US011821015B2

(12) United States Patent
Douchin et al.

(10) Patent No.: US 11,821,015 B2
(45) **Date of Patent: *Nov. 21, 2023**

(54) PRODUCTION OF STEVIOL GLYCOSIDES IN RECOMBINANT HOSTS

(71) Applicant: EVOLVA SA, Reinach (CH)

(72) Inventors: Veronique Douchin, Frederiksberg (DK); Swee Chuang Lim Hallwyl, Vallensbaek Strand (DK); Kim Olsson, Copenhagen (DK)

(73) Assignee: Evolva SA, Reinach (CH)

( * ) Notice: Subject to any disclaimer, the term of this patent is extended or adjusted under 35 U.S.C. 154(b) by 138 days.

This patent is subject to a terminal disclaimer.

(21) Appl. No.: 17/200,673

(22) Filed: Mar. 12, 2021

(65) Prior Publication Data

US 2021/0403970 A1 Dec. 30, 2021

Related U.S. Application Data

(62) Division of application No. 16/091,536, filed as application No. PCT/EP2017/059028 on Apr. 13, 2017, now Pat. No. 10,982,249.

(60) Provisional application No. 62/321,850, filed on Apr. 13, 2016.

(51) Int. Cl.

| | |
|---|---|
| ***C12N 15/63*** | (2006.01) |
| ***C12P 19/56*** | (2006.01) |
| ***A23L 2/60*** | (2006.01) |
| ***A23L 27/30*** | (2016.01) |
| ***G01N 30/02*** | (2006.01) |

(52) U.S. Cl.

CPC ................. *C12P 19/56* (2013.01); *A23L 2/60* (2013.01); *A23L 27/36* (2016.08); *C12N 15/63* (2013.01); *G01N 30/02* (2013.01); *G01N 2030/027* (2013.01)

(58) Field of Classification Search

CPC ................................ C12P 19/56; C12N 15/63

See application file for complete search history.

(56) References Cited

U.S. PATENT DOCUMENTS

| | | | | |
|---|---|---|---|---|
| 4,590,160 | A | 5/1986 | Nishihashi et al. | |
| 5,198,360 | A | 3/1993 | Ballou | |
| 5,204,253 | A | 4/1993 | Sanford et al. | |
| 5,306,862 | A | 4/1994 | Chappell et al. | |
| 5,460,949 | A | 10/1995 | Saunders et al. | |
| 5,538,880 | A | 7/1996 | Lundquist et al. | |
| 6,013,863 | A | 1/2000 | Lundquist et al. | |
| 6,215,051 | B1 | 4/2001 | Yu et al. | |
| 6,255,557 | B1 | 7/2001 | Brandle | |
| 6,284,493 | B1 | 9/2001 | Roth | |
| 6,284,506 | B1 | 9/2001 | Hoshino et al. | |
| 6,329,571 | B1 | 12/2001 | Hiei | |
| 6,586,202 | B2 | 7/2003 | Hoshino et al. | |
| 6,660,507 | B2 | 12/2003 | Cheng et al. | |
| 6,806,076 | B1 | 10/2004 | Miyake et al. | |
| 6,969,595 | B2 | 11/2005 | Brzostowicz et al. | |
| 7,034,140 | B2 | 4/2006 | Bramucci et al. | |
| 7,056,717 | B2 | 6/2006 | Cheng et al. | |
| 7,098,000 | B2 | 8/2006 | Cheng et al. | |
| 7,129,392 | B2 | 10/2006 | Hahn et al. | |
| 7,132,268 | B2 | 11/2006 | Miyake et al. | |
| 7,172,886 | B2 | 2/2007 | Keasling et al. | |
| 7,183,089 | B2 | 2/2007 | Keasling et al. | |
| 7,186,891 | B1 | 3/2007 | Chappell et al. | |
| 7,208,298 | B2 | 4/2007 | Miyake et al. | |
| 7,335,815 | B2 | 2/2008 | Boronat et al. | |
| 7,364,885 | B2 | 4/2008 | Miyake et al. | |
| 7,422,884 | B2 | 9/2008 | Bai et al. | |
| 7,514,597 | B2 | 4/2009 | Nakamura et al. | |
| 7,569,389 | B2 | 9/2009 | Feldmann et al. | |
| 7,692,065 | B2 | 4/2010 | Harper et al. | |
| 7,838,287 | B2 | 11/2010 | Goldsmith et al. | |
| 7,923,541 | B2 | 4/2011 | Yang et al. | |
| 7,927,851 | B2 | 4/2011 | Brandle et al. | |
| 7,981,647 | B2 | 7/2011 | Berry et al. | |
| 9,562,251 | B2 | 2/2017 | Kishore et al. | |
| 9,957,540 | B2 | 5/2018 | Mikkelsen et al. | |
| 10,947,515 | B2 | 3/2021 | Boer et al. | |
| 10,982,249 | B2 * | 4/2021 | Douchin | A23L 27/36 |
| 2002/0142408 | A1 | 10/2002 | DiCosimo et al. | |
| 2003/0033626 | A1 | 2/2003 | Hahn et al. | |
| 2003/0148416 | A1 | 8/2003 | Berry et al. | |
| 2003/0148479 | A1 | 8/2003 | Keasling et al. | |
| 2003/0190734 | A1 | 10/2003 | Hoshino et al. | |
| 2003/0219798 | A1 | 11/2003 | Gokarn et al. | |
| 2004/0010815 | A1 | 1/2004 | Lange et al. | |
| 2004/0072311 | A1 | 4/2004 | DiCosimo et al. | |

(Continued)

FOREIGN PATENT DOCUMENTS

| | | |
|---|---|---|
| CN | 101720910 | 6/2010 |
| CN | 102216313 | 10/2011 |

(Continued)

OTHER PUBLICATIONS

International Search Report issued by the International Searching Authority for International Application No. PCT/US2011/038967, dated Sep. 1, 2011 (10 pages).

Written Opinion of the International Searching Authority for International Application No. PCT/US2011/038967, dated Sep. 1, 2011 (12 pages).

International Preliminary Report on Patentability issued by the International Bureau for International Application No. PCT/US2011/038967, dated Dec. 4, 2012 (13 pages).

Third-Party Submission under 37 CFR 1.290 for U.S. Appl. No. 13/701,406, dated Mar. 7, 2014 (238 pages).

(Continued)

*Primary Examiner* — Tekchand Saidha

(74) *Attorney, Agent, or Firm* — McDonnell Boehnen Hulbert & Berghoff LLP

(57) ABSTRACT

The invention relates to recombinant microorganisms and methods for producing steviol glycosides and steviol glycoside precursors.

22 Claims, 3 Drawing Sheets

Specification includes a Sequence Listing.

(56) References Cited

U.S. PATENT DOCUMENTS

| | | | |
|---|---|---|---|
| 2004/0078846 | A1 | 4/2004 | Desouza et al. |
| 2004/0176570 | A1 | 9/2004 | Bacher et al. |
| 2004/0194162 | A1 | 9/2004 | Hahn et al. |
| 2005/0003474 | A1 | 1/2005 | Desouza et al. |
| 2005/0032169 | A1 | 2/2005 | Miyake et al. |
| 2006/0014264 | A1 | 1/2006 | Sauer et al. |
| 2006/0079476 | A1 | 4/2006 | Keasling et al. |
| 2006/0083838 | A1 | 4/2006 | Jackson et al. |
| 2007/0004000 | A1 | 1/2007 | Miyake et al. |
| 2007/0077616 | A1 | 4/2007 | Keasling et al. |
| 2007/0099261 | A1 | 5/2007 | Keasling et al. |
| 2007/0118916 | A1 | 5/2007 | Puzio et al. |
| 2007/0128311 | A1 | 6/2007 | Prakash et al. |
| 2007/0166782 | A1 | 7/2007 | Keasling et al. |
| 2007/0202579 | A1 | 8/2007 | Berry et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2007/0269857 | A1 | 11/2007 | Miyake et al. |
| 2007/0286850 | A1 | 12/2007 | Bai et al. |
| 2008/0064063 | A1 | 3/2008 | Brandle et al. |
| 2008/0081358 | A1 | 4/2008 | Viitanen et al. |
| 2008/0131926 | A1 | 6/2008 | Miyake et al. |
| 2008/0216397 | A1 | 9/2008 | Busby et al. |
| 2008/0261280 | A1 | 10/2008 | Hahn et al. |
| 2008/0271205 | A1 | 10/2008 | Yamaguchi et al. |
| 2008/0286870 | A1 | 11/2008 | Viitanen et al. |
| 2008/0292775 | A1 | 11/2008 | Prakash et al. |
| 2008/0318227 | A1 | 12/2008 | Bacher et al. |
| 2009/0004724 | A1 | 1/2009 | Keasling et al. |
| 2009/0047718 | A1 | 2/2009 | Blaschek et al. |
| 2009/0055974 | A1 | 2/2009 | Tanksley et al. |
| 2009/0074935 | A1 | 3/2009 | Lee |
| 2009/0143308 | A1 | 6/2009 | Monk et al. |
| 2009/0286262 | A1 | 11/2009 | Slack |
| 2009/0298706 | A1 | 12/2009 | Lee et al. |
| 2010/0112156 | A1 | 5/2010 | Abelyan et al. |
| 2010/0120096 | A1 | 5/2010 | Kitaoka et al. |
| 2010/0221801 | A1 | 9/2010 | Van Dyk |
| 2010/0297722 | A1 | 11/2010 | Anterola et al. |
| 2010/0316782 | A1 | 12/2010 | Shi et al. |
| 2011/0087011 | A1 | 4/2011 | Chiang et al. |
| 2011/0092684 | A1 | 4/2011 | Abelyan et al. |
| 2011/0126318 | A1 | 5/2011 | Allen et al. |
| 2011/0160311 | A1 | 6/2011 | Prakash et al. |
| 2012/0021111 | A1 | 1/2012 | Pfister et al. |
| 2012/0083593 | A1 | 4/2012 | Liu et al. |
| 2012/0164678 | A1 | 6/2012 | Stephanopoulos et al. |
| 2012/0178169 | A1 | 7/2012 | Voytas et al. |
| 2013/0137138 | A1 | 5/2013 | Hansen |
| 2013/0171328 | A1 | 7/2013 | Kishore et al. |
| 2014/0329281 | A1 | 11/2014 | Houghton-Larsen et al. |
| 2015/0159188 | A1 | 6/2015 | Ono et al. |
| 2015/0342234 | A1 | 12/2015 | Hicks et al. |
| 2016/0186225 | A1 | 6/2016 | Mikkelsen et al. |
| 2021/0147815 | A1 | 5/2021 | Boer et al. |

FOREIGN PATENT DOCUMENTS

| | | |
|---|---|---|
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 59101408 | 6/1984 |
| JP | 3-277275 | 12/1991 |
| JP | 05-115298 | 5/1993 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | WO 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/021261 | 5/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | WO2014/191580 | 12/2014 |
| WO | 2015/011209 | 1/2015 |
| WO | WO 2015/007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | 2016/023844 | 2/2016 |
| WO | WO 2016/038095 | 3/2016 |
| WO | WO2016054544 A1 | 4/2016 |

(56) References Cited

FOREIGN PATENT DOCUMENTS

| | | |
|---|---|---|
| WO | WO 2016/120486 | 8/2016 |
| WO | WO 2017/025362 | 2/2017 |
| WO | WO 2017/098017 | 6/2017 |

OTHER PUBLICATIONS

Extended European Search Report and Opinion issued by the European Patent Office for European Application No. 11790428.4, dated Dec. 20, 2013.

Non-Final Office Action for U.S. Appl. No. 14/237,540, dated Dec. 30, 2015 (pp. 1-19).

International Search Report issued by the International Searching Authority for International Application No. PCT/US2012/050021, dated Apr. 12, 2013.

Written Opinion of the International Searching Authority for International Application No. PCT/US2012/050021, dated Apr. 12, 2013.

International Preliminary Report on Patentability issued by the International Bureau for International Application No. PCT/US2012/050021, dated Feb. 11, 2014.

Extended European Search Report issued in EP 15193074.0; dated Feb. 12, 2016, pp. 1-9.

International Search Report from the International Searching Authority for International Application No. PCT/EP2014/052363, dated Sep. 22, 2014 (12 pages).

Written Opinion of the International Searching Authority for International Application No. PCT/EP2014/052363, dated Sep. 22, 2014 (10 pages).

International Preliminary Report on Patentability issued by the International Bureau for International Application No. PCT/EP2014/052363, dated Aug. 11, 2015 (11 pages).

International Preliminary Report on Patentability issued by the International Bureau for International Application No. PCT/EP2014/052675, dated Aug. 11, 2015 (8 pages).

International Search Report of the International Searching Authority for International Application No. PCT/EP2013/075587, dated Feb. 20, 2014 (pp. 1-5).

Written Opinion of the International Searching Authority for International Application No. PCT/EP2013/075587, dated Feb. 20, 2014 (pp. 1-9).

International Preliminary Report on Patentability from the International Bureau for International Application No. PCT/EP2013/075587, dated Jun. 9, 2015 (pp. 1-10).

Invitation to Pay Additional Fees and, Where Applicable, Protest Fee by the International Searching Authority for International Application No. PCT/EP2015/070620, dated Nov. 27, 2015 (pp. 1-14).

International Search Report and Written Opinion of the International Searching Authority for International Application No. PCT/EP2015/068314, dated Jan. 20, 2016 (pp. 1-7).

Written Opinion of the International Searching Authority for International Application No. PCT/EP2015/068314, dated Jan. 20, 2016 (pp. 1-9).

Abraham & Bhat, "Permeabilization of baker's yeast with N-lauroyl sarcosine," J Ind Microbial Biotechnol. 35(8):799-804 (2008).

Ageitos et al., "Oily yeasts as oleaginous cell factories," Appl Microbiol Biotechnol. 90(4):1219-27 (May 2011).

Agrawal, "NMR spectroscopy in the structural elucidation of oligosaccharides and glycosides," Phytochemistry 31(10):3307-30 (1992).

Ajikumar et al., "Terpenoids: opportunities for biosynthsis of natural product drugs using engineered microorganisms," Molecular Pharmaceuticals 5(2):167-90 (2008).

Alakomi et al., "Lactic acid permeabilizes gram-negative bacteria by disrupting the outer membrane," Appl Environ Microbiol. 66(5):2001-5 (2000).

Ali et al., "Biochemical investigation during different stages of in vitro propagation of Stevia rebaudiana," Pak J Bot. 42(4):2827-37 (2010).

Bankar et al., "Environmental and industrial applications of Yarrowia lipolytica," Appl Microbiol Biotechnol. 84(5):847-65 (Oct. 2009).

Baykov et al., "A malachite green procedure for orthophosphate determination and its use in alkaline phosphatase-based enzyme immunoassay," Anal Biochem. 171(2):266-70 (Jun. 1988).

Beopoulos et al., "Yarrowia lipolytica: A model and a tool to understand the mechanisms implicated in lipid accumulation," Biochimie 91(6):692-6 (Jun. 2009).

Brandle et al., "Leaf ESTs from Stevia rebaudiana: A Resource for Gene Discovery in Diterpene Synthesis," Plant Mol Biol. 50(4-5):613-22 (2002).

Brandle & Telmer, "Steviol glycoside biosynthesis," Phytochemistry 68(14):1855-63 (2007).

Brochado et al. "Improved vanillin production in baker's yeast through in silico design," Microb Cell Fact. 9:84-98 (2010).

Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).

Chemler et al., "Biosynthesis of isoprenoids, polyunsaturated fatty acids and flavonoids in *Saccharomyces cerevisiae*," Microb Cell Fact. 5:20 (2006).

Chen, "Summary on Study of Stevioside," China Pharmacist, 10(6):598-599 (2007).

Chen et al., "MolProbity: all-atom structure validation for macromolecular crystallography," Acta Crystallogr D Biol Crystallogr 66(Pt 1):12-21 (Jan. 2010).

Chica et al., "Semi-rational approaches to engineering enzyme activity: combining the benefits of directed evolution and rational design," Curr Opin Biotechnol. 16(4):378-84 (2005).

Chow & Palecek, "Enzyme encapsulation in permeabilized *Saccharomyces cerevisiae* cells," Biotechnol Prog. 20(2):449-56 (2004).

Correa et al., "Genetic mapping of 1,3-beta-glucanase-encoding genes in *Saccharomyces cerevisiae*," Current Genet. 22(4):283-8 (1992).

Darise et al., "Enzymic Transglucosylation of Rubusoside and the Structure-Sweetness Relationship of Steviol-Bisglycosides," Agric. Biol. Chem. 48(10):2483-8 (Jan. 1984).

Davis et al., "MolProbity: all-atom contacts and structure validation for proteins and nucleic acids," Nucleic Acids Res. 35:W375-83 (Apr. 2007).

Del Sorbo et al., "Fungal transporters involved in efflux of natural toxic compounds and fungicides," Fungal. Genet. Biol. 30(1):1-15 (Jun. 2000).

Diener et al., "*Arabidopsis* ALF5, a multidrug efflux transporter gene family member, confers resistance to toxins," Plant Cell 13(7):1625-38 (Jul. 2001).

Dodhia et al., "Engineering human cytochrome P450 enzymes into catalytically self-sufficient chimeras using molecular Lego," J Biol Inorg Chem. 11(7):903-16 (Oct. 2006).

Dubey, et al., An overview of the non-mevalonate pathway for terpenoid biosynthesis in plants, J. Biosci. 28(5):637-46 (2003).

Dubois & Stephenson, "Diterpenoid sweeteners. Synthesis and sensory evaluation of stevioside analogues with Improved organoleptic properties," J. Med. Chem. 28(1):93-8 (Jan. 1985).

EFSA Panel on Food Additives and Nutrient Sources added to Food (ANS), "Scientific Opinion on the safety of steviol glycosides for the proposed uses as a food additive," EFSA Journal 8(4):1537 (2010).

Eisenreich et al., "Biosynthesis of isoprenoids via the non-mevalonate pathway," Cell Mol Life Sci. 61(12):1401-6 (2004).

EMBOSS Needle results for Pairwise Sequence Alignment of UGT91D1 and UGT91D2; dated Apr. 4, 2016, 2 pages.

Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).

Estrada De Martin et al., "Ice2p is important for the distribution and structure of the cortical ER network in *Saccharomyces cerevisiae*," J Cell Sci. 118(Pt 1):65-77 (Oct. 2006).

(56) References Cited

OTHER PUBLICATIONS

Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: Implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2) 151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).

(56) References Cited

OTHER PUBLICATIONS

EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* $288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31(13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. AEE36246, dated Oct. 6, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Ohta et al., MassBank Accession No. FU000299 (May 2016).
Ohta et al., MassBank Accession No. FU000332 (May 2016).
Third Party Submission in U.S. Appl. No. 14/648,747; dated Mar. 28, 2016, pp. 1-231.
International Search Report and Written Opinion of International Search Authority for International Application No. PCTEP2017/059028; dated Jun. 27, 2017, pp. 1-15.
International Preliminary Report on Patentability from the International Bureau for International Application PCTEP2017/059028; dated Oct. 16, 2018 (pp. 1-7).
Garber et al., "Computational methods for transcriptome annotation and quantification using RNA-seq," Nat Methods 8(6):469-77 (2011).
Kawai et al., "Transformation of *Saccharomyces cerevisiae* and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320 (5881 ): 1344-9 (2008).
Nikko & Pelham, "Arrestin-mediated endocytosis of yeast plasma membrane transporters," Traffic 10(12):1856-67 (2009).
Nikko et al. "Arrestin-like proteins mediate ubiquitination and endocytosis of the yeast metal transporter Smf1," EMBO Rep. 9(12):1216-21 (2008).
Olsson et al., "Microbial production of next-generation stevia sweeteners," Microbial Cell Factories, 15:11-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Bioi. 11(3):R25 (2010).
Saier Jr. et al., "The transporter classification database," Nucl. Acids Res., 42(1):D251-258 (2014).
Wang et al., "RNA-Seq: a revolutionary tool for transcriptomics," Nat Rev Genet. 10(1):57-63 (2009).
Wilhelm et al., "Defining transcribed regions using RNA-seq," Nature Protocols 5:255-66 (2010).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Arnold, F. H. "Combinatorial and computational challenges for biocatalyst design," Nature 409(6817):253-257 (2001).
Bruyn et al., "Metabolic engineering of *Escherichia coli* into a versatile glycosylation platform: production of bio-active quercetin glycosides," Microb Cell Fact., 14:138 (2015).
Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Duetz, "Microtiter plates as mini-bioreactors: miniaturization of fermentation methods," Trends Microbiol 15(10):469-75 (2007).
François et al., "Reserve carbohydrates metabolism in the yeast *Saccharomyces cerevisiae*," FEMS Microbiol Rev., 25(1):125-45 (2001).
Li et al., "Production of rebaudioside A from stevioside catalyzed by the engineered *Saccharomyces cerevisiae*," Appl Biochem Biotechnol., 178(8):1586-98 (2016).

(56) References Cited

OTHER PUBLICATIONS

Mikayama et al., "Molecular cloning and functional expression of a cDNA encoding glycosylation-inhibiting factor," Proc Natl Acad Sci U S A. 90(21):10056-60 (1993).
Rudinger et al., "Characteristics of the amino acids as components of a peptide hormone sequence," Peptide Hormones. Biol. Council. pp. 5-7 (1976).
Saier, "Families of transmembrane sugar transport proteins," Mol Microbiol., 35(4):699-710 (2000).
Tiwari et al., "Plant secondary metabolism linked glycosyltransferases: An update on expaning knowledge and scopes", Biotechnology Advances, 34:714-739 (May 2016).
GenBank Accession No. AZF53544, dated Apr. 14, 2011 (2 pages).
UniProt Accession No. B5MEX6, Nov. 4, 2008 (1 page).
UniProt Accession No. E4MVV7, Feb. 8, 2011 (1 page).
UniProt Accession No. F6KWJ2, Jul. 27, 2011 (1 page).
UniProt Accession No. H9BYK3, May 16, 2012 (1 page).
International Preliminary Report on Patentability from the International Bureau for International Application PCT/EP2015/070620; dated March 14, 2017 (pp. 1-25).
International Preliminary Report on Patentability from the International Bureau for International Application PCTEP2015/068314; dated Feb. 14, 2017 (pp. 1-10).
International Search Report and Written Opinion of the International Searching Authority for International Application No. PCT/EP2015/052007; dated Jul. 4, 2016, pp. 1-24.
International Preliminary Report on Patentability from the International Bureau for International Application PCT/EP2015/052007; dated Aug. 1, 2017 (pp. 1-16).
International Search Report and Written Opinion of the International Searching Authority for International Application No. PCT/EP2016/068259; dated Jan. 24, 2017, pp. 1-18.
International Preliminary Report on Patentability from the International Bureau for International Application PCT/EP2016/068259; dated Feb. 13, 2018 (pp. 1-11).
International Search Report and Written Opinion of International Search Authority for International Application No. PCTEP2016/080516; dated Mar. 15, 2017, pp. 1-22.
International Preliminary Report on Patentability from the International Bureau for International Application PCTEP2016/080516; dated Jun. 12, 2018 (pp. 1-11).
International Search Report and Written Opinion of the International Searching Authority for International Application No. PCT/EP2017/061775; dated Sep. 6, 2017, pp. 1-17.
International Preliminary Report on Patentability from the International Bureau for International Application PCT/EP2017/061775; dated Nov. 20, 2018 (pp. 1-9).
International Search Report of the International Searching Authority for International Application No. PCT/EP2017/061774; dated Aug. 30, 2017, pp. 1-20.
Written Opinion of the International Searching Authority for International Application No. PCT/EP2017/061774; dated Aug. 30, 2017, pp. 1-13.
International Preliminary Report on Patentability from then International Search Authority for International Application No. PCT/EP2017/061774; dated Nov. 20, 2018, pp. 1-14.
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008).
Devos et al., "Practical limits of function prediction," Proteins: Structure, Function, and Genetics, vol. 41: 98-107 (2000).
Pearson & Lipman, "Improved tools for biological sequence comparison," Proc Natl Acad Sci. 85(8):2444-8 (1988).
Seffernick et al., "Melamine deaminase and Atrazine chlorohydrolase: 98 percent identical but functionally different," J. Bacterial., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from *Saccharomyces cerevisiae*," Eur J Biochem. 233(2):520-30 (Jul. 1995).
Husar et al., "Overexpression of the UGT73C6 alters brassinosteriod glucoside formation in *Arabidopsis thaliana*", BMC Plant Biology, 11:1-14 (2011).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).
Mao et al., "Produce steviol glycosides in engineered yeast", 2015 Synthetic Biology: Engineering, Evolution & Design (SEED), Poster Abstract (Jun. 2015).
Nagatoshi et al., "UGT75L6 and UGT94E5 mediate sequential glucosylation of crocetin to crocin in Gardenia iasminoides", FEBS Letters, 586:1055-1061 (2012).
Wang et al., "Pathway mining-based integration of critical enzyme parts for de novo biosynthesis of steviol glycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "Design and construction of artificial biological systems for complex natural products biosynthesis", Chinese Journal of Biotechnology, 29:1146-1160 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: in-house validation and application to wheat," Journal of Chromatography A, 1423, pp. 183-189 (2015).
Yang et al., "Base substitution mutations in uridinediphosphate-dependent glycosyltransferase 76G1 gene of Stevia rebaudioside A; Mustation in UGT76G1, a key gene of steviol glycoside synthesis", Plant Physiology and Biochemistry, 80:220-225 (2014).
Examination Report issued by the European Patent Office for European Application No. 12750513.9, dated Nov. 26, 2014.
Ceunen & Geuns, "Steviol glycosides: chemical diversity, metabolism, and function," J. Nat. Prod. 76(6):1201-28 (Jun. 2013).
Olsson et al., "Microbial production of next-generation stevia sweeteners," Microbial Cell Factories, 15:1-14 (2016).
Song et al., "The Aspergillus fumigatus 1-29 damage resistance protein family coordinately regulates ergosterol biosynthesis and azole susceptibility," MBIO, 7:1-13 (2016).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).

(56) References Cited

OTHER PUBLICATIONS

Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-concepción & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
GenBank Accession No. AAS07253.1, dated Jan. 31, 2004 (3 pages).
Gloster, "Advances in understanding glycosyltransferases from a structural perspective," Curr Opin Struct Biol. 28:131-41 (2014).
Guo et al., "Protein tolerance to random amino acid change", Proceedings of the National Academy of Sciences USA, vol. 101, No. 25, pp. 9205-9210 (2004).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Ni et al., "Outer membrane mutation effects on UDP-glucose permeability and whole-cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Unligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
Wang, et al., "Glycosylation and Glycosyltransferase of Small Molecular Compounds of Plan", Plant Physiology Communications 44(5):997-1003, Oct. 2008.
Liu et al., "Functional and Biochemical Characteritzation of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 60(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of

(56) References Cited

OTHER PUBLICATIONS the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1(3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4, 11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for *Aspergillus nidulans*," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from Intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Jones et al., "UGT73C6 and UGT78D1, Glycosyltransferases Involved in Flavonol Glycoside Biosynthesis in *Arabidopsis thaliana**," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone 4-0-Glucoside, Appl. Environ. Microbial., vol. 72, pp. 4404-4410 (2006).

* cited by examiner

GGPP

*ent*-Copalyl-PP

*ent*-Kaurene

*ent*-Kaurenoic acid

Steviol

Steviol
Steviol-13-O-glucoside
Steviol-19-O-Glucoside
Steviol-1,3-bioside
Steviol-1,2-bioside
Rubusoside
RebB
1,3-Stevioside (RebG)
Stevioside
RebQ
RebA
RebE
RebI
RebD
RebM

SEQUENCE LISTING

<160> NUMBER OF SEQ ID NOS: 155

<210> SEQ ID NO 1
<211> LENGTH: 1713
<212> TYPE: DNA
<213> ORGANISM: Saccharomyces cerevisiae

<400> SEQUENCE: 1
atgtcacttc taatagattc tgtaccaaca gttgcttata aggaccaaaa accgggtact 60
tcaggtttac gtaagaagac caaggttttc atggatgagc ctcattatac tgagaacttc 120
attcaagcaa caatgcaatc tatccctaat ggctcagagg gaaccacttt agttgttgga 180
ggagatggtc gtttctacaa cgatgttatc atgaacaaga ttgccgcagt aggtgctgca 240
aacggtgtca gaaagttagt cattggtcaa ggcggtttac tttcaacacc agctgcttct 300
catataatta gaacatacga ggaaaagtgt accggtggtg gtatcatatt aactgcctca 360
cacaacccag gcggtccaga gaatgattta ggtatcaagt ataatttacc taatggtggg 420
ccagctccag agagtgtcac taacgctatc tgggaagcgt ctaaaaaatt aactcactat 480
aaaattataa agaacttccc caagttgaat ttgaacaagc ttggtaaaaa ccaaaaatat 540
ggcccattgt tagtggacat aattgatcct gccaaagcat acgttcaatt tctgaaggaa 600
atttttgatt ttgacttaat taaaagcttc ttagcgaaac agcgcaaaga caaagggtgg 660
aagttgttgt ttgactcctt aaatggtatt acaggaccat atggtaaggc tatatttgtt 720
gatgaatttg gtttaccggc agaggaagtt cttcaaaatt ggcacccttt acctgatttc 780
ggcggtttac atcccgatcc gaatctaacc tatgcacgaa ctcttgttga cagggttgac 840
cgcgaaaaaa ttgcctttgg agcagcctcc gatggtgatg gtgataggaa tatgatttac 900
ggttatggcc ctgctttcgt ttcgccaggt gattctgttg ccattattgc cgaatatgca 960
cccgaaattc catacttcgc caaacaaggt atttatggct tggcacgttc atttcctaca 1020
tcctcagcca ttgatcgtgt tgcagcaaaa aagggattaa gatgttacga agttccaacc 1080

-continued

```
ggctggaaat tcttctgtgc cttatttgat gctaaaaagc tatcaatctg tggtgaagaa   1140

tccttcggta caggttccaa tcatatcaga gaaaaggacg gtctatgggc cattattgct   1200

tggttaaata tcttggctat ctaccatagg cgtaaccctg aaaaggaagc ttcgatcaaa   1260

actattcagg acgaattttg gaacgagtat ggccgtactt tcttcacaag atacgattac   1320

gaacatatcg aatgcgagca ggccgaaaaa gttgtagctc ttttgagtga atttgtatca   1380

aggccaaacg tttgtggctc ccacttccca gctgatgagt ctttaaccgt tatcgattgt   1440

ggtgattttt cgtatagaga tctagatggc tccatctctg aaaatcaagg ccttttcgta   1500

aagttttcga atgggactaa atttgttttg aggttatccg gcacaggcag ttctggtgca   1560

acaataagat tatacgtaga aaagtatact gataaaaagg agaactatgg ccaaacagct   1620

gacgtcttct tgaaacccgt catcaactcc attgtaaaat tcttaagatt taaagaaatt   1680

ttaggaacag acgaaccaac agtccgcaca tag                                 1713
```

<210> SEQ ID NO 2
<211> LENGTH: 570
<212> TYPE: PRT
<213> ORGANISM: Saccharomyces cerevisiae

<400> SEQUENCE: 2

```
Met Ser Leu Leu Ile Asp Ser Val Pro Thr Val Ala Tyr Lys Asp Gln
1               5                   10                  15

Lys Pro Gly Thr Ser Gly Leu Arg Lys Lys Thr Lys Val Phe Met Asp
            20                  25                  30

Glu Pro His Tyr Thr Glu Asn Phe Ile Gln Ala Thr Met Gln Ser Ile
        35                  40                  45

Pro Asn Gly Ser Glu Gly Thr Thr Leu Val Val Gly Gly Asp Gly Arg
    50                  55                  60

Phe Tyr Asn Asp Val Ile Met Asn Lys Ile Ala Ala Val Gly Ala Ala
65                  70                  75                  80

Asn Gly Val Arg Lys Leu Val Ile Gly Gln Gly Gly Leu Leu Ser Thr
                85                  90                  95

Pro Ala Ala Ser His Ile Ile Arg Thr Tyr Glu Glu Lys Cys Thr Gly
            100                 105                 110

Gly Gly Ile Ile Leu Thr Ala Ser His Asn Pro Gly Gly Pro Glu Asn
        115                 120                 125

Asp Leu Gly Ile Lys Tyr Asn Leu Pro Asn Gly Gly Pro Ala Pro Glu
    130                 135                 140

Ser Val Thr Asn Ala Ile Trp Glu Ala Ser Lys Lys Leu Thr His Tyr
145                 150                 155                 160

Lys Ile Ile Lys Asn Phe Pro Lys Leu Asn Leu Asn Lys Leu Gly Lys
                165                 170                 175

Asn Gln Lys Tyr Gly Pro Leu Leu Val Asp Ile Ile Asp Pro Ala Lys
            180                 185                 190

Ala Tyr Val Gln Phe Leu Lys Glu Ile Phe Asp Phe Asp Leu Ile Lys
        195                 200                 205

Ser Phe Leu Ala Lys Gln Arg Lys Asp Lys Gly Trp Lys Leu Leu Phe
    210                 215                 220

Asp Ser Leu Asn Gly Ile Thr Gly Pro Tyr Gly Lys Ala Ile Phe Val
225                 230                 235                 240

Asp Glu Phe Gly Leu Pro Ala Glu Glu Val Leu Gln Asn Trp His Pro
                245                 250                 255

Leu Pro Asp Phe Gly Gly Leu His Pro Asp Pro Asn Leu Thr Tyr Ala
```

```
            260                 265                 270

Arg Thr Leu Val Asp Arg Val Asp Arg Glu Lys Ile Ala Phe Gly Ala
        275                 280                 285

Ala Ser Asp Gly Asp Gly Asp Arg Asn Met Ile Tyr Gly Tyr Gly Pro
    290                 295                 300

Ala Phe Val Ser Pro Gly Asp Ser Val Ala Ile Ile Ala Glu Tyr Ala
305                 310                 315                 320

Pro Glu Ile Pro Tyr Phe Ala Lys Gln Gly Ile Tyr Gly Leu Ala Arg
                325                 330                 335

Ser Phe Pro Thr Ser Ser Ala Ile Asp Arg Val Ala Ala Lys Lys Gly
            340                 345                 350

Leu Arg Cys Tyr Glu Val Pro Thr Gly Trp Lys Phe Phe Cys Ala Leu
        355                 360                 365

Phe Asp Ala Lys Lys Leu Ser Ile Cys Gly Glu Glu Ser Phe Gly Thr
    370                 375                 380

Gly Ser Asn His Ile Arg Glu Lys Asp Gly Leu Trp Ala Ile Ile Ala
385                 390                 395                 400

Trp Leu Asn Ile Leu Ala Ile Tyr His Arg Arg Asn Pro Glu Lys Glu
                405                 410                 415

Ala Ser Ile Lys Thr Ile Gln Asp Glu Phe Trp Asn Glu Tyr Gly Arg
            420                 425                 430

Thr Phe Phe Thr Arg Tyr Asp Tyr Glu His Ile Glu Cys Glu Gln Ala
        435                 440                 445

Glu Lys Val Val Ala Leu Leu Ser Glu Phe Val Ser Arg Pro Asn Val
    450                 455                 460

Cys Gly Ser His Phe Pro Ala Asp Glu Ser Leu Thr Val Ile Asp Cys
465                 470                 475                 480

Gly Asp Phe Ser Tyr Arg Asp Leu Asp Gly Ser Ile Ser Glu Asn Gln
                485                 490                 495

Gly Leu Phe Val Lys Phe Ser Asn Gly Thr Lys Phe Val Leu Arg Leu
            500                 505                 510

Ser Gly Thr Gly Ser Ser Gly Ala Thr Ile Arg Leu Tyr Val Glu Lys
        515                 520                 525

Tyr Thr Asp Lys Lys Glu Asn Tyr Gly Gln Thr Ala Asp Val Phe Leu
    530                 535                 540

Lys Pro Val Ile Asn Ser Ile Val Lys Phe Leu Arg Phe Lys Glu Ile
545                 550                 555                 560

Leu Gly Thr Asp Glu Pro Thr Val Arg Thr
                565                 570


<210> SEQ ID NO 3
<211> LENGTH: 1383
<212> TYPE: DNA
<213> ORGANISM: Stevia rebaudiana

<400> SEQUENCE: 3

atggcagagc aacaaaagat caaaaagtca cctcacgtct tacttattcc atttcctctg      60

caaggacata tcaacccatt catacaattt gggaaaagat tgattagtaa gggtgtaaag     120

acaacactgg taaccactat ccacactttg aattctactc tgaaccactc aaatactact     180

actacaagta tagaaattca agctatatca gacggatgcg atgagggtgg ctttatgtct     240

gccggtgaat cttacttgga aacattcaag caagtgggat ccaagtctct ggccgatcta     300

atcaaaaagt tacagagtga aggcaccaca attgacgcca taatctacga ttctatgaca     360

gagtgggttt tagacgttgc tatcgaattt ggtattgatg gaggttcctt tttcacacaa     420
```

```
gcatgtgttg tgaattctct atactaccat gtgcataaag ggttaatctc tttaccattg    480

ggtgaaactg tttcagttcc aggttttcca gtgttacaac gttgggaaac cccattgatc    540

ttacaaaatc atgaacaaat acaatcacct tggtcccaga tgttgtttgg tcaattcgct    600

aacatcgatc aagcaagatg ggtctttact aattcattct ataagttaga ggaagaggta    660

attgaatgga ctaggaagat ctggaatttg aaagtcattg gtccaacatt gccatcaatg    720

tatttggaca aaagacttga tgatgataaa gataatggtt tcaatttgta caaggctaat    780

catcacgaat gtatgaattg gctggatgac aaaccaaagg aatcagttgt atatgttgct    840

ttcggctctc ttgttaaaca tggtccagaa caagttgagg agattacaag agcacttata    900

gactctgacg taaacttttt gtgggtcatt aagcacaaag aggaggggaa actgccagaa    960

aacctttctg aagtgataaa gaccggaaaa ggtctaatcg ttgcttggtg taaacaattg   1020

gatgttttag ctcatgaatc tgtaggctgt tttgtaacac attgcggatt caactctaca   1080

ctagaagcca tttccttagg cgtacctgtc gttgcaatgc ctcagttctc cgatcagaca   1140

accaacgcta aacttttgga cgaaatacta ggggtgggtg tcagagttaa agcagacgag   1200

aatggtatcg tcagaagagg gaacctagct tcatgtatca aaatgatcat ggaagaggaa   1260

agaggagtta tcataaggaa aaacgcagtt aagtggaagg atcttgcaaa ggttgccgtc   1320

catgaaggcg gctcttcaga taatgatatt gttgaatttg tgtccgaact aatcaaagcc   1380

taa                                                                 1383
```

```
<210> SEQ ID NO 4
<211> LENGTH: 460
<212> TYPE: PRT
<213> ORGANISM: Stevia rebaudiana

<400> SEQUENCE: 4

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
```

```
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460


<210> SEQ ID NO 5
<211> LENGTH: 1586
<212> TYPE: DNA
<213> ORGANISM: Stevia rebaudiana

<400> SEQUENCE: 5

atggatgcaa tggctacaac tgagaagaaa ccacacgtca tcttcatacc atttccagca     60

caaagccaca ttaaagccat gctcaaacta gcacaacttc tccaccacaa aggactccag    120

ataaccttcg tcaacaccga cttcatccac aaccagtttc ttgaatcatc gggcccacat    180

tgtctagacg gtgcaccggg tttccggttc gaaaccattc cggatggtgt ttctcacagt    240

ccggaagcga gcatcccaat cagagaatca ctcttgagat ccattgaaac caacttcttg    300

gatcgtttca ttgatcttgt aaccaaactt ccggatcctc cgacttgtat tatctcagat    360

gggttcttgt cggttttcac aattgacgct gcaaaaaagc ttggaattcc ggtcatgatg    420

tattggacac ttgctgcctg tgggttcatg ggtttttacc atattcattc tctcattgag    480

aaaggatttg caccacttaa agatgcaagt tacttgacaa atgggtattt ggacaccgtc    540

attgattggg ttccgggaat ggaaggcatc cgtctcaagg atttcccgct ggactggagc    600

actgacctca atgacaaagt tttgatgttc actacggaag ctcctcaaag gtcacacaag    660
```

gtttcacatc atattttcca cacgttcgat gagttggagc ctagtattat aaaaactttg 720
tcattgaggt ataatcacat ttacaccatc ggcccactgc aattacttct tgatcaaata 780
cccgaagaga aaaagcaaac tggaattacg agtctccatg gatacagttt agtaaaagaa 840
gaaccagagt gtttccagtg gcttcagtct aaagaaccaa attccgtcgt ttatgtaaat 900
tttggaagta ctacagtaat gtctttagaa gacatgacgg aatttggttg gggacttgct 960
aatagcaacc attatttcct ttggatcatc cgatcaaact tggtgatagg ggaaaatgca 1020
gttttgcccc ctgaacttga ggaacatata aagaaaagag gctttattgc tagctggtgt 1080
tcacaagaaa aggtcttgaa gcacccttcg gttggagggt tcttgactca ttgtgggtgg 1140
ggatcgacca tcgagagctt gtctgctggg gtgccaatga tatgctggcc ttattcgtgg 1200
gaccagctga ccaactgtag gtatatatgc aaagaatggg aggttgggct cgagatggga 1260
accaaagtga aacgagatga agtcaagagg cttgtacaag agttgatggg agaaggaggt 1320
cacaaaatga ggaacaaggc taaagattgg aaagaaaagg ctcgcattgc aatagctcct 1380
aacggttcat cttctttgaa catagacaaa atggtcaagg aaatcaccgt gctagcaaga 1440
aactagttac aaagttgttt cacattgtgc tttctattta agatgtaact ttgttctaat 1500
ttaatattgt ctagatgtat tgaaccataa gtttagttgg tctcaggaat tgatttttaa 1560
tgaaataatg gtcattaggg gtgagt 1586

<210> SEQ ID NO 6
<211> LENGTH: 1446
<212> TYPE: DNA
<213> ORGANISM: Artificial Sequence
<220> FEATURE:
<223> OTHER INFORMATION: Codon-optimized UGT85C2

<400> SEQUENCE: 6
atggatgcaa tggcaactac tgagaaaaag cctcatgtga tcttcattcc atttcctgca 60
caatctcaca taaaggcaat gctaaagtta gcacaactat tacaccataa gggattacag 120
ataactttcg tgaataccga cttcatccat aatcaatttc tggaatctag tggccctcat 180
tgtttggacg gagccccagg gtttagattc gaaacaattc ctgacggtgt ttcacattcc 240
ccagaggcct ccatcccaat aagagagagt ttactgaggt caatagaaac caactttttg 300
gatcgtttca ttgacttggt cacaaaactt ccagacccac caacttgcat aatctctgat 360
ggctttctgt cagtgtttac tatcgacgct gccaaaaagt tgggtatccc agttatgatg 420
tactggactc ttgctgcatg cggtttcatg ggtttctatc acatccattc tcttatcgaa 480
aagggttttg ctccactgaa agatgcatca tacttaacca acggctacct ggatactgtt 540
attgactggg taccaggtat ggaaggtata agacttaaag attttccttt ggattggtct 600
acagacctta atgataaagt attgatgttt actacagaag ctccacaaag atctcataag 660
gtttcacatc atatctttca cacctttgat gaattggaac catcaatcat caaaaccttg 720
tctctaagat acaatcatat ctacactatt ggtccattac aattacttct agatcaaatt 780
cctgaagaga aaaagcaaac tggtattaca tccttacacg gctactcttt agtgaaagag 840
gaaccagaat gttttcaatg gctacaaagt aaagagccta attctgtggt ctacgtcaac 900
ttcggaagta caacagtcat gtccttggaa gatatgactg aatttggttg ggccttgct 960 aattcaaatc attactttct atggattatc aggtccaatt tggtaatagg ggaaaacgcc 1020
gtattacctc cagaattgga ggaacacatc aaaaagagag gtttcattgc ttcctggtgt 1080

```
tctcaggaaa aggtattgaa acatccttct gttggtggtt tccttactca ttgcggttgg   1140

ggctctacaa tcgaatcact aagtgcagga gttccaatga tttgttggcc atattcatgg   1200

gaccaactta caaattgtag gtatatctgt aaagagtggg aagttggatt agaaatggga   1260

acaaaggtta aacgtgatga agtgaaaaga ttggttcagg agttgatggg ggaaggtggc   1320

cacaagatga gaaacaaggc caaagattgg aaggaaaaag ccagaattgc tattgctcct   1380

aacgggtcat cctctctaaa cattgataag atggtcaaag agattacagt cttagccaga   1440

aactaa                                                              1446
```

<210> SEQ ID NO 7
<211> LENGTH: 481
<212> TYPE: PRT
<213> ORGANISM: Stevia rebaudiana

<400> SEQUENCE: 7

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300
```

Thr Val Met Ser Leu Glu Asp Met Thr Glu Phe Gly Trp Gly Leu Ala
305 310 315 320

Asn Ser Asn His Tyr Phe Leu Trp Ile Ile Arg Ser Asn Leu Val Ile
325 330 335

Gly Glu Asn Ala Val Leu Pro Pro Glu Leu Glu Glu His Ile Lys Lys
340 345 350

Arg Gly Phe Ile Ala Ser Trp Cys Ser Gln Glu Lys Val Leu Lys His
355 360 365

Pro Ser Val Gly Gly Phe Leu Thr His Cys Gly Trp Gly Ser Thr Ile
370 375 380

Glu Ser Leu Ser Ala Gly Val Pro Met Ile Cys Trp Pro Tyr Ser Trp
385 390 395 400

Asp Gln Leu Thr Asn Cys Arg Tyr Ile Cys Lys Glu Trp Glu Val Gly
405 410 415

Leu Glu Met Gly Thr Lys Val Lys Arg Asp Glu Val Lys Arg Leu Val
420 425 430

Gln Glu Leu Met Gly Glu Gly Gly His Lys Met Arg Asn Lys Ala Lys
435 440 445

Asp Trp Lys Glu Lys Ala Arg Ile Ala Ile Ala Pro Asn Gly Ser Ser
450 455 460

Ser Leu Asn Ile Asp Lys Met Val Lys Glu Ile Thr Val Leu Ala Arg
465 470 475 480

Asn

<210> SEQ ID NO 8
<211> LENGTH: 1377
<212> TYPE: DNA
<213> ORGANISM: Artificial Sequence
<220> FEATURE:
<223> OTHER INFORMATION: Codon-optimized UGT76G1

<400> SEQUENCE: 8
atggaaaaca agaccgaaac aacagttaga cgtaggcgta gaatcattct gtttccagta 60
ccttttcaag ggcacatcaa tccaatacta caactagcca acgttttgta ctctaaaggt 120
ttttctatta caatctttca caccaatttc aacaaaccaa aaacatccaa ttacccacat 180
ttcacattca gattcatact tgataatgat ccacaagatg aacgtatttc aaacttacct 240
acccacggtc ctttagctgg aatgagaatt ccaatcatca atgaacatgg tgccgatgag 300
cttagaagag aattagagtt acttatgttg gcatccgaag aggacgagga agtctcttgt 360
ctgattactg acgctctatg gtactttgcc caatctgtgg ctgatagttt gaatttgagg 420
agattggtac taatgacatc cagtctgttt aactttcacg ctcatgttag tttaccacaa 480
tttgacgaat tgggatactt ggaccctgat gacaagacta ggttagagga acaggcctct 540
ggttttccta tgttgaaagt caaagatatc aagtctgcct attctaattg gcaaatcttg 600
aaagagatct taggaaagat gatcaaacag acaaaggctt catctggagt gatttggaac 660
agtttcaaag agttagaaga gtctgaattg gagactgtaa tcagagaaat tccagcacct 720
tcattcctga taccattacc aaaacatttg actgcttcct cttcctcttt gttggatcat 780
gacagaacag tttttcaatg gttggaccaa caaccaccta gttctgtttt gtacgtgtca 840
tttggtagta cttctgaagt cgatgaaaag gacttccttg aaatcgcaag aggcttagtc 900
gatagtaagc agtcattcct ttgggtcgtg cgtccaggtt tcgtgaaagg ctcaacatgg 960
gtcgaaccac ttccagatgg ttttctaggc gaaagaggta gaatagtcaa atgggttcct 1020

-continued

```
caacaggaag ttttagctca tggcgctatt ggggcattct ggactcattc cggatggaat   1080

tcaactttag aatcagtatg cgaaggggta cctatgatct tttcagattt tggtcttgat   1140

caaccactga acgcaagata catgtctgat gttttgaaag tgggtgtata tctagaaaat   1200

ggctgggaaa ggggtgaaat agctaatgca ataagacgtg ttatggttga tgaagagggg   1260

gagtatatca gacaaaacgc aagagtgctg aagcaaaagg ccgacgtttc tctaatgaag   1320

ggaggctctt catacgaatc cttagaatct cttgtttcct acatttcatc actgtaa      1377


<210> SEQ ID NO 9
<211> LENGTH: 458
<212> TYPE: PRT
<213> ORGANISM: Stevia rebaudiana

<400> SEQUENCE: 9

Met Glu Asn Lys Thr Glu Thr Thr Val Arg Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320
```

```
Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455


<210> SEQ ID NO 10
<211> LENGTH: 1422
<212> TYPE: DNA
<213> ORGANISM: Artificial Sequence
<220> FEATURE:
<223> OTHER INFORMATION: Codon-optimized UGT91D2e

<400> SEQUENCE: 10

atggctacat ctgattctat tgttgatgac aggaagcagt tgcatgtggc tactttccct     60

tggcttgctt tcggtcatat actgccttac ctacaactat caaaactgat agctgaaaaa    120

ggacataaag tgtcattcct ttcaacaact agaaacattc aaagattatc ttcccacata    180

tcaccattga ttaacgtcgt tcaattgaca cttccaagag tacaggaatt accagaagat    240

gctgaagcta caacagatgt gcatcctgaa gatatccctt acttgaaaaa ggcatccgat    300

ggattacagc ctgaggtcac tagattcctt gagcaacaca gtccagattg gatcatatac    360

gactacactc actattggtt gccttcaatt gcagcatcac taggcatttc tagggcacat    420

ttcagtgtaa ccacaccttg ggccattgct tacatgggtc catccgctga tgctatgatt    480

aacggcagtg atggtagaac taccgttgaa gatttgacaa ccccaccaaa gtggtttcca    540

tttccaacta aagtctgttg gagaaaacac gacttagcaa gactggttcc atacaaggca    600

ccaggaatct cagacggcta tagaatgggt ttagtcctta aagggtctga ctgcctattg    660

tctaagtgtt accatgagtt tggacacaa tggctaccac ttttggaaac attacaccaa    720

gttcctgtcg taccagttgg tctattacct ccagaaatcc ctggtgatga gaaggacgag    780

acttgggttt caatcaaaaa gtggttagac gggaagcaaa aaggctcagt ggtatatgtg    840

gcactgggtt ccgaagtttt agtatctcaa acagaagttg tggaacttgc cttaggtttg    900

gaactatctg gattgccatt tgtctgggcc tacagaaaac caaaaggccc tgcaaagtcc    960

gattcagttg aattgccaga cggctttgtc gagagaacta gagatagagg gttggtatgg   1020

acttcatggg ctccacaatt gagaatcctg agtcacgaat ctgtgtgcgg tttcctaaca   1080

cattgtggtt ctggttctat agttgaagga ctgatgtttg gtcatccact tatcatgttg   1140

ccaatctttg gtgaccagcc tttgaatgca cgtctgttag aagataaaca agttggaatt   1200

gaaatcccac gtaatgagga agatggatgt ttaaccaagg agtctgtggc cagatcatta   1260
```

```
cgttccgttg tcgttgaaaa ggaaggcgaa atctacaagg ccaatgcccg tgaactttca   1320

aagatctaca atgacacaaa agtagagaag gaatatgttt ctcaatttgt agattaccta   1380

gagaaaaacg ctagagccgt agctattgat catgaatcct aa                      1422


<210> SEQ ID NO 11
<211> LENGTH: 473
<212> TYPE: PRT
<213> ORGANISM: Stevia rebaudiana

<400> SEQUENCE: 11

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
```

340 345 350

Glu Ser Val Cys Gly Phe Leu Thr His Cys Gly Ser Gly Ser Ile Val
355 360 365

Glu Gly Leu Met Phe Gly His Pro Leu Ile Met Leu Pro Ile Phe Gly
370 375 380

Asp Gln Pro Leu Asn Ala Arg Leu Leu Glu Asp Lys Gln Val Gly Ile
385 390 395 400

Glu Ile Pro Arg Asn Glu Glu Asp Gly Cys Leu Thr Lys Glu Ser Val
405 410 415

Ala Arg Ser Leu Arg Ser Val Val Val Glu Lys Glu Gly Glu Ile Tyr
420 425 430

Lys Ala Asn Ala Arg Glu Leu Ser Lys Ile Tyr Asn Asp Thr Lys Val
435 440 445

Glu Lys Glu Tyr Val Ser Gln Phe Val Asp Tyr Leu Glu Lys Asn Ala
450 455 460

Arg Ala Val Ala Ile Asp His Glu Ser
465 470

<210> SEQ ID NO 12
<211> LENGTH: 1422
<212> TYPE: DNA
<213> ORGANISM: Artificial Sequence
<220> FEATURE:
<223> OTHER INFORMATION: Codon-optimized UGT91D2e-b

<400> SEQUENCE: 12
atggctactt ctgattccat cgttgacgat agaaagcaat tgcatgttgc tacttttcca 60
tggttggctt tcggtcatat tttgccatac ttgcaattgt ccaagttgat tgctgaaaag 120
ggtcacaagg tttcattctt gtctaccacc agaaacatcc aaagattgtc ctctcatatc 180
tccccattga tcaacgttgt tcaattgact ttgccaagag tccaagaatt gccagaagat 240
gctgaagcta ctactgatgt tcatccagaa gatatccctt acttgaaaaa ggcttccgat 300
ggtttacaac cagaagttac tagattcttg gaacaacatt ccccagattg gatcatctac 360
gattatactc attactggtt gccatccatt gctgcttcat tgggtatttc tagagcccat 420
ttctctgtta ctactccatg ggctattgct tatatgggtc catctgctga tgctatgatt 480
aacggttctg atggtagaac taccgttgaa gatttgacta ctccaccaaa gtggtttcca 540
tttccaacaa aagtctgttg gagaaaacac gatttggcta gattggttcc atacaaagct 600
ccaggtattt ctgatggtta cagaatgggt atggttttga aaggttccga ttgcttgttg 660
tctaagtgct atcatgaatt cggtactcaa tggttgcctt tgttggaaac attgcatcaa 720
gttccagttg ttccagtagg tttgttgcca ccagaaattc caggtgacga aaaagacgaa 780
acttgggttt ccatcaaaaa gtggttggat ggtaagcaaa agggttctgt tgtttatgtt 840
gctttgggtt ccgaagcttt ggtttctcaa accgaagttg ttgaattggc tttgggtttg 900
gaattgtctg gtttgccatt tgtttgggct tacagaaaac ctaaaggtcc agctaagtct 960
gattctgttg aattgccaga tggtttcgtt gaaagaacta gagatagagg tttggtttgg 1020
acttcttggg ctccacaatt gagaattttg tctcatgaat ccgtctgtgg tttcttgact 1080
cattgtggtt ctggttctat cgttgaaggt ttgatgtttg gtcacccatt gattatgttg 1140
ccaatctttg gtgaccaacc attgaacgct agattattgg aagataagca agtcggtatc 1200
gaaatcccaa gaaatgaaga agatggttgc ttgaccaaag aatctgttgc tagatctttg 1260
agatccgttg tcgttgaaaa agaaggtgaa atctacaagg ctaacgctag agaattgtcc 1320
aagatctaca acgataccaa ggtcgaaaaa gaatacgttt cccaattcgt tgactacttg 1380
gaaaagaatg ctagagctgt tgccattgat catgaatctt ga 1422

<210> SEQ ID NO 13
<211> LENGTH: 473
<212> TYPE: PRT
<213> ORGANISM: Artificial Sequence
<220> FEATURE:
<223> OTHER INFORMATION: UGT91D2e-b

<400> SEQUENCE: 13

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
```

```
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470


<210> SEQ ID NO 14
<211> LENGTH: 1389
<212> TYPE: DNA
<213> ORGANISM: Oryza sativa

<400> SEQUENCE: 14

atggactccg gctactcctc ctcctacgcc gccgccgccg ggatgcacgt cgtgatctgc      60

ccgtggctcg ccttcggcca cctgctcccg tgcctcgacc tcgcccagcg cctcgcgtcg     120

cggggccacc gcgtgtcgtt cgtctccacg ccgcggaaca tatcccgcct cccgccggtg     180

cgccccgcgc tcgcgccgct cgtcgccttc gtggcgctgc cgctcccgcg cgtcgagggg     240

ctccccgacg gcgccgagtc caccaacgac gtcccccacg acaggccgga catggtcgag     300

ctccaccgga gggccttcga cgggctcgcc gcgcccttct cggagttctt gggcaccgcg     360

tgcgccgact gggtcatcgt cgacgtcttc caccactggg ccgcagccgc cgctctcgag     420

cacaaggtgc catgtgcaat gatgttgttg ggctctgcac atatgatcgc ttccatagca     480

gacagacggc tcgagcgcgc ggagacagag tcgcctgcgg ctgccgggca gggacgccca     540

gcggcggcgc caacgttcga ggtggcgagg atgaagttga tacgaaccaa aggctcatcg     600

ggaatgtccc tcgccgagcg cttctccttg acgctctcga ggagcagcct cgtcgtcggg     660

cggagctgcg tggagttcga gccggagacc gtcccgctcc tgtcgacgct ccgcggtaag     720

cctattacct tccttggcct tatgccgccg ttgcatgaag gccgccgcga ggacggcgag     780

gatgccaccg tccgctggct cgacgcgcag ccggccaagt ccgtcgtgta cgtcgcgcta     840

ggcagcgagg tgccactggg agtggagaag gtccacgagc tcgcgctcgg gctggagctc     900

gccgggacgc gcttcctctg ggctcttagg aagcccactg gcgtctccga cgccgacctc     960

ctccccgccg gcttcgagga gcgcacgcgc ggccgcggcg tcgtggcgac gagatgggtt    1020

cctcagatga gcatactggc gcacgccgcc gtgggcgcgt tcctgaccca ctgcggctgg    1080

aactcgacca tcgaggggct catgttcggc cacccgctta tcatgctgcc gatcttcggc    1140

gaccagggac cgaacgcgcg gctaatcgag gcgaagaacg ccggattgca ggtggcaaga    1200

aacgacggcg atggatcgtt cgaccgagaa ggcgtcgcgg cggcgattcg tgcagtcgcg    1260

gtggaggaag aaagcagcaa agtgtttcaa gccaaagcca agaagctgca ggagatcgtc    1320

gcggacatgg cctgccatga gaggtacatc gacggattca ttcagcaatt gagatcttac    1380
```

aaggattga 1389

<210> SEQ ID NO 15
<211> LENGTH: 1389
<212> TYPE: DNA
<213> ORGANISM: Artificial Sequence
<220> FEATURE:
<223> OTHER INFORMATION: Codon-optimized EUGT11

<400> SEQUENCE: 15
atggatagtg gctactcctc atcttatgct gctgccgctg gtatgcacgt tgtgatctgc 60
ccttggttgg cctttggtca cctgttacca tgtctggatt tagcccaaag actggcctca 120
agaggccata gagtatcatt tgtgtctact cctagaaata tctctcgttt accaccagtc 180
agacctgctc tagctcctct agttgcattc gttgctcttc cacttccaag agtagaagga 240
ttgccagacg gcgctgaatc tactaatgac gtaccacatg atagacctga catggtcgaa 300
ttgcatagaa gagcctttga tggattggca gctccatttt ctgagttcct gggcacagca 360
tgtgcagact gggttatagt cgatgtattt catcactggg ctgctgcagc cgcattggaa 420
cataaggtgc cttgtgctat gatgttgtta gggtcagcac acatgatcgc atccatagct 480
gatagaagat tggaaagagc tgaaacagaa tccccagccg cagcaggaca aggtaggcca 540
gctgccgccc caacctttga agtggctaga atgaaattga ttcgtactaa aggtagttca 600
gggatgagtc ttgctgaaag gtttctctg acattatcta gatcatcatt agttgtaggt 660
agatcctgcg tcgagttcga acctgaaaca gtacctttac tatctacttt gagaggcaaa 720
cctattactt tccttggtct aatgcctcca ttacatgaag gaaggagaga agatggtgaa 780
gatgctactg ttaggtggtt agatgcccaa cctgctaagt ctgttgttta cgttgcattg 840
ggttctgagg taccactagg ggtggaaaag gtgcatgaat tagcattagg acttgagctg 900
gccggaacaa gattcctttg ggctttgaga aaaccaaccg gtgtttctga cgccgacttg 960
ctaccagctg ggttcgaaga gagaacaaga ggccgtggtg tcgttgctac tagatgggtc 1020
ccacaaatga gtattctagc tcatgcagct gtaggggcct ttctaaccca ttgcggttgg 1080
aactcaacaa tagaaggact gatgtttggt catccactta ttatgttacc aatctttggc 1140
gatcagggac ctaacgcaag attgattgag gcaaagaacg caggtctgca ggttgcacgt 1200
aatgatggtg atggttcctt tgatagagaa ggcgttgcag ctgccatcag agcagtcgcc 1260
gttgaggaag agtcatctaa agttttccaa gctaaggcca aaaaattaca agagattgtg 1320
gctgacatgg cttgtcacga aagatacatc gatggtttca tccaacaatt gagaagttat 1380
aaagactaa 1389

<210> SEQ ID NO 16
<211> LENGTH: 462
<212> TYPE: PRT
<213> ORGANISM: Oryza sativa

<400> SEQUENCE: 16

Met Asp Ser Gly Tyr Ser Ser Ser Tyr Ala Ala Ala Ala Gly Met His
1 5 10 15

Val Val Ile Cys Pro Trp Leu Ala Phe Gly His Leu Leu Pro Cys Leu
20 25 30

Asp Leu Ala Gln Arg Leu Ala Ser Arg Gly His Arg Val Ser Phe Val
35 40 45

Ser Thr Pro Arg Asn Ile Ser Arg Leu Pro Pro Val Arg Pro Ala Leu

```
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
    370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
    450                 455                 460
```

<210> SEQ ID NO 17

<211> LENGTH: 465
<212> TYPE: PRT
<213> ORGANISM: Artificial Sequence
<220> FEATURE:
<223> OTHER INFORMATION: UGT91D2e-b-EUGT11 chimera 3

<400> SEQUENCE: 17

Met Asp Ser Gly Tyr Ser Ser Ser Tyr Ala Ala Ala Ala Gly Met His
1 5 10 15

Val Val Ile Cys Pro Trp Leu Ala Phe Gly His Leu Leu Pro Cys Leu
20 25 30

Asp Leu Ala Gln Arg Leu Ala Ser Arg Gly His Arg Val Ser Phe Val
35 40 45

Ser Thr Pro Arg Asn Ile Ser Arg Leu Pro Pro Val Arg Pro Ala Leu
50 55 60

Ala Pro Leu Val Ala Phe Val Ala Leu Pro Leu Pro Arg Val Glu Gly
65 70 75 80

Leu Pro Asp Gly Ala Glu Ser Thr Asn Asp Val Pro His Asp Arg Pro
85 90 95

Asp Met Val Glu Leu His Arg Arg Ala Phe Asp Gly Leu Ala Ala Pro
100 105 110

Phe Ser Glu Phe Leu Gly Thr Ala Cys Ala Asp Trp Val Ile Val Asp
115 120 125

Val Phe His His Trp Ala Ala Ala Ala Ala Leu Glu His Lys Val Pro
130 135 140

Cys Ala Met Met Leu Leu Gly Ser Ala His Met Ile Ala Ser Ile Ala
145 150 155 160

Asp Arg Arg Leu Glu Arg Ala Glu Thr Glu Ser Pro Ala Ala Ala Gly
165 170 175

Gln Gly Arg Pro Ala Ala Ala Pro Thr Phe Glu Val Ala Arg Met Lys
180 185 190

Leu Ile Arg Thr Lys Gly Ser Ser Gly Met Ser Leu Ala Glu Arg Phe
195 200 205

Ser Leu Thr Leu Ser Arg Ser Ser Leu Val Val Gly Arg Ser Cys Val
210 215 220

Glu Phe Glu Pro Glu Thr Val Pro Leu Leu Ser Thr Leu Arg Gly Lys
225 230 235 240

Pro Ile Thr Phe Leu Gly Leu Leu Pro Pro Glu Ile Pro Gly Asp Glu
245 250 255

Lys Asp Glu Thr Trp Val Ser Ile Lys Lys Trp Leu Asp Gly Lys Gln
260 265 270

Lys Gly Ser Val Val Tyr Val Ala Leu Gly Ser Glu Ala Leu Val Ser
275 280 285

Gln Thr Glu Val Val Glu Leu Ala Leu Gly Leu Glu Leu Ser Gly Leu
290 295 300

Pro Phe Val Trp Ala Tyr Arg Lys Pro Lys Gly Pro Ala Lys Ser Asp
305 310 315 320

Ser Val Glu Leu Pro Asp Gly Phe Val Glu Arg Thr Arg Asp Arg Gly
325 330 335

Leu Val Trp Thr Ser Trp Ala Pro Gln Leu Arg Ile Leu Ser His Glu
340 345 350

Ser Val Cys Gly Phe Leu Thr His Cys Gly Ser Gly Ser Ile Val Glu
355 360 365

Gly Leu Met Phe Gly His Pro Leu Ile Met Leu Pro Ile Phe Gly Asp
370 375 380

```
Gln Pro Leu Asn Ala Arg Leu Leu Glu Asp Lys Gln Val Gly Ile Glu
385                 390                 395                 400

Ile Ala Arg Asn Asp Gly Asp Gly Ser Phe Asp Arg Glu Gly Val Ala
                405                 410                 415

Ala Ala Ile Arg Ala Val Ala Val Glu Glu Glu Ser Ser Lys Val Phe
            420                 425                 430

Gln Ala Lys Ala Lys Lys Leu Gln Glu Ile Val Ala Asp Met Ala Cys
        435                 440                 445

His Glu Arg Tyr Ile Asp Gly Phe Ile Gln Gln Leu Arg Ser Tyr Lys
    450                 455                 460

Asp
465


<210> SEQ ID NO 18
<211> LENGTH: 470
<212> TYPE: PRT
<213> ORGANISM: Artificial Sequence
<220> FEATURE:
<223> OTHER INFORMATION: UGT91D2e-b-EUGT11 chimera 7

<400> SEQUENCE: 18

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Met Pro Pro Leu His Glu Gly Arg
                245                 250                 255

Arg Glu Asp Gly Glu Asp Ala Thr Val Arg Trp Leu Asp Ala Gln Pro
            260                 265                 270
```

```
Ala Lys Ser Val Val Tyr Val Ala Leu Gly Ser Glu Val Pro Leu Gly
        275                 280                 285

Val Glu Lys Val His Glu Leu Ala Leu Gly Leu Glu Leu Ala Gly Thr
    290                 295                 300

Arg Phe Leu Trp Ala Leu Arg Lys Pro Thr Gly Val Ser Asp Ala Asp
305                 310                 315                 320

Leu Leu Pro Ala Gly Phe Glu Glu Arg Thr Arg Gly Arg Gly Val Val
                325                 330                 335

Ala Thr Arg Trp Val Pro Gln Met Ser Ile Leu Ala His Ala Ala Val
            340                 345                 350

Gly Ala Phe Leu Thr His Cys Gly Trp Asn Ser Thr Ile Glu Gly Leu
        355                 360                 365

Met Phe Gly His Pro Leu Ile Met Leu Pro Ile Phe Gly Asp Gln Gly
    370                 375                 380

Pro Asn Ala Arg Leu Ile Glu Ala Lys Asn Ala Gly Leu Gln Val Pro
385                 390                 395                 400

Arg Asn Glu Glu Asp Gly Cys Leu Thr Lys Glu Ser Val Ala Arg Ser
                405                 410                 415

Leu Arg Ser Val Val Val Glu Lys Glu Gly Glu Ile Tyr Lys Ala Asn
            420                 425                 430

Ala Arg Glu Leu Ser Lys Ile Tyr Asn Asp Thr Lys Val Glu Lys Glu
        435                 440                 445

Tyr Val Ser Gln Phe Val Asp Tyr Leu Glu Lys Asn Ala Arg Ala Val
    450                 455                 460

Ala Ile Asp His Glu Ser
465                 470
```

<210> SEQ ID NO 19
<211> LENGTH: 1086
<212> TYPE: DNA
<213> ORGANISM: Artificial Sequence
<220> FEATURE:
<223> OTHER INFORMATION: Codon-optimized GGPPS

<400> SEQUENCE: 19

```
atggctttgg taaacccaac cgctcttttc tatggtacct ctatcagaac aagacctaca     60

aacttactaa atccaactca aaagctaaga ccagtttcat catcttcctt accttctttc    120

tcatcagtta gtgcgattct tactgaaaaa catcaatcta atccttctga gaacaacaat    180

ttgcaaactc atctagaaac tcctttcaac tttgatagtt atatgttgga aaaagtcaac    240

atggttaacg aggcgcttga tgcatctgtc ccactaaaag acccaatcaa aatccatgaa    300

tccatgagat actctttatt ggcaggcggt aagagaatca gaccaatgat gtgtattgca    360

gcctgcgaaa tagtcggagg taatatcctt aacgccatgc cagccgcatg tgccgtggaa    420

atgattcata ctatgtcttt ggtgcatgac gatcttccat gtatggataa tgatgacttc    480

agaagaggta aacctatttc acacaaggtc tacggggagg aaatggcagt attgaccggc    540

gatgctttac taagtttatc tttcgaacat atagctactg ctacaaaggg tgtatcaaag    600

gatagaatcg tcagagctat aggggagttg gcccgttcag ttggctccga aggtttagtg    660

gctggacaag ttgtagatat cttgtcagag ggtgctgatg ttggattaga tcacctagaa    720

tacattcaca tccacaaaac agcaatgttg cttgagtcct cagtagttat tggcgctatc    780

atgggaggag gatctgatca gcagatcgaa aagttgagaa aattcgctag atctattggt    840

ctactattcc aagttgtgga tgacattttg gatgttacaa aatctaccga agagttgggg    900
```

-continued aaaacagctg gtaaggattt gttgacagat aagacaactt acccaaagtt gttaggtata 960
gaaaagtcca gagaatttgc cgaaaaactt aacaaggaag cacaagagca attaagtggc 1020
tttgatagac gtaaggcagc tcctttgatc gcgttagcca actacaatgc gtaccgtcaa 1080
aattga 1086

<210> SEQ ID NO 20
<211> LENGTH: 361
<212> TYPE: PRT
<213> ORGANISM: Stevia rebaudiana

<400> SEQUENCE: 20

Met Ala Leu Val Asn Pro Thr Ala Leu Phe Tyr Gly Thr Ser Ile Arg
1 5 10 15

Thr Arg Pro Thr Asn Leu Leu Asn Pro Thr Gln Lys Leu Arg Pro Val
20 25 30

Ser Ser Ser Ser Leu Pro Ser Phe Ser Ser Val Ser Ala Ile Leu Thr
35 40 45

Glu Lys His Gln Ser Asn Pro Ser Glu Asn Asn Asn Leu Gln Thr His
50 55 60

Leu Glu Thr Pro Phe Asn Phe Asp Ser Tyr Met Leu Glu Lys Val Asn
65 70 75 80

Met Val Asn Glu Ala Leu Asp Ala Ser Val Pro Leu Lys Asp Pro Ile
85 90 95

Lys Ile His Glu Ser Met Arg Tyr Ser Leu Leu Ala Gly Gly Lys Arg
100 105 110

Ile Arg Pro Met Met Cys Ile Ala Ala Cys Glu Ile Val Gly Gly Asn
115 120 125

Ile Leu Asn Ala Met Pro Ala Ala Cys Ala Val Glu Met Ile His Thr
130 135 140

Met Ser Leu Val His Asp Asp Leu Pro Cys Met Asp Asn Asp Asp Phe
145 150 155 160

Arg Arg Gly Lys Pro Ile Ser His Lys Val Tyr Gly Glu Glu Met Ala
165 170 175

Val Leu Thr Gly Asp Ala Leu Leu Ser Leu Ser Phe Glu His Ile Ala
180 185 190

Thr Ala Thr Lys Gly Val Ser Lys Asp Arg Ile Val Arg Ala Ile Gly
195 200 205

Glu Leu Ala Arg Ser Val Gly Ser Glu Gly Leu Val Ala Gly Gln Val
210 215 220

Val Asp Ile Leu Ser Glu Gly Ala Asp Val Gly Leu Asp His Leu Glu
225 230 235 240

Tyr Ile His Ile His Lys Thr Ala Met Leu Leu Glu Ser Ser Val Val
245 250 255

Ile Gly Ala Ile Met Gly Gly Gly Ser Asp Gln Gln Ile Glu Lys Leu
260 265 270

Arg Lys Phe Ala Arg Ser Ile Gly Leu Leu Phe Gln Val Val Asp Asp
275 280 285

Ile Leu Asp Val Thr Lys Ser Thr Glu Glu Leu Gly Lys Thr Ala Gly
290 295 300

Lys Asp Leu Leu Thr Asp Lys Thr Thr Tyr Pro Lys Leu Leu Gly Ile
305 310 315 320

Glu Lys Ser Arg Glu Phe Ala Glu Lys Leu Asn Lys Glu Ala Gln Glu
325 330 335

```
Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360
```

<210> SEQ ID NO 21
<211> LENGTH: 1029
<212> TYPE: DNA
<213> ORGANISM: Artificial Sequence
<220> FEATURE:
<223> OTHER INFORMATION: Codon-optimized GGPPS

<400> SEQUENCE: 21

```
atggctgagc aacaaatatc taacttgctg tctatgtttg atgcttcaca tgctagtcag     60

aaattagaaa ttactgtcca aatgatggac acataccatt acagagaaac gcctccagat    120

tcctcatctt ctgaaggcgg ttcattgtct agatacgacg agagaagagt ctctttgcct    180

ctcagtcata atgctgcctc tccagatatt gtatcacaac tatgtttttc cactgcaatg    240

tcttcagagt tgaatcacag atggaaatct caaagattaa aggtggccga ttctccttac    300

aactatatcc taacattacc atcaaaagga attagaggtg cctttatcga ttccctgaac    360

gtatggttgg aggttccaga ggatgaaaca tcagtcatca aggaagttat tggtatgctc    420

cacaactctt cattaatcat tgatgacttc caagataatt ctccacttag aagaggaaag    480

ccatctaccc atacagtctt cggccctgcc caggctatca atactgctac ttacgttata    540

gttaaagcaa tcgaaaagat acaagacata gtgggacacg atgcattggc agatgttacg    600

ggtactatta caactatttt ccaaggtcag gccatggact tgtggtggac agcaaatgca    660

atcgttccat caatacagga atacttactt atggtaaacg ataaaaccgg tgctctcttt    720

agactgagtt tggagttgtt agctctgaat tccgaagcca gtatttctga ctctgcttta    780

gaaagtttat ctagtgctgt ttccttgcta ggtcaatact tccaaatcag agacgactat    840

atgaacttga tcgataacaa gtatacagat cagaaaggct tctgcgaaga tcttgatgaa    900

ggcaagtact cactaacact tattcatgcc ctccaaactg attcatccga tctactgacc    960

aacatccttt caatgagaag agtgcaagga aagttaacgg cacaaaagag atgttggttc   1020

tggaaatga                                                           1029
```

<210> SEQ ID NO 22
<211> LENGTH: 342
<212> TYPE: PRT
<213> ORGANISM: Gibberella fujikuroi

<400> SEQUENCE: 22

```
Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
            20                  25                  30

His Tyr Arg Glu Thr Pro Pro Asp Ser Ser Ser Ser Glu Gly Gly Ser
        35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
65                  70                  75                  80

Ser Ser Glu Leu Asn His Arg Trp Lys Ser Gln Arg Leu Lys Val Ala
                85                  90                  95
```

-continued

```
Asp Ser Pro Tyr Asn Tyr Ile Leu Thr Leu Pro Ser Lys Gly Ile Arg
            100                 105                 110

Gly Ala Phe Ile Asp Ser Leu Asn Val Trp Leu Glu Val Pro Glu Asp
        115                 120                 125

Glu Thr Ser Val Ile Lys Glu Val Ile Gly Met Leu His Asn Ser Ser
    130                 135                 140

Leu Ile Ile Asp Asp Phe Gln Asp Asn Ser Pro Leu Arg Arg Gly Lys
145                 150                 155                 160

Pro Ser Thr His Thr Val Phe Gly Pro Ala Gln Ala Ile Asn Thr Ala
                165                 170                 175

Thr Tyr Val Ile Val Lys Ala Ile Glu Lys Ile Gln Asp Ile Val Gly
            180                 185                 190

His Asp Ala Leu Ala Asp Val Thr Gly Thr Ile Thr Thr Ile Phe Gln
        195                 200                 205

Gly Gln Ala Met Asp Leu Trp Trp Thr Ala Asn Ala Ile Val Pro Ser
    210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                245                 250                 255

Asp Ser Ala Leu Glu Ser Leu Ser Ser Ala Val Ser Leu Leu Gly Gln
            260                 265                 270

Tyr Phe Gln Ile Arg Asp Asp Tyr Met Asn Leu Ile Asp Asn Lys Tyr
        275                 280                 285

Thr Asp Gln Lys Gly Phe Cys Glu Asp Leu Asp Glu Gly Lys Tyr Ser
    290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                325                 330                 335

Arg Cys Trp Phe Trp Lys
            340


<210> SEQ ID NO 23
<211> LENGTH: 903
<212> TYPE: DNA
<213> ORGANISM: Artificial Sequence
<220> FEATURE:
<223> OTHER INFORMATION: Codon-optimized GGPPS

<400> SEQUENCE: 23

atggaaaaga ctaaggagaa agcagaacgt atcttgctgg agccatacag atacttatta     60

caactaccag gaaagcaagt ccgttctaaa ctatcacaag cgttcaatca ctggttaaaa    120

gttcctgaag ataagttaca aatcattatt gaagtcacag aaatgctaca caatgcttct    180

ttactgatcg atgatataga ggattcttcc aaactgagaa gaggttttcc tgtcgctcat    240

tccatatacg ggtaccaag tgtaatcaac tcagctaatt acgtctactt cttgggattg    300

gaaaaagtat tgacattaga tcatccagac gctgtaaagc tattcaccag acaacttctt    360

gaattgcatc aaggtcaagg tttggatatc tattggagag acacttatac ttgcccaaca    420

gaagaggagt acaaagcaat ggttctacaa aagactggcg gtttgttcgg acttgccgtt    480

ggtctgatgc aacttttctc tgattacaag gaggacttaa agcctctgtt ggataccttg    540

ggcttgtttt tccagattag agatgactac gctaacttac attcaaagga atattcagaa    600

aacaaatcat tctgtgaaga tttgactgaa gggaagttta gttttccaac aatccacgcc    660
```

```
atttggtcaa gaccagaatc tactcaagtg caaaacattc tgcgtcagag aacagagaat    720

attgacatca aaaagtattg tgttcagtac ttggaagatg ttggttcttt tgcttacaca    780

agacatacac ttagagaatt agaggcaaaa gcatacaagc aaatagaagc ctgtggaggc    840

aatccttctc tagtggcatt ggttaaacat ttgtccaaaa tgttcaccga ggaaaacaag    900

taa                                                                  903
```

<210> SEQ ID NO 24
<211> LENGTH: 300
<212> TYPE: PRT
<213> ORGANISM: Mus musculus

<400> SEQUENCE: 24

```
Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
            20                  25                  30

Gln Ala Phe Asn His Trp Leu Lys Val Pro Glu Asp Lys Leu Gln Ile
        35                  40                  45

Ile Ile Glu Val Thr Glu Met Leu His Asn Ala Ser Leu Leu Ile Asp
    50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
            100                 105                 110

Lys Leu Phe Thr Arg Gln Leu Leu Glu Leu His Gln Gly Gln Gly Leu
        115                 120                 125

Asp Ile Tyr Trp Arg Asp Thr Tyr Thr Cys Pro Thr Glu Glu Glu Tyr
    130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175

Leu Asp Thr Leu Gly Leu Phe Phe Gln Ile Arg Asp Asp Tyr Ala Asn
            180                 185                 190

Leu His Ser Lys Glu Tyr Ser Glu Asn Lys Ser Phe Cys Glu Asp Leu
        195                 200                 205

Thr Glu Gly Lys Phe Ser Phe Pro Thr Ile His Ala Ile Trp Ser Arg
    210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
                245                 250                 255

Phe Ala Tyr Thr Arg His Thr Leu Arg Glu Leu Glu Ala Lys Ala Tyr
            260                 265                 270

Lys Gln Ile Glu Ala Cys Gly Gly Asn Pro Ser Leu Val Ala Leu Val
        275                 280                 285

Lys His Leu Ser Lys Met Phe Thr Glu Glu Asn Lys
    290                 295                 300
```

<210> SEQ ID NO 25
<211> LENGTH: 1020

-continued

<212> TYPE: DNA
<213> ORGANISM: Artificial Sequence
<220> FEATURE:
<223> OTHER INFORMATION: Codon-optimized GGPPS

<400> SEQUENCE: 25
atggcaagat tctattttct taacgcacta ttgatggtta tctcattaca atcaactaca 60
gccttcactc cagctaaact tgcttatcca acaacaacaa cagctctaaa tgtcgcctcc 120
gccgaaactt ctttcagtct agatgaatac ttggcctcta agataggacc tatagagtct 180
gccttggaag catcagtcaa atccagaatt ccacagaccg ataagatctg cgaatctatg 240
gcctactctt tgatggcagg aggcaagaga attagaccag tgttgtgtat cgctgcatgt 300
gagatgttcg gtggatccca agatgtcgct atgcctactg ctgtggcatt agaaatgata 360
cacacaatgt ctttgattca tgatgatttg ccatccatgg ataacgatga cttgagaaga 420
ggtaaaccaa caaaccatgt cgttttcggc gaagatgtag ctattcttgc aggtgactct 480
ttattgtcaa cttccttcga gcacgtcgct agagaaacaa aaggagtgtc agcagaaaag 540
atcgtggatg ttatcgctag attaggcaaa tctgttggtg ccgagggcct tgctggcggt 600
caagttatgg acttagaatg tgaagctaaa ccaggtacca cattagacga cttgaaatgg 660
attcatatcc ataaaaccgc tacattgtta caagttgctg tagcttctgg tgcagttcta 720
ggtggtgcaa ctcctgaaga ggttgctgca tgcgagttgt ttgctatgaa tataggtctt 780
gcctttcaag ttgccgacga tatccttgat gtaaccgctt catcagaaga tttgggtaaa 840
actgcaggca aagatgaagc tactgataag acaacttacc caaagttatt aggattagaa 900
gagagtaagg catacgcaag acaactaatc gatgaagcca aggaaagttt ggctcctttt 960
ggagatagag ctgccccttt attggccatt gcagatttca ttattgatag aaagaattga 1020

<210> SEQ ID NO 26
<211> LENGTH: 339
<212> TYPE: PRT
<213> ORGANISM: Thalassiosira pseudonana

<400> SEQUENCE: 26

Met Ala Arg Phe Tyr Phe Leu Asn Ala Leu Leu Met Val Ile Ser Leu
1               5                   10                  15

Gln Ser Thr Thr Ala Phe Thr Pro Ala Lys Leu Ala Tyr Pro Thr Thr
            20                  25                  30

Thr Thr Ala Leu Asn Val Ala Ser Ala Glu Thr Ser Phe Ser Leu Asp
        35                  40                  45

Glu Tyr Leu Ala Ser Lys Ile Gly Pro Ile Glu Ser Ala Leu Glu Ala
    50                  55                  60

Ser Val Lys Ser Arg Ile Pro Gln Thr Asp Lys Ile Cys Glu Ser Met
65                  70                  75                  80

Ala Tyr Ser Leu Met Ala Gly Gly Lys Arg Ile Arg Pro Val Leu Cys
                85                  90                  95

Ile Ala Ala Cys Glu Met Phe Gly Gly Ser Gln Asp Val Ala Met Pro
            100                 105                 110

Thr Ala Val Ala Leu Glu Met Ile His Thr Met Ser Leu Ile His Asp
        115                 120                 125

Asp Leu Pro Ser Met Asp Asn Asp Asp Leu Arg Arg Gly Lys Pro Thr
    130                 135                 140

Asn His Val Val Phe Gly Glu Asp Val Ala Ile Leu Ala Gly Asp Ser
145                 150                 155                 160

```
Leu Leu Ser Thr Ser Phe Glu His Val Ala Arg Glu Thr Lys Gly Val
                165                 170                 175

Ser Ala Glu Lys Ile Val Asp Val Ile Ala Arg Leu Gly Lys Ser Val
            180                 185                 190

Gly Ala Glu Gly Leu Ala Gly Gly Gln Val Met Asp Leu Glu Cys Glu
        195                 200                 205

Ala Lys Pro Gly Thr Thr Leu Asp Asp Leu Lys Trp Ile His Ile His
    210                 215                 220

Lys Thr Ala Thr Leu Leu Gln Val Ala Val Ala Ser Gly Ala Val Leu
225                 230                 235                 240

Gly Gly Ala Thr Pro Glu Glu Val Ala Ala Cys Glu Leu Phe Ala Met
                245                 250                 255

Asn Ile Gly Leu Ala Phe Gln Val Ala Asp Asp Ile Leu Asp Val Thr
            260                 265                 270

Ala Ser Ser Glu Asp Leu Gly Lys Thr Ala Gly Lys Asp Glu Ala Thr
        275                 280                 285

Asp Lys Thr Thr Tyr Pro Lys Leu Leu Gly Leu Glu Glu Ser Lys Ala
    290                 295                 300

Tyr Ala Arg Gln Leu Ile Asp Glu Ala Lys Glu Ser Leu Ala Pro Phe
305                 310                 315                 320

Gly Asp Arg Ala Ala Pro Leu Leu Ala Ile Ala Asp Phe Ile Ile Asp
                325                 330                 335

Arg Lys Asn


<210> SEQ ID NO 27
<211> LENGTH: 1068
<212> TYPE: DNA
<213> ORGANISM: Artificial Sequence
<220> FEATURE:
<223> OTHER INFORMATION: Codon-optimized GGPPS

<400> SEQUENCE: 27

atgcacttag caccacgtag agtccctaga ggtagaagat caccacctga cagagttcct      60

gaaagacaag gtgccttggg tagaagacgt ggagctggct ctactggctg tgcccgtgct     120

gctgctggtg ttcaccgtag aagaggagga ggcgaggctg atccatcagc tgctgtgcat     180

agaggctggc aagccggtgg tggcaccggt ttgcctgatg aggtggtgtc taccgcagcc     240

gccttagaaa tgtttcatgc ttttgcttta atccatgatg atatcatgga tgatagtgca     300

actagaagag gctccccaac tgttcacaga gccctagctg atcgtttagg cgctgctctg     360

gacccagatc aggccggtca actaggagtt tctactgcta tcttggttgg agatctggct     420

ttgacatggt ccgatgaatt gttatacgct ccattgactc cacatagact ggcagcagta     480

ctaccattgg taacagctat gagagctgaa accgttcatg gccaatatct tgatataact     540

agtgctagaa gacctgggac cgatacttct cttgcattga gaatagccag atataagaca     600

gcagcttaca caatggaacg tccactgcac attggtgcag ccctggctgg ggcaagacca     660

gaactattag cagggctttc agcatacgcc ttgccagctg gagaagcctt ccaattggca     720

gatgacctgc taggcgtctt cggtgatcca agacgtacag ggaaacctga cctagatgat     780

cttagaggtg gaaagcatac tgtcttagtc gccttggcaa gagaacatgc cactccagaa     840

cagagacaca cattggatac attattgggt acaccaggtc ttgatagaca aggcgcttca     900

agactaagat gcgtattggt agcaactggt gcaagagccg aagccgaaag acttattaca     960

gagagaagag atcaagcatt aactgcattg aacgcattaa cactgccacc tcctttagct    1020
```

gaggcattag caagattgac attagggtct acagctcatc ctgcctaa 1068

<210> SEQ ID NO 28
<211> LENGTH: 355
<212> TYPE: PRT
<213> ORGANISM: Streptomyces clavuligerus

<400> SEQUENCE: 28

```
Met His Leu Ala Pro Arg Arg Val Pro Arg Gly Arg Arg Ser Pro Pro
1               5                   10                  15

Asp Arg Val Pro Glu Arg Gln Gly Ala Leu Gly Arg Arg Arg Gly Ala
            20                  25                  30

Gly Ser Thr Gly Cys Ala Arg Ala Ala Ala Gly Val His Arg Arg Arg
        35                  40                  45

Gly Gly Gly Glu Ala Asp Pro Ser Ala Ala Val His Arg Gly Trp Gln
    50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
        115                 120                 125

Gly Val Ser Thr Ala Ile Leu Val Gly Asp Leu Ala Leu Thr Trp Ser
    130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
        195                 200                 205

Leu His Ile Gly Ala Ala Leu Ala Gly Ala Arg Pro Glu Leu Leu Ala
    210                 215                 220

Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
                245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
        275                 280                 285

Leu Gly Thr Pro Gly Leu Asp Arg Gln Gly Ala Ser Arg Leu Arg Cys
    290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
                325                 330                 335

Pro Pro Leu Ala Glu Ala Leu Ala Arg Leu Thr Leu Gly Ser Thr Ala
            340                 345                 350

His Pro Ala
        355
```

<210> SEQ ID NO 29
<211> LENGTH: 993
<212> TYPE: DNA
<213> ORGANISM: Artificial Sequence
<220> FEATURE:
<223> OTHER INFORMATION: Codon-optimized GGPPS

<400> SEQUENCE: 29
atgtcatatt tcgataacta cttcaatgag atagttaatt ccgtgaacga catcattaag 60
tcttacatct ctggcgacgt accaaaacta tacgaagcct cctaccattt gtttacatca 120
ggaggaaaga gactaagacc attgatcctt acaatttctt ctgatctttt cggtggacag 180
agagaaagag catactatgc tggcgcagca atcgaagttt tgcacacatt cactttggtt 240
cacgatgata tcatggatca agataacatt cgtagaggtc ttcctactgt acatgtcaag 300
tatggcctac ctttggccat tttagctggt gacttattgc atgcaaaagc ctttcaattg 360
ttgactcagg cattgagagg tctaccatct gaaactatca tcaaggcgtt tgatatcttt 420
acaagatcta tcattatcat atcagaaggt caagctgtcg atatggaatt cgaagataga 480
attgatatca aggaacaaga gtatttggat atgatatctc gtaaaaccgc tgccttattc 540
tcagcttctt cttccattgg ggcgttgata gctggagcta atgataacga tgtgagatta 600
atgtccgatt tcggtacaaa tcttgggatc gcatttcaaa ttgtagatga tatacttggt 660
ttaacagctg atgaaaaaga gctaggaaaa cctgttttca gtgatatcag agaaggtaaa 720
aagaccatat tagtcattaa gactttagaa ttgtgtaagg aagacgagaa aaagattgtg 780
ttaaaagcgc taggcaacaa gtcagcatca aaggaagagt tgatgagttc tgctgacata 840
atcaaaaagt actcattgga ttacgcctac aacttagctg agaaatacta caaaaacgcc 900
atcgattctc taaatcaagt ttcaagtaaa agtgatattc cagggaaggc attgaaatat 960
cttgctgaat tcaccatcag aagacgtaag taa 993

<210> SEQ ID NO 30
<211> LENGTH: 330
<212> TYPE: PRT
<213> ORGANISM: Sulfolobus acidocaldarius

<400> SEQUENCE: 30

Met Ser Tyr Phe Asp Asn Tyr Phe Asn Glu Ile Val Asn Ser Val Asn
1 5 10 15

Asp Ile Ile Lys Ser Tyr Ile Ser Gly Asp Val Pro Lys Leu Tyr Glu
20 25 30

Ala Ser Tyr His Leu Phe Thr Ser Gly Gly Lys Arg Leu Arg Pro Leu
35 40 45

Ile Leu Thr Ile Ser Ser Asp Leu Phe Gly Gly Gln Arg Glu Arg Ala
50 55 60

Tyr Tyr Ala Gly Ala Ala Ile Glu Val Leu His Thr Phe Thr Leu Val
65 70 75 80

His Asp Asp Ile Met Asp Gln Asp Asn Ile Arg Arg Gly Leu Pro Thr
85 90 95

Val His Val Lys Tyr Gly Leu Pro Leu Ala Ile Leu Ala Gly Asp Leu
100 105 110

Leu His Ala Lys Ala Phe Gln Leu Leu Thr Gln Ala Leu Arg Gly Leu
115 120 125

Pro Ser Glu Thr Ile Ile Lys Ala Phe Asp Ile Phe Thr Arg Ser Ile
130 135 140

-continued

Ile Ile Ile Ser Glu Gly Gln Ala Val Asp Met Glu Phe Glu Asp Arg
145 150 155 160

Ile Asp Ile Lys Glu Gln Glu Tyr Leu Asp Met Ile Ser Arg Lys Thr
165 170 175

Ala Ala Leu Phe Ser Ala Ser Ser Ser Ile Gly Ala Leu Ile Ala Gly
180 185 190

Ala Asn Asp Asn Asp Val Arg Leu Met Ser Asp Phe Gly Thr Asn Leu
195 200 205

Gly Ile Ala Phe Gln Ile Val Asp Asp Ile Leu Gly Leu Thr Ala Asp
210 215 220

Glu Lys Glu Leu Gly Lys Pro Val Phe Ser Asp Ile Arg Glu Gly Lys
225 230 235 240

Lys Thr Ile Leu Val Ile Lys Thr Leu Glu Leu Cys Lys Glu Asp Glu
245 250 255

Lys Lys Ile Val Leu Lys Ala Leu Gly Asn Lys Ser Ala Ser Lys Glu
260 265 270

Glu Leu Met Ser Ser Ala Asp Ile Ile Lys Lys Tyr Ser Leu Asp Tyr
275 280 285

Ala Tyr Asn Leu Ala Glu Lys Tyr Tyr Lys Asn Ala Ile Asp Ser Leu
290 295 300

Asn Gln Val Ser Ser Lys Ser Asp Ile Pro Gly Lys Ala Leu Lys Tyr
305 310 315 320

Leu Ala Glu Phe Thr Ile Arg Arg Arg Lys
325 330

<210> SEQ ID NO 31
<211> LENGTH: 894
<212> TYPE: DNA
<213> ORGANISM: Artificial Sequence
<220> FEATURE:
<223> OTHER INFORMATION: Codon-optimized GGPPS

<400> SEQUENCE: 31
atggtcgcac aaactttcaa cctggatacc tacttatccc aaagacaaca acaagttgaa 60
gaggccctaa gtgctgctct tgtgccagct tatcctgaga gaatatacga agctatgaga 120
tactccctcc tggcaggtgg caaaagatta agacctatct tatgtttagc tgcttgcgaa 180
ttggcaggtg gttctgttga acaagccatg ccaactgcgt gtgcacttga aatgatccat 240
acaatgtcac taattcatga tgacctgcca gccatggata acgatgattt cagaagagga 300
aagccaacta atcacaaggt gttcggggaa gatatagcca tcttagcggg tgatgcgctt 360
ttagcttacg cttttgaaca tattgcttct caaacaagag gagtaccacc tcaattggtg 420
ctacaagtta ttgctagaat cggacacgcc gttgctgcaa caggcctcgt tggaggccaa 480
gtcgtagacc ttgaatctga aggtaaagct atttccttag aaacattgga gtatattcac 540
tcacataaga ctggagcctt gctggaagca tcagttgtct caggcggtat tctcgcaggg 600
gcagatgaag agcttttggc cagattgtct cattacgcta gagatatagg cttggctttt 660
caaatcgtcg atgatatcct ggatgttact gctacatctg aacagttggg gaaaaccgct 720
ggtaaagacc aggcagccgc aaaggcaact tatccaagtc tattgggttt agaagcctct 780
agacagaaag cggaagagtt gattcaatct gctaaggaag ccttaagacc ttacggttca 840
caagcagagc cactcctagc gctggcagac ttcatcacac gtcgtcagca ttaa 894

<210> SEQ ID NO 32
<211> LENGTH: 297

<212> TYPE: PRT
<213> ORGANISM: Synechococcus sp.

<400> SEQUENCE: 32

```
Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65                  70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295
```

<210> SEQ ID NO 33
<211> LENGTH: 1680
<212> TYPE: DNA
<213> ORGANISM: Artificial Sequence
<220> FEATURE:
<223> OTHER INFORMATION: Codon-optimized CDPS

<400> SEQUENCE: 33

```
atgaaaaccg ggtttatctc accagcaaca gtatttcatc acagaatctc accagcgacc     60

actttcagac atcacttatc acctgctact acaaactcta caggcattgt cgccttaaga    120

gacatcaact tcagatgtaa agcagtttct aaagagtact ctgatctgtt gcagaaagat    180

gaggcttctt tcacaaaatg ggacgatgac aaggtgaaag atcatcttga taccaacaaa    240
```

-continued

```
aacttatacc caaatgatga gattaaggaa tttgttgaat cagtaaaggc tatgttcggt    300
agtatgaatg acggggagat aaacgtctct gcatacgata ctgcatgggt tgctttggtt    360
caagatgtcg atggatcagg tagtcctcag ttcccttctt ctttagaatg gattgccaac    420
aatcaattgt cagatggatc atggggagat catttgctgt tctcagctca cgatagaatc    480
atcaacacat tagcatgcgt tattgcactt acaagttgga atgttcatcc ttctaagtgt    540
gaaaaaggtt tgaattttct gagagaaaac atttgcaaat tagaagatga aaacgcagaa    600
catatgccaa ttggttttga agtaacattc ccatcactaa ttgatatcgc gaaaaagttg    660
aacattgaag tacctgagga tactccagca cttaaagaga tctacgcacg tagagatatc    720
aagttaacta agatcccaat ggaagttctt cacaaggtac ctactacttt gttacattct    780
ttggaaggaa tgcctgattt ggagtgggaa aaactgttaa agctacaatg taaagatggt    840
agtttcttgt tttccccatc tagtaccgca ttcgccctaa tgcaaacaaa agatgagaaa    900
tgcttacagt atctaacaaa tatcgtcact aagttcaacg gtggcgtgcc taatgtgtac    960
ccagtcgatt tgtttgaaca tatttgggtt gttgatagac tgcagagatt ggggattgcc   1020
agatacttca aatcagagat aaaagattgt gtagagtata tcaataagta ctggaccaaa   1080
aatggaattt gttgggctag aaatactcac gttcaagata tcgatgatac agccatggga   1140
ttcagagtgt tgagagcgca cggttatgac gtcactccag atgtttttag acaatttgaa   1200
aaagatggta aattcgtttg ctttgcaggg caatcaacac aagccgtgac aggaatgttt   1260
aacgtttaca gagcctctca aatgttgttc ccaggggaga gaattttgga agatgccaaa   1320
aagttctctt acaattactt aaaggaaaag caaagtacca acgaattgct ggataaatgg   1380
ataatcgcta aagatctacc tggtgaagtt ggttatgctc tggatatccc atggtatgct   1440
tccttaccaa gattggaaac tcgttattac cttgaacaat acggcggtga agatgatgtc   1500
tggataggca agacattata cagaatgggt tacgtgtcca ataacacata tctagaaatg   1560
gcaaagctgg attacaataa ctatgttgca gtccttcaat tagaatggta cacaatacaa   1620
caatggtacg tcgatattgg tatagagaag ttcgaatctg acaacatcaa gtcagtcctg   1680
```

<210> SEQ ID NO 34
<211> LENGTH: 787
<212> TYPE: PRT
<213> ORGANISM: Stevia rebaudiana

<400> SEQUENCE: 34

```
Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
```

```
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
            180                 185                 190

Lys Leu Glu Asp Glu Asn Ala Glu His Met Pro Ile Gly Phe Glu Val
        195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350

Tyr Ile Asn Lys Tyr Trp Thr Lys Asn Gly Ile Cys Trp Ala Arg Asn
        355                 360                 365

Thr His Val Gln Asp Ile Asp Asp Thr Ala Met Gly Phe Arg Val Leu
    370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
            420                 425                 430

Glu Arg Ile Leu Glu Asp Ala Lys Lys Phe Ser Tyr Asn Tyr Leu Lys
        435                 440                 445

Glu Lys Gln Ser Thr Asn Glu Leu Leu Asp Lys Trp Ile Ile Ala Lys
    450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
            500                 505                 510

Ser Asn Asn Thr Tyr Leu Glu Met Ala Lys Leu Asp Tyr Asn Asn Tyr
        515                 520                 525

Val Ala Val Leu Gln Leu Glu Trp Tyr Thr Ile Gln Gln Trp Tyr Val
    530                 535                 540
```

Asp Ile Gly Ile Glu Lys Phe Glu Ser Asp Asn Ile Lys Ser Val Leu
545 550 555 560

Val Ser Tyr Tyr Leu Ala Ala Ala Ser Ile Phe Glu Pro Glu Arg Ser
565 570 575

Lys Glu Arg Ile Ala Trp Ala Lys Thr Thr Ile Leu Val Asp Lys Ile
580 585 590

Thr Ser Ile Phe Asp Ser Ser Gln Ser Ser Lys Glu Asp Ile Thr Ala
595 600 605

Phe Ile Asp Lys Phe Arg Asn Lys Ser Ser Ser Lys Lys His Ser Ile
610 615 620

Asn Gly Glu Pro Trp His Glu Val Met Val Ala Leu Lys Lys Thr Leu
625 630 635 640

His Gly Phe Ala Leu Asp Ala Leu Met Thr His Ser Gln Asp Ile His
645 650 655

Pro Gln Leu His Gln Ala Trp Glu Met Trp Leu Thr Lys Leu Gln Asp
660 665 670

Gly Val Asp Val Thr Ala Glu Leu Met Val Gln Met Ile Asn Met Thr
675 680 685

Ala Gly Arg Trp Val Ser Lys Glu Leu Leu Thr His Pro Gln Tyr Gln
690 695 700

Arg Leu Ser Thr Val Thr Asn Ser Val Cys His Asp Ile Thr Lys Leu
705 710 715 720

His Asn Phe Lys Glu Asn Ser Thr Thr Val Asp Ser Lys Val Gln Glu
725 730 735

Leu Val Gln Leu Val Phe Ser Asp Thr Pro Asp Asp Leu Asp Gln Asp
740 745 750

Met Lys Gln Thr Phe Leu Thr Val Met Lys Thr Phe Tyr Tyr Lys Ala
755 760 765

Trp Cys Asp Pro Asn Thr Ile Asn Asp His Ile Ser Lys Val Phe Glu
770 775 780

Ile Val Ile
785

<210> SEQ ID NO 35
<211> LENGTH: 1584
<212> TYPE: DNA
<213> ORGANISM: Artificial Sequence
<220> FEATURE:
<223> OTHER INFORMATION: Codon-optimized CDPS

<400> SEQUENCE: 35
atgcctgatg cacacgatgc tccacctcca caaataagac agagaacact agtagatgag 60
gctacccaac tgctaactga gtccgcagaa gatgcatggg gtgaagtcag tgtgtcagaa 120
tacgaaacag caaggctagt tgcccatgct acatggttag gtggacacgc cacaagagtg 180
gccttccttc tggagagaca acacgaagac gggtcatggg gtccaccagg tggatatagg 240
ttagtcccta cattatctgc tgttcacgca ttattgacat gtcttgcctc tcctgctcag 300
gatcatggcg ttccacatga tagactttta agagctgttg acgcaggctt gactgccttg 360
agaagattgg ggacatctga ctccccacct gatactatag cagttgagct ggttatccca 420
tctttgctag agggcattca acacttactg gaccctgctc atcctcatag tagaccagcc 480
ttctctcaac atagaggctc tcttgtttgt cctggtggac tagatgggag aactctagga 540
gctttgagat cacacgccgc agcaggtaca ccagtaccag gaaaagtctg gcacgcttcc 600

```
gagactttgg gcttgagtac cgaagctgct tctcacttgc aaccagccca aggtataatc    660
ggtggctctg ctgctgccac agcaacatgg ctaaccaggg ttgcaccatc tcaacagtca    720
gattctgcca gaagatacct tgaggaatta caacacagat actctggccc agttccttcc    780
attaccccta tcacatactt cgaaagagca tggttattga acaattttgc agcagccggt    840
gttccttgtg aggctccagc tgctttgttg gattccttag aagcagcact tacaccacaa    900
ggtgctcctg ctggagcagg attgcctcca gatgctgatg atacagccgc tgtgttgctt    960
gcattggcaa cacatgggag aggtagaaga ccagaagtac tgatggatta caggactgac   1020
gggtatttcc aatgctttat tggggaaagg actccatcaa tttcaacaaa cgctcacgta   1080
ttggaaacat tagggcatca tgtggcccaa catccacaag atagagccag atacggatca   1140
gccatggata ccgcatcagc ttggctgctg gcagctcaaa agcaagatgg ctcttggtta   1200
gataaatggc atgcctcacc atactacgct actgtttgtt gcacacaagc cctagccgct   1260
catgcaagtc ctgcaactgc accagctaga cagagagctg tcagatgggt tttagccaca   1320
caaagatccg atggcggttg gggtctatgg cattcaactg ttgaagagac tgcttatgcc   1380
ttacagatct tggccccacc ttctggtggt ggcaatatcc cagtccaaca agcacttact   1440
agaggcagag caagattgtg tggagccttg ccactgactc ctttatggca tgataaggat   1500
ttgtatactc cagtaagagt agtcagagct gccagagctg ctgctctgta cactaccaga   1560
gatctattgt taccaccatt gtaa                                          1584
```

<210> SEQ ID NO 36
<211> LENGTH: 527
<212> TYPE: PRT
<213> ORGANISM: Streptomyces clavuligerus

<400> SEQUENCE: 36

```
Met Pro Asp Ala His Asp Ala Pro Pro Pro Gln Ile Arg Gln Arg Thr
1               5                   10                  15

Leu Val Asp Glu Ala Thr Gln Leu Leu Thr Glu Ser Ala Glu Asp Ala
            20                  25                  30

Trp Gly Glu Val Ser Val Ser Glu Tyr Glu Thr Ala Arg Leu Val Ala
        35                  40                  45

His Ala Thr Trp Leu Gly Gly His Ala Thr Arg Val Ala Phe Leu Leu
    50                  55                  60

Glu Arg Gln His Glu Asp Gly Ser Trp Gly Pro Pro Gly Gly Tyr Arg
65                  70                  75                  80

Leu Val Pro Thr Leu Ser Ala Val His Ala Leu Leu Thr Cys Leu Ala
                85                  90                  95

Ser Pro Ala Gln Asp His Gly Val Pro His Asp Arg Leu Leu Arg Ala
            100                 105                 110

Val Asp Ala Gly Leu Thr Ala Leu Arg Arg Leu Gly Thr Ser Asp Ser
        115                 120                 125

Pro Pro Asp Thr Ile Ala Val Glu Leu Val Ile Pro Ser Leu Leu Glu
    130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
                165                 170                 175

Arg Thr Leu Gly Ala Leu Arg Ser His Ala Ala Ala Gly Thr Pro Val
            180                 185                 190

Pro Gly Lys Val Trp His Ala Ser Glu Thr Leu Gly Leu Ser Thr Glu
```

-continued

```
        195                 200                 205

Ala Ala Ser His Leu Gln Pro Ala Gln Gly Ile Ile Gly Gly Ser Ala
    210                 215                 220

Ala Ala Thr Ala Thr Trp Leu Thr Arg Val Ala Pro Ser Gln Gln Ser
225                 230                 235                 240

Asp Ser Ala Arg Arg Tyr Leu Glu Glu Leu Gln His Arg Tyr Ser Gly
                245                 250                 255

Pro Val Pro Ser Ile Thr Pro Ile Thr Tyr Phe Glu Arg Ala Trp Leu
            260                 265                 270

Leu Asn Asn Phe Ala Ala Ala Gly Val Pro Cys Glu Ala Pro Ala Ala
        275                 280                 285

Leu Leu Asp Ser Leu Glu Ala Ala Leu Thr Pro Gln Gly Ala Pro Ala
    290                 295                 300

Gly Ala Gly Leu Pro Pro Asp Ala Asp Asp Thr Ala Ala Val Leu Leu
305                 310                 315                 320

Ala Leu Ala Thr His Gly Arg Gly Arg Arg Pro Glu Val Leu Met Asp
                325                 330                 335

Tyr Arg Thr Asp Gly Tyr Phe Gln Cys Phe Ile Gly Glu Arg Thr Pro
            340                 345                 350

Ser Ile Ser Thr Asn Ala His Val Leu Glu Thr Leu Gly His His Val
        355                 360                 365

Ala Gln His Pro Gln Asp Arg Ala Arg Tyr Gly Ser Ala Met Asp Thr
    370                 375                 380

Ala Ser Ala Trp Leu Leu Ala Ala Gln Lys Gln Asp Gly Ser Trp Leu
385                 390                 395                 400

Asp Lys Trp His Ala Ser Pro Tyr Tyr Ala Thr Val Cys Cys Thr Gln
                405                 410                 415

Ala Leu Ala Ala His Ala Ser Pro Ala Thr Ala Pro Ala Arg Gln Arg
            420                 425                 430

Ala Val Arg Trp Val Leu Ala Thr Gln Arg Ser Asp Gly Gly Trp Gly
        435                 440                 445

Leu Trp His Ser Thr Val Glu Glu Thr Ala Tyr Ala Leu Gln Ile Leu
    450                 455                 460

Ala Pro Pro Ser Gly Gly Gly Asn Ile Pro Val Gln Gln Ala Leu Thr
465                 470                 475                 480

Arg Gly Arg Ala Arg Leu Cys Gly Ala Leu Pro Leu Thr Pro Leu Trp
                485                 490                 495

His Asp Lys Asp Leu Tyr Thr Pro Val Arg Val Val Arg Ala Ala Arg
            500                 505                 510

Ala Ala Ala Leu Tyr Thr Thr Arg Asp Leu Leu Leu Pro Pro Leu
        515                 520                 525
```

<210> SEQ ID NO 37
<211> LENGTH: 1551
<212> TYPE: DNA
<213> ORGANISM: Artificial Sequence
<220> FEATURE:
<223> OTHER INFORMATION: Codon-optimized CDPS

<400> SEQUENCE: 37

```
atgaacgccc tatccgaaca cattttgtct gaattgagaa gattattgtc tgaaatgagt      60

gatggcggat ctgttggtcc atctgtgtat gatacggccc aggccctaag attccacggt     120

aacgtaacag gtagacaaga tgcatatgct tggttgatcg cccagcaaca agcagatgga     180

ggttggggct ctgccgactt tccactcttt agacatgctc caacatgggc tgcacttctc     240
```

```
gcattacaaa gagctgatcc acttcctggc gcagcagacg cagttcagac cgcaacaaga    300

ttcttgcaaa gacaaccaga tccatacgct catgccgttc ctgaggatgc ccctattggt    360

gctgaactga tcttgcctca gttttgtgga gaggctgctt ggttgttggg aggtgtggcc    420

ttccctagac acccagccct attaccatta agacaggctt gtttagtcaa actgggtgca    480

gtcgccatgt tgccttcagg acacccattg ctccactcct gggaggcatg ggtacttct     540

ccaacaacag cctgtccaga cgatgatggt tctataggta tctcaccagc agctacagcc    600

gcctggagag cccaggctgt gaccagaggc tcaactcctc aagtgggcag agctgacgca    660

tacttacaaa tggcttcaag agcaacgaga tcaggcatag aaggagtctt ccctaatgtt    720

tggcctataa acgtattcga accatgctgg tcactgtaca ctctccatct tgccggtctg    780

ttcgcccatc cagcactggc tgaggctgta agagttatcg ttgctcaact tgaagcaaga    840

ttgggagtgc atggcctcgg accagcttta cattttgctg ccgacgctga tgatactgca    900

gttgccttat gcgttctgca tttggctggc agagatcctg cagttgacgc attgagacat    960

tttgaaattg gtgagctctt tgttacattc ccaggagaga gaaatgctag tgtctctacg   1020

aacattcacg ctcttcatgc tttgagattg ttaggtaaac cagctgccgg agcaagtgca   1080

tacgtcgaag caaatagaaa tccacatggt ttgtgggaca acgaaaaatg gcacgtttca   1140

tggctttatc caactgcaca cgccgttgca gctctagctc aaggcaagcc tcaatggaga   1200

gatgaaagag cactagccgc tctactacaa gctcaaagag atgatggtgg ttggggagct   1260

ggtagaggat ccactttcga ggaaaccgcc tacgctcttt tcgctttaca cgttatggac   1320

ggatctgagg aagccacagg cagaagaaga atcgctcaag tcgtcgcaag agccttagaa   1380

tggatgctag ctagacatgc cgcacatgga ttaccacaaa caccactctg gattggtaag   1440

gaattgtact gtcctactag agtcgtaaga gtagctgagc tagctggcct gtggttagca   1500

ttaagatggg gtagaagagt attagctgaa ggtgctggtg ctgcacctta a            1551
```

<210> SEQ ID NO 38
<211> LENGTH: 516
<212> TYPE: PRT
<213> ORGANISM: Bradyrhizobium japonicum

<400> SEQUENCE: 38

```
Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30

Ala Gln Ala Leu Arg Phe His Gly Asn Val Thr Gly Arg Gln Asp Ala
        35                  40                  45

Tyr Ala Trp Leu Ile Ala Gln Gln Gln Ala Asp Gly Gly Trp Gly Ser
    50                  55                  60

Ala Asp Phe Pro Leu Phe Arg His Ala Pro Thr Trp Ala Ala Leu Leu
65                  70                  75                  80

Ala Leu Gln Arg Ala Asp Pro Leu Pro Gly Ala Ala Asp Ala Val Gln
                85                  90                  95

Thr Ala Thr Arg Phe Leu Gln Arg Gln Pro Asp Pro Tyr Ala His Ala
            100                 105                 110

Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140
```

```
Pro Ala Leu Leu Pro Leu Arg Gln Ala Cys Leu Val Lys Leu Gly Ala
145                 150                 155                 160

Val Ala Met Leu Pro Ser Gly His Pro Leu Leu His Ser Trp Glu Ala
                165                 170                 175

Trp Gly Thr Ser Pro Thr Thr Ala Cys Pro Asp Asp Asp Gly Ser Ile
            180                 185                 190

Gly Ile Ser Pro Ala Ala Thr Ala Ala Trp Arg Ala Gln Ala Val Thr
        195                 200                 205

Arg Gly Ser Thr Pro Gln Val Gly Arg Ala Asp Ala Tyr Leu Gln Met
    210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
            260                 265                 270

Ile Val Ala Gln Leu Glu Ala Arg Leu Gly Val His Gly Leu Gly Pro
        275                 280                 285

Ala Leu His Phe Ala Ala Asp Ala Asp Asp Thr Ala Val Ala Leu Cys
    290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Ala Leu Leu Gln Ala Gln Arg Asp Asp Gly
                405                 410                 415

Gly Trp Gly Ala Gly Arg Gly Ser Thr Phe Glu Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Ala Arg Ala Leu Glu Trp Met Leu Ala
    450                 455                 460

Arg His Ala Ala His Gly Leu Pro Gln Thr Pro Leu Trp Ile Gly Lys
465                 470                 475                 480

Glu Leu Tyr Cys Pro Thr Arg Val Val Arg Val Ala Glu Leu Ala Gly
                485                 490                 495

Leu Trp Leu Ala Leu Arg Trp Gly Arg Arg Val Leu Ala Glu Gly Ala
            500                 505                 510

Gly Ala Ala Pro
        515
```

<210> SEQ ID NO 39
<211> LENGTH: 2490
<212> TYPE: DNA
<213> ORGANISM: Artificial Sequence
<220> FEATURE:

-continued

<223> OTHER INFORMATION: Codon-optimized CDPS

<400> SEQUENCE: 39

```
atggttttgt cttcttcttg tactacagta ccacacttat cttcattagc tgtcgtgcaa     60
cttggtcctt ggagcagtag gattaaaaag aaaaccgata ctgttgcagt accagccgct    120
gcaggaaggt ggagaagggc cttggctaga gcacagcaca catcagaatc cgcagctgtc    180
gcaaagggca gcagtttgac ccctatagtg agaactgacg ctgagtcaag gagaacaaga    240
tggccaaccg atgacgatga cgccgaacct ttagtggatg agatcagggc aatgcttact    300
tccatgtctg atggtgacat ttccgtgagc gcatacgata cagcctgggt cggattggtt    360
ccaagattag acggcggtga aggtcctcaa tttccagcag ctgtgagatg gataagaaat    420
aaccagttgc ctgacggaag ttggggcgat gccgcattat tctctgccta tgacaggctt    480
atcaataccc ttgcctgcgt tgtaactttg acaaggtggt ccctagaacc agagatgaga    540
ggtagaggac tatctttttt gggtaggaac atgtggaaat tagcaactga agatgaagag    600
tcaatgccta ttggcttcga attagcattt ccatctttga tagagcttgc taagagccta    660
ggtgtccatg acttccctta tgatcaccag gccctacaag gaatctactc ttcaagagag    720
atcaaaatga agaggattcc aaaagaagtg atgcataccg ttccaacatc aatattgcac    780
agtttggagg gtatgcctgg cctagattgg gctaaactac ttaaactaca gagcagcgac    840
ggaagttttt tgttctcacc agctgccact gcatatgctt taatgaatac cggagatgac    900
aggtgtttta gctacatcga tagaacagta aagaaattca acggcggcgt ccctaatgtt    960
tatccagtgg atctatttga acatatttgg gccgttgata gacttgaaag attaggaatc   1020
tccaggtact tccaaaagga gatcgaacaa tgcatggatt atgtaaacag gcattggact   1080
gaggacggta tttgttgggc aaggaactct gatgtcaaag aggtggacga cacagctatg   1140
gcctttagac ttcttaggtt gcacggctac agcgtcagtc ctgatgtgtt taaaaacttc   1200
gaaaaggacg gtgaattttt cgcatttgtc ggacagtcta atcaagctgt taccggtatg   1260
tacaacttaa acagagcaag ccagatatcc ttcccaggcg aggatgtgct tcatagagct   1320
ggtgccttct catatgagtt cttgaggaga aaagaagcag agggagcttt gagggacaag   1380
tggatcattt ctaaagatct acctggtgaa gttgtgtata ctttggattt tccatggtac   1440
ggcaacttac ctagagtcga ggccagagac tacctagagc aatacggagg tggtgatgac   1500
gtttggattg gcaagacatt gtataggatg ccacttgtaa acaatgatgt atatttggaa   1560
ttggcaagaa tggatttcaa ccactgccag gctttgcatc agttagagtg gcaaggacta   1620
aaaagatggt atactgaaaa taggttgatg gactttggtg tcgcccaaga agatgccctt   1680
agagcttatt ttcttgcagc cgcatctgtt tacgagcctt gtagagctgc cgagaggctt   1740
gcatgggcta gagccgcaat actagctaac gccgtgagca cccacttaag aaatagccca   1800
tcattcagag aaaggttaga gcattctctt aggtgtagac ctagtgaaga gacagatggc   1860
tcctggttta actcctcaag tggctctgat gcagttttag taaaggctgt cttaagactt   1920
actgattcat tagccaggga agcacagcca atccatggag gtgacccaga agatattata   1980
cacaagttgt taagatctgc ttgggccgag tgggttaggg aaaaggcaga cgctgccgat   2040
agcgtgtgca atggtagttc tgcagtagaa caagagggat caagaatggt ccatgataaa   2100
cagacctgtc tattattggc tagaatgatc gaaatttctg ccggtagggc agctggtgaa   2160
gcagccagtg aggacggcga tagaagaata attcaattaa caggctccat ctgcgacagt   2220
cttaagcaaa aaatgctagt ttcacaggac cctgaaaaaa atgaagagat gatgtctcac   2280
```

gtggatgacg aattgaagtt gaggattaga gagttcgttc aatatttgct tagactaggt 2340
gaaaaaaaga ctggatctag cgaaaccagg caaacatttt taagtatagt gaaatcatgt 2400
tactatgctg ctcattgccc acctcatgtc gttgatagac acattagtag agtgattttc 2460
gagccagtaa gtgccgcaaa gtaaccgcgg 2490

<210> SEQ ID NO 40
<211> LENGTH: 827
<212> TYPE: PRT
<213> ORGANISM: Zea mays

<400> SEQUENCE: 40

Met Val Leu Ser Ser Ser Cys Thr Thr Val Pro His Leu Ser Ser Leu
1 5 10 15

Ala Val Val Gln Leu Gly Pro Trp Ser Ser Arg Ile Lys Lys Lys Thr
20 25 30

Asp Thr Val Ala Val Pro Ala Ala Ala Gly Arg Trp Arg Arg Ala Leu
35 40 45

Ala Arg Ala Gln His Thr Ser Glu Ser Ala Ala Val Ala Lys Gly Ser
50 55 60

Ser Leu Thr Pro Ile Val Arg Thr Asp Ala Glu Ser Arg Arg Thr Arg
65 70 75 80

Trp Pro Thr Asp Asp Asp Asp Ala Glu Pro Leu Val Asp Glu Ile Arg
85 90 95

Ala Met Leu Thr Ser Met Ser Asp Gly Asp Ile Ser Val Ser Ala Tyr
100 105 110

Asp Thr Ala Trp Val Gly Leu Val Pro Arg Leu Asp Gly Gly Glu Gly
115 120 125

Pro Gln Phe Pro Ala Ala Val Arg Trp Ile Arg Asn Asn Gln Leu Pro
130 135 140

Asp Gly Ser Trp Gly Asp Ala Ala Leu Phe Ser Ala Tyr Asp Arg Leu
145 150 155 160

Ile Asn Thr Leu Ala Cys Val Val Thr Leu Thr Arg Trp Ser Leu Glu
165 170 175

Pro Glu Met Arg Gly Arg Gly Leu Ser Phe Leu Gly Arg Asn Met Trp
180 185 190

Lys Leu Ala Thr Glu Asp Glu Glu Ser Met Pro Ile Gly Phe Glu Leu
195 200 205

Ala Phe Pro Ser Leu Ile Glu Leu Ala Lys Ser Leu Gly Val His Asp
210 215 220

Phe Pro Tyr Asp His Gln Ala Leu Gln Gly Ile Tyr Ser Ser Arg Glu
225 230 235 240

Ile Lys Met Lys Arg Ile Pro Lys Glu Val Met His Thr Val Pro Thr
245 250 255

Ser Ile Leu His Ser Leu Glu Gly Met Pro Gly Leu Asp Trp Ala Lys
260 265 270

Leu Leu Lys Leu Gln Ser Ser Asp Gly Ser Phe Leu Phe Ser Pro Ala
275 280 285

Ala Thr Ala Tyr Ala Leu Met Asn Thr Gly Asp Asp Arg Cys Phe Ser
290 295 300

Tyr Ile Asp Arg Thr Val Lys Lys Phe Asn Gly Gly Val Pro Asn Val
305 310 315 320

Tyr Pro Val Asp Leu Phe Glu His Ile Trp Ala Val Asp Arg Leu Glu
325 330 335

-continued

```
Arg Leu Gly Ile Ser Arg Tyr Phe Gln Lys Glu Ile Glu Gln Cys Met
            340                 345                 350

Asp Tyr Val Asn Arg His Trp Thr Glu Asp Gly Ile Cys Trp Ala Arg
        355                 360                 365

Asn Ser Asp Val Lys Glu Val Asp Asp Thr Ala Met Ala Phe Arg Leu
    370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
            420                 425                 430

Gly Glu Asp Val Leu His Arg Ala Gly Ala Phe Ser Tyr Glu Phe Leu
        435                 440                 445

Arg Arg Lys Glu Ala Glu Gly Ala Leu Arg Asp Lys Trp Ile Ile Ser
    450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
            500                 505                 510

Val Asn Asn Asp Val Tyr Leu Glu Leu Ala Arg Met Asp Phe Asn His
        515                 520                 525

Cys Gln Ala Leu His Gln Leu Glu Trp Gln Gly Leu Lys Arg Trp Tyr
    530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ala Ser Val Tyr Glu Pro Cys Arg Ala
                565                 570                 575

Ala Glu Arg Leu Ala Trp Ala Arg Ala Ala Ile Leu Ala Asn Ala Val
            580                 585                 590

Ser Thr His Leu Arg Asn Ser Pro Ser Phe Arg Glu Arg Leu Glu His
        595                 600                 605

Ser Leu Arg Cys Arg Pro Ser Glu Glu Thr Asp Gly Ser Trp Phe Asn
    610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
        675                 680                 685

Val Glu Gln Glu Gly Ser Arg Met Val His Asp Lys Gln Thr Cys Leu
    690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750
```

```
Lys Asn Glu Glu Met Met Ser His Val Asp Asp Glu Leu Lys Leu Arg
        755                 760                 765

Ile Arg Glu Phe Val Gln Tyr Leu Leu Arg Leu Gly Glu Lys Lys Thr
    770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825
```

<210> SEQ ID NO 41
<211> LENGTH: 2570
<212> TYPE: DNA
<213> ORGANISM: Artificial Sequence
<220> FEATURE:
<223> OTHER INFORMATION: Codon-optimized CDPS

<400> SEQUENCE: 41

```
cttcttcact aaatacttag acagagaaaa cagagctttt taaagccatg tctcttcagt     60

atcatgttct aaactccatt ccaagtacaa cctttctcag ttctactaaa acaacaatat    120

cttcttcttt ccttaccatc tcaggatctc ctctcaatgt cgctagagac aaatccagaa    180

gcggttccat acattgttca aagcttcgaa ctcaagaata cattaattct caagaggttc    240

aacatgattt gcctctaata catgagtggc aacagcttca aggagaagat gctcctcaga    300

ttagtgttgg aagtaatagt aatgcattca aagaagcagt gaagagtgtg aaaacgatct    360

tgagaaacct aacggacggg gaaattacga tatcggctta cgatacagct tgggttgcat    420

tgatcgatgc cggagataaa actccggcgt ttccctccgc cgtgaaatgg atcgccgaga    480

accaactttc cgatggttct tggggagatg cgtatctctt ctcttatcat gatcgtctca    540

tcaataccct tgcatgcgtc gttgctctaa gatcatggaa tctctttcct catcaatgca    600

acaaaggaat cacgtttttc cgggaaaata ttgggaagct agaagacgaa aatgatgagc    660

atatgccaat cggattcgaa gtagcattcc catcgttgct tgagatagct cgaggaataa    720

acattgatgt accgtacgat tctccggtct taaaagatat atacgccaag aaagagctaa    780

agcttacaag gataccaaaa gagataatgc acaagatacc aacaacattg ttgcatagtt    840

tggaggggat gcgtgattta gattgggaaa agctcttgaa acttcaatct caagacggat    900

ctttcctctt ctctccttcc tctaccgctt ttgcattcat gcagacccga gacagtaact    960

gcctcgagta tttgcgaaat gccgtcaaac gtttcaatgg aggagttccc aatgtctttc   1020

ccgtggatct tttcgagcac atatggatag tggatcggtt acaacgttta gggatatcga   1080

gatactttga agaagagatt aaagagtgtc ttgactatgt ccacagatat tggaccgaca   1140

atggcatatg ttgggctaga tgttcccatg tccaagacat cgatgataca gccatggcat   1200

ttaggctctt aagacaacat ggataccaag tgtccgcaga tgtattcaag aactttgaga   1260

aagagggaga gtttttctgc tttgtggggc aatcaaacca agcagtaacc ggtatgttca   1320

acctataccg ggcatcacaa ttggcgtttc caagggaaga gatattgaaa aacgccaaag   1380

agttttctta taattatctg ctagaaaaac gggagagaga ggagttgatt gataagtgga   1440

ttataatgaa agacttacct ggcgagattg ggtttgcgtt agagattcca tggtacgcaa   1500

gcttgcctcg agtagagacg agattctata ttgatcaata tggtggagaa aacgacgttt   1560

ggattggcaa gactctttat aggatgccat acgtgaacaa taatggatat ctggaattag   1620
```

-continued

```
caaaacaaga ttacaacaat tgccaagctc agcatcagct cgaatgggac atattccaaa   1680

agtggtatga agaaaatagg ttaagtgagt ggggtgtgcg cagaagtgag cttctcgagt   1740

gttactactt agcggctgca actatatttg aatcagaaag gtcacatgag agaatggttt   1800

gggctaagtc aagtgtattg gttaaagcca tttcttcttc ttttggggaa tcctctgact   1860

ccagaagaag cttctccgat cagtttcatg aatacattgc caatgctcga cgaagtgatc   1920

atcactttaa tgacaggaac atgagattgg accgaccagg atcggttcag gccagtcggc   1980

ttgccggagt gttaatcggg actttgaatc aaatgtcttt tgaccttttc atgtctcatg   2040

gccgtgacgt taacaatctc ctctatctat cgtggggaga ttggatggaa aaatggaaac   2100

tatatggaga tgaaggagaa ggagagctca tggtgaagat gataattcta atgaagaaca   2160

atgacctaac taacttcttc acccacactc acttcgttcg tctcgcggaa atcatcaatc   2220

gaatctgtct tcctcgccaa tacttaaagg caaggagaaa cgatgagaag gagaagacaa   2280

taaagagtat ggagaaggag atggggaaaa tggttgagtt agcattgtcg gagagtgaca   2340

catttcgtga cgtcagcatc acgtttcttg atgtagcaaa agcattttac tactttgctt   2400

tatgtggcga tcatctccaa actcacatct ccaaagtctt gtttcaaaaa gtctagtaac   2460

ctcatcatca tcatcgatcc attaacaatc agtggatcga tgtatccata gatgcgtgaa   2520

taatatttca tgtagagaag gagaacaaat tagatcatgt agggttatca              2570
```

```
<210> SEQ ID NO 42
<211> LENGTH: 802
<212> TYPE: PRT
<213> ORGANISM: Arabidopsis thaliana

<400> SEQUENCE: 42

Met Ser Leu Gln Tyr His Val Leu Asn Ser Ile Pro Ser Thr Thr Phe
1               5                   10                  15

Leu Ser Ser Thr Lys Thr Thr Ile Ser Ser Ser Phe Leu Thr Ile Ser
            20                  25                  30

Gly Ser Pro Leu Asn Val Ala Arg Asp Lys Ser Arg Ser Gly Ser Ile
        35                  40                  45

His Cys Ser Lys Leu Arg Thr Gln Glu Tyr Ile Asn Ser Gln Glu Val
    50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
                85                  90                  95

Ala Val Lys Ser Val Lys Thr Ile Leu Arg Asn Leu Thr Asp Gly Glu
            100                 105                 110

Ile Thr Ile Ser Ala Tyr Asp Thr Ala Trp Val Ala Leu Ile Asp Ala
        115                 120                 125

Gly Asp Lys Thr Pro Ala Phe Pro Ser Ala Val Lys Trp Ile Ala Glu
    130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
            180                 185                 190

Glu Asn Ile Gly Lys Leu Glu Asp Glu Asn Asp Glu His Met Pro Ile
        195                 200                 205
```

-continued

```
Gly Phe Glu Val Ala Phe Pro Ser Leu Leu Glu Ile Ala Arg Gly Ile
    210                 215                 220

Asn Ile Asp Val Pro Tyr Asp Ser Pro Val Leu Lys Asp Ile Tyr Ala
225                 230                 235                 240

Lys Lys Glu Leu Lys Leu Thr Arg Ile Pro Lys Glu Ile Met His Lys
                245                 250                 255

Ile Pro Thr Thr Leu Leu His Ser Leu Glu Gly Met Arg Asp Leu Asp
            260                 265                 270

Trp Glu Lys Leu Leu Lys Leu Gln Ser Gln Asp Gly Ser Phe Leu Phe
        275                 280                 285

Ser Pro Ser Ser Thr Ala Phe Ala Phe Met Gln Thr Arg Asp Ser Asn
    290                 295                 300

Cys Leu Glu Tyr Leu Arg Asn Ala Val Lys Arg Phe Asn Gly Gly Val
305                 310                 315                 320

Pro Asn Val Phe Pro Val Asp Leu Phe Glu His Ile Trp Ile Val Asp
                325                 330                 335

Arg Leu Gln Arg Leu Gly Ile Ser Arg Tyr Phe Glu Glu Glu Ile Lys
            340                 345                 350

Glu Cys Leu Asp Tyr Val His Arg Tyr Trp Thr Asp Asn Gly Ile Cys
        355                 360                 365

Trp Ala Arg Cys Ser His Val Gln Asp Ile Asp Asp Thr Ala Met Ala
    370                 375                 380

Phe Arg Leu Leu Arg Gln His Gly Tyr Gln Val Ser Ala Asp Val Phe
385                 390                 395                 400

Lys Asn Phe Glu Lys Glu Gly Glu Phe Phe Cys Phe Val Gly Gln Ser
                405                 410                 415

Asn Gln Ala Val Thr Gly Met Phe Asn Leu Tyr Arg Ala Ser Gln Leu
            420                 425                 430

Ala Phe Pro Arg Glu Glu Ile Leu Lys Asn Ala Lys Glu Phe Ser Tyr
        435                 440                 445

Asn Tyr Leu Leu Glu Lys Arg Glu Arg Glu Glu Leu Ile Asp Lys Trp
    450                 455                 460

Ile Ile Met Lys Asp Leu Pro Gly Glu Ile Gly Phe Ala Leu Glu Ile
465                 470                 475                 480

Pro Trp Tyr Ala Ser Leu Pro Arg Val Glu Thr Arg Phe Tyr Ile Asp
                485                 490                 495

Gln Tyr Gly Gly Glu Asn Asp Val Trp Ile Gly Lys Thr Leu Tyr Arg
            500                 505                 510

Met Pro Tyr Val Asn Asn Asn Gly Tyr Leu Glu Leu Ala Lys Gln Asp
        515                 520                 525

Tyr Asn Asn Cys Gln Ala Gln His Gln Leu Glu Trp Asp Ile Phe Gln
    530                 535                 540

Lys Trp Tyr Glu Glu Asn Arg Leu Ser Glu Trp Gly Val Arg Arg Ser
545                 550                 555                 560

Glu Leu Leu Glu Cys Tyr Tyr Leu Ala Ala Ala Thr Ile Phe Glu Ser
                565                 570                 575

Glu Arg Ser His Glu Arg Met Val Trp Ala Lys Ser Ser Val Leu Val
            580                 585                 590

Lys Ala Ile Ser Ser Ser Phe Gly Glu Ser Ser Asp Ser Arg Arg Ser
        595                 600                 605

Phe Ser Asp Gln Phe His Glu Tyr Ile Ala Asn Ala Arg Arg Ser Asp
    610                 615                 620

His His Phe Asn Asp Arg Asn Met Arg Leu Asp Arg Pro Gly Ser Val
```

625 630 635 640

Gln Ala Ser Arg Leu Ala Gly Val Leu Ile Gly Thr Leu Asn Gln Met
645 650 655

Ser Phe Asp Leu Phe Met Ser His Gly Arg Asp Val Asn Asn Leu Leu
660 665 670

Tyr Leu Ser Trp Gly Asp Trp Met Glu Lys Trp Lys Leu Tyr Gly Asp
675 680 685

Glu Gly Glu Gly Glu Leu Met Val Lys Met Ile Ile Leu Met Lys Asn
690 695 700

Asn Asp Leu Thr Asn Phe Phe Thr His Thr His Phe Val Arg Leu Ala
705 710 715 720

Glu Ile Ile Asn Arg Ile Cys Leu Pro Arg Gln Tyr Leu Lys Ala Arg
725 730 735

Arg Asn Asp Glu Lys Glu Lys Thr Ile Lys Ser Met Glu Lys Glu Met
740 745 750

Gly Lys Met Val Glu Leu Ala Leu Ser Glu Ser Asp Thr Phe Arg Asp
755 760 765

Val Ser Ile Thr Phe Leu Asp Val Ala Lys Ala Phe Tyr Tyr Phe Ala
770 775 780

Leu Cys Gly Asp His Leu Gln Thr His Ile Ser Lys Val Leu Phe Gln
785 790 795 800

Lys Val

<210> SEQ ID NO 43
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 43
atgaatttga gtttgtgtat agcatctcca ctattgacca aatctaatag accagctgct 60
ttatcagcaa ttcatacagc tagtacatcc catggtggcc aaaccaaccc tacgaatctg 120
ataatcgata cgaccaagga gagaatacaa aaacaattca aaaatgttga aatttcagtt 180
tcttcttatg atactgcgtg ggttgccatg gttccatcac ctaattctcc aaagtctcca 240
tgtttcccag aatgtttgaa ttggctgatt aacaaccagt tgaatgatgg atcttggggt 300
ttagtcaatc acacgcacaa tcacaaccat ccacttttga aagattcttt atcctcaact 360
ttggcttgca tcgtggccct aaagagatgg aacgtaggtg aggatcagat taacaagggg 420
cttagtttca ttgaatctaa cttggcttcc gcgactgaaa aatctcaacc atctccaata 480
ggattcgata tcatctttcc aggtctgtta gagtacgcca aaaatctaga tatcaactta 540
ctgtctaagc aaactgattt ctcactaatg ttacacaaga gagaattaga acaaaagaga 600
tgtcattcaa acgaaatgga tggttaccta gcttatatct ctgaaggtct tggtaatctt 660
tacgattgga atatggtgaa aaagtaccag atgaaaaatg gctcagtttt caattcccct 720
tctgcaactg cggcagcatt cattaaccat caaaatccag gatgcctgaa ctatttgaat 780
tcactactag acaaattcgg caacgcagtt ccaactgtat accctcacga tttgtttatc 840
agattgagta tggtggatac aattgaaaga cttggtatat cccaccactt tagagtcgag 900
atcaaaaatg ttttggatga gacataccgt tgttgggtgg agagagatga acaaatcttt 960
atggatgttg tgacgtgcgc gttggccttt agattgttgc gtattaacgg ttacgaagtt 1020
agtccagatc cacttgccga aattacaaac gaattagctt taaaggatga atacgccgct 1080
cttgaaacat atcatgcgtc acatatcctt taccaagagg acttatcatc tggaaaacaa 1140
attcttaaat ctgctgattt cctgaaggaa atcatatcca ctgatagtaa tagactgtcc 1200
aaactgatcc ataaagaggt tgaaaatgca cttaagttcc ctattaacac cggcttagaa 1260
cgtattaaca caagacgtaa catccagctt tacaacgtag acaatactag aatcttgaaa 1320
accacttacc attcttccaa catatcaaac actgattacc taagattagc tgttgaagat 1380
ttctacacat gtcagtctat ctatagagaa gagctgaaag gattagagag atgggtcgtt 1440
gagaataagc tagatcaatt gaaatttgcc agacaaaaga cagcttattg ttacttctca 1500
gttgccgcca ctttatcaag tccagaattg tcagatgcac gtatttcttg ggctaaaaac 1560
ggaattttga caactgttgt tgatgatttc tttgatattg gcgggacaat cgacgaattg 1620
acaaacctga ttcaatgcgt tgaaaagtgg aatgtcgatg tcgataaaga ctgttgctca 1680
gaacatgtta gaatactgtt cttggctctg aaagatgcta tctgttggat cggggatgag 1740
gctttcaaat ggcaagctag agatgtgacg tctcacgtca ttcaaacctg gctagaactg 1800
atgaactcta tgttgagaga agcaatttgg actagagatg catacgttcc tacattaaac 1860
gagtatatgg aaaacgctta tgtctccttt gctttgggtc ctatcgttaa gcctgccata 1920
tactttgtag gaccaaagct atccgaggaa atcgtcgaat catcagaata ccataacttg 1980
ttcaagttaa tgtccacaca aggcagatta cttaatgata ttcattcttt caaaagagag 2040
tttaaggaag gaaagttaaa tgctgttgct ctgcatcttt ctaatggcga aagtggtaaa 2100
gtcgaagagg aagtagttga ggaaatgatg atgatgatca aaaacaagag aaaggagttg 2160
atgaaactaa tcttcgaaga gaacggttca attgttccta gagcatgtaa ggatgcattt 2220
tggaacatgt gtcatgtgct aaactttttc tacgcaaacg acgatggttt tactgggaac 2280
acaatactag atacagtaaa agacatcata tacaaccctt tggtcttagt aaacgaaaac 2340
gaggagcaaa gataa 2355

<210> SEQ ID NO 44
<211> LENGTH: 784
<212> TYPE: PRT
<213> ORGANISM: Stevia rebaudiana

<400> SEQUENCE: 44

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

```
Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Met Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
            340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560
```

-continued

```
Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
        755                 760                 765

Ile Ile Tyr Asn Pro Leu Val Leu Val Asn Glu Asn Glu Glu Gln Arg
    770                 775                 780
```

<210> SEQ ID NO 45
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 45

```
atgaatctgt ccctttgtat agctagtcca ctgttgacaa aatcttctag accaactgct     60

ctttctgcaa ttcatactgc cagtactagt catggaggtc aaacaaaccc aacaaatttg    120

ataatcgata ctactaagga gagaatccaa aagctattca aaaatgttga aatctcagta    180

tcatcttatg acaccgcatg ggttgcaatg gtgccatcac ctaattcccc aaaaagtcca    240

tgttttccag agtgcttgaa ttggttaatc aataatcagt taaacgatgg ttcttggggt    300

ttagtcaacc acactcataa ccacaatcat ccattattga aggactcttt atcatcaaca    360

ttagcctgta ttgttgcatt gaaaagatgg aatgtaggtg aagatcaaat caacaagggt    420

ttatcattca tagaatccaa tctagcttct gctaccgaca aatcacaacc atctccaatc    480

gggttcgaca taatcttccc tggtttgctg gagtatgcca aaaaccttga tatcaactta    540

ctgtctaaac aaacagattt ctctttgatg ctacacaaaa gagagttaga gcagaaaaga    600

tgccattcta acgaaattga cgggtactta gcatatatct cagaaggttt gggtaatttg    660

tatgactgga acatggtcaa aaagtatcag atgaaaaatg gatccgtatt caattctcct    720

tctgcaactg ccgcagcatt cattaatcat caaaaccctg ggtgtcttaa ctacttgaac    780

tcactattag ataagtttgg aaatgcagtt ccaacagtct atcctttgga cttgtacatc    840
```

-continued

```
agattatcta tggttgacac tatagagaga ttaggtattt ctcatcattt cagagttgag     900
atcaaaaatg ttttggacga gacatacaga tgttgggtcg aaagagatga gcaaatcttt     960
atggatgtcg tgacctgcgc tctggctttt agattgctaa ggatacacgg atacaaagta    1020
tctcctgatc aactggctga gattacaaac gaactggctt tcaaagacga atacgccgca    1080
ttagaaacat accatgcatc ccaaatactt taccaggaag acctaagttc aggaaaacaa    1140
atcttgaagt ctgcagattt cctgaaaggc attctgtcta cagatagtaa taggttgtct    1200
aaattgatac acaaggaagt agaaaacgca ctaaagtttc ctattaacac tggtttagag    1260
agaatcaata ctaggagaaa cattcagctg tacaacgtag ataatacaag gattcttaag    1320
accacctacc atagttcaaa catttccaac acctattact taagattagc tgtcgaagac    1380
ttttacactt gtcaatcaat ctacagagag gagttaaagg gcctagaaag atgggtagtt    1440
caaaacaagt tggatcaact gaagtttgct agacagaaga cagcatactg ttatttctct    1500
gttgctgcta ccctttcatc cccagaattg tctgatgcca gaataagttg ggccaaaaat    1560
ggtattctta caactgtagt cgatgatttc tttgatattg gaggtactat tgatgaactg    1620
acaaatctta ttcaatgtgt tgaaaagtgg aacgtggatg tagataagga ttgctgcagt    1680
gaacatgtga gaatactttt cctggctcta aaagatgcaa tatgttggat tggcgacgag    1740
gccttcaagt ggcaagctag agatgttaca tctcatgtca tccaaacttg gcttgaactg    1800
atgaactcaa tgctaagaga agcaatctgg acaagagatg catacgttcc aacattgaac    1860
gaatacatgg aaaacgctta cgtctcattt gccttgggtc ctattgttaa gccagccata    1920
tactttgttg ggccaaagtt atccgaagag attgttgagt cttccgaata tcataaccta    1980
ttcaagttaa tgtcaacaca aggcagactt ctgaacgata tccactcctt caaaagagaa    2040
ttcaaggaag gtaagctaaa cgctgttgct ttgcacttgt ctaatggtga atctggcaaa    2100
gtggaagagg aagtcgttga ggaaatgatg atgatgatca aaaacaagag aaaggaattg    2160
atgaaattga ttttcgagga aaatggttca atcgtaccta gagcttgtaa agatgctttt    2220
tggaatatgt gccatgttct taacttcttt tacgctaatg atgatggctt cactggaaat    2280
acaatattgg atacagttaa agatatcatc tacaacccac ttgttttggt caatgagaac    2340
gaggaacaaa gataa                                                     2355
```

<210> SEQ ID NO 46
<211> LENGTH: 784
<212> TYPE: PRT
<213> ORGANISM: Stevia rebaudiana

<400> SEQUENCE: 46

```
Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Leu Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95
```

-continued

```
Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro Leu Asp Leu Tyr Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
```

515 520 525

Asp Phe Phe Asp Ile Gly Gly Thr Ile Asp Glu Leu Thr Asn Leu Ile
530 535 540

Gln Cys Val Glu Lys Trp Asn Val Asp Val Asp Lys Asp Cys Cys Ser
545 550 555 560

Glu His Val Arg Ile Leu Phe Leu Ala Leu Lys Asp Ala Ile Cys Trp
565 570 575

Ile Gly Asp Glu Ala Phe Lys Trp Gln Ala Arg Asp Val Thr Ser His
580 585 590

Val Ile Gln Thr Trp Leu Glu Leu Met Asn Ser Met Leu Arg Glu Ala
595 600 605

Ile Trp Thr Arg Asp Ala Tyr Val Pro Thr Leu Asn Glu Tyr Met Glu
610 615 620

Asn Ala Tyr Val Ser Phe Ala Leu Gly Pro Ile Val Lys Pro Ala Ile
625 630 635 640

Tyr Phe Val Gly Pro Lys Leu Ser Glu Glu Ile Val Glu Ser Ser Glu
645 650 655

Tyr His Asn Leu Phe Lys Leu Met Ser Thr Gln Gly Arg Leu Leu Asn
660 665 670

Asp Ile His Ser Phe Lys Arg Glu Phe Lys Glu Gly Lys Leu Asn Ala
675 680 685

Val Ala Leu His Leu Ser Asn Gly Glu Ser Gly Lys Val Glu Glu Glu
690 695 700

Val Val Glu Glu Met Met Met Met Ile Lys Asn Lys Arg Lys Glu Leu
705 710 715 720

Met Lys Leu Ile Phe Glu Glu Asn Gly Ser Ile Val Pro Arg Ala Cys
725 730 735

Lys Asp Ala Phe Trp Asn Met Cys His Val Leu Asn Phe Phe Tyr Ala
740 745 750

Asn Asp Asp Gly Phe Thr Gly Asn Thr Ile Leu Asp Thr Val Lys Asp
755 760 765

Ile Ile Tyr Asn Pro Leu Val Leu Val Asn Glu Asn Glu Glu Gln Arg
770 775 780

<210> SEQ ID NO 47
<211> LENGTH: 1773
<212> TYPE: DNA
<213> ORGANISM: Artificial Sequence
<220> FEATURE:
<223> OTHER INFORMATION: Codon-optimized KS

<400> SEQUENCE: 47
atggctatgc cagtgaagct aacacctgcg tcattatcct taaaagctgt gtgctgcaga 60
ttctcatccg gtggccatgc tttgagattc gggagtagtc tgccatgttg gagaaggacc 120
cctacccaaa gatctacttc ttcctctact actagaccag ctgccgaagt gtcatcaggt 180
aagagtaaac aacatgatca ggaagctagt gaagcgacta tcagacaaca attacaactt 240
gtggatgtcc tggagaatat gggaatatcc agacattttg ctgcagagat aaagtgcata 300
ctagacagaa cttacagatc ttggttacaa agacacgagg aaatcatgct ggacactatg 360
acatgtgcta tggcttttag aatcctaaga ttgaacggat acaacgtttc atcagatgaa 420
ctataccacg ttgtagaggc atctggtctg cataattctt tgggtgggta tcttaacgat 480
accagaacac tacttgaatt acacaaggct tcaacagtta gtatctctga ggatgaatct 540
atcttagatt caattggctc tagatccaga acattgctta gagaacaatt ggagtctggt 600

```
ggcgcactga gaaagccttc tttattcaaa gaggttgaac atgcactgga tggacctttt    660

tacaccacac ttgatagact tcatcatagg tggaatattg aaaacttcaa cattattgag    720

caacacatgt tggagactcc atacttatct aaccagcata catcaaggga tatcctagca    780

ttgtcaatta gagatttttc ctcctcacaa ttcacttatc aacaagagct acagcatctg    840

gagagttggg ttaaggaatg tagattagat caactacagt tcgcaagaca gaaattagcg    900

tacttttacc tatcagccgc aggcaccatg ttttctcctg agctttctga tgcgagaaca    960

ttatgggcca aaaacggggt gttgacaact attgttgatg atttctttga tgttgccggt   1020

tctaaagagg aattggaaaa cttagtcatg ctggtcgaaa tgtgggatga acatcacaaa   1080

gttgaattct attctgagca ggtcgaaatc atcttctctt ccatctacga ttctgtcaac   1140

caattgggtg agaaggcctc tttggttcaa gacagatcaa ttacaaaaca ccttgttgaa   1200

atatggttag acttgttaaa gtccatgatg acggaagttg aatggagact gtcaaaatac   1260

gtgcctacag aaaaggaata catgattaat gcctctctta tcttcggcct aggtccaatc   1320

gttttaccag ctttgtattt cgttggtcca aagatttcag aaagtatagt aaaggaccca   1380

gaatatgatg aattgttcaa actaatgtca acatgtggta gattgttgaa tgacgtgcaa   1440

acgttcgaaa gagaatacaa tgagggtaaa ctgaattctg tcagtctatt ggttcttcac   1500

ggaggcccaa tgtctatttc agacgcaaag aggaaattac aaaagcctat tgatacgtgt   1560

agaagagatc ttctttcttt ggtccttaga gaagagtctg tagtaccaag accatgtaag   1620

gaactattct ggaaaatgtg taaagtgtgc tatttctttt actcaacaac tgatgggttt   1680

tctagtcaag tcgaaagagc aaaagaggta gacgctgtca taaatgagcc actgaagttg   1740

caaggttctc atacactggt atctgatgtt taa                                1773
```

<210> SEQ ID NO 48
<211> LENGTH: 590
<212> TYPE: PRT
<213> ORGANISM: Zea mays

<400> SEQUENCE: 48

```
Met Ala Met Pro Val Lys Leu Thr Pro Ala Ser Leu Ser Leu Lys Ala
1               5                   10                  15

Val Cys Cys Arg Phe Ser Ser Gly Gly His Ala Leu Arg Phe Gly Ser
            20                  25                  30

Ser Leu Pro Cys Trp Arg Arg Thr Pro Thr Gln Arg Ser Thr Ser Ser
        35                  40                  45

Ser Thr Thr Arg Pro Ala Ala Glu Val Ser Ser Gly Lys Ser Lys Gln
    50                  55                  60

His Asp Gln Glu Ala Ser Glu Ala Thr Ile Arg Gln Gln Leu Gln Leu
65                  70                  75                  80

Val Asp Val Leu Glu Asn Met Gly Ile Ser Arg His Phe Ala Ala Glu
                85                  90                  95

Ile Lys Cys Ile Leu Asp Arg Thr Tyr Arg Ser Trp Leu Gln Arg His
            100                 105                 110

Glu Glu Ile Met Leu Asp Thr Met Thr Cys Ala Met Ala Phe Arg Ile
        115                 120                 125

Leu Arg Leu Asn Gly Tyr Asn Val Ser Ser Asp Glu Leu Tyr His Val
    130                 135                 140

Val Glu Ala Ser Gly Leu His Asn Ser Leu Gly Gly Tyr Leu Asn Asp
145                 150                 155                 160
```

-continued

```
Thr Arg Thr Leu Leu Glu Leu His Lys Ala Ser Thr Val Ser Ile Ser
                165                 170                 175

Glu Asp Glu Ser Ile Leu Asp Ser Ile Gly Ser Arg Ser Arg Thr Leu
            180                 185                 190

Leu Arg Glu Gln Leu Glu Ser Gly Gly Ala Leu Arg Lys Pro Ser Leu
        195                 200                 205

Phe Lys Glu Val Glu His Ala Leu Asp Gly Pro Phe Tyr Thr Thr Leu
    210                 215                 220

Asp Arg Leu His His Arg Trp Asn Ile Glu Asn Phe Asn Ile Ile Glu
225                 230                 235                 240

Gln His Met Leu Glu Thr Pro Tyr Leu Ser Asn Gln His Thr Ser Arg
                245                 250                 255

Asp Ile Leu Ala Leu Ser Ile Arg Asp Phe Ser Ser Ser Gln Phe Thr
            260                 265                 270

Tyr Gln Gln Glu Leu Gln His Leu Glu Ser Trp Val Lys Glu Cys Arg
        275                 280                 285

Leu Asp Gln Leu Gln Phe Ala Arg Gln Lys Leu Ala Tyr Phe Tyr Leu
    290                 295                 300

Ser Ala Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Asp Phe Phe
                325                 330                 335

Asp Val Ala Gly Ser Lys Glu Glu Leu Glu Asn Leu Val Met Leu Val
            340                 345                 350

Glu Met Trp Asp Glu His His Lys Val Glu Phe Tyr Ser Glu Gln Val
        355                 360                 365

Glu Ile Ile Phe Ser Ser Ile Tyr Asp Ser Val Asn Gln Leu Gly Glu
    370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
        435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Gly Pro Met Ser Ile Ser Asp Ala Lys Arg Lys
            500                 505                 510

Leu Gln Lys Pro Ile Asp Thr Cys Arg Arg Asp Leu Leu Ser Leu Val
        515                 520                 525

Leu Arg Glu Glu Ser Val Val Pro Arg Pro Cys Lys Glu Leu Phe Trp
    530                 535                 540

Lys Met Cys Lys Val Cys Tyr Phe Phe Tyr Ser Thr Thr Asp Gly Phe
545                 550                 555                 560

Ser Ser Gln Val Glu Arg Ala Lys Glu Val Asp Ala Val Ile Asn Glu
                565                 570                 575

Pro Leu Lys Leu Gln Gly Ser His Thr Leu Val Ser Asp Val
```

580 585 590

<210> SEQ ID NO 49
<211> LENGTH: 2232
<212> TYPE: DNA
<213> ORGANISM: Artificial Sequence
<220> FEATURE:
<223> OTHER INFORMATION: Codon-optimized KS

<400> SEQUENCE: 49
atgcagaact tccatggtac aaaggaaagg atcaaaaaga tgtttgacaa gattgaattg 60
tccgtttctt cttatgatac agcctgggtt gcaatggtcc catcccctga ttgcccagaa 120
acaccttgtt ttccagaatg tactaaatgg atcctagaaa atcagttggg tgatggtagt 180
tggtcacttc ctcatggcaa tccacttcta gttaaagatg cattatcttc cactcttgct 240
tgtattctgg ctcttaaaag atggggaatc ggtgaggaac agattaacaa aggactgaga 300
ttcatagaac tcaactctgc tagtgtaacc gataacgaac aacacaaacc aattggattt 360
gacattatct ttccaggtat gattgaatac gctatagact tagacctgaa tctaccacta 420
aaaccaactg acattaactc catgttgcat cgtagagccc ttgaattgac atcaggtgga 480
ggcaaaaatc tagaaggtag aagagcttac ttggcctacg tctctgaagg aatcggtaag 540
ctgcaagatt gggaaatggc tatgaaatac caacgtaaaa acggatctct gttcaatagt 600
ccatcaacaa ctgcagctgc attcatccat atacaagatg ctgaatgcct ccactatatt 660
cgttctcttc tccagaaatt tggaaacgca gtccctacaa tataccctct cgatatctat 720
gccagacttt caatggtaga tgccctggaa cgtcttggta ttgatagaca tttcagaaag 780
gagagaaagt tcgttctgga tgaaacatac agattttggt tgcaaggaga agaggagatt 840
ttctccgata acgcaacctg tgctttggcc ttcagaatat tgagacttaa tggttacgat 900
gtctctcttg aagatcactt ctctaactct ctgggcggtt acttaaagga ctcaggagca 960
gctttagaac tgtacagagc cctccaattg tcttacccag acgagtccct cctggaaaag 1020
caaaattcta gaacttctta cttcttaaaa caaggtttat ccaatgtctc cctctgtggt 1080
gacagattgc gtaaaaacat aattggagag gtgcatgatg ctttaaactt ttccgaccac 1140
gctaacttac aaagattagc tattcgtaga aggattaagc attacgctac tgacgataca 1200
aggattctaa aaacttccta cagatgctca acaatcggta accaagattt tctaaaactt 1260
gcagtggaag atttcaatat ctgtcaatca atacaaagag aggaattcaa gcatattgaa 1320
agatgggtcg ttgaaagacg tctagacaag ttaaagttcg ctagacaaaa agaggcctat 1380
tgctatttct cagccgcagc aacattgttt gcccctgaat tgtctgatgc tagaatgtct 1440
tgggccaaaa atggtgtatt gacaactgtg gttgatgatt tcttcgatgt cggaggctct 1500
gaagaggaat tagttaactt gatagaattg atcgagcgtt gggatgtgaa tggcagtgca 1560
gatttttgta gtgaggaagt tgagattatc tattctgcta tccactcaac tatctctgaa 1620
ataggtgata agtcatttgg ctggcaaggt agagatgtaa agtctcaagt tatcaagatc 1680
tggctggact tattgaaatc aatgttaact gaagctcaat ggtcttcaaa caagtctgtt 1740
cctaccctag atgagtatat gacaaccgcc catgtttcat tcgcacttgg tccaattgta 1800
cttccagcct tatacttcgt tggcccaaag ttgtcagaag aggttgcagg tcatcctgaa 1860
ctactaaacc tctacaaagt cacatctact tgtggcagac tactgaatga ttggagaagt 1920
tttaagagag aatccgagga aggtaagctc aacgctatta gtttatacat gatccactcc 1980
ggtggtgctt ctacagaaga ggaaacaatc gaacatttca aaggtttgat tgattctcag 2040

```
agaaggcaac tgttacaatt ggtgttgcaa gagaaggata gtatcatacc tagaccatgt   2100

aaagatctat tttggaatat gattaagtta ttacacactt tctacatgaa agatgatggc   2160

ttcacctcaa atgagatgag gaatgtagtt aaggcaatca ttaacgaacc aatctcactg   2220

gatgaattat ga                                                       2232


<210> SEQ ID NO 50
<211> LENGTH: 775
<212> TYPE: PRT
<213> ORGANISM: Populus trichocarpa

<400> SEQUENCE: 50

Met Ser Cys Ile Arg Pro Trp Phe Cys Pro Ser Ser Ile Ser Ala Thr
1               5                   10                  15

Leu Thr Asp Pro Ala Ser Lys Leu Val Thr Gly Glu Phe Lys Thr Thr
            20                  25                  30

Ser Leu Asn Phe His Gly Thr Lys Glu Arg Ile Lys Lys Met Phe Asp
        35                  40                  45

Lys Ile Glu Leu Ser Val Ser Ser Tyr Asp Thr Ala Trp Val Ala Met
    50                  55                  60

Val Pro Ser Pro Asp Cys Pro Glu Thr Pro Cys Phe Pro Glu Cys Thr
65                  70                  75                  80

Lys Trp Ile Leu Glu Asn Gln Leu Gly Asp Gly Ser Trp Ser Leu Pro
                85                  90                  95

His Gly Asn Pro Leu Leu Val Lys Asp Ala Leu Ser Ser Thr Leu Ala
            100                 105                 110

Cys Ile Leu Ala Leu Lys Arg Trp Gly Ile Gly Glu Glu Gln Ile Asn
        115                 120                 125

Lys Gly Leu Arg Phe Ile Glu Leu Asn Ser Ala Ser Val Thr Asp Asn
    130                 135                 140

Glu Gln His Lys Pro Ile Gly Phe Asp Ile Ile Phe Pro Gly Met Ile
145                 150                 155                 160

Glu Tyr Ala Lys Asp Leu Asp Leu Asn Leu Pro Leu Lys Pro Thr Asp
                165                 170                 175

Ile Asn Ser Met Leu His Arg Arg Ala Leu Glu Leu Thr Ser Gly Gly
            180                 185                 190

Gly Lys Asn Leu Glu Gly Arg Arg Ala Tyr Leu Ala Tyr Val Ser Glu
        195                 200                 205

Gly Ile Gly Lys Leu Gln Asp Trp Glu Met Ala Met Lys Tyr Gln Arg
    210                 215                 220

Lys Asn Gly Ser Leu Phe Asn Ser Pro Ser Thr Thr Ala Ala Ala Phe
225                 230                 235                 240

Ile His Ile Gln Asp Ala Glu Cys Leu His Tyr Ile Arg Ser Leu Leu
                245                 250                 255

Gln Lys Phe Gly Asn Ala Val Pro Thr Ile Tyr Pro Leu Asp Ile Tyr
            260                 265                 270

Ala Arg Leu Ser Met Val Asp Ala Leu Glu Arg Leu Gly Ile Asp Arg
        275                 280                 285

His Phe Arg Lys Glu Arg Lys Phe Val Leu Asp Glu Thr Tyr Arg Phe
    290                 295                 300

Trp Leu Gln Gly Glu Glu Glu Ile Phe Ser Asp Asn Ala Thr Cys Ala
305                 310                 315                 320

Leu Ala Phe Arg Ile Leu Arg Leu Asn Gly Tyr Asp Val Ser Leu Glu
                325                 330                 335
```

```
Asp His Phe Ser Asn Ser Leu Gly Gly Tyr Leu Lys Asp Ser Gly Ala
            340                 345                 350

Ala Leu Glu Leu Tyr Arg Ala Leu Gln Leu Ser Tyr Pro Asp Glu Ser
        355                 360                 365

Leu Leu Glu Lys Gln Asn Ser Arg Thr Ser Tyr Phe Leu Lys Gln Gly
    370                 375                 380

Leu Ser Asn Val Ser Leu Cys Gly Asp Arg Leu Arg Lys Asn Ile Ile
385                 390                 395                 400

Gly Glu Val His Asp Ala Leu Asn Phe Pro Asp His Ala Asn Leu Gln
                405                 410                 415

Arg Leu Ala Ile Arg Arg Arg Ile Lys His Tyr Ala Thr Asp Asp Thr
            420                 425                 430

Arg Ile Leu Lys Thr Ser Tyr Arg Cys Ser Thr Ile Gly Asn Gln Asp
        435                 440                 445

Phe Leu Lys Leu Ala Val Glu Asp Phe Asn Ile Cys Gln Ser Ile Gln
    450                 455                 460

Arg Glu Glu Phe Lys His Ile Glu Arg Trp Val Val Glu Arg Arg Leu
465                 470                 475                 480

Asp Lys Leu Lys Phe Ala Arg Gln Lys Glu Ala Tyr Cys Tyr Phe Ser
                485                 490                 495

Ala Ala Ala Thr Leu Phe Ala Pro Glu Leu Ser Asp Ala Arg Met Ser
            500                 505                 510

Trp Ala Lys Asn Gly Val Leu Thr Thr Val Val Asp Asp Phe Phe Asp
        515                 520                 525

Val Gly Gly Ser Glu Glu Glu Leu Val Asn Leu Ile Glu Leu Ile Glu
    530                 535                 540

Arg Trp Asp Val Asn Gly Ser Ala Asp Phe Cys Ser Glu Glu Val Glu
545                 550                 555                 560

Ile Ile Tyr Ser Ala Ile His Ser Thr Ile Ser Glu Ile Gly Asp Lys
                565                 570                 575

Ser Phe Gly Trp Gln Gly Arg Asp Val Lys Ser His Val Ile Lys Ile
            580                 585                 590

Trp Leu Asp Leu Leu Lys Ser Met Leu Thr Glu Ala Gln Trp Ser Ser
        595                 600                 605

Asn Lys Ser Val Pro Thr Leu Asp Glu Tyr Met Thr Thr Ala His Val
    610                 615                 620

Ser Phe Ala Leu Gly Pro Ile Val Leu Pro Ala Leu Tyr Phe Val Gly
625                 630                 635                 640

Pro Lys Leu Ser Glu Glu Val Ala Gly His Pro Glu Leu Leu Asn Leu
                645                 650                 655

Tyr Lys Val Met Ser Thr Cys Gly Arg Leu Leu Asn Asp Trp Arg Ser
            660                 665                 670

Phe Lys Arg Glu Ser Glu Glu Gly Lys Leu Asn Ala Ile Ser Leu Tyr
        675                 680                 685

Met Ile His Ser Gly Gly Ala Ser Thr Glu Glu Glu Thr Ile Glu His
    690                 695                 700

Phe Lys Gly Leu Ile Asp Ser Gln Arg Arg Gln Leu Leu Gln Leu Val
705                 710                 715                 720

Leu Gln Glu Lys Asp Ser Ile Ile Pro Arg Pro Cys Lys Asp Leu Phe
                725                 730                 735

Trp Asn Met Ile Lys Leu Leu His Thr Phe Tyr Met Lys Asp Asp Gly
            740                 745                 750
```

Phe Thr Ser Asn Glu Met Arg Asn Val Val Lys Ala Ile Ile Asn Glu
        755                 760                 765

Pro Ile Ser Leu Asp Glu Leu
    770                 775

<210> SEQ ID NO 51
<211> LENGTH: 2358
<212> TYPE: DNA
<213> ORGANISM: Artificial Sequence
<220> FEATURE:
<223> OTHER INFORMATION: Codon-optimized KS

<400> SEQUENCE: 51
atgtctatca accttcgctc ctccggttgt tcgtctccga tctcagctac tttggaacga 60
ggattggact cagaagtaca gacaagagct aacaatgtga gctttgagca aacaaaggag 120
aagattagga agatgttgga gaaagtggag ctttctgttt cggcctacga tactagttgg 180
gtagcaatgg ttccatcacc gagctcccaa aatgctccac ttttcccaca gtgtgtgaaa 240
tggttattgg ataatcaaca tgaagatgga tcttggggac ttgataacca tgaccatcaa 300
tctcttaaga aggatgtgtt atcatctaca ctggctagta tcctcgcgtt aaagaagtgg 360
ggaattggtg aaagacaaat aaacaagggt ctccagttta ttgagctgaa ttctgcatta 420
gtcactgatg aaaccataca gaaaccaaca gggtttgata ttatatttcc tgggatgatt 480
aaatatgcta gagatttgaa tctgacgatt ccattgggct cagaagtggt ggatgacatg 540
atacgaaaaa gagatctgga tcttaaatgt gatagtgaaa agttttcaaa gggaagagaa 600
gcatatctgg cctatgtttt agaggggaca agaaacctaa aagattggga tttgatagtc 660
aaatatcaaa ggaaaaatgg gtcactgttt gattctccag ccacaacagc agctgctttt 720
actcagtttg ggaatgatgg ttgtctccgt tatctctgtt ctctccttca gaaattcgag 780
gctgcagttc cttcagttta tccatttgat caatatgcac gccttagtat aattgtcact 840
cttgaaagct taggaattga tagagatttc aaaaccgaaa tcaaaagcat attggatgaa 900
acctatagat attggcttcg tggggatgaa gaaatatgtt tggacttggc cacttgtgct 960
ttggctttcc gattattgct tgctcatggc tatgatgtgt cttacgatcc gctaaaacca 1020
tttgcagaag aatctggttt ctctgatact ttggaaggat atgttaagaa tacgttttct 1080
gtgttagaat tatttaaggc tgctcaaagt tatccacatg aatcagcttt gaagaagcag 1140
tgttgttgga ctaaacaata tctggagatg gaattgtcca gctgggttaa gacctctgtt 1200
cgagataaat acctcaagaa agaggtcgag gatgctcttg cttttccctc ctatgcaagc 1260
ctagaaagat cagatcacag gagaaaaata ctcaatggtt ctgctgtgga aaacaccaga 1320
gttacaaaaa cctcatatcg tttgcacaat atttgcacct ctgatatcct gaagttagct 1380
gtggatgact tcaatttctg ccagtccata caccgtgaag aaatggaacg tcttgatagg 1440
tggattgtgg agaatagatt gcaggaactg aaatttgcca gacagaagct ggcttactgt 1500
tatttctctg ggctgcaac tttattttct ccagaactat ctgatgctcg tatatcgtgg 1560
gccaaaggtg gagtacttac aacggttgta gacgacttct ttgatgttgg agggtccaaa 1620
gaagaactgg aaaacctcat acacttggtc gaaaagtggg atttgaacgg tgttcctgag 1680
tacagctcag aacatgttga gatcatattc tcagttctaa gggacaccat tctcgaaaca 1740
ggagacaaag cattcaccta tcaaggacgc aatgtgacac accacattgt gaaaatttgg 1800
ttggatctgc tcaagtctat gttgagagaa gccgagtggt ccagtgacaa gtcaacacca 1860
agcttggagg attacatgga aaatgcgtac atatcatttg cattaggacc aattgtcctc 1920
ccagctacct atctgatcgg acctccactt ccagagaaga cagtcgatag ccaccaatat 1980
aatcagctct acaagctcgt gagcactatg ggtcgtcttc taaatgacat acaaggtttt 2040
aagagagaaa gcgcggaagg gaagctgaat gcggtttcat tgcacatgaa acacgagaga 2100
gacaatcgca gcaaagaagt gatcatagaa tcgatgaaag gtttagcaga gagaaagagg 2160
gaagaattgc ataagctagt tttggaggag aaaggaagtg tggttccaag ggaatgcaaa 2220
gaagcgttct tgaaaatgag caaagtgttg aacttatttt acaggaagga cgatggattc 2280
acatcaaatg atctgatgag tcttgttaaa tcagtgatct acgagcctgt tagcttacag 2340
aaagaatctt taacttga 2358

<210> SEQ ID NO 52
<211> LENGTH: 785
<212> TYPE: PRT
<213> ORGANISM: Arabidopsis thaliana

<400> SEQUENCE: 52

Met Ser Ile Asn Leu Arg Ser Ser Gly Cys Ser Ser Pro Ile Ser Ala
1 5 10 15

Thr Leu Glu Arg Gly Leu Asp Ser Glu Val Gln Thr Arg Ala Asn Asn
20 25 30

Val Ser Phe Glu Gln Thr Lys Glu Lys Ile Arg Lys Met Leu Glu Lys
35 40 45

Val Glu Leu Ser Val Ser Ala Tyr Asp Thr Ser Trp Val Ala Met Val
50 55 60

Pro Ser Pro Ser Ser Gln Asn Ala Pro Leu Phe Pro Gln Cys Val Lys
65 70 75 80

Trp Leu Leu Asp Asn Gln His Glu Asp Gly Ser Trp Gly Leu Asp Asn
85 90 95

His Asp His Gln Ser Leu Lys Lys Asp Val Leu Ser Ser Thr Leu Ala
100 105 110

Ser Ile Leu Ala Leu Lys Lys Trp Gly Ile Gly Glu Arg Gln Ile Asn
115 120 125

Lys Gly Leu Gln Phe Ile Glu Leu Asn Ser Ala Leu Val Thr Asp Glu
130 135 140

Thr Ile Gln Lys Pro Thr Gly Phe Asp Ile Ile Phe Pro Gly Met Ile
145 150 155 160

Lys Tyr Ala Arg Asp Leu Asn Leu Thr Ile Pro Leu Gly Ser Glu Val
165 170 175

Val Asp Asp Met Ile Arg Lys Arg Asp Leu Asp Leu Lys Cys Asp Ser
180 185 190

Glu Lys Phe Ser Lys Gly Arg Glu Ala Tyr Leu Ala Tyr Val Leu Glu
195 200 205

Gly Thr Arg Asn Leu Lys Asp Trp Asp Leu Ile Val Lys Tyr Gln Arg
210 215 220

Lys Asn Gly Ser Leu Phe Asp Ser Pro Ala Thr Thr Ala Ala Ala Phe
225 230 235 240

Thr Gln Phe Gly Asn Asp Gly Cys Leu Arg Tyr Leu Cys Ser Leu Leu
245 250 255

Gln Lys Phe Glu Ala Ala Val Pro Ser Val Tyr Pro Phe Asp Gln Tyr
260 265 270

Ala Arg Leu Ser Ile Ile Val Thr Leu Glu Ser Leu Gly Ile Asp Arg
275 280 285

```
Asp Phe Lys Thr Glu Ile Lys Ser Ile Leu Asp Glu Thr Tyr Arg Tyr
    290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
```

705 710 715 720

Glu Glu Leu His Lys Leu Val Leu Glu Glu Lys Gly Ser Val Val Pro
725 730 735

Arg Glu Cys Lys Glu Ala Phe Leu Lys Met Ser Lys Val Leu Asn Leu
740 745 750

Phe Tyr Arg Lys Asp Asp Gly Phe Thr Ser Asn Asp Leu Met Ser Leu
755 760 765

Val Lys Ser Val Ile Tyr Glu Pro Val Ser Leu Gln Lys Glu Ser Leu
770 775 780

Thr
785

<210> SEQ ID NO 53
<211> LENGTH: 2952
<212> TYPE: DNA
<213> ORGANISM: Artificial Sequence
<220> FEATURE:
<223> OTHER INFORMATION: Codon-optimized CDPS-KS

<400> SEQUENCE: 53
atggaatttg atgaaccatt ggttgacgaa gcaagatctt tagtgcagcg tactttacaa 60
gattatgatg acagatacgg cttcggtact atgtcatgtg ctgcttatga tacagcctgg 120
gtgtctttag ttacaaaaac agtcgatggg agaaaacaat ggcttttccc agagtgtttt 180
gaatttctac tagaaacaca atctgatgcc ggaggatggg aaatcgggaa ttcagcacca 240
atcgacggta tattgaatac agctgcatcc ttacttgctc taaaacgtca cgttcaaact 300
gagcaaatca tccaacctca acatgaccat aaggatctag caggtagagc tgaacgtgcc 360
gctgcatctt tgagagcaca attggctgca ttggatgtgt ctacaactga acacgtcggt 420
tttgagataa ttgttcctgc aatgctagac ccattagaag ccgaagatcc atctctagtt 480
ttcgattttc cagctaggaa acctttgatg aagattcatg atgctaagat gagtagattc 540
aggccagaat acttgtatgg caaacaacca atgaccgcct tacattcatt agaggctttc 600
ataggcaaaa tcgacttcga taaggtaaga caccaccgta cccatgggtc tatgatgggt 660
tctccttcat ctaccgcagc ctacttaatg cacgcttcac aatgggatgg tgactcagag 720
gcttacctta gacacgtgat taaacacgca gcagggcagg gaactggtgc tgtaccatct 780
gctttcccat caacacattt tgagtcatct tggattctta ccacattgtt tagagctgga 840
ttttcagctt ctcatcttgc ctgtgatgag ttgaacaagt tggtcgagat acttgagggc 900
tcattcgaga aggaaggtgg ggcaatcggt tacgctccag ggtttcaagc agatgttgat 960
gatactgcta aaacaataag tacattagca gtccttggaa gagatgctac accaagacaa 1020
atgatcaagg tatttgaagc taatacacat tttagaacat accctggtga aagagatcct 1080
tctttgacag ctaattgtaa tgctctatca gccttactac accaaccaga tgcagcaatg 1140
tatggatctc aaattcaaaa gattaccaaa tttgtctgtg actattggtg gaagtctgat 1200
ggtaagatta aagataagtg gaacacttgc tacttgtacc catctgtctt attagttgag 1260
gttttggttg atcttgttag tttattggag cagggtaaat tgcctgatgt tttggatcaa 1320
gagcttcaat acagagtcgc catcacattg ttccaagcat gtttaaggcc attactagac 1380
caagatgccg aaggatcatg gaacaagtct atcgaagcca cagcctacgg catccttatc 1440
ctaactgaag ctaggagagt ttgtttcttc gacagattgt ctgagccatt gaatgaggca 1500
atccgtagag gtatcgcttt cgccgactct atgtctggaa ctgaagctca gttgaactac 1560
atttggatcg aaaaggttag ttacgcacct gcattattga ctaaatccta tttgttagca 1620
gcaagatggg ctgctaagtc tcctttaggc gcttccgtag gctcttcttt gtggactcca 1680
ccaagagaag gattggataa gcatgtcaga ttattccatc aagctgagtt attcagatcc 1740
cttccagaat gggaattaag agcctccatg attgaagcag ctttgttcac accacttcta 1800
agagcacata gactagacgt tttccctaga caagatgtag gtgaagacaa atatcttgat 1860
gtagttccat tcttttggac tgccgctaac aacagagata gaacttacgc ttccactcta 1920
ttcctttacg atatgtgttt tatcgcaatg ttaaacttcc agttagacga attcatggag 1980
gccacagccg gtatcttatt cagagatcat atggatgatt tgaggcaatt gattcatgat 2040
cttttggcag agaaaacttc cccaaagagt tctggtagaa gtagtcaggg cacaaaagat 2100
gctgactcag gtatagagga agacgtgtca atgtccgatt cagcttcaga ttcccaggat 2160
agaagtccag aatacgactt ggttttcagt gcattgagta cctttacaaa acatgtcttg 2220
caacacccat ctatacaaag tgcctctgta tgggatagaa aactacttgc tagagagatg 2280
aaggcttact tacttgctca tatccaacaa gcagaagatt caactccatt gtctgaattg 2340
aaagatgtgc ctcaaaagac tgatgtaaca agagtttcta catctactac taccttcttt 2400
aactgggtta gaacaacttc cgcagaccat atatcctgcc catactcctt ccactttgta 2460
gcatgccatc taggcgcagc attgtcacct aaagggtcta acggtgattg ctatccttca 2520
gctggtgaga agttcttggc agctgcagtc tgcagacatt tggccaccat gtgtagaatg 2580
tacaacgatc ttggatcagc tgaacgtgat tctgatgaag gtaatttgaa ctccttggac 2640
ttccctgaat tcgccgattc cgcaggaaac ggagggatag aaattcagaa ggccgctcta 2700
ttaaggttag ctgagtttga gagagattca tacttagagg ccttccgtcg tttacaagat 2760
gaatccaata gagttcacgg tccagccggt ggtgatgaag ccagattgtc cagaaggaga 2820
atggcaatcc ttgaattctt cgcccagcag gtagatttgt acggtcaagt atacgtcatt 2880
agggatattt ccgctcgtat tcctaaaaac gaggttgaga aaaagagaaa attggatgat 2940
gctttcaatt ga 2952

<210> SEQ ID NO 54
<211> LENGTH: 983
<212> TYPE: PRT
<213> ORGANISM: Phomopsis amygdali

<400> SEQUENCE: 54

Met Glu Phe Asp Glu Pro Leu Val Asp Glu Ala Arg Ser Leu Val Gln
1 5 10 15

Arg Thr Leu Gln Asp Tyr Asp Asp Arg Tyr Gly Phe Gly Thr Met Ser
20 25 30

Cys Ala Ala Tyr Asp Thr Ala Trp Val Ser Leu Val Thr Lys Thr Val
35 40 45

Asp Gly Arg Lys Gln Trp Leu Phe Pro Glu Cys Phe Glu Phe Leu Leu
50 55 60

Glu Thr Gln Ser Asp Ala Gly Gly Trp Glu Ile Gly Asn Ser Ala Pro
65 70 75 80

Ile Asp Gly Ile Leu Asn Thr Ala Ala Ser Leu Leu Ala Leu Lys Arg
85 90 95

His Val Gln Thr Glu Gln Ile Ile Gln Pro Gln His Asp His Lys Asp
100 105 110

Leu Ala Gly Arg Ala Glu Arg Ala Ala Ala Ser Leu Arg Ala Gln Leu
115 120 125

-continued

```
Ala Ala Leu Asp Val Ser Thr Thr Glu His Val Gly Phe Glu Ile Ile
    130                 135                 140

Val Pro Ala Met Leu Asp Pro Leu Glu Ala Glu Asp Pro Ser Leu Val
145                 150                 155                 160

Phe Asp Phe Pro Ala Arg Lys Pro Leu Met Lys Ile His Asp Ala Lys
                165                 170                 175

Met Ser Arg Phe Arg Pro Glu Tyr Leu Tyr Gly Lys Gln Pro Met Thr
            180                 185                 190

Ala Leu His Ser Leu Glu Ala Phe Ile Gly Lys Ile Asp Phe Asp Lys
        195                 200                 205

Val Arg His His Arg Thr His Gly Ser Met Met Gly Ser Pro Ser Ser
    210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
                245                 250                 255

Ala Val Pro Ser Ala Phe Pro Ser Thr His Phe Glu Ser Ser Trp Ile
            260                 265                 270

Leu Thr Thr Leu Phe Arg Ala Gly Phe Ser Ala Ser His Leu Ala Cys
        275                 280                 285

Asp Glu Leu Asn Lys Leu Val Glu Ile Leu Glu Gly Ser Phe Glu Lys
    290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Thr Leu Ala Val Leu Gly Arg Asp Ala
                325                 330                 335

Thr Pro Arg Gln Met Ile Lys Val Phe Glu Ala Asn Thr His Phe Arg
            340                 345                 350

Thr Tyr Pro Gly Glu Arg Asp Pro Ser Leu Thr Ala Asn Cys Asn Ala
        355                 360                 365

Leu Ser Ala Leu Leu His Gln Pro Asp Ala Ala Met Tyr Gly Ser Gln
    370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
                405                 410                 415

Leu Leu Val Glu Val Leu Val Asp Leu Val Ser Leu Leu Glu Gln Gly
            420                 425                 430

Lys Leu Pro Asp Val Leu Asp Gln Glu Leu Gln Tyr Arg Val Ala Ile
        435                 440                 445

Thr Leu Phe Gln Ala Cys Leu Arg Pro Leu Leu Asp Gln Asp Ala Glu
    450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
                485                 490                 495

Leu Asn Glu Ala Ile Arg Arg Gly Ile Ala Phe Ala Asp Ser Met Ser
            500                 505                 510

Gly Thr Glu Ala Gln Leu Asn Tyr Ile Trp Ile Glu Lys Val Ser Tyr
        515                 520                 525

Ala Pro Ala Leu Leu Thr Lys Ser Tyr Leu Leu Ala Ala Arg Trp Ala
    530                 535                 540
```

-continued

```
Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
                565                 570                 575

Leu Phe Arg Ser Leu Pro Glu Trp Glu Leu Arg Ala Ser Met Ile Glu
            580                 585                 590

Ala Ala Leu Phe Thr Pro Leu Leu Arg Ala His Arg Leu Asp Val Phe
        595                 600                 605

Pro Arg Gln Asp Val Gly Glu Asp Lys Tyr Leu Asp Val Val Pro Phe
    610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
            660                 665                 670

Asp Leu Arg Gln Leu Ile His Asp Leu Leu Ala Glu Lys Thr Ser Pro
        675                 680                 685

Lys Ser Ser Gly Arg Ser Ser Gln Gly Thr Lys Asp Ala Asp Ser Gly
    690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
            740                 745                 750

Arg Lys Leu Leu Ala Arg Glu Met Lys Ala Tyr Leu Leu Ala His Ile
        755                 760                 765

Gln Gln Ala Glu Asp Ser Thr Pro Leu Ser Glu Leu Lys Asp Val Pro
    770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
            820                 825                 830

Ser Asn Gly Asp Cys Tyr Pro Ser Ala Gly Glu Lys Phe Leu Ala Ala
        835                 840                 845

Ala Val Cys Arg His Leu Ala Thr Met Cys Arg Met Tyr Asn Asp Leu
    850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Gly Ile Glu Ile Gln
                885                 890                 895

Lys Ala Ala Leu Leu Arg Leu Ala Glu Phe Glu Arg Asp Ser Tyr Leu
            900                 905                 910

Glu Ala Phe Arg Arg Leu Gln Asp Glu Ser Asn Arg Val His Gly Pro
        915                 920                 925

Ala Gly Gly Asp Glu Ala Arg Leu Ser Arg Arg Arg Met Ala Ile Leu
    930                 935                 940

Glu Phe Phe Ala Gln Gln Val Asp Leu Tyr Gly Gln Val Tyr Val Ile
945                 950                 955                 960

Arg Asp Ile Ser Ala Arg Ile Pro Lys Asn Glu Val Glu Lys Lys Arg
```

965 970 975

Lys Leu Asp Asp Ala Phe Asn
980

<210> SEQ ID NO 55
<211> LENGTH: 2646
<212> TYPE: DNA
<213> ORGANISM: Artificial Sequence
<220> FEATURE:
<223> OTHER INFORMATION: Codon-optimized CDPS-KS

<400> SEQUENCE: 55
atggcttcta gtacacttat ccaaaacaga tcatgtggcg tcacatcatc tatgtcaagt 60
tttcaaatct tcagaggtca accactaaga tttcctggca ctagaacccc agctgcagtt 120
caatgcttga aaaagaggag atgccttagg ccaaccgaat ccgtactaga atcatctcct 180
ggctctggtt catatagaat agtaactggc ccttctggaa ttaaccctag ttctaacggg 240
cacttgcaag agggttcctt gactcacagg ttaccaatac caatggaaaa atctatcgat 300
aacttccaat ctactctata tgtgtcagat atttggtctg aaacactaca gagaactgaa 360
tgtttgctac aagtaactga aaacgtccag atgaatgagt ggattgagga aattagaatg 420
tactttagaa atatgacttt aggtgaaatt tccatgtccc cttacgacac tgcttgggtg 480
gctagagttc cagcgttgga cggttctcat gggcctcaat tccacagatc tttgcaatgg 540
attatcgaca accaattacc agatggggac tggggcgaac cttctctttt cttgggttac 600
gatagagttt gtaatacttt agcctgtgtg attgcgttga aaacatgggg tgttggggca 660
caaaacgttg aaagaggaat tcagttccta caatctaaca tatacaagat ggaggaagat 720
gacgctaatc atatgccaat aggattcgaa atcgtattcc ctgctatgat ggaagatgcc 780
aaagcattag gtttggattt gccatacgat gctactattt tgcaacagat ttcagccgaa 840
agagagaaaa agatgaaaaa gatcccaatg gcaatggtgt acaaataccc aaccacttta 900
cttcactcct tagaaggctt gcatagagaa gttgattgga ataagttgtt acaattacaa 960
tctgaaaatg gtagttttct ttattcacct gcttcaaccg catgcgcctt aatgtacact 1020
aaggacgtta aatgttttga ttacttaaac cagttgttga tcaagttcga ccacgcatgc 1080
ccaaatgtat atccagtcga tctattcgaa agattatgga tggttgacag attgcagaga 1140
ttagggatct ccagatactt tgaaagagag attagagatt gtttacaata cgtctacaga 1200
tattggaaag attgtggaat cggatgggct tctaactctt ccgtacaaga tgttgatgat 1260
acagccatgg cgtttagact tttaaggact catggtttcg acgtaaagga agattgcttt 1320
agacagtttt tcaaggacgg agaattcttc tgcttcgcag gccaatcatc tcaagcagtt 1380
acaggcatgt ttaatctttc aagagccagt caaacattgt ttccaggaga atctttattg 1440
aaaaaggcta gaaccttctc tagaaacttc ttgagaacaa agcatgagaa caacgaatgt 1500
ttcgataaat ggatcattac taaagatttg gctggtgaag tcgagtataa cttgaccttc 1560
ccatggtatg cctctttgcc tagattagaa cataggacat acttagatca atatggaatc 1620
gatgatatct ggataggcaa atctttatac aaaatgcctg ctgttaccaa cgaagttttc 1680
ctaaagttgg caaaggcaga ctttaacatg tgtcaagctc tacacaaaaa ggaattggaa 1740
caagtgataa agtggaacgc gtcctgtcaa ttcagagatc ttgaattcgc cagacaaaaa 1800
tcagtagaat gctattttgc tggtgcagcc acaatgttcg aaccagaaat ggttcaagct 1860
agattagtct gggcaagatg ttgtgtattg acaactgtct tagacgatta ctttgaccac 1920

```
gggacacctg ttgaggaact tagagtgttt gttcaagctg tcagaacatg gaatccagag   1980

ttgatcaacg gtttgccaga gcaagctaaa atcttgttta tgggcttata caaaacagtt   2040

aacacaattg cagaggaagc attcatggca cagaaaagag acgtccatca tcatttgaaa   2100

cactattggg acaagttgat aacaagtgcc ctaaaggagg ccgaatgggc agagtcaggt   2160

tacgtcccaa catttgatga atacatggaa gtagctgaaa tttctgttgc tctagaacca   2220

attgtctgta gtaccttgtt ctttgcgggt catagactag atgaggatgt tctagatagt   2280

tacgattacc atctagttat gcatttggta aacagagtcg gtagaatctt gaatgatata   2340

caaggcatga agagggaggc ttcacaaggt aagatctcat cagttcaaat ctacatggag   2400

gaacatccat ctgttccatc tgaggccatg gcgatcgctc atcttcaaga gttagttgat   2460

aattcaatgc agcaattgac atacgaagtt cttaggttca ctgcggttcc aaaaagttgt   2520

aagagaatcc acttgaatat ggctaaaatc atgcatgcct tctacaagga tactgatgga   2580

ttctcatccc ttactgcaat gacaggattc gtcaaaaagg ttcttttcga acctgtgcct   2640

gagtaa                                                              2646
```

```
<210> SEQ ID NO 56
<211> LENGTH: 881
<212> TYPE: PRT
<213> ORGANISM: Physcomitrella patens

<400> SEQUENCE: 56

Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Ser Pro Gly Ser Gly Ser
    50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140

Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
    210                 215                 220

Arg Gly Ile Gln Phe Leu Gln Ser Asn Ile Tyr Lys Met Glu Glu Asp
225                 230                 235                 240
```

```
Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285

Pro Met Ala Met Val Tyr Lys Tyr Pro Thr Thr Leu Leu His Ser Leu
    290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

Leu Met Tyr Thr Lys Asp Val Lys Cys Phe Asp Tyr Leu Asn Gln Leu
            340                 345                 350

Leu Ile Lys Phe Asp His Ala Cys Pro Asn Val Tyr Pro Val Asp Leu
        355                 360                 365

Phe Glu Arg Leu Trp Met Val Asp Arg Leu Gln Arg Leu Gly Ile Ser
    370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
        435                 440                 445

Phe Phe Cys Phe Ala Gly Gln Ser Ser Gln Ala Val Thr Gly Met Phe
    450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
            500                 505                 510

Glu Val Glu Tyr Asn Leu Thr Phe Pro Trp Tyr Ala Ser Leu Pro Arg
        515                 520                 525

Leu Glu His Arg Thr Tyr Leu Asp Gln Tyr Gly Ile Asp Asp Ile Trp
    530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
        595                 600                 605

Ala Ala Thr Met Phe Glu Pro Glu Met Val Gln Ala Arg Leu Val Trp
    610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
                645                 650                 655

Trp Asn Pro Glu Leu Ile Asn Gly Leu Pro Glu Gln Ala Lys Ile Leu
```

660 665 670

Phe Met Gly Leu Tyr Lys Thr Val Asn Thr Ile Ala Glu Glu Ala Phe
675 680 685

Met Ala Gln Lys Arg Asp Val His His His Leu Lys His Tyr Trp Asp
690 695 700

Lys Leu Ile Thr Ser Ala Leu Lys Glu Ala Glu Trp Ala Glu Ser Gly
705 710 715 720

Tyr Val Pro Thr Phe Asp Glu Tyr Met Glu Val Ala Glu Ile Ser Val
725 730 735

Ala Leu Glu Pro Ile Val Cys Ser Thr Leu Phe Phe Ala Gly His Arg
740 745 750

Leu Asp Glu Asp Val Leu Asp Ser Tyr Asp Tyr His Leu Val Met His
755 760 765

Leu Val Asn Arg Val Gly Arg Ile Leu Asn Asp Ile Gln Gly Met Lys
770 775 780

Arg Glu Ala Ser Gln Gly Lys Ile Ser Ser Val Gln Ile Tyr Met Glu
785 790 795 800

Glu His Pro Ser Val Pro Ser Glu Ala Met Ala Ile Ala His Leu Gln
805 810 815

Glu Leu Val Asp Asn Ser Met Gln Gln Leu Thr Tyr Glu Val Leu Arg
820 825 830

Phe Thr Ala Val Pro Lys Ser Cys Lys Arg Ile His Leu Asn Met Ala
835 840 845

Lys Ile Met His Ala Phe Tyr Lys Asp Thr Asp Gly Phe Ser Ser Leu
850 855 860

Thr Ala Met Thr Gly Phe Val Lys Lys Val Leu Phe Glu Pro Val Pro
865 870 875 880

Glu

<210> SEQ ID NO 57
<211> LENGTH: 2859
<212> TYPE: DNA
<213> ORGANISM: Artificial Sequence
<220> FEATURE:
<223> OTHER INFORMATION: Codon-optimized CDPS-KS

<400> SEQUENCE: 57
atgcctggta aaattgaaaa tggtacccca aaggacctca agactggaaa tgattttgtt 60
tctgctgcta agagtttact agatcgagct ttcaaaagtc atcattccta ctacggatta 120
tgctcaactt catgtcaagt ttatgataca gcttgggttg caatgattcc aaaaacaaga 180
gataatgtaa aacagtggtt gtttccagaa tgtttccatt acctcttaaa aacacaagcc 240
gcagatggct catggggttc attgcctaca acacagacag cgggtatcct agatacagcc 300
tcagctgtgc tggcattatt gtgccacgca caagagcctt tacaaatatt ggatgtatct 360
ccagatgaaa tggggttgag aatagaacac ggtgtcacat ccttgaaacg tcaattagca 420
gtttggaatg atgtggagga caccaaccat attggcgtcg agtttatcat accagcctta 480
ctttccatgc tagaaaagga attagatgtt ccatcttttg aatttccatg taggtccatc 540
ttagagagaa tgcacgggga gaaattaggt catttcgacc tggaacaagt ttacggcaag 600
ccaagctcat tgttgcactc attggaagca tttctcggta agctagattt tgatcgacta 660
tcacatcacc tataccacgg cagtatgatg gcatctccat cttcaacggc tgcttatctt 720
attggggcta caaaatggga tgacgaagcc gaagattacc taagacatgt aatgcgtaat 780

```
ggtgcaggac atgggaatgg aggtatttct ggtacatttc caactactca tttcgaatgt    840

agctggatta tagcaacgtt gttaaaggtt ggctttactt tgaagcaaat tgacggcgat    900

ggcttaagag gtttatcaac catcttactt gaggcgcttc gtgatgagaa tggtgtcata    960

ggctttgccc ctagaacagc agatgtagat gacacagcca aagctctatt ggccttgtca   1020

ttggtaaacc agccagtgtc acctgatatc atgattaagg tctttgaggg caaagaccat   1080

tttaccactt ttggttcaga aagagatcca tcattgactt ccaacctgca cgtcctttta   1140

tctttactta aacaatctaa cttgtctcaa taccatcctc aaatcctcaa aacaacatta   1200

ttcacttgta gatggtggtg gggttccgat cattgtgtca aagacaaatg gaatttgagt   1260

cacctatatc caactatgtt gttggttgaa gccttcactg aagtgctcca tctcattgac   1320

ggtggtgaat tgtctagtct gtttgatgaa tcctttaagt gtaagattgg tcttagcatc   1380

tttcaagcgg tacttagaat aatcctcacc caagacaacg acggctcttg gagaggatac   1440

agagaacaga cgtgttacgc aatattggct ttagttcaag cgagacatgt atgctttttc   1500

actcacatgg ttgacagact gcaatcatgt gttgatcgag gtttctcatg gttgaaatct   1560

tgctcttttc attctcaaga cctgacttgg acctctaaaa cagcttatga agtgggtttc   1620

gtagctgaag catataaact agctgcttta caatctgctt ccctggaggt tcctgctgcc   1680

accattggac attctgtcac gtctgccgtt ccatcaagtg atcttgaaaa atacatgaga   1740

ttggtgagaa aaactgcgtt attctctcca ctggatgagt ggggtctaat ggcttctatc   1800

atcgaatctt catttttcgt accattactg caggcacaaa gagttgaaat ataccctaga   1860

gataatatca aggtggacga agataagtac ttgtctatta tcccattcac atgggtcgga   1920

tgcaataata ggtctagaac tttcgcaagt aacagatggc tatacgatat gatgtacctt   1980

tcattactcg gctatcaaac cgacgagtac atggaagctg tagctgggcc agtgtttggg   2040

gatgtttcct tgttacatca aacaattgat aaggtgattg ataatacaat gggtaacctt   2100

gcgagagcca atggaacagt acacagtggt aatggacatc agcacgaatc tcctaatata   2160

ggtcaagtcg aggacacctt gactcgtttc acaaattcag tcttgaatca caaagacgtc   2220

cttaactcta gctcatctga tcaagatact ttgagaagag agtttagaac attcatgcac   2280

gctcatataa cacaaatcga agataactca cgattcagta agcaagcctc atccgatgcg   2340

ttttcctctc ctgaacaatc ttactttcaa tgggtgaact caactggtgg ctcacatgtc   2400

gcttgcgcct attcatttgc cttctctaat tgcctcatgt ctgcaaattt gttgcagggt   2460

aaagacgcat ttccaagcgg aacgcaaaag tacttaatct cctctgttat gagacatgcc   2520

acaaacatgt gtagaatgta taacgacttt ggctctattg ccagagacaa cgctgagaga   2580

aatgttaata gtattcattt tcctgagttt actctctgta acggaacttc tcaaaaccta   2640

gatgaaagga aggaaagact tctgaaaatc gcaacttacg aacaagggta tttggataga   2700

gcactagagg ccttggaaag acagagtaga gatgatgccg gagacagagc tggatctaaa   2760

gatatgagaa agttgaaaat cgttaagtta ttctgtgatg ttacggactt atacgatcag   2820

ctctacgtta tcaaagattt gtcatcctct atgaagtaa                          2859
```

<210> SEQ ID NO 58
<211> LENGTH: 952
<212> TYPE: PRT
<213> ORGANISM: Gibberella fujikuroi

<400> SEQUENCE: 58

Met Pro Gly Lys Ile Glu Asn Gly Thr Pro Lys Asp Leu Lys Thr Gly

-continued

```
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
    50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
            100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
    130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
            180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
    210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
            260                 265                 270

Phe Pro Thr Thr His Phe Glu Cys Ser Trp Ile Ile Ala Thr Leu Leu
        275                 280                 285

Lys Val Gly Phe Thr Leu Lys Gln Ile Asp Gly Asp Gly Leu Arg Gly
    290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Asp Thr Ala Lys Ala Leu
                325                 330                 335

Leu Ala Leu Ser Leu Val Asn Gln Pro Val Ser Pro Asp Ile Met Ile
            340                 345                 350

Lys Val Phe Glu Gly Lys Asp His Phe Thr Thr Phe Gly Ser Glu Arg
        355                 360                 365

Asp Pro Ser Leu Thr Ser Asn Leu His Val Leu Leu Ser Leu Leu Lys
    370                 375                 380

Gln Ser Asn Leu Ser Gln Tyr His Pro Gln Ile Leu Lys Thr Thr Leu
385                 390                 395                 400

Phe Thr Cys Arg Trp Trp Trp Gly Ser Asp His Cys Val Lys Asp Lys
                405                 410                 415

Trp Asn Leu Ser His Leu Tyr Pro Thr Met Leu Leu Val Glu Ala Phe
            420                 425                 430
```

-continued

```
Thr Glu Val Leu His Leu Ile Asp Gly Gly Glu Leu Ser Ser Leu Phe
        435                 440                 445

Asp Glu Ser Phe Lys Cys Lys Ile Gly Leu Ser Ile Phe Gln Ala Val
    450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
                485                 490                 495

Val Cys Phe Phe Thr His Met Val Asp Arg Leu Gln Ser Cys Val Asp
            500                 505                 510

Arg Gly Phe Ser Trp Leu Lys Ser Cys Ser Phe His Ser Gln Asp Leu
        515                 520                 525

Thr Trp Thr Ser Lys Thr Ala Tyr Glu Val Gly Phe Val Ala Glu Ala
    530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
                565                 570                 575

Lys Tyr Met Arg Leu Val Arg Lys Thr Ala Leu Phe Ser Pro Leu Asp
            580                 585                 590

Glu Trp Gly Leu Met Ala Ser Ile Ile Glu Ser Ser Phe Phe Val Pro
        595                 600                 605

Leu Leu Gln Ala Gln Arg Val Glu Ile Tyr Pro Arg Asp Asn Ile Lys
    610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
                645                 650                 655

Met Met Tyr Leu Ser Leu Leu Gly Tyr Gln Thr Asp Glu Tyr Met Glu
            660                 665                 670

Ala Val Ala Gly Pro Val Phe Gly Asp Val Ser Leu Leu His Gln Thr
        675                 680                 685

Ile Asp Lys Val Ile Asp Asn Thr Met Gly Asn Leu Ala Arg Ala Asn
    690                 695                 700

Gly Thr Val His Ser Gly Asn Gly His Gln His Glu Ser Pro Asn Ile
705                 710                 715                 720

Gly Gln Val Glu Asp Thr Leu Thr Arg Phe Thr Asn Ser Val Leu Asn
                725                 730                 735

His Lys Asp Val Leu Asn Ser Ser Ser Ser Asp Gln Asp Thr Leu Arg
            740                 745                 750

Arg Glu Phe Arg Thr Phe Met His Ala His Ile Thr Gln Ile Glu Asp
        755                 760                 765

Asn Ser Arg Phe Ser Lys Gln Ala Ser Ser Asp Ala Phe Ser Ser Pro
    770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
            820                 825                 830

Ile Ser Ser Val Met Arg His Ala Thr Asn Met Cys Arg Met Tyr Asn
        835                 840                 845
```

Asp Phe Gly Ser Ile Ala Arg Asp Asn Ala Glu Arg Asn Val Asn Ser
    850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                885                 890                 895

Tyr Leu Asp Arg Ala Leu Glu Ala Leu Glu Arg Gln Ser Arg Asp Asp
            900                 905                 910

Ala Gly Asp Arg Ala Gly Ser Lys Asp Met Arg Lys Leu Lys Ile Val
        915                 920                 925

Lys Leu Phe Cys Asp Val Thr Asp Leu Tyr Asp Gln Leu Tyr Val Ile
    930                 935                 940

Lys Asp Leu Ser Ser Ser Met Lys
945                 950

<210> SEQ ID NO 59
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 59
atggatgctg tgacgggttt gttaactgtc ccagcaaccg ctataactat tggtggaact 60
gctgtagcat tggcggtagc gctaatcttt tggtacctga aatcctacac atcagctaga 120
agatcccaat caaatcatct tccaagagtg cctgaagtcc caggtgttcc attgttagga 180
aatctgttac aattgaagga gaaaaagcca tacatgactt ttacgagatg ggcagcgaca 240
tatggaccta tctatagtat caaaactggg gctacaagta tggttgtggt atcatctaat 300
gagatagcca aggaggcatt ggtgaccaga ttccaatcca tatctacaag gaacttatct 360
aaagccctga aagtacttac agcagataag acaatggtcg caatgtcaga ttatgatgat 420
tatcataaaa cagttaagag acacatactg accgccgtct tgggtcctaa tgcacagaaa 480
aagcatagaa ttcacagaga tatcatgatg gataacatat ctactcaact tcatgaattc 540
gtgaaaaaca acccagaaca ggaagaggta gaccttagaa aaatctttca atctgagtta 600
ttcggcttag ctatgagaca agccttagga aaggatgttg aaagtttgta cgttgaagac 660
ctgaaaatca ctatgaatag agacgaaatc tttcaagtcc ttgttgttga tccaatgatg 720
ggagcaatcg atgttgattg gagagacttc tttccatacc taaagtgggt cccaaacaaa 780
aagttcgaaa atactattca acaaatgtac atcagaagag aagctgttat gaaatcttta 840
atcaaagagc acaaaaagag aatagcgtca ggcgaaaagc taaatagtta tatcgattac 900
cttttatctg aagctcaaac tttaaccgat cagcaactat tgatgtcctt gtgggaacca 960
atcattgaat cttcagatac aacaatggtc acaacagaat gggcaatgta cgaattagct 1020
aaaaacccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag gaatggaacc cagaaagatt catgaaagag 1320
aatgagacaa ttgattttca aaagacgatg gccttcggtg gtggtaagag agtttgtgct 1380
ggttccttgc aagccctttt aactgcatct attgggattg ggagaatggt tcaagagttc 1440

-continued gaatggaaac tgaaggatat gactcaagag gaagtgaaca cgataggcct aactacacaa 1500
atgttaagac cattgagagc tattatcaaa cctaggatct aa 1542

<210> SEQ ID NO 60
<211> LENGTH: 513
<212> TYPE: PRT
<213> ORGANISM: Stevia rebaudiana

<400> SEQUENCE: 60

Met Asp Ala Val Thr Gly Leu Leu Thr Val Pro Ala Thr Ala Ile Thr
1 5 10 15

Ile Gly Gly Thr Ala Val Ala Leu Ala Val Ala Leu Ile Phe Trp Tyr
20 25 30

Leu Lys Ser Tyr Thr Ser Ala Arg Arg Ser Gln Ser Asn His Leu Pro
35 40 45

Arg Val Pro Glu Val Pro Gly Val Pro Leu Leu Gly Asn Leu Leu Gln
50 55 60

Leu Lys Glu Lys Lys Pro Tyr Met Thr Phe Thr Arg Trp Ala Ala Thr
65 70 75 80

Tyr Gly Pro Ile Tyr Ser Ile Lys Thr Gly Ala Thr Ser Met Val Val
85 90 95

Val Ser Ser Asn Glu Ile Ala Lys Glu Ala Leu Val Thr Arg Phe Gln
100 105 110

Ser Ile Ser Thr Arg Asn Leu Ser Lys Ala Leu Lys Val Leu Thr Ala
115 120 125

Asp Lys Thr Met Val Ala Met Ser Asp Tyr Asp Asp Tyr His Lys Thr
130 135 140

Val Lys Arg His Ile Leu Thr Ala Val Leu Gly Pro Asn Ala Gln Lys
145 150 155 160

Lys His Arg Ile His Arg Asp Ile Met Met Asp Asn Ile Ser Thr Gln
165 170 175

Leu His Glu Phe Val Lys Asn Asn Pro Glu Gln Glu Glu Val Asp Leu
180 185 190

Arg Lys Ile Phe Gln Ser Glu Leu Phe Gly Leu Ala Met Arg Gln Ala
195 200 205

Leu Gly Lys Asp Val Glu Ser Leu Tyr Val Glu Asp Leu Lys Ile Thr
210 215 220

Met Asn Arg Asp Glu Ile Phe Gln Val Leu Val Val Asp Pro Met Met
225 230 235 240

Gly Ala Ile Asp Val Asp Trp Arg Asp Phe Phe Pro Tyr Leu Lys Trp
245 250 255

Val Pro Asn Lys Lys Phe Glu Asn Thr Ile Gln Gln Met Tyr Ile Arg
260 265 270

Arg Glu Ala Val Met Lys Ser Leu Ile Lys Glu His Lys Lys Arg Ile
275 280 285

Ala Ser Gly Glu Lys Leu Asn Ser Tyr Ile Asp Tyr Leu Leu Ser Glu
290 295 300

Ala Gln Thr Leu Thr Asp Gln Gln Leu Leu Met Ser Leu Trp Glu Pro
305 310 315 320

Ile Ile Glu Ser Ser Asp Thr Thr Met Val Thr Thr Glu Trp Ala Met
325 330 335

Tyr Glu Leu Ala Lys Asn Pro Lys Leu Gln Asp Arg Leu Tyr Arg Asp
340 345 350

Ile Lys Ser Val Cys Gly Ser Glu Lys Ile Thr Glu Glu His Leu Ser

```
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile
```

<210> SEQ ID NO 61
<211> LENGTH: 1566
<212> TYPE: DNA
<213> ORGANISM: Artificial Sequence
<220> FEATURE:
<223> OTHER INFORMATION: Codon-optimized KO

<400> SEQUENCE: 61

```
aagcttacta gtaaaatgga cggtgtcatc gatatgcaaa ccattccatt gagaaccgct     60

attgctattg gtggtactgc tgttgctttg gttgttgcat tatacttttg gttcttgaga    120

tcctacgctt ccccatctca tcattctaat catttgccac cagtacctga agttccaggt    180

gttccagttt tgggtaattt gttgcaattg aaagaaaaaa agccttacat gaccttcacc    240

aagtgggctg aaatgtatgg tccaatctac tctattagaa ctggtgctac ttccatggtt    300

gttgtctctt ctaacgaaat cgccaaagaa gttgttgtta ccagattccc atctatctct    360

accagaaaat tgtcttacgc cttgaaggtt ttgaccgaag ataagtctat ggttgccatg    420

tctgattatc acgattacca taagaccgtc aagagacata ttttgactgc tgttttgggt    480

ccaaacgccc aaaaaaagtt tagagcacat agagacacca tgatggaaaa cgtttccaat    540

gaattgcatg ccttcttcga aaagaaccca aatcaagaag tcaacttgag aaagatcttc    600

caatcccaat tattcggttt ggctatgaag caagccttgg gtaaagatgt tgaatccatc    660

tacgttaagg atttggaaac caccatgaag agagaagaaa tcttcgaagt tttggttgtc    720

gatccaatga tgggtgctat tgaagttgat tggagagact tttttcccata cttgaaatgg    780

gttccaaaca agtccttcga aaacatcatc catagaatgt acactagaag agaagctgtt    840

atgaaggcct tgatccaaga acacaagaaa agaattgcct ccggtgaaaa cttgaactcc    900

tacattgatt acttgttgtc tgaagcccaa accttgaccg ataagcaatt attgatgtct    960

ttgtgggaac ctattatcga atcttctgat accactatgg ttactactga atgggctatg   1020

tacgaattgg ctaagaatcc aaacatgcaa gacagattat acgaagaaat ccaatccgtt   1080

tgcggttccg aaaagattac tgaagaaaac ttgtcccaat tgccatactt gtacgctgtt   1140
```

-continued

```
ttccaagaaa ctttgagaaa gcactgtcca gttcctatta tgccattgag atatgttcac   1200

gaaaacaccg ttttgggtgg ttatcatgtt ccagctggta ctgaagttgc tattaacatc   1260

tacggttgca acatggataa gaaggtctgg gaaaatccag aagaatggaa tccagaaaga   1320

ttcttgtccg aaaaagaatc catggacttg tacaaaacta tggcttttgg tggtggtaaa   1380

agagtttgcg ctggttcttt acaagccatg gttatttctt gcattggtat cggtagattg   1440

gtccaagatt ttgaatggaa gttgaaggat gatgccgaag aagatgttaa cactttgggt   1500

ttgactaccc aaaagttgca tccattattg gccttgatta acccaagaaa gtaactcgag   1560

ccgcgg                                                              1566
```

<210> SEQ ID NO 62
<211> LENGTH: 512
<212> TYPE: PRT
<213> ORGANISM: Lactuca sativa

<400> SEQUENCE: 62

```
Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
            20                  25                  30

Phe Leu Arg Ser Tyr Ala Ser Pro Ser His His Ser Asn His Leu Pro
        35                  40                  45

Pro Val Pro Glu Val Pro Gly Val Pro Val Leu Gly Asn Leu Leu Gln
    50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
    130                 135                 140

Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                165                 170                 175

Leu His Ala Phe Phe Glu Lys Asn Pro Asn Gln Glu Val Asn Leu Arg
            180                 185                 190

Lys Ile Phe Gln Ser Gln Leu Phe Gly Leu Ala Met Lys Gln Ala Leu
        195                 200                 205

Gly Lys Asp Val Glu Ser Ile Tyr Val Lys Asp Leu Glu Thr Thr Met
    210                 215                 220

Lys Arg Glu Glu Ile Phe Glu Val Leu Val Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
            260                 265                 270

Glu Ala Val Met Lys Ala Leu Ile Gln Glu His Lys Lys Arg Ile Ala
        275                 280                 285

Ser Gly Glu Asn Leu Asn Ser Tyr Ile Asp Tyr Leu Leu Ser Glu Ala
```

```
    290                 295                 300

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
            340                 345                 350

Gln Ser Val Cys Gly Ser Glu Lys Ile Thr Glu Glu Asn Leu Ser Gln
        355                 360                 365

Leu Pro Tyr Leu Tyr Ala Val Phe Gln Glu Thr Leu Arg Lys His Cys
    370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
            420                 425                 430

Pro Glu Arg Phe Leu Ser Glu Lys Glu Ser Met Asp Leu Tyr Lys Thr
        435                 440                 445

Met Ala Phe Gly Gly Gly Lys Arg Val Cys Ala Gly Ser Leu Gln Ala
    450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510
```

<210> SEQ ID NO 63
<211> LENGTH: 1535
<212> TYPE: DNA
<213> ORGANISM: Rubus suavissimus

<400> SEQUENCE: 63

```
atggccaccc tccttgagca tttccaagct atgccctttg ccatccctat tgcactggct      60

gctctgtctt ggctgttcct cttttacatc aaagtttcat tcttttccaa caagagtgct     120

caggctaagc tccctcctgt gccagtggtt cctgggctgc cggtgattgg gaatttactg     180

caactcaagg agaagaaacc ctaccagact tttacaaggt gggctgagga gtatggacca     240

atctattcta tcaggactgg tgcttccacc atggtcgttc tcaataccac ccaagttgca     300

aaagaggcca tggtgaccag atatttatcc atctcaacca gaaagctatc aaacgcacta     360

aagattctta ctgctgataa atgtatggtt gcaataagtg actacaacga ttttcacaag     420

atgataaagc gatacatact ctcaaatgtt cttggaccta gtgctcagaa gcgtcaccgg     480

agcaacagag ataccttgag agctaatgtc tgcagccgat tgcattctca agtaaagaac     540

tctcctcgag aagctgtgaa tttcagaaga gtttttgagt gggaactctt tggaattgca     600

ttgaagcaag cctttggaaa ggacatagaa aagcccattt atgtggagga acttggcact     660

acactgtcaa gagatgagat ctttaaggtt ctagtgcttg acataatgga gggtgcaatt     720

gaggttgatt ggagagattt cttccccttac ctgagatgga ttccgaatac gcgcatggaa     780

acaaaaattc agcgactcta tttccgcagg aaagcagtga tgactgccct gatcaacgag     840

cagaagaagc gaattgcttc aggagaggaa atcaactgtt atatcgactt cttgcttaag     900
```

gaagggaaga cactgacaat ggaccaaata agtatgttgc tttgggagac ggttattgaa 960
acagcagata ctacaatggt aacgacagaa tgggctatgt atgaagttgc taaagactca 1020
aagcgtcagg atcgtctcta tcaggaaatc caaaaggttt gtggatcgga gatggttaca 1080
gaggaatact tgtcccaact gccgtacctg aatgcagttt tccatgaaac gctaaggaag 1140
cacagtccgg ctgcgttagt tcctttaaga tatgcacatg aagataccca actaggaggt 1200
tactacattc cagctggaac tgagattgct ataaacatat acgggtgtaa catggacaag 1260
catcaatggg aaagccctga ggaatggaaa ccggagagat tttggaccc gaaatttgat 1320 cctatggatt tgtacaagac catggctttt ggggctggaa agagggtatg tgctggttct 1380
cttcaggcaa tgttaatagc gtgcccgacg attggtaggc tggtgcagga gtttgagtgg 1440
aagctgagag atggagaaga agaaaatgta gatactgttg ggctcaccac tcacaaacgc 1500
tatccaatgc atgcaatcct gaagccaaga agtta 1535

<210> SEQ ID NO 64
<211> LENGTH: 1536
<212> TYPE: DNA
<213> ORGANISM: Artificial Sequence
<220> FEATURE:
<223> OTHER INFORMATION: Codon-optimized KO

<400> SEQUENCE: 64
atggctacct tgttggaaca ttttcaagct atgccattcg ctattccaat tgctttggct 60
gctttgtctt ggttgttttt gttctacatc aaggtttctt tcttctccaa caaatccgct 120
caagctaaat tgccaccagt tccagttgtt ccaggtttgc cagttattgg taatttgttg 180
caattgaaag aaaagaagcc ataccaaacc ttcactagat gggctgaaga atatggtcca 240
atctactcta ttagaactgg tgcttctact atggttgtct tgaacactac tcaagttgcc 300
aaagaagcta tggttaccag atacttgtct atctctacca gaaagttgtc caacgccttg 360
aaaattttga ccgctgataa gtgcatggtt gccatttctg attacaacga tttccacaag 420
atgatcaaga gatatatctt gtctaacgtt ttgggtccat ctgcccaaaa aagacataga 480
tctaacagag ataccttgag agccaacgtt tgttctagat tgcattccca agttaagaac 540
tctccaagag aagctgtcaa ctttagaaga gttttcgaat gggaattatt cggtatcgct 600
ttgaaacaag ccttcggtaa ggatattgaa aagccaatct acgtcgaaga attgggtact 660
actttgtcca gagatgaaat cttcaaggtt ttggtcttgg acattatgga aggtgccatt 720
gaagttgatt ggagagattt tttcccatac ttgcgttgga ttccaaacac cagaatggaa 780
actaagatcc aaagattata ctttagaaga aaggccgtta tgaccgcctt gattaacgaa 840
caaaagaaaa gaattgcctc cggtgaagaa atcaactgct acatcgattt cttgttgaaa 900
gaaggtaaga ccttgaccat ggaccaaatc tctatgttgt tgtgggaaac cgttattgaa 960
actgctgata ccacaatggt tactactgaa tgggctatgt acgaagttgc taaggattct 1020
aaaagacaag acagattata ccaagaaatc caaaaggtct gcggttctga aatggttaca 1080
gaagaatact tgtcccaatt gccatacttg aatgctgttt tccacgaaac tttgagaaaa 1140
cattctccag ctgctttggt tccattgaga tatgctcatg aagatactca attgggtggt 1200
tattacattc cagccggtac tgaaattgcc attaacatct acggttgcaa catggacaaa 1260
caccaatggg aatctccaga agaatggaag ccagaaagat tttggatcc taagtttgac 1320 ccaatggact tgtacaaaac tatggctttt ggtgctggta aaagagtttg cgctggttct 1380
ttacaagcta tgttgattgc ttgtccaacc atcggtagat tggttcaaga atttgaatgg 1440
aagttgagag atggtgaaga agaaaacgtt gatactgttg gtttgaccac ccataagaga 1500
tatccaatgc atgctatttt gaagccaaga tcttaa 1536

<210> SEQ ID NO 65
<211> LENGTH: 1572
<212> TYPE: DNA
<213> ORGANISM: Artificial Sequence
<220> FEATURE:
<223> OTHER INFORMATION: Codon-optimized KO

<400> SEQUENCE: 65
aagcttacta gtaaaatggc ctccatcacc catttcttac aagattttca agctactcca 60
ttcgctactg cttttgctgt tggtggtgtt tctttgttga tattcttctt cttcatccgt 120
ggtttccact ctactaagaa aaacgaatat tacaagttgc caccagttcc agttgttcca 180
ggtttgccag ttgttggtaa tttgttgcaa ttgaaagaaa agaagccata caagactttc 240
ttgagatggg ctgaaattca tggtccaatc tactctatta gaactggtgc ttctaccatg 300
gttgttgtta actctactca tgttgccaaa gaagctatgg ttaccagatt ctcttcaatc 360
tctaccagaa agttgtccaa ggctttggaa ttattgacct ccaacaaatc tatggttgcc 420
acctctgatt acaacgaatt tcacaagatg gtcaagaagt acatcttggc cgaattattg 480
ggtgctaatg ctcaaaagag acacagaatt catagagaca ccttgatcga aaacgtcttg 540
aacaaattgc atgcccatac caagaattct ccattgcaag ctgttaactt cagaaagatc 600
ttcgaatctg aattattcgg tttggctatg aagcaagcct tgggttatga tgttgattcc 660
ttgttcgttg aagaattggg tactaccttg tccagagaag aaatctacaa cgttttggtc 720
agtgacatgt tgaagggtgc tattgaagtt gattggagag actttttccc atacttgaaa 780
tggatcccaa acaagtcctt cgaaatgaag attcaaagat tggcctctag aagacaagcc 840
gttatgaact ctattgtcaa agaacaaaag aagtccattg cctctggtaa gggtgaaaac 900
tgttacttga attacttgtt gtccgaagct aagactttga ccgaaaagca aatttccatt 960
ttggcctggg aaaccattat tgaaactgct gatacaactg ttgttaccac tgaatgggct 1020
atgtacgaat tggctaaaaa cccaaagcaa caagacagat tatacaacga aatccaaaac 1080
gtctgcggta ctgataagat taccgaagaa catttgtcca agttgcctta cttgtctgct 1140
gtttttcacg aaaccttgag aaagtattct ccatctccat tggttccatt gagatacgct 1200
catgaagata ctcaattggg tggttattat gttccagccg gtactgaaat tgctgttaat 1260
atctacggtt gcaacatgga caagaatcaa tgggaaactc cagaagaatg gaagccagaa 1320
agatttttgg acgaaaagta cgatccaatg gacatgtaca agactatgtc ttttggttcc 1380
ggtaaaagag tttgcgctgg ttctttacaa gctagtttga ttgcttgtac ctccatcggt 1440
agattggttc aagaatttga atggagattg aaagacggtg aagttgaaaa cgttgatacc 1500
ttgggtttga ctacccataa gttgtatcca atgcaagcta tcttgcaacc tagaaactga 1560
ctcgagccgc gg 1572

<210> SEQ ID NO 66
<211> LENGTH: 514
<212> TYPE: PRT
<213> ORGANISM: Castanea mollissima

<400> SEQUENCE: 66

Met Ala Ser Ile Thr His Phe Leu Gln Asp Phe Gln Ala Thr Pro Phe
1 5 10 15

-continued

```
Ala Thr Ala Phe Ala Val Gly Gly Val Ser Leu Leu Ile Phe Phe Phe
            20                  25                  30

Phe Ile Arg Gly Phe His Ser Thr Lys Lys Asn Glu Tyr Tyr Lys Leu
        35                  40                  45

Pro Pro Val Pro Val Val Pro Gly Leu Pro Val Val Gly Asn Leu Leu
    50                  55                  60

Gln Leu Lys Glu Lys Lys Pro Tyr Lys Thr Phe Leu Arg Trp Ala Glu
65                  70                  75                  80

Ile His Gly Pro Ile Tyr Ser Ile Arg Thr Gly Ala Ser Thr Met Val
                85                  90                  95

Val Val Asn Ser Thr His Val Ala Lys Glu Ala Met Val Thr Arg Phe
            100                 105                 110

Ser Ser Ile Ser Thr Arg Lys Leu Ser Lys Ala Leu Glu Leu Leu Thr
        115                 120                 125

Ser Asn Lys Ser Met Val Ala Thr Ser Asp Tyr Asn Glu Phe His Lys
    130                 135                 140

Met Val Lys Lys Tyr Ile Leu Ala Glu Leu Leu Gly Ala Asn Ala Gln
145                 150                 155                 160

Lys Arg His Arg Ile His Arg Asp Thr Leu Ile Glu Asn Val Leu Asn
                165                 170                 175

Lys Leu His Ala His Thr Lys Asn Ser Pro Leu Gln Ala Val Asn Phe
            180                 185                 190

Arg Lys Ile Phe Glu Ser Glu Leu Phe Gly Leu Ala Met Lys Gln Ala
        195                 200                 205

Leu Gly Tyr Asp Val Asp Ser Leu Phe Val Glu Glu Leu Gly Thr Thr
    210                 215                 220

Leu Ser Arg Glu Glu Ile Tyr Asn Val Leu Val Ser Asp Met Leu Lys
225                 230                 235                 240

Gly Ala Ile Glu Val Asp Trp Arg Asp Phe Phe Pro Tyr Leu Lys Trp
                245                 250                 255

Ile Pro Asn Lys Ser Phe Glu Met Lys Ile Gln Arg Leu Ala Ser Arg
            260                 265                 270

Arg Gln Ala Val Met Asn Ser Ile Val Lys Glu Gln Lys Lys Ser Ile
        275                 280                 285

Ala Ser Gly Lys Gly Glu Asn Cys Tyr Leu Asn Tyr Leu Leu Ser Glu
    290                 295                 300

Ala Lys Thr Leu Thr Glu Lys Gln Ile Ser Ile Leu Ala Trp Glu Thr
305                 310                 315                 320

Ile Ile Glu Thr Ala Asp Thr Thr Val Val Thr Thr Glu Trp Ala Met
                325                 330                 335

Tyr Glu Leu Ala Lys Asn Pro Lys Gln Gln Asp Arg Leu Tyr Asn Glu
            340                 345                 350

Ile Gln Asn Val Cys Gly Thr Asp Lys Ile Thr Glu Glu His Leu Ser
        355                 360                 365

Lys Leu Pro Tyr Leu Ser Ala Val Phe His Glu Thr Leu Arg Lys Tyr
    370                 375                 380

Ser Pro Ser Pro Leu Val Pro Leu Arg Tyr Ala His Glu Asp Thr Gln
385                 390                 395                 400

Leu Gly Gly Tyr Tyr Val Pro Ala Gly Thr Glu Ile Ala Val Asn Ile
                405                 410                 415

Tyr Gly Cys Asn Met Asp Lys Asn Gln Trp Glu Thr Pro Glu Glu Trp
            420                 425                 430
```

-continued

```
Lys Pro Glu Arg Phe Leu Asp Glu Lys Tyr Asp Pro Met Asp Met Tyr
        435                 440                 445

Lys Thr Met Ser Phe Gly Ser Gly Lys Arg Val Cys Ala Gly Ser Leu
    450                 455                 460

Gln Ala Ser Leu Ile Ala Cys Thr Ser Ile Gly Arg Leu Val Gln Glu
465                 470                 475                 480

Phe Glu Trp Arg Leu Lys Asp Gly Glu Val Glu Asn Val Asp Thr Leu
                485                 490                 495

Gly Leu Thr Thr His Lys Leu Tyr Pro Met Gln Ala Ile Leu Gln Pro
            500                 505                 510

Arg Asn


<210> SEQ ID NO 67
<211> LENGTH: 1512
<212> TYPE: DNA
<213> ORGANISM: Artificial Sequence
<220> FEATURE:
<223> OTHER INFORMATION: Codon-optimized KO

<400> SEQUENCE: 67

atgatttcct tgttgttggg ttttgttgtc tcctccttct tgtttatctt cttcttgaaa      60

aaattgttgt tcttcttcag tcgtcacaaa atgtccgaag tttctagatt gccatctgtt     120

ccagttccag gttttccatt gattggtaac ttgttgcaat tgaaagaaaa gaagccacac     180

aagactttca ccaagtggtc tgaattatat ggtccaatct actctatcaa gatgggttcc     240

tcttctttga tcgtcttgaa ctctattgaa accgccaaag aagctatggt cagtagattc     300

tcttcaatct ctaccagaaa gttgtctaac gctttgactg ttttgacctg caacaaatct     360

atggttgcta cctctgatta cgatgacttt cataagttcg tcaagagatg cttgttgaac     420

ggtttgttgg gtgctaatgc tcaagaaaga aaaagacatt acagagatgc cttgatcgaa     480

aacgttacct ctaaattgca tgcccatacc agaaatcatc cacaagaacc agttaacttc     540

agagccattt tcgaacacga attattcggt gttgctttga aacaagcctt cggtaaagat     600

gtcgaatcca tctatgtaaa agaattgggt gtcaccttgt ccagagatga aattttcaag     660

gttttggtcc acgacatgat ggaaggtgct attgatgttg attggagaga tttcttccca     720

tacttgaaat ggatcccaaa caactctttc gaagccagaa ttcaacaaaa gcacaagaga     780

agattggctg ttatgaacgc cttgatccaa gacagattga atcaaaacga ttccgaatcc     840

gatgatgact gctacttgaa tttcttgatg tctgaagcta agaccttgac catggaacaa     900

attgctattt tggtttggga aaccattatc gaaactgctg ataccacttt ggttactact     960

gaatgggcta tgtacgaatt ggccaaacat caatctgttc aagatagatt attcaaagaa    1020

atccaatccg tctgcggtgg tgaaaagatc aaagaagaac aattgccaag attgccttac    1080

gtcaatggtg tttttcacga aaccttgaga aagtattctc cagctccatt ggttccaatt    1140

agatacgctc atgaagatac ccaaattggt ggttatcata ttccagccgg ttctgaaatt    1200

gccattaaca tctacggttg caacatggat aagaagagat gggaaagacc tgaagaatgg    1260

tggccagaaa gatttttgga agatagatac gaatcctccg acttgcataa gactatggct    1320

tttggtgctg gtaaaagagt ttgtgctggt gctttacaag ctagtttgat ggctggtatt    1380

gctatcggta gattggttca agaattcgaa tggaagttga gagatggtga agaagaaaac    1440

gttgatactt acggtttgac ctcccaaaag ttgtatccat tgatggccat tatcaaccca    1500

agaagatctt aa                                                        1512
```

<210> SEQ ID NO 68
<211> LENGTH: 506
<212> TYPE: PRT
<213> ORGANISM: Thellungiella halophila

<400> SEQUENCE: 68

Met Ala Ser Met Ile Ser Leu Leu Leu Gly Phe Val Val Ser Ser Phe
1 5 10 15

Leu Phe Ile Phe Phe Leu Lys Lys Leu Leu Phe Phe Phe Ser Arg His
20 25 30

Lys Met Ser Glu Val Ser Arg Leu Pro Ser Val Pro Val Pro Gly Phe
35 40 45

Pro Leu Ile Gly Asn Leu Leu Gln Leu Lys Glu Lys Lys Pro His Lys
50 55 60

Thr Phe Thr Lys Trp Ser Glu Leu Tyr Gly Pro Ile Tyr Ser Ile Lys
65 70 75 80

Met Gly Ser Ser Ser Leu Ile Val Leu Asn Ser Ile Glu Thr Ala Lys
85 90 95

Glu Ala Met Val Ser Arg Phe Ser Ser Ile Ser Thr Arg Lys Leu Ser
100 105 110

Asn Ala Leu Thr Val Leu Thr Cys Asn Lys Ser Met Val Ala Thr Ser
115 120 125

Asp Tyr Asp Asp Phe His Lys Phe Val Lys Arg Cys Leu Leu Asn Gly
130 135 140

Leu Leu Gly Ala Asn Ala Gln Glu Arg Lys Arg His Tyr Arg Asp Ala
145 150 155 160

Leu Ile Glu Asn Val Thr Ser Lys Leu His Ala His Thr Arg Asn His
165 170 175

Pro Gln Glu Pro Val Asn Phe Arg Ala Ile Phe Glu His Glu Leu Phe
180 185 190

Gly Val Ala Leu Lys Gln Ala Phe Gly Lys Asp Val Glu Ser Ile Tyr
195 200 205

Val Lys Glu Leu Gly Val Thr Leu Ser Arg Asp Glu Ile Phe Lys Val
210 215 220

Leu Val His Asp Met Met Glu Gly Ala Ile Asp Val Asp Trp Arg Asp
225 230 235 240

Phe Phe Pro Tyr Leu Lys Trp Ile Pro Asn Asn Ser Phe Glu Ala Arg
245 250 255

Ile Gln Gln Lys His Lys Arg Arg Leu Ala Val Met Asn Ala Leu Ile
260 265 270

Gln Asp Arg Leu Asn Gln Asn Asp Ser Glu Ser Asp Asp Asp Cys Tyr
275 280 285

Leu Asn Phe Leu Met Ser Glu Ala Lys Thr Leu Thr Met Glu Gln Ile
290 295 300

Ala Ile Leu Val Trp Glu Thr Ile Ile Glu Thr Ala Asp Thr Thr Leu
305 310 315 320

Val Thr Thr Glu Trp Ala Met Tyr Glu Leu Ala Lys His Gln Ser Val
325 330 335

Gln Asp Arg Leu Phe Lys Glu Ile Gln Ser Val Cys Gly Gly Glu Lys
340 345 350

Ile Lys Glu Glu Gln Leu Pro Arg Leu Pro Tyr Val Asn Gly Val Phe
355 360 365

His Glu Thr Leu Arg Lys Tyr Ser Pro Ala Pro Leu Val Pro Ile Arg
370 375 380

```
Tyr Ala His Glu Asp Thr Gln Ile Gly Gly Tyr His Ile Pro Ala Gly
385                 390                 395                 400

Ser Glu Ile Ala Ile Asn Ile Tyr Gly Cys Asn Met Asp Lys Lys Arg
                405                 410                 415

Trp Glu Arg Pro Glu Glu Trp Trp Pro Glu Arg Phe Leu Glu Asp Arg
            420                 425                 430

Tyr Glu Ser Ser Asp Leu His Lys Thr Met Ala Phe Gly Ala Gly Lys
        435                 440                 445

Arg Val Cys Ala Gly Ala Leu Gln Ala Ser Leu Met Ala Gly Ile Ala
    450                 455                 460

Ile Gly Arg Leu Val Gln Glu Phe Glu Trp Lys Leu Arg Asp Gly Glu
465                 470                 475                 480

Glu Glu Asn Val Asp Thr Tyr Gly Leu Thr Ser Gln Lys Leu Tyr Pro
                485                 490                 495

Leu Met Ala Ile Ile Asn Pro Arg Arg Ser
            500                 505


<210> SEQ ID NO 69
<211> LENGTH: 1554
<212> TYPE: DNA
<213> ORGANISM: Artificial Sequence
<220> FEATURE:
<223> OTHER INFORMATION: Codon-optimized KO

<400> SEQUENCE: 69

aagcttacta gtaaaatgga catgatgggt attgaagctg ttccatttgc tactgctgtt     60

gttttgggtg gtatttcctt ggttgttttg atcttcatca gaagattcgt ttccaacaga    120

aagagatccg ttgaaggttt gccaccagtt ccagatattc caggtttacc attgattggt    180

aacttgttgc aattgaaaga aaagaagcca cataagacct ttgctagatg ggctgaaact    240

tacggtccaa ttttctctat tagaactggt gcttctacca tgatcgtctt gaattcttct    300

gaagttgcca aagaagctat ggtcactaga ttctcttcaa tctctaccag aaagttgtcc    360

aacgccttga agattttgac cttcgataag tgtatggttg ccacctctga ttacaacgat    420

tttcacaaaa tggtcaaggg tttcatcttg agaaacgttt taggtgctcc agcccaaaaa    480

agacatagat gtcatagaga taccttgatc gaaaacatct ctaagtactt gcatgcccat    540

gttaagactt ctccattgga accagttgtc ttgaagaaga ttttcgaatc cgaaattttc    600

ggtttggctt tgaaacaagc cttgggtaag gatatcgaat ccatctatgt tgaagaattg    660

ggtactacct tgtccagaga agaaattttt gccgttttgg ttgttgatcc aatggctggt    720

gctattgaag ttgattggag agatttttc ccatacttgt cctggattcc aaacaagtct    780

atggaaatga agatccaaag aatggatttt agaagaggtg ctttgatgaa ggccttgatt    840

ggtgaacaaa agaaaagaat cggttccggt gaagaaaaga actcctacat tgatttcttg    900

ttgtctgaag ctaccacttt gaccgaaaag caaattgcta tgttgatctg ggaaaccatc    960

atcgaaattt ccgatacaac tttggttacc tctgaatggg ctatgtacga attggctaaa   1020

gacccaaata gacaagaaat cttgtacaga gaaatccaca aggtttgcgg ttctaacaag   1080

ttgactgaag aaaacttgtc caagttgcca tacttgaact ctgttttcca cgaaaccttg   1140

agaaagtatt ctccagctcc aatggttcca gttagatatg ctcatgaaga tactcaattg   1200

ggtggttacc atattccagc tggttctcaa attgccatta acatctacgg ttgcaacatg   1260

aacaaaaagc aatgggaaaa tcctgaagaa tggaagccag aaagattctt ggacgaaaag   1320
```

```
tatgacttga tggacttgca taagactatg gcttttggtg gtggtaaaag agtttgtgct   1380

ggtgctttac aagcaatgtt gattgcttgc acttccatcg gtagattcgt tcaagaattt   1440

gaatggaagt tgatgggtgg tgaagaagaa aacgttgata ctgttgcttt gacctcccaa   1500

aaattgcatc caatgcaagc cattattaag gccagagaat gactcgagcc gcgg         1554


<210> SEQ ID NO 70
<211> LENGTH: 508
<212> TYPE: PRT
<213> ORGANISM: Vitis vinifera

<400> SEQUENCE: 70

Met Asp Met Met Gly Ile Glu Ala Val Pro Phe Ala Thr Ala Val Val
1               5                   10                  15

Leu Gly Gly Ile Ser Leu Val Val Leu Ile Phe Ile Arg Arg Phe Val
            20                  25                  30

Ser Asn Arg Lys Arg Ser Val Glu Gly Leu Pro Pro Val Pro Asp Ile
        35                  40                  45

Pro Gly Leu Pro Leu Ile Gly Asn Leu Leu Gln Leu Lys Glu Lys Lys
    50                  55                  60

Pro His Lys Thr Phe Ala Arg Trp Ala Glu Thr Tyr Gly Pro Ile Phe
65                  70                  75                  80

Ser Ile Arg Thr Gly Ala Ser Thr Met Ile Val Leu Asn Ser Ser Glu
                85                  90                  95

Val Ala Lys Glu Ala Met Val Thr Arg Phe Ser Ser Ile Ser Thr Arg
            100                 105                 110

Lys Leu Ser Asn Ala Leu Lys Ile Leu Thr Phe Asp Lys Cys Met Val
        115                 120                 125

Ala Thr Ser Asp Tyr Asn Asp Phe His Lys Met Val Lys Gly Phe Ile
    130                 135                 140

Leu Arg Asn Val Leu Gly Ala Pro Ala Gln Lys Arg His Arg Cys His
145                 150                 155                 160

Arg Asp Thr Leu Ile Glu Asn Ile Ser Lys Tyr Leu His Ala His Val
                165                 170                 175

Lys Thr Ser Pro Leu Glu Pro Val Val Leu Lys Lys Ile Phe Glu Ser
            180                 185                 190

Glu Ile Phe Gly Leu Ala Leu Lys Gln Ala Leu Gly Lys Asp Ile Glu
        195                 200                 205

Ser Ile Tyr Val Glu Glu Leu Gly Thr Thr Leu Ser Arg Glu Glu Ile
    210                 215                 220

Phe Ala Val Leu Val Val Asp Pro Met Ala Gly Ala Ile Glu Val Asp
225                 230                 235                 240

Trp Arg Asp Phe Phe Pro Tyr Leu Ser Trp Ile Pro Asn Lys Ser Met
                245                 250                 255

Glu Met Lys Ile Gln Arg Met Asp Phe Arg Arg Gly Ala Leu Met Lys
            260                 265                 270

Ala Leu Ile Gly Glu Gln Lys Lys Arg Ile Gly Ser Gly Glu Glu Lys
        275                 280                 285

Asn Ser Tyr Ile Asp Phe Leu Leu Ser Glu Ala Thr Thr Leu Thr Glu
    290                 295                 300

Lys Gln Ile Ala Met Leu Ile Trp Glu Thr Ile Ile Glu Ile Ser Asp
305                 310                 315                 320

Thr Thr Leu Val Thr Ser Glu Trp Ala Met Tyr Glu Leu Ala Lys Asp
                325                 330                 335
```

```
Pro Asn Arg Gln Glu Ile Leu Tyr Arg Glu Ile His Lys Val Cys Gly
            340                 345                 350

Ser Asn Lys Leu Thr Glu Glu Asn Leu Ser Lys Leu Pro Tyr Leu Asn
        355                 360                 365

Ser Val Phe His Glu Thr Leu Arg Lys Tyr Ser Pro Ala Pro Met Val
    370                 375                 380

Pro Val Arg Tyr Ala His Glu Asp Thr Gln Leu Gly Gly Tyr His Ile
385                 390                 395                 400

Pro Ala Gly Ser Gln Ile Ala Ile Asn Ile Tyr Gly Cys Asn Met Asn
                405                 410                 415

Lys Lys Gln Trp Glu Asn Pro Glu Glu Trp Lys Pro Glu Arg Phe Leu
            420                 425                 430

Asp Glu Lys Tyr Asp Leu Met Asp Leu His Lys Thr Met Ala Phe Gly
        435                 440                 445

Gly Gly Lys Arg Val Cys Ala Gly Ala Leu Gln Ala Met Leu Ile Ala
    450                 455                 460

Cys Thr Ser Ile Gly Arg Phe Val Gln Glu Phe Glu Trp Lys Leu Met
465                 470                 475                 480

Gly Gly Glu Glu Glu Asn Val Asp Thr Val Ala Leu Thr Ser Gln Lys
                485                 490                 495

Leu His Pro Met Gln Ala Ile Ile Lys Ala Arg Glu
            500                 505
```

<210> SEQ ID NO 71
<211> LENGTH: 1593
<212> TYPE: DNA
<213> ORGANISM: Artificial Sequence
<220> FEATURE:
<223> OTHER INFORMATION: Codon-optimized KO

<400> SEQUENCE: 71

```
aagcttaaaa tgagtaagtc taatagtatg aattctacat cacacgaaac cctttttcaa     60

caattggtct tgggtttgga ccgtatgcca ttgatggatg ttcactggtt gatctacgtt    120

gctttcggcg catggttatg ttcttatgtg atacatgttt tatcatcttc ctctacagta    180

aaagtgccag ttgttggata caggtctgta ttcgaaccta catggttgct tagacttaga    240

ttcgtctggg aaggtggctc tatcataggt caagggtaca ataagtttaa agactctatt    300

ttccaagtta ggaaattggg aactgatatt gtcattatac cacctaacta tattgatgaa    360

gtgagaaaat tgtcacagga caagactaga tcagttgaac ctttcattaa tgattttgca    420

ggtcaataca caagaggcat ggttttcttg caatctgact tacaaaaccg tgttatacaa    480

caaagactaa ctccaaaatt ggtttccttg accaaggtca tgaaggaaga gttggattat    540

gctttaacaa aagagatgcc tgatatgaaa aatgacgaat gggtagaagt agatatcagt    600

agtataatgg tgagattgat ttccaggatc tccgccagag tctttctagg gcctgaacac    660

tgtcgtaacc aggaatggtt gactactaca gcagaatatt cagaatcact tttcattaca    720

gggtttatct taagagttgt acctcatatc ttaagaccat tcatcgcccc tctattacct    780

tcatacagga ctctacttag aaacgtttca agtggtagaa gagtcatcgg tgacatcata    840

agatctcagc aaggggatgg taacgaagat atactttcct ggatgagaga tgctgccaca    900

ggagaggaaa agcaaatcga taacattgct cagagaatgt taattctttc tttagcatca    960

atccacacta ctgcgatgac catgacacat gccatgtacg atctatgtgc ttgccctgag   1020

tacattgaac cattaagaga tgaagttaaa tctgttgttg ggcttctggg ctgggacaag   1080
```

-continued acagcgttaa acagatttca taagttggac tccttcctaa aagagtcaca aagattcaac 1140
ccagtattct tattgacatt caatagaatc taccatcaat ctatgacctt atcagatggc 1200
actaacattc catctggaac acgtattgct gttccatcac acgcaatgtt gcaagattct 1260
gcacatgtcc caggtccaac cccacctact gaatttgatg gattcagata tagtaagata 1320
cgttctgata gtaactacgc acaaaagtac ctattctcca tgaccgattc ttcaaacatg 1380
gctttcggat acggcaagta tgcttgtcca ggtagatttt acgcgtctaa tgagatgaaa 1440
ctaacattag ccattttgtt gctacaattt gagttcaaac taccagatgg taaaggtcgt 1500
cctagaaata tcactatcga ttctgatatg attccagacc caagagctag actttgcgtc 1560
agaaaaagat cacttagaga tgaatgaccg cgg 1593

<210> SEQ ID NO 72
<211> LENGTH: 525
<212> TYPE: PRT
<213> ORGANISM: Gibberella fujikuroi

<400> SEQUENCE: 72

Met Ser Lys Ser Asn Ser Met Asn Ser Thr Ser His Glu Thr Leu Phe
1 5 10 15

Gln Gln Leu Val Leu Gly Leu Asp Arg Met Pro Leu Met Asp Val His
20 25 30

Trp Leu Ile Tyr Val Ala Phe Gly Ala Trp Leu Cys Ser Tyr Val Ile
35 40 45

His Val Leu Ser Ser Ser Ser Thr Val Lys Val Pro Val Val Gly Tyr
50 55 60

Arg Ser Val Phe Glu Pro Thr Trp Leu Leu Arg Leu Arg Phe Val Trp
65 70 75 80

Glu Gly Gly Ser Ile Ile Gly Gln Gly Tyr Asn Lys Phe Lys Asp Ser
85 90 95

Ile Phe Gln Val Arg Lys Leu Gly Thr Asp Ile Val Ile Ile Pro Pro
100 105 110

Asn Tyr Ile Asp Glu Val Arg Lys Leu Ser Gln Asp Lys Thr Arg Ser
115 120 125

Val Glu Pro Phe Ile Asn Asp Phe Ala Gly Gln Tyr Thr Arg Gly Met
130 135 140

Val Phe Leu Gln Ser Asp Leu Gln Asn Arg Val Ile Gln Gln Arg Leu
145 150 155 160

Thr Pro Lys Leu Val Ser Leu Thr Lys Val Met Lys Glu Glu Leu Asp
165 170 175

Tyr Ala Leu Thr Lys Glu Met Pro Asp Met Lys Asn Asp Glu Trp Val
180 185 190

Glu Val Asp Ile Ser Ser Ile Met Val Arg Leu Ile Ser Arg Ile Ser
195 200 205

Ala Arg Val Phe Leu Gly Pro Glu His Cys Arg Asn Gln Glu Trp Leu
210 215 220

Thr Thr Thr Ala Glu Tyr Ser Glu Ser Leu Phe Ile Thr Gly Phe Ile
225 230 235 240

Leu Arg Val Val Pro His Ile Leu Arg Pro Phe Ile Ala Pro Leu Leu
245 250 255

Pro Ser Tyr Arg Thr Leu Leu Arg Asn Val Ser Ser Gly Arg Arg Val
260 265 270

Ile Gly Asp Ile Ile Arg Ser Gln Gln Gly Asp Gly Asn Glu Asp Ile
275 280 285

Leu Ser Trp Met Arg Asp Ala Ala Thr Gly Glu Glu Lys Gln Ile Asp
290 295 300

Asn Ile Ala Gln Arg Met Leu Ile Leu Ser Leu Ala Ser Ile His Thr
305 310 315 320

Thr Ala Met Thr Met Thr His Ala Met Tyr Asp Leu Cys Ala Cys Pro
325 330 335

Glu Tyr Ile Glu Pro Leu Arg Asp Glu Val Lys Ser Val Val Gly Ala
340 345 350

Ser Gly Trp Asp Lys Thr Ala Leu Asn Arg Phe His Lys Leu Asp Ser
355 360 365

Phe Leu Lys Glu Ser Gln Arg Phe Asn Pro Val Phe Leu Leu Thr Phe
370 375 380

Asn Arg Ile Tyr His Gln Ser Met Thr Leu Ser Asp Gly Thr Asn Ile
385 390 395 400

Pro Ser Gly Thr Arg Ile Ala Val Pro Ser His Ala Met Leu Gln Asp
405 410 415

Ser Ala His Val Pro Gly Pro Thr Pro Pro Thr Glu Phe Asp Gly Phe
420 425 430

Arg Tyr Ser Lys Ile Arg Ser Asp Ser Asn Tyr Ala Gln Lys Tyr Leu
435 440 445

Phe Ser Met Thr Asp Ser Ser Asn Met Ala Phe Gly Tyr Gly Lys Tyr
450 455 460

Ala Cys Pro Gly Arg Phe Tyr Ala Ser Asn Glu Met Lys Leu Thr Leu
465 470 475 480

Ala Ile Leu Leu Leu Gln Phe Glu Phe Lys Leu Pro Asp Gly Lys Gly
485 490 495

Arg Pro Arg Asn Ile Thr Ile Asp Ser Asp Met Ile Pro Asp Pro Arg
500 505 510

Ala Arg Leu Cys Val Arg Lys Arg Ser Leu Arg Asp Glu
515 520 525

<210> SEQ ID NO 73
<211> LENGTH: 1515
<212> TYPE: DNA
<213> ORGANISM: Artificial Sequence
<220> FEATURE:
<223> OTHER INFORMATION: Codon-optimized KO

<400> SEQUENCE: 73
aagcttaaaa tggaagatcc tactgtctta tatgcttgtc ttgccattgc agttgcaact 60
ttcgttgtta gatggtacag agatccattg agatccatcc caacagttgg tggttccgat 120
ttgcctattc tatcttacat cggcgcacta agatggacaa gacgtggcag agagatactt 180
caagagggat atgatggcta cagaggatct acattcaaaa tcgcgatgtt agaccgttgg 240
atcgtgatcg caaatggtcc taaactagct gatgaagtca gacgtagacc agatgaagag 300
ttaaacttta tggacggatt aggagcattc gtccaaacta agtacacctt aggtgaagct 360
attcataacg atccatacca tgtcgatatc ataagagaaa aactaacaag aggccttcca 420
gccgtgcttc ctgatgtcat tgaagagttg acacttgcgg ttagacagta cattccaaca 480
gaaggtgatg aatgggtgtc cgtaaactgt tcaaaggccg caagagatat tgttgctaga 540
gcttctaata gagtctttgt aggtttgcct gcttgcagaa accaaggtta cttagatttg 600
gcaatagact ttacattgtc tgttgtcaag gatagagcca tcatcaatat gtttccagaa 660
ttgttgaagc caatagttgg cagagttgta ggtaacgcca ccagaaatgt tcgtagagct 720
gttccttttg ttgctccatt ggtggaggaa agacgtagac ttatggaaga gtacggtgaa 780
gactggtctg aaaaacctaa tgatatgtta cagtggataa tggatgaagc tgcatccaga 840
gatagttcag tgaaggcaat cgcagagaga ttgttaatgg tgaacttcgc ggctattcat 900
acctcatcaa acactatcac tcatgctttg taccaccttg ccgaaatgcc tgaaactttg 960
caaccactta gagaagagat cgaaccatta gtcaaagagg agggctggac caaggctgct 1020
atgggaaaaa tgtggtggtt agattcattt ctaagagaat ctcaaagata caatggcatt 1080
aacatcgtat ctttaactag aatggctgac aaagatatta cattgagtga tggcacattt 1140
ttgccaaaag gtactctagt ggccgttcca gcgtattcta ctcatagaga tgatgctgtc 1200
tacgctgatg ccttagtatt cgatcctttc agattctcac gtatgagagc gagagaaggt 1260
gaaggtacaa agcaccagtt cgttaatact tcagtcgagt acgttccatt tggtcacgga 1320
aagcatgctt gtccaggaag attcttcgcc gcaaacgaat tgaaagcaat gttggcttac 1380
attgttctaa actatgatgt aaagttgcct ggtgacggta aacgtccatt gaacatgtat 1440
tggggtccaa cagttttgcc tgcaccagca ggccaagtat tgttcagaaa gagacaagtt 1500
agtctataac cgcgg 1515

<210> SEQ ID NO 74
<211> LENGTH: 499
<212> TYPE: PRT
<213> ORGANISM: Trametes versicolor

<400> SEQUENCE: 74

Met Glu Asp Pro Thr Val Leu Tyr Ala Cys Leu Ala Ile Ala Val Ala
1 5 10 15

Thr Phe Val Val Arg Trp Tyr Arg Asp Pro Leu Arg Ser Ile Pro Thr
20 25 30

Val Gly Gly Ser Asp Leu Pro Ile Leu Ser Tyr Ile Gly Ala Leu Arg
35 40 45

Trp Thr Arg Arg Gly Arg Glu Ile Leu Gln Glu Gly Tyr Asp Gly Tyr
50 55 60

Arg Gly Ser Thr Phe Lys Ile Ala Met Leu Asp Arg Trp Ile Val Ile
65 70 75 80

Ala Asn Gly Pro Lys Leu Ala Asp Glu Val Arg Arg Arg Pro Asp Glu
85 90 95

Glu Leu Asn Phe Met Asp Gly Leu Gly Ala Phe Val Gln Thr Lys Tyr
100 105 110

Thr Leu Gly Glu Ala Ile His Asn Asp Pro Tyr His Val Asp Ile Ile
115 120 125

Arg Glu Lys Leu Thr Arg Gly Leu Pro Ala Val Leu Pro Asp Val Ile
130 135 140

Glu Glu Leu Thr Leu Ala Val Arg Gln Tyr Ile Pro Thr Glu Gly Asp
145 150 155 160

Glu Trp Val Ser Val Asn Cys Ser Lys Ala Ala Arg Asp Ile Val Ala
165 170 175

Arg Ala Ser Asn Arg Val Phe Val Gly Leu Pro Ala Cys Arg Asn Gln
180 185 190

Gly Tyr Leu Asp Leu Ala Ile Asp Phe Thr Leu Ser Val Val Lys Asp
195 200 205

Arg Ala Ile Ile Asn Met Phe Pro Glu Leu Leu Lys Pro Ile Val Gly
210 215 220

Arg Val Val Gly Asn Ala Thr Arg Asn Val Arg Arg Ala Val Pro Phe
225 230 235 240

Val Ala Pro Leu Val Glu Glu Arg Arg Arg Leu Met Glu Glu Tyr Gly
245 250 255

Glu Asp Trp Ser Glu Lys Pro Asn Asp Met Leu Gln Trp Ile Met Asp
260 265 270

Glu Ala Ala Ser Arg Asp Ser Ser Val Lys Ala Ile Ala Glu Arg Leu
275 280 285

Leu Met Val Asn Phe Ala Ala Ile His Thr Ser Ser Asn Thr Ile Thr
290 295 300

His Ala Leu Tyr His Leu Ala Glu Met Pro Glu Thr Leu Gln Pro Leu
305 310 315 320

Arg Glu Glu Ile Glu Pro Leu Val Lys Glu Glu Gly Trp Thr Lys Ala
325 330 335

Ala Met Gly Lys Met Trp Trp Leu Asp Ser Phe Leu Arg Glu Ser Gln
340 345 350

Arg Tyr Asn Gly Ile Asn Ile Val Ser Leu Thr Arg Met Ala Asp Lys
355 360 365

Asp Ile Thr Leu Ser Asp Gly Thr Phe Leu Pro Lys Gly Thr Leu Val
370 375 380

Ala Val Pro Ala Tyr Ser Thr His Arg Asp Asp Ala Val Tyr Ala Asp
385 390 395 400

Ala Leu Val Phe Asp Pro Phe Arg Phe Ser Arg Met Arg Ala Arg Glu
405 410 415

Gly Glu Gly Thr Lys His Gln Phe Val Asn Thr Ser Val Glu Tyr Val
420 425 430

Pro Phe Gly His Gly Lys His Ala Cys Pro Gly Arg Phe Phe Ala Ala
435 440 445

Asn Glu Leu Lys Ala Met Leu Ala Tyr Ile Val Leu Asn Tyr Asp Val
450 455 460

Lys Leu Pro Gly Asp Gly Lys Arg Pro Leu Asn Met Tyr Trp Gly Pro
465 470 475 480

Thr Val Leu Pro Ala Pro Ala Gly Gln Val Leu Phe Arg Lys Arg Gln
485 490 495

Val Ser Leu

<210> SEQ ID NO 75
<211> LENGTH: 1530
<212> TYPE: DNA
<213> ORGANISM: Artificial Sequence
<220> FEATURE:
<223> OTHER INFORMATION: Codon-optimized KO

<400> SEQUENCE: 75
atggcatttt tctctatgat ttcaattttg ttgggatttg ttatttcttc tttcatcttc 60
atctttttct tcaaaaagtt acttagtttt agtaggaaaa acatgtcaga agtttctact 120
ttgccaagtg ttccagtagt gcctggtttt ccagttattg ggaatttgtt gcaactaaag 180
gagaaaaagc ctcataaaac tttcactaga tggtcagaga tatatggacc tatctactct 240
ataaagatgg gttcttcatc tcttattgta ttgaacagta cagaaactgc taaggaagca 300
atggtcacta gattttcatc aatatctacc agaaaattgt caaacgccct aacagttcta 360
acctgcgata agtctatggt cgccacttct gattatgatg acttccacaa attagttaag 420
agatgtttgc taaatggact tcttggtgct aatgctcaaa agagaaaaag acactacaga 480

```
gatgctttga ttgaaaatgt gagttccaag ctacatgcac acgctagaga tcatccacaa    540
gagccagtta actttagagc aattttcgaa cacgaattgt ttggtgtagc attaaagcaa    600
gccttcggta aagacgtaga atccatatac gtcaaggagt taggcgtaac attatcaaaa    660
gatgaaatct ttaaggtgct tgtacatgat atgatggagg gtgcaattga tgtagattgg    720
agagatttct tcccatattt gaaatggatc cctaataagt cttttgaagc taggatacaa    780
caaaagcaca agagaagact agctgttatg aacgcactta tacaggacag attgaagcaa    840
aatgggtctg aatcagatga tgattgttac cttaacttct taatgtctga ggctaaaaca    900
ttgactaagg aacagatcgc aatccttgtc tgggaaacaa tcattgaaac agcagatact    960
accttagtca caactgaatg ggccatatac gagctagcca aacatccatc tgtgcaagat   1020
aggttgtgta aggagatcca gaacgtgtgt ggtggagaga aattcaagga agagcagttg   1080
tcacaagttc cttaccttaa cggcgttttc catgaaacct tgagaaaata ctcacctgca   1140
ccattagttc ctattagata cgcccacgaa gatacacaaa tcggtggcta ccatgttcca   1200
gctgggtccg aaattgctat aaacatctac gggtgcaaca tggacaaaaa gagatgggaa   1260
agaccagaag attggtggcc agaaagattc ttagatgatg gcaaatatga aacatctgat   1320
ttgcataaaa caatggcttt cggagctggc aaaagagtgt gtgccggtgc tctacaagcc   1380
tccctaatgg ctggtatcgc tattggtaga ttggtccaag agttcgaatg gaaacttaga   1440
gatggtgaag aggaaaatgt cgatacttat gggttaacat ctcaaaagtt atacccacta   1500
atggcaatca tcaatcctag aagatcctaa                                    1530
```

<210> SEQ ID NO 76
<211> LENGTH: 509
<212> TYPE: PRT
<213> ORGANISM: Arabidopsis thaliana

<400> SEQUENCE: 76

```
Met Ala Phe Phe Ser Met Ile Ser Ile Leu Leu Gly Phe Val Ile Ser
1               5                   10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190
```

Leu Phe Gly Val Ala Leu Lys Gln Ala Phe Gly Lys Asp Val Glu Ser
195 200 205

Ile Tyr Val Lys Glu Leu Gly Val Thr Leu Ser Lys Asp Glu Ile Phe
210 215 220

Lys Val Leu Val His Asp Met Met Glu Gly Ala Ile Asp Val Asp Trp
225 230 235 240

Arg Asp Phe Phe Pro Tyr Leu Lys Trp Ile Pro Asn Lys Ser Phe Glu
245 250 255

Ala Arg Ile Gln Gln Lys His Lys Arg Arg Leu Ala Val Met Asn Ala
260 265 270

Leu Ile Gln Asp Arg Leu Lys Gln Asn Gly Ser Glu Ser Asp Asp Asp
275 280 285

Cys Tyr Leu Asn Phe Leu Met Ser Glu Ala Lys Thr Leu Thr Lys Glu
290 295 300

Gln Ile Ala Ile Leu Val Trp Glu Thr Ile Ile Glu Thr Ala Asp Thr
305 310 315 320

Thr Leu Val Thr Thr Glu Trp Ala Ile Tyr Glu Leu Ala Lys His Pro
325 330 335

Ser Val Gln Asp Arg Leu Cys Lys Glu Ile Gln Asn Val Cys Gly Gly
340 345 350

Glu Lys Phe Lys Glu Glu Gln Leu Ser Gln Val Pro Tyr Leu Asn Gly
355 360 365

Val Phe His Glu Thr Leu Arg Lys Tyr Ser Pro Ala Pro Leu Val Pro
370 375 380

Ile Arg Tyr Ala His Glu Asp Thr Gln Ile Gly Gly Tyr His Val Pro
385 390 395 400

Ala Gly Ser Glu Ile Ala Ile Asn Ile Tyr Gly Cys Asn Met Asp Lys
405 410 415

Lys Arg Trp Glu Arg Pro Glu Asp Trp Trp Pro Glu Arg Phe Leu Asp
420 425 430

Asp Gly Lys Tyr Glu Thr Ser Asp Leu His Lys Thr Met Ala Phe Gly
435 440 445

Ala Gly Lys Arg Val Cys Ala Gly Ala Leu Gln Ala Ser Leu Met Ala
450 455 460

Gly Ile Ala Ile Gly Arg Leu Val Gln Glu Phe Glu Trp Lys Leu Arg
465 470 475 480

Asp Gly Glu Glu Glu Asn Val Asp Thr Tyr Gly Leu Thr Ser Gln Lys
485 490 495

Leu Tyr Pro Leu Met Ala Ile Ile Asn Pro Arg Arg Ser
500 505

<210> SEQ ID NO 77
<211> LENGTH: 2133
<212> TYPE: DNA
<213> ORGANISM: Artificial Sequence
<220> FEATURE:
<223> OTHER INFORMATION: Codon-optimized CPR

<400> SEQUENCE: 77
atgcaatcag attcagtcaa agtctctcca tttgatttgg tttccgctgc tatgaatggc 60
aaggcaatgg aaaagttgaa cgctagtgaa tctgaagatc caacaacatt gcctgcacta 120
aagatgctag ttgaaaatag agaattgttg acactgttca caacttcctt cgcagttctt 180
attgggtgtc ttgtatttct aatgtggaga cgttcatcct ctaaaaagct ggtacaagat 240

-continued

```
ccagttccac aagttatcgt tgtaaagaag aaagagaagg agtcagaggt tgatgacggg    300

aaaaagaaag tttctatttt ctacggcaca caaacaggaa ctgccgaagg ttttgctaaa    360

gcattagtcg aggaagcaaa agtgagatat gaaaagacct ctttcaaggt tatcgatcta    420

gatgactacg ctgcagatga tgatgaatat gaggaaaaac tgaaaaagga atccttagcc    480

ttcttcttct tggccacata cggtgatggt gaacctactg ataatgctgc taacttctac    540

aagtggttca cagaaggcga cgataaaggt gaatggctga aaaagttaca atacggagta    600

tttggtttag gtaacagaca atatgaacat ttcaacaaga tcgctattgt agttgatgat    660

aaacttactg aaatgggagc caaaagatta gtaccagtag gattagggga tgatgatcag    720

tgtatagaag atgacttcac cgcctggaag gaattggtat ggccagaatt ggatcaactt    780

ttaagggacg aagatgatac ttctgtgact accccataca ctgcagccgt attggagtac    840

agagtggttt accatgataa accagcagac tcatatgctg aagatcaaac ccatacaaac    900

ggtcatgttg ttcatgatgc acagcatcct tcaagatcta atgtggcttt caaaaaggaa    960

ctacacacct ctcaatcaga taggtcttgt actcacttag aattcgatat ttctcacaca   1020

ggactgtctt acgaaactgg cgatcacgtt ggcgtttatt ccgagaactt gtccgaagtt   1080

gtcgatgaag cactaaaact gttagggtta tcaccagaca catacttctc agtccatgct   1140

gataaggagg atgggacacc tatcggtggt gcttcactac caccaccttt tcctccttgc   1200

acattgagag acgctctaac cagatacgca gatgtcttat cctcacctaa aaaggtagct   1260

ttgctggcat tggctgctca tgctagtgat cctagtgaag ccgataggtt aaagttcctg   1320

gcttcaccag ccggaaaaga tgaatatgca caatggatcg tcgccaacca acgttctttg   1380

ctagaagtga tgcaaagttt tccatctgcc aagcctccat taggtgtgtt cttcgcagca   1440

gtagctccac gtttacaacc aagatactac tctatcagtt catctcctaa gatgtctcct   1500

aacagaatac atgttacatg tgctttggtg tacgagacta ctccagcagg cagaattcac   1560

agaggattgt gttcaacctg gatgaaaaat gctgtccctt taacagagtc acctgattgc   1620

tctcaagcat ccattttcgt tagaacatca aatttcagac ttccagtgga tccaaaagtt   1680

ccagtcatta tgataggacc aggcactggt cttgccccat tcaggggctt tcttcaagag   1740

agattggcct tgaaggaatc tggtacagaa ttgggttctt ctatcttttt ctttggttgc   1800

cgtaatagaa aagttgactt tatctacgag gacgagctta acaattttgt tgagacagga   1860

gcattgtcag aattgatcgt cgcattttca agagaaggga ctgccaaaga gtacgttcag   1920

cacaagatga gtcaaaaagc ctccgatata tggaaacttc taagtgaagg tgcctatctt   1980

tatgtctgtg gcgatgcaaa gggcatggcc aaggatgtcc atagaactct gcatacaatt   2040

gttcaggaac aagggagtct ggattcttcc aaggctgaat tgtacgtcaa aaacttacag   2100

atgtctggaa gatacttaag agatgtttgg taa                                 2133
```

<210> SEQ ID NO 78
<211> LENGTH: 710
<212> TYPE: PRT
<213> ORGANISM: Stevia rebaudiana

<400> SEQUENCE: 78

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
```

-continued

```
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Ser Lys Lys Leu Val Gln Asp
65                  70                  75                  80

Pro Val Pro Gln Val Ile Val Val Lys Lys Lys Glu Lys Glu Ser Glu
                85                  90                  95

Val Asp Asp Gly Lys Lys Lys Val Ser Ile Phe Tyr Gly Thr Gln Thr
            100                 105                 110

Gly Thr Ala Glu Gly Phe Ala Lys Ala Leu Val Glu Glu Ala Lys Val
        115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
            260                 265                 270

Tyr Thr Ala Ala Val Leu Glu Tyr Arg Val Val Tyr His Asp Lys Pro
        275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp
    370                 375                 380

Gly Thr Pro Ile Gly Gly Ala Ser Leu Pro Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460
```

```
Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710
```

<210> SEQ ID NO 79
<211> LENGTH: 2106
<212> TYPE: DNA
<213> ORGANISM: Siraitia grosvenorii

<400> SEQUENCE: 79

```
atgaaggtca gtccattcga attcatgtcc gctattatca agggtagaat ggacccatct      60

aactcctcat ttgaatctac tggtgaagtt gcctccgtta tctttgaaaa cagagaattg     120

gttgccatct tgaccacttc tattgctgtt atgattggtt gcttcgttgt cttgatgtgg     180

agaagagctg gttctagaaa ggttaagaat gtcgaattgc caaagccatt gattgtccat     240

gaaccagaac ctgaagttga agatggtaag aagaaggttt ccatcttctt cggtactcaa     300

actggtactg ctgaaggttt tgctaaggct ttggctgatg aagctaaagc tagatacgaa     360

aaggctacct tcagagttgt tgatttggat gattatgctg ccgatgatga ccaatacgaa     420

gaaaaattga agaacgaatc cttcgccgtt ttcttgttgg ctacttatgg tgatggtgaa     480

cctactgata atgctgctag attttacaag tggttcgccg aaggtaaaga aagaggtgaa     540

tggttgcaaa acttgcacta tgctgttttt ggtttgggta acagacaata cgaacacttc     600

aacaagattg ctaaggttgc cgacgaatta ttggaagctc aaggtggtaa tagattggtt     660
```

-continued

```
aaggttggtt taggtgatga cgatcaatgc atcgaagatg atttttctgc ttggagagaa     720

tctttgtggc cagaattgga tatgttgttg agagatgaag atgatgctac tactgttact     780

actccatata ctgctgctgt cttggaatac agagttgtct ttcatgattc tgctgatgtt     840

gctgctgaag ataagtcttg gattaacgct aatggtcatg ctgttcatga tgctcaacat     900

ccattcagat ctaacgttgt cgtcagaaaa gaattgcata cttctgcctc tgatagatcc     960

tgttctcatt tggaattcaa catttccggt tccgctttga attacgaaac tggtgatcat    1020

gttggtgtct actgtgaaaa cttgactgaa actgttgatg aagccttgaa cttgttgggt    1080

ttgtctccag aaacttactt ctctatctac accgataacg aagatggtac tccattgggt    1140

ggttcttcat tgccaccacc atttccatca tgtactttga gaactgcttt gaccagatac    1200

gctgatttgt tgaactctcc aaaaaagtct gctttgttgg ctttagctgc tcatgcttct    1260

aatccagttg aagctgatag attgagatac ttggcttctc cagctggtaa agatgaatat    1320

gcccaatctg ttatcggttc ccaaaagtct ttgttggaag ttatggctga attcccatct    1380

gctaaaccac cattaggtgt ttttttgct gctgttgctc caagattgca acctagattc    1440

tactccattt catcctctcc aagaatggct ccatctagaa tccatgttac ttgtgctttg    1500

gtttacgata agatgccaac tggtagaatt cataagggtg tttgttctac ctggatgaag    1560

aattctgttc caatggaaaa gtcccatgaa tgttcttggg ctccaatttt cgttagacaa    1620

tccaatttta agttgccagc cgaatccaag gttccaatta tcatggttgg tccaggtact    1680

ggtttggctc cttttagagg ttttttacaa gaaagattgg ccttgaaaga atccggtgtt    1740

gaattgggtc catccatttt gtttttcggt tgcagaaaca gaagaatgga ttacatctac    1800

gaagatgaat tgaacaactt cgttgaaacc ggtgctttgt ccgaattggt tattgctttt    1860

tctagagaag gtcctaccaa agaatacgtc caacataaga tggctgaaaa ggcttctgat    1920

atctggaact tgatttctga aggtgcttac ttgtacgttt gtggtgatgc taaaggtatg    1980

gctaaggatg ttcatagaac cttgcatacc atcatgcaag aacaaggttc tttggattct    2040

tccaaagctg aatccatggt caagaacttg caaatgaatg gtagatactt aagagatgtt    2100

tggtaa                                                               2106
```

<210> SEQ ID NO 80
<211> LENGTH: 701
<212> TYPE: PRT
<213> ORGANISM: Siraitia grosvenorii

<400> SEQUENCE: 80

```
Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Lys Val Ser Ile Phe
                85                  90                  95

Phe Gly Thr Gln Thr Gly Thr Ala Glu Gly Phe Ala Lys Ala Leu Ala
            100                 105                 110
```

```
Asp Glu Ala Lys Ala Arg Tyr Glu Lys Ala Thr Phe Arg Val Val Asp
        115                 120                 125

Leu Asp Asp Tyr Ala Ala Asp Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300

Asn Val Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
        435                 440                 445

Lys Ser Leu Leu Glu Val Met Ala Glu Phe Pro Ser Ala Lys Pro Pro
    450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
                485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
        515                 520                 525

His Glu Cys Ser Trp Ala Pro Ile Phe Val Arg Gln Ser Asn Phe Lys
```

-continued

```
    530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
        595                 600                 605

Glu Thr Gly Ala Leu Ser Glu Leu Val Ile Ala Phe Ser Arg Glu Gly
    610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
            660                 665                 670

Gln Glu Gln Gly Ser Leu Asp Ser Ser Lys Ala Glu Ser Met Val Lys
        675                 680                 685

Asn Leu Gln Met Asn Gly Arg Tyr Leu Arg Asp Val Trp
    690                 695                 700


<210> SEQ ID NO 81
<211> LENGTH: 2142
<212> TYPE: DNA
<213> ORGANISM: Artificial Sequence
<220> FEATURE:
<223> OTHER INFORMATION: Codon-optimized CPR

<400> SEQUENCE: 81

atggcagaat tagatacact tgatatagta gtattaggtg ttatcttttt gggtactgtg      60

gcatacttta ctaagggtaa attgtggggt gttaccaagg atccatacgc taacggattc     120

gctgcaggtg gtgcttccaa gcctggcaga actagaaaca tcgtcgaagc tatggaggaa     180

tcaggtaaaa actgtgttgt tttctacggc agtcaaacag gtacagcgga ggattacgca     240

tcaagacttg caaaggaagg aaagtccaga ttcggtttga acactatgat cgccgatcta     300

gaagattatg acttcgataa cttagacact gttccatctg ataacatcgt tatgtttgta     360

ttggctactt acggtgaagg cgaaccaaca gataacgccg tggatttcta tgagttcatt     420

actggcgaag atgcctcttt caatgagggc aacgatcctc cactaggtaa cttgaattac     480

gttgcgttcg gtctgggcaa caatacctac gaacactaca actcaatggt caggaacgtt     540

aacaaggctc tagaaaagtt aggagctcat agaattggag aagcaggtga gggtgacgac     600

ggagctggaa ctatggaaga ggactttta gcttggaaag atccaatgtg ggaagccttg     660

gctaaaaaga tgggcttgga ggaaagagaa gctgtatatg aacctatttt cgctatcaat     720

gagagagatg atttgacccc tgaagcgaat gaggtatact tgggagaacc taataagcta     780

cacttggaag gtacagcgaa aggtccattc aactcccaca acccatatat cgcaccaatt     840

gcagaatcat acgaactttt ctcagctaag gatagaaatt gtctgcatat ggaaattgat     900

atttctggta gtaatctaaa gtatgaaaca ggcgaccata tcgcgatctg gcctaccaac     960

ccaggtgaag aggtcaacaa atttcttgac attctagatc tgtctggtaa gcaacattcc    1020

gtcgtaacag tgaaagcctt agaacctaca gccaaagttc cttttccaaa tccaactacc    1080

tacgatgcta tattgagata ccatctggaa atatgcgctc cagtttctag acagtttgtc    1140
```

```
tcaactttag cagcattcgc ccctaatgat gatatcaaag ctgagatgaa ccgtttggga   1200

tcagacaaag attacttcca cgaaaagaca ggaccacatt actacaatat cgctagattt   1260

ttggcctcag tctctaaagg tgaaaaatgg acaaagatac cattttctgc tttcatagaa   1320

ggccttacaa aactacaacc aagatactat tctatctctt cctctagttt agttcagcct   1380

aaaaagatta gtattactgc tgttgtcgaa tctcagcaaa ttccaggtag agatgaccca   1440

ttcagaggtg tagcgactaa ctacttgttc gctttgaagc agaaacaaaa cggtgatcca   1500

aatccagctc cttttggcca atcatacgag ttgacaggac caaggaataa gtatgatggt   1560

atacatgttc cagtccatgt aagacattct aactttaagc taccatctga tccaggcaaa   1620

cctattatca tgatcggtcc aggtaccggt gttgcccctt ttagaggctt cgtccaagag   1680

agggcaaaac aagccagaga tggtgtagaa gttggtaaaa cactgctgtt ctttggatgt   1740

agaaagagta cagaagattt catgtatcaa aaagagtggc aagagtacaa ggaagctctt   1800

ggcgacaaat tcgaaatgat tacagctttt tcaagagaag gatctaaaaa ggtttatgtt   1860

caacacagac tgaaggaaag atcaaaggaa gtttctgatc ttctatccca aaaagcatac   1920

ttctacgttt gcggagacgc cgcacatatg gcacgtgaag tgaacactgt gttagcacag   1980

atcatagcag aaggccgtgg tgtatcagaa gccaagggtg aggaaattgt caaaaacatg   2040

agatcagcaa atcaatacca agtgtgttct gatttcgtaa ctttacactg taaagagaca   2100

acatacgcga attcagaatt gcaagaggat gtctggagtt aa                      2142
```

```
<210> SEQ ID NO 82
<211> LENGTH: 713
<212> TYPE: PRT
<213> ORGANISM: Gibberella fujikuroi

<400> SEQUENCE: 82

Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
            20                  25                  30

Lys Asp Pro Tyr Ala Asn Gly Phe Ala Ala Gly Gly Ala Ser Lys Pro
        35                  40                  45

Gly Arg Thr Arg Asn Ile Val Glu Ala Met Glu Glu Ser Gly Lys Asn
    50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190
```

```
Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
    210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
            260                 265                 270

His Asn Pro Tyr Ile Ala Pro Ile Ala Glu Ser Tyr Glu Leu Phe Ser
        275                 280                 285

Ala Lys Asp Arg Asn Cys Leu His Met Glu Ile Asp Ile Ser Gly Ser
    290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
        355                 360                 365

Leu Glu Ile Cys Ala Pro Val Ser Arg Gln Phe Val Ser Thr Leu Ala
    370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
            420                 425                 430

Ile Pro Phe Ser Ala Phe Ile Glu Gly Leu Thr Lys Leu Gln Pro Arg
        435                 440                 445

Tyr Tyr Ser Ile Ser Ser Ser Ser Leu Val Gln Pro Lys Lys Ile Ser
    450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
        595                 600                 605

Ala Phe Ser Arg Glu Gly Ser Lys Lys Val Tyr Val Gln His Arg Leu
```

-continued

```
    610                 615                 620

Lys Glu Arg Ser Lys Glu Val Ser Asp Leu Leu Ser Gln Lys Ala Tyr
625                 630                 635                 640

Phe Tyr Val Cys Gly Asp Ala Ala His Met Ala Arg Glu Val Asn Thr
                645                 650                 655

Val Leu Ala Gln Ile Ile Ala Glu Gly Arg Gly Val Ser Glu Ala Lys
            660                 665                 670

Gly Glu Glu Ile Val Lys Asn Met Arg Ser Ala Asn Gln Tyr Gln Val
        675                 680                 685

Cys Ser Asp Phe Val Thr Leu His Cys Lys Glu Thr Thr Tyr Ala Asn
    690                 695                 700

Ser Glu Leu Gln Glu Asp Val Trp Ser
705                 710


<210> SEQ ID NO 83
<211> LENGTH: 2130
<212> TYPE: DNA
<213> ORGANISM: Stevia rebaudiana

<400> SEQUENCE: 83

atgcaatcgg aatccgttga agcatcgacg attgatttga tgactgctgt tttgaaggac     60

acagtgatcg atacagcgaa cgcatctgat aacggagact caaagatgcc gccggcgttg    120

gcgatgatgt tcgaaattcg tgatctgttg ctgattttga ctacgtcagt tgctgttttg    180

gtcggatgtt tcgttgtttt ggtgtggaag agatcgtccg ggaagaagtc cggcaaggaa    240

ttggagccgc cgaagatcgt tgtgccgaag aggcggctgg agcaggaggt tgatgatggt    300

aagaagaagg ttacgatttt cttcggaaca caaactggaa cggctgaagg tttcgctaag    360

gcacttttcg aagaagcgaa agcgcgatat gaaaaggcag cgtttaaagt gattgatttg    420

gatgattatg ctgctgattt ggatgagtat gcagagaagc tgaagaagga aacatatgct    480

ttcttcttct tggctacata tggagatggt gagccaactg ataatgctgc caaattttat    540

aaatggttta ctgagggaga cgagaaaggc gtttggcttc aaaaacttca atatggagta    600

tttggtcttg gcaacagaca atatgaacat ttcaacaaga ttggaatagt ggttgatgat    660

ggtctcaccg agcagggtgc aaaacgcatt gttcccgttg gtcttggaga cgacgatcaa    720

tcaattgaag acgatttttc ggcatggaaa gagttagtgt ggcccgaatt ggatctattg    780

cttcgcgatg aagatgacaa agctgctgca actccttaca cagctgcaat ccctgaatac    840

cgcgtcgtat ttcatgacaa acccgatgcg ttttctgatg atcatactca aaccaatggt    900

catgctgttc atgatgctca acatccatgc agatccaatg tggctgttaa aaaagagctt    960

catactcctg aatccgatcg ttcatgcaca catcttgaat ttgacatttc tcacactgga   1020

ttatcttatg aaactgggga tcatgttggt gtatactgtg aaaacctaat tgaagtagtg   1080

gaagaagctg ggaaattgtt aggattatca acagatactt atttctcgtt acatattgat   1140

aacgaagatg gttcaccact tggtggacct tcattacaac ctccttttcc tccttgtact   1200

ttaagaaaag cattgactaa ttatgcagat ctgttaagct ctcccaaaaa gtcaactttg   1260

cttgctctag ctgctcatgc ttccgatccc actgaagctg atcgtttaag atttcttgca   1320

tctcgcgagg gcaaggatga atatgctgaa tgggttgttg caaaccaaag aagtcttctt   1380

gaagtcatgg aagctttccc gtcagctaga ccgccacttg gtgttttctt tgcagcggtt   1440

gcaccgcgtt tacagcctcg ttactactct atttcttcct ccccaaagat ggaaccaaac   1500

aggattcatg ttacttgcgc gttggtttat gaaaaaactc ccgcaggtcg tatccacaaa   1560
```

```
ggaatctgct caacctggat gaagaacgct gtacctttga ccgaaagtca agattgcagt   1620

tgggcaccga tttttgttag aacatcaaac ttcagacttc caattgaccc gaaagtcccg   1680

gttatcatga ttggtcctgg aaccgggttg gctccattta ggggttttct tcaagaaaga   1740

ttggctctta aagaatccgg aaccgaactc gggtcatcta ttttattctt cggttgtaga   1800

aaccgcaaag tggattacat atatgagaat gaactcaaca actttgttga aaatggtgcg   1860

ctttctgagc ttgatgttgc tttctcccgc gatggcccga cgaaagaata cgtgcaacat   1920

aaaatgaccc aaaaggcttc tgaaatatgg aatatgcttt ctgagggagc atatttatat   1980

gtatgtggtg atgctaaagg catggctaaa gatgtacacc gtacacttca caccattgtg   2040

caagaacagg gaagtttgga ctcgtctaaa gcggagttgt atgtgaagaa tctacaaatg   2100

tcaggaagat acctccgtga tgtttggtaa                                    2130
```

<210> SEQ ID NO 84
<211> LENGTH: 709
<212> TYPE: PRT
<213> ORGANISM: Stevia rebaudiana

<400> SEQUENCE: 84

```
Met Gln Ser Glu Ser Val Glu Ala Ser Thr Ile Asp Leu Met Thr Ala
1               5                   10                  15

Val Leu Lys Asp Thr Val Ile Asp Thr Ala Asn Ala Ser Asp Asn Gly
            20                  25                  30

Asp Ser Lys Met Pro Pro Ala Leu Ala Met Met Phe Glu Ile Arg Asp
        35                  40                  45

Leu Leu Leu Ile Leu Thr Thr Ser Val Ala Val Leu Val Gly Cys Phe
    50                  55                  60

Val Val Leu Val Trp Lys Arg Ser Ser Gly Lys Lys Ser Gly Lys Glu
65                  70                  75                  80

Leu Glu Pro Pro Lys Ile Val Val Pro Lys Arg Arg Leu Glu Gln Glu
                85                  90                  95

Val Asp Asp Gly Lys Lys Lys Val Thr Ile Phe Phe Gly Thr Gln Thr
            100                 105                 110

Gly Thr Ala Glu Gly Phe Ala Lys Ala Leu Phe Glu Glu Ala Lys Ala
        115                 120                 125

Arg Tyr Glu Lys Ala Ala Phe Lys Val Ile Asp Leu Asp Asp Tyr Ala
    130                 135                 140

Ala Asp Leu Asp Glu Tyr Ala Glu Lys Leu Lys Lys Glu Thr Tyr Ala
145                 150                 155                 160

Phe Phe Phe Leu Ala Thr Tyr Gly Asp Gly Glu Pro Thr Asp Asn Ala
                165                 170                 175

Ala Lys Phe Tyr Lys Trp Phe Thr Glu Gly Asp Glu Lys Gly Val Trp
            180                 185                 190

Leu Gln Lys Leu Gln Tyr Gly Val Phe Gly Leu Gly Asn Arg Gln Tyr
        195                 200                 205

Glu His Phe Asn Lys Ile Gly Ile Val Val Asp Asp Gly Leu Thr Glu
    210                 215                 220

Gln Gly Ala Lys Arg Ile Val Pro Val Gly Leu Gly Asp Asp Asp Gln
225                 230                 235                 240

Ser Ile Glu Asp Asp Phe Ser Ala Trp Lys Glu Leu Val Trp Pro Glu
                245                 250                 255

Leu Asp Leu Leu Leu Arg Asp Glu Asp Asp Lys Ala Ala Ala Thr Pro
            260                 265                 270
```

```
Tyr Thr Ala Ala Ile Pro Glu Tyr Arg Val Val Phe His Asp Lys Pro
        275                 280                 285

Asp Ala Phe Ser Asp Asp His Thr Gln Thr Asn Gly His Ala Val His
    290                 295                 300

Asp Ala Gln His Pro Cys Arg Ser Asn Val Ala Val Lys Lys Glu Leu
305                 310                 315                 320

His Thr Pro Glu Ser Asp Arg Ser Cys Thr His Leu Glu Phe Asp Ile
                325                 330                 335

Ser His Thr Gly Leu Ser Tyr Glu Thr Gly Asp His Val Gly Val Tyr
            340                 345                 350

Cys Glu Asn Leu Ile Glu Val Val Glu Glu Ala Gly Lys Leu Leu Gly
        355                 360                 365

Leu Ser Thr Asp Thr Tyr Phe Ser Leu His Ile Asp Asn Glu Asp Gly
    370                 375                 380

Ser Pro Leu Gly Gly Pro Ser Leu Gln Pro Pro Phe Pro Pro Cys Thr
385                 390                 395                 400

Leu Arg Lys Ala Leu Thr Asn Tyr Ala Asp Leu Leu Ser Ser Pro Lys
                405                 410                 415

Lys Ser Thr Leu Leu Ala Leu Ala Ala His Ala Ser Asp Pro Thr Glu
            420                 425                 430

Ala Asp Arg Leu Arg Phe Leu Ala Ser Arg Glu Gly Lys Asp Glu Tyr
        435                 440                 445

Ala Glu Trp Val Val Ala Asn Gln Arg Ser Leu Leu Glu Val Met Glu
    450                 455                 460

Ala Phe Pro Ser Ala Arg Pro Pro Leu Gly Val Phe Phe Ala Ala Val
465                 470                 475                 480

Ala Pro Arg Leu Gln Pro Arg Tyr Tyr Ser Ile Ser Ser Ser Pro Lys
                485                 490                 495

Met Glu Pro Asn Arg Ile His Val Thr Cys Ala Leu Val Tyr Glu Lys
            500                 505                 510

Thr Pro Ala Gly Arg Ile His Lys Gly Ile Cys Ser Thr Trp Met Lys
        515                 520                 525

Asn Ala Val Pro Leu Thr Glu Ser Gln Asp Cys Ser Trp Ala Pro Ile
    530                 535                 540

Phe Val Arg Thr Ser Asn Phe Arg Leu Pro Ile Asp Pro Lys Val Pro
545                 550                 555                 560

Val Ile Met Ile Gly Pro Gly Thr Gly Leu Ala Pro Phe Arg Gly Phe
                565                 570                 575

Leu Gln Glu Arg Leu Ala Leu Lys Glu Ser Gly Thr Glu Leu Gly Ser
            580                 585                 590

Ser Ile Leu Phe Phe Gly Cys Arg Asn Arg Lys Val Asp Tyr Ile Tyr
        595                 600                 605

Glu Asn Glu Leu Asn Asn Phe Val Glu Asn Gly Ala Leu Ser Glu Leu
    610                 615                 620

Asp Val Ala Phe Ser Arg Asp Gly Pro Thr Lys Glu Tyr Val Gln His
625                 630                 635                 640

Lys Met Thr Gln Lys Ala Ser Glu Ile Trp Asn Met Leu Ser Glu Gly
                645                 650                 655

Ala Tyr Leu Tyr Val Cys Gly Asp Ala Lys Gly Met Ala Lys Asp Val
            660                 665                 670

His Arg Thr Leu His Thr Ile Val Gln Glu Gln Gly Ser Leu Asp Ser
        675                 680                 685
```

```
Ser Lys Ala Glu Leu Tyr Val Lys Asn Leu Gln Met Ser Gly Arg Tyr
    690                 695                 700

Leu Arg Asp Val Trp
705


<210> SEQ ID NO 85
<211> LENGTH: 2124
<212> TYPE: DNA
<213> ORGANISM: Artificial Sequence
<220> FEATURE:
<223> OTHER INFORMATION: Codon-optimized CPR

<400> SEQUENCE: 85

atgcaatcta actccgtgaa gatttcgccg cttgatctgg taactgcgct gtttagcggc     60

aaggttttgg acacatcgaa cgcatcggaa tcgggagaat ctgctatgct gccgactata    120

gcgatgatta tggagaatcg tgagctgttg atgatactca caacgtcggt tgctgtattg    180

atcggatgcg ttgtcgtttt ggtgtggcgg agatcgtcta cgaagaagtc ggcgttggag    240

ccaccggtga ttgtggttcc gaagagagtg caagaggagg aagttgatga tggtaagaag    300

aaagttacgg ttttcttcgg cacccaaact ggaacagctg aaggcttcgc taaggcactt    360

gttgaggaag ctaaagctcg atatgaaaag gctgtcttta aagtaattga tttggatgat    420

tatgctgctg atgacgatga gtatgaggag aaactaaaga aagaatcttt ggcctttttc    480

tttttggcta cgtatggaga tggtgagcca acagataatg ctgccagatt ttataaatgg    540

tttactgagg gagatgcgaa aggagaatgg cttaataagc ttcaatatgg agtatttggt    600

ttgggtaaca gacaatatga acattttaac aagatcgcaa aagtggttga tgatggtctt    660

gtagaacagg gtgcaaagcg tcttgttcct gttggacttg gagatgatga tcaatgtatt    720

gaagatgact tcaccgcatg gaaagagtta gtatggccgg agttggatca attacttcgt    780

gatgaggatg acacaactgt tgctactcca tacacagctg ctgttgcaga atatcgcgtt    840

gtttttcatg aaaaaccaga cgcgctttct gaagattata gttatacaaa tggccatgct    900

gttcatgatg ctcaacatcc atgcagatcc aacgtggctg tcaaaaagga acttcatagt    960

cctgaatctg accggtcttg cactcatctt gaatttgaca tctcgaacac cggactatca   1020

tatgaaactg ggaccatgt tggagtttac tgtgaaaact tgagtgaagt tgtgaatgat   1080

gctgaaagat tagtaggatt accaccagac acttactcct ccatccacac tgatagtgaa   1140

gacgggtcgc cacttggcgg agcctcattg ccgcctcctt tcccgccatg cactttaagg   1200

aaagcattga cgtgttatgc tgatgttttg agttctccca agaagtcggc tttgcttgca   1260

ctagctgctc atgccaccga tcccagtgaa gctgatagat tgaaatttct tgcatccccc   1320

gccggaaagg atgaatattc tcaatggata gttgcaagcc aaagaagtct ccttgaagtc   1380

atggaagcat tcccgtcagc taagccttca cttggtgttt tctttgcatc tgttgccccg   1440

cgcttacaac caagatacta ctctatttct tcctcaccca agatggcacc ggataggatt   1500

catgttacat gtgcattagt ctatgagaaa acacctgcag gccgcatcca caaaggagtt   1560

tgttcaactt ggatgaagaa cgcagtgcct atgaccgaga gtcaagattg cagttgggcc   1620

ccaatatacg tccgaacatc caatttcaga ctaccatctg accctaaggt cccggttatc   1680

atgattggac ctggcactgg tttggctcct tttagaggtt tccttcaaga gcggttagct   1740

ttaaaggaag ccggaactga cctcggttta tccattttat tcttcggatg taggaatcgc   1800

aaagtggatt tcatatatga aaacgagctt aacaactttg tggagactgg tgctctttct   1860

gagcttattg ttgctttctc ccgtgaaggc ccgactaagg aatatgtgca acacaagatg   1920
```

agtgagaagg cttcggatat ctggaacttg ctttctgaag gagcatattt atacgtatgt 1980
ggtgatgcca aaggcatggc caaagatgta catcgaaccc tccacacaat tgtgcaagaa 2040
cagggatctc ttgactcgtc aaaggcagaa ctctacgtga agaatctaca aatgtcagga 2100
agatacctcc gtgacgtttg gtaa 2124

<210> SEQ ID NO 86
<211> LENGTH: 707
<212> TYPE: PRT
<213> ORGANISM: Stevia rebaudiana

<400> SEQUENCE: 86

Met Gln Ser Asn Ser Val Lys Ile Ser Pro Leu Asp Leu Val Thr Ala
1 5 10 15

Leu Phe Ser Gly Lys Val Leu Asp Thr Ser Asn Ala Ser Glu Ser Gly
20 25 30

Glu Ser Ala Met Leu Pro Thr Ile Ala Met Ile Met Glu Asn Arg Glu
35 40 45

Leu Leu Met Ile Leu Thr Thr Ser Val Ala Val Leu Ile Gly Cys Val
50 55 60

Val Val Leu Val Trp Arg Arg Ser Ser Thr Lys Lys Ser Ala Leu Glu
65 70 75 80

Pro Pro Val Ile Val Val Pro Lys Arg Val Gln Glu Glu Glu Val Asp
85 90 95

Asp Gly Lys Lys Lys Val Thr Val Phe Phe Gly Thr Gln Thr Gly Thr
100 105 110

Ala Glu Gly Phe Ala Lys Ala Leu Val Glu Glu Ala Lys Ala Arg Tyr
115 120 125

Glu Lys Ala Val Phe Lys Val Ile Asp Leu Asp Asp Tyr Ala Ala Asp
130 135 140

Asp Asp Glu Tyr Glu Glu Lys Leu Lys Lys Glu Ser Leu Ala Phe Phe
145 150 155 160

Phe Leu Ala Thr Tyr Gly Asp Gly Glu Pro Thr Asp Asn Ala Ala Arg
165 170 175

Phe Tyr Lys Trp Phe Thr Glu Gly Asp Ala Lys Gly Glu Trp Leu Asn
180 185 190

Lys Leu Gln Tyr Gly Val Phe Gly Leu Gly Asn Arg Gln Tyr Glu His
195 200 205

Phe Asn Lys Ile Ala Lys Val Val Asp Asp Gly Leu Val Glu Gln Gly
210 215 220

Ala Lys Arg Leu Val Pro Val Gly Leu Gly Asp Asp Asp Gln Cys Ile
225 230 235 240

Glu Asp Asp Phe Thr Ala Trp Lys Glu Leu Val Trp Pro Glu Leu Asp
245 250 255

Gln Leu Leu Arg Asp Glu Asp Asp Thr Thr Val Ala Thr Pro Tyr Thr
260 265 270

Ala Ala Val Ala Glu Tyr Arg Val Val Phe His Glu Lys Pro Asp Ala
275 280 285

Leu Ser Glu Asp Tyr Ser Tyr Thr Asn Gly His Ala Val His Asp Ala
290 295 300

Gln His Pro Cys Arg Ser Asn Val Ala Val Lys Lys Glu Leu His Ser
305 310 315 320

Pro Glu Ser Asp Arg Ser Cys Thr His Leu Glu Phe Asp Ile Ser Asn
325 330 335

```
Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
        515                 520                 525

Val Pro Met Thr Glu Ser Gln Asp Cys Ser Trp Ala Pro Ile Tyr Val
    530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
            580                 585                 590

Leu Phe Phe Gly Cys Arg Asn Arg Lys Val Asp Phe Ile Tyr Glu Asn
        595                 600                 605

Glu Leu Asn Asn Phe Val Glu Thr Gly Ala Leu Ser Glu Leu Ile Val
    610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
    690                 695                 700

Asp Val Trp
705
```

<210> SEQ ID NO 87
<211> LENGTH: 2070
<212> TYPE: DNA
<213> ORGANISM: Artificial Sequence
<220> FEATURE:

<223> OTHER INFORMATION: Codon-optimized CPR

<400> SEQUENCE: 87
atgtcctcca actccgattt ggtcagaaga ttggaatctg ttttgggtgt ttctttcggt 60
ggttctgtta ctgattccgt tgttgttatt gctaccacct ctattgcttt ggttatcggt 120
gttttggttt tgttgtggag aagatcctct gacagatcta gagaagttaa gcaattggct 180
gttccaaagc cagttactat cgttgaagaa gaagatgaat tcgaagttgc ttctggtaag 240
accagagttt ctattttcta cggtactcaa actggtactg ctgaaggttt tgctaaggct 300
ttggctgaag aaatcaaagc cagatacgaa aaagctgccg ttaaggttat tgatttggat 360
gattacacag ccgaagatga caaatacggt gaaaagttga agaaagaaac tatggccttc 420
ttcatgttgg ctacttatgg tgatggtgaa cctactgata atgctgctag attttacaag 480
tggttcaccg aaggtactga tagaggtgtt tggttggaac atttgagata cggtgtattc 540
ggtttgggta acagacaata cgaacacttc aacaagattg ccaaggttgt tgatgatttg 600
ttggttgaac aaggtgccaa gagattggtt actgttggtt tgggtgatga tgatcaatgc 660
atcgaagatg atttctccgc ttggaaagaa gccttgtggc cagaattgga tcaattattg 720
caagatgata ccaacaccgt ttctactcca tacactgctg ttattccaga atacagagtt 780
gttatccacg atccatctgt tacctcttat gaagatccat actctaacat ggctaacggt 840
aatgcctctt acgatattca tcatccatgt agagctaacg ttgccgtcca aaaagaattg 900
cataagccag aatctgacag aagttgcatc catttggaat tcgatatttt cgctactggt 960
ttgacttacg aaaccggtga tcatgttggt gtttacgctg ataattgtga tgatactgta 1020
gaagaagccg ctaagttgtt gggtcaacca ttggatttgt tgttctccat tcataccgat 1080
aacaacgacg gtacttcttt gggttcttct ttgccaccac catttccagg tccatgtact 1140
ttgagaactg ctttggctag atatgccgat ttgttgaatc caccaaaaaa ggctgctttg 1200
attgctttag ctgctcatgc tgatgaacca tctgaagctg aaagattgaa gttcttgtca 1260
tctccacaag gtaaggacga atattctaaa tgggttgtcg gttcccaaag atccttggtt 1320
gaagttatgg ctgaatttcc atctgctaaa ccaccattgg gtgtattttt tgctgctgtt 1380
gttcctagat tgcaacctag atattactcc atctcttcca gtccaagatt tgctccacat 1440
agagttcatg ttacttgcgc tttggtttat ggtccaactc caactggtag aattcacaga 1500
ggtgtatgtt cattctggat gaagaatgtt gtcccattgg aaaagtctca aaactgttct 1560
tgggccccaa ttttcatcag acaatctaat ttcaagttgc cagccgatca ttctgttcca 1620
atagttatgg ttggtccagg tactggttta gctcctttta gaggtttctt acaagaaaga 1680
ttggccttga aagaagaagg tgctcaagtt ggtcctgctt tgttgttttt tggttgcaga 1740
aacagacaaa tggacttcat ctacgaagtc gaattgaaca actttgtcga acaaggtgct 1800
ttgtccgaat tgatcgttgc tttttcaaga gaaggtccat ccaaagaata cgtccaacat 1860
aagatggttg aaaaggcagc ttacatgtgg aacttgattt ctcaaggtgg ttacttctac 1920
gtttgtggtg atgctaaagg tatggctaga gatgttcata gaacattgca taccatcgtc 1980
caacaagaag aaaaggttga ttctaccaag gccgaatcca tcgttaagaa attgcaaatg 2040
gacggtagat acttgagaga tgtttggtga 2070

<210> SEQ ID NO 88
<211> LENGTH: 689
<212> TYPE: PRT
<213> ORGANISM: Rubus suavissimus

<400> SEQUENCE: 88

Met Ser Ser Asn Ser Asp Leu Val Arg Arg Leu Glu Ser Val Leu Gly
1               5                   10                  15

Val Ser Phe Gly Gly Ser Val Thr Asp Ser Val Val Val Ile Ala Thr
            20                  25                  30

Thr Ser Ile Ala Leu Val Ile Gly Val Leu Val Leu Leu Trp Arg Arg
        35                  40                  45

Ser Ser Asp Arg Ser Arg Glu Val Lys Gln Leu Ala Val Pro Lys Pro
    50                  55                  60

Val Thr Ile Val Glu Glu Glu Asp Glu Phe Glu Val Ala Ser Gly Lys
65                  70                  75                  80

Thr Arg Val Ser Ile Phe Tyr Gly Thr Gln Thr Gly Thr Ala Glu Gly
                85                  90                  95

Phe Ala Lys Ala Leu Ala Glu Glu Ile Lys Ala Arg Tyr Glu Lys Ala
            100                 105                 110

Ala Val Lys Val Ile Asp Leu Asp Asp Tyr Thr Ala Glu Asp Asp Lys
        115                 120                 125

Tyr Gly Glu Lys Leu Lys Lys Glu Thr Met Ala Phe Phe Met Leu Ala
    130                 135                 140

Thr Tyr Gly Asp Gly Glu Pro Thr Asp Asn Ala Ala Arg Phe Tyr Lys
145                 150                 155                 160

Trp Phe Thr Glu Gly Thr Asp Arg Gly Val Trp Leu Glu His Leu Arg
                165                 170                 175

Tyr Gly Val Phe Gly Leu Gly Asn Arg Gln Tyr Glu His Phe Asn Lys
            180                 185                 190

Ile Ala Lys Val Val Asp Asp Leu Leu Val Glu Gln Gly Ala Lys Arg
        195                 200                 205

Leu Val Thr Val Gly Leu Gly Asp Asp Asp Gln Cys Ile Glu Asp Asp
    210                 215                 220

Phe Ser Ala Trp Lys Glu Ala Leu Trp Pro Glu Leu Asp Gln Leu Leu
225                 230                 235                 240

Gln Asp Asp Thr Asn Thr Val Ser Thr Pro Tyr Thr Ala Val Ile Pro
                245                 250                 255

Glu Tyr Arg Val Val Ile His Asp Pro Ser Val Thr Ser Tyr Glu Asp
            260                 265                 270

Pro Tyr Ser Asn Met Ala Asn Gly Asn Ala Ser Tyr Asp Ile His His
        275                 280                 285

Pro Cys Arg Ala Asn Val Ala Val Gln Lys Glu Leu His Lys Pro Glu
    290                 295                 300

Ser Asp Arg Ser Cys Ile His Leu Glu Phe Asp Ile Phe Ala Thr Gly
305                 310                 315                 320

Leu Thr Tyr Glu Thr Gly Asp His Val Gly Val Tyr Ala Asp Asn Cys
                325                 330                 335

Asp Asp Thr Val Glu Glu Ala Ala Lys Leu Leu Gly Gln Pro Leu Asp
            340                 345                 350

Leu Leu Phe Ser Ile His Thr Asp Asn Asn Asp Gly Thr Ser Leu Gly
        355                 360                 365

Ser Ser Leu Pro Pro Pro Phe Pro Gly Pro Cys Thr Leu Arg Thr Ala
    370                 375                 380

Leu Ala Arg Tyr Ala Asp Leu Leu Asn Pro Pro Lys Lys Ala Ala Leu
385                 390                 395                 400

Ile Ala Leu Ala Ala His Ala Asp Glu Pro Ser Glu Ala Glu Arg Leu

-continued

```
                405                 410                 415

Lys Phe Leu Ser Ser Pro Gln Gly Lys Asp Glu Tyr Ser Lys Trp Val
            420                 425                 430

Val Gly Ser Gln Arg Ser Leu Val Glu Val Met Ala Glu Phe Pro Ser
        435                 440                 445

Ala Lys Pro Pro Leu Gly Val Phe Phe Ala Ala Val Val Pro Arg Leu
    450                 455                 460

Gln Pro Arg Tyr Tyr Ser Ile Ser Ser Ser Pro Arg Phe Ala Pro His
465                 470                 475                 480

Arg Val His Val Thr Cys Ala Leu Val Tyr Gly Pro Thr Pro Thr Gly
                485                 490                 495

Arg Ile His Arg Gly Val Cys Ser Phe Trp Met Lys Asn Val Val Pro
            500                 505                 510

Leu Glu Lys Ser Gln Asn Cys Ser Trp Ala Pro Ile Phe Ile Arg Gln
        515                 520                 525

Ser Asn Phe Lys Leu Pro Ala Asp His Ser Val Pro Ile Val Met Val
    530                 535                 540

Gly Pro Gly Thr Gly Leu Ala Pro Phe Arg Gly Phe Leu Gln Glu Arg
545                 550                 555                 560

Leu Ala Leu Lys Glu Glu Gly Ala Gln Val Gly Pro Ala Leu Leu Phe
                565                 570                 575

Phe Gly Cys Arg Asn Arg Gln Met Asp Phe Ile Tyr Glu Val Glu Leu
            580                 585                 590

Asn Asn Phe Val Glu Gln Gly Ala Leu Ser Glu Leu Ile Val Ala Phe
        595                 600                 605

Ser Arg Glu Gly Pro Ser Lys Glu Tyr Val Gln His Lys Met Val Glu
    610                 615                 620

Lys Ala Ala Tyr Met Trp Asn Leu Ile Ser Gln Gly Gly Tyr Phe Tyr
625                 630                 635                 640

Val Cys Gly Asp Ala Lys Gly Met Ala Arg Asp Val His Arg Thr Leu
                645                 650                 655

His Thr Ile Val Gln Gln Glu Glu Lys Val Asp Ser Thr Lys Ala Glu
            660                 665                 670

Ser Ile Val Lys Lys Leu Gln Met Asp Gly Arg Tyr Leu Arg Asp Val
        675                 680                 685

Trp
```

<210> SEQ ID NO 89
<211> LENGTH: 2079
<212> TYPE: DNA
<213> ORGANISM: Artificial Sequence
<220> FEATURE:
<223> OTHER INFORMATION: Codon-optimized CPR

<400> SEQUENCE: 89

```
atgacttctg cactttatgc ctccgatctt ttcaaacaat tgaaaagtat catgggaacg     60

gattctttgt ccgatgatgt tgtattagtt attgctacaa cttctctggc actggttgct    120

ggtttcgttg tcttattgtg gaaaaagacc acggcagatc gttccggcga gctaaagcca    180

ctaatgatcc ctaagtctct gatggcgaaa gatgaggatg atgacttaga tctaggttct    240

ggaaaaacga gagtctctat cttcttcggc acacaaaccg gaacagccga aggattcgct    300

aaagcacttt cagaagagat caaagcaaga tacgaaaagg cggctgtaaa agtaatcgat    360

ttggatgatt acgctgccga tgatgaccaa tatgaggaaa agttgaaaaa ggaaacattg    420
```

```
gctttctttt gtgtagccac gtatggtgat ggtgaaccaa ccgataacgc cgcaagattc    480

tacaagtggt ttactgaaga gaacgaaaga gatatcaagt tgcagcaact tgcttacggc    540

gtttttgcct taggtaacag acaatacgag cactttaaca agataggtat tgtcttagat    600

gaagagttat gcaaaaaggg tgcgaagaga ttgattgaag tcggtttagg agatgatgat    660

caatctatcg aggatgactt taatgcatgg aaggaatctt tgtggtctga attagataag    720

ttacttaagg acgaagatga taaatccgtt gccactccat acacagccgt cattccagaa    780

tatagagtag ttactcatga tccaagattc acaacacaga aatcaatgga aagtaatgtg    840

gctaatggta atactaccat cgatattcat catccatgta gagtagacgt tgcagttcaa    900

aaggaattgc acactcatga atcagacaga tcttgcatac atcttgaatt tgatatatca    960

cgtactggta tcacttacga aacaggtgat cacgtgggtg tctacgctga aaaccatgtt   1020

gaaattgtag aggaagctgg aaagttgttg ggccatagtt tagatcttgt tttctcaatt   1080

catgccgata aagaggatgg ctcaccacta gaaagtgcag tgcctccacc atttccagga   1140

ccatgcaccc taggtaccgg tttagctcgt tacgcggatc tgttaaatcc tccacgtaaa   1200

tcagctctag tggccttggc tgcgtacgcc acagaacctt ctgaggcaga aaaactgaaa   1260

catctaactt caccagatgg taaggatgaa tactcacaat ggatagtagc tagtcaacgt   1320

tctttactag aagttatggc tgctttccca tccgctaaac ctcctttggg tgttttcttc   1380

gccgcaatag cgcctagact gcaaccaaga tactattcaa tttcatcctc acctagactg   1440

gcaccatcaa gagttcatgt cacatccgct ttagtgtacg gtccaactcc tactggtaga   1500

atccataagg gcgtttgttc aacatggatg aaaaacgcgg ttccagcaga gaagtctcac   1560

gaatgttctg gtgctccaat ctttatcaga gcctccaact tcaaactgcc ttccaatcct   1620

tctactccta ttgtcatggt cggtcctggt acaggtcttg ctccattcag aggtttctta   1680

caagagagaa tggccttaaa ggaggatggt gaagagttgg gatcttcttt gttgtttttc   1740

ggctgtagaa acagacaaat ggatttcatc tacgaagatg aactgaataa ctttgtagat   1800

caaggagtta tttcagagtt gataatggct ttttctagag aaggtgctca gaaggagtac   1860

gtccaacaca aaatgatgga aaaggccgca caagtttggg acttaatcaa agaggaaggc   1920

tatctatatg tctgtggtga tgcaaagggt atggcaagag atgttcacag aacacttcat   1980

actatagtcc aggaacagga aggcgttagt tcttctgaag cggaagcaat tgtgaaaaag   2040

ttacaaacag agggaagata cttgagagat gtgtggtaa                          2079
```

<210> SEQ ID NO 90
<211> LENGTH: 692
<212> TYPE: PRT
<213> ORGANISM: Arabidopsis thaliana

<400> SEQUENCE: 90

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Asp Leu Asp Leu Gly Ser
65                  70                  75                  80
```

-continued

```
Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Ser Pro Arg Leu
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
```

```
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690
```

<210> SEQ ID NO 91
<211> LENGTH: 2139
<212> TYPE: DNA
<213> ORGANISM: Artificial Sequence
<220> FEATURE:
<223> OTHER INFORMATION: Codon-optimized CPR

<400> SEQUENCE: 91

```
atgtcttcct cttcctcttc cagtacctct atgattgatt tgatggctgc tattattaaa     60

ggtgaaccag ttatcgtctc cgacccagca aatgcctctg cttatgaatc agttgctgca    120

gaattgtctt caatgttgat cgaaaacaga caattcgcca tgatcgtaac tacatcaatc    180

gctgttttga tcggttgtat tgtcatgttg gtatggagaa gatccggtag tggtaattct    240

aaaagagtcg aacctttgaa accattagta attaagccaa gagaagaaga aatagatgac    300

ggtagaaaga aagttacaat atttttcggt acccaaactg gtacagctga aggttttgca    360

aaagccttag gtgaagaagc taaggcaaga tacgaaaaga ctagattcaa gatagtcgat    420

ttggatgact atgccgctga tgacgatgaa tacgaagaaa agttgaagaa agaagatgtt    480

gcatttttct tttggcaac ctatggtgac ggtgaaccaa ctgacaatgc agccagattc    540

tacaaatggt ttacagaggg taatgatcgt ggtgaatggt tgaaaaactt aaagtacggt    600

gttttcggtt tgggtaacag acaatacgaa catttcaaca aagttgcaaa ggttgtcgac    660

gatattttgg tcgaacaagg tgctcaaaga ttagtccaag taggtttggg tgacgatgac    720

caatgtatag aagatgactt tactgcctgg agagaagctt tgtggcctga attagacaca    780

atcttgagag aagaaggtga caccgccgtt gctaccccat atactgctgc agtattagaa    840

tacagagttt ccatccatga tagtgaagac gcaaagttta atgatatcac tttggccaat    900

ggtaacggtt atacagtttt cgatgcacaa caccttaca aagctaacgt tgcagtcaag     960
```

```
agagaattac atacaccaga atccgacaga agttgtatac acttggaatt tgatatcgct   1020
ggttccggtt taaccatgaa gttgggtgac catgtaggtg ttttatgcga caatttgtct   1080
gaaactgttg atgaagcatt gagattgttg gatatgtccc ctgacactta ttttagtttg   1140
cacgctgaaa aagaagatgg tacaccaatt tccagttctt taccacctcc attccctcca   1200
tgtaacttaa gaacagcctt gaccagatac gcttgcttgt tatcatcccc taaaaagtcc   1260
gccttggttg ctttagccgc tcatgctagt gatcctactg aagcagaaag attgaaacac   1320
ttagcatctc cagccggtaa agatgaatat tcaaagtggg tagttgaatc tcaaagatca   1380
ttgttagaag ttatggcaga atttccatct gccaagcctc cattaggtgt cttctttgct   1440
ggtgtagcac ctagattgca accaagattc tactcaatca gttcttcacc taagatcgct   1500
gaaactagaa ttcatgttac atgtgcatta gtctacgaaa agatgccaac cggtagaatt   1560
cacaagggtg tatgctctac ttggatgaaa aatgctgttc cttacgaaaa atcagaaaag   1620
ttgttcttag gtagaccaat cttcgtaaga caatcaaact tcaagttgcc ttctgattca   1680
aaggttccaa taatcatgat aggtcctggt acaggtttag ccccattcag aggtttcttg   1740
caagaaagat tggctttagt tgaatctggt gtcgaattag gtccttcagt tttgttcttt   1800
ggttgtagaa acagaagaat ggatttcatc tatgaagaag aattgcaaag attcgtcgaa   1860
tctggtgcat tggccgaatt atctgtagct tttcaagag aaggtccaac taaggaatac   1920
gttcaacata agatgatgga taaggcatcc gacatatgga acatgatcag tcaaggtgct   1980
tatttgtacg tttgcggtga cgcaaagggt atggccagag atgtccatag atctttgcac   2040
acaattgctc aagaacaagg ttccatggat agtaccaaag ctgaaggttt cgtaaagaac   2100
ttacaaactt ccggtagata cttgagagat gtctggtga                          2139
```

<210> SEQ ID NO 92
<211> LENGTH: 712
<212> TYPE: PRT
<213> ORGANISM: Arabidopsis thaliana

<400> SEQUENCE: 92

```
Met Ser Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160
```

```
Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Lys Leu Phe Leu Gly
    530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
```

-continued

```
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710
```

<210> SEQ ID NO 93
<211> LENGTH: 1503
<212> TYPE: DNA
<213> ORGANISM: Artificial Sequence
<220> FEATURE:
<223> OTHER INFORMATION: Codon-optimized KAH

<400> SEQUENCE: 93

```
atggaagcct cttacctata catttctatt ttgcttttac tggcatcata cctgttcacc     60
actcaactta gaaggaagag cgctaatcta ccaccaaccg tgtttccatc aataccaatc    120
attggacact tatacttact caaaaagcct ctttatagaa ctttagcaaa aattgccgct    180
aagtacggac caatactgca attacaactc ggctacagac gtgttctggt gatttcctca    240
ccatcagcag cagaagagtg ctttaccaat aacgatgtaa tcttcgcaaa tagacctaag    300
acattgtttg gcaaaatagt gggtggaaca tcccttggca gtttatccta cggcgatcaa    360
tggcgtaatc taaggagagt agcttctatc gaaatcctat cagttcatag gttgaacgaa    420
tttcatgata tcagagtgga tgagaacaga ttgttaatta gaaaacttag aagttcatct    480
tctcctgtta ctcttataac agtcttttat gctctaacat tgaacgtcat tatgagaatg    540
atctctggca aaagatattt cgacagtggg gatagagaat tggaggagga aggtaagaga    600
tttcgagaaa tcttagacga aacgttgctt ctagccggtg cttctaatgt tggcgactac    660
ttaccaatat tgaactggtt gggagttaag tctcttgaaa agaaattgat cgctttgcag    720
aaaaagagag atgacttttt ccagggtttg attgaacagg ttagaaaatc tcgtggtgct    780
aaagtaggca aaggtagaaa aacgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg gtaataacag attgattgac   1020
gagtcagaca ttggaaatat cccttacatc gggtgtatta tcaatgaaac tctaagactc   1080
tatccagcag ggccattgtt gttcccacat gaaagttctg ccgactgcgt tatttccggt   1140
tacaatatac ctagaggtac aatgttaatc gtaaaccaat gggcgattca tcacgatcct   1200
aaagtctggg atgatcctga aacctttaaa cctgaaagat ttcaaggatt agaaggaact   1260
agagatggtt tcaaacttat gccattcggt tctgggagaa gaggatgtcc aggtgaaggt   1320
```

ttggcaataa ggctgttagg gatgacacta ggctcagtga tccaatgttt tgattgggag 1380
agagtaggag atgagatggt tgacatgaca gaaggtttgg gtgtcacact tcctaaggcc 1440
gttccattag ttgccaaatg taagccacgt tccgaaatga ctaatctcct atccgaactt 1500
taa 1503

<210> SEQ ID NO 94
<211> LENGTH: 500
<212> TYPE: PRT
<213> ORGANISM: Stevia rebaudiana

<400> SEQUENCE: 94

Met Glu Ala Ser Tyr Leu Tyr Ile Ser Ile Leu Leu Leu Leu Ala Ser
1 5 10 15

Tyr Leu Phe Thr Thr Gln Leu Arg Arg Lys Ser Ala Asn Leu Pro Pro
20 25 30

Thr Val Phe Pro Ser Ile Pro Ile Ile Gly His Leu Tyr Leu Leu Lys
35 40 45

Lys Pro Leu Tyr Arg Thr Leu Ala Lys Ile Ala Ala Lys Tyr Gly Pro
50 55 60

Ile Leu Gln Leu Gln Leu Gly Tyr Arg Arg Val Leu Val Ile Ser Ser
65 70 75 80

Pro Ser Ala Ala Glu Glu Cys Phe Thr Asn Asn Asp Val Ile Phe Ala
85 90 95

Asn Arg Pro Lys Thr Leu Phe Gly Lys Ile Val Gly Gly Thr Ser Leu
100 105 110

Gly Ser Leu Ser Tyr Gly Asp Gln Trp Arg Asn Leu Arg Arg Val Ala
115 120 125

Ser Ile Glu Ile Leu Ser Val His Arg Leu Asn Glu Phe His Asp Ile
130 135 140

Arg Val Asp Glu Asn Arg Leu Leu Ile Arg Lys Leu Arg Ser Ser Ser
145 150 155 160

Ser Pro Val Thr Leu Ile Thr Val Phe Tyr Ala Leu Thr Leu Asn Val
165 170 175

Ile Met Arg Met Ile Ser Gly Lys Arg Tyr Phe Asp Ser Gly Asp Arg
180 185 190

Glu Leu Glu Glu Glu Gly Lys Arg Phe Arg Glu Ile Leu Asp Glu Thr
195 200 205

Leu Leu Leu Ala Gly Ala Ser Asn Val Gly Asp Tyr Leu Pro Ile Leu
210 215 220

Asn Trp Leu Gly Val Lys Ser Leu Glu Lys Lys Leu Ile Ala Leu Gln
225 230 235 240

Lys Lys Arg Asp Asp Phe Phe Gln Gly Leu Ile Glu Gln Val Arg Lys
245 250 255

Ser Arg Gly Ala Lys Val Gly Lys Gly Arg Lys Thr Met Ile Glu Leu
260 265 270

Leu Leu Ser Leu Gln Glu Ser Glu Pro Glu Tyr Tyr Thr Asp Ala Met
275 280 285

Ile Arg Ser Phe Val Leu Gly Leu Leu Ala Ala Gly Ser Asp Thr Ser
290 295 300

Ala Gly Thr Met Glu Trp Ala Met Ser Leu Leu Val Asn His Pro His
305 310 315 320

Val Leu Lys Lys Ala Gln Ala Glu Ile Asp Arg Val Ile Gly Asn Asn
325 330 335

```
Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
    370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
    450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500
```

<210> SEQ ID NO 95
<211> LENGTH: 1572
<212> TYPE: DNA
<213> ORGANISM: Rubus suavissimus

<400> SEQUENCE: 95

```
atggaagtaa cagtagctag tagtgtagcc ctgagcctgg tctttattag catagtagta     60

agatgggcat ggagtgtggt gaattgggtg tggtttaagc cgaagaagct ggaaagattt    120

ttgagggagc aaggccttaa aggcaattcc tacaggtttt tatatggaga catgaaggag    180

aactctatcc tgctcaaaca agcaagatcc aaacccatga acctctccac ctcccatgac    240

atagcacctc aagtcacccc ttttgtcgac caaaccgtga aagcttacgg taagaactct    300

tttaattggg ttggccccat accaagggtg aacataatga atccagaaga tttgaaggac    360

gtcttaacaa aaaatgttga ctttgttaag ccaatatcaa acccacttat caagttgcta    420

gctacaggta ttgcaatcta tgaaggtgag aaatggacta aacacagaag gattatcaac    480

ccaacattcc attcggagag gctaaagcgt atgttacctt catttcacca aagttgtaat    540

gagatggtca aggaatggga gagcttggtg tcaaaagagg gttcatcatg tgagttggat    600

gtctggcctt ttcttgaaaa tatgtcggca gatgtgatct cgagaacagc atttggaact    660

agctacaaaa aaggacagaa aatctttgaa ctcttgagag agcaagtaat atatgtaacg    720

aaaggctttc aaagttttta cattccagga tggaggtttc tcccaactaa gatgaacaag    780

aggatgaatg agattaacga agaaataaaa ggattaatca ggggtattat aattgacaga    840

gagcaaatca ttaaggcagg tgaagaaacc aacgatgact tattaggtgc acttatggag    900

tcaaacttga aggacattcg ggaacatggg aaaaacaaca aaaatgttgg gatgagtatt    960

gaagatgtaa ttcaggagtg taagctgttt tactttgctg ggcaagaaac cacttcagtg   1020

ttgctggctt ggacaatggt tttacttggt caaaatcaga actggcaaga tcgagcaaga   1080

caagaggttt tgcaagtctt tggaagcagc aagccagatt ttgatggtct agctcacctt   1140
```

aaagtcgtaa ccatgatttt gcttgaagtt cttcgattat acccaccagt cattgaactt 1200
attcgaacca ttcacaagaa aacacaactt gggaagctct cactaccaga aggagttgaa 1260
gtccgcttac caacactgct cattcaccat gacaaggaac tgtggggtga tgatgcaaac 1320
cagttcaatc cagagaggtt ttcggaagga gtttccaaag caacaaagaa ccgactctca 1380
ttcttcccct tcggagccgg tccacgcatt tgcattggac agaacttttc tatgatggaa 1440
gcaaagttgg ccttagcatt gatcttgcaa cacttcacct ttgagctttc tccatctcat 1500
gcacatgctc cttcccatcg tataaccctt caaccacagt atggtgttcg tatcatttta 1560
catcgacgtt ag 1572

<210> SEQ ID NO 96
<211> LENGTH: 1572
<212> TYPE: DNA
<213> ORGANISM: Artificial Sequence
<220> FEATURE:
<223> OTHER INFORMATION: Codon-optimized KAH

<400> SEQUENCE: 96
atggaagtca ctgtcgcctc ttctgtcgct ttatccttag tcttcatttc cattgtcgtc 60
agatgggctt ggtccgttgt caactgggtt tggttcaaac caaagaagtt ggaaagattc 120
ttgagagagc aaggtttgaa gggtaattct tatagattct tgtacggtga catgaaggaa 180
aattctattt tgttgaagca agccagatcc aaaccaatga acttgtctac ctctcatgat 240
attgctccac aagttactcc attcgtcgat caaactgtta aagcctacgg taagaactct 300
ttcaattggg ttggtccaat tcctagagtt aacatcatga acccagaaga tttgaaggat 360
gtcttgacca agaacgttga cttcgttaag ccaatttcca acccattgat taaattgttg 420
gctactggta ttgccattta cgaaggtgaa aagtggacta agcatagaag aatcatcaac 480
cctaccttcc actctgaaag attgaagaga atgttaccat ctttccatca atcctgtaat 540
gaaatggtta aggaatggga atccttggtt tctaaagaag gttcttcttg cgaattggat 600
gtttggccat tcttggaaaa tatgtctgct gatgtcattt ccagaaccgc tttcggtacc 660
tcctacaaga agggtcaaaa gattttcgaa ttgttgagag agcaagttat ttacgttacc 720
aagggtttcc aatccttcta catcccaggt tggagattct tgccaactaa aatgaacaag 780
cgtatgaacg agatcaacga agaaattaaa ggtttgatca gaggtattat tatcgacaga 840
gaacaaatta ttaaagctgg tgaagaaacc aacgatgatt tgttgggtgc tttgatggag 900
tccaacttga aggatattag agaacatggt aagaacaaca agaatgttgg tatgtctatt 960
gaagatgtta ttcaagaatg taagttattc tacttcgctg gtcaagagac cacttctgtt 1020
ttgttagcct ggactatggt cttgttaggt caaaaccaaa attggcaaga tagagctaga 1080
caagaagttt tgcaagtctt cggttcttcc aagccagact ttgatggttt ggcccacttg 1140
aaggttgtta ctatgatttt gttagaagtt ttgagattgt acccaccagt cattgagtta 1200
atcagaacca ttcataaaaa gactcaattg ggtaaattat ctttgccaga aggtgttgaa 1260
gtcagattac caaccttgtt gattcaccac gataaggaat tatggggtga cgacgctaat 1320
caatttaatc cagaaagatt ttccgaaggt gtttccaagg ctaccaaaaa ccgtttgtcc 1380
ttcttcccat ttggtgctgg tccacgtatt tgtatcggtc aaaacttttc catgatggaa 1440
gccaagttgg ctttggcttt aatcttgcaa cacttcactt tcgaattgtc tccatcccat 1500
gcccacgctc cttctcatag aatcacttta caaccacaat acggtgtcag aatcatctta 1560
cacagaagat aa 1572

<210> SEQ ID NO 97
<211> LENGTH: 523
<212> TYPE: PRT
<213> ORGANISM: Rubus suavissimus

<400> SEQUENCE: 97

Met Glu Val Thr Val Ala Ser Ser Val Ala Leu Ser Leu Val Phe Ile
1               5                   10                  15

Ser Ile Val Val Arg Trp Ala Trp Ser Val Val Asn Trp Val Trp Phe
            20                  25                  30

Lys Pro Lys Lys Leu Glu Arg Phe Leu Arg Glu Gln Gly Leu Lys Gly
        35                  40                  45

Asn Ser Tyr Arg Phe Leu Tyr Gly Asp Met Lys Glu Asn Ser Ile Leu
    50                  55                  60

Leu Lys Gln Ala Arg Ser Lys Pro Met Asn Leu Ser Thr Ser His Asp
65                  70                  75                  80

Ile Ala Pro Gln Val Thr Pro Phe Val Asp Gln Thr Val Lys Ala Tyr
                85                  90                  95

Gly Lys Asn Ser Phe Asn Trp Val Gly Pro Ile Pro Arg Val Asn Ile
            100                 105                 110

Met Asn Pro Glu Asp Leu Lys Asp Val Leu Thr Lys Asn Val Asp Phe
        115                 120                 125

Val Lys Pro Ile Ser Asn Pro Leu Ile Lys Leu Leu Ala Thr Gly Ile
    130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
            180                 185                 190

Glu Gly Ser Ser Cys Glu Leu Asp Val Trp Pro Phe Leu Glu Asn Met
        195                 200                 205

Ser Ala Asp Val Ile Ser Arg Thr Ala Phe Gly Thr Ser Tyr Lys Lys
    210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
                245                 250                 255

Lys Met Asn Lys Arg Met Asn Glu Ile Asn Glu Glu Ile Lys Gly Leu
            260                 265                 270

Ile Arg Gly Ile Ile Ile Asp Arg Glu Gln Ile Ile Lys Ala Gly Glu
        275                 280                 285

Glu Thr Asn Asp Asp Leu Leu Gly Ala Leu Met Glu Ser Asn Leu Lys
    290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                325                 330                 335

Thr Thr Ser Val Leu Leu Ala Trp Thr Met Val Leu Leu Gly Gln Asn
            340                 345                 350

Gln Asn Trp Gln Asp Arg Ala Arg Gln Glu Val Leu Gln Val Phe Gly
        355                 360                 365

```
Ser Ser Lys Pro Asp Phe Asp Gly Leu Ala His Leu Lys Val Val Thr
    370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                405                 410                 415

Glu Gly Val Glu Val Arg Leu Pro Thr Leu Leu Ile His His Asp Lys
            420                 425                 430

Glu Leu Trp Gly Asp Asp Ala Asn Gln Phe Asn Pro Glu Arg Phe Ser
        435                 440                 445

Glu Gly Val Ser Lys Ala Thr Lys Asn Arg Leu Ser Phe Phe Pro Phe
    450                 455                 460

Gly Ala Gly Pro Arg Ile Cys Ile Gly Gln Asn Phe Ser Met Met Glu
465                 470                 475                 480

Ala Lys Leu Ala Leu Ala Leu Ile Leu Gln His Phe Thr Phe Glu Leu
                485                 490                 495

Ser Pro Ser His Ala His Ala Pro Ser His Arg Ile Thr Leu Gln Pro
            500                 505                 510

Gln Tyr Gly Val Arg Ile Ile Leu His Arg Arg
        515                 520
```

<210> SEQ ID NO 98
<211> LENGTH: 1566
<212> TYPE: DNA
<213> ORGANISM: Prunus avium

<400> SEQUENCE: 98

```
atggaagcat caagggctag ttgtgttgcg ctatgtgttg tttgggtgag catagtaatt     60

acattggcat ggagggtgct gaattgggtg tggttgaggc caaagaaact agaaagatgc    120

ttgagggagc aaggccttac aggcaattct tacaggcttt tgtttggaga caccaaggat    180

ctctcgaaga tgctggaaca aacacaatcc aaacccatca aactctccac ctcccatgat    240

atagcgccac gagtcacccc atttttccat cgaactgtga actctaatgg caagaattct    300

tttgtttgga tgggccctat accaagagtg cacatcatga atccagaaga tttgaaagat    360

gccttcaaca gacatgatga ttttcataag acagtaaaaa atcctatcat gaagtctcca    420

ccaccgggca ttgtaggcat tgaaggtgag caatgggcta aacacagaaa gattatcaac    480

ccagcattcc atttagagaa gctaaagggt atggtaccaa tattttacca aagttgtagc    540

gagatgatta acaaatggga gagcttggtg tccaaagaga gttcatgtga gttggatgtg    600

tggccttatc ttgaaaattt taccagcgat gtgatttccc gagctgcatt tggaagtagc    660

tatgaagagg gaaggaaaat atttcaacta ctaagagagg aagcaaaagt ttattcggta    720

gctctacgaa gtgtttacat tccaggatgg aggtttctac caaccaagca gaacaagaag    780

acgaaggaaa ttcacaatga aattaaaggc ttacttaagg gcattataaa taaaagggaa    840

gaggcgatga aggcagggga agccactaaa gatgacttac taggaatact tatggagtcc    900

aacttcaggg aaattcagga acatgggaac aacaaaaatg ctggaatgag tattgaagat    960

gtaattggag agtgtaagtt gttttacttt gctgggcaag agaccacttc ggtgttgctt   1020

gtttggacaa tgattttact aagccaaaat caggattggc aagctcgtgc aagagaagag   1080

gtcttgaaag tctttggaag caacatccca acctatgaag agctaagtca cctaaaagtt   1140

gtgaccatga ttttacttga agttcttcga ttatacccat cagtcgttgc gcttcctcga   1200

accactcaca agaaaacaca gcttggaaaa ttatcattac cagctggagt ggaagtctcc   1260
```

ttgcccatac tgcttgttca ccatgacaaa gagttgtggg gtgaggatgc aaatgagttc 1320
aagccagaga ggttttcaga gggagtttca aaggcaacaa agaacaaatt tacatactta 1380
cctttcggag ggggtccaag gatttgcatt ggacaaaact ttgccatggt ggaagctaaa 1440
ttggccttgg ccctgatttt acaacacttt gcctttgagc tttctccatc ctatgctcat 1500
gctccttctg cagttataac ccttcaacct caatttggtg ctcatatcat tttgcataaa 1560
cgttga 1566

<210> SEQ ID NO 99
<211> LENGTH: 1567
<212> TYPE: DNA
<213> ORGANISM: Artificial Sequence
<220> FEATURE:
<223> OTHER INFORMATION: Codon-optimized KAH

<400> SEQUENCE: 99
atggaagctt ctagagcatc ttgtgttgct ttgtgtgttg tttgggtttc catcgttatt 60
actttggctt ggagagtttt gaattgggtc tggttaagac caaaaaagtt ggaaagatgc 120
ttgagagaac aaggtttgac tggtaactct tacagattgt tgttcggtga taccaaggac 180
ttgtctaaga tgttggaaca aactcaatcc aagcctatca agttgtctac ctctcatgat 240
attgctccaa gagttactcc attcttccat agaactgtta actccaacgg taagaactct 300
tttgtttgga tgggtccaat tccaagagtc catattatga accctgaaga tttgaaggac 360
gctttcaaca gacatgatga tttccataag accgtcaaga acccaattat gaagtctcca 420
ccaccaggta tagttggtat tgaaggtgaa caatgggcca aacatagaaa gattattaac 480
ccagccttcc acttggaaaa gttgaaaggt atggttccaa tcttctacca atcctgctct 540
gaaatgatta acaagtggga atccttggtt tccaaagaat cttcctgtga attggatgtc 600
tggccatatt tggaaaactt cacctccgat gttatttcca gagctgcttt tggttcttct 660
tacgaagaag gtagaaagat cttccaatta ttgagagaag aagccaaggt ttactccgtt 720
gctttgagat ctgtttacat tccaggttgg agattcttgc caactaagca aaacaaaaag 780
accaaagaaa tccacaacga aatcaagggt ttgttgaagg gtatcatcaa caagagagaa 840
gaagctatga aggctggtga agctacaaaa gatgatttgt tgggtatctt gatggaatcc 900
aacttcagag aaatccaaga acacggtaac aacaagaatg ccggtatgtc tattgaagat 960
gttatcggtg aatgcaagtt gttctacttt gctggtcaag aaactacctc cgttttgttg 1020
gtttggacca tgattttgtt gtcccaaaat caagattggc aagctagagc tagagaagaa 1080
gtcttgaaag ttttcggttc taacatccca acctacgaag aattgtctca cttgaaggtt 1140
gtcactatga tcttgttgga agtattgaga ttatacccat ccgttgttgc attgccaaga 1200
actactcata agaaaactca attgggtaaa ttgtccttgc cagctggtgt tgaagtttct 1260
ttgccaattt tgttagtcca ccacgacaaa gaattgtggg gtgaagatgc taatgaattc 1320
aagccagaaa gattctccga aggtgtttct aaagctacca agaacaagtt cacttacttg 1380
ccatttggtg gtggtccaag aatatgtatt ggtcaaaatt tcgctatggt cgaagctaaa 1440
ttggctttgg ctttgatctt gcaacatttc gctttcgaat tgtcaccatc ttatgctcat 1500
gctccatctg ctgttattac attgcaacca caatttggtg cccatatcat cttgcataag 1560
agataac 1567

<210> SEQ ID NO 100

<211> LENGTH: 521
<212> TYPE: PRT
<213> ORGANISM: Prunus avium

<400> SEQUENCE: 100

```
Met Glu Ala Ser Arg Ala Ser Cys Val Ala Leu Cys Val Val Trp Val
1               5                   10                  15

Ser Ile Val Ile Thr Leu Ala Trp Arg Val Leu Asn Trp Val Trp Leu
            20                  25                  30

Arg Pro Lys Lys Leu Glu Arg Cys Leu Arg Glu Gln Gly Leu Thr Gly
        35                  40                  45

Asn Ser Tyr Arg Leu Leu Phe Gly Asp Thr Lys Asp Leu Ser Lys Met
    50                  55                  60

Leu Glu Gln Thr Gln Ser Lys Pro Ile Lys Leu Ser Thr Ser His Asp
65                  70                  75                  80

Ile Ala Pro Arg Val Thr Pro Phe Phe His Arg Thr Val Asn Ser Asn
                85                  90                  95

Gly Lys Asn Ser Phe Val Trp Met Gly Pro Ile Pro Arg Val His Ile
            100                 105                 110

Met Asn Pro Glu Asp Leu Lys Asp Ala Phe Asn Arg His Asp Asp Phe
        115                 120                 125

His Lys Thr Val Lys Asn Pro Ile Met Lys Ser Pro Pro Pro Gly Ile
    130                 135                 140

Val Gly Ile Glu Gly Glu Gln Trp Ala Lys His Arg Lys Ile Ile Asn
145                 150                 155                 160

Pro Ala Phe His Leu Glu Lys Leu Lys Gly Met Val Pro Ile Phe Tyr
                165                 170                 175

Gln Ser Cys Ser Glu Met Ile Asn Lys Trp Glu Ser Leu Val Ser Lys
            180                 185                 190

Glu Ser Ser Cys Glu Leu Asp Val Trp Pro Tyr Leu Glu Asn Phe Thr
        195                 200                 205

Ser Asp Val Ile Ser Arg Ala Ala Phe Gly Ser Ser Tyr Glu Glu Gly
    210                 215                 220

Arg Lys Ile Phe Gln Leu Leu Arg Glu Glu Ala Lys Val Tyr Ser Val
225                 230                 235                 240

Ala Leu Arg Ser Val Tyr Ile Pro Gly Trp Arg Phe Leu Pro Thr Lys
                245                 250                 255

Gln Asn Lys Lys Thr Lys Glu Ile His Asn Glu Ile Lys Gly Leu Leu
            260                 265                 270

Lys Gly Ile Ile Asn Lys Arg Glu Glu Ala Met Lys Ala Gly Glu Ala
        275                 280                 285

Thr Lys Asp Asp Leu Leu Gly Ile Leu Met Glu Ser Asn Phe Arg Glu
    290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
                325                 330                 335

Ser Val Leu Leu Val Trp Thr Met Ile Leu Leu Ser Gln Asn Gln Asp
            340                 345                 350

Trp Gln Ala Arg Ala Arg Glu Glu Val Leu Lys Val Phe Gly Ser Asn
        355                 360                 365

Ile Pro Thr Tyr Glu Glu Leu Ser His Leu Lys Val Val Thr Met Ile
    370                 375                 380

Leu Leu Glu Val Leu Arg Leu Tyr Pro Ser Val Val Ala Leu Pro Arg
```

385 390 395 400

Thr Thr His Lys Lys Thr Gln Leu Gly Lys Leu Ser Leu Pro Ala Gly
405 410 415

Val Glu Val Ser Leu Pro Ile Leu Leu Val His His Asp Lys Glu Leu
420 425 430

Trp Gly Glu Asp Ala Asn Glu Phe Lys Pro Glu Arg Phe Ser Glu Gly
435 440 445

Val Ser Lys Ala Thr Lys Asn Lys Phe Thr Tyr Leu Pro Phe Gly Gly
450 455 460

Gly Pro Arg Ile Cys Ile Gly Gln Asn Phe Ala Met Val Glu Ala Lys
465 470 475 480

Leu Ala Leu Ala Leu Ile Leu Gln His Phe Ala Phe Glu Leu Ser Pro
485 490 495

Ser Tyr Ala His Ala Pro Ser Ala Val Ile Thr Leu Gln Pro Gln Phe
500 505 510

Gly Ala His Ile Ile Leu His Lys Arg
515 520

<210> SEQ ID NO 101
<211> LENGTH: 517
<212> TYPE: PRT
<213> ORGANISM: Prunus mume

<400> SEQUENCE: 101

Ala Ser Trp Val Ala Val Leu Ser Val Val Trp Val Ser Met Val Ile
1 5 10 15

Ala Trp Ala Trp Arg Val Leu Asn Trp Val Trp Leu Arg Pro Lys Lys
20 25 30

Leu Glu Lys Cys Leu Arg Glu Gln Gly Leu Ala Gly Asn Ser Tyr Arg
35 40 45

Leu Leu Phe Gly Asp Thr Lys Asp Leu Ser Lys Met Leu Glu Gln Thr
50 55 60

Gln Ser Lys Pro Ile Lys Leu Ser Thr Ser His Asp Ile Ala Pro His
65 70 75 80

Val Thr Pro Phe Phe His Gln Thr Val Asn Ser Tyr Gly Lys Asn Ser
85 90 95

Phe Val Trp Met Gly Pro Ile Pro Arg Val His Ile Met Asn Pro Glu
100 105 110

Asp Leu Lys Asp Thr Phe Asn Arg His Asp Asp Phe His Lys Val Val
115 120 125

Lys Asn Pro Ile Met Lys Ser Leu Pro Gln Gly Ile Val Gly Ile Glu
130 135 140

Gly Glu Gln Trp Ala Lys His Arg Lys Ile Ile Asn Pro Ala Phe His
145 150 155 160

Leu Glu Lys Leu Lys Gly Met Val Pro Ile Phe Tyr Arg Ser Cys Ser
165 170 175

Glu Met Ile Asn Lys Trp Glu Ser Leu Val Ser Lys Glu Ser Ser Cys
180 185 190

Glu Leu Asp Val Trp Pro Tyr Leu Glu Asn Phe Thr Ser Asp Val Ile
195 200 205

Ser Arg Ala Ala Phe Gly Ser Ser Tyr Glu Glu Gly Arg Lys Ile Phe
210 215 220

Gln Leu Leu Arg Glu Glu Ala Lys Ile Tyr Thr Val Ala Met Arg Ser
225 230 235 240

Val Tyr Ile Pro Gly Trp Arg Phe Leu Pro Thr Lys Gln Asn Lys Lys
245 250 255

Ala Lys Glu Ile His Asn Glu Ile Lys Gly Leu Leu Lys Gly Ile Ile
260 265 270

Asn Lys Arg Glu Glu Ala Met Lys Ala Gly Glu Ala Thr Lys Asp Asp
275 280 285

Leu Leu Gly Ile Leu Met Glu Ser Asn Phe Arg Glu Ile Gln Glu His
290 295 300

Gly Asn Asn Lys Asn Ala Gly Met Ser Ile Glu Asp Val Ile Gly Glu
305 310 315 320

Cys Lys Leu Phe Tyr Phe Ala Gly Gln Glu Thr Thr Ser Val Leu Leu
325 330 335

Val Trp Thr Met Val Leu Leu Ser Gln Asn Gln Asp Trp Gln Ala Arg
340 345 350

Ala Arg Glu Glu Val Leu Gln Val Phe Gly Ser Asn Ile Pro Thr Tyr
355 360 365

Glu Glu Leu Ser Gln Leu Lys Val Val Thr Met Ile Leu Leu Glu Val
370 375 380

Leu Arg Leu Tyr Pro Ser Val Val Ala Leu Pro Arg Thr Thr His Lys
385 390 395 400

Lys Thr Gln Leu Gly Lys Leu Ser Leu Pro Ala Gly Val Glu Val Ser
405 410 415

Leu Pro Ile Leu Leu Val His His Asp Lys Glu Leu Trp Gly Glu Asp
420 425 430

Ala Asn Glu Phe Lys Pro Glu Arg Phe Ser Glu Gly Val Ser Lys Ala
435 440 445

Thr Lys Asn Gln Phe Thr Tyr Phe Pro Phe Gly Gly Pro Arg Ile
450 455 460

Cys Ile Gly Gln Asn Phe Ala Met Met Glu Ala Lys Leu Ala Leu Ser
465 470 475 480

Leu Ile Leu Arg His Phe Ala Leu Glu Leu Ser Pro Leu Tyr Ala His
485 490 495

Ala Pro Ser Val Thr Ile Thr Leu Gln Pro Gln Tyr Gly Ala His Ile
500 505 510

Ile Leu His Lys Arg
515

<210> SEQ ID NO 102
<211> LENGTH: 521
<212> TYPE: PRT
<213> ORGANISM: Prunus mume

<400> SEQUENCE: 102

Met Glu Ala Ser Arg Pro Ser Cys Val Ala Leu Ser Val Val Leu Val
1 5 10 15

Ser Ile Val Ile Ala Trp Ala Trp Arg Val Leu Asn Trp Val Trp Leu
20 25 30

Arg Pro Asn Lys Leu Glu Arg Cys Leu Arg Glu Gln Gly Leu Thr Gly
35 40 45

Asn Ser Tyr Arg Leu Leu Phe Gly Asp Thr Lys Glu Ile Ser Met Met
50 55 60

Val Glu Gln Ala Gln Ser Lys Pro Ile Lys Leu Ser Thr Thr His Asp
65 70 75 80

Ile Ala Pro Arg Val Ile Pro Phe Ser His Gln Ile Val Tyr Thr Tyr
85 90 95

```
Gly Arg Asn Ser Phe Val Trp Met Gly Pro Thr Pro Arg Val Thr Ile
            100                 105                 110

Met Asn Pro Glu Asp Leu Lys Asp Ala Phe Asn Lys Ser Asp Glu Phe
        115                 120                 125

Gln Arg Ala Ile Ser Asn Pro Ile Val Lys Ser Ile Ser Gln Gly Leu
    130                 135                 140

Ser Ser Leu Glu Gly Glu Lys Trp Ala Lys His Arg Lys Ile Ile Asn
145                 150                 155                 160

Pro Ala Phe His Leu Glu Lys Leu Lys Gly Met Leu Pro Thr Phe Tyr
                165                 170                 175

Gln Ser Cys Ser Glu Met Ile Asn Lys Trp Glu Ser Leu Val Phe Lys
            180                 185                 190

Glu Gly Ser Arg Glu Met Asp Val Trp Pro Tyr Leu Glu Asn Leu Thr
        195                 200                 205

Ser Asp Val Ile Ser Arg Ala Ala Phe Gly Ser Ser Tyr Glu Glu Gly
    210                 215                 220

Arg Lys Ile Phe Gln Leu Leu Arg Glu Glu Ala Lys Phe Tyr Thr Ile
225                 230                 235                 240

Ala Ala Arg Ser Val Tyr Ile Pro Gly Trp Arg Phe Leu Pro Thr Lys
                245                 250                 255

Gln Asn Lys Arg Met Lys Glu Ile His Lys Glu Val Arg Gly Leu Leu
            260                 265                 270

Lys Gly Ile Ile Asn Lys Arg Glu Asp Ala Ile Lys Ala Gly Glu Ala
        275                 280                 285

Ala Lys Gly Asn Leu Leu Gly Ile Leu Met Glu Ser Asn Phe Arg Glu
    290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
                325                 330                 335

Ser Val Leu Leu Val Trp Thr Leu Val Leu Leu Ser Gln Asn Gln Asp
            340                 345                 350

Trp Gln Ala Arg Ala Arg Glu Glu Val Leu Gln Val Phe Gly Thr Asn
        355                 360                 365

Ile Pro Thr Tyr Asp Gln Leu Ser His Leu Lys Val Val Thr Met Ile
    370                 375                 380

Leu Leu Glu Val Leu Arg Leu Tyr Pro Ala Val Val Glu Leu Pro Arg
385                 390                 395                 400

Thr Thr Tyr Lys Lys Thr Gln Leu Gly Lys Phe Leu Leu Pro Ala Gly
                405                 410                 415

Val Glu Val Ser Leu His Ile Met Leu Ala His His Asp Lys Glu Leu
            420                 425                 430

Trp Gly Glu Asp Ala Lys Glu Phe Lys Pro Glu Arg Phe Ser Glu Gly
        435                 440                 445

Val Ser Lys Ala Thr Lys Asn Gln Phe Thr Tyr Phe Pro Phe Gly Ala
    450                 455                 460

Gly Pro Arg Ile Cys Ile Gly Gln Asn Phe Ala Met Leu Glu Ala Lys
465                 470                 475                 480

Leu Ala Leu Ser Leu Ile Leu Gln His Phe Thr Phe Glu Leu Ser Pro
                485                 490                 495

Ser Tyr Ala His Ala Pro Ser Val Thr Ile Thr Leu His Pro Gln Phe
            500                 505                 510
```

Gly Ala His Phe Ile Leu His Lys Arg
515 520

<210> SEQ ID NO 103
<211> LENGTH: 514
<212> TYPE: PRT
<213> ORGANISM: Prunus mume

<400> SEQUENCE: 103

Cys Val Ala Leu Ser Val Val Leu Val Ser Ile Val Ile Ala Trp Ala
1 5 10 15

Trp Arg Val Leu Asn Trp Val Trp Leu Arg Pro Asn Lys Leu Glu Arg
20 25 30

Cys Leu Arg Glu Gln Gly Leu Thr Gly Asn Ser Tyr Arg Leu Leu Phe
35 40 45

Gly Asp Thr Lys Glu Ile Ser Met Met Val Glu Gln Ala Gln Ser Lys
50 55 60

Pro Ile Lys Leu Ser Thr Thr His Asp Ile Ala Pro Arg Val Ile Pro
65 70 75 80

Phe Ser His Gln Ile Val Tyr Thr Tyr Gly Arg Asn Ser Phe Val Trp
85 90 95

Met Gly Pro Thr Pro Arg Val Thr Ile Met Asn Pro Glu Asp Leu Lys
100 105 110

Asp Ala Phe Asn Lys Ser Asp Glu Phe Gln Arg Ala Ile Ser Asn Pro
115 120 125

Ile Val Lys Ser Ile Ser Gln Gly Leu Ser Ser Leu Glu Gly Glu Lys
130 135 140

Trp Ala Lys His Arg Lys Ile Ile Asn Pro Ala Phe His Leu Glu Lys
145 150 155 160

Leu Lys Gly Met Leu Pro Thr Phe Tyr Gln Ser Cys Ser Glu Met Ile
165 170 175

Asn Lys Trp Glu Ser Leu Val Phe Lys Glu Gly Ser Arg Glu Met Asp
180 185 190

Val Trp Pro Tyr Leu Glu Asn Leu Thr Ser Asp Val Ile Ser Arg Ala
195 200 205

Ala Phe Gly Ser Ser Tyr Glu Glu Gly Arg Lys Ile Phe Gln Leu Leu
210 215 220

Arg Glu Glu Ala Lys Phe Tyr Thr Ile Ala Ala Arg Ser Val Tyr Ile
225 230 235 240

Pro Gly Trp Arg Phe Leu Pro Thr Lys Gln Asn Lys Arg Met Lys Glu
245 250 255

Ile His Lys Glu Val Arg Gly Leu Leu Lys Gly Ile Ile Asn Lys Arg
260 265 270

Glu Asp Ala Ile Lys Ala Gly Glu Ala Ala Lys Gly Asn Leu Leu Gly
275 280 285

Ile Leu Met Glu Ser Asn Phe Arg Glu Ile Gln Glu His Gly Asn Asn
290 295 300

Lys Asn Ala Gly Met Ser Ile Glu Asp Val Ile Gly Glu Cys Lys Leu
305 310 315 320

Phe Tyr Phe Ala Gly Gln Glu Thr Thr Ser Val Leu Leu Val Trp Thr
325 330 335

Leu Val Leu Leu Ser Gln Asn Gln Asp Trp Gln Ala Arg Ala Arg Glu
340 345 350

Glu Val Leu Gln Val Phe Gly Thr Asn Ile Pro Thr Tyr Asp Gln Leu
355 360 365

```
Ser His Leu Lys Val Val Thr Met Ile Leu Leu Glu Val Leu Arg Leu
    370                 375                 380

Tyr Pro Ala Val Val Glu Leu Pro Arg Thr Thr Tyr Lys Lys Thr Gln
385                 390                 395                 400

Leu Gly Lys Phe Leu Leu Pro Ala Gly Val Glu Val Ser Leu His Ile
                405                 410                 415

Met Leu Ala His His Asp Lys Glu Leu Trp Gly Glu Asp Ala Lys Glu
            420                 425                 430

Phe Lys Pro Glu Arg Phe Ser Glu Gly Val Ser Lys Ala Thr Lys Asn
        435                 440                 445

Gln Phe Thr Tyr Phe Pro Phe Gly Ala Gly Pro Arg Ile Cys Ile Gly
    450                 455                 460

Gln Asn Phe Ala Met Leu Glu Ala Lys Leu Ala Leu Ser Leu Ile Leu
465                 470                 475                 480

Gln His Phe Thr Phe Glu Leu Ser Pro Ser Tyr Ala His Ala Pro Ser
                485                 490                 495

Val Thr Ile Thr Leu His Pro Gln Phe Gly Ala His Phe Ile Leu His
            500                 505                 510

Lys Arg


<210> SEQ ID NO 104
<211> LENGTH: 418
<212> TYPE: PRT
<213> ORGANISM: Prunus persica

<400> SEQUENCE: 104

Met Gly Pro Ile Pro Arg Val His Ile Met Asn Pro Glu Asp Leu Lys
1               5                   10                  15

Asp Thr Phe Asn Arg His Asp Asp Phe His Lys Val Val Lys Asn Pro
            20                  25                  30

Ile Met Lys Ser Leu Pro Gln Gly Ile Val Gly Ile Glu Gly Asp Gln
        35                  40                  45

Trp Ala Lys His Arg Lys Ile Ile Asn Pro Ala Phe His Leu Glu Lys
    50                  55                  60

Leu Lys Gly Met Val Pro Ile Phe Tyr Gln Ser Cys Ser Glu Met Ile
65                  70                  75                  80

Asn Ile Trp Lys Ser Leu Val Ser Lys Glu Ser Ser Cys Glu Leu Asp
                85                  90                  95

Val Trp Pro Tyr Leu Glu Asn Phe Thr Ser Asp Val Ile Ser Arg Ala
            100                 105                 110

Ala Phe Gly Ser Ser Tyr Glu Glu Gly Arg Lys Ile Phe Gln Leu Leu
        115                 120                 125

Arg Glu Glu Ala Lys Val Tyr Thr Val Ala Val Arg Ser Val Tyr Ile
    130                 135                 140

Pro Gly Trp Arg Phe Leu Pro Thr Lys Gln Asn Lys Lys Thr Lys Glu
145                 150                 155                 160

Ile His Asn Glu Ile Lys Gly Leu Leu Lys Gly Ile Ile Asn Lys Arg
                165                 170                 175

Glu Glu Ala Met Lys Ala Gly Glu Ala Thr Lys Asp Asp Leu Leu Gly
            180                 185                 190

Ile Leu Met Glu Ser Asn Phe Arg Glu Ile Gln Glu His Gly Asn Asn
        195                 200                 205

Lys Asn Ala Gly Met Ser Ile Glu Asp Val Ile Gly Glu Cys Lys Leu
    210                 215                 220
```

```
Phe Tyr Phe Ala Gly Gln Glu Thr Thr Ser Val Leu Leu Val Trp Thr
225                 230                 235                 240

Met Val Leu Leu Ser Gln Asn Gln Asp Trp Gln Ala Arg Ala Arg Glu
                245                 250                 255

Glu Val Leu Gln Val Phe Gly Ser Asn Ile Pro Thr Tyr Glu Glu Leu
            260                 265                 270

Ser His Leu Lys Val Val Thr Met Ile Leu Leu Glu Val Leu Arg Leu
        275                 280                 285

Tyr Pro Ser Val Val Ala Leu Pro Arg Thr Thr His Lys Lys Thr Gln
    290                 295                 300

Leu Gly Lys Leu Ser Leu Pro Ala Gly Val Glu Val Ser Leu Pro Ile
305                 310                 315                 320

Leu Leu Val His His Asp Lys Glu Leu Trp Gly Glu Asp Ala Asn Glu
                325                 330                 335

Phe Lys Pro Glu Arg Phe Ser Glu Gly Val Ser Lys Ala Thr Lys Asn
            340                 345                 350

Gln Phe Thr Tyr Phe Pro Phe Gly Gly Gly Pro Arg Ile Cys Ile Gly
        355                 360                 365

Gln Asn Phe Ala Met Met Glu Ala Lys Leu Ala Leu Ser Leu Ile Leu
    370                 375                 380

Gln His Phe Thr Phe Glu Leu Ser Pro Gln Tyr Ser His Ala Pro Ser
385                 390                 395                 400

Val Thr Ile Thr Leu Gln Pro Gln Tyr Gly Ala His Leu Ile Leu His
                405                 410                 415

Lys Arg


<210> SEQ ID NO 105
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 105

atgggtttgt tcccattaga ggattcctac gcgctggtct ttgaaggact agcaataaca     60

ctggctttgt actatctact gtctttcatc tacaaaacat ctaaaaagac atgtacacct    120

cctaaagcat ctggtgaaat cattccaatt acaggaatca tattgaatct gctatctggc    180

tcaagtggtc tacctattat cttagcactt gcctctttag cagacagatg tggtcctatt    240

ttcaccatta ggctgggtat taggagagtg ctagtagtat caaattggga aatcgctaag    300

gagattttca ctacccacga tttgatagtt tctaatagac caaaatactt agccgctaag    360

attcttggtt tcaattatgt ttcattctct ttcgctccat acggcccata ttgggtcgga    420

atcagaaaga ttattgctac aaaactaatg tcttcttcca gacttcagaa gttgcaattt    480

gtaagagttt ttgaactaga aaactctatg aaatctatca gagaatcatg gaaggagaaa    540

aaggatgaag agggaaaggt attagttgag atgaaaaagt ggttctggga actgaatatg    600

aacatagtgt taaggacagt tgctggtaaa caatacactg gtacagttga tgatgccgat    660

gcaaagcgta tctccgagtt attcagagaa tggtttcact acactggcag atttgtcgtt    720

ggagacgctt ttccttttct aggttggttg gacctgggcg gatacaaaaa gacaatggaa    780

ttagttgcta gtagattgga ctcaatggtc agtaaatggt tagatgagca tcgtaaaaag    840

caagctaacg atgacaaaaa ggaggatatg gatttcatgg atatcatgat ctccatgaca    900
```

```
gaagcaaatt caccacttga aggatacggc actgatacta ttatcaagac cacatgtatg    960

actttgattg tttcaggagt tgatacaacc tcaatcgtac ttacttgggc cttatcactt   1020

ttgttaaaca acagagatac tttgaaaaag gcacaagagg aattagatat gtgcgtaggt   1080

aaaggaagac aagtcaacga gtctgatctt gttaacttga tatacttgga agcagtgctt   1140

aaagaggctt taagacttta cccagcagcg ttcttaggcg gaccaagagc attcttggaa   1200

gattgtactg ttgctggtta tagaattcca aagggcacct gcttgttgat taacatgtgg   1260

aaactgcata gagatccaaa catttggagt gatccttgcg aattcaagcc agaaagattt   1320

ttgacaccta atcaaaagga tgttgatgtg atcggtatgg atttcgaatt gataccattt   1380

ggtgccggca gaagatattg tccaggtact agattggctt tacagatgtt gcatatcgta   1440

ttagcgacat tgctgcaaaa cttcgaaatg tcaacaccaa acgatgcgcc agtcgatatg   1500

actgcttctg ttggcatgac aaatgccaaa gcatcacctt tagaagtctt gctatcacct   1560

cgtgttaaat ggtcctaa                                                 1578
```

```
<210> SEQ ID NO 106
<211> LENGTH: 522
<212> TYPE: PRT
<213> ORGANISM: Stevia rebaudiana

<400> SEQUENCE: 106

Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
            20                  25                  30

Thr Ser Lys Lys Thr Cys Thr Pro Pro Lys Ala Ser Gly Glu His Pro
        35                  40                  45

Ile Thr Gly His Leu Asn Leu Leu Ser Gly Ser Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
        195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255
```

```
Glu Leu Val Ala Ser Arg Leu Asp Ser Met Val Ser Lys Trp Leu Asp
            260                 265                 270

Glu His Arg Lys Lys Gln Ala Asn Asp Asp Lys Lys Glu Asp Met Asp
        275                 280                 285

Phe Met Asp Ile Met Ile Ser Met Thr Glu Ala Asn Ser Pro Leu Glu
    290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
            325                 330                 335

Leu Leu Leu Asn Asn Arg Asp Thr Leu Lys Lys Ala Gln Glu Glu Leu
            340                 345                 350

Asp Met Cys Val Gly Lys Gly Arg Gln Val Asn Glu Ser Asp Leu Val
        355                 360                 365

Asn Leu Ile Tyr Leu Glu Ala Val Leu Lys Glu Ala Leu Arg Leu Tyr
    370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
            405                 410                 415

Trp Lys Leu His Arg Asp Pro Asn Ile Trp Ser Asp Pro Cys Glu Phe
            420                 425                 430

Lys Pro Glu Arg Phe Leu Thr Pro Asn Gln Lys Asp Val Asp Val Ile
        435                 440                 445

Gly Met Asp Phe Glu Leu Ile Pro Phe Gly Ala Gly Arg Arg Tyr Cys
    450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
            485                 490                 495

Met Thr Ala Ser Val Gly Met Thr Asn Ala Lys Ala Ser Pro Leu Glu
            500                 505                 510

Val Leu Leu Ser Pro Arg Val Lys Trp Ser
        515                 520


<210> SEQ ID NO 107
<211> LENGTH: 1431
<212> TYPE: DNA
<213> ORGANISM: Artificial Sequence
<220> FEATURE:
<223> OTHER INFORMATION: Codon-optimized KAH

<400> SEQUENCE: 107

atgatacaag ttttaactcc aattctactc ttcctcatct tcttcgtttt ctggaaagtc      60

tacaaacatc aaaagactaa aatcaatcta ccaccaggtt ccttcggctg gccatttttg     120

ggtgaaacct tagccttact tagagcaggc tgggattctg agccagaaag attcgtaaga     180

gagcgtatca aaaagcatgg atctccactt gttttcaaga catcactatt tggagacaga     240

ttcgctgttc tttgcggtcc agctggtaat aagtttttgt tctgcaacga aaacaaatta     300

gtggcatctt ggtggccagt ccctgtaagg aagttgttcg gtaaaagttt actcacaata     360

agaggagatg aagcaaaatg gatgagaaaa atgctattgt cttacttggg tccagatgca     420

tttgccacac attatgccgt tactatggat gttgtaacac gtagacatat tgatgtccat     480

tggaggggca aggaggaagt taatgtattt caaacagtta agttgtacgc attcgaatta     540
```

```
gcttgtagat tattcatgaa cctagatgac ccaaaccaca tcgcgaaact cggtagtctt    600

ttcaacattt tcctcaaagg gatcatcgag cttcctatag acgttcctgg aactagattt    660

tactccagta aaaaggccgc agctgccatt agaattgaat tgaaaaagct cattaaagct    720

agaaaactcg aattgaagga gggtaaggcg tcttcttcac aggacttgct ttctcatcta    780

ttaacatcac ctgatgagaa tgggatgttc ttgacagaag aggaaatagt cgataacatt    840

ctacttttgt tattcgctgg tcacgatacc tctgcactat caataacact tttgatgaaa    900

accttaggtg aacacagtga tgtgtacgac aaggttttga aggaacaatt agaaatttcc    960

aaaacaaagg aggcttggga atcactaaag tgggaagata tccagaagat gaagtactca   1020

tggtcagtaa tctgtgaagt catgagattg aatcctcctg tcatagggac atacagagag   1080

gcgttggttg atatcgacta tgctggttac actatcccaa aaggatggaa gttgcattgg   1140

tcagctgttt ctactcaaag agacgaagcc aatttcgaag atgtaactag attcgatcca   1200

tccagatttg aaggggcagg ccctactcca ttcacatttg tgcctttcgg tggaggtcct   1260

agaatgtgtt taggcaaaga gtttgccagg ttagaagtgt tagcatttct ccacaacatt   1320

gttaccaact ttaagtggga tcttctaatc cctgatgaga agatcgaata tgatccaatg   1380

gctactccag ctaagggctt gccaattaga cttcatccac accaagtcta a            1431
```

<210> SEQ ID NO 108
<211> LENGTH: 476
<212> TYPE: PRT
<213> ORGANISM: Stevia rebaudiana

<400> SEQUENCE: 108

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190

His Ile Ala Lys Leu Gly Ser Leu Phe Asn Ile Phe Leu Lys Gly Ile
        195                 200                 205

Ile Glu Leu Pro Ile Asp Val Pro Gly Thr Arg Phe Tyr Ser Ser Lys
```

```
    210                 215                 220

Lys Ala Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Ser Gln Asp Leu
                245                 250                 255

Leu Ser His Leu Leu Thr Ser Pro Asp Glu Asn Gly Met Phe Leu Thr
            260                 265                 270

Glu Glu Glu Ile Val Asp Asn Ile Leu Leu Leu Leu Phe Ala Gly His
        275                 280                 285

Asp Thr Ser Ala Leu Ser Ile Thr Leu Leu Met Lys Thr Leu Gly Glu
    290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

Gly Tyr Thr Ile Pro Lys Gly Trp Lys Leu His Trp Ser Ala Val Ser
    370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
        435                 440                 445

Leu Ile Pro Asp Glu Lys Ile Glu Tyr Asp Pro Met Ala Thr Pro Ala
    450                 455                 460

Lys Gly Leu Pro Ile Arg Leu His Pro His Gln Val
465                 470                 475
```

<210> SEQ ID NO 109
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 109

```
atggagtctt tagtggttca tacagtaaat gctatctggt gtattgtaat cgtcgggatt     60

ttctcagttg gttatcacgt ttacggtaga gctgtggtcg aacaatggag aatgagaaga    120

tcactgaagc tacaaggtgt taaaggccca ccaccatcca tcttcaatgg taacgtctca    180

gaaatgcaac gtatccaatc cgaagctaaa cactgctctg gcgataacat tatctcacat    240

gattattctt cttcattatt cccacacttc gatcactgga gaaaacagta cggcagaatc    300

tacacatact ctactggatt aaagcaacac ttgtacatca atcatccaga aatggtgaag    360

gagctatctc agactaacac attgaacttg ggtagaatca cccatataac caaaagattg    420

aatcctatct taggtaacgg aatcataacc tctaatggtc ctcattgggc ccatcagcgt    480

agaattatcg cctacgagtt tactcatgat aagatcaagg gtatggttgg tttgatggtt    540

gagtctgcta tgcctatgtt gaataagtgg gaggagatgg taaagagagg cggagaaatg    600
```

```
ggatgcgaca taagagttga tgaggacttg aaagatgttt cagcagatgt gattgcaaaa    660

gcctgtttcg gatcctcatt ttctaaaggt aaggctattt tctctatgat aagagatttg    720

cttacagcta tcacaaagag aagtgttcta ttcagattca acggattcac tgatatggtc    780

tttgggagta aaaagcatgg tgacgttgat atagacgctt tagaaatgga attggaatca    840

tccatttggg aaactgtcaa ggaacgtgaa atagaatgta aagatactca caaaaaggat    900

ctgatgcaat tgattttgga aggggcaatg cgttcatgtg acggtaacct ttgggataaa    960

tcagcatata gaagatttgt tgtagataat tgtaaatcta tctacttcgc agggcatgat   1020

agtacagctg tctcagtgtc atggtgtttg atgttactgg ccctaaaccc atcatggcaa   1080

gttaagatcc gtgatgaaat tctgtcttct tgcaaaaatg gtattccaga tgccgaaagt   1140

atcccaaacc ttaaaacagt gactatggtt attcaagaga caatgagatt ataccctcca   1200

gcaccaatcg tcgggagaga agcctctaaa gatatcagat tgggcgatct agttgttcct   1260

aaaggcgtct gtatatggac actaatacca gctttacaca gagatcctga gatttgggga   1320

ccagatgcaa acgatttcaa accagaaaga ttttctgaag gaatttcaaa ggcttgtaag   1380

tatcctcaaa gttacattcc atttggtctg ggtcctagaa catgcgttgg taaaaacttt   1440

ggcatgatgg aagtaaaggt tcttgtttcc ctgattgtct ccaagttctc tttcactcta   1500

tctcctacct accaacatag tcctagtcac aaacttttag tagaaccaca acatggggtg   1560

gtaattagag tggtttaa                                                 1578
```

<210> SEQ ID NO 110
<211> LENGTH: 525
<212> TYPE: PRT
<213> ORGANISM: Arabidopsis thaliana

<400> SEQUENCE: 110

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190
```

```
Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Ile Glu Cys Lys Asp Thr His Lys Lys Asp Leu Met Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
        355                 360                 365

Ser Ser Cys Lys Asn Gly Ile Pro Asp Ala Glu Ser Ile Pro Asn Leu
    370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ser
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525
```

<210> SEQ ID NO 111
<211> LENGTH: 1590
<212> TYPE: DNA
<213> ORGANISM: Artificial Sequence
<220> FEATURE:
<223> OTHER INFORMATION: Codon-optimized KAH

<400> SEQUENCE: 111

```
atgtacttcc tactacaata cctcaacatc acaaccgttg gtgtctttgc cacattgttt      60

ctctcttatt gtttacttct ctggagaagt agagcgggta acaaaaagat tgccccagaa     120

gctgccgctg catggcctat tatcggccac ctccacttac ttgcaggtgg atcccatcaa     180
```

```
ctaccacata ttacattggg taacatggca gataagtacg gtcctgtatt cacaatcaga    240
ataggcttgc atagagctgt agttgtctca tcttgggaaa tggcaaagga atgttcaaca    300
gctaatgatc aagtgtcttc ttcaagacct gaactattag cttctaagtt gttgggttat    360
aactacgcca tgtttggttt ttcaccatac ggttcatact ggagagaaat gagaaagatc    420
atctctctcg aattactatc taattccaga ttggaactat tgaaagatgt tagagcctca    480
gaagttgtca catctattaa ggaactatac aaattgtggg cggaaaagaa gaatgagtca    540
ggattggttt ctgtcgagat gaaacaatgg ttcggagatt tgactttaaa cgtgatcttg    600
agaatggtgg ctggtaaaag atacttctcc gcgagtgacg cttcagaaaa caaacaggcc    660
cagcgttgta gaagagtctt cagagaattc ttccatctct ccggcttgtt tgtggttgct    720
gatgctatac cttttcttgg atggctcgat tggggaagac acgagaagac cttgaaaaag    780
accgccatag aaatggattc catcgcccag gagtggcttg aggaacatag acgtagaaaa    840
gattctggag atgataattc tacccaagat ttcatggacg ttatgcaatc tgtgctagat    900
ggcaaaaatc taggcggata cgatgctgat acgattaaca aggctacatg cttaactctt    960
atatcaggtg gcagtgatac tactgtagtt tctttgacat gggctcttag tcttgtgtta   1020
aacaatagag atactttgaa aaaggcacag gaagagttag acatccaagt cggtaaggaa   1080
agattggtta acgagcaaga catcagtaag ttagtttact tgcaagcaat agtaaaagag   1140
acactcagac tttatccacc aggtcctttg ggtggtttga gacaattcac tgaagattgt   1200
acactaggtg gctatcacgt ttcaaaagga actagattaa tcatgaactt atccaagatt   1260
caaaaagatc cacgtatttg gtctgatcct actgaattcc aaccagagag attccttacg   1320
actcataaag atgtcgatcc acgtggtaaa cactttgaat tcattccatt cggtgcagga   1380
agacgtgcat gtcctggtat cacattcgga ttacaagtac tacatctaac attggcatct   1440
ttcttgcatg cgtttgaatt ttcaacacca tcaaatgagc aggttaacat gagagaatca   1500
ttaggtctta cgaatatgaa atctacccca ttagaagttt tgatttctcc aagactatcc   1560
cttaattgct tcaaccttat gaaaatttga                                     1590
```

<210> SEQ ID NO 112
<211> LENGTH: 526
<212> TYPE: PRT
<213> ORGANISM: Vitis vinifera

<400> SEQUENCE: 112

```
Met Tyr Phe Leu Leu Gln Tyr Leu Asn Ile Thr Thr Val Gly Val Phe
1               5                   10                  15

Ala Thr Leu Phe Leu Ser Tyr Cys Leu Leu Leu Trp Arg Ser Arg Ala
            20                  25                  30

Gly Asn Lys Lys Ile Ala Pro Glu Ala Ala Ala Ala Trp Pro Ile Ile
        35                  40                  45

Gly His Leu His Leu Leu Ala Gly Gly Ser His Gln Leu Pro His Ile
    50                  55                  60

Thr Leu Gly Asn Met Ala Asp Lys Tyr Gly Pro Val Phe Thr Ile Arg
65                  70                  75                  80

Ile Gly Leu His Arg Ala Val Val Val Ser Ser Trp Glu Met Ala Lys
                85                  90                  95

Glu Cys Ser Thr Ala Asn Asp Gln Val Ser Ser Ser Arg Pro Glu Leu
            100                 105                 110

Leu Ala Ser Lys Leu Leu Gly Tyr Asn Tyr Ala Met Phe Gly Phe Ser
        115                 120                 125
```

```
Pro Tyr Gly Ser Tyr Trp Arg Glu Met Arg Lys Ile Ile Ser Leu Glu
    130                 135                 140

Leu Leu Ser Asn Ser Arg Leu Glu Leu Leu Lys Asp Val Arg Ala Ser
145                 150                 155                 160

Glu Val Val Thr Ser Ile Lys Glu Leu Tyr Lys Leu Trp Ala Glu Lys
                165                 170                 175

Lys Asn Glu Ser Gly Leu Val Ser Val Glu Met Lys Gln Trp Phe Gly
            180                 185                 190

Asp Leu Thr Leu Asn Val Ile Leu Arg Met Val Ala Gly Lys Arg Tyr
        195                 200                 205

Phe Ser Ala Ser Asp Ala Ser Glu Asn Lys Gln Ala Gln Arg Cys Arg
    210                 215                 220

Arg Val Phe Arg Glu Phe Phe His Leu Ser Gly Leu Phe Val Val Ala
225                 230                 235                 240

Asp Ala Ile Pro Phe Leu Gly Trp Leu Asp Trp Gly Arg His Glu Lys
                245                 250                 255

Thr Leu Lys Lys Thr Ala Ile Glu Met Asp Ser Ile Ala Gln Glu Trp
            260                 265                 270

Leu Glu Glu His Arg Arg Arg Lys Asp Ser Gly Asp Asp Asn Ser Thr
        275                 280                 285

Gln Asp Phe Met Asp Val Met Gln Ser Val Leu Asp Gly Lys Asn Leu
    290                 295                 300

Gly Gly Tyr Asp Ala Asp Thr Ile Asn Lys Ala Thr Cys Leu Thr Leu
305                 310                 315                 320

Ile Ser Gly Gly Ser Asp Thr Thr Val Val Ser Leu Thr Trp Ala Leu
                325                 330                 335

Ser Leu Val Leu Asn Asn Arg Asp Thr Leu Lys Lys Ala Gln Glu Glu
            340                 345                 350

Leu Asp Ile Gln Val Gly Lys Glu Arg Leu Val Asn Glu Gln Asp Ile
        355                 360                 365

Ser Lys Leu Val Tyr Leu Gln Ala Ile Val Lys Glu Thr Leu Arg Leu
    370                 375                 380

Tyr Pro Pro Gly Pro Leu Gly Gly Leu Arg Gln Phe Thr Glu Asp Cys
385                 390                 395                 400

Thr Leu Gly Gly Tyr His Val Ser Lys Gly Thr Arg Leu Ile Met Asn
                405                 410                 415

Leu Ser Lys Ile Gln Lys Asp Pro Arg Ile Trp Ser Asp Pro Thr Glu
            420                 425                 430

Phe Gln Pro Glu Arg Phe Leu Thr Thr His Lys Asp Val Asp Pro Arg
        435                 440                 445

Gly Lys His Phe Glu Phe Ile Pro Phe Gly Ala Gly Arg Arg Ala Cys
    450                 455                 460

Pro Gly Ile Thr Phe Gly Leu Gln Val Leu His Leu Thr Leu Ala Ser
465                 470                 475                 480

Phe Leu His Ala Phe Glu Phe Ser Thr Pro Ser Asn Glu Gln Val Asn
                485                 490                 495

Met Arg Glu Ser Leu Gly Leu Thr Asn Met Lys Ser Thr Pro Leu Glu
            500                 505                 510

Val Leu Ile Ser Pro Arg Leu Ser Ser Cys Ser Leu Tyr Asn
        515                 520                 525
```

<210> SEQ ID NO 113
<211> LENGTH: 1440

<212> TYPE: DNA
<213> ORGANISM: Artificial Sequence
<220> FEATURE:
<223> OTHER INFORMATION: Codon-optimized KAH

<400> SEQUENCE: 113

```
atggaaccta acttttactt gtcattacta ttgttgttcg tgaccttcat ttctttaagt     60

ctgtttttca tcttttacaa acaaaagtcc ccattgaatt tgccaccagg gaaaatgggt    120

taccctatca taggtgaaag tttagaattc ctatccacag gctggaaggg acatcctgaa    180

aagttcatat ttgatagaat gcgtaagtac agtagtgagt tattcaagac ttctattgta    240

ggcgaatcca cagttgtttg ctgtggggca gctagtaaca aattcctatt ctctaacgaa    300

aacaaactgg taactgcctg gtggccagat tctgttaaca aaatcttccc aacaacttca    360

ctggattcta atttgaagga ggaatctata aagatgagaa agttgctgcc acagttcttc    420

aaaccagaag cacttcaaag atacgtcggc gttatggatg taatcgcaca aagacatttt    480

gtcactcact gggacaacaa aaatgagatc acagtttatc cacttgctaa aagatacact    540

ttcttgcttg cgtgtagact gttcatgtct gttgaggatg aaaatcatgt ggcgaaattc    600

tcagacccat tccaactaat cgctgcaggc atcatttcac ttcctatcga tcttcctggt    660

actccattca acaaggccat aaaggcttca aatttcatta gaaaagagct gataaagatt    720

atcaaacaaa gacgtgttga tctggcagag ggtacagcat ctccaaccca ggatatcttg    780

tcacatatgc tattaacatc tgatgaaaac ggtaaatcta tgaacgagtt gaacattgcc    840

gacaagattc ttggactatt gataggaggc cacgatacag cttcagtagc ttgcacattt    900

ctagtgaagt acttaggaga attaccacat atctacgata aagtctacca agagcaaatg    960

gaaattgcca agtccaaacc tgctggggaa ttgttgaatt gggatgactt gaaaaagatg   1020

aagtattcat ggaatgtggc atgtgaggta atgagattgt caccaccttt acaaggtggt   1080

tttagagagg ctataactga ctttatgttt aacggtttct ctattccaaa agggtggaag   1140

ttatactggt ccgccaactc tacacacaaa aatgcagaat gtttcccaat gcctgagaaa   1200

ttcgatccta ccagatttga aggtaatggt ccagcgcctt atacatttgt accattcggt   1260

ggaggcccta gaatgtgtcc tggaaaggaa tacgctagat tagaaatctt ggttttcatg   1320

cataatctgg tcaaacgttt taagtgggaa aaggttattc cagacgaaaa gattattgtc   1380

gatccattcc caatcccagc taaagatctt ccaatccgtt tgtatcctca caaagcttaa   1440
```

<210> SEQ ID NO 114
<211> LENGTH: 479
<212> TYPE: PRT
<213> ORGANISM: Medicago truncatula

<400> SEQUENCE: 114

```
Met Glu Pro Asn Phe Tyr Leu Ser Leu Leu Leu Leu Phe Val Thr Phe
1               5                   10                  15

Ile Ser Leu Ser Leu Phe Phe Ile Phe Tyr Lys Gln Lys Ser Pro Leu
            20                  25                  30

Asn Leu Pro Pro Gly Lys Met Gly Tyr Pro Ile Ile Gly Glu Ser Leu
        35                  40                  45

Glu Phe Leu Ser Thr Gly Trp Lys Gly His Pro Glu Lys Phe Ile Phe
    50                  55                  60

Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
```

-continued

```
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
        115                 120                 125

Ser Ile Lys Met Arg Lys Leu Leu Pro Gln Phe Phe Lys Pro Glu Ala
    130                 135                 140

Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475
```

<210> SEQ ID NO 115
<211> LENGTH: 1116
<212> TYPE: DNA
<213> ORGANISM: Artificial Sequence
<220> FEATURE:
<223> OTHER INFORMATION: Codon-optimized GGPPS

<400> SEQUENCE: 115
atggcctctg ttactttggg ttcctggatc gtcgtccacc accataacca tcaccatcca 60
tcatctatcc taactaaatc tcgttcaaga tcctgtccta ttacactaac caaaccaatc 120
tcttttcgtt caaagagaac agtttcctct agtagttcta tcgtgtcctc tagtgtcgtc 180
actaaggaag acaatctgag acagtctgaa ccttcttcct ttgatttcat gtcatatatc 240
attactaagg cagaactagt gaataaggct cttgattcag cagttccatt aagagagcca 300
ttgaaaatcc atgaagcaat gagatactct cttctagctg gcgggaagag agtcagacct 360
gtactctgca tagcagcgtg cgaattagtt ggtggcgagg aatcaaccgc tatgcctgcc 420
gcttgtgctg tagaaatgat tcatacaatg tcactgatac acgatgattt gccatgtatg 480
gataacgatg atctgagaag ggtaagcca actaaccata aggttttcgg cgaagatgtt 540
gccgtcttag ctggtgatgc tttgttatct ttcgcgttcg aacatttggc atccgcaaca 600
tcaagtgatg ttgtgtcacc agtaagagta gttagagcag ttggagaact ggctaaagct 660
attggaactg agggtttagt tgcaggtcaa gtcgtcgata tctcttccga aggtcttgat 720
ttgaatgatg taggtcttga acatctcgaa ttcatccatc ttcacaagac agctgcactt 780
ttagaagcca gtgcggttct cggcgcaatt gttggcggag ggagtgatga cgaaattgag 840
agattgagga agtttgctag atgtatagga ttactgttcc aagtagtaga cgatatacta 900
gatgtgacaa agtcttccaa agagttggga aaaacagctg gtaaagattt gattgccgac 960
aaattgacct accctaagat tatggggcta gaaaaatcaa gagaatttgc cgagaaactc 1020
aatagagagg cgcgtgatca actgttgggt ttcgattctg ataaagttgc accactctta 1080
gccttagcca actacatcgc ttacagacaa aactaa 1116

<210> SEQ ID NO 116
<211> LENGTH: 371
<212> TYPE: PRT
<213> ORGANISM: Arabidopsis thaliana

<400> SEQUENCE: 116

Met Ala Ser Val Thr Leu Gly Ser Trp Ile Val Val His His His Asn
1 5 10 15

His His His Pro Ser Ser Ile Leu Thr Lys Ser Arg Ser Arg Ser Cys
20 25 30

Pro Ile Thr Leu Thr Lys Pro Ile Ser Phe Arg Ser Lys Arg Thr Val
35 40 45

Ser Ser Ser Ser Ser Ile Val Ser Ser Ser Val Val Thr Lys Glu Asp
50 55 60

Asn Leu Arg Gln Ser Glu Pro Ser Ser Phe Asp Phe Met Ser Tyr Ile
65 70 75 80

Ile Thr Lys Ala Glu Leu Val Asn Lys Ala Leu Asp Ser Ala Val Pro
85 90 95

Leu Arg Glu Pro Leu Lys Ile His Glu Ala Met Arg Tyr Ser Leu Leu
100 105 110

Ala Gly Gly Lys Arg Val Arg Pro Val Leu Cys Ile Ala Ala Cys Glu
115 120 125

Leu Val Gly Gly Glu Glu Ser Thr Ala Met Pro Ala Ala Cys Ala Val
130 135 140

Glu Met Ile His Thr Met Ser Leu Ile His Asp Asp Leu Pro Cys Met 145 150 155 160

Asp Asn Asp Asp Leu Arg Arg Gly Lys Pro Thr Asn His Lys Val Phe
165 170 175

Gly Glu Asp Val Ala Val Leu Ala Gly Asp Ala Leu Leu Ser Phe Ala
180 185 190

Phe Glu His Leu Ala Ser Ala Thr Ser Ser Asp Val Val Ser Pro Val
195 200 205

Arg Val Val Arg Ala Val Gly Glu Leu Ala Lys Ala Ile Gly Thr Glu
210 215 220

Gly Leu Val Ala Gly Gln Val Val Asp Ile Ser Ser Glu Gly Leu Asp
225 230 235 240

Leu Asn Asp Val Gly Leu Glu His Leu Glu Phe Ile His Leu His Lys
245 250 255

Thr Ala Ala Leu Leu Glu Ala Ser Ala Val Leu Gly Ala Ile Val Gly
260 265 270

Gly Gly Ser Asp Asp Glu Ile Glu Arg Leu Arg Lys Phe Ala Arg Cys
275 280 285

Ile Gly Leu Leu Phe Gln Val Val Asp Asp Ile Leu Asp Val Thr Lys
290 295 300

Ser Ser Lys Glu Leu Gly Lys Thr Ala Gly Lys Asp Leu Ile Ala Asp
305 310 315 320

Lys Leu Thr Tyr Pro Lys Ile Met Gly Leu Glu Lys Ser Arg Glu Phe
325 330 335

Ala Glu Lys Leu Asn Arg Glu Ala Arg Asp Gln Leu Leu Gly Phe Asp
340 345 350

Ser Asp Lys Val Ala Pro Leu Leu Ala Leu Ala Asn Tyr Ile Ala Tyr
355 360 365

Arg Gln Asn
370

<210> SEQ ID NO 117
<211> LENGTH: 511
<212> TYPE: PRT
<213> ORGANISM: Rubus suavissimus

<400> SEQUENCE: 117

Met Ala Thr Leu Leu Glu His Phe Gln Ala Met Pro Phe Ala Ile Pro
1 5 10 15

Ile Ala Leu Ala Ala Leu Ser Trp Leu Phe Leu Phe Tyr Ile Lys Val
20 25 30

Ser Phe Phe Ser Asn Lys Ser Ala Gln Ala Lys Leu Pro Pro Val Pro
35 40 45

Val Val Pro Gly Leu Pro Val Ile Gly Asn Leu Leu Gln Leu Lys Glu
50 55 60

Lys Lys Pro Tyr Gln Thr Phe Thr Arg Trp Ala Glu Glu Tyr Gly Pro
65 70 75 80

Ile Tyr Ser Ile Arg Thr Gly Ala Ser Thr Met Val Val Leu Asn Thr
85 90 95

Thr Gln Val Ala Lys Glu Ala Met Val Thr Arg Tyr Leu Ser Ile Ser
100 105 110

Thr Arg Lys Leu Ser Asn Ala Leu Lys Ile Leu Thr Ala Asp Lys Cys
115 120 125

Met Val Ala Ile Ser Asp Tyr Asn Asp Phe His Lys Met Ile Lys Arg
130 135 140

-continued

```
Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met
    450                 455                 460

Leu Ile Ala Cys Pro Thr Ile Gly Arg Leu Val Gln Glu Phe Glu Trp
465                 470                 475                 480

Lys Leu Arg Asp Gly Glu Glu Glu Asn Val Asp Thr Val Gly Leu Thr
                485                 490                 495

Thr His Lys Arg Tyr Pro Met His Ala Ile Leu Lys Pro Arg Ser
            500                 505                 510
```

<210> SEQ ID NO 118
<211> LENGTH: 1710
<212> TYPE: DNA
<213> ORGANISM: Saccharomyces cerevisiae

<400> SEQUENCE: 118

```
atgtcatttc aaattgaaac ggttcccacc aaaccatatg aagaccaaaa gcctggtacc      60
```

tctggtttgc gtaagaagac aaaggtgttt aaagacgaac ctaactacac agaaaatttc 120
attcaatcga tcatggaagc tattccagag ggttctaaag gtgccactct tgttgtcggt 180
ggtgatgggc gttactacaa tgatgtcatt cttcataaga ttgccgctat cggtgctgcc 240
aacggtatta aaaagttagt tattggccag catggtcttc tgtctacgcc agccgcttct 300
cacatcatga gaacctacga ggaaaaatgt actggtggta ttatcttaac cgcctcacat 360
aatccaggtg gtccagaaaa tgacatgggt attaagtata acttatccaa tgggggtcct 420
gctcctgaat ccgtcacaaa tgctatttgg gagatttcca aaaagcttac cagctataag 480
attatcaaag acttcccaga actagacttg ggtacgatag gcaagaacaa gaaatacggt 540
ccattactcg ttgacattat cgatattaca aaagattatg tcaacttctt gaaggaaatc 600
ttcgatttcg acttaatcaa gaaattcatc gataatcaac gttctactaa gaattggaag 660
ttactgtttg acagtatgaa cggtgtaact ggaccatacg gtaaggctat tttcgttgat 720
gaatttggtt taccggcgga tgaggtttta caaaactggc atccttctcc ggattttggt 780
ggtatgcatc cagatccaaa cttaacttat gccagttcgt tagtgaaaag agtagatcgt 840
gaaaagattg agtttggtgc tgcatccgat ggtgatggtg atagaaatat gatttacggt 900
tacggcccat ctttcgtttc tccaggtgac tccgtcgcaa ttattgccga atatgcagct 960
gaaatcccat atttcgccaa gcaaggtata tatggtctgg cccgttcatt ccctacctca 1020
ggagccatag accgtgttgc caaggcccat ggtctaaact gttatgaggt cccaactggc 1080
tggaaatttt tctgtgcttt gttcgacgct aaaaaattat ctatttgtgg tgaagaatcg 1140
tttggtactg gttccaacca cgtaagggaa aaggacggtg tttgggccat tatggcgtgg 1200
ttgaacatct tggccattta caacaagcat catccggaga acgaagcttc tattaagacg 1260
atacagaatg aattctgggc aaagtacggc cgtactttct tcactcgtta tgattttgaa 1320
aaagttgaaa cagaaaaagc taacaagatt gtcgatcaat tgagagcata tgttaccaaa 1380
tcgggtgttg ttaattccgc cttcccagcc gatgagtctc ttaaggtcac cgattgtggt 1440
gatttttcat acacagattt ggacggttct gtttctgacc atcaaggttt atatgtcaag 1500
ctttccaatg gtgcaagatt cgttctaaga ttgtcaggta caggttcttc aggtgctacc 1560
attagattgt acattgaaaa atactgcgat gataaatcac aataccaaaa gacagctgaa 1620
gaatacttga agccaattat taactcggtc atcaagttct tgaactttaa acaagtttta 1680
ggaactgaag aaccaacggt tcgtacttaa 1710

<210> SEQ ID NO 119
<211> LENGTH: 569
<212> TYPE: PRT
<213> ORGANISM: Saccharomyces cerevisiae

<400> SEQUENCE: 119

Met Ser Phe Gln Ile Glu Thr Val Pro Thr Lys Pro Tyr Glu Asp Gln
1               5                   10                  15

Lys Pro Gly Thr Ser Gly Leu Arg Lys Lys Thr Lys Val Phe Lys Asp
            20                  25                  30

Glu Pro Asn Tyr Thr Glu Asn Phe Ile Gln Ser Ile Met Glu Ala Ile
        35                  40                  45

Pro Glu Gly Ser Lys Gly Ala Thr Leu Val Val Gly Gly Asp Gly Arg
    50                  55                  60

Tyr Tyr Asn Asp Val Ile Leu His Lys Ile Ala Ala Ile Gly Ala Ala
65                  70                  75                  80

-continued

```
Asn Gly Ile Lys Lys Leu Val Ile Gly Gln His Gly Leu Leu Ser Thr
                85                  90                  95

Pro Ala Ala Ser His Ile Met Arg Thr Tyr Glu Glu Lys Cys Thr Gly
            100                 105                 110

Gly Ile Ile Leu Thr Ala Ser His Asn Pro Gly Gly Pro Glu Asn Asp
        115                 120                 125

Met Gly Ile Lys Tyr Asn Leu Ser Asn Gly Gly Pro Ala Pro Glu Ser
    130                 135                 140

Val Thr Asn Ala Ile Trp Glu Ile Ser Lys Lys Leu Thr Ser Tyr Lys
145                 150                 155                 160

Ile Ile Lys Asp Phe Pro Glu Leu Asp Leu Gly Thr Ile Gly Lys Asn
                165                 170                 175

Lys Lys Tyr Gly Pro Leu Leu Val Asp Ile Ile Asp Ile Thr Lys Asp
            180                 185                 190

Tyr Val Asn Phe Leu Lys Glu Ile Phe Asp Phe Asp Leu Ile Lys Lys
        195                 200                 205

Phe Ile Asp Asn Gln Arg Ser Thr Lys Asn Trp Lys Leu Leu Phe Asp
    210                 215                 220

Ser Met Asn Gly Val Thr Gly Pro Tyr Gly Lys Ala Ile Phe Val Asp
225                 230                 235                 240

Glu Phe Gly Leu Pro Ala Asp Glu Val Leu Gln Asn Trp His Pro Ser
                245                 250                 255

Pro Asp Phe Gly Gly Met His Pro Asp Pro Asn Leu Thr Tyr Ala Ser
            260                 265                 270

Ser Leu Val Lys Arg Val Asp Arg Glu Lys Ile Glu Phe Gly Ala Ala
        275                 280                 285

Ser Asp Gly Asp Gly Asp Arg Asn Met Ile Tyr Gly Tyr Gly Pro Ser
    290                 295                 300

Phe Val Ser Pro Gly Asp Ser Val Ala Ile Ile Ala Glu Tyr Ala Ala
305                 310                 315                 320

Glu Ile Pro Tyr Phe Ala Lys Gln Gly Ile Tyr Gly Leu Ala Arg Ser
                325                 330                 335

Phe Pro Thr Ser Gly Ala Ile Asp Arg Val Ala Lys Ala His Gly Leu
            340                 345                 350

Asn Cys Tyr Glu Val Pro Thr Gly Trp Lys Phe Phe Cys Ala Leu Phe
        355                 360                 365

Asp Ala Lys Lys Leu Ser Ile Cys Gly Glu Glu Ser Phe Gly Thr Gly
    370                 375                 380

Ser Asn His Val Arg Glu Lys Asp Gly Val Trp Ala Ile Met Ala Trp
385                 390                 395                 400

Leu Asn Ile Leu Ala Ile Tyr Asn Lys His His Pro Glu Asn Glu Ala
                405                 410                 415

Ser Ile Lys Thr Ile Gln Asn Glu Phe Trp Ala Lys Tyr Gly Arg Thr
            420                 425                 430

Phe Phe Thr Arg Tyr Asp Phe Glu Lys Val Glu Thr Glu Lys Ala Asn
        435                 440                 445

Lys Ile Val Asp Gln Leu Arg Ala Tyr Val Thr Lys Ser Gly Val Val
    450                 455                 460

Asn Ser Ala Phe Pro Ala Asp Glu Ser Leu Lys Val Thr Asp Cys Gly
465                 470                 475                 480

Asp Phe Ser Tyr Thr Asp Leu Asp Gly Ser Val Ser Asp His Gln Gly
                485                 490                 495

Leu Tyr Val Lys Leu Ser Asn Gly Ala Arg Phe Val Leu Arg Leu Ser
```

500 505 510

Gly Thr Gly Ser Ser Gly Ala Thr Ile Arg Leu Tyr Ile Glu Lys Tyr
515 520 525

Cys Asp Asp Lys Ser Gln Tyr Gln Lys Thr Ala Glu Glu Tyr Leu Lys
530 535 540

Pro Ile Ile Asn Ser Val Ile Lys Phe Leu Asn Phe Lys Gln Val Leu
545 550 555 560

Gly Thr Glu Glu Pro Thr Val Arg Thr
565

<210> SEQ ID NO 120
<211> LENGTH: 1500
<212> TYPE: DNA
<213> ORGANISM: Saccharomyces cerevisiae

<400> SEQUENCE: 120
atgtccacta agaagcacac caaaacacat tccacttatg cattcgagag caacacaaac 60
agcgttgctg cctcacaaat gagaaacgcc ttaaacaagt tggcggactc tagtaaactt 120
gacgatgctg ctcgcgctaa gtttgagaac gaactggatt cgtttttcac gcttttcagg 180
agatatttgg tagagaagtc ttctagaacc accttggaat gggacaagat caagtctccc 240
aacccggatg aagtggttaa gtatgaaatt atttctcagc agcccgagaa tgtctcaaac 300
ctttccaaat tggctgtttt gaagttgaac ggtgggctgg gtacctccat gggctgcgtt 360
ggccctaaat ctgttattga agtgagagag ggaaacacct tttggattt gtctgttcgt 420 caaattgaat acttgaacag acagtacgat agcgacgtgc cattgttatt gatgaattct 480
ttcaacactg acaaggatac ggaacacttg attaagaagt attccgctaa cagaatcaga 540
atcagatctt tcaatcaatc caggttccca agagtctaca aggattcttt attgcctgtc 600
cccaccgaat acgattctcc actggatgct tggtatccac caggtcacgg tgatttgttt 660
gaatctttac acgtatctgg tgaactggat gccttaattg cccaaggaag agaaatatta 720
tttgtttcta acggtgacaa cttgggtgct accgtcgact taaaaatttt aaaccacatg 780
atcgagactg gtgccgaata tataatggaa ttgactgata agaccagagc cgatgttaaa 840
ggtggtactt tgatttctta cgatggtcaa gtccgtttat tggaagtcgc ccaagttcca 900
aaagaacaca ttgacgaatt caaaaatatc agaaagttta ccaacttcaa cacgaataac 960
ttatggatca atctgaaagc agtaaagagg ttgatcgaat cgagcaattt ggagatggaa 1020
atcattccaa accaaaaaac tataacaaga gacggtcatg aaattaatgt cttacaatta 1080
gaaaccgctt gtggtgctgc tatcaggcat tttgatggtg ctcacggtgt tgtcgttcca 1140
agatcaagat tcttgcctgt caagacctgt tccgatttgt tgctggttaa atcagatcta 1200
ttccgtctgg aacacggttc tttgaagtta gacccatccc gttttggtcc aaacccatta 1260
atcaagttgg gctcgcattt caaaaaggtt tctggtttta acgcaagaat ccctcacatc 1320
ccaaaaatcg tcgagctaga tcatttgacc atcactggta acgtcttttt aggtaaagat 1380
gtcactttga ggggtactgt catcatcgtt tgctccgacg gtcataaaat cgatattcca 1440
aacggctcca tattggaaaa tgttgtcgtt actggtaatt tgcaaatctt ggaacattga 1500

<210> SEQ ID NO 121
<211> LENGTH: 499
<212> TYPE: PRT
<213> ORGANISM: Saccharomyces cerevisiae

<400> SEQUENCE: 121

-continued

```
Met Ser Thr Lys Lys His Thr Lys Thr His Ser Thr Tyr Ala Phe Glu
1               5                   10                  15

Ser Asn Thr Asn Ser Val Ala Ala Ser Gln Met Arg Asn Ala Leu Asn
            20                  25                  30

Lys Leu Ala Asp Ser Ser Lys Leu Asp Asp Ala Ala Arg Ala Lys Phe
        35                  40                  45

Glu Asn Glu Leu Asp Ser Phe Phe Thr Leu Phe Arg Arg Tyr Leu Val
    50                  55                  60

Glu Lys Ser Ser Arg Thr Thr Leu Glu Trp Asp Lys Ile Lys Ser Pro
65                  70                  75                  80

Asn Pro Asp Glu Val Val Lys Tyr Glu Ile Ile Ser Gln Gln Pro Glu
                85                  90                  95

Asn Val Ser Asn Leu Ser Lys Leu Ala Val Leu Lys Leu Asn Gly Gly
            100                 105                 110

Leu Gly Thr Ser Met Gly Cys Val Gly Pro Lys Ser Val Ile Glu Val
        115                 120                 125

Arg Glu Gly Asn Thr Phe Leu Asp Leu Ser Val Arg Gln Ile Glu Tyr
    130                 135                 140

Leu Asn Arg Gln Tyr Asp Ser Asp Val Pro Leu Leu Leu Met Asn Ser
145                 150                 155                 160

Phe Asn Thr Asp Lys Asp Thr Glu His Leu Ile Lys Lys Tyr Ser Ala
                165                 170                 175

Asn Arg Ile Arg Ile Arg Ser Phe Asn Gln Ser Arg Phe Pro Arg Val
            180                 185                 190

Tyr Lys Asp Ser Leu Leu Pro Val Pro Thr Glu Tyr Asp Ser Pro Leu
        195                 200                 205

Asp Ala Trp Tyr Pro Pro Gly His Gly Asp Leu Phe Glu Ser Leu His
    210                 215                 220

Val Ser Gly Glu Leu Asp Ala Leu Ile Ala Gln Gly Arg Glu Ile Leu
225                 230                 235                 240

Phe Val Ser Asn Gly Asp Asn Leu Gly Ala Thr Val Asp Leu Lys Ile
                245                 250                 255

Leu Asn His Met Ile Glu Thr Gly Ala Glu Tyr Ile Met Glu Leu Thr
            260                 265                 270

Asp Lys Thr Arg Ala Asp Val Lys Gly Gly Thr Leu Ile Ser Tyr Asp
        275                 280                 285

Gly Gln Val Arg Leu Leu Glu Val Ala Gln Val Pro Lys Glu His Ile
    290                 295                 300

Asp Glu Phe Lys Asn Ile Arg Lys Phe Thr Asn Phe Asn Thr Asn Asn
305                 310                 315                 320

Leu Trp Ile Asn Leu Lys Ala Val Lys Arg Leu Ile Glu Ser Ser Asn
                325                 330                 335

Leu Glu Met Glu Ile Ile Pro Asn Gln Lys Thr Ile Thr Arg Asp Gly
            340                 345                 350

His Glu Ile Asn Val Leu Gln Leu Glu Thr Ala Cys Gly Ala Ala Ile
        355                 360                 365

Arg His Phe Asp Gly Ala His Gly Val Val Val Pro Arg Ser Arg Phe
    370                 375                 380

Leu Pro Val Lys Thr Cys Ser Asp Leu Leu Leu Val Lys Ser Asp Leu
385                 390                 395                 400

Phe Arg Leu Glu His Gly Ser Leu Lys Leu Asp Pro Ser Arg Phe Gly
                405                 410                 415
```

```
Pro Asn Pro Leu Ile Lys Leu Gly Ser His Phe Lys Lys Val Ser Gly
            420                 425                 430

Phe Asn Ala Arg Ile Pro His Ile Pro Lys Ile Val Glu Leu Asp His
        435                 440                 445

Leu Thr Ile Thr Gly Asn Val Phe Leu Gly Lys Asp Val Thr Leu Arg
    450                 455                 460

Gly Thr Val Ile Ile Val Cys Ser Asp Gly His Lys Ile Asp Ile Pro
465                 470                 475                 480

Asn Gly Ser Ile Leu Glu Asn Val Val Val Thr Gly Asn Leu Gln Ile
                485                 490                 495

Leu Glu His
```

```
<210> SEQ ID NO 122
<211> LENGTH: 462
<212> TYPE: DNA
<213> ORGANISM: Saccharomyces cerevisiae

<400> SEQUENCE: 122

atgtctagtc aaacagaaag aacttttatt gcggtaaaac cagatggtgt ccagaggggc      60

ttagtatctc aaattctatc tcgttttgaa aaaaaaggtt acaaactagt tgctattaaa     120

ttagttaaag cggatgataa attactagag caacattacg cagagcatgt tggtaaacca     180

tttttcccaa agatggtatc ctttatgaag tctggtccca ttttggccac ggtctgggag     240

ggaaaagatg tggttagaca aggaagaact attcttggtg ctactaatcc tttgggcagt     300

gcaccaggta ccattagagg tgatttcggt attgacctag gcagaaacgt ctgtcacggc     360

agtgattctg ttgatagcgc tgaacgtgaa atcaatttgt ggtttaagaa ggaagagtta     420

gttgattggg aatctaatca agctaagtgg atttatgaat ga                        462
```

```
<210> SEQ ID NO 123
<211> LENGTH: 153
<212> TYPE: PRT
<213> ORGANISM: Saccharomyces cerevisiae

<400> SEQUENCE: 123

Met Ser Ser Gln Thr Glu Arg Thr Phe Ile Ala Val Lys Pro Asp Gly
1               5                   10                  15

Val Gln Arg Gly Leu Val Ser Gln Ile Leu Ser Arg Phe Glu Lys Lys
            20                  25                  30

Gly Tyr Lys Leu Val Ala Ile Lys Leu Val Lys Ala Asp Asp Lys Leu
        35                  40                  45

Leu Glu Gln His Tyr Ala Glu His Val Gly Lys Pro Phe Phe Pro Lys
    50                  55                  60

Met Val Ser Phe Met Lys Ser Gly Pro Ile Leu Ala Thr Val Trp Glu
65                  70                  75                  80

Gly Lys Asp Val Val Arg Gln Gly Arg Thr Ile Leu Gly Ala Thr Asn
                85                  90                  95

Pro Leu Gly Ser Ala Pro Gly Thr Ile Arg Gly Asp Phe Gly Ile Asp
            100                 105                 110

Leu Gly Arg Asn Val Cys His Gly Ser Asp Ser Val Asp Ser Ala Glu
        115                 120                 125

Arg Glu Ile Asn Leu Trp Phe Lys Lys Glu Glu Leu Val Asp Trp Glu
    130                 135                 140

Ser Asn Gln Ala Lys Trp Ile Tyr Glu
145                 150
```

<210> SEQ ID NO 124
<211> LENGTH: 1413
<212> TYPE: DNA
<213> ORGANISM: Stevia rebaudiana

<400> SEQUENCE: 124
atggctgctg ctgatactga aaagttgaac aatttgagat ccgccgtttc tggtttgacc 60
caaatttctg ataacgaaaa gtccggtttc atcaacttgg tcagtagata tttgtctggt 120
gaagctcaac acgttgaatg gtctaaaatt caaactccaa ccgataagat cgttgttcca 180
tacgatactt tgtctgctgt tccagaagat gctgctcaaa caaaatcttt gttggataag 240
ttggtcgtct tgaagttgaa cggtggtttg ggtactacta tgggttgtac tggtccaaag 300
tctgttatcg aagttagaaa cggtttgacc ttcttggatt tgatcgtcat ccaaatcgaa 360
tccttgaaca agaagtacgg ttgttctgtt cctttgttgt tgatgaactc tttcaacacc 420
catgaagata cccaaaagat cgtcgaaaag tactccggtt ctaacattga agttcacacc 480
ttcaatcaat cccaataccc aagattggtt gtcgatgaat tttgccatt gccatctaaa 540 ggtgaaactg gtaaagatgg ttggtatcca ccaggtcatg gtgatgtttt tccatccttg 600
atgaattccg gtaagttgga tgctttgttg tcccaaggta aagaatacgt tttcgttgcc 660
aactctgata acttgggtgc agttgttgat ttgaagatct tgaaccactt gatccaaaac 720
aagaacgaat actgcatgga agttactcca aagactttgg ctgatgttaa gggtggtact 780
ttgatttctt acgatggtaa ggttcaatta ttggaaatcg cccaagttcc agatgaacac 840
gttaatgaat tcaagtccat cgaaaagttt aagatcttta acactaacaa cttgtgggtc 900
aacttgaacg ccattaagag attggttcaa gctgatgctt tgaagatgga aattattcca 960
aatccaaaag aagtcaacgg tgtcaaggta ttgcaattgg aaactgctgc tggtgctgct 1020
attaagtttt tcgataatgc catcggtatc aacgtcccaa gatctagatt tttgcctgtt 1080
aaggcttcct ctgacttgtt gttagttcaa tcagacttgt acaccgaaaa ggatggttac 1140
gttattagaa acccagctag aaaggatcca gctaacccat ctattgaatt gggtccagaa 1200
ttcaaaaagg tcggtgattt cttgaagaga ttcaagtcta tcccatccat catcgaattg 1260
gactcattga aagtttctgg tgatgtctgg tttggttcca acgttgtttt gaaaggtaag 1320
gttgttgttg ctgccaaatc cggtgaaaaa ttggaaattc cagatggtgc cttgattgaa 1380
aacaaagaag ttcatggtgc ctccgacatt tga 1413

<210> SEQ ID NO 125
<211> LENGTH: 470
<212> TYPE: PRT
<213> ORGANISM: Stevia rebaudiana

<400> SEQUENCE: 125

Met Ala Ala Ala Asp Thr Glu Lys Leu Asn Asn Leu Arg Ser Ala Val
1 5 10 15

Ser Gly Leu Thr Gln Ile Ser Asp Asn Glu Lys Ser Gly Phe Ile Asn
20 25 30

Leu Val Ser Arg Tyr Leu Ser Gly Glu Ala Gln His Val Glu Trp Ser
35 40 45

Lys Ile Gln Thr Pro Thr Asp Lys Ile Val Val Pro Tyr Asp Thr Leu
50 55 60

Ser Ala Val Pro Glu Asp Ala Ala Gln Thr Lys Ser Leu Leu Asp Lys
65 70 75 80

```
Leu Val Val Leu Lys Leu Asn Gly Gly Leu Gly Thr Thr Met Gly Cys
                85                  90                  95

Thr Gly Pro Lys Ser Val Ile Glu Val Arg Asn Gly Leu Thr Phe Leu
            100                 105                 110

Asp Leu Ile Val Ile Gln Ile Glu Ser Leu Asn Lys Lys Tyr Gly Cys
        115                 120                 125

Ser Val Pro Leu Leu Leu Met Asn Ser Phe Asn Thr His Glu Asp Thr
    130                 135                 140

Gln Lys Ile Val Glu Lys Tyr Ser Gly Ser Asn Ile Glu Val His Thr
145                 150                 155                 160

Phe Asn Gln Ser Gln Tyr Pro Arg Leu Val Val Asp Glu Phe Leu Pro
                165                 170                 175

Leu Pro Ser Lys Gly Glu Thr Gly Lys Asp Gly Trp Tyr Pro Pro Gly
            180                 185                 190

His Gly Asp Val Phe Pro Ser Leu Met Asn Ser Gly Lys Leu Asp Ala
        195                 200                 205

Leu Leu Ser Gln Gly Lys Glu Tyr Val Phe Val Ala Asn Ser Asp Asn
    210                 215                 220

Leu Gly Ala Val Val Asp Leu Lys Ile Leu Asn His Leu Ile Gln Asn
225                 230                 235                 240

Lys Asn Glu Tyr Cys Met Glu Val Thr Pro Lys Thr Leu Ala Asp Val
                245                 250                 255

Lys Gly Gly Thr Leu Ile Ser Tyr Asp Gly Lys Val Gln Leu Leu Glu
            260                 265                 270

Ile Ala Gln Val Pro Asp Glu His Val Asn Glu Phe Lys Ser Ile Glu
        275                 280                 285

Lys Phe Lys Ile Phe Asn Thr Asn Asn Leu Trp Val Asn Leu Asn Ala
    290                 295                 300

Ile Lys Arg Leu Val Gln Ala Asp Ala Leu Lys Met Glu Ile Ile Pro
305                 310                 315                 320

Asn Pro Lys Glu Val Asn Gly Val Lys Val Leu Gln Leu Glu Thr Ala
                325                 330                 335

Ala Gly Ala Ala Ile Lys Phe Phe Asp Asn Ala Ile Gly Ile Asn Val
            340                 345                 350

Pro Arg Ser Arg Phe Leu Pro Val Lys Ala Ser Ser Asp Leu Leu Leu
        355                 360                 365

Val Gln Ser Asp Leu Tyr Thr Glu Lys Asp Gly Tyr Val Ile Arg Asn
    370                 375                 380

Pro Ala Arg Lys Asp Pro Ala Asn Pro Ser Ile Glu Leu Gly Pro Glu
385                 390                 395                 400

Phe Lys Lys Val Gly Asp Phe Leu Lys Arg Phe Lys Ser Ile Pro Ser
                405                 410                 415

Ile Ile Glu Leu Asp Ser Leu Lys Val Ser Gly Asp Val Trp Phe Gly
            420                 425                 430

Ser Asn Val Val Leu Lys Gly Lys Val Val Val Ala Ala Lys Ser Gly
        435                 440                 445

Glu Lys Leu Glu Ile Pro Asp Gly Ala Leu Ile Glu Asn Lys Glu Val
    450                 455                 460

His Gly Ala Ser Asp Ile
465                 470
```

<210> SEQ ID NO 126
<211> LENGTH: 1551
<212> TYPE: DNA

<213> ORGANISM: Aureobasidium pullulans

<400> SEQUENCE: 126
atgtcctctg aaatggctac tcatttgaaa cctaatggtg gtgccgaatt cgaaaaaaga 60
catcatggta agacccaatc ccatgttgct tttgaaaaca cttctacatc tgttgctgcc 120
tcccaaatga gaaatgcttt gaatactttg tgcgattccg ttactgatcc agctgaaaag 180
caaagattcg aaaccgaaat ggataacttc ttcgccttgt ttagaagata cttgaacgat 240
aaggctaagg gtaacgaaat cgaatggtct agaattgctc caccaaaacc agaacaagtt 300
gttgcttatc aagacttgcc tgaacaagaa tccgttgaat tcttgaacaa attggccgtc 360
ttgaagttga atggtggttt gggtacttct atgggttgtg ttggtccaaa gtctgttatc 420
gaagttagag atggtatgtc cttcttggat ttgtccgtta gacaaatcga atacttgaat 480
agaacctacg gtgttaacgt tccattcgtc ttgatgaatt ctttcaacac tgatgctgat 540
accgccaaca ttatcaaaaa gtacgaaggt cacaacatcg acatcatgac cttcaatcaa 600
tctagatacc caagaatctt gaaggattct ttgttgccag ctccaaaatc tgccaactct 660
caaatttctg attggtatcc accaggtcat ggtgacgttt ttgaatcctt gtacaactct 720
ggtatcttgg ataagttgtt ggaaagaggt gtcgaaatcg ttttcttgtc caatgctgat 780
aatttgggtg ccgttgttga tttgaagatc ttgcaacata tggttgatac caaggccgaa 840
tatatcatgg aattgactga taagactaag gccgatgtta agggtggtac tattattgac 900
tatgaaggtc aagccagatt attggaaatt gcccaagttc caaaagaaca cgtcaacgaa 960
ttcaagtcca tcaagaagtt taagtacttc aacaccaaca acatctggat gaacttgaga 1020
gctgttaaga gaatcgtcga aaacaacgaa ttggccatgg aaattatccc aaacggtaaa 1080
tctattccag ccgacaaaaa aggtgaagcc gatgtttcta tagttcaatt ggaaactgct 1140
gttggtgctg ccattagaca ttttaacaat gctcatggtg tcaacgtccc aagaagaaga 1200
tttttgccag ttaagacctg ctccgatttg atgttggtta agtctgactt gtacactttg 1260
aagcacggtc aattgattat ggacccaaat agatttggtc cagccccatt gattaagttg 1320
ggtggtgatt ttaagaaggt ttcctcattc caatccagaa tcccatccat tcctaaaatc 1380
ttggaattgg atcatttgac cattaccggt ccagttaact tgggtagagg tgttactttt 1440
aagggtactg ttattatcgt tgcctccgaa ggtcaaacca ttgatattcc acctggttcc 1500
attttggaaa acgttgttgt tcaaggttcc ttgagattat tagaacatta a 1551

<210> SEQ ID NO 127
<211> LENGTH: 516
<212> TYPE: PRT
<213> ORGANISM: Aureobasidium pullulans

<400> SEQUENCE: 127

Met Ser Ser Glu Met Ala Thr His Leu Lys Pro Asn Gly Gly Ala Glu
1 5 10 15

Phe Glu Lys Arg His His Gly Lys Thr Gln Ser His Val Ala Phe Glu
20 25 30

Asn Thr Ser Thr Ser Val Ala Ala Ser Gln Met Arg Asn Ala Leu Asn
35 40 45

Thr Leu Cys Asp Ser Val Thr Asp Pro Ala Glu Lys Gln Arg Phe Glu
50 55 60

Thr Glu Met Asp Asn Phe Phe Ala Leu Phe Arg Arg Tyr Leu Asn Asp
65 70 75 80

-continued

```
Lys Ala Lys Gly Asn Glu Ile Glu Trp Ser Arg Ile Ala Pro Pro Lys
                85                  90                  95

Pro Glu Gln Val Val Ala Tyr Gln Asp Leu Pro Glu Gln Glu Ser Val
            100                 105                 110

Glu Phe Leu Asn Lys Leu Ala Val Leu Lys Leu Asn Gly Gly Leu Gly
        115                 120                 125

Thr Ser Met Gly Cys Val Gly Pro Lys Ser Val Ile Glu Val Arg Asp
    130                 135                 140

Gly Met Ser Phe Leu Asp Leu Ser Val Arg Gln Ile Glu Tyr Leu Asn
145                 150                 155                 160

Arg Thr Tyr Gly Val Asn Val Pro Phe Val Leu Met Asn Ser Phe Asn
                165                 170                 175

Thr Asp Ala Asp Thr Ala Asn Ile Ile Lys Lys Tyr Glu Gly His Asn
            180                 185                 190

Ile Asp Ile Met Thr Phe Asn Gln Ser Arg Tyr Pro Arg Ile Leu Lys
        195                 200                 205

Asp Ser Leu Leu Pro Ala Pro Lys Ser Ala Asn Ser Gln Ile Ser Asp
    210                 215                 220

Trp Tyr Pro Pro Gly His Gly Asp Val Phe Glu Ser Leu Tyr Asn Ser
225                 230                 235                 240

Gly Ile Leu Asp Lys Leu Leu Glu Arg Gly Val Glu Ile Val Phe Leu
                245                 250                 255

Ser Asn Ala Asp Asn Leu Gly Ala Val Val Asp Leu Lys Ile Leu Gln
            260                 265                 270

His Met Val Asp Thr Lys Ala Glu Tyr Ile Met Glu Leu Thr Asp Lys
        275                 280                 285

Thr Lys Ala Asp Val Lys Gly Gly Thr Ile Ile Asp Tyr Glu Gly Gln
    290                 295                 300

Ala Arg Leu Leu Glu Ile Ala Gln Val Pro Lys Glu His Val Asn Glu
305                 310                 315                 320

Phe Lys Ser Ile Lys Lys Phe Lys Tyr Phe Asn Thr Asn Asn Ile Trp
                325                 330                 335

Met Asn Leu Arg Ala Val Lys Arg Ile Val Glu Asn Asn Glu Leu Ala
            340                 345                 350

Met Glu Ile Ile Pro Asn Gly Lys Ser Ile Pro Ala Asp Lys Lys Gly
        355                 360                 365

Glu Ala Asp Val Ser Ile Val Gln Leu Glu Thr Ala Val Gly Ala Ala
    370                 375                 380

Ile Arg His Phe Asn Asn Ala His Gly Val Asn Val Pro Arg Arg Arg
385                 390                 395                 400

Phe Leu Pro Val Lys Thr Cys Ser Asp Leu Met Leu Val Lys Ser Asp
                405                 410                 415

Leu Tyr Thr Leu Lys His Gly Gln Leu Ile Met Asp Pro Asn Arg Phe
            420                 425                 430

Gly Pro Ala Pro Leu Ile Lys Leu Gly Gly Asp Phe Lys Lys Val Ser
        435                 440                 445

Ser Phe Gln Ser Arg Ile Pro Ser Ile Pro Lys Ile Leu Glu Leu Asp
    450                 455                 460

His Leu Thr Ile Thr Gly Pro Val Asn Leu Gly Arg Gly Val Thr Phe
465                 470                 475                 480

Lys Gly Thr Val Ile Ile Val Ala Ser Glu Gly Gln Thr Ile Asp Ile
                485                 490                 495

Pro Pro Gly Ser Ile Leu Glu Asn Val Val Val Gln Gly Ser Leu Arg
```

```
        500                 505                 510

Leu Leu Glu His
        515


<210> SEQ ID NO 128
<211> LENGTH: 1410
<212> TYPE: DNA
<213> ORGANISM: Arabidopsis thaliana

<400> SEQUENCE: 128

atggctgcta ctactgaaaa cttgccacaa ttgaaatctg ccgttgatgg tttgactgaa      60

atgtccgaat ctgaaaagtc cggtttcatc tctttggtca gtagatattt gtctggtgaa     120

gcccaacata tcgaatggtc taaaattcaa actccaaccg acgaaatcgt tgtcccatac     180

gaaaaaatga ctccagtttc tcaagatgtc gccgaaacta agaatttgtt ggataagttg     240

gtcgtcttga agttgaatgg tggtttgggt actactatgg gttgtactgg tccaaagtct     300

gttatcgaag ttagagatgg tttaaccttc ttggacttga tcgtcatcca aatcgaaaac     360

ttgaacaaca agtacggttg caaggttcca ttggtcttga tgaattcttt caacacccat     420

gatgataccc acaagatcgt tgaaaagtac accaactcca acgttgatat ccacaccttc     480

aatcaatcta agtacccaag agttgttgcc gatgaatttg ttccatggcc atctaaaggt     540

aagactgaca aagaaggttg gtatccacca ggtcatggtg atgtttttcc agctttaatg     600

aactccggta agttggatac tttcttgtcc caaggtaaag aatacgtttt cgttgccaac     660

tctgataact tgggtgctat agttgatttg accatcttga agcacttgat ccaaaaacaag    720

aacgaatact gcatggaagt tactccaaag actttggctg atgttaaggg tggtactttg     780

atttcttacg aaggtaaggt tcaattattg gaaatcgccc aagttccaga tgaacacgtt     840

aatgaattca agtccatcga aaagttcaag atcttcaaca ccaacaactt gtgggttaac     900

ttgaaggcca tcaagaaatt ggttgaagct gatgctttga agatggaaat tatcccaaac     960

ccaaaagaag ttgacggtgt taaggtattg caattggaaa ctgctgctgg tgctgctatt    1020

agatttttcg ataatgccat cggtgttaac gtcccaagat ctagattttt gccagttaag    1080

gcttcctccg atttgttgtt ggttcaatct gacttgtaca ccttggttga cggttttgtt    1140

acaagaaaca aggctagaac taacccatcc aacccatcta ttgaattggg tccagaattc    1200

aaaaaggttg ccacattctt gtccagattc aagtctattc catccatcgt cgaattggac    1260

tcattgaaag tttctggtga tgtctggttt ggttcctcta tagttttgaa gggtaaggtt    1320

actgttgctg ctaaatctgg tgttaagttg gaaattccag atagagccgt tgtcgaaaac    1380

aaaaacatta acggtcctga agatttgtga                                     1410


<210> SEQ ID NO 129
<211> LENGTH: 469
<212> TYPE: PRT
<213> ORGANISM: Arabidopsis thaliana

<400> SEQUENCE: 129

Met Ala Ala Thr Thr Glu Asn Leu Pro Gln Leu Lys Ser Ala Val Asp
1               5                   10                  15

Gly Leu Thr Glu Met Ser Glu Ser Glu Lys Ser Gly Phe Ile Ser Leu
            20                  25                  30

Val Ser Arg Tyr Leu Ser Gly Glu Ala Gln His Ile Glu Trp Ser Lys
        35                  40                  45

Ile Gln Thr Pro Thr Asp Glu Ile Val Val Pro Tyr Glu Lys Met Thr
```

-continued

```
    50                  55                  60

Pro Val Ser Gln Asp Val Ala Glu Thr Lys Asn Leu Leu Asp Lys Leu
65                  70                  75                  80

Val Val Leu Lys Leu Asn Gly Gly Leu Gly Thr Thr Met Gly Cys Thr
                85                  90                  95

Gly Pro Lys Ser Val Ile Glu Val Arg Asp Gly Leu Thr Phe Leu Asp
            100                 105                 110

Leu Ile Val Ile Gln Ile Glu Asn Leu Asn Asn Lys Tyr Gly Cys Lys
        115                 120                 125

Val Pro Leu Val Leu Met Asn Ser Phe Asn Thr His Asp Asp Thr His
    130                 135                 140

Lys Ile Val Glu Lys Tyr Thr Asn Ser Asn Val Asp Ile His Thr Phe
145                 150                 155                 160

Asn Gln Ser Lys Tyr Pro Arg Val Val Ala Asp Glu Phe Val Pro Trp
                165                 170                 175

Pro Ser Lys Gly Lys Thr Asp Lys Glu Gly Trp Tyr Pro Pro Gly His
            180                 185                 190

Gly Asp Val Phe Pro Ala Leu Met Asn Ser Gly Lys Leu Asp Thr Phe
        195                 200                 205

Leu Ser Gln Gly Lys Glu Tyr Val Phe Val Ala Asn Ser Asp Asn Leu
    210                 215                 220

Gly Ala Ile Val Asp Leu Thr Ile Leu Lys His Leu Ile Gln Asn Lys
225                 230                 235                 240

Asn Glu Tyr Cys Met Glu Val Thr Pro Lys Thr Leu Ala Asp Val Lys
                245                 250                 255

Gly Gly Thr Leu Ile Ser Tyr Glu Gly Lys Val Gln Leu Leu Glu Ile
            260                 265                 270

Ala Gln Val Pro Asp Glu His Val Asn Glu Phe Lys Ser Ile Glu Lys
        275                 280                 285

Phe Lys Ile Phe Asn Thr Asn Asn Leu Trp Val Asn Leu Lys Ala Ile
    290                 295                 300

Lys Lys Leu Val Glu Ala Asp Ala Leu Lys Met Glu Ile Ile Pro Asn
305                 310                 315                 320

Pro Lys Glu Val Asp Gly Val Lys Val Leu Gln Leu Glu Thr Ala Ala
                325                 330                 335

Gly Ala Ala Ile Arg Phe Phe Asp Asn Ala Ile Gly Val Asn Val Pro
            340                 345                 350

Arg Ser Arg Phe Leu Pro Val Lys Ala Ser Ser Asp Leu Leu Leu Val
        355                 360                 365

Gln Ser Asp Leu Tyr Thr Leu Val Asp Gly Phe Val Thr Arg Asn Lys
    370                 375                 380

Ala Arg Thr Asn Pro Ser Asn Pro Ser Ile Glu Leu Gly Pro Glu Phe
385                 390                 395                 400

Lys Lys Val Ala Thr Phe Leu Ser Arg Phe Lys Ser Ile Pro Ser Ile
                405                 410                 415

Val Glu Leu Asp Ser Leu Lys Val Ser Gly Asp Val Trp Phe Gly Ser
            420                 425                 430

Ser Ile Val Leu Lys Gly Lys Val Thr Val Ala Ala Lys Ser Gly Val
        435                 440                 445

Lys Leu Glu Ile Pro Asp Arg Ala Val Val Glu Asn Lys Asn Ile Asn
    450                 455                 460

Gly Pro Glu Asp Leu
465
```

<210> SEQ ID NO 130
<211> LENGTH: 909
<212> TYPE: DNA
<213> ORGANISM: Escherichia coli

<400> SEQUENCE: 130
atggctgcta ttaacaccaa ggttaagaag gctgttattc cagttgctgg tttgggtact 60
agaatgttgc cagctacaaa agccattcca aaagaaatgt taccattggt cgataagcca 120
ttgatccaat acgttgtcaa cgaatgtatt gctgctggta ttaccgaaat cgttttggtt 180
actcactcct ccaagaactc cattgaaaat catttcgaca cctcattcga attggaagcc 240
atgttggaaa agagagtcaa gagacaatta ttggacgaag tccaatctat ttgcccacca 300
catgttacta tcatgcaagt tagacaaggt ttggctaaag gtttgggtca tgctgttttg 360
tgtgctcatc cagttgttgg tgatgaacca gttgcagtta ttttgccaga tgttatcttg 420
gacgaatacg aatccgattt gtctcaagat aacttggctg aaatgatcag aagattcgac 480
gaaactggtc actcccaaat tatggttgaa cctgttgctg atgttactgc ttatggtgtt 540
gttgattgca agggtgttga attggctcca ggtgaatctg ttccaatggt tggtgttgta 600
gaaaagccaa aagctgatgt tgctccatct aatttggcta tcgttggtag atatgttttg 660
tccgctgata tttggccttt gttggctaaa actccaccag gtgctggtga cgaaattcaa 720
ttgactgatg ctatcgacat gttgatcgaa aaagaaaccg ttgaagccta ccacatgaag 780
ggtaaatctc atgattgtgg taacaagttg ggttacatgc aagcttttgt tgaatacggt 840
atcagacata acaccttagg tactgaattc aaggcttggt tggaagaaga aatgggtatc 900
aagaagtaa 909

<210> SEQ ID NO 131
<211> LENGTH: 302
<212> TYPE: PRT
<213> ORGANISM: Escherichia coli

<400> SEQUENCE: 131

Met Ala Ala Ile Asn Thr Lys Val Lys Lys Ala Val Ile Pro Val Ala
1 5 10 15

Gly Leu Gly Thr Arg Met Leu Pro Ala Thr Lys Ala Ile Pro Lys Glu
20 25 30

Met Leu Pro Leu Val Asp Lys Pro Leu Ile Gln Tyr Val Val Asn Glu
35 40 45

Cys Ile Ala Ala Gly Ile Thr Glu Ile Val Leu Val Thr His Ser Ser
50 55 60

Lys Asn Ser Ile Glu Asn His Phe Asp Thr Ser Phe Glu Leu Glu Ala
65 70 75 80

Met Leu Glu Lys Arg Val Lys Arg Gln Leu Leu Asp Glu Val Gln Ser
85 90 95

Ile Cys Pro Pro His Val Thr Ile Met Gln Val Arg Gln Gly Leu Ala
100 105 110

Lys Gly Leu Gly His Ala Val Leu Cys Ala His Pro Val Val Gly Asp
115 120 125

Glu Pro Val Ala Val Ile Leu Pro Asp Val Ile Leu Asp Glu Tyr Glu
130 135 140

Ser Asp Leu Ser Gln Asp Asn Leu Ala Glu Met Ile Arg Arg Phe Asp
145 150 155 160

```
Glu Thr Gly His Ser Gln Ile Met Val Glu Pro Val Ala Asp Val Thr
                165                 170                 175

Ala Tyr Gly Val Val Asp Cys Lys Gly Val Glu Leu Ala Pro Gly Glu
            180                 185                 190

Ser Val Pro Met Val Gly Val Val Glu Lys Pro Lys Ala Asp Val Ala
        195                 200                 205

Pro Ser Asn Leu Ala Ile Val Gly Arg Tyr Val Leu Ser Ala Asp Ile
    210                 215                 220

Trp Pro Leu Leu Ala Lys Thr Pro Pro Gly Ala Gly Asp Glu Ile Gln
225                 230                 235                 240

Leu Thr Asp Ala Ile Asp Met Leu Ile Glu Lys Glu Thr Val Glu Ala
                245                 250                 255

Tyr His Met Lys Gly Lys Ser His Asp Cys Gly Asn Lys Leu Gly Tyr
            260                 265                 270

Met Gln Ala Phe Val Glu Tyr Gly Ile Arg His Asn Thr Leu Gly Thr
        275                 280                 285

Glu Phe Lys Ala Trp Leu Glu Glu Glu Met Gly Ile Lys Lys
    290                 295                 300


<210> SEQ ID NO 132
<211> LENGTH: 1416
<212> TYPE: DNA
<213> ORGANISM: Rubus suavissimus

<400> SEQUENCE: 132

atggctgctg ttgctactga taagatctct aagttgaagt ctgaagttgc tgccttgtcc      60

caaatttctg aaaacgaaaa gtccggtttc atcaacttgg tcagtagata tttgtctggt     120

actgaagcta ctcacgttga atggtctaaa attcaaactc caaccgatga agttgttgtt     180

ccatatgata ctttggctcc aactccagaa gatccagctg aaactaagaa gttgttagat     240

aagttggtcg tcttgaagtt gaacggtggt ttgggtacta ctatgggttg tactggtcca     300

aagtctgtta tcgaagttag aaacggtttg accttcttgg atttgatcgt cattcaaatc     360

gaaaccttga acaacaagta cggttgtaac gttcctttgt tgttgatgaa ctctttcaac     420

acccatgatg acaccttcaa gatcgttgaa agatacacca agtccaacgt tcaaatccat     480

accttcaatc aatcccaata cccaagattg gttgtcgaag ataattctcc attgccatct     540

aagggtcaaa ctggtaaaga tggttggtat ccaccaggtc atggtgatgt ttttccatct     600

ttgagaaact ccggtaagtt ggatttgttg ttatcccaag gtaaagaata cgttttcatc     660

tccaactctg ataacttggg tgcagttgtt gatttgaaga tcttgtccca tttggtccaa     720

aaaaagaacg aatactgcat ggaagttacc ccaaaaactt tggctgatgt taagggtggt     780

actttgattt cttacgaagg tagaacccaa ttattggaaa ttgcccaagt tccagatcaa     840

cacgttaacg aattcaagtc catcgaaaag ttcaagatct ttaacaccaa caatttgtgg     900

gtcaacttga acgccattaa gagattagtt gaagctgatg ccttgaaaat ggaaatcatc     960

ccaaatccaa aagaagtcga cggtattaag gtcttgcaat tggaaactgc tgctggtgct    1020

gctattagat tttcaatca tgccatcggt atcaacgtcc caagatctag atttttgcca    1080

gttaaggcta cctccgattt gttattggtt caatctgact tgtacaccgt cgaagatggt    1140

ttcgttatta gaaacactgc tagaaagaat ccagccaacc catctgttga attgggtcca    1200

gaattcaaaa aggttgccaa cttcttgtcc agattcaagt ctattccatc catcatcgaa    1260

ttggactcat tgaaggttgt tggtgatgta tggtttggtg ctggtgttgt tttgaaaggt    1320
```

```
aaggttacta ttactgctaa gccaggtgtt aagttggaaa ttccagataa ggctgtcttg   1380

gaaaacaagg atattaacgg tcctgaagat ttgtga                             1416


<210> SEQ ID NO 133
<211> LENGTH: 471
<212> TYPE: PRT
<213> ORGANISM: Rubus suavissimus

<400> SEQUENCE: 133

Met Ala Ala Val Ala Thr Asp Lys Ile Ser Lys Leu Lys Ser Glu Val
1               5                   10                  15

Ala Ala Leu Ser Gln Ile Ser Glu Asn Glu Lys Ser Gly Phe Ile Asn
            20                  25                  30

Leu Val Ser Arg Tyr Leu Ser Gly Thr Glu Ala Thr His Val Glu Trp
        35                  40                  45

Ser Lys Ile Gln Thr Pro Thr Asp Glu Val Val Val Pro Tyr Asp Thr
    50                  55                  60

Leu Ala Pro Thr Pro Glu Asp Pro Ala Glu Thr Lys Lys Leu Leu Asp
65                  70                  75                  80

Lys Leu Val Val Leu Lys Leu Asn Gly Gly Leu Gly Thr Thr Met Gly
                85                  90                  95

Cys Thr Gly Pro Lys Ser Val Ile Glu Val Arg Asn Gly Leu Thr Phe
            100                 105                 110

Leu Asp Leu Ile Val Ile Gln Ile Glu Thr Leu Asn Asn Lys Tyr Gly
        115                 120                 125

Cys Asn Val Pro Leu Leu Leu Met Asn Ser Phe Asn Thr His Asp Asp
    130                 135                 140

Thr Phe Lys Ile Val Glu Arg Tyr Thr Lys Ser Asn Val Gln Ile His
145                 150                 155                 160

Thr Phe Asn Gln Ser Gln Tyr Pro Arg Leu Val Val Glu Asp Asn Ser
                165                 170                 175

Pro Leu Pro Ser Lys Gly Gln Thr Gly Lys Asp Gly Trp Tyr Pro Pro
            180                 185                 190

Gly His Gly Asp Val Phe Pro Ser Leu Arg Asn Ser Gly Lys Leu Asp
        195                 200                 205

Leu Leu Leu Ser Gln Gly Lys Glu Tyr Val Phe Ile Ser Asn Ser Asp
    210                 215                 220

Asn Leu Gly Ala Val Val Asp Leu Lys Ile Leu Ser His Leu Val Gln
225                 230                 235                 240

Lys Lys Asn Glu Tyr Cys Met Glu Val Thr Pro Lys Thr Leu Ala Asp
                245                 250                 255

Val Lys Gly Gly Thr Leu Ile Ser Tyr Glu Gly Arg Thr Gln Leu Leu
            260                 265                 270

Glu Ile Ala Gln Val Pro Asp Gln His Val Asn Glu Phe Lys Ser Ile
        275                 280                 285

Glu Lys Phe Lys Ile Phe Asn Thr Asn Asn Leu Trp Val Asn Leu Asn
    290                 295                 300

Ala Ile Lys Arg Leu Val Glu Ala Asp Ala Leu Lys Met Glu Ile Ile
305                 310                 315                 320

Pro Asn Pro Lys Glu Val Asp Gly Ile Lys Val Leu Gln Leu Glu Thr
                325                 330                 335

Ala Ala Gly Ala Ala Ile Arg Phe Phe Asn His Ala Ile Gly Ile Asn
            340                 345                 350

Val Pro Arg Ser Arg Phe Leu Pro Val Lys Ala Thr Ser Asp Leu Leu
```

```
        355                 360                 365

Leu Val Gln Ser Asp Leu Tyr Thr Val Glu Asp Gly Phe Val Ile Arg
    370                 375                 380

Asn Thr Ala Arg Lys Asn Pro Ala Asn Pro Ser Val Glu Leu Gly Pro
385                 390                 395                 400

Glu Phe Lys Lys Val Ala Asn Phe Leu Ser Arg Phe Lys Ser Ile Pro
                405                 410                 415

Ser Ile Ile Glu Leu Asp Ser Leu Lys Val Val Gly Asp Val Trp Phe
            420                 425                 430

Gly Ala Gly Val Val Leu Lys Gly Lys Val Thr Ile Thr Ala Lys Pro
        435                 440                 445

Gly Val Lys Leu Glu Ile Pro Asp Lys Ala Val Leu Glu Asn Lys Asp
    450                 455                 460

Ile Asn Gly Pro Glu Asp Leu
465                 470
```

<210> SEQ ID NO 134
<211> LENGTH: 1422
<212> TYPE: DNA
<213> ORGANISM: Hordeum vulgare

<400> SEQUENCE: 134

```
atggctgctg ctgcagttgc tgctgattct aaaattgatg gtttgagaga tgctgttgcc      60

aagttgggtg aaatttctga aaacgaaaag gccggtttca tctccttggt ttctagatat     120

ttgtctggtg aagccgaaca aatcgaatgg tctaaaattc aaactccaac cgatgaagtt     180

gttgttccat atgatacttt ggctccacca cctgaagatt tggatgctat gaaggctttg     240

ttggataagt tggttgtctt gaagttgaat ggtggtttgg gtactactat gggttgtact     300

ggtccaaagt ctgttatcga agttagaaac ggtttcacct tcttggattt gatcgttatc     360

caaattgaat ccttgaacaa gaagtacggt tgctctgttc ctttgttgtt gatgaactct     420

ttcaacaccc atgatgacac ccaaaagatc gttgaaaagt actccaactc caacatcgaa     480

atccacacct tcaatcaatc tcaataccca agaatcgtca ccgaagattt tttgccattg     540

ccatctaaag gtcaaactgg taaagatggt tggtatccac caggtcatgg tgatgttttt     600

ccatctttga acaactccgg taagttggat accttgttgt ctcaaggtaa agaatacgtt     660

ttcgttgcca actctgataa cttgggtgct atcgttgata ttaagatctt gaaccacttg     720

atccacaatc aaaacgaata ctgcatggaa gttactccaa agactttggc tgatgttaag     780

ggtggtactt tgatttctta cgaaggtaga gttcaattat tggaaatcgc ccaagttcca     840

gatgaacacg ttgatgaatt caagtccatc gaaaagttca aaatcttcaa caccaacaac     900

ttgtgggtta acttgaaggc cattaagaga ttggttgatg ctgaagcttt gaaaatggaa     960

atcatcccaa accctaaaga agttgacggt gttaaggtat tgcaattgga aactgctgct    1020

ggtgctgcta ttagattctt tgaaaaagcc atcggtatca acgtcccaag atctagattt    1080

ttgccagtta aggctacctc tgacttgttg ttggttcaat cagacttgta caccttggtt    1140

gacggttacg ttattagaaa tccagctaga gttaagccat ccaacccatc tattgaattg    1200

ggtccagaat tcaagaaggt cgctaatttc ttggctagat tcaagtctat cccatccatc    1260

gttgaattgg actcattgaa agtttctggt gatgtctctt ttggttccgg tgttgttttg    1320

aagggtaatg ttactattgc tgctaaggct ggtgttaagt tggaaattcc agatggtgct    1380

gttttggaaa acaaggatat taacggtcca gaagatattt ga                        1422
```

<210> SEQ ID NO 135
<211> LENGTH: 473
<212> TYPE: PRT
<213> ORGANISM: Hordeum vulgare

<400> SEQUENCE: 135

Met Ala Ala Ala Ala Val Ala Ala Asp Ser Lys Ile Asp Gly Leu Arg
1               5                   10                  15

Asp Ala Val Ala Lys Leu Gly Glu Ile Ser Glu Asn Glu Lys Ala Gly
            20                  25                  30

Phe Ile Ser Leu Val Ser Arg Tyr Leu Ser Gly Glu Ala Glu Gln Ile
        35                  40                  45

Glu Trp Ser Lys Ile Gln Thr Pro Thr Asp Glu Val Val Val Pro Tyr
    50                  55                  60

Asp Thr Leu Ala Pro Pro Pro Glu Asp Leu Asp Ala Met Lys Ala Leu
65                  70                  75                  80

Leu Asp Lys Leu Val Val Leu Lys Leu Asn Gly Gly Leu Gly Thr Thr
                85                  90                  95

Met Gly Cys Thr Gly Pro Lys Ser Val Ile Glu Val Arg Asn Gly Phe
            100                 105                 110

Thr Phe Leu Asp Leu Ile Val Ile Gln Ile Glu Ser Leu Asn Lys Lys
        115                 120                 125

Tyr Gly Cys Ser Val Pro Leu Leu Leu Met Asn Ser Phe Asn Thr His
    130                 135                 140

Asp Asp Thr Gln Lys Ile Val Glu Lys Tyr Ser Asn Ser Asn Ile Glu
145                 150                 155                 160

Ile His Thr Phe Asn Gln Ser Gln Tyr Pro Arg Ile Val Thr Glu Asp
                165                 170                 175

Phe Leu Pro Leu Pro Ser Lys Gly Gln Thr Gly Lys Asp Gly Trp Tyr
            180                 185                 190

Pro Pro Gly His Gly Asp Val Phe Pro Ser Leu Asn Asn Ser Gly Lys
        195                 200                 205

Leu Asp Thr Leu Leu Ser Gln Gly Lys Glu Tyr Val Phe Val Ala Asn
    210                 215                 220

Ser Asp Asn Leu Gly Ala Ile Val Asp Ile Lys Ile Leu Asn His Leu
225                 230                 235                 240

Ile His Asn Gln Asn Glu Tyr Cys Met Glu Val Thr Pro Lys Thr Leu
                245                 250                 255

Ala Asp Val Lys Gly Gly Thr Leu Ile Ser Tyr Glu Gly Arg Val Gln
            260                 265                 270

Leu Leu Glu Ile Ala Gln Val Pro Asp Glu His Val Asp Glu Phe Lys
        275                 280                 285

Ser Ile Glu Lys Phe Lys Ile Phe Asn Thr Asn Asn Leu Trp Val Asn
    290                 295                 300

Leu Lys Ala Ile Lys Arg Leu Val Asp Ala Glu Ala Leu Lys Met Glu
305                 310                 315                 320

Ile Ile Pro Asn Pro Lys Glu Val Asp Gly Val Lys Val Leu Gln Leu
                325                 330                 335

Glu Thr Ala Ala Gly Ala Ala Ile Arg Phe Phe Glu Lys Ala Ile Gly
            340                 345                 350

Ile Asn Val Pro Arg Ser Arg Phe Leu Pro Val Lys Ala Thr Ser Asp
        355                 360                 365

Leu Leu Leu Val Gln Ser Asp Leu Tyr Thr Leu Val Asp Gly Tyr Val
    370                 375                 380

Ile Arg Asn Pro Ala Arg Val Lys Pro Ser Asn Pro Ser Ile Glu Leu
385 390 395 400

Gly Pro Glu Phe Lys Lys Val Ala Asn Phe Leu Ala Arg Phe Lys Ser
405 410 415

Ile Pro Ser Ile Val Glu Leu Asp Ser Leu Lys Val Ser Gly Asp Val
420 425 430

Ser Phe Gly Ser Gly Val Val Leu Lys Gly Asn Val Thr Ile Ala Ala
435 440 445

Lys Ala Gly Val Lys Leu Glu Ile Pro Asp Gly Ala Val Leu Glu Asn
450 455 460

Lys Asp Ile Asn Gly Pro Glu Asp Ile
465 470

<210> SEQ ID NO 136
<211> LENGTH: 1404
<212> TYPE: DNA
<213> ORGANISM: Oryza sativa

<400> SEQUENCE: 136
atggctgacg aaaaattggc caaattgaga gaagctgttg ctggtttgtc tcaaatctct 60
gataacgaaa agtccggttt catttccttg gttgctagat atttgtccgg tgaagaagaa 120
catgttgaat gggctaaaat tcatacccca accgatgaag ttgttgttcc atatgatact 180
ttggaagctc caccagaaga tttggaagaa acaaaaaagt tgttgaacaa gttggccgtc 240
ttgaagttga atggtggttt gggtactact atgggttgta ctggtccaaa gtctgttatc 300
gaagttagaa acggtttcac cttcttggat ttgatcgtca tccaaatcga atccttgaac 360
aaaaagtacg gttccaacgt tcctttgttg ttgatgaact ctttcaacac ccatgaagat 420
accttgaaga tcgttgaaaa gtacaccaac tccaacatcg aagttcacac cttcaatcaa 480
tctcaatacc caagagttgt tgccgatgaa tttttgccat ggccatctaa aggtaagact 540
tgtaaagatg gttggtatcc accaggtcat ggtgatattt ttccatcctt gatgaacagt 600
ggtaagttgg acttgttgtt gtcccaaggt aaagaatacg ttttcattgc caactccgat 660
aacttgggtg ctatagttga tatgaagatt ttgaaccact tgatccacaa gcaaaacgaa 720
tactgtatgg aagttactcc aaagactttg gctgatgtta agggtggtac tttgatctct 780
tacgaagata aggttcaatt attggaaatc gcccaagttc cagatgctca tgttaatgaa 840
ttcaagtcca tcgaaaagtt caagatcttt aacaccaaca acttgtgggt taacttgaag 900
gccattaaga gattagttga agctgacgct ttgaagatgg aaattatccc aaacccaaaa 960
gaagttgacg gtgttaaggt attgcaattg gaaactgctg ctggtgctgc tattagattt 1020
ttcgatcatg ctatcggtat caacgtccca agatctagat ttttaccagt taaggctacc 1080
tccgacttgc aattagttca atctgacttg tacaccttgg ttgatggttt cgttactaga 1140
aatccagcta gaactaatcc atccaaccca tctattgaat tgggtccaga attcaagaag 1200
gttggttgtt ttttgggtag attcaagtct atcccatcca tcgttgaatt ggacactttg 1260
aaagtttctg gtgatgtttg gttcggttcc tccattacat tgaaaggtaa ggttactatt 1320
accgctcaac caggtgttaa gttggaaatt ccagatggtg ctgtcatcga aaacaaggat 1380
attaacggtc ctgaagattt gtga 1404

<210> SEQ ID NO 137
<211> LENGTH: 467
<212> TYPE: PRT

<213> ORGANISM: Oryza sativa

<400> SEQUENCE: 137

Met Ala Asp Glu Lys Leu Ala Lys Leu Arg Glu Ala Val Ala Gly Leu
1               5                   10                  15

Ser Gln Ile Ser Asp Asn Glu Lys Ser Gly Phe Ile Ser Leu Val Ala
            20                  25                  30

Arg Tyr Leu Ser Gly Glu Glu Glu His Val Glu Trp Ala Lys Ile His
        35                  40                  45

Thr Pro Thr Asp Glu Val Val Val Pro Tyr Asp Thr Leu Glu Ala Pro
    50                  55                  60

Pro Glu Asp Leu Glu Glu Thr Lys Lys Leu Leu Asn Lys Leu Ala Val
65                  70                  75                  80

Leu Lys Leu Asn Gly Gly Leu Gly Thr Thr Met Gly Cys Thr Gly Pro
                85                  90                  95

Lys Ser Val Ile Glu Val Arg Asn Gly Phe Thr Phe Leu Asp Leu Ile
            100                 105                 110

Val Ile Gln Ile Glu Ser Leu Asn Lys Lys Tyr Gly Ser Asn Val Pro
        115                 120                 125

Leu Leu Leu Met Asn Ser Phe Asn Thr His Glu Asp Thr Leu Lys Ile
    130                 135                 140

Val Glu Lys Tyr Thr Asn Ser Asn Ile Glu Val His Thr Phe Asn Gln
145                 150                 155                 160

Ser Gln Tyr Pro Arg Val Val Ala Asp Glu Phe Leu Pro Trp Pro Ser
                165                 170                 175

Lys Gly Lys Thr Cys Lys Asp Gly Trp Tyr Pro Pro Gly His Gly Asp
            180                 185                 190

Ile Phe Pro Ser Leu Met Asn Ser Gly Lys Leu Asp Leu Leu Leu Ser
        195                 200                 205

Gln Gly Lys Glu Tyr Val Phe Ile Ala Asn Ser Asp Asn Leu Gly Ala
    210                 215                 220

Ile Val Asp Met Lys Ile Leu Asn His Leu Ile His Lys Gln Asn Glu
225                 230                 235                 240

Tyr Cys Met Glu Val Thr Pro Lys Thr Leu Ala Asp Val Lys Gly Gly
                245                 250                 255

Thr Leu Ile Ser Tyr Glu Asp Lys Val Gln Leu Leu Glu Ile Ala Gln
            260                 265                 270

Val Pro Asp Ala His Val Asn Glu Phe Lys Ser Ile Glu Lys Phe Lys
        275                 280                 285

Ile Phe Asn Thr Asn Asn Leu Trp Val Asn Leu Lys Ala Ile Lys Arg
    290                 295                 300

Leu Val Glu Ala Asp Ala Leu Lys Met Glu Ile Ile Pro Asn Pro Lys
305                 310                 315                 320

Glu Val Asp Gly Val Lys Val Leu Gln Leu Glu Thr Ala Ala Gly Ala
                325                 330                 335

Ala Ile Arg Phe Phe Asp His Ala Ile Gly Ile Asn Val Pro Arg Ser
            340                 345                 350

Arg Phe Leu Pro Val Lys Ala Thr Ser Asp Leu Gln Leu Val Gln Ser
        355                 360                 365

Asp Leu Tyr Thr Leu Val Asp Gly Phe Val Thr Arg Asn Pro Ala Arg
    370                 375                 380

Thr Asn Pro Ser Asn Pro Ser Ile Glu Leu Gly Pro Glu Phe Lys Lys
385                 390                 395                 400

```
Val Gly Cys Phe Leu Gly Arg Phe Lys Ser Ile Pro Ser Ile Val Glu
            405                 410                 415

Leu Asp Thr Leu Lys Val Ser Gly Asp Val Trp Phe Gly Ser Ser Ile
        420                 425                 430

Thr Leu Lys Gly Lys Val Thr Ile Thr Ala Gln Pro Gly Val Lys Leu
    435                 440                 445

Glu Ile Pro Asp Gly Ala Val Ile Glu Asn Lys Asp Ile Asn Gly Pro
    450                 455                 460

Glu Asp Leu
465
```

<210> SEQ ID NO 138
<211> LENGTH: 1434
<212> TYPE: DNA
<213> ORGANISM: Solanum tuberosum

<400> SEQUENCE: 138

```
atggctactg ctactacttt gtctccagct gatgctgaaa agttgaacaa tttgaaatct     60

gctgtcgccg gtttgaatca aatctctgaa aacgaaaagt ccggtttcat caacttggtt    120

ggtagatatt tgtctggtga agcccaacat attgactggt ctaaaattca aactccaacc    180

gatgaagttg ttgtcccata tgataagttg gctccattgt ctgaagatcc agctgaaaca    240

aaaaagttgt tggacaagtt ggtcgtcttg aagttgaatg gtggtttggg tactactatg    300

ggttgtactg gtccaaagtc tgttatcgaa gttagaaacg gtttgacctt cttggatttg    360

atcgtcaagc aaattgaagc tttgaacgct aagttcggtt gttctgttcc tttgttgttg    420

atgaactctt tcaacaccca tgatgacacc ttgaagatcg ttgaaaagta cgccaactcc    480

aacattgata tccacacctt caatcaatcc caatacccaa gattggttac cgaagatttt    540

gctccattgc catgtaaagg taactctggt aaagatggtt ggtatccacc aggtcatggt    600

gatgtttttc catccttgat gaattccggt aagttggatg ctttgttggc taagggtaaa    660

gaatacgttt tcgttgccaa ctctgataac ttgggtgcta tcgttgattt gaaaatcttg    720

aaccacttga tcttgaacaa gaacgaatac tgcatggaag ttactccaaa gactttggct    780

gatgttaagg gtggtacttt gatttcttac gaaggtaagg ttcaattatt ggaaatcgcc    840

caagttccag atgaacacgt taatgaattc aagtccatcg aaaagtttaa gatcttcaac    900

actaacaact tgtgggtcaa cttgtctgcc attaagagat tggttgaagc tgatgccttg    960

aaaatggaaa ttattccaaa cccaaaagaa gtcgatggtg tcaaagtatt gcaattggaa   1020

actgctgctg gtgctgctat taagtttttc gatagagcta ttggtgccaa cgttccaaga   1080

tctagatttt tgccagttaa ggctacctct gacttgttgt tggttcaatc agacttgtac   1140

actttgactg atgaaggtta cgttattaga aacccagcta gatccaatcc atccaaccca   1200

tctattgaat tgggtccaga attcaagaag gtagccaatt ttttgggtag attcaagtct   1260

atcccatcca tcatcgattt ggattctttg aaagttactg gtgatgtctg gtttggttct   1320

ggtgttactt tgaaaggtaa agttaccgtt gctgctaagt caggtgttaa gttggaaatt   1380

ccagatggtg ctgttattgc caacaaggat attaacggtc cagaagatat ctaa         1434
```

<210> SEQ ID NO 139
<211> LENGTH: 477
<212> TYPE: PRT
<213> ORGANISM: Solanum tuberosum

<400> SEQUENCE: 139

-continued

```
Met Ala Thr Ala Thr Thr Leu Ser Pro Ala Asp Ala Glu Lys Leu Asn
1               5                   10                  15

Asn Leu Lys Ser Ala Val Ala Gly Leu Asn Gln Ile Ser Glu Asn Glu
            20                  25                  30

Lys Ser Gly Phe Ile Asn Leu Val Gly Arg Tyr Leu Ser Gly Glu Ala
        35                  40                  45

Gln His Ile Asp Trp Ser Lys Ile Gln Thr Pro Thr Asp Glu Val Val
    50                  55                  60

Val Pro Tyr Asp Lys Leu Ala Pro Leu Ser Glu Asp Pro Ala Glu Thr
65                  70                  75                  80

Lys Lys Leu Leu Asp Lys Leu Val Val Leu Lys Leu Asn Gly Gly Leu
                85                  90                  95

Gly Thr Thr Met Gly Cys Thr Gly Pro Lys Ser Val Ile Glu Val Arg
            100                 105                 110

Asn Gly Leu Thr Phe Leu Asp Leu Ile Val Lys Gln Ile Glu Ala Leu
        115                 120                 125

Asn Ala Lys Phe Gly Cys Ser Val Pro Leu Leu Leu Met Asn Ser Phe
    130                 135                 140

Asn Thr His Asp Asp Thr Leu Lys Ile Val Glu Lys Tyr Ala Asn Ser
145                 150                 155                 160

Asn Ile Asp Ile His Thr Phe Asn Gln Ser Gln Tyr Pro Arg Leu Val
                165                 170                 175

Thr Glu Asp Phe Ala Pro Leu Pro Cys Lys Gly Asn Ser Gly Lys Asp
            180                 185                 190

Gly Trp Tyr Pro Pro Gly His Gly Asp Val Phe Pro Ser Leu Met Asn
        195                 200                 205

Ser Gly Lys Leu Asp Ala Leu Leu Ala Lys Gly Lys Glu Tyr Val Phe
    210                 215                 220

Val Ala Asn Ser Asp Asn Leu Gly Ala Ile Val Asp Leu Lys Ile Leu
225                 230                 235                 240

Asn His Leu Ile Leu Asn Lys Asn Glu Tyr Cys Met Glu Val Thr Pro
                245                 250                 255

Lys Thr Leu Ala Asp Val Lys Gly Gly Thr Leu Ile Ser Tyr Glu Gly
            260                 265                 270

Lys Val Gln Leu Leu Glu Ile Ala Gln Val Pro Asp Glu His Val Asn
        275                 280                 285

Glu Phe Lys Ser Ile Glu Lys Phe Lys Ile Phe Asn Thr Asn Asn Leu
    290                 295                 300

Trp Val Asn Leu Ser Ala Ile Lys Arg Leu Val Glu Ala Asp Ala Leu
305                 310                 315                 320

Lys Met Glu Ile Ile Pro Asn Pro Lys Glu Val Asp Gly Val Lys Val
                325                 330                 335

Leu Gln Leu Glu Thr Ala Ala Gly Ala Ala Ile Lys Phe Phe Asp Arg
            340                 345                 350

Ala Ile Gly Ala Asn Val Pro Arg Ser Arg Phe Leu Pro Val Lys Ala
        355                 360                 365

Thr Ser Asp Leu Leu Leu Val Gln Ser Asp Leu Tyr Thr Leu Thr Asp
    370                 375                 380

Glu Gly Tyr Val Ile Arg Asn Pro Ala Arg Ser Asn Pro Ser Asn Pro
385                 390                 395                 400

Ser Ile Glu Leu Gly Pro Glu Phe Lys Lys Val Ala Asn Phe Leu Gly
                405                 410                 415

Arg Phe Lys Ser Ile Pro Ser Ile Ile Asp Leu Asp Ser Leu Lys Val
```

```
            420                 425                 430

Thr Gly Asp Val Trp Phe Gly Ser Gly Val Thr Leu Lys Gly Lys Val
        435                 440                 445

Thr Val Ala Ala Lys Ser Gly Val Lys Leu Glu Ile Pro Asp Gly Ala
    450                 455                 460

Val Ile Ala Asn Lys Asp Ile Asn Gly Pro Glu Asp Ile
465                 470                 475


<210> SEQ ID NO 140
<211> LENGTH: 1818
<212> TYPE: DNA
<213> ORGANISM: Arabidopsis thaliana

<400> SEQUENCE: 140

atgttcttgt tggttacctc ttgcttcttg ccagattctg gttcttctgt taaggtcagt     60

ttgttcatct tcggtgtctc attggtttct acctctccaa ttgatggtca aaaaccaggt    120

acttctggtt tgagaaagaa ggtcaaggtt ttcaagcaac ctaactactt ggaaaacttc    180

gttcaagcta ctttcaacgc tttgactacc gaaaaagtta agggtgctac tttggttgtt    240

tctggtgatg gtagatatta ctccgaacaa gccattcaaa tcatcgttaa gatggctgct    300

gctaacggtg ttagaagagt ttgggttggt caaaactctt tgttgtctac tccagctgtt    360

tccgccatta ttagagaaag agttggtgct gatggttcta aagctactgg tgctttcatt    420

ttgactgctt ctcataatcc aggtggtcca actgaagatt tcggtattaa gtacaacatg    480

gaaaatggtg gtccagcccc agaatctatt actgataaga tatacgaaaa caccaagacc    540

atcaaagaat acccaattgc agaagatttg ccaagagttg atatctctac tatcggtatc    600

acttctttcg aaggtcctga aggtaaattc gacgttgaag tttttgattc cgctgatgat    660

tacgtcaagt tgatgaagtc catcttcgac ttcgaatcca tcaagaagtt gttgtcttac    720

ccaaagttca ccttttgtta cgatgcattg catggtgttg ctggtgctta tgctcataga    780

attttcgttg aagaattggg tgctccagaa tcctctttat tgaactgtgt tccaaaagaa    840

gattttggtg gtggtcatcc agatccaaat ttgacttatg ccaaagaatt ggttgccaga    900

atgggtttgt ctaagactga tgatgctggt ggtgaaccac ctgaatttgg tgctgctgca    960

gatggtgatg ctgatagaaa tatgatcttg ggtaaaagat tcttcgtcac cccatctgat   1020

tccgttgcta ttattgctgc taatgctgtt ggtgctattc catacttttc atccggtttg   1080

aaaggtgttg ctagatctat gccaacttct gctgctttgg atgttgttgc taagaatttg   1140

ggtttgaagt tcttcgaagt tccaactggt tggaaattct tcggtaattt gatggatgca   1200

ggtatgtgtt ctgtttgcgg tgaagaatca tttggtactg gttccgatca tatcagagaa   1260

aaggatggta tttgggctgt tttggcttgg ttgtctattt tggctcacaa gaacaaagaa   1320

accttggatg gtaatgccaa gttggttact gttgaagata tcgttagaca acattgggct   1380

acttacggta gacattacta cactagatac gactacgaaa acgttgatgc tacagctgct   1440

aaagaattga tgggtttatt ggtcaagttg caatcctcat tgccagaagt taacaagatc   1500

atcaagggta tccatcctga agttgctaat gttgcttctg ctgatgaatt cgaatacaag   1560

gatccagttg atggttccgt ttctaaacat caaggtatca gatacttgtt tgaagatggt   1620

tccagattgg ttttcagatt gtctggtaca ggttctgaag gtgctactat tagattgtac   1680

atcgaacaat acgaaaagga cgcctctaag attggtagag attctcaaga tgctttgggt   1740

ccattggttg atgttgcttt gaagttgtcc aagatgcaag aattcactgg tagatcttct   1800
```

ccaaccgtta ttacctga 1818

<210> SEQ ID NO 141
<211> LENGTH: 605
<212> TYPE: PRT
<213> ORGANISM: Arabidopsis thaliana

<400> SEQUENCE: 141

Met Phe Leu Leu Val Thr Ser Cys Phe Leu Pro Asp Ser Gly Ser Ser
1 5 10 15

Val Lys Val Ser Leu Phe Ile Phe Gly Val Ser Leu Val Ser Thr Ser
20 25 30

Pro Ile Asp Gly Gln Lys Pro Gly Thr Ser Gly Leu Arg Lys Lys Val
35 40 45

Lys Val Phe Lys Gln Pro Asn Tyr Leu Glu Asn Phe Val Gln Ala Thr
50 55 60

Phe Asn Ala Leu Thr Thr Glu Lys Val Lys Gly Ala Thr Leu Val Val
65 70 75 80

Ser Gly Asp Gly Arg Tyr Tyr Ser Glu Gln Ala Ile Gln Ile Ile Val
85 90 95

Lys Met Ala Ala Ala Asn Gly Val Arg Arg Val Trp Val Gly Gln Asn
100 105 110

Ser Leu Leu Ser Thr Pro Ala Val Ser Ala Ile Ile Arg Glu Arg Val
115 120 125

Gly Ala Asp Gly Ser Lys Ala Thr Gly Ala Phe Ile Leu Thr Ala Ser
130 135 140

His Asn Pro Gly Gly Pro Thr Glu Asp Phe Gly Ile Lys Tyr Asn Met
145 150 155 160

Glu Asn Gly Gly Pro Ala Pro Glu Ser Ile Thr Asp Lys Ile Tyr Glu
165 170 175

Asn Thr Lys Thr Ile Lys Glu Tyr Pro Ile Ala Glu Asp Leu Pro Arg
180 185 190

Val Asp Ile Ser Thr Ile Gly Ile Thr Ser Phe Glu Gly Pro Glu Gly
195 200 205

Lys Phe Asp Val Glu Val Phe Asp Ser Ala Asp Asp Tyr Val Lys Leu
210 215 220

Met Lys Ser Ile Phe Asp Phe Glu Ser Ile Lys Lys Leu Leu Ser Tyr
225 230 235 240

Pro Lys Phe Thr Phe Cys Tyr Asp Ala Leu His Gly Val Ala Gly Ala
245 250 255

Tyr Ala His Arg Ile Phe Val Glu Glu Leu Gly Ala Pro Glu Ser Ser
260 265 270

Leu Leu Asn Cys Val Pro Lys Glu Asp Phe Gly Gly Gly His Pro Asp
275 280 285

Pro Asn Leu Thr Tyr Ala Lys Glu Leu Val Ala Arg Met Gly Leu Ser
290 295 300

Lys Thr Asp Asp Ala Gly Gly Glu Pro Pro Glu Phe Gly Ala Ala Ala
305 310 315 320

Asp Gly Asp Ala Asp Arg Asn Met Ile Leu Gly Lys Arg Phe Phe Val
325 330 335

Thr Pro Ser Asp Ser Val Ala Ile Ile Ala Ala Asn Ala Val Gly Ala
340 345 350

Ile Pro Tyr Phe Ser Ser Gly Leu Lys Gly Val Ala Arg Ser Met Pro
355 360 365

```
Thr Ser Ala Ala Leu Asp Val Val Ala Lys Asn Leu Gly Leu Lys Phe
    370                 375                 380

Phe Glu Val Pro Thr Gly Trp Lys Phe Phe Gly Asn Leu Met Asp Ala
385                 390                 395                 400

Gly Met Cys Ser Val Cys Gly Glu Glu Ser Phe Gly Thr Gly Ser Asp
                405                 410                 415

His Ile Arg Glu Lys Asp Gly Ile Trp Ala Val Leu Ala Trp Leu Ser
            420                 425                 430

Ile Leu Ala His Lys Asn Lys Glu Thr Leu Asp Gly Asn Ala Lys Leu
        435                 440                 445

Val Thr Val Glu Asp Ile Val Arg Gln His Trp Ala Thr Tyr Gly Arg
    450                 455                 460

His Tyr Tyr Thr Arg Tyr Asp Tyr Glu Asn Val Asp Ala Thr Ala Ala
465                 470                 475                 480

Lys Glu Leu Met Gly Leu Leu Val Lys Leu Gln Ser Ser Leu Pro Glu
                485                 490                 495

Val Asn Lys Ile Ile Lys Gly Ile His Pro Glu Val Ala Asn Val Ala
            500                 505                 510

Ser Ala Asp Glu Phe Glu Tyr Lys Asp Pro Val Asp Gly Ser Val Ser
        515                 520                 525

Lys His Gln Gly Ile Arg Tyr Leu Phe Glu Asp Gly Ser Arg Leu Val
    530                 535                 540

Phe Arg Leu Ser Gly Thr Gly Ser Glu Gly Ala Thr Ile Arg Leu Tyr
545                 550                 555                 560

Ile Glu Gln Tyr Glu Lys Asp Ala Ser Lys Ile Gly Arg Asp Ser Gln
                565                 570                 575

Asp Ala Leu Gly Pro Leu Val Asp Val Ala Leu Lys Leu Ser Lys Met
            580                 585                 590

Gln Glu Phe Thr Gly Arg Ser Ser Pro Thr Val Ile Thr
        595                 600                 605
```

<210> SEQ ID NO 142
<211> LENGTH: 1641
<212> TYPE: DNA
<213> ORGANISM: Escherichia coli

<400> SEQUENCE: 142

```
atggccattc ataatagagc tggtcaacca gcacaacaat ccgatttgat taacgttgct      60

caattgaccg cccaatatta cgttttgaaa cctgaagctg gtaacgctga acatgctgtt     120

aagtttggta cttctggtca tagaggttct gctgctagac attcttttaa cgaaccacat     180

attttggcta tcgctcaagc tattgctgaa gaaagagcta agaacggtat tactggtcca     240

tgttacgttg gtaaagatac ccatgctttg tctgaaccag ctttcatttc tgttttggaa     300

gttttggctg ctaacggtgt tgatgttatc gttcaagaaa acaacggttt cactccaact     360

ccagctgttt ctaatgctat tttggttcac aacaaaaagg gtggtccatt ggctgatggt     420

atagttatta ctccatctca taacccacct gaagatggtg gtattaagta caatccacca     480

aatggtggtc cagctgatac aaatgttact aaggttgttg aagatagagc caacgctttg     540

ttagctgatg gtttgaaagg tgtcaagaga atctctttgg atgaagctat ggcttcaggt     600

catgtcaaag aacaagattt ggttcaacca ttcgttgaag gtttggctga tatagttgat     660

atggctgcta ttcaaaaggc tggtttgact ttgggtgttg atccattggg tggttctggt     720

attgaatact ggaaaagaat cggtgaatat tacaacttga acttgaccat cgtcaacgat     780
```

-continued

```
caagttgacc aaactttcag attcatgcac ttggataagg atggtgctat tagaatggac    840

tgttcttctg aatgtgctat ggctggttta ttggctttga gagataagtt cgatttggct    900

tttgctaacg atccagatta cgatagacat ggtatcgtta ctccagcagg tttgatgaat    960

ccaaatcatt acttggctgt tgccatcaac tacttgtttc aacatagacc acaatggggt   1020

aaggatgttg ctgttggtaa aactttggtt tcctccgcta tgatcgatag agttgttaac   1080

gatttgggta gaaagttggt tgaagttcca gttggtttca agtggtttgt tgacggtttg   1140

tttgatggtt cttttggttt tggtggtgaa gaatctgctg gtgcttcatt tttgagattt   1200

gatggtactc catggtccac tgacaaagat ggtattatca tgtgtttgtt ggctgctgaa   1260

attactgctg ttactggtaa gaatccacaa gaacactaca acgaattggc taagagattt   1320

ggtgctccat cttacaatag attgcaagct gctgctactt ctgctcaaaa agctgcttta   1380

tctaagttgt ccccagaaat ggtttctgct tctactttag ctggtgatcc aattacagct   1440

agattgactg ctgctccagg taatggtgct tctattggtg gtttaaaggt tatgactgat   1500

aacggttggt ttgctgcaag accatctggt actgaagatg cttacaaaat ctactgcgaa   1560

tccttcttgg gtgaagaaca tagaaagcaa attgaaaaag aagccgtcga aatcgtcagt   1620

gaagttttga agaatgccta a                                             1641
```

<210> SEQ ID NO 143
<211> LENGTH: 546
<212> TYPE: PRT
<213> ORGANISM: Escherichia coli

<400> SEQUENCE: 143

```
Met Ala Ile His Asn Arg Ala Gly Gln Pro Ala Gln Gln Ser Asp Leu
1               5                   10                  15

Ile Asn Val Ala Gln Leu Thr Ala Gln Tyr Tyr Val Leu Lys Pro Glu
            20                  25                  30

Ala Gly Asn Ala Glu His Ala Val Lys Phe Gly Thr Ser Gly His Arg
        35                  40                  45

Gly Ser Ala Ala Arg His Ser Phe Asn Glu Pro His Ile Leu Ala Ile
    50                  55                  60

Ala Gln Ala Ile Ala Glu Glu Arg Ala Lys Asn Gly Ile Thr Gly Pro
65                  70                  75                  80

Cys Tyr Val Gly Lys Asp Thr His Ala Leu Ser Glu Pro Ala Phe Ile
                85                  90                  95

Ser Val Leu Glu Val Leu Ala Ala Asn Gly Val Asp Val Ile Val Gln
            100                 105                 110

Glu Asn Asn Gly Phe Thr Pro Thr Pro Ala Val Ser Asn Ala Ile Leu
        115                 120                 125

Val His Asn Lys Lys Gly Gly Pro Leu Ala Asp Gly Ile Val Ile Thr
    130                 135                 140

Pro Ser His Asn Pro Pro Glu Asp Gly Gly Ile Lys Tyr Asn Pro Pro
145                 150                 155                 160

Asn Gly Gly Pro Ala Asp Thr Asn Val Thr Lys Val Val Glu Asp Arg
                165                 170                 175

Ala Asn Ala Leu Leu Ala Asp Gly Leu Lys Gly Val Lys Arg Ile Ser
            180                 185                 190

Leu Asp Glu Ala Met Ala Ser Gly His Val Lys Glu Gln Asp Leu Val
        195                 200                 205

Gln Pro Phe Val Glu Gly Leu Ala Asp Ile Val Asp Met Ala Ala Ile
    210                 215                 220
```

Gln Lys Ala Gly Leu Thr Leu Gly Val Asp Pro Leu Gly Gly Ser Gly
225 230 235 240

Ile Glu Tyr Trp Lys Arg Ile Gly Glu Tyr Tyr Asn Leu Asn Leu Thr
245 250 255

Ile Val Asn Asp Gln Val Asp Gln Thr Phe Arg Phe Met His Leu Asp
260 265 270

Lys Asp Gly Ala Ile Arg Met Asp Cys Ser Ser Glu Cys Ala Met Ala
275 280 285

Gly Leu Leu Ala Leu Arg Asp Lys Phe Asp Leu Ala Phe Ala Asn Asp
290 295 300

Pro Asp Tyr Asp Arg His Gly Ile Val Thr Pro Ala Gly Leu Met Asn
305 310 315 320

Pro Asn His Tyr Leu Ala Val Ala Ile Asn Tyr Leu Phe Gln His Arg
325 330 335

Pro Gln Trp Gly Lys Asp Val Ala Val Gly Lys Thr Leu Val Ser Ser
340 345 350

Ala Met Ile Asp Arg Val Val Asn Asp Leu Gly Arg Lys Leu Val Glu
355 360 365

Val Pro Val Gly Phe Lys Trp Phe Val Asp Gly Leu Phe Asp Gly Ser
370 375 380

Phe Gly Phe Gly Gly Glu Glu Ser Ala Gly Ala Ser Phe Leu Arg Phe
385 390 395 400

Asp Gly Thr Pro Trp Ser Thr Asp Lys Asp Gly Ile Ile Met Cys Leu
405 410 415

Leu Ala Ala Glu Ile Thr Ala Val Thr Gly Lys Asn Pro Gln Glu His
420 425 430

Tyr Asn Glu Leu Ala Lys Arg Phe Gly Ala Pro Ser Tyr Asn Arg Leu
435 440 445

Gln Ala Ala Ala Thr Ser Ala Gln Lys Ala Ala Leu Ser Lys Leu Ser
450 455 460

Pro Glu Met Val Ser Ala Ser Thr Leu Ala Gly Asp Pro Ile Thr Ala
465 470 475 480

Arg Leu Thr Ala Ala Pro Gly Asn Gly Ala Ser Ile Gly Gly Leu Lys
485 490 495

Val Met Thr Asp Asn Gly Trp Phe Ala Ala Arg Pro Ser Gly Thr Glu
500 505 510

Asp Ala Tyr Lys Ile Tyr Cys Glu Ser Phe Leu Gly Glu Glu His Arg
515 520 525

Lys Gln Ile Glu Lys Glu Ala Val Glu Ile Val Ser Glu Val Leu Lys
530 535 540

Asn Ala
545

<210> SEQ ID NO 144
<211> LENGTH: 1749
<212> TYPE: DNA
<213> ORGANISM: Rubus suavissimus

<400> SEQUENCE: 144
atgtcctccg gtaagattaa gagagttcaa actactccat tcgacggtca aaaaccaggt 60
acttctggtt tgagaaagaa ggttaaggtt ttcacccaac ctaactactt gcaaaacttc 120
gttcaatcta ccttcaacgc tttgccatct gataaggtaa aaggtgctag attggttgtt 180
tctggtgatg gtagatactt ctccaaagaa gccattcaaa tcatcattaa gatggctgct 240

```
ggtaacggtg ttaagtctgt ttgggttggt caaaatggtt tgttgtctac tccagctgtt    300

tctgctgttg ttagagaaag agttggtgct gatggttgta aagcttctgg tgctttcatt    360

ttgactgctt ctcataatcc aggtggtcca aatgaagatt tcggtatcaa gtacaacatg    420

gaaaatggtg gtccagctcc agaatctatt accaacaaaa tctacgaaaa caccacccaa    480

atcaaagaat acttgaccgt tgatttgcca gaagttgata ttactaagcc aggtgttact    540

accttcgaag ttgaaggtgg tactttcact gttgatgttt tcgattctgc ttccgattac    600

gtcaagttga tgaagtccat tttcgacttc gaatccatca gaaagttgtt gtcctctcca    660

aagttcacct tttgttttga tgcattgcat ggtgttggtg gtgcttacgc taaaagaatt    720

ttcgttgaag aattgggtgc caaagaatcc tctttgttga actgtgttcc taaagaagat    780

tttggtggtg gtcatccaga tccaaatttg acatatgcta aagaattggt cgccagaatg    840

ggtttgtcta agtctaatac tcaaaacgaa ccaccagaat ttggtgctgc tgcagatggt    900

gatgctgata gaaatatggt tttgggtaag agattcttcg ttaccccatc tgattccgtt    960

gctattattg ctgctaatgc tgttgaagct atcccatact tttctactgg tttgaaaggt   1020

gttgctagat ctatgccaac ttctgctgct ttggatgttg ttgctaaaca cttgaacttg   1080

aagttcttcg aagtaccaac tggttggaag tttttcggta atttgatgga tgctggtttg   1140

tgttctgttt gcggtgaaga atcttttggt actggttccg atcatatcag agaaaaggat   1200

ggtatttggg ctgttttggc ttggttgtca attattgcca tcaagaacaa ggataacatc   1260

ggtggtgata agttggttac cgttgaagat atcgttagaa aacattgggc tacttacggt   1320

agacattact acactagata cgattacgaa aacgttgatg ctggtaaggc taaagatttg   1380

atggcatcat tggtcaactt gcaatcatct ttgcctgaag ttaacaagat cgttaagggt   1440

atctgttccg atgttgcaaa tgttgttggt gccgatgaat tcgaatacaa ggattctgtt   1500

gatggttcca tctccaaaca tcaaggtatc agatacttgt tcgaagatgg ttcaagattg   1560

gttttcagat tgtctggtac aggttctgaa ggtgctacta ttagattgta catcgaacaa   1620

tacgaaaatg acccatccaa gatctccaga gaatcttctg aagctttggc tccattggtt   1680

gaagttgctt tgaaattgtc caagatgcaa gaattcactg gtagatcagc tccaactgtt   1740

attacctga                                                           1749
```

<210> SEQ ID NO 145
<211> LENGTH: 582
<212> TYPE: PRT
<213> ORGANISM: Rubus suavissimus

<400> SEQUENCE: 145

```
Met Ser Ser Gly Lys Ile Lys Arg Val Gln Thr Thr Pro Phe Asp Gly
1               5                   10                  15

Gln Lys Pro Gly Thr Ser Gly Leu Arg Lys Lys Val Lys Val Phe Thr
            20                  25                  30

Gln Pro Asn Tyr Leu Gln Asn Phe Val Gln Ser Thr Phe Asn Ala Leu
        35                  40                  45

Pro Ser Asp Lys Val Lys Gly Ala Arg Leu Val Val Ser Gly Asp Gly
    50                  55                  60

Arg Tyr Phe Ser Lys Glu Ala Ile Gln Ile Ile Ile Lys Met Ala Ala
65                  70                  75                  80

Gly Asn Gly Val Lys Ser Val Trp Val Gly Gln Asn Gly Leu Leu Ser
                85                  90                  95
```

```
Thr Pro Ala Val Ser Ala Val Val Arg Glu Arg Val Gly Ala Asp Gly
            100                 105                 110

Cys Lys Ala Ser Gly Ala Phe Ile Leu Thr Ala Ser His Asn Pro Gly
        115                 120                 125

Gly Pro Asn Glu Asp Phe Gly Ile Lys Tyr Asn Met Glu Asn Gly Gly
    130                 135                 140

Pro Ala Pro Glu Ser Ile Thr Asn Lys Ile Tyr Glu Asn Thr Thr Gln
145                 150                 155                 160

Ile Lys Glu Tyr Leu Thr Val Asp Leu Pro Glu Val Asp Ile Thr Lys
                165                 170                 175

Pro Gly Val Thr Thr Phe Glu Val Glu Gly Gly Thr Phe Thr Val Asp
            180                 185                 190

Val Phe Asp Ser Ala Ser Asp Tyr Val Lys Leu Met Lys Ser Ile Phe
        195                 200                 205

Asp Phe Glu Ser Ile Arg Lys Leu Leu Ser Ser Pro Lys Phe Thr Phe
    210                 215                 220

Cys Phe Asp Ala Leu His Gly Val Gly Gly Ala Tyr Ala Lys Arg Ile
225                 230                 235                 240

Phe Val Glu Glu Leu Gly Ala Lys Glu Ser Ser Leu Leu Asn Cys Val
                245                 250                 255

Pro Lys Glu Asp Phe Gly Gly Gly His Pro Asp Pro Asn Leu Thr Tyr
            260                 265                 270

Ala Lys Glu Leu Val Ala Arg Met Gly Leu Ser Lys Ser Asn Thr Gln
        275                 280                 285

Asn Glu Pro Pro Glu Phe Gly Ala Ala Ala Asp Gly Asp Ala Asp Arg
    290                 295                 300

Asn Met Val Leu Gly Lys Arg Phe Phe Val Thr Pro Ser Asp Ser Val
305                 310                 315                 320

Ala Ile Ile Ala Ala Asn Ala Val Glu Ala Ile Pro Tyr Phe Ser Thr
                325                 330                 335

Gly Leu Lys Gly Val Ala Arg Ser Met Pro Thr Ser Ala Ala Leu Asp
            340                 345                 350

Val Val Ala Lys His Leu Asn Leu Lys Phe Phe Glu Val Pro Thr Gly
        355                 360                 365

Trp Lys Phe Phe Gly Asn Leu Met Asp Ala Gly Leu Cys Ser Val Cys
    370                 375                 380

Gly Glu Glu Ser Phe Gly Thr Gly Ser Asp His Ile Arg Glu Lys Asp
385                 390                 395                 400

Gly Ile Trp Ala Val Leu Ala Trp Leu Ser Ile Ile Ala Ile Lys Asn
                405                 410                 415

Lys Asp Asn Ile Gly Gly Asp Lys Leu Val Thr Val Glu Asp Ile Val
            420                 425                 430

Arg Lys His Trp Ala Thr Tyr Gly Arg His Tyr Tyr Thr Arg Tyr Asp
        435                 440                 445

Tyr Glu Asn Val Asp Ala Gly Lys Ala Lys Asp Leu Met Ala Ser Leu
    450                 455                 460

Val Asn Leu Gln Ser Ser Leu Pro Glu Val Asn Lys Ile Val Lys Gly
465                 470                 475                 480

Ile Cys Ser Asp Val Ala Asn Val Val Gly Ala Asp Glu Phe Glu Tyr
                485                 490                 495

Lys Asp Ser Val Asp Gly Ser Ile Ser Lys His Gln Gly Ile Arg Tyr
            500                 505                 510

Leu Phe Glu Asp Gly Ser Arg Leu Val Phe Arg Leu Ser Gly Thr Gly
```

515 520 525

Ser Glu Gly Ala Thr Ile Arg Leu Tyr Ile Glu Gln Tyr Glu Asn Asp
530 535 540

Pro Ser Lys Ile Ser Arg Glu Ser Ser Glu Ala Leu Ala Pro Leu Val
545 550 555 560

Glu Val Ala Leu Lys Leu Ser Lys Met Gln Glu Phe Thr Gly Arg Ser
565 570 575

Ala Pro Thr Val Ile Thr
580

<210> SEQ ID NO 146
<211> LENGTH: 1749
<212> TYPE: DNA
<213> ORGANISM: Stevia rebaudiana

<400> SEQUENCE: 146
atggcctctt tcaaggttaa cagagttgaa tcctctccaa tcgaaggtca aaaaccaggt 60
acttctggtt tgagaaagaa ggttaaggtt ttcacccaac cacattactt gcacaacttc 120
gttcaatcta ctttcaacgc tttgtctgcc gaaaaagtta agggttctac tttggttgtt 180
tccggtgatg gtagatatta ctccaaggat gccattcaaa tcatcattaa gatggctgct 240
gctaacggtg ttagaagagt ttgggttggt caaaatggtt tgttgtctac tccagctgtt 300
tctgctgttg ttagagaaag agttggtgct gatggttcta aatctaacgg tgctttcatt 360
ttgactgcct ctcataatcc aggtggtcca aatgaagatt tcggtatcaa gtacaacatg 420
gaaaatggtg gtccagctcc agaaggtatt actgataaga tttttgaaaa caccaagacc 480
atcaaagaat acttcattgc tgaaggtttg ccagacgttg atatttccgc tattggtatc 540
tcttcattct ctggtccaga tggtcaattc gatgttgatg ttttcgattc ctcttccgac 600
tacgtcaaat tgatgaagtc catcttcgac ttccaatcca tcaagaagtt gattacctcc 660
ccacaatttt ctttctgtta cgatgcttta catggtgttg gtggtgctta tgctaagcca 720
atttttgttg atgaattggg tgccaaagaa tcctctttgt tgaactgtgt tcctaaagaa 780
gattttggtg gtggtcatcc agatccaaat ttgacttacg ctaaagaatt ggtttccaga 840
atgggtttgg gtaagaatcc agattctaat ccaccagaat ttggtgctgc tgcagatggt 900
gatgctgata gaaatatgat cttgggtaaa agattcttcg tcaccccatc tgattccgtt 960
gctattattg ctgctaatgc cgttcaatca atcccatact tttcatccgg tttgaaaggt 1020
gttgctagat ctatgccaac ttctgctgct ttggatgttg ttgctaagtc tttgaacttg 1080
aagttcttcg aagttccaac tggttggaag tttttcggta atttgatgga tgctggtttg 1140
tgttctgttt gcggtgaaga atcatttggt actggttccg atcatatcag agaaaaggat 1200
ggtatttggg ctgttttggc ttggttgtct attttggctc ataagaacaa ggacaacttg 1260
aacggtggta acttggttac tgttgaagat atcgttaagc aacattgggc tacttacggt 1320
agacattact acactagata cgactacgaa aacgttgatg ctggtgctgc aaaagaattg 1380
atggctcatt tggttaagtt gcaatcctcc atctctgatg ttaacacctt cattaagggt 1440
atcagatccg atgttgctaa tgttgcatct gctgatgaat tcgaatacaa ggatccagtt 1500
gacggttcta tttccaaaca tcaaggtatt agatacttgt ttgaagatgg ttccagattg 1560
gttttcagat tgtctggtac aggttctgaa ggtgctacta ttagattgta catcgaacaa 1620
tacgaaaagg attcctctaa gaccggtaga gattctcaag aagctttggc tccattagtt 1680
gaagttgcct tgaaattgtc caagatgcaa gaattcactg gtagatctgc tccaactgtt 1740
attacctga 1749

<210> SEQ ID NO 147
<211> LENGTH: 582
<212> TYPE: PRT
<213> ORGANISM: Stevia rebaudiana

<400> SEQUENCE: 147

Met Ala Ser Phe Lys Val Asn Arg Val Glu Ser Ser Pro Ile Glu Gly
1               5                   10                  15

Gln Lys Pro Gly Thr Ser Gly Leu Arg Lys Lys Val Lys Val Phe Thr
            20                  25                  30

Gln Pro His Tyr Leu His Asn Phe Val Gln Ser Thr Phe Asn Ala Leu
        35                  40                  45

Ser Ala Glu Lys Val Lys Gly Ser Thr Leu Val Val Ser Gly Asp Gly
    50                  55                  60

Arg Tyr Tyr Ser Lys Asp Ala Ile Gln Ile Ile Ile Lys Met Ala Ala
65                  70                  75                  80

Ala Asn Gly Val Arg Arg Val Trp Val Gly Gln Asn Gly Leu Leu Ser
                85                  90                  95

Thr Pro Ala Val Ser Ala Val Val Arg Glu Arg Val Gly Ala Asp Gly
            100                 105                 110

Ser Lys Ser Asn Gly Ala Phe Ile Leu Thr Ala Ser His Asn Pro Gly
        115                 120                 125

Gly Pro Asn Glu Asp Phe Gly Ile Lys Tyr Asn Met Glu Asn Gly Gly
    130                 135                 140

Pro Ala Pro Glu Gly Ile Thr Asp Lys Ile Phe Glu Asn Thr Lys Thr
145                 150                 155                 160

Ile Lys Glu Tyr Phe Ile Ala Glu Gly Leu Pro Asp Val Asp Ile Ser
                165                 170                 175

Ala Ile Gly Ile Ser Ser Phe Ser Gly Pro Asp Gly Gln Phe Asp Val
            180                 185                 190

Asp Val Phe Asp Ser Ser Ser Asp Tyr Val Lys Leu Met Lys Ser Ile
        195                 200                 205

Phe Asp Phe Gln Ser Ile Lys Lys Leu Ile Thr Ser Pro Gln Phe Ser
    210                 215                 220

Phe Cys Tyr Asp Ala Leu His Gly Val Gly Gly Ala Tyr Ala Lys Pro
225                 230                 235                 240

Ile Phe Val Asp Glu Leu Gly Ala Lys Glu Ser Ser Leu Leu Asn Cys
                245                 250                 255

Val Pro Lys Glu Asp Phe Gly Gly Gly His Pro Asp Pro Asn Leu Thr
            260                 265                 270

Tyr Ala Lys Glu Leu Val Ser Arg Met Gly Leu Gly Lys Asn Pro Asp
        275                 280                 285

Ser Asn Pro Pro Glu Phe Gly Ala Ala Ala Asp Gly Asp Ala Asp Arg
    290                 295                 300

Asn Met Ile Leu Gly Lys Arg Phe Phe Val Thr Pro Ser Asp Ser Val
305                 310                 315                 320

Ala Ile Ile Ala Ala Asn Ala Val Gln Ser Ile Pro Tyr Phe Ser Ser
                325                 330                 335

Gly Leu Lys Gly Val Ala Arg Ser Met Pro Thr Ser Ala Ala Leu Asp
            340                 345                 350

Val Val Ala Lys Ser Leu Asn Leu Lys Phe Phe Glu Val Pro Thr Gly
        355                 360                 365

```
Trp Lys Phe Phe Gly Asn Leu Met Asp Ala Gly Leu Cys Ser Val Cys
    370                 375                 380

Gly Glu Glu Ser Phe Gly Thr Gly Ser Asp His Ile Arg Glu Lys Asp
385                 390                 395                 400

Gly Ile Trp Ala Val Leu Ala Trp Leu Ser Ile Leu Ala His Lys Asn
                405                 410                 415

Lys Asp Asn Leu Asn Gly Gly Asn Leu Val Thr Val Glu Asp Ile Val
            420                 425                 430

Lys Gln His Trp Ala Thr Tyr Gly Arg His Tyr Tyr Thr Arg Tyr Asp
        435                 440                 445

Tyr Glu Asn Val Asp Ala Gly Ala Ala Lys Glu Leu Met Ala His Leu
    450                 455                 460

Val Lys Leu Gln Ser Ser Ile Ser Asp Val Asn Thr Phe Ile Lys Gly
465                 470                 475                 480

Ile Arg Ser Asp Val Ala Asn Val Ala Ser Ala Asp Glu Phe Glu Tyr
                485                 490                 495

Lys Asp Pro Val Asp Gly Ser Ile Ser Lys His Gln Gly Ile Arg Tyr
            500                 505                 510

Leu Phe Glu Asp Gly Ser Arg Leu Val Phe Arg Leu Ser Gly Thr Gly
        515                 520                 525

Ser Glu Gly Ala Thr Ile Arg Leu Tyr Ile Glu Gln Tyr Glu Lys Asp
    530                 535                 540

Ser Ser Lys Thr Gly Arg Asp Ser Gln Glu Ala Leu Ala Pro Leu Val
545                 550                 555                 560

Glu Val Ala Leu Lys Leu Ser Lys Met Gln Glu Phe Thr Gly Arg Ser
                565                 570                 575

Ala Pro Thr Val Ile Thr
            580
```

<210> SEQ ID NO 148
<211> LENGTH: 426
<212> TYPE: DNA
<213> ORGANISM: Artificial Sequence
<220> FEATURE:
<223> OTHER INFORMATION: pTEF1 promoter nucleotide sequence

<400> SEQUENCE: 148

```
gcacacacca tagcttcaaa atgtttctac tcctttttta ctcttccaga ttttctcgga      60

ctccgcgcat cgccgtacca cttcaaaaca cccaagcaca gcatactaaa tttcccctct     120

ttcttcctct agggtgtcgt taattacccg tactaaaggt ttggaaaaga aaaaagagac     180

cgcctcgttt ctttttcttc gtcgaaaaag gcaataaaaa tttttatcac gtttcttttt     240

cttgaaaatt tttttttttg atttttttct ctttcgatga cctcccattg atatttaagt     300

taataaacgg tcttcaattt ctcaagtttc agtttcattt ttcttgttct attacaactt     360

tttttacttc ttgctcatta gaaagaaagc atagcaatct aatctaagtt ttaattacaa     420

ggatcc                                                                426
```

<210> SEQ ID NO 149
<211> LENGTH: 984
<212> TYPE: DNA
<213> ORGANISM: Artificial Sequence
<220> FEATURE:
<223> OTHER INFORMATION: pPGK1 promoter nucleotide sequence

<400> SEQUENCE: 149

```
ggaagtacct tcaaagaatg gggtcttatc ttgttttgca agtaccactg agcaggataa     60

taatagaaat gataatatac tatagtagag ataacgtcga tgacttccca tactgtaatt    120

gcttttagtt gtgtattttt agtgtgcaag tttctgtaaa tcgattaatt tttttttctt    180

tcctcttttt attaacctta atttttattt tagattcctg acttcaactc aagacgcaca    240

gatattataa catctgcata ataggcattt gcaagaatta ctcgtgagta aggaaagagt    300

gaggaactat cgcatacctg catttaaaga tgccgatttg ggcgcgaatc ctttattttg    360

gcttcaccct catactatta tcagggccag aaaaaggaag tgtttccctc cttcttgaat    420

tgatgttacc ctcataaagc acgtggcctc ttatcgagaa agaaattacc gtcgctcgtg    480

atttgtttgc aaaaagaaca aaactgaaaa aacccagaca cgctcgactt cctgtcttcc    540

tattgattgc agcttccaat ttcgtcacac aacaaggtcc tagcgacggc tcacaggttt    600

tgtaacaagc aatcgaaggt tctggaatgg cgggaaaggg tttagtacca catgctatga    660

tgcccactgt gatctccaga gcaaagttcg ttcgatcgta ctgttactct ctctctttca    720

aacagaattg tccgaatcgt gtgacaacaa cagcctgttc tcacacactc ttttcttcta    780

accaaggggg tggtttagtt tagtagaacc tcgtgaaact tacatttaca tatatataaa    840

cttgcataaa ttggtcaatg caagaaatac atatttggtc ttttctaatt cgtagttttt    900

caagttctta gatgctttct tttctctttt tttacagatc atcaaggaag taattatcta    960

ctttttacaa caaatataaa acaa                                           984
```

<210> SEQ ID NO 150
<211> LENGTH: 666
<212> TYPE: DNA
<213> ORGANISM: Artificial Sequence
<220> FEATURE:
<223> OTHER INFORMATION: pTDH3 promoter nucleotide sequence

<400> SEQUENCE: 150

```
cattatcaat actgccattt caaagaatac gtaaataatt aatagtagtg attttcctaa     60

ctttatttag tcaaaaaatt agccttttaa ttctgctgta acccgtacat gcccaaaata    120

gggggcgggt tacacagaat atataacatc gtaggtgtct gggtgaacag tttattcctg    180

gcatccacta aatataatgg agcccgcttt ttaagctggc atccagaaaa aaaaagaatc    240

ccagcaccaa aatattgttt tcttcaccaa ccatcagttc ataggtccat tctcttagcg    300

caactacaga gaacaggggc acaaacaggc aaaaaacggg cacaacctca atggagtgat    360

gcaacctgcc tggagtaaat gatgacacaa ggcaattgac ccacgcatgt atctatctca    420

ttttcttaca ccttctatta ccttctgctc tctctgattt ggaaaaagct gaaaaaaaag    480

gttgaaacca gttccctgaa attattcccc tacttgacta ataagtatat aaagacggta    540

ggtattgatt gtaattctgt aaatctattt cttaaacttc ttaaattcta cttttatagt    600

tagtcttttt tttagtttta aaacaccaag aacttagttt cgaataaaca cacataaaca    660

aacaaa                                                               666
```

<210> SEQ ID NO 151
<211> LENGTH: 565
<212> TYPE: DNA
<213> ORGANISM: Artificial Sequence
<220> FEATURE:
<223> OTHER INFORMATION: pTEF2 promoter nucleotide sequence

<400> SEQUENCE: 151

```
gatctgggcc gtatacttac atatagtaga tgtcaagcgt aggcgcttcc cctgccggct     60
```

gtgagggcgc cataaccaag gtatctatag accgccaatc agcaaactac ctccgtacat 120
tcatgttgca cccacacatt tatacaccca gaccgcgaca aattacccat aaggttgttt 180
gtgacggcgt cgtacaagag aacgtgggaa ctttttaggc tcaccaaaaa agaaagaaaa 240
aatacgagtt gctgacagaa gcctcaagaa aaaaaaaatt cttcttcgac tatgctggag 300
gcagagatga tcgagccggt agttaactat atatagctaa attggttcca tcaccttctt 360
ttctggtgtc gctccttcta gtgctatttc tggcttttcc tatttttttt tttccatttt 420
tctttctctc tttctaatat ataaattctc ttgcattttc tatttttctc tctatctatt 480
ctacttgttt attcccttca aggttttttt ttaaggagta cttgttttta gaatatacgg 540
tcaacgaact ataattaact aaaca 565

<210> SEQ ID NO 152
<211> LENGTH: 532
<212> TYPE: DNA
<213> ORGANISM: Artificial Sequence
<220> FEATURE:
<223> OTHER INFORMATION: pTPI1 promoter nucleotide sequence

<400> SEQUENCE: 152
agttataata atcctacgtt agtgtgagcg ggatttaaac tgtgaggacc ttaatacatt 60
cagacacttc tgcggtatca ccctacttat tcccttcgag attatatcta ggaacccatc 120
aggttggtgg aagattaccc gttctaagac ttttcagctt cctctattga tgttacacct 180
ggacacccct tttctggcat ccagttttta atcttcagtg gcatgtgaga ttctccgaaa 240
ttaattaaag caatcacaca attctctcgg ataccacctc ggttgaaact gacaggtggt 300
ttgttacgca tgctaatgca aaggagccta tatacctttg gctcggctgc tgtaacaggg 360
aatataaagg gcagcataat ttaggagttt agtgaacttg caacatttac tattttccct 420
tcttacgtaa atatttttct ttttaattct aaatcaatct tttcaattt tttgtttgta 480 ttcttttctt gcttaaatct ataactacaa aaaacacata cataaactaa aa 532

<210> SEQ ID NO 153
<211> LENGTH: 805
<212> TYPE: DNA
<213> ORGANISM: Artificial Sequence
<220> FEATURE:
<223> OTHER INFORMATION: pPDC1 promoter nucleotide sequence

<400> SEQUENCE: 153
gatctatgcg actgggtgag catatgttcc gctgatgtga tgtgcaagat aaacaagcaa 60
ggcagaaact aacttcttct tcatgtaata aacacacccc gcgtttattt acctatctct 120
aaacttcaac accttatatc ataactaata tttcttgaga taagcacact gcacccatac 180
cttccttaaa aacgtagctt ccagtttttg gtggttccgg cttccttccc gattccgccc 240
gctaaacgca tatttttgtt gcctggtggc atttgcaaaa tgcataacct atgcatttaa 300
aagattatgt atgctcttct gacttttcgt gtgatgaggc tcgtggaaaa aatgaataat 360
ttatgaattt gagaacaatt ttgtgttgtt acggtatttt actatggaat aatcaatcaa 420
ttgaggattt tatgcaaata tcgtttgaat atttttccga ccctttgagt acttttcttc 480
ataattgcat aatattgtcc gctgcccctt tttctgttag acggtgtctt gatctacttg 540
ctatcgttca acaccacctt attttctaac tatttttttt ttagctcatt tgaatcagct 600
tatggtgatg gcacattttt gcataaacct agctgtcctc gttgaacata ggaaaaaaaa 660

-continued

```
atatataaac aaggctcttt cactctcctt gcaatcagat ttgggtttgt tccctttatt    720

ttcatatttc ttgtcatatt cctttctcaa ttattatttt ctactcataa cctcacgcaa    780

aataacacag tcaaatctat caaaa                                          805


<210> SEQ ID NO 154
<211> LENGTH: 192
<212> TYPE: DNA
<213> ORGANISM: Artificial Sequence
<220> FEATURE:
<223> OTHER INFORMATION: tCYC1 terminator nucleotide sequence

<400> SEQUENCE: 154

atccgctcta accgaaaagg aaggagttag acaacctgaa gtctaggtcc ctatttattt     60

tttttaatag ttatgttagt attaagaacg ttatttatat ttcaaatttt tctttttttt    120

ctgtacaaac gcgtgtacgc atgtaacatt atactgaaaa ccttgcttga gaaggttttg    180

ggacgctcga ag                                                        192


<210> SEQ ID NO 155
<211> LENGTH: 195
<212> TYPE: DNA
<213> ORGANISM: Artificial Sequence
<220> FEATURE:
<223> OTHER INFORMATION: tADH1 terminator nucleotide sequence

<400> SEQUENCE: 155

gtagatacgt tgttgacact tctaaataag cgaatttctt atgatttatg atttttatta     60

ttaaataagt tataaaaaaa ataagtgtat acaaatttta aagtgactct taggttttaa    120

aacgaaaatt cttattcttg agtaactctt tcctgtaggt caggttgctt tctcaggtat    180

agcatgaggt cgctc                                                     195
```

PRODUCTION OF STEVIOL GLYCOSIDES IN RECOMBINANT HOSTS

This application is a divisional of U.S. application Ser. No. 16/091,536, filed on Oct. 5, 2018 and issued as U.S. Pat. No. 10,982,249 on Apr. 20, 2021, which is a U.S. National Stage Application of International Application No. PCT/EP2017/059028, filed on Apr. 13, 2017, and claims the benefit of U.S. Provisional Application No. 62/321,850, filed on Apr. 13, 2016, the disclosures of each of which are explicitly incorporated by reference herein in their entirety.

BACKGROUND OF THE INVENTION

Field of the Invention

This disclosure relates to recombinant production of steviol glycosides and steviol glycoside precursors in recombinant hosts. In particular, this disclosure relates to production of steviol glycosides comprising steviol-13-O-glucoside (13-SMG), rubusoside, rebaudioside B (RebB), rebaudioside A (RebA), rebaudioside D (RebD), and rebaudioside M (RebM) in recombinant hosts comprising genes involved in uridine diphosphate (UDP)-glucose formation.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. *Stevia* extract is a natural sweetener that can be isolated and extracted from a perennial shrub, *Stevia rebaudiana. Stevia* is commonly grown in South America and Asia for commercial production of *stevia* extract. *Stevia* extract, purified to various degrees, is used commercially as a high intensity sweetener in foods and in blends or alone as a tabletop sweetener. Extracts of the *Stevia* plant generally comprise steviol glycosides that contribute to the sweet flavor, although the amount of each steviol glycoside often varies, inter alia, among different production batches.

Chemical structures for several steviol glycosides are shown in FIG. 2, including the diterpene steviol and various steviol glycosides. Extracts of the *Stevia* plant generally comprise steviol glycosides that contribute to the sweet flavor, although the amount of each steviol glycoside often varies, inter alia, among different production batches.

As recovery and purification of steviol glycosides from the *Stevia* plant have proven to be labor intensive and inefficient, there remains a need for a recombinant production system that can accumulate high yields of desired steviol glycosides, such as RebM. There also remains a need for improved production of steviol glycosides in recombinant hosts for commercial uses. As well, there remains a need for increasing UDP-glucose formation in recombinant hosts in order to produce higher yields of steviol glycosides, including RebM.

SUMMARY OF THE INVENTION

It is against the above background that the present invention provides certain advantages and advancements over the prior art.

Although this invention as disclosed herein is not limited to specific advantages or functionalities, the invention provides a recombinant host cell capable of producing one or more steviol glycosides or a steviol glycoside composition in a cell culture, comprising:

(a) a recombinant gene encoding a polypeptide capable of synthesizing uridine 5'-triphosphate (UTP) from uridine diphosphate (UDP);

(b) a recombinant gene encoding a polypeptide capable of converting glucose-6-phosphate to glucose-1-phosphate; and/or (c) a recombinant gene encoding a polypeptide capable of synthesizing uridine diphosphate glucose (UDP-glucose) from UTP and glucose-1-phosphate.

In one aspect of the recombinant host cell disclosed herein:

(a) the polypeptide capable of synthesizing UTP from UDP comprises a polypeptide having at least 60% sequence identity to the amino acid sequence set forth in SEQ ID NO:123;

(b) the polypeptide capable of converting glucose-6-phosphate to glucose-1-phosphate comprises a polypeptide having at least 60% sequence identity to the amino acid sequence set forth in SEQ ID NO:2, SEQ ID NO:119, SEQ ID NO:143 or a polypeptide having at least 55% sequence identity to the amino acid sequence set forth in SEQ ID NO:141, SEQ ID NO:145, or SEQ ID NO:147; and/or (c) the polypeptide capable of synthesizing UDP-glucose from UTP and glucose-1-phosphate comprises a polypeptide having at least 60% sequence identity to the amino acid sequence set forth in SEQ ID NO:121, SEQ ID NO:127, a polypeptide having at least 55% sequence identity to the amino acid sequence set forth in SEQ ID NO:125, SEQ ID NO:129, SEQ ID NO:133, SEQ ID NO:135, SEQ ID NO:137, or SEQ ID NO:139 or a polypeptide having at least 70% sequence identity to the amino acid sequence set forth in SEQ ID NO:131.

In one aspect, the recombinant host cell disclosed herein further comprises:

(a) a gene encoding a polypeptide capable of glycosylating steviol or a steviol glycoside at its C-13 hydroxyl group thereof;

(b) a gene encoding a polypeptide capable of beta 1,3 glycosylation of the C3' of the 13-O-glucose, 19-O-glucose, or both 13-O-glucose and 19-O-glucose of a steviol glycoside;

(c) a gene encoding a polypeptide capable of glycosylating steviol or a steviol glycoside at its C-19 carboxyl group thereof; and/or (d) a gene encoding a polypeptide capable of beta 1,2 glycosylation of the C2' of the 13-O-glucose, 19-O-glucose, or both 13-O-glucose and 19-O-glucose of a steviol glycoside.

In one aspect, the recombinant host cell disclosed herein further comprises:

(e) a gene encoding a polypeptide capable of synthesizing geranylgeranyl pyrophosphate (GGPP) from farnesyl diphosphate (FPP) and isopentenyl diphosphate (IPP);

(f) a gene encoding a polypeptide capable of synthesizing ent-copalyl diphosphate from GGPP;

(g) a gene encoding an a polypeptide capable of synthesizing ent-kaurene from ent-copalyl diphosphate;

(h) a gene encoding a polypeptide capable of synthesizing ent-kaurenoic acid from ent-kaurene;

(i) a gene encoding a polypeptide capable of reducing cytochrome P450 complex; and/or (j) a gene encoding a polypeptide capable of synthesizing steviol from ent-kaurenoic acid.

In one aspect of the recombinant host cell disclosed herein:

(a) the polypeptide capable of glycosylating steviol or a steviol glycoside at its C-13 hydroxyl group thereof comprises a polypeptide having at least 55% sequence identity to the amino acid sequence set forth in SEQ ID NO:7;

(b) the polypeptide capable of beta 1,3 glycosylation of the C3' of the 13-O-glucose, 19-O-glucose, or both 13-O-glucose and 19-O-glucose of a steviol glycoside comprises a polypeptide having at least 50% sequence identity to the amino acid sequence set forth in SEQ ID NO:9;

(c) the polypeptide capable of glycosylating steviol or a steviol glycoside at its C-19 carboxyl group thereof comprises a polypeptide having at least 55% sequence identity to the amino acid sequence set forth in SEQ ID NO:4;

(d) the polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16;

(e) the polypeptide capable of synthesizing GGPP comprises a polypeptide having at least 70% sequence identity to the amino acid sequence set forth in SEQ ID NO:20, SEQ ID NO:22, SEQ ID NO:24, SEQ ID NO:26, SEQ ID NO:28, SEQ ID NO:30, SEQ ID NO:32, or SEQ ID NO:116;

(f) the polypeptide capable of synthesizing ent-copalyl diphosphate comprises a polypeptide having at least 70% sequence identity to the amino acid sequence set forth in SEQ ID NO:34, SEQ ID NO:36, SEQ ID NO:38, SEQ ID NO:40, SEQ ID NO:42, or SEQ ID NO:120;

(g) the polypeptide capable of synthesizing ent-kaurene comprises a polypeptide having at least 70% sequence identity to the amino acid sequence set forth in SEQ ID NO:44, SEQ ID NO:46, SEQ ID NO:48, SEQ ID NO:50, or SEQ ID NO:52;

(h) the polypeptide capable of synthesizing ent-kaurenoic acid comprises a polypeptide having at least 70% sequence identity to the amino acid sequence set forth in SEQ ID NO:60, SEQ ID NO:62, SEQ ID NO:117, SEQ ID NO:66, SEQ ID NO:68, SEQ ID NO:70, SEQ ID NO:72, SEQ ID NO:74, or SEQ ID NO:76;

(i) the polypeptide capable of reducing cytochrome P450 complex comprises a polypeptide having at least 70% sequence identity to the amino acid sequence set forth in SEQ ID NO:78, SEQ ID NO:80, SEQ ID NO:82, SEQ ID NO:84, SEQ ID NO:86, SEQ ID NO:88, SEQ ID NO:90, SEQ ID NO:92; and/or (k) the polypeptide capable of synthesizing steviol comprises a polypeptide having at least 70% sequence identity to the amino acid sequence set forth in SEQ ID NO:94, SEQ ID NO:97, SEQ ID NO:100, SEQ ID NO:101, SEQ ID NO:102, SEQ ID NO:103, SEQ ID NO:104, SEQ ID NO:106, SEQ ID NO:108, SEQ ID NO:110, SEQ ID NO:112, or SEQ ID NO:114.

In one aspect, the recombinant host cell disclosed herein comprises:

(a) a gene encoding a polypeptide capable of synthesizing uridine 5'-triphosphate (UTP) from uridine diphosphate (UDP) having at least 60% sequence identity to the amino acid sequence set forth in SEQ ID NO:123;

(b) one or more genes encoding a polypeptide capable of converting glucose-6-phosphate to glucose-1-phosphate, each having at least 60% sequence identity to the amino acid sequence set forth in SEQ ID NO:2 and/or SEQ ID NO:119; and (c) a gene encoding a polypeptide capable of synthesizing UDP-glucose from UTP and glucose-1-phosphate having at least 60% sequence identity to the amino acid sequence set forth in SEQ ID NO:121.

In one aspect, the recombinant host cell disclosed herein comprises:

(a) a gene encoding a polypeptide capable of synthesizing uridine 5'-triphosphate (UTP) from uridine diphosphate (UDP);

(b) a gene encoding a polypeptide capable of converting glucose-6-phosphate to glucose-1-phosphate;

(c) a gene encoding a polypeptide capable of synthesizing UDP-glucose from UTP and glucose-1-phosphate having at least 60% sequence identity to the amino acid sequence set forth in SEQ ID NO:121;

(d) a gene encoding a polypeptide capable of synthesizing UDP-glucose from UTP and glucose-1-phosphate having at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; at least 60% sequence identity to the amino acid sequence set forth in SEQ ID NO:127; or at least 70% sequence identity to the amino acid sequence set forth in SEQ ID NO:131; and one or more of:

(e) a gene encoding a polypeptide capable of glycosylating steviol or a steviol glycoside at its C-13 hydroxyl group thereof having at least 55% sequence identity to the amino acid sequence set forth in SEQ ID NO:7;

(b) a gene encoding a polypeptide capable of beta 1,3 glycosylation of the C3' of the 13-O-glucose, 19-O-glucose, or both 13-O-glucose and 19-O-glucose of a steviol glycoside having at least 50% sequence identity to the amino acid sequence set forth in SEQ ID NO:9;

(c) a gene encoding a polypeptide capable of glycosylating steviol or a steviol glycoside at its C-19 carboxyl group thereof having at least 55% sequence identity to the amino acid sequence set forth in SEQ ID NO:4;

(d) a gene encoding a polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16.

In one aspect, the recombinant host cell disclosed herein comprises:

(a) a recombinant gene encoding a polypeptide capable of synthesizing uridine 5'-triphosphate (UTP) from uridine diphosphate (UDP) having at least 60% sequence identity to the amino acid sequence set forth in SEQ ID NO:123;

(b) one or more recombinant genes encoding a polypeptide capable of converting glucose-6-phosphate to glucose-1-phosphate, each having at least 60% sequence identity to the amino acid sequence set forth in SEQ ID NO:2 and/or SEQ ID NO:119; and/or (c) a recombinant gene encoding a polypeptide capable of synthesizing UDP-glucose from UTP and glucose-1-phosphate having at least 60% sequence identity to the amino acid sequence set forth in SEQ ID NO:121;

wherein the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed relative to a corresponding host cell lacking the one or more recombinant genes.

In one aspect of the recombinant host cell disclosed herein, the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed by at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% relative to a corresponding host cell lacking the one or more recombinant genes.

In one aspect of the recombinant host cell disclosed herein, expression of the one or more recombinant genes increase the amount of UDP-glucose accumulated by the cell relative to a corresponding host lacking the one or more recombinant genes.

In one aspect of the recombinant host cell disclosed herein, expression of the one or more recombinant genes increases the amount of UDP-glucose accumulated by the cell by at least about 10%, at least about 25%, or at least about 50%, at least about 100%, at least about 150%, at least about 200%, or at least about 250% relative to a corresponding host lacking the one or more recombinant genes.

In one aspect of the recombinant host cell disclosed herein, expression of the one or more recombinant genes increases an amount of the one or more steviol glycosides or the steviol glycoside composition produced by the cell relative to a corresponding host lacking the one or more recombinant genes.

In one aspect of the recombinant host cell disclosed herein, expression of the one or more recombinant genes increases the amount of the one or more steviol glycosides produced by the cell by at least about 5%, at least about 10%, at least about 25%, at least about 50%, at least about 75%, or at least about 100% relative to a corresponding host lacking the one or more recombinant genes.

In one aspect of the recombinant host cell disclosed herein, expression of the one or more recombinant genes increases the amount of RebA, RebB, Reb D, and/or RebM produced by the cell relative to a corresponding host lacking the one or more recombinant genes.

In one aspect of the recombinant host cell disclosed herein, expression of the one or more recombinant genes decreases the one of one or more steviol glycosides or the steviol glycoside composition accumulated by the cell relative to a corresponding host lacking the one or more recombinant genes.

In one aspect of the recombinant host cell disclosed herein, expression of the one or more recombinant genes decreases the amount of the one or more steviol glycosides accumulated by the cell by at least about 5%, at least about 10%, at least about 25%, or at least about 50% relative to a corresponding host lacking the one or more recombinant genes.

In one aspect of the recombinant host cell disclosed herein, expression of the one or more recombinant genes decreases the amount of RebB, RebD, and/or 13-SMG accumulated by the cell relative to a corresponding host lacking the one or more recombinant genes.

In one aspect of the recombinant host cell disclosed herein, expression of the one or more recombinant genes increases or decreases the amount of total steviol glycosides produced by the cell by less than 5%, less than 2.5%, or less than 1% relative to a corresponding host lacking the one or more recombinant genes.

In one aspect of the recombinant host cell disclosed herein, expression of the one or more recombinant genes increases the amount of total steviol glycosides produced by the cell by at least about 5%, at least about 10%, or at least about 25% relative to a corresponding host lacking the one or more recombinant genes.

In one aspect of the recombinant host cell disclosed herein, the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-Stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, and/or an isomer thereof.

In one aspect of the recombinant host cell disclosed herein, the recombinant host cell is a plant cell, a mammalian cell, an insect cell, a fungal cell, an algal cell or a bacterial cell.

The invention also provides method of producing one or more steviol glycosides or a steviol glycoside composition in a cell culture, comprising culturing the recombinant host cell disclosed herein, under conditions in which the genes are expressed, and wherein the one or more steviol glycosides or the steviol glycoside composition is produced by the recombinant host cell.

In one aspect of the methods disclosed herein, the genes are constitutively expressed and/or expression of the genes is induced.

In one aspect of the methods disclosed herein, the amount of UDP-glucose accumulated by the cell is increased by at least by at least about 10% relative to a corresponding host lacking the one or more recombinant genes.

In one aspect of the methods disclosed herein, the amount of RebA, RebB, RebD, and/or RebM produced by the cell is increased by at least about 5% relative to a corresponding host lacking the one or more recombinant genes.

In one aspect of the methods disclosed herein, the amount of RebB, RebD, and/or 13-SMG accumulated by the cell is decreased by at least about 5% relative to a corresponding host lacking the one or more recombinant genes.

In one aspect of the methods disclosed herein, the amount of total steviol glycosides produced by the cell is increased or decreased by less than about 5% relative to a corresponding host lacking the one or more recombinant genes.

In one aspect of the methods disclosed herein, the amount of total steviol glycosides produced by the cell is increased by at least about 5% relative to a corresponding host lacking the one or more recombinant genes.

In one aspect of the methods disclosed herein, the recombinant host cell is grown in a fermentor at a temperature for a period of time, wherein the temperature and period of time facilitate the production of the one or more steviol glycosides or the steviol glycoside composition.

In one aspect of the methods disclosed herein, the amount of UDP-glucose present in the cell culture is increased by at least about 10%, at least about 25%, or at least about 50%, at least about 100%, at least about 150%, at least about 200%, or at least about 250% at any point throughout the period of time.

In one aspect, the methods disclosed herein further comprise isolating the produced one or more steviol glycosides or the steviol glycoside composition from the cell culture.

In one aspect of the methods disclosed herein, the isolating step comprises:

(a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) providing one or more adsorbent resins, comprising providing the adsorbent resins in a packed column; and
(d) contacting the supernatant of step (b) with the one or more adsorbent resins in order to obtain at least a portion of the produced one or more steviol glycosides or the steviol glycoside composition, thereby isolating the produced one or more steviol glycosides or the steviol glycoside composition;

or (a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) providing one or more ion exchange or ion exchange or reversed-phase chromatography columns; and
(d) contacting the supernatant of step (b) with the one or more ion exchange or ion exchange or reversed-phase chromatography columns in order to obtain at least a portion of the produced one or more steviol glycosides or the steviol glycoside composition, thereby isolating the produced one or more steviol glycosides or the steviol glycoside composition;

or (a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) crystallizing or extracting the produced one or more steviol glycosides or the steviol glycoside composition, thereby isolating the produced one or more steviol glycosides or the steviol glycoside composition.

In one aspect, the methods disclosed herein further comprise recovering the one or more steviol glycosides or the steviol glycoside composition from the cell culture.

In one aspect of the methods disclosed herein, the recovered one or more steviol glycosides or the steviol glycoside composition has a reduced level of *Stevia* plant-derived components relative to a plant-derived *Stevia* extract.

The invention also provides a method for producing one or more steviol glycosides or a steviol glycoside composition, comprising whole-cell bioconversion of plant-derived or synthetic steviol and/or steviol glycosides in a cell culture medium of a recombinant host cell using:

(a) a polypeptide capable of synthesizing UTP from UDP having at least 60% sequence identity to the amino acid sequence set forth in SEQ ID NO:123;
(b) a polypeptide capable of converting glucose-6-phosphate to glucose-1-phosphate having at least 60% sequence identity to the amino acid sequence set forth in SEQ ID NO:2, SEQ ID NO:119, or SEQ ID NO:143; at least 55% sequence identity to the amino acid sequence set forth in SEQ ID NO:141, SEQ ID NO:145, or SEQ ID NO:147; and/or
(c) a polypeptide capable of synthesizing UDP-glucose from UTP and glucose-1-phosphate having at least 60% sequence identity to the amino acid sequence set forth in SEQ ID NO:121, SEQ ID NO:127; at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; or at least 70% sequence identity to the amino acid sequence set forth in SEQ ID NO:131; and one or more of:

(d) a polypeptide capable of glycosylating steviol or a steviol glycoside at its C-13 hydroxyl group thereof;
(e) a polypeptide capable of beta 1,3 glycosylation of the C3' of the 13-O-glucose, 19-O-glucose, or both 13-O-glucose and 19-O-glucose of a steviol glycoside;
(f) a polypeptide capable of glycosylating steviol or a steviol glycoside at its C-19 carboxyl group thereof; and/or
(g) a polypeptide capable of beta 1,2 glycosylation of the C2' of the 13-O-glucose, 19-O-glucose, or both 13-O-glucose and 19-O-glucose of a steviol glycoside;
wherein at least one of the polypeptides is a recombinant polypeptide expressed in the recombinant host cell; and producing the one or more steviol glycosides or the steviol glycoside composition thereby.

In one aspect of the methods disclosed herein:

(d) the polypeptide capable of glycosylating steviol or a steviol glycoside at its C-13 hydroxyl group thereof comprises a polypeptide having at least 55% sequence identity to the amino acid sequence set forth in SEQ ID NO:7;
(e) the polypeptide capable of beta 1,3 glycosylation of the C3' of the 13-O-glucose, 19-O-glucose, or both 13-O-glucose and 19-O-glucose of a steviol glycoside comprises a polypeptide having at least 50% sequence identity to the amino acid sequence set forth in SEQ ID NO:9;
(f) the polypeptide capable of glycosylating steviol or a steviol glycoside at its C-19 carboxyl group thereof comprises a polypeptide having at least 55% sequence identity to the amino acid sequence set forth in SEQ ID NO:4;
(g) the polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16.

In one aspect of the methods disclosed herein, the recombinant host cell is a plant cell, a mammalian cell, an insect cell, a fungal cell, an algal cell or a bacterial cell.

In one aspect of the methods disclosed herein, the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, and/or an isomer thereof.

The invention also provides a cell culture, comprising the recombinant host cell disclosed herein, the cell culture further comprising:

(a) the one or more steviol glycosides or the steviol glycoside composition produced by the recombinant host cell;
(b) glucose, fructose, sucrose, xylose, rhamnose, UDP-glucose, UDP-rhamnose, UDP-xylose, and/or N-acetyl-glucosamine; and
(c) supplemental nutrients comprising trace metals, vitamins, salts, YNB, and/or amino acids;
    wherein the one or more steviol glycosides or the steviol glycoside composition is present at a concentration of at least 1 mg/liter of the cell culture;

wherein the cell culture is enriched for the one or more steviol glycosides or the steviol glycoside composition relative to a steviol glycoside composition from a *Stevia* plant and has a reduced level of *Stevia* plant-derived components relative to a plant-derived *Stevia* extract.

The invention also provides a cell culture, comprising the recombinant host cell disclosed herein, the cell culture further comprising:

(a) the one or more steviol glycosides or the steviol glycoside composition produced by the recombinant host cell;
(b) glucose, fructose, sucrose, xylose, rhamnose, UDP-glucose, UDP-rhamnose, UDP-xylose, and/or N-acetyl-glucosamine; and
(c) supplemental nutrients comprising trace metals, vitamins, salts, YNB, and/or amino acids;
    wherein UDP-glucose is present in the cell culture at a concentration of at least 100 μM;
    wherein the cell culture is enriched for UGP-glucose relative to a steviol glycoside composition from a *Stevia* plant and has a reduced level of *Stevia* plant-derived components relative to a plant-derived *Stevia* extract.

The invention also provides cell lysate from the recombinant host cell disclosed herein grown in the cell culture, comprising:

(a) the one or more steviol glycosides or the steviol glycoside composition produced by the recombinant host cell;
(b) glucose, fructose, sucrose, xylose, rhamnose, UDP-glucose, UDP-rhamnose, UDP-xylose, and/or N-acetyl-glucosamine; and/or
(c) supplemental nutrients comprising trace metals, vitamins, salts, yeast nitrogen base, YNB, and/or amino acids;
    wherein the one or more steviol glycosides or the steviol glycoside composition produced by the recombinant host cell is present at a concentration of at least 1 mg/liter of the cell culture.

The invention also provides one or more steviol glycosides produced by the recombinant host cell disclosed herein;

wherein the one or more steviol glycosides produced by the recombinant host cell are present in relative amounts that are different from a steviol glycoside composition from a *Stevia* plant and have a reduced level of *Stevia* plant-derived components relative to a plant-derived *Stevia* extract.

The invention also provides one or more steviol glycosides produced by the method disclosed herein;

wherein the one or more steviol glycosides produced by the recombinant host cell are present in relative amounts that are different from a steviol glycoside composition from a *Stevia* plant and have a reduced level of *Stevia* plant-derived components relative to a plant-derived *Stevia* extract.

The invention also provides a sweetener composition, comprising the one or more steviol glycosides disclosed herein.

The invention also provides a food product comprising, the sweetener composition disclosed herein.

The invention also provides a beverage or a beverage concentrate, comprising the sweetener composition disclosed herein.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
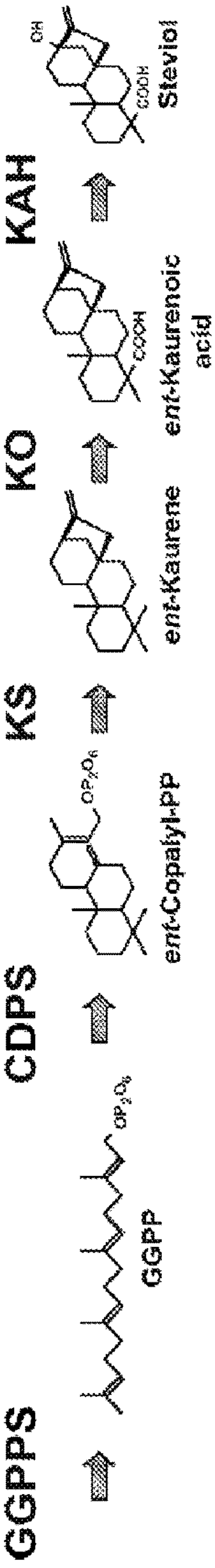
FIG. 1 shows the biochemical pathway for producing steviol from geranylgeranyl diphosphate using geranylgeranyl diphosphate synthase (GGPPS), ent-copalyl diphosphate synthase (CDPS), ent-kaurene synthase (KS), ent-kaurene oxidase (KO), and ent-kaurenoic acid hydroxylase (KAH) polypeptides.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, CA).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae.*

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, *Genetics* 190:841-54. See, e.g., Giaever & Nislow, 2014, *Genetics* 197(2):451-65. In some aspects, overexpression can be performed by integration using the USER cloning system; see, e.g., Nour-Eldin et al., 2010, Methods Mol Biol. 643:185-200. As used herein, the terms "deletion," "deleted," "knockout," and "knocked out" can be used interchangeably to refer to an endogenous gene that has been manipulated to no longer be expressed in an organism, including, but not limited to, *S. cerevisiae.*

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Figure 2:
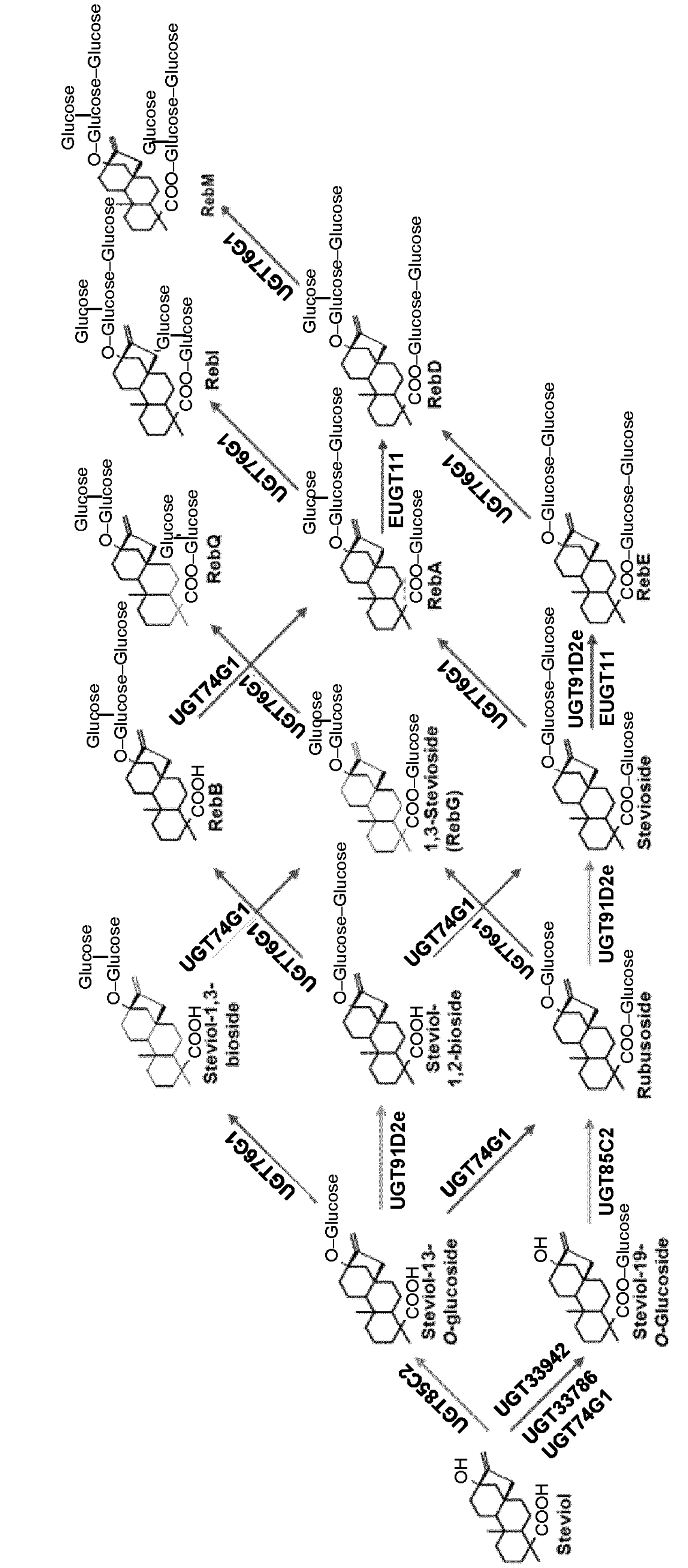
FIG. 2 shows representative primary steviol glycoside glycosylation reactions catalyzed by suitable UGT enzymes and chemical structures for several of the compounds found in *Stevia* extracts.

As used herein, the term "steviol glycoside" refers to rebaudioside A (RebA) (CAS #58543-16-1), rebaudioside B (RebB) (CAS #58543-17-2), rebaudioside C (RebC) (CAS #63550-99-2), rebaudioside D (RebD) (CAS #63279-13-0), rebaudioside E (RebE) (CAS #63279-14-1), rebaudioside F (RebF) (CAS #438045-89-7), rebaudioside M (RebM) (CAS #1220616-44-3), Rubusoside (CAS #63849-39-4), Dulcoside A (CAS #64432-06-0), rebaudioside I (RebI) (MassBank Record: FU000332), rebaudioside Q (RebQ), 1,2-Stevioside (CAS #57817-89-7), 1,3-Stevioside (RebG), Steviol-1,2-Bioside (MassBank Record: FU000299), Steviol-1,3-Bioside, Steviol-13-O-glucoside (13-SMG), Steviol-19-O-glucoside (19-SMG), a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof. See FIG. 2; see also, Steviol Glycosides Chemical and Technical Assessment 69th JECFA, 2007, prepared by Harriet Wallin, Food Agric. Org.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenal, ent-kaurenoic acid, and steviol. See FIG. 1. In some embodiments, steviol glycoside precursors are themselves steviol glycoside compounds. For example, 19-SMG, rubusoside, 1,2-stevioside, and RebE are steviol glycoside precursors of RebM. See FIG. 2.

Also as used herein, the terms "steviol precursor" and "steviol precursor compound" are used to refer to intermediate compounds in the steviol biosynthetic pathway. Steviol precursors may also be steviol glycoside precursors, and include, but are not limited to, geranylgeranyl diphosphate (GGPP), ent-copalyl-diphosphate, ent-kaurene, ent-kaurenol, ent-kaurenal, and ent-kaurenoic acid. Steviol glycosides and/or steviol glycoside precursors can be produced in vivo (i.e., in a recombinant host), in vitro (i.e., enzymatically), or by whole cell bioconversion. As used herein, the terms "produce" and "accumulate" can be used interchangeably to describe synthesis of steviol glycosides and steviol glycoside precursors in vivo, in vitro, or by whole cell bioconversion.

As used herein, the terms "culture broth," "culture medium," and "growth medium" can be used interchangeably to refer to a liquid or solid that supports growth of a cell. A culture broth can comprise glucose, fructose, sucrose, trace metals, vitamins, salts, yeast nitrogen base (YNB), and/or amino acids. The trace metals can be divalent cations, including, but not limited to, $Mn^{2+}$ and/or $Mg^{2+}$. In some embodiments, $Mn^{2+}$ can be in the form of $MnCl_2$ dihydrate and range from approximately 0.01 g/L to 100 g/L. In some embodiments, $Mg^{2+}$ can be in the form of $MgSO_4$ heptahydrate and range from approximately 0.01 g/L to 100 g/L. For example, a culture broth can comprise i) approximately 0.02-0.03 g/L $MnCl_2$ dihydrate and approximately 0.5-3.8 g/L $MgSO_4$ heptahydrate, ii) approximately 0.03-0.06 g/L $MnCl_2$ dihydrate and approximately 0.5-3.8 g/L $MgSO_4$ heptahydrate, and/or iii) approximately 0.03-0.17 g/L $MnCl_2$ dihydrate and approximately 0.5-7.3 g/L $MgSO_4$ heptahydrate. Additionally, a culture broth can comprise one or more steviol glycosides produced by a recombinant host, as described herein.

Recombinant steviol glycoside-producing *Saccharomyces cerevisiae* (*S. cerevisiae*) strains are described in WO 2011/153378, WO 2013/022989, WO 2014/122227, and WO 2014/122328, each of which is incorporated by reference in their entirety. Methods of producing steviol glycosides in recombinant hosts, by whole cell bio-conversion, and in vitro are also described in WO 2011/153378, WO 2013/022989, WO 2014/122227, and WO 2014/122328.

In some embodiments, a recombinant host comprising a gene encoding a polypeptide capable of synthesizing geranylgeranyl pyrophosphate (GGPP) from farnesyl diphosphate (FPP) and isopentenyl diphosphate (IPP) (e.g., geranylgeranyl diphosphate synthase (GGPPS)); a gene encoding a polypeptide capable of synthesizing ent-copalyl diphosphate from GGPP (e.g., ent-copalyl diphosphate synthase (CDPS)); a gene encoding a polypeptide capable of synthesizing ent-kaurene from ent-copalyl diphosphate (e.g., kaurene synthase (KS)); a gene encoding a polypeptide capable of synthesizing ent-kaurenoic acid, ent-kaurenol, and/or ent-kaurenal from ent-kaurene (e.g., kaurene oxidase (KO)); a gene encoding a polypeptide capable of reducing cytochrome P450 complex (e.g., cytochrome P450 reductase (CPR) or P450 oxidoreductase (POR); for example, but not limited to a polypeptide capable of electron transfer from NADPH to cytochrome P450 complex during conversion of NADPH to $NADP^+$, which is utilized as a cofactor for terpenoid biosynthesis); a gene encoding a polypeptide capable of synthesizing steviol from ent-kaurenoic acid (e.g., steviol synthase (KAH)); and/or a gene encoding a bifunctional polypeptide capable of synthesizing ent-copalyl diphosphate from GGPP and synthesizing ent-kaurene from ent-copalyl diphosphate (e.g., an ent-copalyl diphosphate synthase (CDPS)—ent-kaurene synthase (KS) polypeptide)

can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In some embodiments, a recombinant host comprising a gene encoding a polypeptide capable of glycosylating steviol or a steviol glycoside at its C-13 hydroxyl group (e.g., UGT85C2 polypeptide); a gene encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide); a gene encoding a polypeptide capable of glycosylating steviol or a steviol glycoside at its C-19 carboxyl group (e.g., UGT74G1 polypeptide); and/or a gene encoding a polypeptide capable of beta 1,2 glycosylation of the C2' of the 13-O-glucose, 19-O-glucose, or both 13-O-glucose and 19-O-glucose of a steviol glycoside (e.g., UGT91D2 and EUGT11 polypeptide) can produce a steviol glycoside in vivo. The skilled worker will appreciate that one or more of these genes can be endogenous to the host provided that at least one (and in some embodiments, all) of these genes is a recombinant gene introduced into the recombinant host.

In some embodiments, steviol glycosides and/or steviol glycoside precursors are produced in vivo through expression of one or more enzymes involved in the steviol glycoside biosynthetic pathway in a recombinant host. For example, a recombinant host comprising a gene encoding a polypeptide capable of synthesizing geranylgeranyl pyrophosphate (GGPP) from farnesyl diphosphate (FPP) and isopentenyl diphosphate (IPP); a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a bifunctional polypeptide capable of synthesizing ent-copalyl diphosphate from GGPP and synthesizing ent-kaurene from ent-copalyl diphosphate; a gene encoding a polypeptide capable of glycosylating steviol or a steviol glycoside at its C-13 hydroxyl group (e.g., UGT85C2 polypeptide); a gene encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide); a gene encoding a polypeptide capable of glycosylating steviol or a steviol glycoside at its C-19 carboxyl group (e.g., UGT74G1 polypeptide); and/or a gene encoding a polypeptide capable of beta 1,2 glycosylation of the C2' of the 13-O-glucose, 19-O-glucose, or both 13-O-glucose and 19-O-glucose of a steviol glycoside (e.g., UGT91D2 and EUGT11 polypeptide) can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In some embodiments, a steviol-producing recombinant microorganism comprises heterologous nucleic acids encoding a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside.

In some embodiments, a steviol-producing recombinant microorganism comprises heterologous nucleic acids encoding a polypeptide capable of glycosylating steviol or a steviol glycoside at its C-13 hydroxyl group, a polypeptide capable of beta 1,3 glycosylation of the C3' of the 13-O-glucose, 19-O-glucose, or both 13-O-glucose and 19-O-glucose of a steviol glycoside, and a polypeptide capable of beta 1,2 glycosylation of the C2' of the 13-O-glucose, 19-O-glucose, or both 13-O-glucose and 19-O-glucose of a steviol glycoside polypeptides.

In some aspects, a polypeptide capable of glycosylating steviol or a steviol glycoside at its C-13 hydroxyl group, a polypeptide capable of beta 1,3 glycosylation of the C3' of the 13-O-glucose, 19-O-glucose, or both 13-O-glucose and 19-O-glucose of a steviol glycoside, a polypeptide capable of glycosylating steviol or a steviol glycoside at its C-19 carboxyl group, and/or a polypeptide capable of beta 1,2 glycosylation of the C2' of the 13-O-glucose, 19-O-glucose, or both 13-O-glucose and 19-O-glucose of a steviol glycoside, transfers a glucose molecule from uridine diphosphate glucose (UDP-glucose) to steviol and/or a steviol glycoside.

Figure 3:
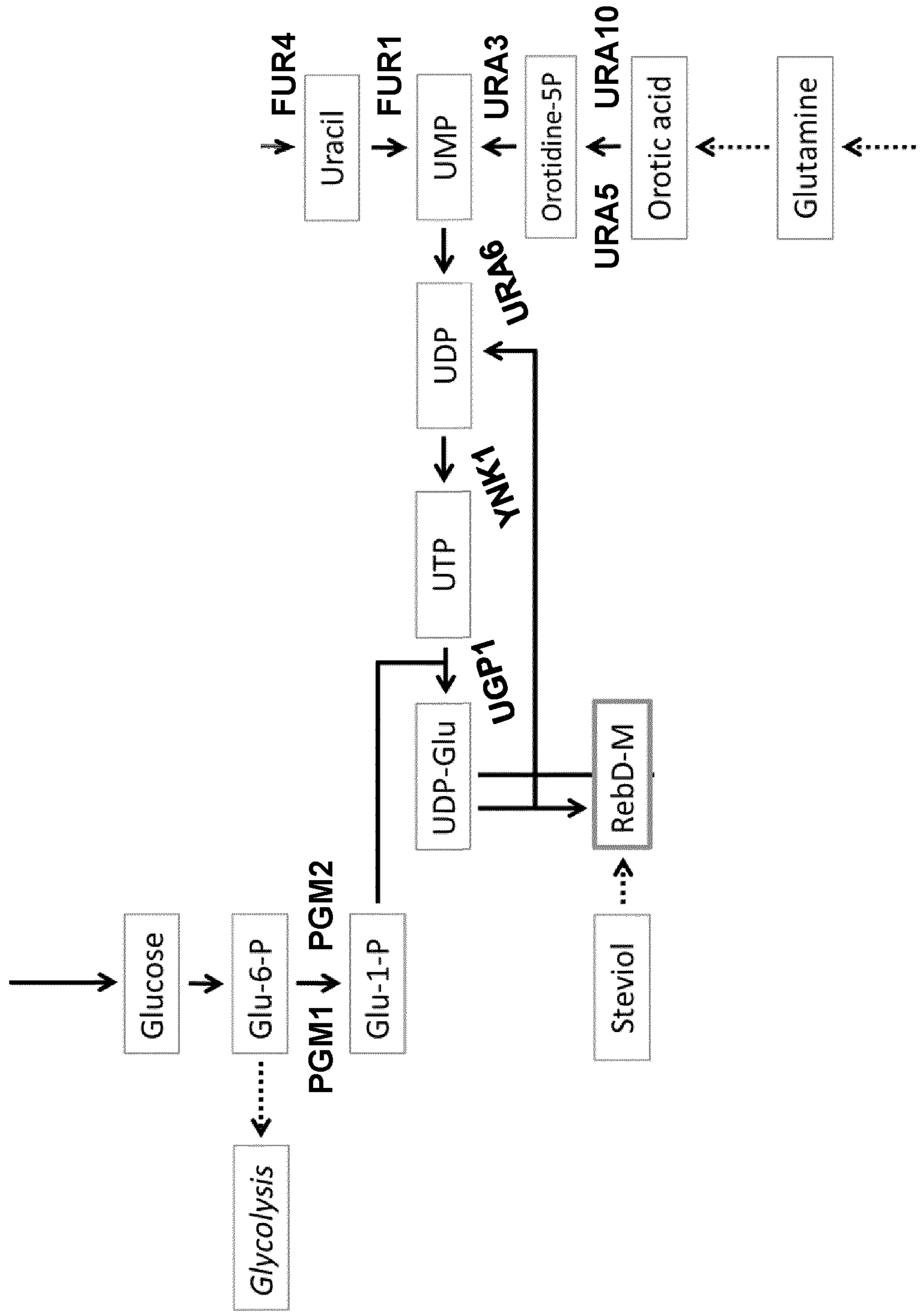
FIG. 3 shows representative reactions catalyzed by enzymes involved in the UDP-glucose biosynthetic pathway, including uracil permease (FUR4), uracil phosphoribosyltransferase (FUR1), orotate phosphoribosyltransferase 1 (URA5), orotate phosphoribosyltransferase 2 (URA10), orotidine 5'-phosphate decarboxylase (URA3), uridylate kinase (URA6), nucleoside diphosphate kinase (YNK1), phosphoglucomutase-1 (PGM1), phosphoglucomutase-2 (PGM2), and UTP-glucose-1-phosphate uridylyltransferase (UGP1). See, e.g., Daran et al., 1995, *Eur J Biochem.* 233(2):520-30.

In some aspects, UDP-glucose is produced in vivo through expression of one or more enzymes involved in the UDP-glucose biosynthetic pathway in a recombinant host. For example, a recombinant host comprising a gene encoding a polypeptide capable of transporting uracil into the host cell (e.g., uracil permease (FUR4)); a gene encoding a polypeptide capable of synthesizing uridine monophosphate (UMP) from uracil (e.g., uracil phosphoribosyltransferase (FUR1)); a gene encoding a polypeptide capable of synthesizing orotidine monophosphate (OMP) from orotate or orotic acid (e.g., orotate phosphoribosyltransferase 1 (URA5) and orotate phosphoribosyltransferase 2 (URA10)); a gene encoding a polypeptide capable of synthesizing UMP from OMP (e.g., orotidine 5'-phosphate decarboxylase (URA3)); a gene encoding a polypeptide capable of synthesizing uridine diphosphate (UDP) from UMP (e.g., uridylate kinase (URA6)); a gene encoding a polypeptide capable of synthesizing uridine 5'-triphosphate (UTP) from UDP (i.e., a polypeptide capable of catalyzing the transfer of gamma phosphates from nucleoside triphosphates, e.g., nucleoside diphosphate kinase (YNK1)); a gene encoding a polypeptide capable of converting glucose-6-phosphate to glucose-1-phosphate (e.g., phosphoglucomutase-1 (PGM1) and phosphoglucomutase-2 (PGM2)); and/or a gene encoding a polypeptide capable of synthesizing UDP-glucose from UTP and glucose-1-phosphate (e.g., UTP-glucose-1-phosphate uridylyltransferase (UGP1) can produce UDP-glucose in vivo. See, e.g., FIG. 3. The skilled worker will appreciate that one or more of these genes may be endogenous to the host.

In some embodiments, a recombinant host comprises a gene encoding a polypeptide capable of synthesizing UTP from UDP. In some aspects, the gene encoding a polypeptide capable of synthesizing UTP from UDP is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of synthesizing UTP from UDP results in a total expression level of genes encoding a polypeptide capable of synthesizing UTP from UDP that is higher than the expression level of endogenous genes encoding a polypeptide capable of synthesizing UTP from UDP, i.e., an overexpression of a polypeptide capable of synthesizing UTP from UDP.

In some aspects, the gene encoding the polypeptide capable of synthesizing UTP from UDP is a gene present in the same species as the recombinant host, i.e., an endogenous gene. In some embodiments, the wild-type promoter of an endogenous gene encoding the polypeptide capable of synthesizing UTP from UDP can be exchanged for a strong promoter. In some aspects, the strong promoter drives high expression of the endogenous gene (i.e., overexpression of the gene). In other embodiments, the wild-type enhancer of an endogenous gene encoding a polypeptide capable of synthesizing UTP from UDP can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of synthesizing UTP from UDP (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of synthesizing UTP from UDP, operably linked to a wild-type promoter, further comprises a recombinant gene encoding a polypeptide capable of synthesizing UTP from UDP, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of synthesizing UTP from UDP, operably linked to a wild-type promoter, further comprises a recombinant gene encoding a polypeptide capable of synthesizing UTP from UDP, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polypeptide capable of synthesizing UTP from UDP, operably linked to, e.g., a strong promoter native to the host, or a heterologous promoter.

The person of ordinary skill in the art will appreciate that, e.g., expression of a recombinant gene encoding a polypeptide capable of synthesizing UTP from UDP; expression of a recombinant gene and an endogenous gene encoding a polypeptide capable of synthesizing UTP from UDP, and expression of an endogenous gene encoding a polypeptide capable of synthesizing UTP from UDP, wherein the wild-type promoter and/or enhancer of the endogenous gene are exchanged for a strong promoter and/or enhancer, each result in overexpression of a polypeptide capable of synthesizing UTP from UDP relative to a corresponding host not expressing a recombinant gene encoding a polypeptide capable of synthesizing UTP from UDP and/or a corresponding host expressing only a native gene encoding a polypeptide capable of synthesizing UTP from UDP, operably linked to the wild-type promoter and enhancer—i.e., as used herein, the term "expression" may include "overexpression."

In some embodiments, a polypeptide capable of synthesizing UTP from UDP is overexpressed such that the total expression level of genes encoding the polypeptide capable of synthesizing UTP from UDP is at least 5% higher than the expression level of endogenous genes encoding a polypeptide capable of synthesizing UTP from UDP. In some embodiments, the total expression level of genes encoding a polypeptide capable of synthesizing UTP from UDP is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of synthesizing UTP from UDP.

In some embodiments, a recombinant host comprises a gene encoding a polypeptide capable of converting glucose-6-phosphate to glucose-1-phosphate. In some aspects, the gene encoding a polypeptide capable of converting glucose-6-phosphate to glucose-1-phosphate is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of converting glucose-6-phosphate to glucose-1-phosphate results in a total expression level of genes encoding a polypeptide capable of converting glucose-6-phosphate to glucose-1-phosphate that is higher than the expression level of endogenous genes encoding a polypeptide capable of converting glucose-6-phosphate to glucose-1-phosphate, i.e., an overexpression of a polypeptide capable of converting glucose-6-phosphate to glucose-1-phosphate.

In some aspects, the gene encoding the polypeptide capable of converting glucose-6-phosphate to glucose-1-phosphate is a gene present in the same species as the recombinant host, i.e., an endogenous gene. In some embodiments, the wild-type promoter of an endogenous gene encoding the polypeptide capable of converting glucose-6-phosphate to glucose-1-phosphate can be exchanged for a strong promoter. In some aspects, the strong promoter drives high expression of the endogenous gene (i.e., overexpression of the gene). In other embodiments, the wild-type enhancer of an endogenous gene encoding a polypeptide capable of converting glucose-6-phosphate to glucose-1-phosphate can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of converting glucose-6-phosphate to glucose-1-phosphate (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of converting glucose-6-phosphate to glucose-1-phosphate, operably linked to a wild-type promoter, further comprises a recombinant gene encoding a polypeptide capable of converting glucose-6-phosphate to glucose-1-phosphate, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of converting glucose-6-phosphate to glucose-1-phosphate, operably linked to a wild-type promoter, further comprises a recombinant gene encoding a polypeptide capable of converting glucose-6-phosphate to glucose-1-phosphate, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polpeptide capable of converting glucose-6-phosphate to glucose-1-phosphate, operably linked to, e.g., a strong promoter native to the host, or a heterologous promoter.

In some embodiments, a polypeptide capable of converting glucose-6-phosphate to glucose-1-phosphate is overexpressed such that the total expression level of genes encoding the polypeptide capable of converting glucose-6-phosphate to glucose-1-phosphate is at least 5% higher than the expression level of endogenous genes encoding a polypeptide capable of converting glucose-6-phosphate to glucose-1-phosphate. In some embodiments, the total expression level of genes encoding a polypeptide capable of converting glucose-6-phosphate to glucose-1-phosphate is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of converting glucose-6-phosphate to glucose-1-phosphate.

In some embodiments, a recombinant host comprises a gene encoding a polypeptide capable of synthesizing UDP-glucose from UTP and glucose-1-phosphate. In some aspects, the gene encoding a polypeptide capable of synthesizing UDP-glucose from UTP and glucose-1-phosphate is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of synthesizing UDP-glucose from UTP and glucose-1-phosphate results in a total expression level of genes encoding a polypeptide capable of synthesizing UDP-glucose from UTP and glucose-1-phosphate that is higher than the expression level of endogenous genes encoding a polypeptide capable of synthesizing UDP-glucose from UTP and glucose-1-phosphate, i.e., an overexpression of a polypeptide capable of synthesizing UDP-glucose from UTP and glucose-1-phosphate.

In some aspects, the gene encoding the polypeptide capable of synthesizing UDP-glucose from UTP and glucose-1-phosphate is a gene present in the same species as the recombinant host, i.e., an endogenous gene. In some embodiments, the wild-type promoter of an endogenous gene encoding the polypeptide capable of synthesizing UDP-glucose from UTP and glucose-1-phosphate can be exchanged for a strong promoter. In some aspects, the strong promoter drives high expression of the endogenous gene (i.e., overexpression of the gene). In other embodiments, the wild-type enhancer of an endogenous gene encoding a polypeptide capable of synthesizing UDP-glucose from UTP and glucose-1-phosphate can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of synthesizing UDP-glucose from UTP and glucose-1-phosphate (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of synthesizing UDP-glucose from UTP and glucose-1-phosphate, operably linked to a wild-type promoter, further comprises a recombinant gene encoding a polypeptide capable of synthesizing UDP-glucose from UTP and glucose-1-phosphate, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of synthesizing UDP-glucose from UTP and glucose-1-phosphate, operably linked to a wild-type promoter, further comprises a recombinant gene encoding a polypeptide capable of synthesizing UDP-glucose from UTP and glucose-1-phosphate, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polypeptide capable of synthesizing UDP-glucose from UTP and glucose-1-phosphate, operably linked to, e.g., a strong promoter native to the host, or a heterologous promoter.

In some embodiments, a recombinant host comprising a polypeptide capable of synthesizing UDP-glucose from UTP and glucose-1-phosphate is overexpressed such that the total expression level of genes encoding the polypeptide capable of synthesizing UDP-glucose from UTP and glucose-1-phosphate is at least 5% higher than the expression level of endogenous genes encoding a polypeptide capable of synthesizing UDP-glucose from UTP and glucose-1-phosphate. In some embodiments, the total expression level of genes encoding a polypeptide capable of synthesizing UDP-glucose from UTP and glucose-1-phosphate is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of synthesizing UDP-glucose from UTP and glucose-1-phosphate.

In some aspects, a recombinant host comprising one or more genes encoding one or more polypeptides capable of synthesizing UTP from UDP, one or more genes encoding one or more polypeptides capable of converting glucose-6-phosphate to glucose-1-phosphate, and/or one or more genes encoding one or more polypeptides capable of synthesizing UDP-glucose from UTP and glucose-1-phosphate may further comprise a recombinant gene encoding a polypeptide capable of transporting uracil into the host cell; a recombinant gene encoding a polypeptide capable of synthesizing uridine monophosphate (UMP) from uracil; a recombinant gene encoding a polypeptide capable of synthesizing orotidine monophosphate (OMP) from orotate or orotic acid; a recombinant gene encoding a polypeptide capable of synthesizing UMP from OMP; and/or a recombinant gene encoding a polypeptide capable of synthesizing uridine diphosphate (UDP) from UMP. In some embodiments, a recombinant host comprising one or more genes encoding one or more polypeptides capable of synthesizing UTP from UDP, one or more genes encoding one or more polypeptides capable of converting glucose-6-phosphate to glucose-1-phosphate, and/or one or more genes encoding one or more polypeptides capable of synthesizing UDP-glucose from UTP and glucose-1-phosphate may overexpress a gene encoding a polypeptide capable of transporting uracil into the host cell; a gene encoding a polypeptide capable of synthesizing uridine monophosphate (UMP) from uracil; a gene encoding a polypeptide capable of synthesizing orotidine monophosphate (OMP) from orotate or orotic acid; a gene encoding a polypeptide capable of synthesizing UMP from OMP; and/or a gene encoding a polypeptide capable of synthesizing uridine diphosphate (UDP) from UMP.

In some aspects, the polypeptide capable of synthesizing UTP from UDP comprises a polypeptide having the amino acid sequence set forth in SEQ ID NO:123 (which can be encoded by the nucleotide sequence set forth in SEQ ID NO:122).

In some aspects, the polypeptide capable of converting glucose-6-phosphate to glucose-1-phosphate comprises a polypeptide having the amino acid sequence set forth in SEQ ID NO:2 (which can be encoded by the nucleotide sequence set forth in SEQ ID NO:1), SEQ ID NO:119 (encoded by the nucleotide sequence set forth in SEQ ID NO:118), SEQ ID NO:141 (encoded by the nucleotide sequence set forth in SEQ ID NO:140), SEQ ID NO:143 (encoded by the nucleotide sequence set forth in SEQ ID NO:142), SEQ ID NO:145 (encoded by the nucleotide sequence set forth in SEQ ID NO:144), or SEQ ID NO:147 (encoded by the nucleotide sequence set forth in SEQ ID NO:146).

In some aspects, the polypeptide capable of synthesizing UDP-glucose from UTP and glucose-1-phosphate comprises a polypeptide having the amino acid sequence set forth in SEQ ID NO:121 (which can be encoded by the nucleotide sequence set forth in SEQ ID NO:120), SEQ ID NO:125 (encoded by the nucleotide sequence set forth in SEQ ID NO:124), SEQ ID NO:127 (encoded by the nucleotide sequence set forth in SEQ ID NO:126), SEQ ID NO:129 (encoded by the nucleotide sequence set forth in SEQ ID NO:128), SEQ ID NO:131 (encoded by the nucleotide sequence set forth in SEQ ID NO:130), SEQ ID NO:133 (encoded by the nucleotide sequence set forth in SEQ ID NO:132), SEQ ID NO:135 (encoded by the nucleotide sequence set forth in SEQ ID NO:134), SEQ ID NO:137 (encoded by the nucleotide sequence set forth in SEQ ID NO:136), or SEQ ID NO:139 (encoded by the nucleotide sequence set forth in SEQ ID NO:138).

In some embodiments, a recombinant host comprises a recombinant gene encoding a polypeptide capable of synthesizing UTP from UDP and a recombinant gene encoding a polypeptide capable of converting glucose-6-phosphate to glucose-1-phosphate. In some embodiments, a recombinant host comprises a recombinant gene encoding a polypeptide capable of synthesizing UTP from UDP and a recombinant gene encoding a polypeptide capable of synthesizing UDP-glucose from UTP and glucose-1-phosphate. In some embodiments, a recombinant host comprises a recombinant gene encoding a polypeptide capable of converting glucose-6-phosphate to glucose-1-phosphate and a recombinant gene encoding a polypeptide capable of synthesizing UDP-glucose from UTP and glucose-1-phosphate. In some embodiments, a recombinant host comprises a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate.

In some embodiments, a recombinant host comprises two or more recombinant genes encoding a polypeptide involved in the UDP-glucose biosynthetic pathway, e.g., a gene encoding a polypeptide capable of converting glucose-6-phosphate having a first amino acid sequence and a gene encoding a polypeptide capable of converting glucose-6-phosphate having a second amino acid sequence distinct from the first amino acid sequence. For example, in some embodiments, a recombinant host comprises a gene encoding a polypeptide having the amino acid sequence of PGM1 (e.g., a polypeptide having the amino acid sequence set forth in SEQ ID NO:2) and a gene encoding a polypeptide having the amino acid sequence of PGM2 (e.g., a polypeptide having the amino acid sequence set forth in SEQ ID NO:119, SEQ ID NO:141, SEQ ID NO:143, SEQ ID NO:145, or SEQ ID NO:147). In certain such embodiments, the two or more genes encoding a polypeptide involved in the UDP-glucose biosynthetic pathway comprise nucleotide sequences native to the recombinant host cell (e.g., a recombinant *S. cerevisiae* host cell comprising a gene encoding a polypeptide having the amino acid sequence set forth in SEQ ID NO:2 and a gene encoding a polypeptide having the amino acid sequence set forth in SEQ ID NO:119). In other such embodiments, one of the two or more genes encoding a polypeptide involved in the UDP-glucose biosynthetic pathway comprises a nucleotide sequence native to the recombinant host cell, while one or more of the two or more genes encoding a polypeptide involved in the UDP-glucose biosynthetic pathway comprises a heterologous nucleotide sequence. For example, in some embodiments, a recombinant *S. cerevisiae* host cell expressing a recombinant gene encoding a polypeptide capable of synthesizing UDP-glucose from UTP and glucose-1-phosphate having the amino acid sequence set forth in SEQ ID NO:121 (i.e., a recombinant host overexpressing the polypeptide) further expresses a recombinant gene encoding a polypeptide capable of synthesizing UDP-glucose from UTP and glucose-1-phosphate having the amino acid sequence set forth in, e.g., SEQ ID NO:125, SEQ ID NO:127, SEQ ID NO:129, SEQ ID NO:131, SEQ ID NO:133, SEQ ID NO:135, SEQ ID NO:137, or SEQ ID NO:139. In another example, in some embodiments, a recombinant *S. cerevisiae* host cell expressing a recombinant gene encoding a polypeptide capable of converting glucose-6-phosphate to glucose-1-phosphate having the amino acid sequence set forth in SEQ ID NO:119 (i.e., a recombinant host overexpressing the polypeptide) further expresses a recombinant gene encoding a polypeptide capable of converting glucose-6-phosphate to glucose-1-phosphate having the amino acid sequence set forth in, e.g., SEQ ID NO:141, SEQ ID NO:143, SEQ ID NO:145, or SEQ ID NO:147. Accordingly, as used herein, the term "a recombinant gene" may include "one or more recombinant genes."

In some embodiments, a recombinant host comprises two or more copies of a recombinant gene encoding a polypeptide involved in the UDP-glucose biosynthetic pathway or the steviol glycoside biosynthetic pathway. In some embodiments, a recombinant host is preferably transformed with, e.g., two copies, three copies, four copies, or five copies of a recombinant gene encoding a polypeptide involved in the UDP-glucose biosynthetic pathway or the steviol glycoside biosynthetic pathway. For example, in some embodiments, a recombinant host is transformed with two copies of a recombinant gene encoding a polypeptide capable of synthesizing UTP from UDP (e.g., a polypeptide having the amino acid sequence set forth in SEQ ID NO:123). The person of ordinary skill in the art will appreciate that, in some embodiments, recombinant genes may be replicated in a host cell independently of cell replication; accordingly, a recombinant host cell may comprise, e.g., more copies of a recombinant gene than the number of copies the cell was transformed with. Accordingly, as used herein, the term "a recombinant gene" may include "one or more copies of a recombinant gene."

In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a recombinant host cell increases the amount of UDP-glucose produced by the cell. In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a recombinant host cell maintains, or even increases, the pool of UDP-glucose available for, e.g., glycosylation of steviol or a steviol glycoside. In some aspects, expression of a polypeptide capable of synthesizing UTP from UDP, a polypeptide capable of converting glucose-6-phosphate to glucose-1-phosphate, and/or a polypeptide capable sunthesizing UDP-glucose from UTP and glucose-1-phosphate in a recombinant host cell increases the speed which UDP-glucose is regenerated, thus maintaining, or even increasing, the UDP-glucose pool, which can be used to synthesize one or more steviol glycosides.

In some embodiments, expression of a recombinant gene encoding a polypeptide capable of synthesizing UTP from UDP (e.g., a polypeptide having the amino acid sequence set forth in SEQ ID NO:123), a recombinant gene encoding a polypeptide capable of converting glucose-6-phosphate to glucose-1-phosphate (e.g. a polypeptide having the amino acid sequence set forth in SEQ ID NO:2, SEQ ID NO:119, SEQ ID NO:141, SEQ ID NO:143, SEQ ID NO:145, or SEQ ID NO:147), and a recombinant gene encoding a polypeptide capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, or SEQ ID NO:139) in a recombinant host cell increases the amount of UDP-glucose produced by the cell by at least about 10%, e.g., at least about 25%, or at least about 50%, or at least about 75%, or at least about 100%, or at least about 125%, or at least about 150%, or at least about 175%, or at least about 200%, or at least about 225%, or at least about 250%, or at least about 275%, or at least about 300%, calculated as an increase in intracellular UDP-glucose concentration relative to a corresponding host lacking the recombinant genes.

In certain such embodiments, one or more of the recombinant gene encoding a polypeptide capable of synthesizing UTP from UDP, the recombinant gene encoding a polypeptide capable of converting glucose-6-phosphate to glucose-1-phosphate, and the recombinant gene encoding a polypeptide capable of synthesizing UDP-glucose from UTP and glucose-1-phosphate comprise a nucleotide sequence native to the host cell. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2 and/or SEQ ID NO:119, and a recombinant gene encoding a polypeptide capable of synthesizing UDP-glucose from UTP and glucose-1-phosphate having the amino acid sequence set forth in SEQ ID NO:121 in a steviol glycoside-producing *S. cerevisiae* host cell (i.e., providing a recombinant host overexpressing the polypeptides) increases the amount of UDP-glucose produced by the cell by at least about 10%, e.g., at least about 25%, or at least about 50%, or at least about 75%, or at least about 100%, or at least about 125%, or at least about 150%, or at least about 175%, or at least about 200%, or at least about 225%, or at least about 250%, or at least about 275%, or at least about 300%, calculated as an increase in intracellular UDP-glucose concentration relative to a corresponding host lacking the recombinant genes.

In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a steviol-glycoside producing recombinant host cell further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside, increases the amount of one or more steviol glycosides produced by the cell, and/or decreases the amount of one or more steviol glycosides produced by the cell. In some embodiments, the steviol glycoside-producing host further expresses a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; and a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate.

In some aspects, the polypeptide capable of synthesizing geranylgeranyl pyrophosphate (GGPP) from farnesyl diphosphate (FPP) and isopentenyl diphosphate (IPP) comprises a polypeptide having an amino acid sequence set forth in SEQ ID NO:20 (which can be encoded by the nucleotide sequence set forth in SEQ ID NO:19), SEQ ID NO:22 (encoded by the nucleotide sequence set forth in SEQ ID NO:21), SEQ ID NO:24 (encoded by the nucleotide sequence set forth in SEQ ID NO:23), SEQ ID NO:26 (encoded by the nucleotide sequence set forth in SEQ ID NO:25), SEQ ID NO:28 (encoded by the nucleotide sequence set forth in SEQ ID NO:27), SEQ ID NO:30 (encoded by the nucleotide sequence set forth in SEQ ID NO:29), SEQ ID NO:32 (encoded by the nucleotide sequence set forth in SEQ ID NO:31), or SEQ ID NO:116 (encoded by the nucleotide sequence set forth in SEQ ID NO:115). In some embodiments, a recombinant host comprising a gene encoding a polypeptide capable of synthesizing geranylgeranyl pyrophosphate (GGPP) from farnesyl diphosphate (FPP) and isopentenyl diphosphate (IPP) further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-copalyl diphosphate from GGPP comprises a polypeptide having an amino acid sequence set forth in SEQ ID NO:34 (which can be encoded by the nucleotide sequence set forth in SEQ ID NO:33), SEQ ID NO:36 (encoded by the nucleotide sequence set forth in SEQ ID NO:35), SEQ ID NO:38 (encoded by the nucleotide sequence set forth in SEQ ID NO:37), SEQ ID NO:40 (encoded by the nucleotide sequence set forth in SEQ ID NO:39), or SEQ ID NO:42 (encoded by the nucleotide sequence set forth in SEQ ID NO:41). In some embodiments, the polypeptide capable of synthesizing ent-copalyl diphosphate from GGPP lacks a chloroplast transit peptide. In some embodiments, a recombinant host comprising a gene encoding a polypeptide capable of synthesizing ent-copalyl diphosphate from GGPP further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-kaurene from ent-copalyl diphosphate comprises a polypeptide having an amino acid sequence set forth in SEQ ID NO:44 (which can be encoded by the nucleotide sequence set forth in SEQ ID NO:43), SEQ ID NO:46 (encoded by the nucleotide sequence set forth in SEQ ID NO:45), SEQ ID NO:48 (encoded by the nucleotide sequence set forth in SEQ ID NO:47), SEQ ID NO:50 (encoded by the nucleotide sequence set forth in SEQ ID NO:49), or SEQ ID NO:52 (encoded by the nucleotide sequence set forth in SEQ ID NO:51). In some embodiments, a recombinant host comprising a gene encoding a polypeptide capable of synthesizing ent-kaurene from ent-copalyl diphosphate further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some embodiments, a recombinant host comprises a gene encoding a bifunctional polypeptide capable of synthesizing ent-copalyl diphosphate from GGPP and synthesizing ent-kaurene from ent-copalyl diphosphate. In some aspects, the bifunctional polypeptide comprises a polypeptide having an amino acid sequence set forth in SEQ ID NO:54 (which can be encoded by the nucleotide sequence set forth in SEQ ID NO:53), SEQ ID NO:56 (encoded by the nucleotide sequence set forth in SEQ ID NO:55), or SEQ ID NO:58 (encoded by the nucleotide sequence set forth in SEQ ID NO:57). In some embodiments, a recombinant host comprising a gene encoding a bifunctional polypeptide capable of synthesizing ent-copalyl diphosphate from GGPP and synthesizing ent-kaurene from ent-copalyl diphosphate further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-kaurenoic acid, ent-kaurenol, and/or ent-kaurenal from ent-kaurene comprises a polypeptide having an amino acid sequence set forth in SEQ ID NO:60 (which can be encoded by the nucleotide sequence set forth in SEQ ID NO:59), SEQ ID NO:62 (encoded by the nucleotide sequence set forth in SEQ ID NO:61), SEQ ID NO:117 (encoded by the nucleotide sequence set forth in SEQ ID NO:63 or SEQ ID NO:64), SEQ ID NO:66 (encoded by the nucleotide sequence set forth in SEQ ID NO:65), SEQ ID NO:68 (encoded by the nucleotide sequence set forth in SEQ ID NO:67), SEQ ID NO:70 (encoded by the nucleotide sequence set forth in SEQ ID NO:69), SEQ ID NO:72 (encoded by the nucleotide sequence set forth in SEQ ID NO:71), SEQ ID NO:74 (encoded by the nucleotide sequence set forth in SEQ ID NO:73), or SEQ ID NO:76 (encoded by the nucleotide sequence set forth in SEQ ID NO:75). In some embodiments, a recombinant host comprising a gene encoding a polypeptide capable of synthesizing ent-kaurenoic acid, ent-kaurenol, and/or ent-kaurenal from ent-kaurene further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of reducing cytochrome P450 complex comprises a polypeptide having an amino acid sequence set forth in SEQ ID NO:78 (which can be encoded by the nucleotide sequence set forth in SEQ ID NO:77), SEQ ID NO:80 (encoded by the nucleotide sequence set forth in SEQ ID NO:79), SEQ ID NO:82 (encoded by the nucleotide sequence set forth in SEQ ID NO:81), SEQ ID NO:84 (encoded by the nucleotide sequence set forth in SEQ ID NO:83), SEQ ID NO:86 (encoded by the nucleotide sequence set forth in SEQ ID NO:85), SEQ ID NO:88 (encoded by the nucleotide sequence set forth in SEQ ID NO:87), SEQ ID NO:90 (encoded by the nucleotide sequence set forth in SEQ ID NO:89), or SEQ ID NO:92 (encoded by the nucleotide sequence set forth in SEQ ID NO:91). In some embodiments, a recombinant host comprising a gene encoding a polypeptide capable of reducing cytochrome P450 complex further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing steviol from ent-kaurenoic acid comprises a polypeptide having an amino acid sequence set forth in SEQ ID NO:94 (which can be encoded by the nucleotide sequence set forth in SEQ ID NO:93), SEQ ID NO:97 (encoded by the nucleotide sequence set forth in SEQ ID NO:95 or SEQ ID NO:96), SEQ ID NO:100 (encoded by the nucleotide sequence set forth in SEQ ID NO:98 or SEQ ID NO:99), SEQ ID NO:101, SEQ ID NO:102, SEQ ID NO:103, SEQ ID NO:104, SEQ ID NO:106 (encoded by the nucleotide sequence set forth in SEQ ID NO:105), SEQ ID NO:108 (encoded by the nucleotide sequence set forth in SEQ ID NO:107), SEQ ID NO:110 (encoded by the nucleotide sequence set forth in SEQ ID NO:109), SEQ ID NO:112 (encoded by the nucleotide sequence set forth in SEQ ID NO:111), or SEQ ID NO:114 (encoded by the nucleotide sequence set forth in SEQ ID NO:113). In some embodiments, a recombinant host comprising a gene encoding a polypeptide capable of synthesizing steviol from ent-kaurenoic acid further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some embodiments, a recombinant host comprises a nucleic acid encoding a polypeptide capable of glycosylating steviol or a steviol glycoside at its C-13 hydroxyl group (e.g., UGT85C2 polypeptide) (SEQ ID NO:7), a nucleic acid encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide) (SEQ ID NO:9), a nucleic acid encoding a polypeptide capable of glycosylating steviol or a steviol glycoside at its C-19 carboxyl group (e.g., UGT74G1 polypeptide) (SEQ ID NO:4), a nucleic acid encoding a polypeptide capable of beta 1,2 glycosylation of the C2' of the 13-O-glucose, 19-O-glucose, or both 13-O-glucose and 19-O-glucose of a steviol glycoside (e.g., EUGT11 polypeptide) (SEQ ID NO:16). In some aspects, the polypeptide capable of beta 1,2 glycosylation of the C2' of the 13-O-glucose, 19-O-glucose, or both 13-O-glucose and 19-O-glucose of a steviol glycoside (e.g., UGT91D2 polypeptide) can be a UGT91D2e polypeptide (SEQ ID NO:11) or a UGT91D2e-b polypeptide (SEQ ID NO:13). In some embodiments, a recombinant host comprising a gene encoding a polypeptide capable of glycosylating steviol or a steviol glycoside further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of glycosylating steviol or a steviol glycoside at its C-13 hydroxyl group is encoded by the nucleotide sequence set forth in SEQ ID NO:5 or SEQ ID NO:6, the polypeptide capable of beta 1,3 glycosylation of the C3' of the 13-O-glucose, 19-O-glucose, or both 13-O-glucose and 19-O-glucose of a steviol glycoside is encoded by the nucleotide sequence set forth in SEQ ID NO:8, the polypeptide capable of glycosylating steviol or a steviol glycoside at its C-19 carboxyl group is encoded by the nucleotide sequence set forth in SEQ ID NO:3, the polypeptide capable of beta 1,2 glycosylation of the C2' of the 13-O-glucose, 19-O-glucose, or both 13-O-glucose and 19-O-glucose of a steviol glycoside is encoded by the nucleotide sequence set forth in SEQ ID NO:10, SEQ ID NO:12, SEQ ID NO:14, or SEQ ID NO:15. The skilled worker will appreciate that expression of these genes may be necessary to produce a particular steviol glycoside but that one or more of these genes can be endogenous to the host provided that at least one (and in some embodiments, all) of these genes is a recombinant gene introduced into the recombinant host.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host increases the amount of one or more steviol glycosides, e.g., rubusoside, RebB, RebA, RebD, and RebM, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, or at least about 60%, or at least about 70%, or at least about 80%, or at least about 90%, or at least about 100%, calculated as an increase in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP (e.g., a polypeptide having the amino acid sequence set forth in SEQ ID NO:123), a recombinant gene encoding a polypeptide capable of converting glucose-6-phosphate to glucose-1-phosphate (e.g. a polypeptide having the amino acid sequence set forth in SEQ ID NO:2, SEQ ID NO:119, SEQ ID NO:141, SEQ ID NO:143, SEQ ID NO:145, or SEQ ID NO:147), and a recombinant gene encoding a polypeptide capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, or SEQ ID NO:139) in a steviol glycoside-producing host increases the amount of one or more steviol glycosides, e.g., rubusoside, RebB, RebA, RebD, and RebM, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, or at least about 60%, or at least about 70%, or at least about 80%, or at least about 90%, or at least about 100%, calculated as an increase in intracellular glycoside concentration relative to a corresponding steviol glycoside-producing host lacking the recombinant genes.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host decreases the amount of one or more steviol glycosides, e.g., 13-SMG and RebD, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, calculated as a decrease in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121, and further expression of a recombinant gene encoding a polypeptide capable of synthesizing UDP-glucose from UTP and glucose-1-phosphate having the amino acid sequence set forth in, e.g., SEQ ID NO:127, SEQ ID NO:133, SEQ ID NO:129, SEQ ID NO:125, SEQ ID NO:139, or SEQ ID NO:135, in a steviol glycoside-producing recombinant host decreases the amount of 13-SMG produced by the cell by at least about 5%, e.g., at least about 7.5%, or at least about 10%, or at least about 15%, or at least about 20%, or at least about 25%, or at least about 30%, or at least about 35%.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host increases the total amount of steviol glycosides (i.e., the total amount of mono-, di-, tri-, tetra- penta-, hexa-, and hepta-glycosylated steviol compounds) by at least about 5%, e.g., at least about 7.5%, or at least about 10%, or at least about 12.5%, or at least about 15%, or at least about 17.5%, or at least about 20%, or at least about 25%, or at least about 27.5%, or at least about 30%, or at least about 35%, calculated as an increase in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121, and further expression of a recombinant gene encoding a polypeptide capable of synthesizing UDP-glucose from UTP and glucose-1-phosphate having the amino acid sequence set forth in, e.g., SEQ ID NO:133, SEQ ID NO:129, SEQ ID NO:131, SEQ ID NO:125, SEQ ID NO:139, or SEQ ID NO:135, in a steviol glycoside-producing recombinant host increases the total amount of steviol glycosides (i.e., the total amount of mono-, di-, tri-, tetra- penta-, hexa-, and hepta-glycosylated steviol compounds) by at least about 5%, e.g., at least about 7.5%, or at least about 10%, or at least about 12.5%, or at least about 15%, or at least about 17.5%, or at least about 20%, or at least about 25%, or at least about 27.5%, or at least about 30%, or at least about 35%, calculated as an increase in intracellular steviol glycoside concentration relative to a corresponding steviol glycoside-producing host lacking the recombinant genes.

In some other embodiments, the total amount of steviol glycosides produced by a steviol glycoside-producing recombinant host cell is unchanged (i.e., increased or decreased by less than about 5%, or less than about 4%, or less than about 3%, or less than about 2%, or less than about 1%) by expression in the host of a recombinant gene encoding a polypeptide capable of synthesizing UTP from UDP, a recombinant gene encoding a polypeptide capable of converting glucose-6-phosphate to glucose-1-phosphate, and/or a recombinant gene encoding a polypeptide capable of synthesizing UDP-glucose from UTP and glucose-1-phosphate. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121 in a steviol glycoside-producing recombinant host increases the total amount of steviol glycosides produced by the host by less than about 5%, e.g., less than about 4%, or less than about 3%, or less than about 2%.

The person of ordinary skill in the art will appreciate that, in such embodiments, expression of one or more genes encoding a polypeptide involved in the involved in the UDP-glucose biosynthetic pathway may affect the relative levels of steviol glycosides produced by the recombinant host, e.g., by increasing the level of UDP-glucose available as a substrate for a polypeptide capable of glycosylating steviol or a steviol glycoside. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121 in a steviol glycoside-producing recombinant host increases the total amount of steviol glycosides produced by the host by less than about 5%, e.g., less than about 4%, or less than about 3%, or less than about 2%, increases the amount of RebM produced by the host by at least about 50%, e.g., at least about 60%, or at least about 70%, or at least about 80%, or at least about 90%, and decreases the amount of RebD produced by the host by at least about 10%, e.g., at least about 20%, or at least about 30%, or at least about 40%.

In some embodiments, a recombinant host cell comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain embodiments, a recombinant host comprises one or more recombinant genes having a nucleotide sequence native to the host that encode one or more polypeptides capable of synthesizing UTP from UDP, one or more polypeptides capable of converting glucose-6-phosphate to glucose-1-phosphate, and/or one or more polypeptides capable of synthesizing UDP-glucose from UTP and glucose-1-phosphate, i.e., a recombinant host overexpresses one or more polypeptides capable of synthesizing UTP from UDP, one or more polypeptides capable of converting glucose-6-phosphate to glucose-1-phosphate, and/or one or more polypeptides capable of synthesizing UDP-glucose from UTP and glucose-1-phosphate.

In certain such embodiments, a recombinant host cell overexpresses one or more genes encoding one or more polypeptides capable of synthesizing UTP from UDP (e.g., an *S. cerevisiae* host cell expressing a recombinant gene encoding a polypeptide having the amino acid sequence set forth in SEQ ID NO:123), one or more genes encoding one or more polypeptides capable of converting glucose-6-phosphate to glucose-1-phosphate (e.g., an *S. cerevisiae* host cell expressing a recombinant gene encoding a polypeptide having the amino acid sequence set forth in SEQ ID NO:2, and/or SEQ ID NO:119), and/or one or more genes encoding one or more polypeptides capable of synthesizing UDP-glucose from UTP and glucose-1-phosphate (e.g., an *S. cerevisiae* host cell expressing a recombinant gene encoding a polypeptide having the amino acid sequence set forth in SEQ ID NO:121). In one example, a recombinant *S. cerevisiae* host cell overexpresses a gene encoding a polypeptide having the amino acid sequence set forth in SEQ ID NO:123, a gene encoding a polypeptide having the amino acid sequence set forth in SEQ ID NO:2, a gene encoding a polypeptide having the amino acid sequence set forth in SEQ ID NO:119, and a gene encoding a polypeptide having the amino acid sequence set forth in SEQ ID NO:121.

In certain embodiments, a recombinant host cell comprising one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139), further comprises a gene encoding a polypeptide capable of glycosylating steviol or a steviol glycoside at its C-13 hydroxyl group (e.g., a polypeptide having the amino acid sequence set forth in SEQ ID NO:7); a gene encoding a polypeptide capable of beta 1,3 glycosylation of the C3' of the 13-O-glucose, 19-O-glucose, or both 13-O-glucose and 19-O-glucose of a steviol glycoside (e.g., a polypeptide having the amino acid sequence set forth in SEQ ID NO:9); a gene encoding a polypeptide capable of glycosylating steviol or a steviol glycoside at its C-19 carboxyl group (e.g., a polypeptide having the amino acid sequence set forth in SEQ ID NO:4); and/or a gene encoding a polypeptide capable of beta 1,2 glycosylation of the C2' of the 13-O-glucose, 19-O-glucose, or both 13-O-glucose and 19-O-glucose of a steviol glycoside (e.g., a polypeptide having the amino acid sequence set forth in SEQ ID NO:11, SEQ ID NO:13, or SEQ ID NO:16). In certain such embodiments, the recombinant host cell further comprises a gene encoding a polypeptide capable of synthesizing GGPP from FPP and IPP (e.g., a polypeptide having the amino acid sequence set forth in SEQ ID NO:20); a gene encoding a polypeptide capable of synthesizing ent-copalyl diphosphate from GGPP (e.g., a polypeptide having the amino acid sequence set forth in SEQ ID NO:40); a gene encoding a polypeptide capable of synthesizing ent-kaurene from ent-copalyl diphosphate (e.g., a polypeptide having the amino acid sequence set forth in SEQ ID NO:52); a gene encoding a polypeptide capable of synthesizing ent-kaurenoic acid, ent-kaurenol, and/or ent-kaurenal from ent-kaurene (e.g., a polypeptide having the amino acid sequence set forth in SEQ ID NO:60 or SEQ ID NO:117); a gene encoding a polypeptide capable of reducing cytochrome P450 complex (e.g., a polypeptide having the amino acid sequence set forth in SEQ ID NO:78, SEQ ID NO:86, or SEQ ID NO:92); and/or a gene encoding a polypeptide capable of synthesizing steviol from ent-kaurenoic acid (e.g., a polypeptide having the amino acid sequence set forth in SEQ ID NO:94).

In some embodiments, a recombinant host comprises two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain such embodiments, a recombinant host comprises two or more genes encoding two or more polypeptides capable of converting glucose-6-phosphate to glucose-1-phosphate, e.g., two or more genes encoding two or more polypeptides having the amino acid sequence set forth in SEQ ID NO:2, SEQ ID NO:119, SEQ ID NO:141, SEQ ID NO:143, SEQ ID NO:145, and/or SEQ ID NO:147. In one example, a recombinant host comprises a gene encoding a polypeptide having the amino acid sequence set forth in SEQ ID NO:2 and a polypeptide having the amino acid sequence set forth in SEQ ID NO:119. In another example, a recombinant host comprises a gene encoding a polypeptide having the amino acid sequence set forth in SEQ ID NO:2, a polypeptide having the amino acid sequence set forth in SEQ ID NO:119, and a polypeptide having the amino acid sequence set forth in SEQ ID NO:145. In some embodiments, the recombinant host further comprises a gene encoding a polypeptide capable of synthesizing UTP from UDP (e.g., a polypeptide having the amino acid sequence set forth in SEQ ID NO:123) and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain such embodiments, a recombinant host comprises two or more genes encoding two or more polypeptides capable of synthesizing UDP-glucose from UTP and glucose-1-phosphate, e.g., two or more genes encoding two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139. In one example, a recombinant host comprises a gene encoding a polypeptide having the amino acid sequence set forth in SEQ ID NO:121 and a polypeptide having the amino acid sequence set forth in SEQ ID NO:125. In another example, a recombinant host comprises a gene encoding a polypeptide having the amino acid sequence set forth in SEQ ID NO:121 and a polypeptide having the amino acid sequence set forth in SEQ ID NO:127. In another example, a recombinant host comprises a gene encoding a polypeptide having the amino acid sequence set forth in SEQ ID NO:121 and a polypeptide having the amino acid sequence set forth in SEQ ID NO:129. In another example, a recombinant host comprises a gene encoding a polypeptide having the amino acid sequence set forth in SEQ ID NO:121 and a polypeptide having the amino acid sequence set forth in SEQ ID NO:131. In another example, a recombinant host comprises a gene encoding a polypeptide having the amino acid sequence set forth in SEQ ID NO:121 and a gene encoding a gene encoding a polypeptide having the amino acid sequence set forth in SEQ ID NO:133. In another example, a recombinant host comprises a gene encoding a polypeptide having the amino acid sequence set forth in SEQ ID NO:121 and a gene encoding a polypeptide having the amino acid sequence set forth in SEQ ID NO:135. In another example, a recombinant host comprises a gene encoding a polypeptide having the amino acid sequence set forth in SEQ ID NO:121 and a gene encoding a polypeptide having the amino acid sequence set forth in SEQ ID NO:137. In another example, a recombinant host comprises a gene encoding a polypeptide having the amino acid sequence set forth in SEQ ID NO:121 and a gene encoding a polypeptide having the amino acid sequence set forth in SEQ ID NO:139. In some embodiments, the recombinant host further comprises a gene encoding a polypeptide capable of synthesizing UTP from UDP (e.g., a polypeptide having the amino acid sequence set forth in SEQ ID NO:123) and/or one or more genes encoding one or more polypeptides capable of converting glucose-6-phosphate to glucose-1-phosphate (e.g., one or more polypeptides having the amino acid sequence set forth in SEQ ID NO:2, SEQ ID NO:119, SEQ ID NO:141, SEQ ID NO:143, SEQ ID NO:145, and/or SEQ ID NO:147).

In certain such embodiments, a recombinant host comprising two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139) is a host cell overexpressing one or more genes encoding one or more polypeptides involved in the UDP-glucose biosynthetic pathway (e.g., an *S. cerevisiae* host cell expressing one or more genes encoding one or more polypeptides having the amino acid sequence set forth in SEQ ID NO:2, SEQ ID NO:119, SEQ ID NO:121, and/or SEQ ID NO:123).

In certain embodiments, a recombinant host cell comprising two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139), further comprises a gene encoding polypeptide capable of synthesizing UTP from UDP (e.g., a polypeptide having the amino acid sequence set forth in SEQ ID NO:123), a gene encoding a polypeptide capable of glycosylating steviol or a steviol glycoside at its C-13 hydroxyl group (e.g., a polypeptide having the amino acid sequence set forth in SEQ ID NO:7); a gene encoding a polypeptide capable of beta 1,3 glycosylation of the C3' of the 13-O-glucose, 19-O-glucose, or both 13-O-glucose and 19-O-glucose of a steviol glycoside (e.g., a polypeptide having the amino acid sequence set forth in SEQ ID NO:9); a gene encoding a polypeptide capable of glycosylating steviol or a steviol glycoside at its C-19 carboxyl group (e.g., a polypeptide having the amino acid sequence set forth in SEQ ID NO:4); and/or a gene encoding a polypeptide capable of beta 1,2 glycosylation of the C2' of the 13-O-glucose, 19-O-glucose, or both 13-O-glucose and 19-O-glucose of a steviol glycoside (e.g., a polypeptide having the amino acid sequence set forth in SEQ ID NO:11, SEQ ID NO:13, or SEQ ID NO:16). In certain such embodiments, the recombinant host cell further comprises a gene encoding a polypeptide capable of synthesizing GGPP from FPP and IPP (e.g., a polypeptide having the amino acid sequence set forth in SEQ ID NO:20); a gene encoding a polypeptide capable of synthesizing ent-copalyl diphosphate from GGPP (e.g., a polypeptide having the amino acid sequence set forth in SEQ ID NO:40); a gene encoding a polypeptide capable of synthesizing ent-kaurene from ent-copalyl diphosphate (e.g., a polypeptide having the amino acid sequence set forth in SEQ ID NO:52); a gene encoding a polypeptide capable of synthesizing ent-kaurenoic acid, ent-kaurenol, and/or ent-kaurenal from ent-kaurene (e.g., a polypeptide having the amino acid sequence set forth in SEQ ID NO:60 or SEQ ID NO:117); a gene encoding a polypeptide capable of reducing cytochrome P450 complex (e.g., a polypeptide having the amino acid sequence set forth in SEQ ID NO:78, SEQ ID NO:86, or SEQ ID NO:92); and/or a gene encoding a polypeptide capable of synthesizing steviol from ent-kaurenoic acid (e.g., a polypeptide having the amino acid sequence set forth in SEQ ID NO:94).

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a polypeptide capable of synthesizing UTP from UDP, a gene encoding a polypeptide capable of converting glucose-6-phosphate to glucose-1-phosphate, and/or a gene encoding a polypeptide capable of synthesizing UDP-glucose from UTP and glucose-1-phosphate; and further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside can take up steviol and glycosylate steviol in the cell; following glycosylation in vivo, a steviol glycoside can be excreted into the culture medium. In certain such embodiments, the host cell may further express a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate.

In some embodiments, the method for producing one or more steviol glycosides or a steviol glycoside composition disclosed herein comprises whole-cell bioconversion of plant-derived or synthetic steviol and/or steviol glycosides in a cell culture medium of a recombinant host cell using: (a) a polypeptide capable of synthesizing UTP from UDP; (b) a polypeptide capable of converting glucose-6-phosphate to glucose-1-phosphate; and/or (c) a polypeptide capable of synthesizing UDP-glucose from UTP and glucose-1-phosphate, and one or more of: (d) a polypeptide capable of glycosylating steviol or a steviol glycoside at its C-13 hydroxyl group thereof; (e) a polypeptide capable of beta 1,3 glycosylation of the C3' of the 13-O-glucose, 19-O-glucose, or both 13-O-glucose and 19-O-glucose of a steviol glycoside; (f) a polypeptide capable of glycosylating steviol or a steviol glycoside at its C-19 carboxyl group thereof; and/or (g) a polypeptide capable of beta 1,2 glycosylation of the C2' of the 13-O-glucose, 19-O-glucose, or both 13-O-glucose and 19-O-glucose of a steviol glycoside; wherein at least one of the polypeptides is a recombinant polypeptide expressed in the recombinant host cell; and producing the one or more steviol glycosides or the steviol glycoside composition thereby.

In some embodiments of the methods for producing one or more steviol glycosides or a steviol glycoside composition disclosed herein comprises whole-cell bioconversion of plant-derived or synthetic steviol and/or steviol glycosides in a cell culture medium of a recombinant host cell disclosed herein, the polypeptide capable of synthesizing UTP from UDP comprises a polypeptide having at least 60% sequence identity to the amino acid sequence set forth in SEQ ID NO:123; the polypeptide capable of converting glucose-6-phosphate to glucose-1-phosphate comprises a polypeptide having at least 60% sequence identity to the amino acid sequence set forth in SEQ ID NO:2, SEQ ID NO:119, or SEQ ID NO:143; or at least 55% sequence identity to the amino acid sequence set forth in SEQ ID NO:141, SEQ ID NO:145, or SEQ ID NO:147; and/or the polypeptide capable of synthesizing UDP-glucose from UTP and glucose-1-phosphate comprises a polypeptide having at least 60% sequence identity to the amino acid sequence set forth in SEQ ID NO:121, SEQ ID NO:127; at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; or at least 70% sequence identity to the amino acid sequence set forth in SEQ ID NO:131.

In some embodiments, a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate can be displayed on the surface of the recombinant host cells disclosed herein by fusing it with the anchoring motifs.

In some embodiments, the cell is permeabilized to take up a substrate to be modified or to excrete a modified product. In some embodiments, a permeabilizing agent can be added to aid the feedstock entering into the host and product getting out. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. For example, a crude lysate of the cultured microorganism can be centrifuged to obtain a supernatant. The resulting supernatant can then be applied to a chromatography column, e.g., a C18 column, and washed with water to remove hydrophilic compounds, followed by elution of the compound(s) of interest with a solvent such as methanol. The compound(s) can then be further purified by preparative HPLC. See also, WO 2009/140394.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host expressing a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate and a host expressing a gene encoding a polypeptide capable of synthesizing UTP from UDP, a gene encoding a polypeptide capable of converting glucose-6-phosphate to glucose-1- phosphate, and/or a gene encoding a polypeptide capable of synthesizing UDP-glucose from UTP and glucose-1-phosphate; and further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside, produce one or more steviol glycosides.

In some embodiments, the steviol glycoside comprises, for example, but not limited to, 13-SMG, steviol-1,2-bioside, steviol-1,3-bioside, 19-SMG, 1,2-stevioside, 1,3-stevioside (RebG), rubusoside, RebA, RebB, RebC, RebD, RebE, RebF, RebM, RebQ, RebI, dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

In some embodiments, a steviol glycoside or steviol glycoside precursor composition produced in vivo, in vitro, or by whole cell bioconversion does not comprise or comprises a reduced amount or reduced level of plant-derived components than a *Stevia* extract from, inter alia, a *Stevia* plant. Plant-derived components can contribute to off-flavors and include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin. In some embodiments, the plant-derived components referred to herein are non-glycoside compounds.

As used herein, the terms "detectable amount," "detectable concentration," "measurable amount," and "measurable concentration" refer to a level of steviol glycosides measured in AUC, $\mu M/OD_{600}$, mg/L, μM, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a steviol glycoside or steviol glycoside precursor composition.

After the recombinant microorganism has been grown in culture for the period of time, wherein the temperature and period of time facilitate the production of a steviol glycoside, steviol and/or one or more steviol glycosides can then be recovered from the culture using various techniques known in the art. Steviol glycosides can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron prior to further purification, such as by preparative chromatography. The fermentation media or cell-free lysate can optionally be treated to remove low molecular weight compounds such as salt; and can optionally be dried prior to purification and re-dissolved in a mixture of water and solvent.

The supernatant or cell-free lysate can be purified as follows: a column can be filled with, for example, HP20 Diaion resin (aromatic type Synthetic Adsorbent; Supelco) or other suitable non-polar adsorbent or reversed-phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e. g., 0%→100% methanol). The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization. For example, steviol glycosides can be isolated by methods not limited to ion exchange chromatography, reversed-phase chromatography (i.e., using a C18 column), extraction, crystallization, and carbon columns and/or decoloring steps.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.,* 26:320-322 (1998); Sonnhammer et al., Proteins, 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of UGTs.

Methods to modify the substrate specificity of, for example, a UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine a % identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGT proteins (e.g., a polypeptide capable of glycosylating steviol or a steviol glycoside at its C-19 carboxyl group) can include additional amino acids that are not involved in the enzymatic activities carried out by the enzymes. In some embodiments, UGT proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a UGT polypeptide (e.g., a polypeptide capable of glycosylating steviol or a steviol glycoside at its C-19 carboxyl group) can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, CT). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a UGT polypeptide (e.g., a polypeptide capable of glycosylating steviol or a steviol glycoside at its C-19 carboxyl group) is altered by domain swapping.

In some embodiments, a fusion protein is a protein altered by circular permutation, which consists in the covalent attachment of the ends of a protein that would be opened elsewhere afterwards. Thus, the order of the sequence is altered without causing changes in the amino acids of the protein. In some embodiments, a targeted circular permutation can be produced, for example but not limited to, by designing a spacer to join the ends of the original protein. Once the spacer has been defined, there are several possibilities to generate permutations through generally accepted molecular biology techniques, for example but not limited to, by producing concatemers by means of PCR and subsequent amplification of specific permutations inside the concatemer or by amplifying discrete fragments of the protein to exchange to join them in a different order. The step of generating permutations can be followed by creating a circular gene by binding the fragment ends and cutting back at random, thus forming collections of permutations from a unique construct. In some embodiments, DAPI polypeptide is altered by circular permutation.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for the producing steviol glycosides, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate the production of a steviol glycoside. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans*, and *Yarrowia lipolytica.*

In some embodiments, a microorganism can be a prokaryote such as *Escherichia* bacteria cells, for example, *Escherichia coli* cells; *Lactobacillus* bacteria cells; *Lactococcus* bacteria cells; *Comebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *S. cerevisiae.*

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella salina,*

*Haematococcus pluvialis, Chlorella* sp., *Undaria pinnatifida, Sargassum, Laminaria japonica, Scenedesmus almeriensis.*

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g., alkanes, fatty acids, oils) and can grow on sugars. It has a high potential for industrial applications and is an oleaginous microorgamism. *Yarrowia lipolyptica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

It can be appreciated that the recombinant host cell disclosed herein can comprise a plant cell, comprising a plant cell that is grown in a plant, a mammalian cell, an insect cell, a fungal cell, comprising a yeast cell, wherein the yeast cell is a cell from *Saccharomyces cerevisiae, Schizosaccharomyces pombe, Yarrowia lipolytica, Candida*

*glabrata*, *Ashbya gossypii*, *Cyberlindnera jadinii*, *Pichia pastoris*, *Kluyveromyces lactis*, *Hansenula polymorpha*, *Candida boidinii*, *Arxula adeninivorans*, *Xanthophyllomyces dendrorhous*, or *Candida albicans* species or is a Saccharomycete or is a *Saccharomyces cerevisiae* cell, an algal cell or a bacterial cell, comprising *Escherichia* cells, *Lactobacillus* cells, *Lactococcus* cells, *Comebacterium* cells, *Acetobacter* cells, *Acinetobacter* cells, or *Pseudomonas* cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a *stevia* plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in *Stevia* extracts. Thus, steviol glycoside compositions produced by the recombinant hosts described herein are distinguishable from compositions derived from *Stevia* plants.

The amount of an individual steviol glycoside (e.g., RebA, RebB, RebD, or RebM) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside can exceed 7,000 mg/L. The amount of a combination of steviol glycosides (e.g., RebA, RebB, RebD, or RebM) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated 2s, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current *Stevia* products.

In another alternative, a substantially pure steviol or steviol glycoside can be incorporated into a food product along with other sweeteners, e.g., saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, *EFSA Journal* 8(4):1537; U.S. Food and Drug Administration GRAS Notice 323; U.S Food and Drug Administration GRAS Notice 329; WO 2011/037959; WO 2010/146463; WO 2011/046423; and WO 2011/056834.

For example, such a steviol glycoside composition can have from 90-99 weight % RebA and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of *stevia* plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of *stevia* plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of *stevia* plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1: Strain Engineering

Steviol glycoside-producing *S. cerevisiae* strains were constructed as described in WO 2011/153378, WO 2013/022989, WO 2014/122227, and WO 2014/122328, each of which is incorporated by reference in its entirety. For example, yeast strains comprising and expressing a native gene encoding a YNK1 polypeptide (SEQ ID NO:122, SEQ ID NO:123), a native gene encoding a PGM1 polypeptide (SEQ ID NO:1, SEQ ID NO:2), a native gene encoding a PGM2 polypeptide (SEQ ID NO:118, SEQ ID NO:119), a native gene encoding a UGP1 polypeptide (SEQ ID NO:120, SEQ ID NO:121), a recombinant gene encoding a GGPPS polypeptide (SEQ ID NO:19, SEQ ID NO:20), a recombinant gene encoding a truncated CDPS polypeptide (SEQ ID NO:39, SEQ ID NO:40), a recombinant gene encoding a KS polypeptide (SEQ ID NO:51, SEQ ID NO:52), a recombinant gene encoding a KO polypeptide (SEQ ID NO:59, SEQ ID NO:60), a recombinant gene encoding a KO polypeptide (SEQ ID NO:63, SEQ ID NO:64), a recombinant gene encoding an ATR2 polypeptide (SEQ ID NO:91, SEQ ID NO:92), a recombinant gene encoding a KAHe1 polypeptide (SEQ ID NO:93, SEQ ID NO:94), a recombinant gene encoding a CPR8 polypeptide (SEQ ID NO:85, SEQ ID NO:86), a recombinant gene encoding a CPR1 polypeptide (SEQ ID NO:77, SEQ ID NO:78), a recombinant gene encoding a UGT76G1 polypeptide (SEQ ID NO:8, SEQ ID NO:9), a recombinant gene encoding a UGT85C2 polypeptide (SEQ ID NO:5/SEQ ID NO:6, SEQ ID NO:7), a recombinant gene encoding a UGT74G1 polypeptide (SEQ ID NO:3, SEQ ID NO:4), a recombinant gene encoding a UGT91d2e-b polypeptide (SEQ ID NO:12, SEQ ID NO:13) and a recombinant gene encoding an EUGT11 polypeptide (SEQ ID NO:14, SEQ ID NO:15, SEQ ID NO:16) were engineered to accumulate steviol glycosides.

Example 2: Overexpression of PGM1, PGM2, UGP1, and YNK1

A steviol glycoside-producing *S. cerevisiae* strain as described in Example 1, further engineered to comprise and express a recombinant gene encoding a KAH polypeptide (SEQ ID NO:96, SEQ ID NO:97) and a recombinant gene encoding a KO polypeptide (SEQ ID NO:117, SEQ ID NO:64), was transformed with vectors comprising an additional copy of the gene encoding a YNK1 polypeptide (SEQ ID NO:122, SEQ ID NO:123), operably linked to a pTEF1 promoter (SEQ ID NO:148) and a CYC1 terminator (SEQ ID NO:154), an additional copy of the gene encoding a PGM1 polypeptide (SEQ ID NO:1, SEQ ID NO:2), operably linked to a pTEF1 promoter (SEQ ID NO:148) and a CYC1 terminator (SEQ ID NO:154), an additional copy of the gene encoding a PGM2 polypeptide (SEQ ID NO:118, SEQ ID NO:119), operably linked to a pPGK1 promoter (SEQ ID NO:149) and a tADH1 terminator (SEQ ID NO:155), and an additional copy of the gene encoding a UGP1 polypeptide (SEQ ID NO:120, SEQ ID NO:121), operably linked to a pPGK1 promoter (SEQ ID NO:149) and a tADH1 terminator (SEQ ID NO:155).

Fed-batch fermentation with cultures of the transformed *S. cerevisiae* strain and a control *S. cerevisiae* strain (a steviol glycoside-producing *S. cerevisiae* strain as described in Example 2, further engineered to comprise and express a recombinant gene encoding a KAH polypeptide and a recombinant gene encoding a KO polypeptide) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Extractions of whole culture samples (without cell removal) were performed and extracts were analyzed by LC-UV to determine levels of steviol glycosides.

LC-UV was conducted with an Agilent 1290 instrument comprising a variable wavelength detector (VWD), a thermostated column compartment (TCC), an autosampler, an autosampler cooling unit, and a binary pump, using SB-C18 rapid resolution high definition (RRHD) 2.1 mm×300 mm, 1.8 μm analytical columns (two 150 mm columns in series; column temperature of 65° C.). Steviol glycosides were separated by a reversed-phase C18 column followed by detection by UV absorbance at 210 mm. Quantification of steviol glycosides was done by comparing the peak area of each analyte to standards of RebA and applying a correction factor for species with differing molar absorptivities. For LC-UV, 0.5 mL cultures were spun down, the supernatant was removed, and the wet weight of the pellets was calculated. The LC-UV results were normalized by pellet wet weight. Total steviol glycoside values of the fed-batch fermentation were calculated based upon the measured levels of steviol glycosides calculated as a sum (in g/L RebD equivalents) of measured RebA, RebB, RebD, RebE, RebM, 13-SMG, rubusoside, steviol-1,2-bioside, di-glycosylated steviol, tri-glycosylated steviol, tetra-glycosylated steviol, penta-glycosylated steviol, hexa-glycosylated steviol, and hepta-glycosylated steviol. Results are shown in Table 1.

TABLE 1

Steviol Glycoside accumulation by transformed *S. cerevisiae* strain and *S. cerevisiae* control strain.

| | Transformed Strain | | Control Strain | |
|---|---|---|---|---|
| | Accumulation (g/L RebD Equiv.) | Std. Error (g/L RebD Equiv.) | Accumulation (g/L RebD Equiv.) | Std. Error (g/L RebD Equiv.) |
| 13-SMG | 2.40 | 0.14 | 4.2 | 0.02 |
| RebA | 0.59 | 0.007 | 0.45 | 0.07 |
| RebD | 1.21 | 0.16 | 2.16 | 0.12 |
| RebM | 6.31 | 0.22 | 3.22 | 0.06 |
| Total SG | 11.90 | 0.33 | 11.76 | 0.34 |

A decrease in 13-SMG and RebD accumulation, and an increase in RebA and RebM accumulation were observed for the *S. cerevisiae* strain overexpressing UGP1, YNK1, PGM1, and PGM2, relative to the control strain. Furthermore, RebD+RebM accumulation levels increased upon overexpression of UGP1, YNK1, PGM1, and PGM2, while the total steviol glycosides produced by the experimental strain increased negligibly. In addition, RebD/RebM ratios of 0.2 and below were observed for the *S. cerevisiae* strain overexpressing UGP1, YNK1, PGM1, and PGM2, relative to the control strain.

Example 3: UGP1, PGM2 Activity Assay

Fed-batch fermentation with cultures of a *S. cerevisiae* strain overexpressing PGM1, PGM2, UGP1, and YNK1, as described in Example 2, and a control *S. cerevisiae* strain (a steviol glycoside-producing *S. cerevisiae* strain as described in Example 1) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed to determine the activity levels of PGM and UGP.

For both assays, frozen fermentation cell pellets were resuspended in CelLytic™ Y Cell Lysis Reagent (Sigma) to an $OD_{600}$ of 44. Samples were shaken 30 min at 25° C. and then centrifuged at 13,000 rpm for 10 min. The supernatant was recovered and stored on ice.

The PGM enzyme assay relies on a coupled activity assay wherein supplied glucose-1-phosphate is first converted to glucose-6-phosphate by a PGM polypeptide/PGM polypeptide containing cell lysate, followed by glucose-6-phosphate conversion by a glucose-6-phosphate dehydrogenase (added to the assay as a purified enzyme in excess) to phosphogluconolactone under β-$NADP^+$ consumption. The kinetics of the concomitant 6-NAPDH released are recorded by monitoring the absorbance at 340 nm.

180 mM glycylglycine, pH 7.4 (adjusted with NaOH/HCl); 5.0 mM glucose-1-phosphate; 3.00 mM β-$NADP^+$; 0.4 mM G1,6-bisphosphate; 30 mM $MgCl_2$, 43 mM L-cysteine; 0.65 U/ml G6P-DH, and previously stored cell lysate were mixed together at 30° C. at different cell-lysate/buffer concentrations (0.5% (v/v), 1% (v/v), 2% (v/v), and 3% (v/v)). The kinetics for the release of β-NAPDH were followed over a maximum of 1000 sec. for each concentration of supernatant added. PGM activity for each cell-lysate/buffer concentration was defined by the maximum slope of the curve of $OD_{340}$ versus time. Cell-lysate/buffer concentration corrected PGM activity was defined as the slope of the curve of OD340/sec as a function of Cell-lysate/buffer concentrations. The value obtained in this way for a certain strain can be compared to the values from other strains and differences in PGM activity can be pointed out. The increase in activity of the cell-lysate of the *S. cerevisiae* strain overexpressing PGM1, PGM2, UGP1, and YNK1 is shown in Table 3, below, relative to that of the control strain.

The UGP assay relies on a coupled activity assay of the yeast UDP-glucose pyrophosphorylase wherein supplied glucose-1-phosphate is first converted to UDP-glucose by a UGP polypeptide/UGP polypeptide-containing cell-lysate under UTP consumption, followed by UDP-glucose conversion to UDP-Glucuronate and β-NADH by UDP-glucose dehydrogenase (added to the assay as a purified enzyme in excess) under β-$NAD^+$ consumption. The kinetics for the release of β-NADH are followed by monitoring the change in absorbance at 340 nm. Alternative UGP assays using, for example but not limited to, hydrophilic interaction liquid chromatography coupled with tandem mass spectrometry for the quantification of UDP-glucose (see Warth et al., Journal of Chromatography A, 1423, pp. 183-189 (2016)) may be used as well.

100 mM Tris/HCl, pH 8.5; 10 mM MgCl2; 100 mM NaCl; 5.0 mM β-$NAD^+$; 2 mM UTP; 2 mM ATP; 0.12 mg/ml UDPG-DH; 5 mM; and previously stored cell lysate were mixed together at 30° C. at different supernatant/buffer concentrations (0.5% (v/v), 1% (v/v), 1.5% (v/v), and 2% (v/v)). The kinetics for the release of β-NADH were followed over a maximum of 1000 sec. for each supernatant/buffer concentration. UGP activity for each cell-lysate/buffer concentration was defined by the maximum slope of the curve of $OD_{340}$ versus time. Cell-lysate/buffer concentration corrected UGP activity was defined as the slope of the curve of OD340/sec as a function of Cell-lysate/buffer concentrations. The value obtained in this way for a certain strain can be compared to the values from other strains and differences in UGP activity can be pointed out. The increase in activity of the lysate of the *S. cerevisiae* strain overexpressing PGM1, PGM2, UGP1, and YNK1 is shown in Table 2, below, relative to that of the control strain.

TABLE 2

Relative UGP and PGM activity

| | Transformed Strain | Control Strain |
|---|---|---|
| UGP Activity relative to control strain | 250% | 100% |
| PGM Activity relative to control stain | 160% | 100% |

Individual and total steviol glycoside values of the fed-batch fermentation were calculated according to Example 2. Results are shown in Table 3.

TABLE 3

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 2.19 | 1.21 |
| RebM | 5.71 | 5.12 |
| Total SG | 12.10 | 9.43 |

An increase in both UGP and PGM activity was observed for the *S. cerevisiae* strain overexpressing UGP1, YNK1, PGM1, and PGM2, relative to the control strain. As shown in Table 3, RebD and total steviol glycoside accumulation increased upon overexpression of UGP1, YNK1, PGM1, and PGM2. Without being bound to a particular theory, the results suggest that increasing UGP and PGM activity (i.e., by expressing genes encoding polypeptides involved in the UDP-glucose biosynthetic pathway) allows for conversion of partially glycosylated steviol glycosides to higher moleculae weight steviol glycosides, including, e.g., RebD.

Example 4: LC-MS Analytical Procedures (UDP-Glucose Analysis)

LC-MS analyses were performed on a Thermo Scientific Accela UPLC (Ultra Performance Liquid Chromatography system; Thermo Scientific) with a Thermo Scientific PAL autosampler system (Thermo Scientific) SeQuant ZIC-cHILIC column (2.1 mm×150 mm, 3.0 μm analytical column, 100 Å pore size) coupled to a Thermo Scientific Exactive Orbitrap mass spectrometer with electrospray ionization (ESI) operated in negative ionization mode. Compound separation was achieved using a gradient of the two mobile phases: A (water with 0.1% ammonium acetate) and B (MeCN). Separation was achieved by using a gradient from time 0 min with 15% A holding until 0.5 min and increasing to 50% A at time 15.50 min, holding until time 17.50 min, and reducing to 15% A at time 17.60 min, equilibrating at 15% A until 25.50 min. The flow rate was 0.3 mL/min, and the column was maintained at room temperature. UDP-glucose was monitored by full-scan analysis in the mass range 130-1400 m/z. EIC (Extracted ion chromatogram) of 565.04492-565.05058 corresponding to UDP-glucose was extracted and quantified by comparing against authentic standards. See Table 4 for m/z trace and retention time values of UDP-glucose.

TABLE 4

LC-MS Analytical Data for UDP-glucose

| Compound | MS Trace | RT (mins) |
|---|---|---|
| UDP-glucose | 565.04775 | 8.4 |

To determine the intracellular concentration of UDP-Glucose, full fermentation broth was sampled (via syringe) at desired time points during different stages of fermentation. Biomass (cells) was quickly separated by centrifugation and supernatant was removed. Cell pellets were quenched and extracted using a mixture of methanol, chloroform and an aqueous buffer solution. The final intracellular extracts were stored at −80° C. prior to LC-MS analysis.

Example 5: UDP-Glucose Accumulation Quantification

Fed-batch fermentation with cultures of a *S. cerevisiae* strain overexpressing PGM1, PGM2, UGP1, and YNK1, as described in Example 2, and a control *S. cerevisiae* strain (a *S. cerevisiae* strain comprising and expressing a native gene encoding a YNK1 polypeptide (SEQ ID NO:122, SEQ ID NO:123), a native gene encoding a PGM1 polypeptide (SEQ ID NO:1, SEQ ID NO:2), a native gene encoding a PGM2 polypeptide (SEQ ID NO:118, SEQ ID NO:119), a native gene encoding a UGP1 polypeptide (SEQ ID NO:120, SEQ ID NO:121), a recombinant gene encoding a GGPPS polypeptide (SEQ ID NO:19, SEQ ID NO:20), a recombinant gene encoding a truncated CDPS polypeptide (SEQ ID NO:39, SEQ ID NO:40), a recombinant gene encoding a KS polypeptide (SEQ ID NO:51, SEQ ID NO:52), a recombinant gene encoding a KO polypeptide (SEQ ID NO:59, SEQ ID NO:60), a recombinant gene encoding a KAHe1 polypeptide (SEQ ID NO:93, SEQ ID NO:94), a recombinant gene encoding a CPR8 polypeptide (SEQ ID NO:85, SEQ ID NO:86), a recombinant gene encoding a CPR1 polypeptide (SEQ ID NO:77, SEQ ID NO:78), a recombinant gene encoding an ATR2 polypeptide (SEQ ID NO:91, SEQ ID NO:92), a recombinant gene encoding a UGT85C2 polypeptide (SEQ ID NO:5/SEQ ID NO:6, SEQ ID NO:7), and a recombinant gene encoding a UGT74G1 polypeptide (SEQ ID NO:3, SEQ ID NO:4)) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed by LC-UV to determine the levels of steviol glycosides, according to Example 2, and by LC-MS to analyze the intracellular level of UDP-glucose, according to Example 4. Results are shown in Tables 5-6.

TABLE 5

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 1.05 | 1.92 |
| RebM | 5.75 | 2.23 |
| Total SG | 10.18 | 7.40 |

TABLE 6

UDP-glucose accumulation by transformed *S. cerevisiae* strain and *S. cerevisiae* control strain.

| | Transformed Strain | | Control Strain | |
|---|---|---|---|---|
| Time (h) | UDP-glucose Accumulation (μM) | Std. Deviation (μM) | UDP-glucose Accumulation (μM) | Std. Deviation (μM) |
| 22 | 450.52 | 54.96 | 306.50 | 51.75 |
| 30 | 495.66 | 10.83 | 198.88 | 36.95 |
| 46 | 518.26 | 26.13 | 241.30 | 45.69 |
| 55 | 425.39 | 70.01 | 221.35 | 64.36 |
| 72 | 398.08 | 41.85 | 206.26 | 19.54 |
| 76 | 299.16 | 33.57 | 159.96 | 5.06 |
| 96 | 270.53 | 82.67 | 160.74 | 9.19 |
| 104 | 310.97 | 24.57 | 132.08 | 21.17 |
| 120 | 359.92 | 24.30 | 119.32 | 37.39 |

An increase in UDP-glucose accumulation, by up to 300%, was observed for the *S. cerevisiae* strain overexpressing UGP1, YNK1, PGM1, and PGM2, relative to the control strain. RebD+RebM accumulation levels increased upon overexpression of UGP1, YNK1, PGM1, and PGM2; this result further demonstrates a beneficial effect of expression of UDP-glucose biosynthetic pathway genes on the production of higher molecular weight steviol glycosides such as RebD or RebM.

One of skill in the art would appreciate a distinction between improving the total amount of UDP-glucose as compared to the recycling of UDP-glucose. As shown in Table 6 above, taking the highest and lowest number over fermentation time, the worst decrease in parental strain is 2.5 while the worst decrease in UDP-glucose boosted strain (i.e., the *S. cerevisiae* strain overexpressing UGP1, YNK1, PGM1, and PGM2) is 1.9 times. This demonstrates that overexpressing UGP1, YNK1, PGM1, and PGM2 increases the UDP-glucose pool and UDP-glucose. In fact, the net increase (consumption/formation) is higher is the UDP-glucose boosted strain.

Without being bound to a particular theory, the results observed in Examples 2-5 suggest that increasing UDP-glucose levels (i.e., by expressing genes encoding polypeptides involved in the UDP-glucose biosynthetic pathway) allows for conversion of 13-SMG and other partially glycosylated steviol glycosides to higher molecular weight steviol glycosides, including, e.g., RebM. Furthermore, the difference between the magnitude of the increase in accumulation levels of, e.g., RebM and/or RebD and that of the increase in accumulation levels of the total steviol glycosides suggests that maintaining and/or increasing UDP-glucose levels allows for more efficient production of higher molecular weight steviol glycosides, including, e.g., RebM (i.e., by shifting the profile of produced steviol glycosides away from lower molecular weight steviol glycosides).

Example 6: Expression of Heterologous UGP1 and PGM2

A steviol glycoside-producing *S. cerevisiae* strain overexpressing UGP1, YNK1, PGM1, and PGM2, as described in Example 2, was transformed with vectors comprising a gene encoding a UGP1 polypeptide (SEQ ID NO:132, SEQ ID NO:133) operably linked to a pPDC1 promoter (SEQ ID NO:153) and a tCYC1 terminator (SEQ ID NO:154) and a gene encoding a PGM2 polypeptide (SEQ ID NO:144, SEQ ID NO:145), operably linked to a pTPI1 promoter (SEQ ID NO:152) and an tADH1 terminator (SEQ ID NO:155).

Fed-batch fermentation with cultures of the transformed *S. cerevisiae* strain and a control *S. cerevisiae* strain (a steviol glycoside-producing *S. cerevisiae* strain as described in Example 2, further engineered to comprise and express a recombinant gene encoding a KAH polypeptide and a recombinant gene encoding a KO polypeptide) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed by LC-UV to determine levels of steviol glycosides, as described in Example 2. Results are shown in Table 7.

TABLE 7

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 2.27 | 1.80 |
| RebM | 5.33 | 4.50 |
| Total SG | 14.27 | 12.39 |

An increase in RebD and RebM accumulation were observed for the *S. cerevisiae* strain expressing PGM2 and UGP1, relative to the control strain. Furthermore, total steviol glycosides produced by the experimental strain also increased. Without being bound to a particular theory, the results observed in Table 7 suggest that increasing UDP-glucose levels (i.e., by expressing genes encoding polypeptides involved in the UDP-glucose biosynthetic pathway) allows for conversion of 13-SMG and other partially glycosylated steviol glycosides to higher molecular weight steviol glycosides, including, e.g., RebM.

Example 7: LC-MS Analytical Procedures (Steviol Glycoside Analysis)

LC-MS analyses were performed on a Waters ACQUITY UPLC (Ultra Performance Liquid Chromatography system; Waters Corporation) with a Waters ACQUITY UPLC (Ultra Performance Liquid Chromatography system; Waters Corporation) BEH C18 column (2.1×50 mm, 1.7 μm particles, 130 Å pore size) equipped with a pre-column (2.1×5 mm, 1.7 μm particles, 130 Å pore size) coupled to a Waters ACQUITY TQD triple quadropole mass spectrometer with electrospray ionization (ESI) operated in negative ionization mode. Compound separation was achieved using a gradient of the two mobile phases, A (water with 0.1% formic acid) and B (MeCN with 0.1% formic acid), by increasing from 20% to 50% B between 0.3 to 2.0 min, increasing to 100% B at 2.01 min and holding 100% B for 0.6 min, and re-equilibrating for 0.6 min. The flow rate was 0.6 mL/min, and the column temperature was set at 55° C. Steviol glycosides were monitored using SIM (Single Ion Monitoring) and quantified by comparing against authentic standards. See Table 1 for m/z trace and retention time values of steviol glycosides and glycosides of steviol precursors detected.

TABLE 8

LC-MS Analytical Data for Steviol and Glycosides of Steviol and Steviol Precursors

| Compound | MS Trace | RT (mins) |
|---|---|---|
| steviol + 5Glc (#22) [also referred to as compound 5.22] | 1127.48 | 0.85 |
| steviol + 6Glc (isomer 1) [also referred to as compound 6.1] | 1289.53 | 0.87 |
| steviol + 7Glc (isomer 2) [also referred to as compound 7.2] | 1451.581 | 0.94 |
| steviol + 6Glc (#23) [also referred to as compound 6.23] | 1289.53 | 0.97 |
| RebE | 965.42 | 1.06 |
| RebD | 1127.48 | 1.08 |
| RebM | 1289.53 | 1.15 |
| steviol + 7Glc (isomer 5) [also referred to as compound 7.5] | 1451.581 | 1.09 |
| steviol + 4Glc (#26) [also referred to as compound 4.26] | 965.42 | 1.21 |
| steviol + 5Glc (#24) [also referred to as compound 5.24] | 1127.48 | 1.18 |
| steviol + 4Glc (#25) [also referred to as compound 5.25] | 1127.48 | 1.40 |
| RebA | 965.42 | 1.43 |
| 1,2-Stevioside | 803.37 | 1.43 |
| steviol + 4Glc (#33) [also referred to as compound 4.33] | 965.42 | 1.49 |
| steviol + 3Glc (#1) [also referred to as compound 3.1] | 803.37 | 1.52 |
| steviol + 2Glc (#57) [also referred to as compound 2.57] | 641.32 | 1.57 |
| RebQ | 965.42 | 1.59 |
| 1,3-Stevioside (RebG) | 803.37 | 1.60 |
| Rubusoside | 641.32 | 1.67 |
| RebB | 803.37 | 1.76 |
| Steviol-1,2-Bioside | 641.32 | 1.80 |
| Steviol-1,3-Bioside | 641.32 | 1.95 |
| 19-SMG | 525.27 | 1.98 |
| 13-SMG | 479.26 | 2.04 |
| ent-kaurenoic acid + 3Glc (isomer 1) [also referred to as compound KA3.1] | 787.37 | 2.16 |
| ent-kaurenoic acid + 3Glc (isomer 2) [also referred to as compound KA3.2] | 787.37 | 2.28 |
| ent-kaurenol + 3Glc (isomer 1) co-eluted with ent-kaurenol + 3Glc (#6) [also referred to as compounds KL3.1 and KL3.6] | 773.4 | 2.36 |
| ent-kaurenoic acid + 2Glc (#7) [also referred to as compound KA2.7] | 625.32 | 2.35 |
| ent-kaurenol + 2Glc (#8) [also referred to as compound KL2.8] | 611.34 | 2.38 |
| Steviol | 317.21 | 2.39 |

Steviol glycosides can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron filter prior to further purification, such as by preparative chromatography. The fermentation media or cell-free lysate can optionally be treated to remove low molecular weight compounds such as salt, and can optionally be dried prior to purification and re-dissolved in a mixture of water and solvent. The supernatant or cell-free lysate can be purified as follows: a column can be filled with, for example, HP20 Diaion resin (aromatic-type Synthetic Adsorbent; Supelco) or another suitable non-polar adsorbent or reverse phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e.g., 0%→100% methanol. The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization.

Example 8: Expression of Heterologous UGP1

A steviol glycoside-producing *S. cerevisiae* strain overexpressing UGP1, YNK1, PGM1, and PGM2, as described in Example 2, was transformed with a vector comprising a codon-optimized nucleotide sequence encoding a UGP1 polypeptide (SEQ ID NO:132, SEQ ID NO:133) operably linked to a pTDH3 promoter (SEQ ID NO:150) and a tCYC1 terminator (SEQ ID NO:154), as summarized in Table 9, below.

TABLE 9

UGP1 Polypeptides Expressed

| Strain | SEQ ID |
|---|---|
| 1 | 126, 127 |
| 2 | 132, 133 |
| 3 | 128, 129 |
| 4 | 130, 131 |
| 5 | 124, 125 |
| 6 | 138, 139 |
| 7 | 136, 137 |
| 8 | 134, 135 |

Single colonies of the transformed strains provided in Table 9, and a control strain, transformed with a blank vector, were grown in 500 μL of Delft medium in a 96-well plate for 2 days at 30° C., shaking at 280 rpm. 50 μL of the cell culture of each strain was then transferred to a second 96-well plate and grown in 450 μL Feed-in-Time medium (m2p-labs GmbH, Baesweiler, Germany) for 4 days at 30° C., shaking at 280 rpm. Samples for LC-MS analysis were prepared by extracting 100 μL of cell solution with 100 μL of DMSO, vortexing until mixed, and incubating at 80° C. for 10 minutes. The resultant extract was clarified by centrifugation at 15,000 g for 10 min. 20 μL of the supernatant was diluted with 140 μL of 50% (v/v) DMSO for LC-MS injection. LC-MS data was normalized to the $OD_{600}$ of a mixture of 100 μL of the cell solution and 100 μL of water, measured on an ENVISION® Multilabel Reader (PerkinElmer, Waltham, MA).

LC-MS analysis was performed according to Example 7. Whole culture accumulation of compounds in μM/$OD_{600}$ was quantified by LC-MS against a known standard. Results are shown in Table 10, below. Each value is an average of 6 independent clones.

TABLE 10

| Concentration of Steviol Glycosides | | | | | | | |
|---|---|---|---|---|---|---|---|
| | Accumulated Concentration (μM/$OD_{600}$) | | | | | | |
| Strain | 13-SMG | Rubu. | RebB | RebA | RebD | RebM | Total |
| Control | 9.96 ± 2.19 | 0.05 ± 0.08 | 0.67 ± 0.14 | 1.95 ± 0.79 | 3.89 ± 0.60 | 20.73 ± 4.48 | 37.38 ± 6.71 |
| 1 | 6.15 ± 1.83 | 0.26 ± 0.04 | 0.59 ± 0.09 | 2.37 ± 0.65 | 1.49 ± 0.36 | 25.91 ± 1.35 | 37.38 ± 3.03 |
| 2 | 7.06 ± 2.48 | 0.23 ± 0.12 | 0.76 ± 0.30 | 2.03 ± 0.37 | 1.34 ± 0.24 | 27.99 ± 3.17 | 39.43 ± 5.88 |
| 3 | 8.73 ± 3.20 | 0.25 ± 0.08 | 0.69 ± 0.24 | 2.50 + 0.81 | 1.69 ± 0.43 | 29.41 ± 6.19 | 43.34 ± 9.22 |
| 4 | 13.02 ± 2.39 | 0.14 ± 0.08 | 0.99 ± 0.23 | 2.88 ± 0.51 | 4.89 ± 0.75 | 30.41 ± 5.90 | 52.50 ± 9.51 |
| 5 | 7.91 ± 2.30 | 0.28 ± 0.08 | 0.62 ± 0.14 | 2.55 ± 0.96 | 1.42 ± 0.33 | 29.54 ± 4.23 | 42.37 ± 5.98 |
| 6 | 8.89 ± 2.94 | 0.28 ± 0.04 | 0.68 ± 0.18 | 2.36 ± 0.66 | 1.43 ± 0.49 | 27.64 ± 3.49 | 41.32 ± 5.08 |
| 7 | 5.68 ± 2.05 | 0.23 ± 0.09 | 0.51 ± 0.19 | 2.04 ± 0.50 | 1.26 ± 0.28 | 23.63 ± 2.27 | 33.38 ± 4.98 |
| 8 | 6.59 ± 2.65 | 0.22 ± 0.12 | 0.63 ± 0.17 | 2.28 ± 1.03 | 1.49 ± 0.59 | 26.64 ± 6.51 | 37.90 ± 10.21 |

Increases in steviol glycoside accumulation, by up to about 600%, was observed for the *S. cereivisiae* strain overexpressing UGP1, YNK1, PGM1, and PGM2, and further expressing heterologous UGP1, relative to the control strain. RebD+RebM accumulation levels increased upon expression of heterologous UGP1, further demonstrating a beneficial effect of expression of heterologous UDP-glucose biosynthetic pathway genes on the production of higher molecular weight steviol glycosides such as RebD or RebM.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 11

| Sequences disclosed herein. |
|---|
| SEQ ID NO: 1 |
| *S. cerevisiae* |
| atgtcacttc taatagattc tgtaccaaca gttgcttata aggaccaaaa accgggtact 60 |
| tcaggtttac gtaagaagac caaggttttc atggatgagc ctcattatac tgagaacttc 120 |
| attcaagcaa caatgcaatc tatccctaat ggctcagagg gaaccacttt agttgttgga 180 |
| ggagatggtc gtttctacaa cgatgttatc atgaacaaga ttgccgcagt aggtgctgca 240 |
| aacggtgtca gaaagttagt cattggtcaa ggcggtttac tttcaacacc agctgcttct 300 |
| catataatta gaacatacga ggaaaagtgt accggtggtg gtatcatatt aactgcctca 360 |
| cacaacccag gcggtccaga gaatgattta ggtatcaagt ataatttacc taatggtggg 420 |
| ccagctccag agagtgtcac taacgctatc tgggaagcgt ctaaaaaatt aactcactat 480 |
| aaaattataa agaacttccc caagttgaat ttgaacaagc ttggtaaaaa ccaaaaatat 540 |
| ggcccattgt tagtggacat aattgatcct gccaaagcat acgttcaatt tctgaaggaa 600 |
| atttttgatt ttgacttaat taaaagcttc ttagcgaaac agcgcaaaga caaagggtgg 660 |
| aagttgttgt ttgactcctt aaatggtatt acaggaccat atggtaaggc tatatttgtt 720 |
| gatgaatttg gtttaccggc agaggaagtt cttcaaaatt ggcacccttt acctgatttc 780 |
| ggcggtttac atcccgatcc gaatctaacc tatgcacgaa ctcttgttga cagggttgac 840 |
| cgcgaaaaaa ttgcctttgg agcagcctcc gatggtgatg gtgataggaa tatgatttac 900 |
| ggttatggcc ctgctttcgt ttcgccaggt gattctgttg ccattattgc cgaatatgca 960 |
| cccgaaattc catacttcgc caaacaaggt atttatggct tggcacgttc atttcctaca 1020 |
| tcctcagcca ttgatcgtgt tgcagcaaaa aagggattaa gatgttacga agttccaacc 1080 |
| ggctggaaat tcttctgtgc cttatttgat gctaaaaagc tatcaatctg tggtgaagaa 1140 |
| tccttcggta caggttccaa tcatatcaga gaaaaggacg gtctatgggc cattattgct 1200 |
| tggttaaata tcttggctat ctaccatagg cgtaaccctg aaaaggaagc ttcgatcaaa 1260 |
| actattcagg acgaattttg gaacgagtat ggccgtactt tcttcacaag atacgattac 1320 |
| gaacatatcg aatgcgagca ggccgaaaaa gttgtagctc ttttgagtga atttgtatca 1380 |
| aggccaaacg tttgtggctc ccacttccca gctgatgagt ctttaaccgt tatcgattgt 1440 |
| ggtgattttt cgtatagaga tctagatggc tccatctctg aaaatcaagg ccttttcgta 1500 |
| aagttttcga atgggactaa atttgttttg aggttatccg gcacaggcag ttctggtgca 1560 |
| acaataagat tatacgtaga aaagtatact gataaaaagg agaactatgg ccaaacagct 1620 |
| gacgtcttct tgaaacccgt catcaactcc attgtaaaat tcttaagatt taaagaaatt 1680 |
| ttaggaacag acgaaccaac agtccgcaca tag 1713 |
| SEQ ID NO: 2 |
| *S. cerevisiae* |
| MSLLIDSVPT VAYKDQKPGT SGLRKKTKVF MDEPHYTENF IQATMQSIPN GSEGTTLVVG 60 |
| GDGRFYNDVI MNKIAAVGAA NGVRKLVIGQ GGLLSTPAAS HIIRTYEEKC TGGGIILTAS 120 |
| HNPGGPENDL GIKYNLPNGG PAPESVTNAI WEASKKLTHY KIIKNFPKLN LNKLGKNQKY 180 |
| GPLLVDIIDP AKAYVQFLKE IFDFDLIKSF LAKQRKDKGW KLLFDSLNGI TGPYGKAIFV 240 |
| DEFGLPAEEV LQNWHPLPDF GGLHPDPNLT YARTLVDRVD REKIAFGAAS DGDGDRNMIY 300 |
| GYGPAFVSPG DSVAIIAEYA PEIPYFAKQG IYGLARSFPT SSAIDRVAAK KGLRCYEVPT 360 |
| GWKFFCALFD AKKLSICGEE SFGTGSNHIR EKDGLWAIIA WLNILAIYHR RNPEKEASIK 420 |
| TIQDEFWNEY GRTFFTRYDY EHIECEQAEK VVALLSEFVS RPNVCGSHFP ADESLTVIDC 480 |
| GDFSYRDLDG SISENQGLFV KFSNGTKFVL RLSGTGSSGA TIRLYVEKYT DKKENYGQTA 540 |
| DVFLKPVINS IVKFLRFKEI LGTDEPTVRT 570 |

TABLE 11-continued

| Sequences disclosed herein. |
| --- |

SEQ ID NO: 3
*S. rebaudiana*
atggcagagc aacaaaagat caaaaagtca cctcacgtct tacttattcc atttcctctg 60
caaggacata tcaacccatt catacaattt gggaaaagat tgattagtaa gggtgtaaag 120
acaacactgg taaccactat ccacactttg aattctactc tgaaccactc aaatactact 180
actacaagta tagaaattca agctatatca gacggatgcg atgagggtgg ctttatgtct 240
gccggtgaat cttacttgga aacattcaag caagtgggat ccaagtctct ggccgatcta 300
atcaaaaagt tacagagtga aggcaccaca attgacgcca taatctacga ttctatgaca 360
gagtgggttt tagacgttgc tatcgaattt ggtattgatg gaggttcctt tttcacacaa 420
gcatgtgttg tgaattctct atactaccat gtgcataaag ggttaatctc tttaccattg 480
ggtgaaactg tttcagttcc aggttttcca gtgttacaac gttgggaaac cccattgatc 540
ttacaaaatc atgaacaaat acaatcacct tggtcccaga tgttgtttgg tcaattcgct 600
aacatcgatc aagcaagatg ggtctttact aattcattct ataagttaga ggaagaggta 660
attgaatgga ctaggaagat ctggaatttg aaagtcattg gtccaacatt gccatcaatg 720
tatttggaca aaagacttga tgatgataaa gataatggtt tcaatttgta caaggctaat 780
catcacgaat gtatgaattg gctggatgac aaaccaaagg aatcagttgt atatgttgct 840
ttcggctctc ttgttaaaca tggtccagaa caagttgagg agattacaag agcacttata 900
gactctgacg taaacttttt gtgggtcatt aagcacaaag aggaggggaa actgccagaa 960
aacctttctg aagtgataaa gaccggaaaa ggtctaatcg ttgcttggtg taaacaattg 1020
gatgttttag ctcatgaatc tgtaggctgt tttgtaacac attgcggatt caactctaca 1080
ctagaagcca tttccttagg cgtacctgtc gttgcaatgc ctcagttctc cgatcagaca 1140
accaacgcta aacttttgga cgaaatacta ggggtgggtg tcagagttaa agcagacgag 1200
aatggtatcg tcagaagagg gaacctagct tcatgtatca aaatgatcat ggaagaggaa 1260
agaggagtta tcataaggaa aaacgcagtt aagtggaagg atcttgcaaa ggttgccgtc 1320
catgaaggcg gctcttcaga taatgatatt gttgaatttg tgtccgaact aatcaaagcc 1380
taa 1383

SEQ ID NO: 4
*S. rebaudiana*
MAEQQKIKKS PHVLLIPFPL QGHINPFIQF GKRLISKGVK TTLVTTIHTL NSTLNHSNTT 60
TTSIEIQAIS DGCDEGGFMS AGESYLETFK QVGSKSLADL IKKLQSEGTT IDAIIYDSMT 120
EWVLDVAIEF GIDGGSFFTQ ACVVNSLYYH VHKGLISLPL GETVSVPGFP VLQRWETPLI 180
LQNHEQIQSP WSQMLFGQFA NIDQARWVFT NSFYKLEEEV IEWTRKIWNL KVIGPTLPSM 240
YLDKRLDDDK DNGFNLYKAN HHECMNWLDD KPKESVVYVA FGSLVKHGPE QVEEITRALI 300
DSDVNFLWVI KHKEEGKLPE NLSEVIKTGK GLIVAWCKQL DVLAHESVGC FVTHCGFNST 360
LEAISLGVPV VAMPQFSDQT TNAKLLDEIL GVGVRVKADE NGIVRRGNLA SCIKMIMEEE 420
RGVIIRKNAV KWKDLAKVAV HEGGSSDNDI VEFVSELIKA 460

SEQ ID NO: 5
*S. rebaudiana*
atggatgcaa tggctacaac tgagaagaaa ccacacgtca tcttcatacc atttccagca 60
caaagccaca ttaaagccat gctcaaacta gcacaacttc tccaccacaa aggactccag 120
ataaccttcg tcaacaccga cttcatccac aaccagtttc ttgaatcatc gggcccacat 180
tgtctagacg gtgcaccggg tttccggttc gaaaccattc cggatggtgt ttctcacagt 240
ccggaagcga gcatcccaat cagagaatca ctcttgagat ccattgaaac caacttcttg 300
gatcgtttca ttgatcttgt aaccaaactt ccggatcctc cgacttgtat tatctcagat 360
gggttcttgt cggttttcac aattgacgct gcaaaaaagc ttggaattcc ggtcatgatg 420
tattggacac ttgctgcctg tgggttcatg ggtttttacc atattcattc tctcattgag 480
aaaggatttg caccacttaa agatgcaagt tacttgacaa atgggtattt ggacaccgtc 540
attgattggg ttccgggaat ggaaggcatc cgtctcaagg atttcccgct ggactggagc 600
actgacctca atgacaaagt tttgatgttc actacggaag ctcctcaaag gtcacacaag 660
gtttcacatc atattttcca cacgttcgat gagttggagc ctagtattat aaaaactttg 720
tcattgaggt ataatcacat ttacaccatc ggcccactgc aattacttct tgatcaaata 780
cccgaagaga aaaagcaaac tggaattacg agtctccatg gatacagttt agtaaaagaa 840
gaaccagagt gtttccagtg gcttcagtct aaagaaccaa attccgtcgt ttatgtaaat 900
tttggaagta ctacagtaat gtctttagaa gacatgacgg aatttggttg gggacttgct 960
aatagcaacc attatttcct ttggatcatc cgatcaaact tggtgatagg ggaaaatgca 1020
gttttgcccc ctgaacttga ggaacatata aagaaaagag gctttattgc tagctggtgt 1080
tcacaagaaa aggtcttgaa gcacccttcg gttggagggt tcttgactca ttgtgggtgg 1140
ggatcgacca tcgagagctt gtctgctggg gtgccaatga tatgctggcc ttattcgtgg 1200
gaccagctga ccaactgtag gtatatatgc aaagaatggg aggttgggct cgagatggga 1260
accaaagtga aacgagatga agtcaagagg cttgtacaag agttgatggg agaaggaggt 1320
cacaaaatga ggaacaaggc taaagattgg aaagaaaagg ctcgcattgc aatagctcct 1380
aacggttcat cttctttgaa catagacaaa atggtcaagg aaatcaccgt gctagcaaga 1440
aactagttac aaagttgttt cacattgtgc tttctattta agatgtaact ttgttctaat 1500
ttaatattgt ctagatgtat tgaaccataa gtttagttgg tctcaggaat tgatttttaa 1560
tgaaataatg gtcattaggg gtgagt 1586

SEQ ID NO: 6
*S. rebaudiana*
atggatgcaa tggcaactac tgagaaaaag cctcatgtga tcttcattcc atttcctgca 60
caatctcaca taaaggcaat gctaaagtta gcacaactat tacaccataa gggattacag 120
ataactttcg tgaataccga cttcatccat aatcaatttc tggaatctag tggccctcat 180
tgtttggacg gagccccagg gtttagattc gaaacaattc ctgacggtgt ttcacattcc 240
ccagaggcct ccatcccaat aagagagagt ttactgaggt caatagaaac caactttttg 300
gatcgtttca ttgacttggt cacaaaactt ccagacccac caacttgcat aatctctgat 360
ggctttctgt cagtgtttac tatcgacgct gccaaaaagt tgggtatccc agttatgatg 420

TABLE 11-continued

Sequences disclosed herein.

```
tactggactc ttgctgcatg cggtttcatg ggtttctatc acatccattc tcttatcgaa   480
aagggttttg ctccactgaa agatgcatca tacttaacca acggctacct ggatactgtt   540
attgactggg taccaggtat ggaaggtata agacttaaag attttccttt ggattggtct   600
acagacctta atgataaagt attgatgttt actacagaag ctccacaaag atctcataag   660
gtttcacatc atatctttca cacctttgat gaattggaac catcaatcat caaaaccttg   720
tctctaagat acaatcatat ctacactatt ggtccattac aattacttct agatcaaatt   780
cctgaagaga aaaagcaaac tggtattaca tccttacacg gctactcttt agtgaaagag   840
gaaccagaat gttttcaatg gctacaaagt aaagagccta attctgtggt ctacgtcaac   900
ttcggaagta caacagtcat gtccttggaa gatatgactg aatttggttg gggccttgct   960
aattcaaatc attactttct atggattatc aggtccaatt tggtaatagg ggaaaacgcc  1020
gtattacctc cagaattgga ggaacacatc aaaaagagag gtttcattgc ttcctggtgt  1080
tctcaggaaa aggtattgaa acatccttct gttggtggtt tccttactca ttgcggttgg  1140
ggctctacaa tcgaatcact aagtgcagga gttccaatga tttgttggcc atattcatgg  1200
gaccaactta caaattgtag gtatatctgt aaagagtggg aagttggatt agaaatggga  1260
acaaaggtta aacgtgatga agtgaaaaga ttggttcagg agttgatggg ggaaggtggc  1320
cacaagatga gaaacaaggc caaagattgg aaggaaaaag ccagaattgc tattgctcct  1380
aacgggtcat cctctctaaa cattgataag atggtcaaag agattacagt cttagccaga  1440
aactaa                                                             1446
```

SEQ ID NO: 7

*S. rebaudiana*

```
MDAMATTEKK PHVIFIPFPA QSHIKAMLKL AQLLHHKGLQ ITFVNTDFIH NQFLESSGPH    60
CLDGAPGFRF ETIPDGVSHS PEASIPIRES LLRSIETNFL DRFIDLVTKL PDPPTCIISD   120
GFLSVFTIDA AKKLGIPVMM YWTLAACGFM GFYHIHSLIE KGFAPLKDAS YLTNGYLDTV   180
IDWVPGMEGI RLKDFPLDWS TDLNDKVLMF TTEAPQRSHK VSHHIFHTFD ELEPSIIKTL   240
SLRYNHIYTI GPLQLLLDQI PEEKKQTGIT SLHGYSLVKE EPECFQWLQS KEPNSVVYVN   300
FGSTTVMSLE DMTEFGWGLA NSNHYFLWII RSNLVIGENA VLPPELEEHI KKRGFIASWC   360
SQEKVLKHPS VGGFLTHCGW GSTIESLSAG VPMICWPYSW DQLTNCRYIC KEWEVGLEMG   420
TKVKRDEVKR LVQELMGEGG HKMRNKAKDW KEKARIAIAP NGSSSLNIDK MVKEITVLAR   480
N                                                                  481
```

SEQ ID NO: 8

*S. rebaudiana*

```
atggaaaaca agaccgaaac aacagttaga cgtaggcgta gaatcattct gtttccagta    60
ccttttcaag ggcacatcaa tccaatacta caactagcca acgttttgta ctctaaaggt   120
ttttctatta caatctttca caccaatttc aacaaaccaa aaacatccaa ttacccacat   180
ttcacattca gattcatact tgataatgat ccacaagatg aacgtatttc aaacttacct   240
acccacggtc ctttagctgg aatgagaatt ccaatcatca atgaacatgg tgccgatgag   300
cttagaagag aattagagtt acttatgttg gcatccgaag aggacgagga agtctcttgt   360
ctgattactg acgctctatg gtactttgcc caatctgtgg ctgatagttt gaatttgagg   420
agattggtac taatgacatc cagtctgttt aactttcacg ctcatgttag tttaccacaa   480
tttgacgaat tgggatactt ggaccctgat gacaagacta ggttagagga acaggcctct   540
ggttttccta tgttgaaagt caaagatatc aagtctgcct attctaattg gcaaatcttg   600
aaagagatct taggaaagat gatcaaacag acaaaggctt catctggagt gatttggaac   660
agtttcaaag agttagaaga gtctgaattg gagactgtaa tcagagaaat tccagcacct   720
tcattcctga taccattacc aaaacatttg actgcttcct cttcctcttt gttggatcat   780
gacagaacag tttttcaatg gttggaccaa caaccaccta gttctgtttt gtacgtgtca   840
tttggtagta cttctgaagt cgatgaaaag gacttccttg aaatcgcaag aggcttagtc   900
gatagtaagc agtcattcct ttgggtcgtg cgtccaggtt tcgtgaaagg ctcaacatgg   960
gtcgaaccac ttccagatgg ttttctaggc gaaagaggta gaatagtcaa atgggttcct  1020
caacaggaag ttttagctca tggcgctatt ggggcattct ggactcattc cggatggaat  1080
tcaactttag aatcagtatg cgaaggggta cctatgatct tttcagattt tggtcttgat  1140
caaccactga acgcaagata catgtctgat gttttgaaag tgggtgtata tctagaaaat  1200
ggctgggaaa ggggtgaaat agctaatgca ataagacgtg ttatggttga tgaagagggg  1260
gagtatatca gacaaaacgc aagagtgctg aagcaaaagg ccgacgtttc tctaatgaag  1320
ggaggctctt catacgaatc cttagaatct cttgtttcct acatttcatc actgtaa     1377
```

SEQ ID NO: 9

*S. rebaudiana*

```
MENKTETTVR RRRRIILFPV PFQGHINPIL QLANVLYSKG FSITIFHTNF NKPKTSNYPH    60
FTFRFILDND PQDERISNLP THGPLAGMRI PIINEHGADE LRRELELLML ASEEDEEVSC   120
LITDALWYFA QSVADSLNLR RLVLMTSSLF NFHAHVSLPQ FDELGYLDPD DKTRLEEQAS   180
GFPMLKVKDI KSAYSNWQIL KEILGKMIKQ TKASSGVIWN SFKELEESEL ETVIREIPAP   240
SFLIPLPKHL TASSSSLLDH DRTVFQWLDQ QPPSSVLYVS FGSTSEVDEK DFLEIARGLV   300
DSKQSFLWVV RPGFVKGSTW VEPLPDGFLG ERGRIVKWVP QQEVLAHGAI GAFWTHSGWN   360
STLESVCEGV PMIFSDFGLD QPLNARYMSD VLKVGVYLEN GWERGEIANA IRRVMVDEEG   420
EYIRQNARVL KQKADVSLMK GGSSYESLES LVSYISSL                          458
```

SEQ ID NO: 10

```
atggctacat ctgattctat tgttgatgac aggaagcagt tgcatgtggc tactttccct    60
tggcttgctt tcggtcatat actgccttac ctacaactat caaaactgat agctgaaaaa   120
ggacataaag tgtcattcct ttcaacaact agaaacattc aaagattatc ttcccacata   180
tcaccattga ttaacgtcgt tcaattgaca cttccaagag tacaggaatt accagaagat   240
gctgaagcta caacagatgt gcatcctgaa gatatccctt acttgaaaaa ggcatccgat   300
ggattacagc ctgaggtcac tagattcctt gagcaacaca gtccagattg gatcatatac   360
gactacactc actattggtt gccttcaatt gcagcatcac taggcatttc tagggcacat   420
ttcagtgtaa ccacaccttg ggccattgct tacatgggtc catccgctga tgctatgatt   480
aacggcagtg atggtagaac taccgttgaa gatttgacaa ccccaccaaa gtggtttcca   540
```

TABLE 11-continued

Sequences disclosed herein.

```
tttccaacta aagtctgttg gagaaaacac gacttagcaa gactggttcc atacaaggca   600
ccaggaatct cagacggcta tagaatgggt ttagtcctta aagggtctga ctgcctattg   660
tctaagtgtt accatgagtt tgggacacaa tggctaccac ttttggaaac attacaccaa   720
gttcctgtcg taccagttgg tctattacct ccagaaatcc ctggtgatga gaaggacgag   780
acttgggttt caatcaaaaa gtggttagac gggaagcaaa aaggctcagt ggtatatgtg   840
gcactgggtt ccgaagtttt agtatctcaa acagaagttg tggaacttgc cttaggtttg   900
gaactatctg gattgccatt tgtctgggcc tacagaaaac caaaaggccc tgcaaagtcc   960
gattcagttg aattgccaga cggctttgtc gagagaacta gagatagagg gttggtatgg  1020
acttcatggg ctccacaatt gagaatcctg agtcacgaat ctgtgtgcgg tttcctaaca  1080
cattgtggtt ctggttctat agttgaagga ctgatgtttg gtcatccact tatcatgttg  1140
ccaatctttg gtgaccagcc tttgaatgca cgtctgttag aagataaaca agttggaatt  1200
gaaatcccac gtaatgagga agatggatgt ttaaccaagg agtctgtggc cagatcatta  1260
cgttccgttg tcgttgaaaa ggaaggcgaa atctacaagg ccaatgcccg tgaactttca  1320
aagatctaca atgacacaaa agtagagaag gaatatgttt ctcaatttgt agattaccta  1380
gagaaaaacg ctagagccgt agctattgat catgaatcct aa                      1422

SEQ ID NO: 11
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVITPWAIA YMGPSADAMI NGSDGRTTVE DLTTPPKWFP   180
FPTKVCWRKH DLARLVPYKA PGISDGYRMG LVLKGSDCLL SKCYHEFGTQ WLPLLETLHQ   240
VPVVPVGLLP PEIPGDEKDE TWVSIKKWLD GKQKGSVVYV ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473

SEQ ID NO: 12
atggctactt ctgattccat cgttgacgat agaaagcaat tgcatgttgc tacttttcca    60
tggttggctt tcggtcatat tttgccatac ttgcaattgt ccaagttgat tgctgaaaag   120
ggtcacaagg tttcattctt gtctaccacc agaaacatcc aaagattgtc ctctcatatc   180
tccccattga tcaacgttgt tcaattgact ttgccaagag tccaagaatt gccagaagat   240
gctgaagcta ctactgatgt tcatccagaa gatatccctt acttgaaaaa ggcttccgat   300
ggtttacaac cagaagttac tagattcttg gaacaacatt ccccagattg gatcatctac   360
gattatactc attactggtt gccatccatt gctgcttcat tgggtatttc tagagcccat   420
ttctctgtta ctactccatg ggctattgct tatatgggtc catctgctga tgctatgatt   480
aacggttctg atggtagaac taccgttgaa gatttgacta ctccaccaaa gtggtttcca   540
tttccaacaa aagtctgttg gagaaaacac gatttggcta gattggttcc atacaaagct   600
ccaggtattt ctgatggtta cagaatgggt atggttttga aaggttccga ttgcttgttg   660
tctaagtgct atcatgaatt cggtactcaa tggttgcctt tgttggaaac attgcatcaa   720
gttccagttg ttccagtagg tttgttgcca ccagaaattc caggtgacga aaaagacgaa   780
acttgggttt ccatcaaaaa gtggttggat ggtaagcaaa agggttctgt tgtttatgtt   840
gctttgggtt ccgaagcttt ggtttctcaa accgaagttg ttgaattggc tttgggtttg   900
gaattgtctg gtttgccatt tgtttgggct tacagaaaac ctaaaggtcc agctaagtct   960
gattctgttg aattgccaga tggtttcgtt gaaagaacta gagatagagg tttggtttgg  1020
acttcttggg ctccacaatt gagaattttg tctcatgaat ccgtctgtgg tttcttgact  1080
cattgtggtt ctggttctat cgttgaaggt ttgatgtttg gtcacccatt gattatgttg  1140
ccaatctttg gtgaccaacc attgaacgct agattattgg aagataagca agtcggtatc  1200
gaaatcccaa gaaatgaaga agatggttgc ttgaccaaag aatctgttgc tagatctttg  1260
agatccgttg tcgttgaaaa agaaggtgaa atctacaagg ctaacgctag agaattgtcc  1320
aagatctaca acgataccaa ggtcgaaaaa gaatacgttt cccaattcgt tgactacttg  1380
gaaaagaatg ctagagctgt tgccattgat catgaatctt ga                      1422

SEQ ID NO: 13
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG MVLKGSDCLL SKCYHEFGTQ WLPLLETLHQ   240
VPVVPVGLLP PEIPGDEKDE TWVSIKKWLD GKQKGSVVYV ALGSEALVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473
```

SEQ ID NO: 14
*O. sativa*

```
atggactccg gctactcctc ctcctacgcc gccgccgccg ggatgcacgt cgtgatctgc    60
ccgtggctcg ccttcggcca cctgctcccg tgcctcgacc tcgcccagcg cctcgcgtcg   120
cggggccacc gcgtgtcgtt cgtctccacg ccgcggaaca tatcccgcct cccgccggtg   180
cgccccgcgc tcgcgccgct cgtcgccttc gtggcgctgc cgctcccgcg cgtcgagggg   240
ctccccgacg gcgccgagtc caccaacgac gtcccccacg acaggccgga catggtcgag   300
ctccaccgga gggccttcga cgggctcgcc gcgcccttct cggagttctt gggcaccgcg   360
tgcgccgact gggtcatcgt cgacgtcttc caccactggg ccgcagccgc cgctctcgag   420
cacaaggtgc catgtgcaat gatgttgttg ggctctgcac atatgatcgc ttccatagca   480
gacagacggc tcgagcgcgc ggagacagag tcgcctgcgg ctgccgggca gggacgccca   540
gcggcggcgc caacgttcga ggtggcgagg atgaagttga tacgaaccaa aggctcatcg   600
ggaatgtccc tcgccgagcg cttctccttg acgctctcga ggagcagcct cgtcgtcggg   660
cggagctgcg tggagttcga gccggagacc gtcccgctcc tgtcgacgct ccgcggtaag   720
cctattacct tccttggcct tatgccgccg ttgcatgaag gccgccgcga ggacggcgag   780
gatgccaccg tccgctggct cgacgcgcag ccggccaagt ccgtcgtgta cgtcgcgcta   840
```

TABLE 11-continued

| Sequences disclosed herein. |
|---|

```
ggcagcgagg tgccactggg agtggagaag gtccacgagc tcgcgctcgg gctggagctc   900
gccgggacgc gcttcctctg ggctcttagg aagcccactg gcgtctccga cgccgacctc   960
ctccccgccg gcttcgagga gcgcacgcgc ggccgcggcg tcgtggcgac gagatgggtt  1020
cctcagatga gcatactggc gcacgccgcc gtgggcgcgt tcctgaccca ctgcggctgg  1080
aactcgacca tcgaggggct catgttcggc cacccgctta tcatgctgcc gatcttcggc  1140
gaccagggac cgaacgcgcg gctaatcgag gcgaagaacg ccggattgca ggtggcaaga  1200
aacgacggcg atggatcgtt cgaccgagaa ggcgtcgcgg cggcgattcg tgcagtcgcg  1260
gtggaggaag aaagcagcaa agtgtttcaa gccaaagcca agaagctgca ggagatcgtc  1320
gcggacatgg cctgccatga gaggtacatc gacggattca ttcagcaatt gagatcttac  1380
aaggattga                                                          1389
```

SEQ ID NO: 15
*O. sativa*

```
atggatagtg gctactcctc atcttatgct gctgccgctg gtatgcacgt tgtgatctgc    60
ccttggttgg cctttggtca cctgttacca tgtctggatt tagcccaaag actggcctca   120
agaggccata gagtatcatt tgtgtctact cctagaaata tctctcgttt accaccagtc   180
agacctgctc tagctcctct agttgcattc gttgctcttc cacttccaag agtagaagga   240
ttgccagacg gcgctgaatc tactaatgac gtaccacatg atagacctga catggtcgaa   300
ttgcatagaa gagcctttga tggattggca gctccatttt ctgagttcct gggcacagca   360
tgtgcagact gggttatagt cgatgtattt catcactggg ctgctgcagc cgcattggaa   420
cataaggtgc cttgtgctat gatgttgtta gggtcagcac acatgatcgc atccatagct   480
gatagaagat tggaaagagc tgaaacagaa tccccagccg cagcaggaca aggtaggcca   540
gctgccgccc caaccttgga agtggctaga atgaaattga ttcgtactaa aggtagttca   600
gggatgagtc ttgctgaaag gttttctctg acattatcta gatcatcatt agttgtaggt   660
agatcctgcg tcgagttcga acctgaaaca gtacctttac tatctacttt gagaggcaaa   720
cctattactt tccttggtct aatgcctcca ttacatgaag gaaggagaga agatggtgaa   780
gatgctactg ttaggtggtt agatgcccaa cctgctaagt ctgttgttta cgttgcattg   840
ggttctgagg taccactagg ggtggaaaag gtgcatgaat tagcattagg acttgagctg   900
gccggaacaa gattcctttg ggctttgaga aaaccaaccg gtgtttctga cgccgacttg   960
ctaccagctg ggttcgaaga gagaacaaga ggccgtggtg tcgttgctac tagatgggtc  1020
ccacaaatga gtattctagc tcatgcagct gtaggggcct ttctaaccca ttgcggttgg  1080
aactcaacaa tagaaggact gatgtttggt catccactta ttatgttacc aatctttggc  1140
gatcagggac ctaacgcaag attgattgag gcaaagaacg caggtctgca ggttgcacgt  1200
aatgatggtg atggttcctt tgatagagaa ggcgttgcag ctgccatcag agcagtcgcc  1260
gttgaggaag agtcatctaa agttttccaa gctaaggcca aaaaattaca agagattgtg  1320
gctgacatgg cttgtcacga aagatacatc gatggtttca tccaacaatt gagaagttat  1380
aaagactaa                                                          1389
```

SEQ ID NO: 16
*O. sativa*

```
MDSGYSSSYA AAAGMHVVIC PWLAFGHLLP CLDLAQRLAS RGHRVSFVST PRNISRLPPV    60
RPALAPLVAF VALPLPRVEG LPDGAESTND VPHDRPDMVE LHRRAFDGLA APFSEFLGTA   120
CADWVIVDVF HHWAAAAALE HKVPCAMMLL GSAHMIASIA DRRLERAETE SPAAAGQGRP   180
AAAPTFEVAR MKLIRTKGSS GMSLAERFSL TLSRSSLVVG RSCVEFEPET VPLLSTLRGK   240
PITFLGLMPP LHEGRREDGE DATVRWLDAQ PAKSVVYVAL GSEVPLGVEK VHELALGLEL   300
AGTRFLWALR KPTGVSDADL LPAGFEERTR GRGVVATRWV PQMSILAHAA VGAFLTHCGW   360
NSTIEGLMFG HPLIMLPIFG DQGPNARLIE AKNAGLQVAR NDGDGSFDRE GVAAAIRAVA   420
VEEESSKVFQ AKAKKLQEIV ADMACHERYI DGFIQQLRSY KD                      462
```

SEQ ID NO: 17

```
MDSGYSSSYA AAAGMHVVIC PWLAFGHLLP CLDLAQRLAS RGHRVSFVST PRNISRLPPV    60
RPALAPLVAF VALPLPRVEG LPDGAESTND VPHDRPDMVE LHRRAFDGLA APFSEFLGTA   120
CADWVIVDVF HHWAAAAALE HKVPCAMMLL GSAHMIASIA DRRLERAETE SPAAAGQGRP   180
AAAPTFEVAR MKLIRTKGSS GMSLAERFSL TLSRSSLVVG RSCVEFEPET VPLLSTLRGK   240
PITFLGLLPP EIPGDEKDET WVSIKKWLDG KQKGSVVYVA LGSEALVSQT EVVELALGLE   300
LSGLPFVWAY RKPKGPAKSD SVELPDGFVE RTRDRGLVWT SWAPQLRILS HESVCGFLTH   360
CGSGSIVEGL MFGHPLIMLP IFGDQPLNAR LLEDKQVGIE IARNDGDGSF DREGVAAAIR   420
AVAVEEESSK VFQAKAKKLQ EIVADMACHE RYIDGFIQQL RSYKD                   465
```

SEQ ID NO: 18

```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG MVLKGSDCLL SKCYHEFGTQ WLPLLETLHQ   240
VPVVPVGLMP PLHEGRREDG EDATVRWLDA QPAKSVVYVA LGSEVPLGVE KVHELALGLE   300
LAGTRFLWAL RKPTGVSDAD LLPAGFEERT RGRGVVATRW VPQMSILAHA AVGAFLTHCG   360
WNSTIEGLMF GHPLIMLPIF GDQGPNARLI EAKNAGLQVP RNEEDGCLTK ESVARSLRSV   420
VVEKEGEIYK ANARELSKIY NDTKVEKEYV SQFVDYLEKN ARAVAIDHES              470
```

SEQ ID NO: 19
*Synechococcus* sp.

```
atggctttgg taaacccaac cgctcttttc tatggtacct ctatcagaac aagacctaca    60
aacttactaa atccaactca aaagctaaga ccagtttcat catcttcctt accttctttc   120
tcatcagtta gtgcgattct tactgaaaaa catcaatcta atccttctga gaacaacaat   180
ttgcaaactc atctagaaac tcctttcaac tttgatagtt atatgttgga aaaagtcaac   240
atggttaacg aggcgcttga tgcatctgtc ccactaaaag acccaatcaa aatccatgaa   300
tccatgagat actctttatt ggcaggcggt aagagaatca gaccaatgat gtgtattgca   360
gcctgcgaaa tagtcggagg taatatcctt aacgccatgc cagccgcatg tgccgtggaa   420
```

TABLE 11-continued

| Sequences disclosed herein. |
|---|
| atgattcata ctatgtcttt ggtgcatgac gatcttccat gtatggataa tgatgacttc 480<br>agaagaggta aacctatttc acacaaggtc tacggggagg aaatggcagt attgaccggc 540<br>gatgctttac taagtttatc tttcgaacat atagctactg ctacaaaggg tgtatcaaag 600<br>gatagaatcg tcagagctat aggggagttg gcccgttcag ttggctccga aggtttagtg 660<br>gctggacaag ttgtagatat cttgtcagag ggtgctgatg ttggattaga tcacctagaa 720<br>tacattcaca tccacaaaac agcaatgttg cttgagtcct cagtagttat tggcgctatc 780<br>atgggaggag gatctgatca gcagatcgaa aagttgagaa aattcgctag atctattggt 840<br>ctactattcc aagttgtgga tgacattttg gatgttacaa aatctaccga agagttgggg 900<br>aaaacagctg gtaaggattt gttgacagat aagacaactt acccaaagtt gttaggtata 960<br>gaaaagtcca gagaatttgc cgaaaaactt aacaaggaag cacaagagca attaagtggc 1020<br>tttgatagac gtaaggcagc tcctttgatc gcgttagcca actacaatgc gtaccgtcaa 1080<br>aattga 1086 |
| SEQ ID NO: 20<br>*Synechococcus* sp.<br>MALVNPTALF YGTSIRTRPT NLLNPTQKLR PVSSSSLPSF SSVSAILTEK HQSNPSENNN 60<br>LQTHLETPFN FDSYMLEKVN MVNEALDASV PLKDPIKIHE SMRYSLLAGG KRIRPMMCIA 120<br>ACEIVGGNIL NAMPAACAVE MIHTMSLVHD DLPCMDNDDF RRGKPISHKV YGEEMAVLTG 180<br>DALLSLSFEH IATATKGVSK DRIVRAIGEL ARSVGSEGLV AGQVVDILSE GADVGLDHLE 240<br>YIHIHKTAML LESSVVIGAI MGGGSDQQIE KLRKFARSIG LLFQVVDDIL DVTKSTEELG 300<br>KTAGKDLLTD KTTYPKLLGI EKSREFAEKL NKEAQEQLSG FDRRKAAPLI ALANYNAYRQ 360<br>N 361 |
| SEQ ID NO: 21<br>atggctgagc aacaaatatc taacttgctg tctatgtttg atgcttcaca tgctagtcag 60<br>aaattagaaa ttactgtcca aatgatggac acataccatt acagagaaac gcctccagat 120<br>tcctcatctt ctgaaggcgg ttcattgtct agatacgacg agagaagagt ctctttgcct 180<br>ctcagtcata atgctgcctc tccagatatt gtatcacaac tatgtttttc cactgcaatg 240<br>tcttcagagt tgaatcacag atggaaatct caaagattaa aggtggccga ttctccttac 300<br>aactatatcc taacattacc atcaaaagga attagaggtg cctttatcga ttccctgaac 360<br>gtatggttgg aggttccaga ggatgaaaca tcagtcatca aggaagttat tggtatgctc 420<br>cacaactctt cattaatcat tgatgacttc caagataatt ctccacttag aagaggaaag 480<br>ccatctaccc atacagtctt cggccctgcc caggctatca atactgctac ttacgttata 540<br>gttaaagcaa tcgaaaagat acaagacata gtgggacacg atgcattggc agatgttacg 600<br>ggtactatta caactatttt ccaaggtcag gccatggact tgtggtggac agcaaatgca 660<br>atcgttccat caatacagga atacttactt atggtaaacg ataaaaccgg tgctctcttt 720<br>agactgagtt tggagttgtt agctctgaat tccgaagcca gtatttctga ctctgcttta 780<br>gaaagtttat ctagtgctgt ttccttgcta ggtcaatact tccaaatcag agacgactat 840<br>atgaacttga tcgataacaa gtatacagat cagaaaggct tctgcgaaga tcttgatgaa 900<br>ggcaagtact cactaacact tattcatgcc ctccaaactg attcatccga tctactgacc 960<br>aacatccttt caatgagaag agtgcaagga aagttaacgg cacaaaagag atgttggttc 1020<br>tggaaatga 1029 |
| SEQ ID NO: 22<br>MAEQQISNLL SMFDASHASQ KLEITVQMMD TYHYRETPPD SSSSEGGSLS RYDERRVSLP 60<br>LSHNAASPDI VSQLCFSTAM SSELNHRWKS QRLKVADSPY NYILTLPSKG IRGAFIDSLN 120<br>VWLEVPEDET SVIKEVIGML HNSSLIIDDF QDNSPLRRGK PSTHTVFGPA QAINTATYVI 180<br>VKAIEKIQDI VGHDALADVT GTITTIFQGQ AMDLWWTANA IVPSIQEYLL MVNDKTGALF 240<br>RLSLELLALN SEASISDSAL ESLSSAVSLL GQYFQIRDDY MNLIDNKYTD QKGFCEDLDE 300<br>GKYSLTLIHA LQTDSSDLLT NILSMRRVQG KLTAQKRCWF WK 342 |
| SEQ ID NO: 23<br>atggaaaaga ctaaggagaa agcagaacgt atcttgctgg agccatacag atacttatta 60<br>caactaccag gaaagcaagt ccgttctaaa ctatcacaag cgttcaatca ctggttaaaa 120<br>gttcctgaag ataagttaca aatcattatt gaagtcacag aaatgctaca caatgcttct 180<br>ttactgatcg atgatataga ggattcttcc aaactgagaa gaggttttcc tgtcgctcat 240<br>tccatatacg gggtaccaag tgtaatcaac tcagctaatt acgtctactt cttgggattg 300<br>gaaaaagtat tgacattaga tcatccagac gctgtaaagc tattcaccag acaacttctt 360<br>gaattgcatc aaggtcaagg tttggatatc tattggagag acacttatac ttgcccaaca 420<br>gaagaggagt acaaagcaat ggttctacaa aagactggcg gtttgttcgg acttgccgtt 480<br>ggtctgatgc aacttttctc tgattacaag gaggacttaa agcctctgtt ggataccttg 540<br>ggcttgtttt tccagattag agatgactac gctaacttac attcaaagga atattcagaa 600<br>aacaaatcat tctgtgaaga tttgactgaa gggaagttta gttttccaac aatccacgcc 660<br>atttggtcaa gaccagaatc tactcaagtg caaaacattc tgcgtcagag aacagagaat 720<br>attgacatca aaaagtattg tgttcagtac ttggaagatg ttggttcttt tgcttacaca 780<br>agacatacac ttagagaatt agaggcaaaa gcatacaagc aaatagaagc ctgtggaggc 840<br>aatccttctc tagtggcatt ggttaaacat ttgtccaaaa tgttcaccga ggaaaacaag 900<br>taa 903 |
| SEQ ID NO: 24<br>MEKTKEKAER ILLEPYRYLL QLPGKQVRSK LSQAFNHWLK VPEDKLQIII EVTEMLHNAS 60<br>LLIDDIEDSS KLRRGFPVAH SIYGVPSVIN SANYVYFLGL EKVLTLDHPD AVKLFTRQLL 120<br>ELHQGQGLDI YWRDTYTCPT EEEYKAMVLQ KTGGLFGLAV GLMQLFSDYK EDLKPLLDTL 180<br>GLFFQIRDDY ANLHSKEYSE NKSFCEDLTE GKFSFPTIHA IWSRPESTQV QNILRQRTEN 240<br>IDIKKYCVQY LEDVGSFAYT RHTLRELEAK AYKQIEACGG NPSLVALVKH LSKMFTEENK 300 |
| SEQ ID NO: 25<br>atggcaagat tctattttct taacgcacta ttgatggtta tctcattaca atcaactaca 60 |

TABLE 11-continued

| Sequences disclosed herein. |
|---|
| gccttcactc cagctaaact tgcttatcca acaacaacaa cagctctaaa tgtcgcctcc 120<br>gccgaaactt ctttcagtct agatgaatac ttggcctcta agataggacc tatagagtct 180<br>gccttggaag catcagtcaa atccagaatt ccacagaccg ataagatctg cgaatctatg 240<br>gcctactctt tgatggcagg aggcaagaga attagaccag tgttgtgtat cgctgcatgt 300<br>gagatgttcg gtggatccca agatgtcgct atgcctactg ctgtggcatt agaaatgata 360<br>cacacaatgt ctttgattca tgatgatttg ccatccatgg ataacgatga cttgagaaga 420<br>ggtaaaccaa caaaccatgt cgttttcggc gaagatgtag ctattcttgc aggtgactct 480<br>ttattgtcaa cttccttcga gcacgtcgct agagaaacaa aaggagtgtc agcagaaaag 540<br>atcgtggatg ttatcgctag attaggcaaa tctgttggtg ccgagggcct tgctggcggt 600<br>caagttatgg acttagaatg tgaagctaaa ccaggtacca cattagacga cttgaaatgg 660<br>attcatatcc ataaaaccgc tacattgtta caagttgctg tagcttctgg tgcagttcta 720<br>ggtggtgcaa ctcctgaaga ggttgctgca tgcgagttgt ttgctatgaa tataggtctt 780<br>gcctttcaag ttgccgacga tatccttgat gtaaccgctt catcagaaga tttgggtaaa 840<br>actgcaggca aagatgaagc tactgataag acaacttacc caaagttatt aggattagaa 900<br>gagagtaagg catacgcaag acaactaatc gatgaagcca aggaaagttt ggctcctttt 960<br>ggagatagag ctgccccttt attggccatt gcagatttca ttattgatag aaagaattga 1020 |
| SEQ ID NO: 26<br>MARFYFLNAL LMVISLQSTT AFTPAKLAYP TTTTALNVAS AETSFSLDEY LASKIGPIES 60<br>ALEASVKSRI PQTDKICESM AYSLMAGGKR IRPVLCIAAC EMFGGSQDVA MPTAVALEMI 120<br>HTMSLIHDDL PSMDNDDLRR GKPTNHVVFG EDVAILAGDS LLSTSFEHVA RETKGVSAEK 180<br>IVDVIARLGK SVGAEGLAGG QVMDLECEAK PGTTLDDLKW IHIHKTATLL QVAVASGAVL 240<br>GGATPEEVAA CELFAMNIGL AFQVADDILD VTASSEDLGK TAGKDEATDK TTYPKLLGLE 300<br>ESKAYARQLI DEAKESLAPF GDRAAPLLAI ADFIIDRKN 339 |
| SEQ ID NO: 27<br>atgcacttag caccacgtag agtccctaga ggtagaagat caccacctga cagagttcct 60<br>gaaagacaag gtgccttggg tagaagacgt ggagctggct ctactggctg tgcccgtgct 120<br>gctgctggtg ttcaccgtag aagaggagga ggcgaggctg atccatcagc tgctgtgcat 180<br>agaggctggc aagccggtgg tggcaccggt ttgcctgatg aggtggtgtc taccgcagcc 240<br>gccttagaaa tgtttcatgc ttttgcttta atccatgatg atatcatgga tgatagtgca 300<br>actagaagag gctccccaac tgttcacaga gccctagctg atcgtttagg cgctgctctg 360<br>gacccagatc aggccggtca actaggagtt tctactgcta tcttggttgg agatctggct 420<br>ttgacatggt ccgatgaatt gttatacgct ccattgactc cacatagact ggcagcagta 480<br>ctaccattgg taacagctat gagagctgaa accgttcatg gccaatatct tgatataact 540<br>agtgctagaa gacctgggac cgatacttct cttgcattga gaatagccag atataagaca 600<br>gcagcttaca caatggaacg tccactgcac attggtgcag ccctggctgg ggcaagacca 660<br>gaactattag cagggctttc agcatacgcc ttgccagctg gagaagcctt ccaattggca 720<br>gatgacctgc taggcgtctt cggtgatcca agacgtacag ggaaacctga cctagatgat 780<br>cttagaggtg gaaagcatac tgtcttagtc gccttggcaa gagaacatgc cactccagaa 840<br>cagagacaca cattggatac attattgggt acaccaggtc ttgatagaca aggcgcttca 900<br>agactaagat gcgtattggt agcaactggt gcaagagccg aagccgaaag acttattaca 960<br>gagagaagag atcaagcatt aactgcattg aacgcattaa cactgccacc tcctttagct 1020<br>gaggcattag caagattgac attagggtct acagctcatc ctgcctaa 1068 |
| SEQ ID NO: 28<br>MHLAPRRVPR GRRSPPDRVP ERQGALGRRR GAGSTGCARA AAGVHRRRGG GEADPSAAVH 60<br>RGWQAGGGTG LPDEVVSTAA ALEMFHAFAL IHDDIMDDSA TRRGSPTVHR ALADRLGAAL 120<br>DPDQAGQLGV STAILVGDLA LTWSDELLYA PLTPHRLAAV LPLVTAMRAE TVHGQYLDIT 180<br>SARRPGTDTS LALRIARYKT AAYTMERPLH IGAALAGARP ELLAGLSAYA LPAGEAFQLA 240<br>DDLLGVFGDP RRTGKPDLDD LRGGKHTVLV ALAREHATPE QRHTLDTLLG TPGLDRQGAS 300<br>RLRCVLVATG ARAEAERLIT ERRDQALTAL NALTLPPPLA EALARLTLGS TAHPA 355 |
| SEQ ID NO: 29<br>atgtcatatt tcgataacta cttcaatgag atagttaatt ccgtgaacga catcattaag 60<br>tcttacatct ctggcgacgt accaaaacta tacgaagcct cctaccattt gtttacatca 120<br>ggaggaaaga gactaagacc attgatcctt acaatttctt ctgatctttt cggtggacag 180<br>agagaaagag catactatgc tggcgcagca atcgaagttt tgcacacatt cactttggtt 240<br>cacgatgata tcatggatca agataacatt cgtagaggtc ttcctactgt acatgtcaag 300<br>tatggcctac ctttggccat tttagctggt gacttattgc atgcaaaagc ctttcaattg 360<br>ttgactcagg cattgagagg tctaccatct gaaactatca tcaaggcgtt tgatatcttt 420<br>acaagatcta tcattatcat atcagaaggt caagctgtcg atatggaatt cgaagataga 480<br>attgatatca aggaacaaga gtatttggat atgatatctc gtaaaaccgc tgccttattc 540<br>tcagcttctt cttccattgg ggcgttgata gctggagcta atgataacga tgtgagatta 600<br>atgtccgatt tcggtacaaa tcttgggatc gcatttcaaa ttgtagatga tatacttggt 660<br>ttaacagctg atgaaaaaga gctaggaaaa cctgttttca gtgatatcag agaaggtaaa 720<br>aagaccatat tagtcattaa gactttagaa ttgtgtaagg aagacgagaa aaagattgtg 780<br>ttaaaagcgc taggcaacaa gtcagcatca aaggaagagt tgatgagttc tgctgacata 840<br>atcaaaaagt actcattgga ttacgcctac aacttagctg agaaatacta caaaaacgcc 900<br>atcgattctc taaatcaagt ttcaagtaaa agtgatattc cagggaaggc attgaaatat 960<br>cttgctgaat tcaccatcag aagacgtaag taa 993 |
| SEQ ID NO: 30<br>MSYFDNYFNE IVNSVNDIIK SYISGDVPKL YEASYHLFTS GGKRLRPLIL TISSDLFGGQ 60<br>RERAYYAGAA IEVLHTFTLV HDDIMDQDNI RRGLPTVHVK YGLPLAILAG DLLHAKAFQL 120<br>LTQALRGLPS ETIIKAFDIF TRSIIIISEG QAVDMEFEDR IDIKEQEYLD MISRKTAALF 180<br>SASSSIGALI AGANDNDVRL MSDFGTNLGI AFQIVDDILG LTADEKELGK PVFSDIREGK 240 |

TABLE 11-continued

Sequences disclosed herein.

```
KTILVIKTLE LCKEDEKKIV LKALGNKSAS KEELMSSADI IKKYSLDYAY NLAEKYYKNA   300
IDSLNQVSSK SDIPGKALKY LAEFTIRRRK                                    330

SEQ ID NO: 31
atggtcgcac aaactttcaa cctggatacc tacttatccc aaagacaaca acaagttgaa    60
gaggccctaa gtgctgctct tgtgccagct tatcctgaga gaatatacga agctatgaga   120
tactccctcc tggcaggtgg caaaagatta agacctatct tatgtttagc tgcttgcgaa   180
ttggcaggtg gttctgttga acaagccatg ccaactgcgt gtgcacttga aatgatccat   240
acaatgtcac taattcatga tgacctgcca gccatggata acgatgattt cagaagagga   300
aagccaacta atcacaaggt gttcggggaa gatatagcca tcttagcggg tgatgcgctt   360
ttagcttacg cttttgaaca tattgcttct caaacaagag gagtaccacc tcaattggtg   420
ctacaagtta ttgctagaat cggacacgcc gttgctgcaa caggcctcgt tggaggccaa   480
gtcgtagacc ttgaatctga aggtaaagct atttccttag aaacattgga gtatattcac   540
tcacataaga ctggagcctt gctggaagca tcagttgtct caggcggtat tctcgcaggg   600
gcagatgaag agcttttggc cagattgtct cattacgcta gagatatagg cttggctttt   660
caaatcgtcg atgatatcct ggatgttact gctacatctg aacagttggg gaaaaccgct   720
ggtaaagacc aggcagccgc aaaggcaact tatccaagtc tattgggttt agaagcctct   780
agacagaaag cggaagagtt gattcaatct gctaaggaag ccttaagacc ttacggttca   840
caagcagagc cactcctagc gctggcagac ttcatcacac gtcgtcagca ttaa         894

SEQ ID NO: 32
MVAQTFNLDT YLSQRQQQVE EALSAALVPA YPERIYEAMR YSLLAGGKRL RPILCLAACE    60
LAGGSVEQAM PTACALEMIH TMSLIHDDLP AMDNDDFRRG KPTNHKVFGE DIAILAGDAL   120
LAYAFEHIAS QTRGVPPQLV LQVIARIGHA VAATGLVGGQ VVDLESEGKA ISLETLEYIH   180
SHKTGALLEA SVVSGGILAG ADEELLARLS HYARDIGLAF QIVDDILDVT ATSEQLGKTA   240
GKDQAAAKAT YPSLLGLEAS RQKAEELIQS AKEALRPYGS QAEPLLALAD FITRRQH      297

SEQ ID NO: 33
atgaaaaccg ggtttatctc accagcaaca gtatttcatc acagaatctc accagcgacc    60
actttcagac atcacttatc acctgctact acaaactcta caggcattgt cgccttaaga   120
gacatcaact tcagatgtaa agcagtttct aaagagtact ctgatctgtt gcagaaagat   180
gaggcttctt tcacaaaatg ggacgatgac aaggtgaaag atcatcttga taccaacaaa   240
aacttatacc caaatgatga gattaaggaa tttgttgaat cagtaaaggc tatgttcggt   300
agtatgaatg acggggagat aaacgtctct gcatacgata ctgcatgggt tgctttggtt   360
caagatgtcg atggatcagg tagtcctcag ttcccttctt ctttagaatg gattgccaac   420
aatcaattgt cagatggatc atggggagat catttgctgt tctcagctca cgatagaatc   480
atcaacacat tagcatgcgt tattgcactt acaagttgga atgttcatcc ttctaagtgt   540
gaaaaaggtt tgaatttttct gagagaaaac atttgcaaat tagaagatga aaacgcagaa   600
catatgccaa ttggttttga agtaacattc ccatcactaa ttgatatcgc gaaaaagttg   660
aacattgaag tacctgagga tactccagca cttaaagaga tctacgcacg tagagatatc   720
aagttaacta agatcccaat ggaagttctt cacaaggtac ctactacttt gttacattct   780
ttggaaggaa tgcctgattt ggagtgggaa aaactgttaa agctacaatg taaagatggt   840
agtttcttgt tttccccatc tagtaccgca ttcgccctaa tgcaaacaaa agatgagaaa   900
tgcttacagt atctaacaaa tatcgtcact aagttcaacg gtggcgtgcc taatgtgtac   960
ccagtcgatt tgtttgaaca tatttgggtt gttgatagac tgcagagatt ggggattgcc  1020
agatacttca aatcagagat aaaagattgt gtagagtata tcaataagta ctggaccaaa  1080
aatggaattt gttgggctag aaatactcac gttcaagata tcgatgatac agccatggga  1140
ttcagagtgt tgagagcgca cggttatgac gtcactccag atgtttttag acaatttgaa  1200
aaagatggta aattcgtttg ctttgcaggg caatcaacac aagccgtgac aggaatgttt  1260
aacgtttaca gagcctctca aatgttgttc ccaggggaga gaattttgga agatgccaaa  1320
aagttctctt acaattactt aaaggaaaag caaagtacca acgaattgct ggataaatgg  1380
ataatcgcta aagatctacc tggtgaagtt ggttatgctc tggatatccc atggtatgct  1440
tccttaccaa gattggaaac tcgttattac cttgaacaat acggcggtga agatgatgtc  1500
tggataggca agacattata cagaatgggt tacgtgtcca ataacacata tctagaaatg  1560
gcaaagctgg attacaataa ctatgttgca gtccttcaat tagaatggta cacaatacaa  1620
caatggtacg tcgatattgg tatagagaag ttcgaatctg acaacatcaa gtcagtcctg  1680

SEQ ID NO: 34
MKTGFISPAT VFHHRISPAT TFRHHLSPAT INSTGIVALR DINFRCKAVS KEYSDLLQKD    60
EASFTKWDDD KVKDHLDTNK NLYPNDEIKE FVESVKAMFG SMNDGEINVS AYDTAWVALV   120
QDVDGSGSPQ FPSSLEWIAN NQLSDGSWGD HLLFSAHDRI INTLACVIAL TSWNVHPSKC   180
EKGLNFLREN ICKLEDENAE HMPIGFEVTF PSLIDIAKKL NIEVPEDTPA LKEIYARRDI   240
KLTKIPMEVL HKVPTTLLHS LEGMPDLEWE KLLKLQCKDG SFLFSPSSTA FALMQTKDEK   300
CLQYLTNIVT KFNGGVPNVY PVDLFEHIWV VDRLQRLGIA RYFKSEIKDC VEYINKYWTK   360
NGICWARNTH VQDIDDTAMG FRVLRAHGYD VTPDVFRQFE KDGKFVCFAG QSTQAVTGMF   420
NVYRASQMLF PGERILEDAK KFSYNYLKEK QSTNELLDKW IIAKDLPGEV GYALDIPWYA   480
SLPRLETRYY LEQYGGEDDV WIGKTLYRMG YVSNNTYLEM AKLDYNNYVA VLQLEWYTIQ   540
QWYVDIGIEK FESDNIKSVL VSYYLAAASI FEPERSKERI AWAKTTILVD KITSIFDSSQ   600
SSKEDITAFI DKFRNKSSSK KHSINGEPWH EVMVALKKTL HGFALDALMT HSQDIHPQLH   660
QAWEMWLTKL QDGVDVTAEL MVQMINMTAG RWVSKELLTH PQYQRLSTVT NSVCHDITKL   720
HNFKENSTTV DSKVQELVQL VFSDTPDDLD QDMKQTFLTV MKTFYYKAWC DPNTINDHIS   780
KVFEIVI                                                             787

SEQ ID NO: 35
atgcctgatg cacacgatgc tccacctcca caaataagac agagaacact agtagatgag    60
gctacccaac tgctaactga gtccgcagaa gatgcatggg gtgaagtcag tgtgtcagaa   120
tacgaaacag caaggctagt tgcccatgct acatggttag gtggacacgc cacaagagtg   180
gccttccttc tggagagaca acacgaagac gggtcatggg gtccaccagg tggatatagg   240
```

TABLE 11-continued

Sequences disclosed herein.

ttagtcccta cattatctgc tgttcacgca ttattgacat gtcttgcctc tcctgctcag 300
gatcatggcg ttccacatga tagactttta agagctgttg acgcaggctt gactgccttg 360
agaagattgg ggacatctga ctccccacct gatactatag cagttgagct ggttatccca 420
tctttgctag agggcattca acacttactg gaccctgctc atcctcatag tagaccagcc 480
ttctctcaac atagaggctc tcttgtttgt cctggtggac tagatgggag aactctagga 540
gctttgagat cacacgccgc agcaggtaca ccagtaccag gaaaagtctg gcacgcttcc 600
gagactttgg gcttgagtac cgaagctgct tctcacttgc aaccagccca aggtataatc 660
ggtggctctg ctgctgccac agcaacatgg ctaaccaggg ttgcaccatc tcaacagtca 720
gattctgcca gaagatacct tgaggaatta caacacagat actctggccc agttccttcc 780
attaccccta tcacatactt cgaaagagca tggttattga acaattttgc agcagccggt 840
gttccttgtg aggctccagc tgctttgttg gattccttag aagcagcact tacaccacaa 900
ggtgctcctg ctggagcagg attgcctcca gatgctgatg atacagccgc tgtgttgctt 960
gcattggcaa cacatgggag aggtagaaga ccagaagtac tgatggatta caggactgac 1020
gggtatttcc aatgctttat tggggaaagg actccatcaa tttcaacaaa cgctcacgta 1080
ttggaaacat tagggcatca tgtggcccaa catccacaag atagagccag atacggatca 1140
gccatggata ccgcatcagc ttggctgctg gcagctcaaa agcaagatgg ctcttggtta 1200
gataaatggc atgcctcacc atactacgct actgtttgtt gcacacaagc cctagccgct 1260
catgcaagtc ctgcaactgc accagctaga cagagagctg tcagatgggt tttagccaca 1320
caaagatccg atggcggttg ggtctatggc cattcaactg ttgaagagac tgcttatgcc 1380
ttacagatct tggccccacc ttctggtggt ggcaatatcc cagtccaaca agcacttact 1440
agaggcagag caagattgtg tggagccttg ccactgactc ctttatggca tgataaggat 1500
ttgtatactc cagtaagagt agtcagagct gccagagctg ctgctctgta cactaccaga 1560
gatctattgt taccaccatt gtaa 1584

SEQ ID NO: 36
MPDAHDAPPP QIRQRTLVDE ATQLLTESAE DAWGEVSVSE YETARLVAHA TWLGGHATRV 60
AFLLERQHED GSWGPPGGYR LVPTLSAVHA LLTCLASPAQ DHGVPHDRLL RAVDAGLTAL 120
RRLGTSDSPP DTIAVELVIP SLLEGIQHLL DPAHPHSRPA FSQHRGSLVC PGGLDGRTLG 180
ALRSHAAAGT PVPGKVWHAS ETLGLSTEAA SHLQPAQGII GGSAAATATW LTRVAPSQQS 240
DSARRYLEEL QHRYSGPVPS ITPITYFERA WLLNNFAAAG VPCEAPAALL DSLEAALTPQ 300
GAPAGAGLPP DADDTAAVLL ALATHGRGRR PEVLMDYRTD GYFQCFIGER TPSISTNAHV 360
LETLGHHVAQ HPQDRARYGS AMDTASAWLL AAQKQDGSWL DKWHASPYYA TVCCTQALAA 420
HASPATAPAR QRAVRWVLAT QRSDGGWGLW HSTVEETAYA LQILAPPSGG GNIPVQQALT 480
RGRARLCGAL PLTPLWHDKD LYTPVRVVRA ARAAALYTTR DLLLPPL 527

SEQ ID NO: 37
atgaacgccc tatccgaaca cattttgtct gaattgagaa gattattgtc tgaaatgagt 60
gatggcggat ctgttggtcc atctgtgtat gatacggccc aggccctaag attccacggt 120
aacgtaacag gtagacaaga tgcatatgct tggttgatcg cccagcaaca agcagatgga 180
ggttggggct ctgccgactt tccactcttt agacatgctc caacatgggc tgcacttctc 240
gcattacaaa gagctgatcc acttcctggc gcagcagacg cagttcagac cgcaacaaga 300
ttcttgcaaa gacaaccaga tccatacgct catgccgttc ctgaggatgc ccctattggt 360
gctgaactga tcttgcctca gttttgtgga gaggctgctt ggttgttggg aggtgtggcc 420
ttccctagac acccagccct attaccatta agacaggctt gtttagtcaa actgggtgca 480
gtcgccatgt tgccttcagg acacccattg ctccactcct gggaggcatg gggtacttct 540
ccaacaacag cctgtccaga cgatgatggt tctataggta tctcaccagc agctacagcc 600
gcctggagag cccaggctgt gaccagaggc tcaactcctc aagtgggcag agctgacgca 660
tacttacaaa tggcttcaag agcaacgaga tcaggcatag aaggagtctt ccctaatgtt 720
tggcctataa acgtattcga accatgctgg tcactgtaca ctctccatct tgccggtctg 780
ttcgcccatc cagcactggc tgaggctgta agagttatcg ttgctcaact tgaagcaaga 840
ttgggagtgc atggcctcgg accagcttta cattttgctg ccgacgctga tgatactgca 900
gttgccttat gcgttctgca tttggctggc agagatcctg cagttgacgc attgagacat 960
tttgaaattg gtgagctctt tgttacattc ccaggagaga gaaatgctag tgtctctacg 1020
aacattcacg ctcttcatgc tttgagattg ttaggtaaac cagctgccgg agcaagtgca 1080
tacgtcgaag caaatagaaa tccacatggt ttgtgggaca acgaaaaatg gcacgtttca 1140
tggctttatc caactgcaca cgccgttgca gctctagctc aaggcaagcc tcaatggaga 1200
gatgaaagag cactagccgc tctactacaa gctcaaagag atgatggtgg ttggggagct 1260
ggtagaggat ccactttcga ggaaaccgcc tacgctcttt tcgctttaca cgttatggac 1320
ggatctgagg aagccacagg cagaagaaga atcgctcaag tcgtcgcaag agccttagaa 1380
tggatgctag ctagacatgc cgcacatgga ttaccacaaa caccactctg gattggtaag 1440
gaattgtact gtcctactag agtcgtaaga gtagctgagc tagctggcct gtggttagca 1500
ttaagatggg gtagaagagt attagctgaa ggtgctggtg ctgcacctta a 1551

SEQ ID NO: 38
MNALSEHILS ELRRLLSEMS DGGSVGPSVY DTAQALRFHG NVTGRQDAYA WLIAQQQADG 60
GWGSADFPLF RHAPTWAALL ALQRADPLPG AADAVQTATR FLQRQPDPYA HAVPEDAPIG 120
AELILPQFCG EAAWLLGGVA FPRHPALLPL RQACLVKLGA VAMLPSGHPL LHSWEAWGTS 180
PTTACPDDDG SIGISPAATA AWRAQAVTRG STPQVGRADA YLQMASRATR SGIEGVFPNV 240
WPINVFEPCW SLYTLHLAGL FAHPALAEAV RVIVAQLEAR LGVHGLGPAL HFAADADDTA 300
VALCVLHLAG RDPAVDALRH FEIGELFVTF PGERNASVST NIHALHALRL LGKPAAGASA 360
YVEANRNPHG LWDNEKWHVS WLYPTAHAVA ALAQGKPQWR DERALAALLQ AQRDDGGWGA 420
GRGSTFEETA YALFALHVMD GSEEATGRRR IAQVVARALE WMLARHAAHG LPQTPLWIGK 480
ELYCPTRVVR VAELAGLWLA LRWGRRVLAE GAGAAP 516

SEQ ID NO: 39
*Z. mays*
atggttttgt cttcttcttg tactacagta ccacacttat cttcattagc tgtcgtgcaa 60
cttggtcctt ggagcagtag gattaaaaag aaaaccgata ctgttgcagt accagccgct 120

TABLE 11-continued

Sequences disclosed herein.

```
gcaggaaggt ggagaagggc cttggctaga gcacagcaca catcagaatc cgcagctgtc   180
gcaaagggca gcagtttgac ccctatagtg agaactgacg ctgagtcaag gagaacaaga   240
tggccaaccg atgacgatga cgccgaacct ttagtggatg agatcagggc aatgcttact   300
tccatgtctg atggtgacat ttccgtgagc gcatacgata cagcctgggt cggattggtt   360
ccaagattag acggcggtga aggtcctcaa tttccagcag ctgtgagatg gataagaaat   420
aaccagttgc ctgacggaag ttggggcgat gccgcattat tctctgccta tgacaggctt   480
atcaataccc ttgcctgcgt tgtaactttg acaaggtggt ccctagaacc agagatgaga   540
ggtagaggac tatctttttt gggtaggaac atgtggaaat tagcaactga agatgaagag   600
tcaatgccta ttggcttcga attagcattt ccatctttga tagagcttgc taagagccta   660
ggtgtccatg acttccctta tgatcaccag gccctacaag gaatctactc ttcaagagag   720
atcaaaatga agaggattcc aaaagaagtg atgcataccg ttccaacatc aatattgcac   780
agtttggagg gtatgcctgg cctagattgg gctaaactac ttaaactaca gagcagcgac   840
ggaagttttt tgttctcacc agctgccact gcatatgctt taatgaatac cggagatgac   900
aggtgtttta gctacatcga tagaacagta aagaaattca acggcggcgt ccctaatgtt   960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                   2490
```

SEQ ID NO: 40

*Z. mays*

```
MVLSSSCTTV PHLSSLAVVQ LGPWSSRIKK KTDTVAVPAA AGRWRRALAR AQHTSESAAV    60
AKGSSLTPIV RTDAESRRTR WPTDDDDAEP LVDEIRAMLT SMSDGDISVS AYDTAWVGLV   120
PRLDGGEGPQ FPAAVRWIRN NQLPDGSWGD AALFSAYDRL INTLACVVTL TRWSLEPEMR   180
GRGLSFLGRN MWKLATEDEE SMPIGFELAF PSLIELAKSL GVHDFPYDHQ ALQGIYSSRE   240
IKMKRIPKEV MHTVPTSILH SLEGMPGLDW AKLLKLQSSD GSFLFSPAAT AYALMNTGDD   300
RCFSYIDRTV KKFNGGVPNV YPVDLFEHIW AVDRLERLGI SRYFQKEIEQ CMDYVNRHWT   360
EDGICWARNS DVKEVDDTAM AFRLLRLHGY SVSPDVFKNF EKDGEFFAFV GQSNQAVTGM   420
YNLNRASQIS FPGEDVLHRA GAFSYEFLRR KEAEGALRDK WIISKDLPGE VVYTLDFPWY   480
GNLPRVEARD YLEQYGGGDD VWIGKTLYRM PLVNNDVYLE LARMDFNHCQ ALHQLEWQGL   540
KRWYTENRLM DFGVAQEDAL RAYFLAAASV YEPCRAAERL AWARAAILAN AVSTHLRNSP   600
SFRERLEHSL RCRPSEETDG SWFNSSSGSD AVLVKAVLRL TDSLAREAQP IHGGDPEDII   660
HKLLRSAWAE WVREKADAAD SVCNGSSAVE QEGSRMVHDK QTCLLLARMI EISAGRAAGE   720
AASEDGDRRI IQLTGSICDS LKQKMLVSQD PEKNEEMMSH VDDELKLRIR EFVQYLLRLG   780
EKKTGSSETR QTFLSIVKSC YYAAHCPPHV VDRHISRVIF EPVSAAK                 827
```

SEQ ID NO: 41

```
cttcttcact aaatacttag acagagaaaa cagagctttt taaagccatg tctcttcagt    60
atcatgttct aaactccatt ccaagtacaa cctttctcag ttctactaaa acaacaatat   120
cttcttcttt ccttaccatc tcaggatctc ctctcaatgt cgctagagac aaatccagaa   180
gcggttccat acattgttca aagcttcgaa ctcaagaata cattaattct caagaggttc   240
aacatgattt gcctctaata catgagtggc aacagcttca aggagaagat gctcctcaga   300
ttagtgttgg aagtaatagt aatgcattca aagaagcagt gaagagtgtg aaaacgatct   360
tgagaaacct aacggacggg gaaattacga tatcggctta cgatacagct tgggttgcat   420
tgatcgatgc cggagataaa actccggcgt ttccctccgc cgtgaaatgg atcgccgaga   480
accaactttc cgatggttct tggggagatg cgtatctctt ctcttatcat gatcgtctca   540
tcaataccct tgcatgcgtc gttgctctaa gatcatggaa tctctttcct catcaatgca   600
acaaaggaat cacgtttttc cgggaaaata ttgggaagct agaagacgaa aatgatgagc   660
atatgccaat cggattcgaa gtagcattcc catcgttgct tgagatagct cgaggaataa   720
acattgatgt accgtacgat tctccggtct taaaagatat atacgccaag aaagagctaa   780
agcttacaag gataccaaaa gagataatgc acaagatacc aacaacattg ttgcatagtt   840
tggaggggat gcgtgattta gattgggaaa agctcttgaa acttcaatct caagacggat   900
ctttcctctt ctctccttcc tctaccgctt ttgcattcat gcagacccga gacagtaact   960
gcctcgagta tttgcgaaat gccgtcaaac gtttcaatgg aggagttccc aatgtctttc  1020
ccgtggatct tttcgagcac atatggatag tggatcggtt acaacgttta gggatatcga  1080
gatactttga agaagagatt aaagagtgtc ttgactatgt ccacagatat tggaccgaca  1140
```

TABLE 11-continued

| Sequences disclosed herein. |
|---|
| atggcatatg ttgggctaga tgttcccatg tccaagacat cgatgataca gccatggcat 1200<br>ttaggctctt aagacaacat ggataccaag tgtccgcaga tgtattcaag aactttgaga 1260<br>aagagggaga gtttttctgc tttgtggggc aatcaaacca agcagtaacc ggtatgttca 1320<br>acctataccg ggcatcacaa ttggcgtttc caagggaaga gatattgaaa aacgccaaag 1380<br>agttttctta taattatctg ctagaaaaac gggagagaga ggagttgatt gataagtgga 1440<br>ttataatgaa agacttacct ggcgagattg ggtttgcgtt agagattcca tggtacgcaa 1500<br>gcttgcctcg agtagagacg agattctata ttgatcaata tggtggagaa aacgacgttt 1560<br>ggattggcaa gactctttat aggatgccat acgtgaacaa taatggatat ctggaattag 1620<br>caaaacaaga ttacaacaat tgccaagctc agcatcagct cgaatgggac atattccaaa 1680<br>agtggtatga agaaaatagg ttaagtgagt ggggtgtgcg cagaagtgag cttctcgagt 1740<br>gttactactt agcggctgca actatatttg aatcagaaag gtcacatgag agaatggttt 1800<br>gggctaagtc aagtgtattg gttaaagcca tttcttcttc ttttggggaa tcctctgact 1860<br>ccagaagaag cttctccgat cagtttcatg aatacattgc caatgctcga cgaagtgatc 1920<br>atcactttaa tgacaggaac atgagattgg accgaccagg atcggttcag gccagtcggc 1980<br>ttgccggagt gttaatcggg actttgaatc aaatgtcttt tgaccttttc atgtctcatg 2040<br>gccgtgacgt taacaatctc ctctatctat cgtggggaga ttggatggaa aaatggaaac 2100<br>tatatggaga tgaaggagaa ggagagctca tggtgaagat gataattcta atgaagaaca 2160<br>atgacctaac taacttcttc acccacactc acttcgttcg tctcgcggaa atcatcaatc 2220<br>gaatctgtct tcctcgccaa tacttaaagg caaggagaaa cgatgagaag gagaagacaa 2280<br>taaagagtat ggagaaggag atggggaaaa tggttgagtt agcattgtcg gagagtgaca 2340<br>catttcgtga cgtcagcatc acgtttcttg atgtagcaaa agcattttac tactttgctt 2400<br>tatgtggcga tcatctccaa actcacatct ccaaagtctt gtttcaaaaa gtctagtaac 2460<br>ctcatcatca tcatcgatcc attaacaatc agtggatcga tgtatccata gatgcgtgaa 2520<br>taatatttca tgtagagaag gagaacaaat tagatcatgt agggttatca 2570<br><br>SEQ ID NO: 42<br>MSLQYHVLNS IPSTTFLSST KTTISSSFLT ISGSPLNVAR DKSRSGSIHC SKLRTQEYIN 60<br>SQEVQHDLPL IHEWQQLQGE DAPQISVGSN SNAFKEAVKS VKTILRNLTD GEITISAYDT 120<br>AWVALIDAGD KTPAFPSAVK WIAENQLSDG SWGDAYLFSY HDRLINTLAC VVALRSWNLF 180<br>PHQCNKGITF FRENIGKLED ENDEHMPIGF EVAFPSLLEI ARGINIDVPY DSPVLKDIYA 240<br>KKELKLTRIP KEIMHKIPTT LLHSLEGMRD LDWEKLLKLQ SQDGSFLFSP SSTAFAFMQT 300<br>RDSNCLEYLR NAVKRFNGGV PNVFPVDLFE HIWIVDRLQR LGISRYFEEE IKECLDYVHR 360<br>YWTDNGICWA RCSHVQDIDD TAMAFRLLRQ HGYQVSADVF KNFEKEGEFF CFVGQSNQAV 420<br>TGMFNLYRAS QLAFPREEIL KNAKEFSYNY LLEKREREEL IDKWIIMKDL PGEIGFALEI 480<br>PWYASLPRVE TRFYIDQYGG ENDVWIGKTL YRMPYVNNNG YLELAKQDYN NCQAQHQLEW 540<br>DIFQKWYEEN RLSEWGVRRS ELLECYYLAA ATIFESERSH ERMVWAKSSV LVKAISSSFG 600<br>ESSDSRRSFS DQFHEYIANA RRSDHHFNDR NMRLDRPGSV QASRLAGVLI GTLNQMSFDL 660<br>FMSHGRDVNN LLYLSWGDWM EKWKLYGDEG EGELMVKMII LMKNNDLTNF FTHTHEVRLA 720<br>EIINRICLPR QYLKARRNDE KEKTIKSMEK EMGKMVELAL SESDTFRDVS ITFLDVAKAF 780<br>YYFALCGDHL QTHISKVLFQ KV 802<br><br>SEQ ID NO: 43<br>atgaatttga gtttgtgtat agcatctcca ctattgacca aatctaatag accagctgct 60<br>ttatcagcaa ttcatacagc tagtacatcc catggtggcc aaaccaaccc tacgaatctg 120<br>ataatcgata cgaccaagga gagaatacaa aaacaattca aaaatgttga aatttcagtt 180<br>tcttcttatg atactgcgtg ggttgccatg gttccatcac ctaattctcc aaagtctcca 240<br>tgtttcccag aatgtttgaa ttggctgatt aacaaccagt tgaatgatgg atcttggggt 300<br>ttagtcaatc acacgcacaa tcacaaccat ccacttttga aagattcttt atcctcaact 360<br>ttggcttgca tcgtggccct aaagagatgg aacgtaggtg aggatcagat taacaagggg 420<br>cttagtttca ttgaatctaa cttggcttcc gcgactgaaa aatctcaacc atctccaata 480<br>ggattcgata tcatctttcc aggtctgtta gagtacgcca aaaatctaga tatcaactta 540<br>ctgtctaagc aaactgattt ctcactaatg ttacacaaga gagaattaga acaaaagaga 600<br>tgtcattcaa acgaaatgga tggttaccta gcttatatct ctgaaggtct tggtaatctt 660<br>tacgattgga atatggtgaa aaagtaccag atgaaaaatg gctcagtttt caattcccct 720<br>tctgcaactg cggcagcatt cattaaccat caaaatccag gatgcctgaa ctatttgaat 780<br>tcactactag acaaattcgg caacgcagtt ccaactgtat accctcacga tttgtttatc 840<br>agattgagta tggtggatac aattgaaaga cttggtatat ccccaccactt tagagtcgag 900<br>atcaaaaatg ttttggatga gacataccgt tgttgggtgg agagagatga acaaatcttt 960<br>atggatgttg tgacgtgcgc gttggccttt agattgttgc gtattaacgg ttacgaagtt 1020<br>agtccagatc cacttgccga aattacaaac gaattagctt taaaggatga atacgccgct 1080<br>cttgaaacat atcatgcgtc acatatcctt taccaagagg acttatcatc tggaaaacaa 1140<br>attcttaaat ctgctgattt cctgaaggaa atcatatcca ctgatagtaa tagactgtcc 1200<br>aaactgatcc ataaagaggt tgaaaatgca cttaagttcc ctattaacac cggcttagaa 1260<br>cgtattaaca caagacgtaa catccagctt tacaacgtag acaatactag aatcttgaaa 1320<br>accacttacc attcttccaa catatcaaac actgattacc taagattagc tgttgaagat 1380<br>ttctacacat gtcagtctat ctatagagaa gagctgaaag gattagagag atgggtcgtt 1440<br>gagaataagc tagatcaatt gaaatttgcc agacaaaaga cagcttattg ttacttctca 1500<br>gttgccgcca ctttatcaag tccagaattg tcagatgcac gtatttcttg ggctaaaaac 1560<br>ggaattttga caactgttgt tgatgatttc tttgatattg gcgggacaat cgacgaattg 1620<br>acaaacctga ttcaatgcgt tgaaaagtgg aatgtcgatg tcgataaaga ctgttgctca 1680<br>gaacatgtta gaatactgtt cttggctctg aaagatgcta tctgttggat cggggatgag 1740<br>gctttcaaat ggcaagctag agatgtgacg tctcacgtca ttcaaacctg gctagaactg 1800<br>atgaactcta tgttgagaga agcaatttgg actagagatg catacgttcc tacattaaac 1860<br>gagtatatgg aaaacgctta tgtctccttt gctttgggtc ctatcgttaa gcctgccata 1920<br>tactttgtag gaccaaagct atccgaggaa atcgtcgaat catcagaata ccataacttg 1980<br>ttcaagttaa tgtccacaca aggcagatta cttaatgata ttcattcttt caaaagagag 2040<br>tttaaggaag gaaagttaaa tgctgttgct ctgcatcttt ctaatggcga aagtggtaaa 2100<br>gtcgaagagg aagtagttga ggaaatgatg atgatgatca aaaacaagag aaaggagttg 2160 |

TABLE 11-continued

Sequences disclosed herein.

```
atgaaactaa tcttcgaaga gaacggttca attgttccta gagcatgtaa ggatgcattt  2220
tggaacatgt gtcatgtgct aaactttttc tacgcaaacg acgatggttt tactgggaac  2280
acaatactag atacagtaaa agacatcata tacaacccttt tggtcttagt aaacgaaaac  2340
gaggagcaaa gataa                                                 2355

SEQ ID NO: 44
MNLSLCIASP LLTKSNRPAA LSAIHTASTS HGGQTNPTNL IIDTTKERIQ KQFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATEKSQPSPI GFDIIFPGLL EYAKNLDINL   180
LSKQTDFSLM LHKRELEQKR CHSNEMDGYL AYISEGLGNL YDWNMVKKYQ MKNGSVFNSP   240
SATAAAFINH QNPGCLNYLN SLLDKFGNAV PTVYPHDLFI RLSMVDTIER LGISHHFRVE   300
IKNVLDETYR CWVERDEQIF MDVVTCALAF RLLRINGYEV SPDPLAEITN ELALKDEYAA   360
LETYHASHIL YQEDLSSGKQ ILKSADFLKE IISTDSNRLS KLIHKEVENA LKFPINTGLE   420
RINTRRNIQL YNVDNTRILK TTYHSSNISN TDYLRLAVED FYTCQSIYRE ELKGLERWVV   480
ENKLDQLKFA RQKTAYCYFS VAATLSSPEL SDARISWAKN GILTTVVDDF FDIGGTIDEL   540
TNLIQCVEKW NVDVDKDCCS EHVRILFLAL KDAICWIGDE AFKWQARDVT SHVIQTWLEL   600
MNSMLREAIW TRDAYVPTLN EYMENAYVSF ALGPIVKPAI YFVGPKLSEE IVESSEYHNL   660
FKLMSTQGRL LNDIHSFKRE FKEGKLNAVA LHLSNGESGK VEEEVVEEMM MMIKNKRKEL   720
MKLIFEENGS IVPRACKDAF WNMCHVLNFF YANDDGFTGN TILDTVKDII YNPLVLVNEN   780
EEQR                                                              784

SEQ ID NO: 45
atgaatctgt ccctttgtat agctagtcca ctgttgacaa aatcttctag accaactgct    60
ctttctgcaa ttcatactgc cagtactagt catggaggtc aaacaaaccc aacaaatttg   120
ataatcgata ctactaagga gagaatccaa aagctattca aaaatgttga aatctcagta   180
tcatcttatg acaccgcatg ggttgcaatg gtgccatcac ctaattcccc aaaaagtcca   240
tgttttccag agtgcttgaa ttggttaatc aataatcagt taaacgatgg ttcttggggt   300
ttagtcaacc acactcataa ccacaatcat ccattattga aggactcttt atcatcaaca   360
ttagcctgta ttgttgcatt gaaaagatgg aatgtaggtg aagatcaaat caacaagggt   420
ttatcattca tagaatccaa tctagcttct gctaccgaca aatcacaacc atctccaatc   480
gggttcgaca taatcttccc tggtttgctg gagtatgcca aaaaccttga tatcaactta   540
ctgtctaaac aaacagattt ctctttgatg ctacacaaaa gagagttaga gcagaaaaga   600
tgccattcta acgaaattga cgggtactta gcatatatct cagaaggttt gggtaatttg   660
tatgactgga acatggtcaa aaagtatcag atgaaaaatg gatccgtatt caattctcct   720
tctgcaactg ccgcagcatt cattaatcat caaaaccctg ggtgtcttaa ctacttgaac   780
tcactattag ataagtttgg aaatgcagtt ccaacagtct atcctttgga cttgtacatc   840
agattatcta tggttgacac tatagagaga ttaggtattt ctcatcattt cagagttgag   900
atcaaaaatg ttttggacga gacatacaga tgttgggtcg aaagagatga gcaaatcttt   960
atggatgtcg tgacctgcgc tctggctttt agattgctaa ggatacacgg atacaaagta  1020
tctcctgatc aactggctga gattacaaac gaactggctt tcaaagacga atacgccgca  1080
ttagaaacat accatgcatc ccaaatactt taccaggaag acctaagttc aggaaaacaa  1140
atcttgaagt ctgcagattt cctgaaaggc attctgtcta cagatagtaa taggttgtct  1200
aaattgatac acaaggaagt agaaaacgca ctaaagtttc ctattaacac tggtttagag  1260
agaatcaata ctaggagaaa cattcagctg tacaacgtag ataatacaag gattcttaag  1320
accacctacc atagttcaaa catttccaac acctattact taagattagc tgtcgaagac  1380
ttttacactt gtcaatcaat ctacagagag gagttaaagg gcctagaaag atgggtagtt  1440
caaaacaagt tggatcaact gaagtttgct agacagaaga cagcatactg ttatttctct  1500
gttgctgcta ccctttcatc cccagaattg tctgatgcca gaataagttg ggccaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg gcttgaactg  1800
atgaactcaa tgctaagaga agcaatctgg acaagagatg catacgttcc aacattgaac  1860
gaatacatgg aaaacgctta cgtctcattt gccttgggtc ctattgttaa gccagccata  1920
tactttgttg ggccaaagtt atccgaagag attgttgagt cttccgaata tcataaccta  1980
ttcaagttaa tgtcaacaca aggcagactt ctgaacgata tccactcctt caaaagagaa  2040
ttcaaggaag gtaagctaaa cgctgttgct ttgcacttgt ctaatggtga atctggcaaa  2100
gtggaagagg aagtcgttga ggaaatgatg atgatgatca aaaacaagag aaaggaattg  2160
atgaaattga ttttcgagga aaatggttca atcgtaccta gagcttgtaa agatgctttt  2220
tggaatatgt gccatgttct taacttcttt tacgctaatg atgatggctt cactggaaat  2280
acaatattgg atacagttaa agatatcatc tacaacccac ttgttttggt caatgagaac  2340
gaggaacaaa gataa                                                 2355

SEQ ID NO: 46
MNLSLCIASP LLTKSSRPTA LSAIHTASTS HGGQTNPTNL IIDTTKERIQ KLFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATDKSQPSPI GFDIIFPGLL EYAKNLDINL   180
LSKQTDFSLM LHKRELEQKR CHSNEIDGYL AYISEGLGNL YDWNMVKKYQ MKNGSVFNSP   240
SATAAAFINH QNPGCLNYLN SLLDKFGNAV PTVYPLDLYI RLSMVDTIER LGISHHFRVE   300
IKNVLDETYR CWVERDEQIF MDVVTCALAF RLLRIHGYKV SPDQLAEITN ELAFKDEYAA   360
LETYHASQIL YQEDLSSGKQ ILKSADFLKG ILSTDSNRLS KLIHKEVENA LKFPINTGLE   420
RINTRRNIQL YNVDNTRILK TTYHSSNISN TYYLRLAVED FYTCQSIYRE ELKGLERWVV   480
QNKLDQLKFA RQKTAYCYFS VAATLSSPEL SDARISWAKN GILTTVVDDF FDIGGTIDEL   540
TNLIQCVEKW NVDVDKDCCS EHVRILFLAL KDAICWIGDE AFKWQARDVT SHVIQTWLEL   600
MNSMLREAIW TRDAYVPTLN EYMENAYVSF ALGPIVKPAI YFVGPKLSEE IVESSEYHNL   660
FKLMSTQGRL LNDIHSFKRE FKEGKLNAVA LHLSNGESGK VEEEVVEEMM MMIKNKRKEL   720
MKLIFEENGS IVPRACKDAF WNMCHVLNFF YANDDGFTGN TILDTVKDII YNPLVLVNEN   780
EEQR                                                              784
```

TABLE 11-continued

| Sequences disclosed herein. |
|---|

SEQ ID NO: 47
atggctatgc cagtgaagct aacacctgcg tcattatcct taaaagctgt gtgctgcaga 60
ttctcatccg gtggccatgc tttgagattc gggagtagtc tgccatgttg gagaaggacc 120
cctacccaaa gatctacttc ttcctctact actagaccag ctgccgaagt gtcatcaggt 180
aagagtaaac aacatgatca ggaagctagt gaagcgacta tcagacaaca attacaactt 240
gtggatgtcc tggagaatat gggaatatcc agacattttg ctgcagagat aaagtgcata 300
ctagacagaa cttacagatc ttggttacaa agacacgagg aaatcatgct ggacactatg 360
acatgtgcta tggcttttag aatcctaaga ttgaacggat acaacgtttc atcagatgaa 420
ctataccacg ttgtagaggc atctggtctg cataattctt tgggtgggta tcttaacgat 480
accagaacac tacttgaatt acacaaggct tcaacagtta gtatctctga ggatgaatct 540
atcttagatt caattggctc tagatccaga acattgctta gagaacaatt ggagtctggt 600
ggcgcactga gaaagccttc tttattcaaa gaggttgaac atgcactgga tggacctttt 660
tacaccacac ttgatagact tcatcatagg tggaatattg aaaacttcaa cattattgag 720
caacacatgt tggagactcc atacttatct aaccagcata catcaaggga tatcctagca 780
ttgtcaatta gagatttttc ctcctcacaa ttcacttatc aacaagagct acagcatctg 840
gagagttggg ttaaggaatg tagattagat caactacagt tcgcaagaca gaaattagcg 900
tacttttacc tatcagccgc aggcaccatg ttttctcctg agctttctga tgcgagaaca 960
ttatgggcca aaaacggggt gttgacaact attgttgatg atttctttga tgttgccggt 1020
tctaaagagg aattggaaaa cttagtcatg ctggtcgaaa tgtgggatga acatcacaaa 1080
gttgaattct attctgagca ggtcgaaatc atcttctctt ccatctacga ttctgtcaac 1140
caattgggtg agaaggcctc tttggttcaa gacagatcaa ttacaaaaca ccttgttgaa 1200
atatggttag acttgttaaa gtccatgatg acggaagttg aatggagact gtcaaaatac 1260
gtgcctacag aaaaggaata catgattaat gcctctctta tcttcggcct aggtccaatc 1320
gttttaccag ctttgtattt cgttggtcca aagatttcag aaagtatagt aaaggaccca 1380
gaatatgatg aattgttcaa actaatgtca acatgtggta gattgttgaa tgacgtgcaa 1440
acgttcgaaa gagaatacaa tgagggtaaa ctgaattctg tcagtctatt ggttcttcac 1500
ggaggcccaa tgtctatttc agacgcaaag aggaaattac aaaagcctat tgatacgtgt 1560
agaagagatc ttctttcttt ggtccttaga gaagagtctg tagtaccaag accatgtaag 1620
gaactattct ggaaaatgtg taaagtgtgc tatttctttt actcaacaac tgatgggttt 1680
tctagtcaag tcgaaagagc aaaagaggta gacgctgtca taaatgagcc actgaagttg 1740
caaggttctc atacactggt atctgatgtt taa 1773

SEQ ID NO: 48
MAMPVKLTPA SLSLKAVCCR FSSGGHALRF GSSLPCWRRT PTQRSTSSST TRPAAEVSSG 60
KSKQHDQEAS EATIRQQLQL VDVLENMGIS RHFAAEIKCI LDRTYRSWLQ RHEEIMLDTM 120
TCAMAFRILR LNGYNVSSDE LYHVVEASGL HNSLGGYLND TRTLLELHKA STVSISEDES 180
ILDSIGSRSR TLLREQLESG GALRKPSLFK EVEHALDGPF YTTLDRLHHR WNIENFNIIE 240
QHMLETPYLS NQHTSRDILA LSIRDFSSSQ FTYQQELQHL ESWVKECRLD QLQFARQKLA 300
YFYLSAAGTM FSPELSDART LWAKNGVLTT IVDDFFDVAG SKEELENLVM LVEMWDEHHK 360
VEFYSEQVEI IFSSIYDSVN QLGEKASLVQ DRSITKHLVE IWLDLLKSMM TEVEWRLSKY 420
VPTEKEYMIN ASLIFGLGPI VLPALYFVGP KISESIVKDP EYDELFKLMS TCGRLLNDVQ 480
TFEREYNEGK LNSVSLLVLH GGPMSISDAK RKLQKPIDTC RRDLLSLVLR EESVVPRPCK 540
ELFWKMCKVC YFFYSTTDGF SSQVERAKEV DAVINEPLKL QGSHTLVSDV 590

SEQ ID NO: 49
atgcagaact tccatggtac aaaggaaagg atcaaaaaga tgtttgacaa gattgaattg 60
tccgtttctt cttatgatac agcctgggtt gcaatggtcc catcccctga ttgcccagaa 120
acaccttgtt ttccagaatg tactaaatgg atcctagaaa atcagttggg tgatggtagt 180
tggtcacttc ctcatggcaa tccacttcta gttaaagatg cattatcttc cactcttgct 240
tgtattctgg ctcttaaaag atggggaatc ggtgaggaac agattaacaa aggactgaga 300
ttcatagaac tcaactctgc tagtgtaacc gataacgaac aacacaaacc aattggattt 360
gacattatct ttccaggtat gattgaatac gctatagact tagacctgaa tctaccacta 420
aaaccaactg acattaactc catgttgcat cgtagagccc ttgaattgac atcaggtgga 480
ggcaaaaatc tagaaggtag aagagcttac ttggcctacg tctctgaagg aatcggtaag 540
ctgcaagatt gggaaatggc tatgaaatac caacgtaaaa acggatctct gttcaatagt 600
ccatcaacaa ctgcagctgc attcatccat atacaagatg ctgaatgcct ccactatatt 660
cgttctcttc tccagaaatt tggaaacgca gtccctacaa tataccctct cgatatctat 720
gccagacttt caatggtaga tgccctggaa cgtcttggta ttgatagaca tttcagaaag 780
gagagaaagt tcgttctgga tgaaacatac agattttggt tgcaaggaga agaggagatt 840
ttctccgata acgcaacctg tgctttggcc ttcagaatat tgagacttaa tggttacgat 900
gtctctcttg aagatcactt ctctaactct ctgggcggtt acttaaagga ctcaggagca 960
gctttagaac tgtacagagc cctccaattg tcttacccag acgagtccct cctggaaaag 1020
caaaattcta gaacttctta cttcttaaaa caaggtttat ccaatgtctc cctctgtggt 1080
gacagattgc gtaaaaacat aattggagag gtgcatgatg ctttaaactt ttccgaccac 1140
gctaacttac aaagattagc tattcgtaga aggattaagc attacgctac tgacgataca 1200
aggattctaa aaacttccta cagatgctca acaatcggta accaagattt tctaaaactt 1260
gcagtggaag atttcaatat ctgtcaatca atacaaagag aggaattcaa gcatattgaa 1320
agatgggtcg ttgaaagacg tctagacaag ttaaagttcg ctagacaaaa agaggcctat 1380
tgctatttct cagccgcagc aacattgttt gcccctgaat tgtctgatgc tagaatgtct 1440
tgggccaaaa atggtgtatt gacaactgtg gttgatgatt tcttcgatgt cggaggctct 1500
gaagaggaat tagttaactt gatagaattg atcgagcgtt gggatgtgaa tggcagtgca 1560
gatttttgta gtgaggaagt tgagattatc tattctgcta tccactcaac tatctctgaa 1620
ataggtgata agtcatttgg ctggcaaggt agagatgtaa agtctcaagt tatcaagatc 1680
tggctggact tattgaaatc aatgttaact gaagctcaat ggtcttcaaa caagtctgtt 1740
cctaccctag atgagtatat gacaaccgcc catgtttcat tcgcacttgg tccaattgta 1800
cttccagcct tatacttcgt tggcccaaag ttgtcagaag aggttgcagg tcatcctgaa 1860
ctactaaacc tctacaaagt cacatctact tgtggcagac tactgaatga ttggagaagt 1920

TABLE 11-continued

| Sequences disclosed herein. |
|---|
| tttaagagag aatccgagga aggtaagctc aacgctatta gtttatacat gatccactcc 1980<br>ggtggtgctt ctacagaaga ggaaacaatc gaacatttca aaggtttgat tgattctcag 2040<br>agaaggcaac tgttacaatt ggtgttgcaa gagaaggata gtatcatacc tagaccatgt 2100<br>aaagatctat tttggaatat gattaagtta ttacacactt tctacatgaa agatgatggc 2160<br>ttcacctcaa atgagatgag gaatgtagtt aaggcaatca ttaacgaacc aatctcactg 2220<br>gatgaattat ga 2232 |
| SEQ ID NO: 50<br>MSCIRPWFCP SSISATLTDP ASKLVTGEFK TTSLNFHGTK ERIKKMFDKI ELSVSSYDTA 60<br>WVAMVPSPDC PETPCFPECT KWILENQLGD GSWSLPHGNP LLVKDALSST LACILALKRW 120<br>GIGEEQINKG LRFIELNSAS VTDNEQHKPI GFDIIFPGMI EYAKDLDLNL PLKPTDINSM 180<br>LHRRALELTS GGGKNLEGRR AYLAYVSEGI GKLQDWEMAM KYQRKNGSLF NSPSTTAAAF 240<br>IHIQDAECLH YIRSLLQKFG NAVPTIYPLD IYARLSMVDA LERLGIDRHF RKERKFVLDE 300<br>TYRFWLQGEE EIFSDNATCA LAFRILRLNG YDVSLEDHFS NSLGGYLKDS GAALELYRAL 360<br>QLSYPDESLL EKQNSRTSYF LKQGLSNVSL CGDRLRKNII GEVHDALNFP DHANLQRLAI 420<br>RRRIKHYATD DTRILKTSYR CSTIGNQDFL KLAVEDFNIC QSIQREEFKH IERWVVERRL 480<br>DKLKFARQKE AYCYFSAAAT LFAPELSDAR MSWAKNGVLT TVVDDFFDVG GSEEELVNLI 540<br>ELIERWDVNG SADFCSEEVE IIYSAIHSTI SEIGDKSFGW QGRDVKSHVI KIWLDLLKSM 600<br>LTEAQWSSNK SVPTLDEYMT TAHVSFALGP IVLPALYFVG PKLSEEVAGH PELLNLYKVM 660<br>STCGRLLNDW RSFKRESEEG KLNAISLYMI HSGGASTEEE TIEHFKGLID SQRRQLLQLV 720<br>LQEKDSIIPR PCKDLFWNMI KLLHTFYMKD DGFTSNEMRN VVKAIINEPI SLDEL 775 |
| SEQ ID NO: 51<br><br>*A. thaliana*<br>atgtctatca accttcgctc ctccggttgt tcgtctccga tctcagctac tttggaacga 60<br>ggattggact cagaagtaca gacaagagct aacaatgtga gctttgagca aacaaaggag 120<br>aagattagga agatgttgga gaaagtggag ctttctgttt cggcctacga tactagttgg 180<br>gtagcaatgg ttccatcacc gagctcccaa aatgctccac ttttcccaca gtgtgtgaaa 240<br>tggttattgg ataatcaaca tgaagatgga tcttggggac ttgataacca tgaccatcaa 300<br>tctcttaaga aggatgtgtt atcatctaca ctggctagta tcctcgcgtt aaagaagtgg 360<br>ggaattggtg aaagacaaat aaacaagggt ctccagttta ttgagctgaa ttctgcatta 420<br>gtcactgatg aaaccataca gaaaccaaca gggtttgata ttatatttcc tgggatgatt 480<br>aaatatgcta gagatttgaa tctgacgatt ccattgggct cagaagtggt ggatgacatg 540<br>atacgaaaaa gagatctgga tcttaaatgt gatagtgaaa agttttcaaa gggaagagaa 600<br>gcatatctgg cctatgtttt agaggggaca agaaacctaa aagattggga tttgatagtc 660<br>aaatatcaaa ggaaaaatgg gtcactgttt gattctccag ccacaacagc agctgctttt 720<br>actcagtttg ggaatgatgg ttgtctccgt tatctctgtt ctctccttca gaaattcgag 780<br>gctgcagttc cttcagttta tccatttgat caatatgcac gccttagtat aattgtcact 840<br>cttgaaagct taggaattga tagagatttc aaaaccgaaa tcaaaagcat attggatgaa 900<br>acctatagat attggcttcg tggggatgaa gaaatatgtt tggacttggc cacttgtgct 960<br>ttggctttcc gattattgct tgctcatggc tatgatgtgt cttacgatcc gctaaaacca 1020<br>tttgcagaag aatctggttt ctctgatact ttggaaggat atgttaagaa tacgttttct 1080<br>gtgttagaat tatttaaggc tgctcaaagt tatccacatg aatcagcttt gaagaagcag 1140<br>tgttgttgga ctaaacaata tctggagatg gaattgtcca gctgggttaa gacctctgtt 1200<br>cgagataaat acctcaagaa agaggtcgag gatgctcttg cttttccctc ctatgcaagc 1260<br>ctagaaagat cagatcacag gagaaaaata ctcaatggtt ctgctgtgga aaacaccaga 1320<br>gttacaaaaa cctcatatcg tttgcacaat atttgcacct ctgatatcct gaagttagct 1380<br>gtggatgact tcaatttctg ccagtccata caccgtgaag aaatggaacg tcttgatagg 1440<br>tggattgtgg agaatagatt gcaggaactg aaatttgcca gacagaagct ggcttactgt 1500<br>tatttctctg gggctgcaac tttattttct ccagaactat ctgatgctcg tatatcgtgg 1560<br>gccaaaggtg gagtacttac aacggttgta gacgacttct ttgatgttgg agggtccaaa 1620<br>gaagaactgg aaaacctcat acacttggtc gaaaagtggg atttgaacgg tgttcctgag 1680<br>tacagctcag aacatgttga gatcatattc tcagttctaa gggacaccat tctcgaaaca 1740<br>ggagacaaag cattcaccta tcaaggacgc aatgtgacac accacattgt gaaaatttgg 1800<br>ttggatctgc tcaagtctat gttgagagaa gccgagtggt ccagtgacaa gtcaacacca 1860<br>agcttggagg attacatgga aaatgcgtac atatcatttg cattaggacc aattgtcctc 1920<br>ccagctacct atctgatcgg acctccactt ccagagaaga cagtcgatag ccaccaatat 1980<br>aatcagctct acaagctcgt gagcactatg ggtcgtcttc taaatgacat acaaggtttt 2040<br>aagagagaaa gcgcggaagg gaagctgaat gcggtttcat tgcacatgaa acacgagaga 2100<br>gacaatcgca gcaaagaagt gatcatagaa tcgatgaaag gtttagcaga gagaaagagg 2160<br>gaagaattgc ataagctagt tttggaggag aaaggaagtg tggttccaag ggaatgcaaa 2220<br>gaagcgttct tgaaaatgag caaagtgttg aacttatttt acaggaagga cgatggattc 2280<br>acatcaaatg atctgatgag tcttgttaaa tcagtgatct acgagcctgt tagcttacag 2340<br>aaagaatctt taacttga 2358 |
| SEQ ID NO: 52<br><br>*A. thaliana*<br>MSINLRSSGC SSPISATLER GLDSEVQTRA NNVSFEQTKE KIRKMLEKVE LSVSAYDTSW 60<br>VAMVPSPSSQ NAPLFPQCVK WLLDNQHEDG SWGLDNHDHQ SLKKDVLSST LASILALKKW 120<br>GIGERQINKG LQFIELNSAL VTDETIQKPT GFDIIFPGMI KYARDLNLTI PLGSEVVDDM 180<br>IRKRDLDLKC DSEKFSKGRE AYLAYVLEGT RNLKDWDLIV KYQRKNGSLF DSPATTAAAF 240<br>TQFGNDGCLR YLCSLLQKFE AAVPSVYPFD QYARLSIIVT LESLGIDRDF KTEIKSILDE 300<br>TYRYWLRGDE EICLDLATCA LAFRLLLAHG YDVSYDPLKP FAEESGFSDT LEGYVKNTFS 360<br>VLELFKAAQS YPHESALKKQ CCWTKQYLEM ELSSWVKTSV RDKYLKKEVE DALAFPSYAS 420<br>LERSDHRRKI LNGSAVENTR VTKTSYRLHN ICTSDILKLA VDDFNFCQSI HREEMERLDR 480<br>WIVENRLQEL KFARQKLAYC YFSGAATLFS PELSDARISW AKGGVLTTVV DDFFDVGGSK 540<br>EELENLIHLV EKWDLNGVPE YSSEHVEIIF SVLRDTILET GDKAFTYQGR NVTHHIVKIW 600<br>LDLLKSMLRE AEWSSDKSTP SLEDYMENAY ISFALGPIVL PATYLIGPPL PEKTVDSHQY 660 |

TABLE 11-continued

| Sequences disclosed herein. |
|---|

```
NQLYKLVSTM GRLLNDIQGF KRESAEGKLN AVSLHMKHER DNRSKEVIIE SMKGLAERKR   720
EELHKLVLEE KGSVVPRECK EAFLKMSKVL NLFYRKDDGF TSNDLMSLVK SVIYEPVSLQ   780
KESLT                                                              785

SEQ ID NO: 53
atggaatttg atgaaccatt ggttgacgaa gcaagatctt tagtgcagcg tactttacaa    60
gattatgatg acagatacgg cttcggtact atgtcatgtg ctgcttatga tacagcctgg   120
gtgtctttag ttacaaaaac agtcgatggg agaaaacaat ggcttttccc agagtgtttt   180
gaatttctac tagaaacaca atctgatgcc ggaggatggg aaatcgggaa ttcagcacca   240
atcgacggta tattgaatac agctgcatcc ttacttgctc taaaacgtca cgttcaaact   300
gagcaaatca tccaacctca acatgaccat aaggatctag caggtagagc tgaacgtgcc   360
gctgcatctt tgagagcaca attggctgca ttggatgtgt ctacaactga acacgtcggt   420
tttgagataa ttgttcctgc aatgctagac ccattagaag ccgaagatcc atctctagtt   480
ttcgattttc cagctaggaa acctttgatg aagattcatg atgctaagat gagtagattc   540
aggccagaat acttgtatgg caaacaacca atgaccgcct tacattcatt agaggctttc   600
ataggcaaaa tcgacttcga taaggtaaga caccaccgta cccatgggtc tatgatgggt   660
tctccttcat ctaccgcagc ctacttaatg cacgcttcac aatgggatgg tgactcagag   720
gcttacctta gacacgtgat taaacacgca gcagggcagg gaactggtgc tgtaccatct   780
gctttcccat caacacattt tgagtcatct tggattctta ccacattgtt tagagctgga   840
ttttcagctt ctcatcttgc ctgtgatgag ttgaacaagt tggtcgagat acttgagggc   900
tcattcgaga aggaaggtgg ggcaatcggt tacgctccag ggtttcaagc agatgttgat   960
gatactgcta aaacaataag tacattagca gtccttggaa gagatgctac accaagacaa  1020
atgatcaagg tatttgaagc taatacacat tttagaacat accctggtga aagagatcct  1080
tctttgacag ctaattgtaa tgctctatca gccttactac accaaccaga tgcagcaatg  1140
tatggatctc aaattcaaaa gattaccaaa tttgtctgtg actattggtg gaagtctgat  1200
ggtaagatta aagataagtg gaacacttgc tacttgtacc catctgtctt attagttgag  1260
gttttggttg atcttgttag tttattggag cagggtaaat tgcctgatgt tttggatcaa  1320
gagcttcaat acagagtcgc catcacattg ttccaagcat gtttaaggcc attactagac  1380
caagatgccg aaggatcatg gaacaagtct atcgaagcca cagcctacgg catccttatc  1440
ctaactgaag ctaggagagt ttgtttcttc gacagattgt ctgagccatt gaatgaggca  1500
atccgtagag gtatcgcttt cgccgactct atgtctggaa ctgaagctca gttgaactac  1560
atttggatcg aaaaggttag ttacgcacct gcattattga ctaaatccta tttgttagca  1620
gcaagatggg ctgctaagtc tcctttaggc gcttccgtag gctcttcttt gtggactcca  1680
ccaagagaag gattggataa gcatgtcaga ttattccatc aagctgagtt attcagatcc  1740
cttccagaat gggaattaag agcctccatg attgaagcag ctttgttcac accacttcta  1800
agagcacata gactagacgt tttccctaga caagatgtag gtgaagacaa atatcttgat  1860
gtagttccat tcttttggac tgccgctaac aacagagata gaacttacgc ttccactcta  1920
ttcctttacg atatgtgttt tatcgcaatg ttaaacttcc agttagacga attcatggag  1980
gccacagccg gtatcttatt cagagatcat atggatgatt tgaggcaatt gattcatgat  2040
cttttggcag agaaaacttc cccaaagagt tctggtagaa gtagtcaggg cacaaaagat  2100
gctgactcag gtatagagga agacgtgtca atgtccgatt cagcttcaga ttcccaggat  2160
agaagtccag aatacgactt ggttttcagt gcattgagta cctttacaaa acatgtcttg  2220
caacacccat ctatacaaag tgcctctgta tgggatagaa aactacttgc tagagagatg  2280
aaggcttact tacttgctca tatccaacaa gcagaagatt caactccatt gtctgaattg  2340
aaagatgtgc ctcaaaagac tgatgtaaca agagtttcta catctactac taccttcttt  2400
aactgggtta gaacaacttc cgcagaccat atatcctgcc catactcctt ccactttgta  2460
gcatgccatc taggcgcagc attgtcacct aaagggtcta acggtgattg ctatccttca  2520
gctggtgaga agttcttggc agctgcagtc tgcagacatt tggccaccat gtgtagaatg  2580
tacaacgatc ttggatcagc tgaacgtgat tctgatgaag gtaatttgaa ctccttggac  2640
ttccctgaat tcgccgattc cgcaggaaac ggagggatag aaattcagaa ggccgctcta  2700
ttaaggttag ctgagtttga gagagattca tacttagagg ccttccgtcg tttacaagat  2760
gaatccaata gagttcacgg tccagccggt ggtgatgaag ccagattgtc cagaaggaga  2820
atggcaatcc ttgaattctt cgcccagcag gtagatttgt acggtcaagt atacgtcatt  2880
agggatattt ccgctcgtat tcctaaaaac gaggttgaga aaaagagaaa attggatgat  2940
gctttcaatt ga                                                      2952

SEQ ID NO: 54
MEFDEPLVDE ARSLVQRTLQ DYDDRYGFGT MSCAAYDTAW VSLVTKTVDG RKQWLFPECF    60
EFLLETQSDA GGWEIGNSAP IDGILNTAAS LLALKRHVQT EQIIQPQHDH KDLAGRAERA   120
AASLRAQLAA LDVSTTEHVG FEIIVPAMLD PLEAEDPSLV FDFPARKPLM KIHDAKMSRF   180
RPEYLYGKQP MTALHSLEAF IGKIDFDKVR HHRTHGSMMG SPSSTAAYLM HASQWDGDSE   240
AYLRHVIKHA AGQGTGAVPS AFPSTHFESS WILTTLFRAG FSASHLACDE LNKLVEILEG   300
SFEKEGGAIG YAPGFQADVD DTAKTISTLA VLGRDATPRQ MIKVFEANTH FRTYPGERDP   360
SLTANCNALS ALLHQPDAAM YGSQIQKITK FVCDYWWKSD GKIKDKWNTC YLYPSVLLVE   420
VLVDLVSLLE QGKLPDVLDQ ELQYRVAITL FQACLRPLLD QDAEGSWNKS IEATAYGILI   480
LTEARRVCFF DRLSEPLNEA IRRGIAFADS MSGTEAQLNY IWIEKVSYAP ALLTKSYLLA   540
ARWAAKSPLG ASVGSSLWTP PREGLDKHVR LFHQAELFRS LPEWELRASM IEAALFTPLL   600
RAHRLDVFPR QDVGEDKYLD VVPFFWTAAN NRDRTYASTL FLYDMCFIAM LNFQLDEFME   660
ATAGILFRDH MDDLRQLIHD LLAEKTSPKS SGRSSQGTKD ADSGIEEDVS MSDSASDSQD   720
RSPEYDLVFS ALSTFTKHVL QHPSIQSASV WDRKLLAREM KAYLLAHIQQ AEDSTPLSEL   780
KDVPQKTDVT RVSTSTTTFF NWVRTTSADH ISCPYSFHFV ACHLGAALSP KGSNGDCYPS   840
AGEKFLAAAV CRHLATMCRM YNDLGSAERD SDEGNLNSLD FPEFADSAGN GGIEIQKAAL   900
LRLAEFERDS YLEAFRRLQD ESNRVHGPAG GDEARLSRRR MAILEFFAQQ VDLYGQVYVI   960
RDISARIPKN EVEKKRKLDD AFN                                          983

SEQ ID NO: 55
atggcttcta gtacacttat ccaaaacaga tcatgtggcg tcacatcatc tatgtcaagt    60
tttcaaatct tcagaggtca accactaaga tttcctggca ctagaacccc agctgcagtt   120
```

TABLE 11-continued

| Sequences disclosed herein. |
|---|
| caatgcttga aaaagaggag atgccttagg ccaaccgaat ccgtactaga atcatctcct 180<br>ggctctggtt catatagaat agtaactggc ccttctggaa ttaaccctag ttctaacggg 240<br>cacttgcaag agggttcctt gactcacagg ttaccaatac caatggaaaa atctatcgat 300<br>aacttccaat ctactctata tgtgtcagat atttggtctg aaacactaca gagaactgaa 360<br>tgtttgctac aagtaactga aaacgtccag atgaatgagt ggattgagga aattagaatg 420<br>tactttagaa atatgacttt aggtgaaatt tccatgtccc cttacgacac tgcttgggtg 480<br>gctagagttc cagcgttgga cggttctcat gggcctcaat tccacagatc tttgcaatgg 540<br>attatcgaca accaattacc agatggggac tggggcgaac cttctctttt cttgggttac 600<br>gatagagttt gtaatacttt agcctgtgtg attgcgttga aaacatgggg tgttggggca 660<br>caaaacgttg aaagaggaat tcagttccta caatctaaca tatacaagat ggaggaagat 720<br>gacgctaatc atatgccaat aggattcgaa atcgtattcc ctgctatgat ggaagatgcc 780<br>aaagcattag gtttggattt gccatacgat gctactattt tgcaacagat ttcagccgaa 840<br>agagagaaaa agatgaaaaa gatcccaatg gcaatggtgt acaaataccc aaccacttta 900<br>cttcactcct tagaaggctt gcatagagaa gttgattgga ataagttgtt acaattacaa 960<br>tctgaaaatg gtagtttttct ttattcacct gcttcaaccg catgcgcctt aatgtacact 1020<br>aaggacgtta aatgttttga ttacttaaac cagttgttga tcaagttcga ccacgcatgc 1080<br>ccaaatgtat atccagtcga tctattcgaa agattatgga tggttgacag attgcagaga 1140<br>ttagggatct ccagatactt tgaaagagag attagagatt gtttacaata cgtctacaga 1200<br>tattggaaag attgtggaat cggatgggct tctaactctt ccgtacaaga tgttgatgat 1260<br>acagccatgg cgtttagact tttaaggact catggtttcg acgtaaagga agattgcttt 1320<br>agacagtttt tcaaggacgg agaattcttc tgcttcgcag gccaatcatc tcaagcagtt 1380<br>acaggcatgt ttaatctttc aagagccagt caaacattgt ttccaggaga atctttattg 1440<br>aaaaaggcta gaaccttctc tagaaacttc ttgagaacaa agcatgagaa caacgaatgt 1500<br>ttcgataaat ggatcattac taaagatttg gctggtgaag tcgagtataa cttgaccttc 1560<br>ccatggtatg cctctttgcc tagattagaa catagggacat acttagatca atatggaatc 1620<br>gatgatatct ggataggcaa atctttatac aaaatgcctg ctgttaccaa cgaagttttc 1680<br>ctaaagttgg caaaggcaga ctttaacatg tgtcaagctc tacacaaaaa ggaattggaa 1740<br>caagtgataa agtggaacgc gtcctgtcaa ttcagagatc ttgaattcgc cagacaaaaa 1800<br>tcagtagaat gctattttgc tggtgcagcc acaatgttcg aaccagaaat ggttcaagct 1860<br>agattagtct gggcaagatg ttgtgtattg acaactgtct tagacgatta ctttgaccac 1920<br>gggacacctg ttgaggaact tagagtgttt gttcaagctg tcagaacatg gaatccagag 1980<br>ttgatcaacg gtttgccaga gcaagctaaa atcttgttta tggcttata caaaacagtt 2040<br>aacacaattg cagaggaagc attcatggca cagaaaagag acgtccatca tcatttgaaa 2100<br>cactattggg acaagttgat aacaagtgcc ctaaaggagg ccgaatgggc agagtcaggt 2160<br>tacgtcccaa catttgatga atacatggaa gtagctgaaa tttctgttgc tctagaacca 2220<br>attgtctgta gtaccttgtt ctttgcgggt catagactag atgaggatgt tctagatagt 2280<br>tacgattacc atctagttat gcatttggta aacagagtcg gtagaatctt gaatgatata 2340<br>caaggcatga agagggaggc ttcacaaggt aagatctcat cagttcaaat ctacatggag 2400<br>gaacatccat ctgttccatc tgaggccatg gcgatcgctc atcttcaaga gttagttgat 2460<br>aattcaatgc agcaattgac atacgaagtt cttaggttca ctgcggttcc aaaaagttgt 2520<br>aagagaatcc acttgaatat ggctaaaatc atgcatgcct tctacaagga tactgatgga 2580<br>ttctcatccc ttactgcaat gacaggattc gtcaaaaagg ttcttttcga acctgtgcct 2640<br>gagtaa 2646 |
| SEQ ID NO: 56<br>MASSTLIQNR SCGVTSSMSS FQIFRGQPLR FPGTRTPAAV QCLKKRRCLR PTESVLESSP 60<br>GSGSYRIVTG PSGINPSSNG HLQEGSLTHR LPIPMEKSID NFQSTLYVSD IWSETLQRTE 120<br>CLLQVTENVQ MNEWIEEIRM YFRNMTLGEI SMSPYDTAWV ARVPALDGSH GPQFHRSLQW 180<br>IIDNQLPDGD WGEPSLFLGY DRVCNTLACV IALKTWGVGA QNVERGIQFL QSNIYKMEED 240<br>DANHMPIGFE IVFPAMMEDA KALGLDLPYD ATILQQISAE REKKMKKIPM AMVYKYPTTL 300<br>LHSLEGLHRE VDWNKLLQLQ SENGSFLYSP ASTACALMYT KDVKCFDYLN QLLIKFDHAC 360<br>PNVYPVDLFE RLWMVDRLQR LGISRYFERE IRDCLQYVYR YWKDCGIGWA SNSSVQDVDD 420<br>TAMAFRLLRT HGFDVKEDCF RQFFKDGEFF CFAGQSSQAV TGMFNLSRAS QTLFPGESLL 480<br>KKARTFSRNF LRTKHENNEC FDKWIITKDL AGEVEYNLTF PWYASLPRLE HRTYLDQYGI 540<br>DDIWIGKSLY KMPAVTNEVF LKLAKADFNM CQALHKKELE QVIKWNASCQ FRDLEFARQK 600<br>SVECYFAGAA TMFEPEMVQA RLVWARCCVL TTVLDDYFDH GTPVEELRVF VQAVRTWNPE 660<br>LINGLPEQAK ILFMGLYKTV NTIAEEAFMA QKRDVHHHLK HYWDKLITSA LKEAEWAESG 720<br>YVPTFDEYME VAEISVALEP IVCSTLFFAG HRLDEDVLDS YDYHLVMHLV NRVGRILNDI 780<br>QGMKREASQG KISSVQIYME EHPSVPSEAM AIAHLQELVD NSMQQLTYEV LRFTAVPKSC 840<br>KRIHLNMAKI MHAFYKDTDG FSSLTAMTGF VKKVLFEPVP E 881 |
| SEQ ID NO: 57<br>atgcctggta aaattgaaaa tggtacccca aaggacctca agactggaaa tgattttgtt 60<br>tctgctgcta agagtttact agatcgagct ttcaaaagtc atcattccta ctacggatta 120<br>tgctcaactt catgtcaagt ttatgataca gcttgggttg caatgattcc aaaaacaaga 180<br>gataatgtaa aacagtggtt gtttccagaa tgtttccatt acctcttaaa aacacaagcc 240<br>gcagatggct catggggttc attgcctaca acacagacag cgggtatcct agatacagcc 300<br>tcagctgtgc tggcattatt gtgccacgca caagagcctt tacaaatatt ggatgtatct 360<br>ccagatgaaa tggggttgag aatagaacac ggtgtcacat ccttgaaacg tcaattagca 420<br>gtttggaatg atgtggagga caccaaccat attggcgtcg agtttatcat accagcctta 480<br>ctttccatgc tagaaaagga attagatgtt ccatcttttg aatttccatg taggtccatc 540<br>ttagagagaa tgcacgggga gaaattaggt catttcgacc tggaacaagt ttacggcaag 600<br>ccaagctcat tgttgcactc attggaagca tttctcggta agctagattt tgatcgacta 660<br>tcacatcacc tataccacgg cagtatgatg gcatctccat cttcaacggc tgcttatctt 720<br>attggggcta caaaatggga tgacgaagcc gaagattacc taagacatgt aatgcgtaat 780<br>ggtgcaggac atgggaatgg aggtatttct ggtacatttc caactactca tttcgaatgt 840<br>agctggatta tagcaacgtt gttaaaggtt ggctttactt tgaagcaaat tgacggcgat 900<br>ggcttaagag gtttatcaac catcttactt gaggcgcttc gtgatgagaa tggtgtcata 960 |

TABLE 11-continued

| Sequences disclosed herein. |
|---|

```
ggctttgccc ctagaacagc agatgtagat gacacagcca aagctctatt ggccttgtca 1020
ttggtaaacc agccagtgtc acctgatatc atgattaagg tctttgaggg caaagaccat 1080
tttaccactt ttggttcaga aagagatcca tcattgactt ccaacctgca cgtcctttta 1140
tctttactta aacaatctaa cttgtctcaa taccatcctc aaatcctcaa aacaacatta 1200
ttcacttgta gatggtggtg gggttccgat cattgtgtca aagacaaatg gaatttgagt 1260
cacctatatc caactatgtt gttggttgaa gccttcactg aagtgctcca tctcattgac 1320
ggtggtgaat tgtctagtct gtttgatgaa tcctttaagt gtaagattgg tcttagcatc 1380
tttcaagcgg tacttagaat aatcctcacc caagacaacg acggctcttg gagaggatac 1440
agagaacaga cgtgttacgc aatattggct ttagttcaag cgagacatgt atgctttttc 1500
actcacatgg ttgacagact gcaatcatgt gttgatcgag gtttctcatg gttgaaatct 1560
tgctcttttc attctcaaga cctgacttgg acctctaaaa cagcttatga agtgggtttc 1620
gtagctgaag catataaact agctgcttta caatctgctt ccctggaggt tcctgctgcc 1680
accattggac attctgtcac gtctgccgtt ccatcaagtg atcttgaaaa atacatgaga 1740
ttggtgagaa aaactgcgtt attctctcca ctggatgagt ggggtctaat ggcttctatc 1800
atcgaatctt catttttcgt accattactg caggcacaaa gagttgaaat ataccctaga 1860
gataatatca aggtggacga agataagtac ttgtctatta tcccattcac atgggtcgga 1920
tgcaataata ggtctagaac tttcgcaagt aacagatggc tatacgatat gatgtacctt 1980
tcattactcg gctatcaaac cgacgagtac atggaagctg tagctgggcc agtgtttggg 2040
gatgtttcct tgttacatca aacaattgat aaggtgattg ataatacaat gggtaacctt 2100
gcgagagcca atggaacagt acacagtggt aatggacatc agcacgaatc tcctaatata 2160
ggtcaagtcg aggacacctt gactcgtttc acaaattcag tcttgaatca caaagacgtc 2220
cttaactcta gctcatctga tcaagatact ttgagaagag agtttagaac attcatgcac 2280
gctcatataa cacaaatcga agataactca cgattcagta agcaagcctc atccgatgcg 2340
ttttcctctc ctgaacaatc ttactttcaa tgggtgaact caactggtgg ctcacatgtc 2400
gcttgcgcct attcatttgc cttctctaat tgcctcatgt ctgcaaattt gttgcagggt 2460
aaagacgcat ttccaagcgg aacgcaaaag tacttaatct cctctgttat gagacatgcc 2520
acaaacatgt gtagaatgta taacgacttt ggctctattg ccagagacaa cgctgagaga 2580
aatgttaata gtattcattt tcctgagttt actctctgta acggaacttc tcaaaaccta 2640
gatgaaagga aggaaagact tctgaaaatc gcaacttacg aacaagggta tttggataga 2700
gcactagagg ccttggaaag acagagtaga gatgatgccg gagacagagc tggatctaaa 2760
gatatgagaa agttgaaaat cgttaagtta ttctgtgatg ttacggactt atacgatcag 2820
ctctacgtta tcaaagattt gtcatcctct atgaagtaa 2859
```

SEQ ID NO: 58

```
MPGKIENGTP KDLKTGNDFV SAAKSLLDRA FKSHHSYYGL CSTSCQVYDT AWVAMIPKTR 60
DNVKQWLFPE CFHYLLKTQA ADGSWGSLPT TQTAGILDTA SAVLALLCHA QEPLQILDVS 120
PDEMGLRIEH GVTSLKRQLA VWNDVEDTNH IGVEFIIPAL LSMLEKELDV PSFEFPCRSI 180
LERMHGEKLG HFDLEQVYGK PSSLLHSLEA FLGKLDFDRL SHHLYHGSMM ASPSSTAAYL 240
IGATKWDDEA EDYLRHVMRN GAGHGNGGIS GTFPTTHFEC SWIIATLLKV GFTLKQIDGD 300
GLRGLSTILL EALRDENGVI GFAPRTADVD DTAKALLALS LVNQPVSPDI MIKVFEGKDH 360
FTTFGSERDP SLTSNLHVLL SLLKQSNLSQ YHPQILKTTL FTCRWWWGSD HCVKDKWNLS 420
HLYPTMLLVE AFTEVLHLID GGELSSLFDE SFKCKIGLSI FQAVLRIILT QDNDGSWRGY 480
REQTCYAILA LVQARHVCFF THMVDRLQSC VDRGFSWLKS CSFHSQDLTW TSKTAYEVGF 540
VAEAYKLAAL QSASLEVPAA TIGHSVTSAV PSSDLEKYMR LVRKTALFSP LDEWGLMASI 600
IESSFFVPLL QAQRVEIYPR DNIKVDEDKY LSIIPFTWVG CNNRSRTFAS NRWLYDMMYL 660
SLLGYQTDEY MEAVAGPVFG DVSLLHQTID KVIDNTMGNL ARANGTVHSG NGHQHESPNI 720
GQVEDTLTRF TNSVLNHKDV LNSSSSDQDT LRREFRTFMH AHITQIEDNS RFSKQASSDA 780
FSSPEQSYFQ WVNSTGGSHV ACAYSFAFSN CLMSANLLQG KDAFPSGTQK YLISSVMRHA 840
TNMCRMYNDF GSIARDNAER NVNSIHFPEF TLCNGTSQNL DERKERLLKI ATYEQGYLDR 900
ALEALERQSR DDAGDRAGSK DMRKLKIVKL FCDVTDLYDQ LYVIKDLSSS MK 952
```

SEQ ID NO: 59

*S. rebaudiana*

```
atggatgctg tgacgggttt gttaactgtc ccagcaaccg ctataactat tggtggaact 60
gctgtagcat tggcggtagc gctaatcttt tggtacctga aatcctacac atcagctaga 120
agatcccaat caaatcatct tccaagagtg cctgaagtcc caggtgttcc attgttagga 180
aatctgttac aattgaagga gaaaaagcca tacatgactt ttacgagatg ggcagcgaca 240
tatggaccta tctatagtat caaaactggg gctacaagta tggttgtggt atcatctaat 300
gagatagcca aggaggcatt ggtgaccaga ttccaatcca tatctacaag gaacttatct 360
aaagccctga aagtacttac agcagataag acaatggtcg caatgtcaga ttatgatgat 420
tatcataaaa cagttaagag acacatactg accgccgtct tgggtcctaa tgcacagaaa 480
aagcatagaa ttcacagaga tatcatgatg gataacatat ctactcaact tcatgaattc 540
gtgaaaaaca acccagaaca ggaagaggta gaccttagaa aaatctttca atctgagtta 600
ttcggcttag ctatgagaca agccttagga aaggatgttg aaagtttgta cgttgaagac 660
ctgaaaatca ctatgaatag agacgaaatc tttcaagtcc ttgttgttga tccaatgatg 720
ggagcaatcg atgttgattg gagagacttc tttccatacc taaagtgggt cccaaacaaa 780
aagttcgaaa atactattca acaaatgtac atcagaagag aagctgttat gaaatcttta 840
atcaaagagc acaaaaagag aatagcgtca ggcgaaaagc taaatagtta tatcgattac 900
cttttatctg aagctcaaac tttaaccgat cagcaactat tgatgtcctt gtgggaacca 960
atcattgaat cttcagatac aacaatggtc acaacagaat gggcaatgta cgaattagct 1020
aaaaacccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag gaatggaacc cagaaagatt catgaaagag 1320
aatgagacaa ttgattttca aaagacgatg gccttcggtg gtggtaagag agtttgtgct 1380
ggttccttgc aagccctttt aactgcatct attgggattg ggagaatggt tcaagagttc 1440
gaatggaaac tgaaggatat gactcaagag gaagtgaaca cgataggcct aactacacaa 1500
```

TABLE 11-continued

| Sequences disclosed herein. |
|---|
| atgttaagac cattgagagc tattatcaaa cctaggatct aa 1542 |
| SEQ ID NO: 60<br>*S. rebaudiana*<br>MDAVTGLLTV PATAITIGGT AVALAVALIF WYLKSYTSAR RSQSNHLPRV PEVPGVPLLG 60<br>NLLQLKEKKP YMTFTRWAAT YGPIYSIKTG ATSMVVVSSN EIAKEALVTR FQSISTRNLS 120<br>KALKVLTADK TMVAMSDYDD YHKTVKRHIL TAVLGPNAQK KHRIHRDIMM DNISTQLHEF 180<br>VKNNPEQEEV DLRKIFQSEL FGLAMRQALG KDVESLYVED LKITMNRDEI FQVLVVDPMM 240<br>GAIDVDWRDF FPYLKWVPNK KFENTIQQMY IRREAVMKSL IKEHKKRIAS GEKLNSYIDY 300<br>LLSEAQTLTD QQLLMSLWEP IIESSDTTMV TTEWAMYELA KNPKLQDRLY RDIKSVCGSE 360<br>KITEEHLSQL PYITAIFHET LRRHSPVPII PLRHVHEDTV LGGYHVPAGT ELAVNIYGCN 420<br>MDKNVWENPE EWNPERFMKE NETIDFQKTM AFGGGKRVCA GSLQALLTAS IGIGRMVQEF 480<br>EWKLKDMTQE EVNTIGLTTQ MLRPLRAIIK PRI 513 |
| SEQ ID NO: 61<br>aagcttacta gtaaaatgga cggtgtcatc gatatgcaaa ccattccatt gagaaccgct 60<br>attgctattg gtggtactgc tgttgctttg gttgttgcat tatacttttg gttcttgaga 120<br>tcctacgctt ccccatctca tcattctaat catttgccac cagtacctga agttccaggt 180<br>gttccagttt tgggtaattt gttgcaattg aaagaaaaaa agccttacat gaccttcacc 240<br>aagtgggctg aaatgtatgg tccaatctac tctattagaa ctggtgctac ttccatggtt 300<br>gttgtctctt ctaacgaaat cgccaaagaa gttgttgtta ccagattccc atctatctct 360<br>accagaaaat tgtcttacgc cttgaaggtt ttgaccgaag ataagtctat ggttgccatg 420<br>tctgattatc acgattacca taagaccgtc aagagacata ttttgactgc tgttttgggt 480<br>ccaaacgccc aaaaaaagtt tagagcacat agagacacca tgatggaaaa cgtttccaat 540<br>gaattgcatg ccttcttcga aaagaaccca aatcaagaag tcaacttgag aaagatcttc 600<br>caatcccaat tattcggttt ggctatgaag caagccttgg gtaaagatgt tgaatccatc 660<br>tacgttaagg atttggaaac caccatgaag agagaagaaa tcttcgaagt tttggttgtc 720<br>gatccaatga tgggtgctat tgaagttgat tggagagact ttttcccata cttgaaatgg 780<br>gttccaaaca agtccttcga aaacatcatc catagaatgt acactagaag agaagctgtt 840<br>atgaaggcct tgatccaaga acacaagaaa agaattgcct ccggtgaaaa cttgaactcc 900<br>tacattgatt acttgttgtc tgaagcccaa accttgaccg ataagcaatt attgatgtct 960<br>ttgtgggaac ctattatcga atcttctgat accactatgg ttactactga atgggctatg 1020<br>tacgaattgg ctaagaatcc aaacatgcaa gacagattat acgaagaaat ccaatccgtt 1080<br>tgcggttccg aaaagattac tgaagaaaac ttgtcccaat tgccatactt gtacgctgtt 1140<br>ttccaagaaa ctttgagaaa gcactgtcca gttcctatta tgccattgag atatgttcac 1200<br>gaaaacaccg ttttgggtgg ttatcatgtt ccagctggta ctgaagttgc tattaacatc 1260<br>tacggttgca acatggataa gaaggtctgg gaaaatccag aagaatggaa tccagaaaga 1320<br>ttcttgtccg aaaaagaatc catggacttg tacaaaacta tggcttttgg tggtggtaaa 1380<br>agagtttgcg ctggttcttt acaagccatg gttatttctt gcattggtat cggtagattg 1440<br>gtccaagatt ttgaatggaa gttgaaggat gatgccgaag aagatgttaa cactttgggt 1500<br>ttgactaccc aaaagttgca tccattattg gccttgatta acccaagaaa gtaactcgag 1560<br>ccgcgg 1566 |
| SEQ ID NO: 62<br>MDGVIDMQTI PLRTAIAIGG TAVALVVALY FWFLRSYASP SHHSNHLPPV PEVPGVPVLG 60<br>NLLQLKEKKP YMTFTKWAEM YGPIYSIRTG ATSMVVVSSN EIAKEVVVTR FPSISTRKLS 120<br>YALKVLTEDK SMVAMSDYHD YHKTVKRHIL TAVLGPNAQK KFRAHRDTMM ENVSNELHAF 180<br>FEKNPNQEVN LRKIFQSQLF GLAMKQALGK DVESIYVKDL ETTMKREEIF EVLVVDPMMG 240<br>AIEVDWRDFF PYLKWVPNKS FENIIHRMYT RREAVMKALI QEHKKRIASG ENLNSYIDYL 300<br>LSEAQTLTDK QLLMSLWEPI IESSDITMVT TEWAMYELAK NPNMQDRLYE EIQSVCGSEK 360<br>ITEENLSQLP YLYAVFQETL RKHCPVPIMP LRYVHENTVL GGYHVPAGTE VAINIYGCNM 420<br>DKKVWENPEE WNPERFLSEK ESMDLYKTMA FGGGKRVCAG SLQAMVISCI GIGRLVQDFE 480<br>WKLKDDAEED VNTLGLTTQK LHPLLALINP RK 512 |
| SEQ ID NO: 63<br>*R. suavissimus*<br>atggccaccc tccttgagca tttccaagct atgccctttg ccatccctat tgcactggct 60<br>gctctgtctt ggctgttcct cttttacatc aaagtttcat tcttttccaa caagagtgct 120<br>caggctaagc tccctcctgt gccagtggtt cctgggctgc cggtgattgg gaatttactg 180<br>caactcaagg agaagaaacc ctaccagact tttacaaggt gggctgagga gtatggacca 240<br>atctattcta tcaggactgg tgcttccacc atggtcgttc tcaataccac ccaagttgca 300<br>aaagaggcca tggtgaccag atatttatcc atctcaacca gaaagctatc aaacgcacta 360<br>aagattctta ctgctgataa atgtatggtt gcaataagtg actacaacga ttttcacaag 420<br>atgataaagc gatacatact ctcaaatgtt cttggaccta gtgctcagaa gcgtcaccgg 480<br>agcaacagag ataccttgag agctaatgtc tgcagccgat tgcattctca agtaaagaac 540<br>tctcctcgag aagctgtgaa tttcagaaga gtttttgagt gggaactctt tggaattgca 600<br>ttgaagcaag cctttggaaa ggacatagaa aagcccattt atgtggagga acttggcact 660<br>acactgtcaa gagatgagat ctttaaggtt ctagtgcttg acataatgga gggtgcaatt 720<br>gaggttgatt ggagagattt cttcccttac ctgagatgga ttccgaatac gcgcatggaa 780<br>acaaaaattc agcgactcta tttccgcagg aaagcagtga tgactgccct gatcaacgag 840<br>cagaagaagc gaattgcttc aggagaggaa atcaactgtt atatcgactt cttgcttaag 900<br>gaagggaaga cactgacaat ggaccaaata agtatgttgc tttgggagac ggttattgaa 960<br>acagcagata ctacaatggt aacgacagaa tgggctatgt atgaagttgc taaagactca 1020<br>aagcgtcagg atcgtctcta tcaggaaatc caaaaggttt gtggatcgga gatggttaca 1080<br>gaggaatact tgtcccaact gccgtacctg aatgcagttt tccatgaaac gctaaggaag 1140<br>cacagtccgg ctgcgttagt tcctttaaga tatgcacatg aagataccca actaggaggt 1200<br>tactacattc cagctggaac tgagattgct ataaacatat acgggtgtaa catggacaag 1260<br>catcaatggg aaagccctga ggaatggaaa ccggagagat tttggaccc gaaatttgat 1320 |

TABLE 11-continued

Sequences disclosed herein.

```
cctatggatt tgtacaagac catggctttt ggggctggaa agagggtatg tgctggttct  1380
cttcaggcaa tgttaatagc gtgcccgacg attggtaggc tggtgcagga gtttgagtgg  1440
aagctgagag atggagaaga agaaaatgta gatactgttg ggctcaccac tcacaaacgc  1500
tatccaatgc atgcaatcct gaagccaaga agtta                             1535
```

SEQ ID NO: 64

*R. suavissimus*

```
atggctacct tgttggaaca ttttcaagct atgccattcg ctattccaat tgctttggct    60
gctttgtctt ggttgttttt gttctacatc aaggtttctt tcttctccaa caaatccgct   120
caagctaaat tgccaccagt tccagttgtt ccaggtttgc cagttattgg taatttgttg   180
caattgaaag aaaagaagcc ataccaaacc ttcactagat gggctgaaga atatggtcca   240
atctactcta ttagaactgg tgcttctact atggttgtct tgaacactac tcaagttgcc   300
aaagaagcta tggttaccag atacttgtct atctctacca gaaagttgtc caacgccttg   360
aaaattttga ccgctgataa gtgcatggtt gccatttctg attacaacga tttccacaag   420
atgatcaaga gatatatctt gtctaacgtt ttgggtccat ctgcccaaaa aagacataga   480
tctaacagag ataccttgag agccaacgtt tgttctagat tgcattccca agttaagaac   540
tctccaagag aagctgtcaa ctttagaaga gttttcgaat gggaattatt cggtatcgct   600
ttgaaacaag ccttcggtaa ggatattgaa aagccaatct acgtcgaaga attgggtact   660
actttgtcca gagatgaaat cttcaaggtt ttggtcttgg acattatgga aggtgccatt   720
gaagttgatt ggagagattt tttcccatac ttgcgttgga ttccaaacac cagaatggaa   780
actaagatcc aaagattata ctttagaaga aaggccgtta tgaccgcctt gattaacgaa   840
caaaagaaaa gaattgcctc cggtgaagaa atcaactgct acatcgattt cttgttgaaa   900
gaaggtaaga ccttgaccat ggaccaaatc tctatgttgt tgtgggaaac cgttattgaa   960
actgctgata ccacaatggt tactactgaa tgggctatgt acgaagttgc taaggattct  1020
aaaagacaag acagattata ccaagaaatc caaaaggtct gcggttctga aatggttaca  1080
gaagaatact tgtcccaatt gccatacttg aatgctgttt tccacgaaac tttgagaaaa  1140
cattctccag ctgctttggt tccattgaga tatgctcatg aagatactca attgggtggt  1200
tattacattc cagccggtac tgaaattgcc attaacatct acggttgcaa catggacaaa  1260
caccaatggg aatctccaga agaatggaag ccagaaagat tttggatcc taagtttgac   1320
ccaatggact tgtacaaaac tatggctttt ggtgctggta aaagagtttg cgctggttct  1380
ttacaagcta tgttgattgc ttgtccaacc atcggtagat tggttcaaga atttgaatgg  1440
aagttgagag atggtgaaga agaaaacgtt gatactgttg gtttgaccac ccataagaga  1500
tatccaatgc atgctatttt gaagccaaga tcttaa                            1536
```

SEQ ID NO: 65

```
aagcttacta gtaaaatggc ctccatcacc catttcttac aagattttca agctactcca    60
ttcgctactg cttttgctgt tggtggtgtt tctttgttga tattcttctt cttcatccgt   120
ggtttccact ctactaagaa aaacgaatat tacaagttgc caccagttcc agttgttcca   180
ggtttgccag ttgttggtaa tttgttgcaa ttgaaagaaa agaagccata caagactttc   240
ttgagatggg ctgaaattca tggtccaatc tactctatta gaactggtgc ttctaccatg   300
gttgttgtta actctactca tgttgccaaa gaagctatgg ttaccagatt ctcttcaatc   360
tctaccagaa agttgtccaa ggctttggaa ttattgacct ccaacaaatc tatggttgcc   420
acctctgatt acaacgaatt tcacaagatg gtcaagaagt acatcttggc cgaattattg   480
ggtgctaatg ctcaaaagag acacagaatt catagagaca ccttgatcga aaacgtcttg   540
aacaaattgc atgcccatac caagaattct ccattgcaag ctgttaactt cagaaagatc   600
ttcgaatctg aattattcgg tttggctatg aagcaagcct tgggttatga tgttgattcc   660
ttgttcgttg aagaattggg tactaccttg tccagagaag aaatctacaa cgttttggtc   720
agtgacatgt tgaagggtgc tattgaagtt gattggagag acttttttccc atacttgaaa   780
tggatcccaa acaagtcctt cgaaatgaag attcaaagat tggcctctag aagacaagcc   840
gttatgaact ctattgtcaa agaacaaaag aagtccattg cctctggtaa gggtgaaaac   900
tgttacttga attacttgtt gtccgaagct aagactttga ccgaaaagca aatttccatt   960
ttggcctggg aaaccattat tgaaactgct gatacaactg ttgttaccac tgaatgggct  1020
atgtacgaat tggctaaaaa cccaaagcaa caagacagat tatacaacga aatccaaaac  1080
gtctgcggta ctgataagat taccgaagaa catttgtcca agttgcctta cttgtctgct  1140
gtttttcacg aaaccttgag aaagtattct ccatctccat tggttccatt gagatacgct  1200
catgaagata ctcaattggg tggttattat gttccagccg gtactgaaat tgctgttaat  1260
atctacggtt gcaacatgga caagaatcaa tgggaaactc cagaagaatg gaagccagaa  1320
agatttttgg acgaaaagta cgatccaatg gacatgtaca agactatgtc ttttggttcc  1380
ggtaaaagag tttgcgctgg ttctttacaa gctagtttga ttgcttgtac ctccatcggt  1440
agattggttc aagaatttga atggagattg aaagacggtg aagttgaaaa cgttgatacc  1500
ttgggtttga ctacccataa gttgtatcca atgcaagcta tcttgcaacc tagaaactga  1560
ctcgagccgc gg                                                      1572
```

SEQ ID NO: 66

```
MASITHFLQD FQATPFATAF AVGGVSLLIF FFFIRGFHST KKNEYYKLPP VPVVPGLPVV    60
GNLLQLKEKK PYKTFLRWAE IHGPIYSIRT GASTMVVVNS THVAKEAMVT RFSSISTRKL   120
SKALELLTSN KSMVATSDYN EFHKMVKKYI LAELLGANAQ KRHRIHRDTL IENVLNKLHA   180
HTKNSPLQAV NFRKIFESEL FGLAMKQALG YDVDSLFVEE LGTTLSREEI YNVLVSDMLK   240
GAIEVDWRDF FPYLKWIPNK SFEMKIQRLA SRRQAVMNSI VKEQKKSIAS GKGENCYLNY   300
LLSEAKTLTE KQISILAWET IIETADTTVV TTEWAMYELA KNPKQQDRLY NEIQNVCGTD   360
KITEEHLSKL PYLSAVFHET LRKYSPSPLV PLRYAHEDTQ LGGYYVPAGT EIAVNIYGCN   420
MDKNQWETPE EWKPERFLDE KYDPMDMYKT MSFGSGKRVC AGSLQASLIA CTSIGRLVQE   480
FEWRLKDGEV ENVDTLGLTT HKLYPMQAIL QPRN                              514
```

SEQ ID NO: 67

```
atgatttcct tgttgttggg ttttgttgtc tcctccttct tgtttatctt cttcttgaaa    60
aaattgttgt tcttcttcag tcgtcacaaa atgtccgaag tttctagatt gccatctgtt   120
ccagttccag gttttccatt gattggtaac ttgttgcaat tgaaagaaaa gaagccacac   180
```

TABLE 11-continued

| Sequences disclosed herein. |
|---|
| aagactttca ccaagtggtc tgaattatat ggtccaatct actctatcaa gatgggttcc 240<br>tcttctttga tcgtcttgaa ctctattgaa accgccaaag aagctatggt cagtagattc 300<br>tcttcaatct ctaccagaaa gttgtctaac gctttgactg ttttgacctg caacaaatct 360<br>atggttgcta cctctgatta cgatgacttt cataagttcg tcaagagatg cttgttgaac 420<br>ggtttgttgg gtgctaatgc tcaagaaaga aaaagacatt acagagatgc cttgatcgaa 480<br>aacgttacct ctaaattgca tgcccatacc agaaatcatc cacaagaacc agttaacttc 540<br>agagccattt tcgaacacga attattcggt gttgctttga aacaagcctt cggtaaagat 600<br>gtcgaatcca tctatgtaaa agaattgggt gtcaccttgt ccagagatga aattttcaag 660<br>gttttggtcc acgacatgat ggaaggtgct attgatgttg attggagaga tttcttccca 720<br>tacttgaaat ggatcccaaa caactctttc gaagccagaa ttcaacaaaa gcacaagaga 780<br>agattggctg ttatgaacgc cttgatccaa gacagattga atcaaaacga ttccgaatcc 840<br>gatgatgact gctacttgaa tttcttgatg tctgaagcta agaccttgac catggaacaa 900<br>attgctattt tggtttggga aaccattatc gaaactgctg ataccacttt ggttactact 960<br>gaatgggcta tgtacgaatt ggccaaacat caatctgttc aagatagatt attcaaagaa 1020<br>atccaatccg tctgcggtgg tgaaaagatc aaagaagaac aattgccaag attgccttac 1080<br>gtcaatggtg tttttcacga aaccttgaga aagtattctc cagctccatt ggttccaatt 1140<br>agatacgctc atgaagatac ccaaattggt ggttatcata ttccagccgg ttctgaaatt 1200<br>gccattaaca tctacggttg caacatggat aagaagagat gggaaagacc tgaagaatgg 1260<br>tggccagaaa gattttggga agatagatac gaatcctccg acttgcataa gactatggct 1320<br>tttggtgctg gtaaaagagt ttgtgctggt gctttacaag ctagtttgat ggctggtatt 1380<br>gctatcggta gattggttca agaattcgaa tggaagttga gagatggtga agaagaaaac 1440<br>gttgatactt acggtttgac ctcccaaaag ttgtatccat tgatggccat tatcaaccca 1500<br>agaagatctt aa 1512 |
| SEQ ID NO: 68<br>MASMISLLLG FVVSSFLFIF FLKKLLFFFS RHKMSEVSRL PSVPVPGFPL IGNLLQLKEK 60<br>KPHKTFTKWS ELYGPIYSIK MGSSSLIVLN SIETAKEAMV SRFSSISTRK LSNALTVLTC 120<br>NKSMVATSDY DDFHKFVKRC LLNGLLGANA QERKRHYRDA LIENVTSKLH AHTRNHPQEP 180<br>VNFRAIFEHE LFGVALKQAF GKDVESIYVK ELGVTLSRDE IFKVLVHDMM EGAIDVDWRD 240<br>FFPYLKWIPN NSFEARIQQK HKRRLAVMNA LIQDRLNQND SESDDDCYLN FLMSEAKTLT 300<br>MEQIAILVWE TIIETADTTL VTTEWAMYEL AKHQSVQDRL FKEIQSVCGG EKIKEEQLPR 360<br>LPYVNGVFHE TLRKYSPAPL VPIRYAHEDT QIGGYHIPAG SEIAINIYGC NMDKKRWERP 420<br>EEWWPERFLE DRYESSDLHK TMAFGAGKRV CAGALQASLM AGIAIGRLVQ EFEWKLRDGE 480<br>EENVDTYGLT SQKLYPLMAI INPRRS 506 |
| SEQ ID NO: 69<br>aagcttacta gtaaaatgga catgatgggt attgaagctg ttccatttgc tactgctgtt 60<br>gttttgggtg gtatttcctt ggttgttttg atcttcatca gaagattcgt ttccaacaga 120<br>aagagatccg ttgaaggttt gccaccagtt ccagatattc caggtttacc attgattggt 180<br>aacttgttgc aattgaaaga aaagaagcca cataagacct ttgctagatg ggctgaaact 240<br>tacggtccaa ttttctctat tagaactggt gcttctacca tgatcgtctt gaattcttct 300<br>gaagttgcca aagaagctat ggtcactaga ttctcttcaa tctctaccag aaagttgtcc 360<br>aacgccttga agattttgac cttcgataag tgtatggttg ccacctctga ttacaacgat 420<br>tttcacaaaa tggtcaaggg tttcatcttg agaaacgttt taggtgctcc agcccaaaaa 480<br>agacatagat gtcatagaga taccttgatc gaaaacatct ctaagtactt gcatgcccat 540<br>gttaagactt ctccattgga accagttgtc ttgaagaaga ttttcgaatc cgaaattttc 600<br>ggtttggctt tgaaacaagc cttgggtaag gatatcgaat ccatctatgt tgaagaattg 660<br>ggtactacct tgtccagaga agaaattttt gccgttttgg ttgttgatcc aatggctggt 720<br>gctattgaag ttgattggag agatttttttc ccatacttgt cctggattcc aaacaagtct 780<br>atggaaatga agatccaaag aatggatttt agaagaggtg ctttgatgaa ggccttgatt 840<br>ggtgaacaaa agaaaagaat cggttccggt gaagaaaaga actcctacat tgatttcttg 900<br>ttgtctgaag ctaccacttt gaccgaaaag caaattgcta tgttgatctg ggaaaccatc 960<br>atcgaaattt ccgatacaac tttggttacc tctgaatggg ctatgtacga attggctaaa 1020<br>gacccaaata gacaagaaat cttgtacaga gaaatccaca aggtttgcgg ttctaacaag 1080<br>ttgactgaag aaaacttgtc caagttgcca tacttgaact ctgttttcca cgaaaccttg 1140<br>agaaagtatt ctccagctcc aatggttcca gttagatatg ctcatgaaga tactcaattg 1200<br>ggtggttacc atattccagc tggttctcaa attgccatta acatctacgg ttgcaacatg 1260<br>aacaaaaagc aatgggaaaa tcctgaagaa tggaagccag aaagattctt ggacgaaaag 1320<br>tatgacttga tggacttgca taagactatg gcttttggtg gtggtaaaag agtttgtgct 1380<br>ggtgctttac aagcaatgtt gattgcttgc acttccatcg gtagattcgt tcaagaattt 1440<br>gaatggaagt tgatgggtgg tgaagaagaa aacgttgata ctgttgcttt gacctcccaa 1500<br>aaattgcatc caatgcaagc cattattaag gccagagaat gactcgagcc gcgg 1554 |
| SEQ ID NO: 70<br>MDMMGIEAVP FATAVVLGGI SLVVLIFIRR FVSNRKRSVE GLPPVPDIPG LPLIGNLLQL 60<br>KEKKPHKTFA RWAETYGPIF SIRTGASTMI VLNSSEVAKE AMVTRFSSIS TRKLSNALKI 120<br>LTFDKCMVAT SDYNDFHKMV KGFILRNVLG APAQKRHRCH RDTLIENISK YLHAHVKTSP 180<br>LEPVVLKKIF ESEIFGLALK QALGKDIESI YVEELGTTLS REEIFAVLVV DPMAGAIEVD 240<br>WRDFFPYLSW IPNKSMEMKI QRMDFRRGAL MKALIGEQKK RIGSGEEKNS YIDFLLSEAT 300<br>TLTEKQIAML IWETIIEISD TTLVTSEWAM YELAKDPNRQ EILYREIHKV CGSNKLTEEN 360<br>LSKLPYLNSV FHETLRKYSP APMVPVRYAH EDTQLGGYHI PAGSQIAINI YGCNMNKKQW 420<br>ENPEEWKPER FLDEKYDLMD LHKTMAFGGG KRVCAGALQA MLIACTSIGR FVQEFEWKLM 480<br>GGEEENVDTV ALTSQKLHPM QAIIKARE 508 |
| SEQ ID NO: 71<br>aagcttaaaa tgagtaagtc taatagtatg aattctacat cacacgaaac ccttttttcaa 60<br>caattggtct tgggtttgga ccgtatgcca ttgatggatg ttcactggtt gatctacgtt 120<br>gctttcggcg catggttatg ttcttatgtg atacatgttt tatcatcttc ctctacagta 180 |

TABLE 11-continued

Sequences disclosed herein.

```
aaagtgccag ttgttggata caggtctgta ttcgaaccta catggttgct tagacttaga   240
ttcgtctggg aaggtggctc tatcataggt caagggtaca ataagtttaa agactctatt   300
ttccaagtta ggaaattggg aactgatatt gtcattatac cacctaacta tattgatgaa   360
gtgagaaaat tgtcacagga caagactaga tcagttgaac ctttcattaa tgattttgca   420
ggtcaataca caagaggcat ggttttcttg caatctgact tacaaaaccg tgttatacaa   480
caaagactaa ctccaaaatt ggtttccttg accaaggtca tgaaggaaga gttggattat   540
gctttaacaa aagagatgcc tgatatgaaa aatgacgaat gggtagaagt agatatcagt   600
agtataatgg tgagattgat ttccaggatc tccgccagag tctttctagg gcctgaacac   660
tgtcgtaacc aggaatggtt gactactaca gcagaatatt cagaatcact tttcattaca   720
gggtttatct taagagttgt acctcatatc ttaagaccat tcatcgcccc tctattacct   780
tcatacagga ctctacttag aaacgtttca agtggtagaa gagtcatcgg tgacatcata   840
agatctcagc aaggggatgg taacgaagat atactttcct ggatgagaga tgctgccaca   900
ggagaggaaa agcaaatcga taacattgct cagagaatgt taattctttc tttagcatca   960
atccacacta ctgcgatgac catgacacat gccatgtacg atctatgtgc ttgccctgag  1020
tacattgaac cattaagaga tgaagttaaa tctgttgttg gggcttctgg ctgggacaag  1080
acagcgttaa acagatttca taagttggac tccttcctaa aagagtcaca aagattcaac  1140
ccagtattct tattgacatt caatagaatc taccatcaat ctatgacctt atcagatggc  1200
actaacattc catctggaac acgtattgct gttccatcac acgcaatgtt gcaagattct  1260
gcacatgtcc caggtccaac cccacctact gaatttgatg gattcagata tagtaagata  1320
cgttctgata gtaactacgc acaaaagtac ctattctcca tgaccgattc ttcaaacatg  1380
gctttcggat acggcaagta tgcttgtcca ggtagatttt acgcgtctaa tgagatgaaa  1440
ctaacattag ccattttgtt gctacaattt gagttcaaac taccagatgg taaaggtcgt  1500
cctagaaata tcactatcga ttctgatatg attccagacc caagagctag actttgcgtc  1560
agaaaaagat cacttagaga tgaatgaccg cgg                               1593
```

SEQ ID NO: 72

```
MSKSNSMNST SHETLFQQLV LGLDRMPLMD VHWLIYVAFG AWLCSYVIHV LSSSSTVKVP    60
VVGYRSVFEP TWLLRLRFVW EGGSIIGQGY NKFKDSIFQV RKLGTDIVII PPNYIDEVRK   120
LSQDKTRSVE PFINDFAGQY TRGMVFLQSD LQNRVIQQRL TPKLVSLTKV MKEELDYALT   180
KEMPDMKNDE WVEVDISSIM VRLISRISAR VFLGPEHCRN QEWLTTTAEY SESLFITGFI   240
LRVVPHILRP FIAPLLPSYR TLLRNVSSGR RVIGDIIRSQ QGDGNEDILS WMRDAATGEE   300
KQIDNIAQRM LILSLASIHT TAMTMTHAMY DLCACPEYIE PLRDEVKSVV GASGWDKTAL   360
NRFHKLDSFL KESQRFNPVF LLTFNRIYHQ SMTLSDGTNI PSGTRIAVPS HAMLQDSAHV   420
PGPTPPTEFD GFRYSKIRSD SNYAQKYLFS MTDSSNMAFG YGKYACPGRF YASNEMKLTL   480
AILLLQFEFK LPDGKGRPRN ITIDSDMIPD PRARLCVRKR SLRDE                  525
```

SEQ ID NO: 73

```
aagcttaaaa tggaagatcc tactgtctta tatgcttgtc ttgccattgc agttgcaact    60
ttcgttgtta gatggtacag agatccattg agatccatcc caacagttgg tggttccgat   120
ttgcctattc tatcttacat cggcgcacta agatggacaa gacgtggcag agagatactt   180
caagagggat atgatggcta cagaggatct acattcaaaa tcgcgatgtt agaccgttgg   240
atcgtgatcg caaatggtcc taaactagct gatgaagtca gacgtagacc agatgaagag   300
ttaaacttta tggacggatt aggagcattc gtccaaacta agtacacctt aggtgaagct   360
attcataacg atccatacca tgtcgatatc ataagagaaa aactaacaag aggccttcca   420
gccgtgcttc ctgatgtcat tgaagagttg acacttgcgg ttagacagta cattccaaca   480
gaaggtgatg aatgggtgtc cgtaaactgt tcaaaggccg caagagatat tgttgctaga   540
gcttctaata gagtctttgt aggtttgcct gcttgcagaa accaaggtta cttagatttg   600
gcaatagact ttacattgtc tgttgtcaag gatagagcca tcatcaatat gtttccagaa   660
ttgttgaagc caatagttgg cagagttgta ggtaacgcca ccagaaatgt tcgtagagct   720
gttccttttg ttgctccatt ggtggaggaa agacgtagac ttatggaaga gtacggtgaa   780
gactggtctg aaaaacctaa tgatatgtta cagtggataa tggatgaagc tgcatccaga   840
gatagttcag tgaaggcaat cgcagagaga ttgttaatgg tgaacttcgc ggctattcat   900
acctcatcaa acactatcac tcatgctttg taccaccttg ccgaaatgcc tgaaactttg   960
caaccactta gagaagagat cgaaccatta gtcaaagagg agggctggac caaggctgct  1020
atgggaaaaa tgtggtggtt agattcattt ctaagagaat ctcaaagata caatggcatt  1080
aacatcgtat ctttaactag aatggctgac aaagatatta cattgagtga tggcacattt  1140
ttgccaaaag gtactctagt ggccgttcca gcgtattcta ctcatagaga tgatgctgtc  1200
tacgctgatg ccttagtatt cgatcctttc agattctcac gtatgagagc gagagaaggt  1260
gaaggtacaa agcaccagtt cgttaatact tcagtcgagt acgttccatt tggtcacgga  1320
aagcatgctt gtccaggaag attcttcgcc gcaaacgaat tgaaagcaat gttggcttac  1380
attgttctaa actatgatgt aaagttgcct ggtgacggta aacgtccatt gaacatgtat  1440
tggggtccaa cagttttgcc tgcaccagca ggccaagtat tgttcagaaa gagacaagtt  1500
agtctataac cgcgg                                                   1515
```

SEQ ID NO: 74

```
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRR LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                               499
```

SEQ ID NO: 75

```
atggcatttt tctctatgat ttcaattttg ttgggatttg ttatttcttc tttcatcttc    60
atctttttct tcaaaaagtt acttagtttt agtaggaaaa acatgtcaga agtttctact   120
```

TABLE 11-continued

| Sequences disclosed herein. |
|---|
| ttgccaagtg ttccagtagt gcctggtttt ccagttattg ggaatttgtt gcaactaaag 180 |
| gagaaaaagc ctcataaaac tttcactaga tggtcagaga tatatggacc tatctactct 240 |
| ataaagatgg gttcttcatc tcttattgta ttgaacagta cagaaactgc taaggaagca 300 |
| atggtcacta gattttcatc aatatctacc agaaaattgt caaacgccct aacagttcta 360 |
| acctgcgata agtctatggt cgccacttct gattatgatg acttccacaa attagttaag 420 |
| agatgtttgc taaatggact tcttggtgct aatgctcaaa agagaaaaag acactacaga 480 |
| gatgctttga ttgaaaatgt gagttccaag ctacatgcac acgctagaga tcatccacaa 540 |
| gagccagtta actttagagc aattttcgaa cacgaattgt ttggtgtagc attaaagcaa 600 |
| gccttcggta aagacgtaga atccatatac gtcaaggagt taggcgtaac attatcaaaa 660 |
| gatgaaatct ttaaggtgct tgtacatgat atgatggagg gtgcaattga tgtagattgg 720 |
| agagatttct tcccatattt gaaatggatc cctaataagt cttttgaagc taggatacaa 780 |
| caaaagcaca agagaagact agctgttatg aacgcactta tacaggacag attgaagcaa 840 |
| aatgggtctg aatcagatga tgattgttac cttaacttct taatgtctga ggctaaaaca 900 |
| ttgactaagg aacagatcgc aatccttgtc tgggaaacaa tcattgaaac agcagatact 960 |
| accttagtca caactgaatg ggccatatac gagctagcca aacatccatc tgtgcaagat 1020 |
| aggttgtgta aggagatcca gaacgtgtgt ggtggagaga aattcaagga agagcagttg 1080 |
| tcacaagttc cttaccttaa cggcgttttc catgaaacct tgagaaaata ctcacctgca 1140 |
| ccattagttc ctattagata cgcccacgaa gatacacaaa tcggtggcta ccatgttcca 1200 |
| gctgggtccg aaattgctat aaacatctac gggtgcaaca tggacaaaaa gagatgggaa 1260 |
| agaccagaag attggtggcc agaaagattc ttagatgatg gcaaatatga aacatctgat 1320 |
| ttgcataaaa caatggcttt cggagctggc aaaagagtgt gtgccggtgc tctacaagcc 1380 |
| tccctaatgg ctggtatcgc tattggtaga ttggtccaag agttcgaatg gaaacttaga 1440 |
| gatggtgaag aggaaaatgt cgatacttat gggttaacat ctcaaaagtt atacccacta 1500 |
| atggcaatca tcaatcctag aagatcctaa 1530 |
| |
| SEQ ID NO: 76 |
| MAFFSMISIL LGFVISSFIF IFFFKKLLSF SRKNMSEVST LPSVPVVPGF PVIGNLLQLK 60 |
| EKKPHKTFTR WSEIYGPIYS IKMGSSSLIV LNSTETAKEA MVTRFSSIST RKLSNALTVL 120 |
| TCDKSMVATS DYDDFHKLVK RCLLNGLLGA NAQKRKRHYR DALIENVSSK LHAHARDHPQ 180 |
| EPVNFRAIFE HELFGVALKQ AFGKDVESIY VKELGVTLSK DEIFKVLVHD MMEGAIDVDW 240 |
| RDFFPYLKWI PNKSFEARIQ QKHKRRLAVM NALIQDRLKQ NGSESDDDCY LNFLMSEAKT 300 |
| LTKEQIAILV WETIIETADT TLVITEWAIY ELAKHPSVQD RLCKEIQNVC GGEKFKEEQL 360 |
| SQVPYLNGVF HETLRKYSPA PLVPIRYAHE DTQIGGYHVP AGSEIAINIY GCNMDKKRWE 420 |
| RPEDWWPERF LDDGKYETSD LHKTMAFGAG KRVCAGALQA SLMAGIAIGR LVQEFEWKLR 480 |
| DGEEENVDTY GLTSQKLYPL MAIINPRRS 509 |
| |
| SEQ ID NO: 77 |
| *S. rebaudiana* |
| atgcaatcag attcagtcaa agtctctcca tttgatttgg tttccgctgc tatgaatggc 60 |
| aaggcaatgg aaaagttgaa cgctagtgaa tctgaagatc caacaacatt gcctgcacta 120 |
| aagatgctag ttgaaaatag agaattgttg acactgttca caacttcctt cgcagttctt 180 |
| attgggtgtc ttgtatttct aatgtggaga cgttcatcct ctaaaaagct ggtacaagat 240 |
| ccagttccac aagttatcgt tgtaaagaag aaagagaagg agtcagaggt tgatgacggg 300 |
| aaaaagaaag tttctatttt ctacggcaca caaacaggaa ctgccgaagg ttttgctaaa 360 |
| gcattagtcg aggaagcaaa agtgagatat gaaaagacct ctttcaaggt tatcgatcta 420 |
| gatgactacg ctgcagatga tgatgaatat gaggaaaaac tgaaaaagga atccttagcc 480 |
| ttcttcttct tggccacata cggtgatggt gaacctactg ataatgctgc taacttctac 540 |
| aagtggttca cagaaggcga cgataaaggt gaatggctga aaaagttaca atacggagta 600 |
| tttggtttag gtaacagaca atatgaacat ttcaacaaga tcgctattgt agttgatgat 660 |
| aaacttactg aaatgggagc caaaagatta gtaccagtag gattagggga tgatgatcag 720 |
| tgtatagaag atgacttcac cgcctggaag gaattggtat ggccagaatt ggatcaactt 780 |
| ttaagggacg aagatgatac ttctgtgact accccataca ctgcagccgt attggagtac 840 |
| agagtggttt accatgataa accagcagac tcatatgctg aagatcaaac ccatacaaac 900 |
| ggtcatgttg ttcatgatgc acagcatcct tcaagatcta atgtggcttt caaaaaggaa 960 |
| ctacacacct ctcaatcaga taggtcttgt actcacttag aattcgatat ttctcacaca 1020 |
| ggactgtctt acgaaactgg cgatcacgtt ggcgtttatt ccgagaactt gtccgaagtt 1080 |
| gtcgatgaag cactaaaact gttagggtta tcaccagaca catacttctc agtccatgct 1140 |
| gataaggagg atgggacacc tatcggtggt gcttcactac caccaccttt tcctccttgc 1200 |
| acattgagag acgctctaac cagatacgca gatgtcttat cctcacctaa aaaggtagct 1260 |
| ttgctggcat tggctgctca tgctagtgat cctagtgaag ccgataggtt aaagttcctg 1320 |
| gcttcaccag ccggaaaaga tgaatatgca caatggatcg tcgccaacca acgttctttg 1380 |
| ctagaagtga tgcaaagttt tccatctgcc aagcctccat taggtgtgtt cttcgcagca 1440 |
| gtagctccac gtttacaacc aagatactac tctatcagtt catctcctaa gatgtctcct 1500 |
| aacagaatac atgttacatg tgctttggtg tacgagacta ctccagcagg cagaattcac 1560 |
| agaggattgt gttcaacctg gatgaaaaat gctgtccctt taacagagtc acctgattgc 1620 |
| tctcaagcat ccattttcgt tagaacatca aatttcagac ttccagtgga tccaaaagtt 1680 |
| ccagtcatta tgataggacc aggcactggt cttgccccat tcaggggctt tcttcaagag 1740 |
| agattggcct tgaaggaatc tggtacagaa ttgggttctt ctatcttttt ctttggttgc 1800 |
| cgtaatagaa aagttgactt tatctacgag gacgagctta acaattttgt tgagacagga 1860 |
| gcattgtcag aattgatcgt cgcattttca agagaaggga ctgccaaaga gtacgttcag 1920 |
| cacaagatga gtcaaaaagc ctccgatata tggaaacttc taagtgaagg tgcctatctt 1980 |
| tatgtctgtg gcgatgcaaa gggcatggcc aaggatgtcc atagaactct gcatacaatt 2040 |
| gttcaggaac aagggagtct ggattcttcc aaggctgaat tgtacgtcaa aaacttacag 2100 |
| atgtctggaa gatacttaag agatgtttgg taa 2133 |
| |
| SEQ ID NO: 78 |
| *S. rebaudiana* |
| MQSDSVKVSP FDLVSAAMNG KAMEKLNASE SEDPTTLPAL KMLVENRELL TLFTTSFAVL 60 |

TABLE 11-continued

| Sequences disclosed herein. |
|---|

```
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPPC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPERGELQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW              710

SEQ ID NO: 79
atgaaggtca gtccattcga attcatgtcc gctattatca agggtagaat ggacccatct    60
aactcctcat ttgaatctac tggtgaagtt gcctccgtta tctttgaaaa cagagaattg   120
gttgccatct tgaccacttc tattgctgtt atgattggtt gcttcgttgt cttgatgtgg   180
agaagagctg gttctagaaa ggttaagaat gtcgaattgc caaagccatt gattgtccat   240
gaaccagaac ctgaagttga agatggtaag aagaaggttt ccatcttctt cggtactcaa   300
actggtactg ctgaaggttt tgctaaggct ttggctgatg aagctaaagc tagatacgaa   360
aaggctacct tcagagttgt tgatttggat gattatgctg ccgatgatga ccaatacgaa   420
gaaaaattga agaacgaatc cttcgccgtt ttcttgttgg ctacttatgg tgatggtgaa   480
cctactgata atgctgctag attttacaag tggttcgccg aaggtaaaga aagaggtgaa   540
tggttgcaaa acttgcacta tgctgttttt ggtttgggta acagacaata cgaacacttc   600
aacaagattg ctaaggttgc cgacgaatta ttggaagctc aaggtggtaa tagattggtt   660
aaggttggtt taggtgatga cgatcaatgc atcgaagatg atttttctgc ttggagagaa   720
tctttgtggc cagaattgga tatgttgttg agagatgaag atgatgctac tactgttact   780
actccatata ctgctgctgt cttggaatac agagttgtct ttcatgattc tgctgatgtt   840
gctgctgaag ataagtcttg gattaacgct aatggtcatg ctgttcatga tgctcaacat   900
ccattcagat ctaacgttgt cgtcagaaaa gaattgcata cttctgcctc tgatagatcc   960
tgttctcatt tggaattcaa catttccggt tccgctttga attacgaaac tggtgatcat  1020
gttggtgtct actgtgaaaa cttgactgaa actgttgatg aagccttgaa cttgttgggt  1080
ttgtctccag aaacttactt ctctatctac accgataacg aagatggtac tccattgggt  1140
ggttcttcat tgccaccacc atttccatca tgtactttga gaactgcttt gaccagatac  1200
gctgatttgt tgaactctcc aaaaaagtct gctttgttgg ctttagctgc tcatgcttct  1260
aatccagttg aagctgatag attgagatac ttggcttctc cagctggtaa agatgaatat  1320
gcccaatctg ttatcggttc ccaaaagtct ttgttggaag ttatggctga attcccatct  1380
gctaaaccac cattaggtgt ttttttgct gctgttgctc caagattgca acctagattc  1440
tactccattt catcctctcc aagaatggct ccatctagaa tccatgttac ttgtgctttg  1500
gtttacgata agatgccaac tggtagaatt cataagggtg tttgttctac ctggatgaag  1560
aattctgttc caatggaaaa gtcccatgaa tgttcttggg ctccaatttt cgttagacaa  1620
tccaatttta agttgccagc cgaatccaag gttccaatta tcatggttgg tccaggtact  1680
ggtttggctc cttttagagg tttttttacaa gaaagattgg ccttgaaaga atccggtgtt  1740
gaattgggtc catccatttt gtttttcggt tgcagaaaca gaagaatgga ttacatctac  1800
gaagatgaat tgaacaactt cgttgaaacc ggtgctttgt ccgaattggt tattgctttt  1860
tctagagaag gtcctaccaa agaatacgtc caacataaga tggctgaaaa ggcttctgat  1920
atctggaact tgatttctga aggtgcttac ttgtacgttt gtggtgatgc taaaggtatg  1980
gctaaggatg ttcatagaac cttgcatacc atcatgcaag aacaaggttc tttggattct  2040
tccaaagctg aatccatggt caagaacttg caaatgaatg gtagatactt aagagatgtt  2100
tggtaa                                                             2106

SEQ ID NO: 80
MKVSPFEFMS AIIKGRMDPS NSSFESTGEV ASVIFENREL VAILTTSIAV MIGCFVVLMW    60
RRAGSRKVKN VELPKPLIVH EPEPEVEDGK KKVSIFFGTQ TGTAEGFAKA LADEAKARYE   120
KATFRVVDLD DYAADDDQYE EKLKNESFAV FLLATYGDGE PTDNAARFYK WFAEGKERGE   180
WLQNLHYAVF GLGNRQYEHF NKIAKVADEL LEAQGGNRLV KVGLGDDDQC IEDDFSAWRE   240
SLWPELDMLL RDEDDATTVT TPYTAAVLEY RVVFHDSADV AAEDKSWINA NGHAVHDAQH   300
PFRSNVVVRK ELHTSASDRS CSHLEFNISG SALNYETGDH VGVYCENLTE TVDEALNLLG   360
LSPETYFSIY TDNEDGTPLG GSSLPPPFPS CTLRTALTRY ADLLNSPKKS ALLALAAHAS   420
NPVEADRLRY LASPAGKDEY AQSVIGSQKS LLEVMAEFPS AKPPLGVFFA AVAPRLQPRF   480
YSISSSPRMA PSRIHVTCAL VYDKMPTGRI HKGVCSTWMK NSVPMEKSHE CSWAPIFVRQ   540
SNFKLPAESK VPIIMVGPGT GLAPERGELQ ERLALKESGV ELGPSILFFG CRNRRMDYIY   600
EDELNNFVET GALSELVIAF SREGPTKEYV QHKMAEKASD IWNLISEGAY LYVCGDAKGM   660
AKDVHRTLHT IMQEQGSLDS SKAESMVKNL QMNGRYLRDV W                        701

SEQ ID NO: 81
atggcagaat tagatacact tgatatagta gtattaggtg ttatcttttt gggtactgtg    60
gcatacttta ctaagggtaa attgtggggt gttaccaagg atccatacgc taacggattc   120
gctgcaggtg gtgcttccaa gcctggcaga actagaaaca tcgtcgaagc tatggaggaa   180
tcaggtaaaa actgtgttgt tttctacggc agtcaaacag gtacagcgga ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtt   540
aacaaggctc tagaaaagtt aggagctcat agaattggag aagcaggtga gggtgacgac   600
ggagctggaa ctatggaaga ggactttta gcttggaaag atccaatgtg ggaagccttg    660
gctaaaaaga tgggcttgga ggaaagagaa gctgtatatg aacctatttt cgctatcaat   720
gagagagatg atttgacccc tgaagcgaat gaggtatact tgggagaacc taataagcta   780
```

TABLE 11-continued

Sequences disclosed herein.

```
cacttggaag gtacagcgaa aggtccattc aactcccaca acccatatat cgcaccaatt  840
gcagaatcat acgaactttt ctcagctaag gatagaaatt gtctgcatat ggaaattgat  900
atttctggta gtaatctaaa gtatgaaaca ggcgaccata tcgcgatctg gcctaccaac  960
ccaggtgaag aggtcaacaa atttcttgac attctagatc tgtctggtaa gcaacattcc 1020
gtcgtaacag tgaaagcctt agaacctaca gccaaagttc cttttccaaa tccaactacc 1080
tacgatgcta tattgagata ccatctggaa atatgcgctc cagtttctag acagtttgtc 1140
tcaactttag cagcattcgc ccctaatgat gatatcaaag ctgagatgaa ccgtttggga 1200
tcagacaaag attacttcca cgaaaagaca ggaccacatt actacaatat cgctagattt 1260
ttggcctcag tctctaaagg tgaaaaatgg acaaagatac cattttctgc tttcatagaa 1320
ggccttacaa aactacaacc aagatactat tctatctctt cctctagttt agttcagcct 1380
aaaaagatta gtattactgc tgttgtcgaa tctcagcaaa ttccaggtag agatgaccca 1440
ttcagaggtg tagcgactaa ctacttgttc gctttgaagc agaaacaaaa cggtgatcca 1500
aatccagctc cttttggcca atcatacgag ttgacaggac caaggaataa gtatgatggt 1560
atacatgttc cagtccatgt aagacattct aactttaagc taccatctga tccaggcaaa 1620
cctattatca tgatcggtcc aggtaccggt gttgcccctt ttagaggctt cgtccaagag 1680
agggcaaaac aagccagaga tggtgtagaa gttggtaaaa cactgctgtt ctttggatgt 1740
agaaagagta cagaagattt catgtatcaa aaagagtggc aagagtacaa ggaagctctt 1800
ggcgacaaat tcgaaatgat tacagctttt tcaagagaag gatctaaaaa ggtttatgtt 1860
caacacagac tgaaggaaag atcaaaggaa gtttctgatc ttctatccca aaaagcatac 1920
ttctacgttt gcggagacgc cgcacatatg gcacgtgaag tgaacactgt gttagcacag 1980
atcatagcag aaggccgtgg tgtatcagaa gccaagggtg aggaaattgt caaaaacatg 2040
agatcagcaa atcaatacca agtgtgttct gatttcgtaa ctttacactg taaagagaca 2100
acatacgcga attcagaatt gcaagaggat gtctggagtt aa                    2142
```

SEQ ID NO: 82

```
MAELDTLDIV VLGVIFLGTV AYFTKGKLWG VTKDPYANGF AAGGASKPGR TRNIVEAMEE   60
SGKNCVVFYG SQTGTAEDYA SRLAKEGKSR FGLNTMIADL EDYDFDNLDT VPSDNIVMFV  120
LATYGEGEPT DNAVDFYEFI TGEDASFNEG NDPPLGNLNY VAFGLGNNTY EHYNSMVRNV  180
NKALEKLGAH RIGEAGEGDD GAGTMEEDFL AWKDPMWEAL AKKMGLEERE AVYEPIFAIN  240
ERDDLTPEAN EVYLGEPNKL HLEGTAKGPF NSHNPYIAPI AESYELFSAK DRNCLHMEID  300
ISGSNLKYET GDHIAIWPTN PGEEVNKFLD ILDLSGKQHS VVTVKALEPT AKVPFPNPTT  360
YDAILRYHLE ICAPVSRQFV STLAAFAPND DIKAEMNRLG SDKDYFHEKT GPHYYNIARF  420
LASVSKGEKW TKIPFSAFIE GLTKLQPRYY SISSSSLVQP KKISITAVVE SQQIPGRDDP  480
FRGVATNYLF ALKQKQNGDP NPAPFGQSYE LTGPRNKYDG IHVPVHVRHS NFKLPSDPGK  540
PIIMIGPGTG VAPFRGFVQE RAKQARDGVE VGKTLLFFGC RKSTEDFMYQ KEWQEYKEAL  600
GDKFEMITAF SREGSKKVYV QHRLKERSKE VSDLLSQKAY FYVCGDAAHM AREVNTVLAQ  660
IIAEGRGVSE AKGEEIVKNM RSANQYQVCS DFVTLHCKET TYANSELQED VWS          713
```

SEQ ID NO: 83

```
atgcaatcgg aatccgttga agcatcgacg attgatttga tgactgctgt tttgaaggac   60
acagtgatcg atacagcgaa cgcatctgat aacggagact caaagatgcc gccggcgttg  120
gcgatgatgt tcgaaattcg tgatctgttg ctgattttga ctacgtcagt tgctgttttg  180
gtcggatgtt tcgttgtttt ggtgtggaag agatcgtccg ggaagaagtc cggcaaggaa  240
ttggagccgc cgaagatcgt tgtgccgaag aggcggctgg agcaggaggt tgatgatggt  300
aagaagaagg ttacgatttt cttcggaaca caaactggaa cggctgaagg tttcgctaag  360
gcacttttcg aagaagcgaa agcgcgatat gaaaaggcag cgtttaaagt gattgatttg  420
gatgattatg ctgctgattt ggatgagtat gcagagaagc tgaagaagga aacatatgct  480
ttcttcttct tggctacata tggagatggt gagccaactg ataatgctgc caaattttat  540
aaatggttta ctgagggaga cgagaaaggc gtttggcttc aaaaacttca atatggagta  600
tttggtcttg gcaacagaca atatgaacat ttcaacaaga ttggaatagt ggttgatgat  660
ggtctcaccg agcagggtgc aaaacgcatt gttcccgttg gtcttggaga cgacgatcaa  720
tcaattgaag acgatttttc ggcatggaaa gagttagtgt ggcccgaatt ggatctattg  780
cttcgcgatg aagatgacaa agctgctgca actccttaca cagctgcaat ccctgaatac  840
cgcgtcgtat ttcatgacaa acccgatgcg ttttctgatg atcatactca aaccaatggt  900
catgctgttc atgatgctca acatccatgc agatccaatg tggctgttaa aaaagagctt  960
catactcctg aatccgatcg ttcatgcaca catcttgaat ttgacatttc tcacactgga 1020
ttatcttatg aaactgggga tcatgttggt gtatactgtg aaaacctaat tgaagtagtg 1080
gaagaagctg ggaaattgtt aggattatca acagatactt atttctcgtt acatattgat 1140
aacgaagatg gttcaccact tggtggacct tcattacaac ctccttttcc tccttgtact 1200
ttaagaaaag cattgactaa ttatgcagat ctgttaagct ctcccaaaaa gtcaactttg 1260
cttgctctag ctgctcatgc ttccgatccc actgaagctg atcgtttaag atttcttgca 1320
tctcgcgagg gcaaggatga atatgctgaa tgggttgttg caaaccaaag aagtcttctt 1380
gaagtcatgg aagctttccc gtcagctaga ccgccacttg gtgttttctt tgcagcggtt 1440
gcaccgcgtt tacagcctcg ttactactct atttcttcct ccccaaagat ggaaccaaac 1500
aggattcatg ttacttgcgc gttggtttat gaaaaaactc ccgcaggtcg tatccacaaa 1560
ggaatctgct caacctggat gaagaacgct gtacctttga ccgaaagtca agattgcagt 1620
tgggcaccga tttttgttag aacatcaaac ttcagacttc caattgaccc gaaagtcccg 1680
gttatcatga ttggtcctgg aaccgggttg gctccattta ggggttttct tcaagaaaga 1740
ttggctctta aagaatccgg aaccgaactc gggtcatcta ttttattctt cggttgtaga 1800
aaccgcaaag tggattacat atatgagaat gaactcaaca actttgttga aaatggtgcg 1860
ctttctgagc ttgatgttgc tttctcccgc gatggcccga cgaaagaata cgtgcaacat 1920
aaaatgaccc aaaaggcttc tgaaatatgg aatatgcttt ctgagggagc atatttatat 1980
gtatgtggtg atgctaaagg catggctaaa gatgtacacc gtacacttca caccattgtg 2040
caagaacagg gaagtttgga ctcgtctaaa gcggagttgt atgtgaagaa tctacaaatg 2100
tcaggaagat acctccgtga tgtttggtaa                                  2130
```

SEQ ID NO: 84

```
MQSESVEAST IDLMTAVLKD TVIDTANASD NGDSKMPPAL AMMFEIRDLL LILTTSVAVL   60
```

TABLE 11-continued

| Sequences disclosed herein. |
|---|
| VGCFVVLVWK RSSGKKSGKE LEPPKIVVPK RRLEQEVDDG KKKVTIFFGT QTGTAEGFAK 120<br>ALFEEAKARY EKAAFKVIDL DDYAADLDEY AEKLKKETYA FFFLATYGDG EPTDNAAKFY 180<br>KWFTEGDEKG VWLQKLQYGV FGLGNRQYEH FNKIGIVVDD GLTEQGAKRI VPVGLGDDDQ 240<br>SIEDDFSAWK ELVWPELDLL LRDEDDKAAA TPYTAAIPEY RVVFHDKPDA FSDDHTQTNG 300<br>HAVHDAQHPC RSNVAVKKEL HTPESDRSCT HLEFDISHTG LSYETGDHVG VYCENLIEVV 360<br>EEAGKLLGLS TDTYFSLHID NEDGSPLGGP SLQPPFPPCT LRKALTNYAD LLSSPKKSTL 420<br>LALAAHASDP TEADRLRFLA SREGKDEYAE WVVANQRSLL EVMEAFPSAR PPLGVFFAAV 480<br>APRLQPRYYS ISSSPKMEPN RIHVTCALVY EKTPAGRIHK GICSTWMKNA VPLTESQDCS 540<br>WAPIFVRTSN FRLPIDPKVP VIMIGPGTGL APFRGFLQER LALKESGTEL GSSILFFGCR 600<br>NRKVDYIYEN ELNNFVENGA LSELDVAFSR DGPTKEYVQH KMTQKASEIW NMLSEGAYLY 660<br>VCGDAKGMAK DVHRTLHTIV QEQGSLDSSK AELYVKNLQM SGRYLRDVW 709 |
| SEQ ID NO: 85<br>*S. rebaudiana*<br>atgcaatcta actccgtgaa gatttcgccg cttgatctgg taactgcgct gtttagcggc 60<br>aaggttttgg acacatcgaa cgcatcggaa tcgggagaat ctgctatgct gccgactata 120<br>gcgatgatta tggagaatcg tgagctgttg atgatactca caacgtcggt tgctgtattg 180<br>atcggatgcg ttgtcgtttt ggtgtggcgg agatcgtcta cgaagaagtc ggcgttggag 240<br>ccaccggtga ttgtggttcc gaagagagtg caagaggagg aagttgatga tggtaagaag 300<br>aaagttacgg ttttcttcgg cacccaaact ggaacagctg aaggcttcgc taaggcactt 360<br>gttgaggaag ctaaagctcg atatgaaaag gctgtcttta aagtaattga tttggatgat 420<br>tatgctgctg atgacgatga gtatgaggag aaactaaaga aagaatcttt ggcctttttc 480<br>tttttggcta cgtatggaga tggtgagcca acagataatg ctgccagatt ttataaatgg 540<br>tttactgagg gagatgcgaa aggagaatgg cttaataagc ttcaatatgg agtatttggt 600<br>ttgggtaaca gacaatatga acattttaac aagatcgcaa aagtggttga tgatggtctt 660<br>gtagaacagg gtgcaaagcg tcttgttcct gttggacttg gagatgatga tcaatgtatt 720<br>gaagatgact tcaccgcatg gaaagagtta gtatggccgg agttggatca attacttcgt 780<br>gatgaggatg acacaactgt tgctactcca tacacagctg ctgttgcaga atatcgcgtt 840<br>gtttttcatg aaaaaccaga cgcgctttct gaagattata gttatacaaa tggccatgct 900<br>gttcatgatg ctcaacatcc atgcagatcc aacgtggctg tcaaaaagga acttcatagt 960<br>cctgaatctg accggtcttg cactcatctt gaatttgaca tctcgaacac cggactatca 1020<br>tatgaaactg ggaccatgt tggagtttac tgtgaaaact tgagtgaagt tgtgaatgat 1080<br>gctgaaagat tagtaggatt accaccagac acttactcct ccatccacac tgatagtgaa 1140<br>gacgggtcgc cacttggcgg agcctcattg ccgcctcctt tcccgccatg cactttaagg 1200<br>aaagcattga cgtgttatgc tgatgttttg agttctccca agaagtcggc tttgcttgca 1260<br>ctagctgctc atgccaccga tcccagtgaa gctgatagat tgaaatttct tgcatccccc 1320<br>gccggaaagg atgaatattc tcaatggata gttgcaagcc aaagaagtct ccttgaagtc 1380<br>atggaagcat tcccgtcagc taagccttca cttggtgttt tctttgcatc tgttgccccg 1440<br>cgcttacaac caagatacta ctctatttct tcctcaccca agatggcacc ggataggatt 1500<br>catgttacat gtgcattagt ctatgagaaa acacctgcag gccgcatcca caaaggagtt 1560<br>tgttcaactt ggatgaagaa cgcagtgcct atgaccgaga gtcaagattg cagttgggcc 1620<br>ccaatatacg tccgaacatc caatttcaga ctaccatctg accctaaggt cccggttatc 1680<br>atgattggac ctggcactgg tttggctcct tttagaggtt tccttcaaga gcggttagct 1740<br>ttaaaggaag ccggaactga cctcggttta tccattttat tcttcggatg taggaatcgc 1800<br>aaagtggatt tcatatatga aaacgagctt aacaactttg tggagactgg tgctctttct 1860<br>gagcttattg ttgctttctc ccgtgaaggc ccgactaagg aatatgtgca acacaagatg 1920<br>agtgagaagg cttcggatat ctggaacttg ctttctgaag gagcatattt atacgtatgt 1980<br>ggtgatgcca aaggcatggc caaagatgta catcgaaccc tccacacaat tgtgcaagaa 2040<br>cagggatctc ttgactcgtc aaaggcagaa ctctacgtga agaatctaca aatgtcagga 2100<br>agatacctcc gtgacgtttg gtaa 2124 |
| SEQ ID NO: 86<br>*S. rebaudiana*<br>MQSNSVKISP LDLVTALFSG KVLDTSNASE SGESAMLPTI AMIMENRELL MILTTSVAVL 60<br>IGCVVVLVWR RSSTKKSALE PPVIVVPKRV QEEEVDDGKK KVTVFFGTQT GTAEGFAKAL 120<br>VEEAKARYEK AVFKVIDLDD YAADDDEYEE KLKKESLAFF FLATYGDGEP TDNAARFYKW 180<br>FTEGDAKGEW LNKLQYGVFG LGNRQYEHFN KIAKVVDDGL VEQGAKRLVP VGLGDDDQCI 240<br>EDDFTAWKEL VWPELDQLLR DEDDTTVATP YTAAVAEYRV VFHEKPDALS EDYSYTNGHA 300<br>VHDAQHPCRS NVAVKKELHS PESDRSCTHL EFDISNTGLS YETGDHVGVY CENLSEVVND 360<br>AERLVGLPPD TYSSIHTDSE DGSPLGGASL PPPFPPCTLR KALTCYADVL SSPKKSALLA 420<br>LAAHATDPSE ADRLKFLASP AGKDEYSQWI VASQRSLLEV MEAFPSAKPS LGVFFASVAP 480<br>RLQPRYYSIS SSPKMAPDRI HVTCALVYEK TPAGRIHKGV CSTWMKNAVP MTESQDCSWA 540<br>PIYVRTSNFR LPSDPKVPVI MIGPGTGLAP FRGFLQERLA LKEAGTDLGL SILFFGCRNR 600<br>KVDFIYENEL NNFVETGALS ELIVAFSREG PTKEYVQHKM SEKASDIWNL LSEGAYLYVC 660<br>GDAKGMAKDV HRTLHTIVQE QGSLDSSKAE LYVKNLQMSG RYLRDVW 707 |
| SEQ ID NO: 87<br>atgtcctcca actccgattt ggtcagaaga ttggaatctg ttttgggtgt ttctttcggt 60<br>ggttctgtta ctgattccgt tgttgttatt gctaccacct ctattgcttt ggttatcggt 120<br>gttttggttt tgttgtggag aagatcctct gacagatcta gagaagttaa gcaattggct 180<br>gttccaaagc cagttactat cgttgaagaa gaagatgaat tcgaagttgc ttctggtaag 240<br>accagagttt ctattttcta cggtactcaa actggtactg ctgaaggttt tgctaaggct 300<br>ttggctgaag aaatcaaagc cagatacgaa aaagctgccg ttaaggttat tgatttggat 360<br>gattacacag ccgaagatga caaatacggt gaaaagttga agaaagaaac tatggccttc 420<br>ttcatgttgg ctacttatgg tgatggtgaa cctactgata atgctgctag attttacaag 480<br>tggttcaccg aaggtactga tagaggtgtt tggttggaac atttgagata cggtgtattc 540<br>ggtttgggta acagacaata cgaacacttc aacaagattg ccaaggttgt tgatgatttg 600<br>ttggttgaac aaggtgccaa gagattggtt actgttggtt tgggtgatga tgatcaatgc 660 |

TABLE 11-continued

Sequences disclosed herein.

```
atcgaagatg atttctccgc ttggaaagaa gccttgtggc cagaattgga tcaattattg   720
caagatgata ccaacaccgt ttctactcca tacactgctg ttattccaga atacagagtt   780
gttatccacg atccatctgt tacctcttat gaagatccat actctaacat ggctaacggt   840
aatgcctctt acgatattca tcatccatgt agagctaacg ttgccgtcca aaaagaattg   900
cataagccag aatctgacag aagttgcatc catttggaat tcgatatttt cgctactggt   960
ttgacttacg aaaccggtga tcatgttggt gtttacgctg ataattgtga tgatactgta  1020
gaagaagccg ctaagttgtt gggtcaacca ttggatttgt tgttctccat tcataccgat  1080
aacaacgacg gtacttcttt gggttcttct ttgccaccac catttccagg tccatgtact  1140
ttgagaactg ctttggctag atatgccgat ttgttgaatc caccaaaaaa ggctgctttg  1200
attgctttag ctgctcatgc tgatgaacca tctgaagctg aaagattgaa gttcttgtca  1260
tctccacaag gtaaggacga atattctaaa tgggttgtcg gttcccaaag atccttggtt  1320
gaagttatgg ctgaatttcc atctgctaaa ccaccattgg gtgtattttt tgctgctgtt  1380
gttcctagat tgcaacctag atattactcc atctcttcca gtccaagatt tgctccacat  1440
agagttcatg ttacttgcgc tttggtttat ggtccaactc caactggtag aattcacaga  1500
ggtgtatgtt cattctggat gaagaatgtt gtcccattgg aaaagtctca aaactgttct  1560
tgggccccaa ttttcatcag acaatctaat ttcaagttgc cagccgatca ttctgttcca  1620
atagttatgg ttggtccagg tactggttta gctcctttta gaggtttctt acaagaaaga  1680
ttggccttga aagaagaagg tgctcaagtt ggtcctgctt tgttgttttt tggttgcaga  1740
aacagacaaa tggacttcat ctacgaagtc gaattgaaca actttgtcga acaaggtgct  1800
ttgtccgaat tgatcgttgc tttttcaaga gaaggtccat ccaaagaata cgtccaacat  1860
aagatggttg aaaaggcagc ttacatgtgg aacttgattt ctcaaggtgg ttacttctac  1920
gtttgtggtg atgctaaagg tatggctaga gatgttcata gaacattgca taccatcgtc  1980
caacaagaag aaaaggttga ttctaccaag gccgaatcca tcgttaagaa attgcaaatg  2040
gacggtagat acttgagaga tgtttggtga                                   2070

SEQ ID NO: 88
MSSNSDLVRR LESVLGVSFG GSVTDSVVVI ATTSIALVIG VLVLLWRRSS DRSREVKQLA    60
VPKPVTIVEE EDEFEVASGK TRVSIFYGTQ TGTAEGFAKA LAEEIKARYE KAAVKVIDLD   120
DYTAEDDKYG EKLKKETMAF FMLATYGDGE PTDNAARFYK WFTEGTDRGV WLEHLRYGVF   180
GLGNRQYEHF NKIAKVVDDL LVEQGAKRLV TVGLGDDDQC IEDDFSAWKE ALWPELDQLL   240
QDDTNTVSTP YTAVIPEYRV VIHDPSVTSY EDPYSNMANG NASYDIHHPC RANVAVQKEL   300
HKPESDRSCI HLEFDIFATG LTYETGDHVG VYADNCDDTV EEAAKLLGQP LDLLFSIHTD   360
NNDGTSLGSS LPPPFPGPCT LRTALARYAD LLNPPKKAAL IALAAHADEP SEAERLKFLS   420
SPQGKDEYSK WVVGSQRSLV EVMAEFPSAK PPLGVFFAAV VPRLQPRYYS ISSSPRFAPH   480
RVHVTCALVY GPTPTGRIHR GVCSFWMKNV VPLEKSQNCS WAPIFIRQSN FKLPADHSVP   540
IVMVGPGTGL APFRGFLQER LALKEEGAQV GPALLFFGCR NRQMDFIYEV ELNNFVEQGA   600
LSELIVAFSR EGPSKEYVQH KMVEKAAYMW NLISQGGYFY VCGDAKGMAR DVHRTLHTIV   660
QQEEKVDSTK AESIVKKLQM DGRYLRDVW                                    689

SEQ ID NO: 89
atgacttctg cactttatgc ctccgatctt ttcaaacaat tgaaaagtat catgggaacg    60
gattctttgt ccgatgatgt tgtattagtt attgctacaa cttctctggc actggttgct   120
ggtttcgttg tcttattgtg gaaaaagacc acggcagatc gttccggcga gctaaagcca   180
ctaatgatcc ctaagtctct gatggcgaaa gatgaggatg atgacttaga tctaggttct   240
ggaaaaacga gagtctctat cttcttcggc acacaaaccg gaacagccga aggattcgct   300
aaagcacttt cagaagagat caaagcaaga tacgaaaagg cggctgtaaa agtaatcgat   360
ttggatgatt acgctgccga tgatgaccaa tatgaggaaa agttgaaaaa ggaaacattg   420
gctttctttt gtgtagccac gtatggtgat ggtgaaccaa ccgataacgc cgcaagattc   480
tacaagtggt ttactgaaga gaacgaaaga gatatcaagt tgcagcaact tgcttacggc   540
gtttttgcct taggtaacag acaatacgag cactttaaca agataggtat tgtcttagat   600
gaagagttat gcaaaaaggg tgcgaagaga ttgattgaag tcggtttagg agatgatgat   660
caatctatcg aggatgactt taatgcatgg aaggaatctt tgtggtctga attagataag   720
ttacttaagg acgaagatga taaatccgtt gccactccat acacagccgt cattccagaa   780
tatagagtag ttactcatga tccaagattc acaacacaga aatcaatgga aagtaatgtg   840
gctaatggta atactaccat cgatattcat catccatgta gagtagacgt tgcagttcaa   900
aaggaattgc acactcatga atcagacaga tcttgcatac atcttgaatt tgatatatca   960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tgcgtacgcc acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctcctttggg tgtttcttc   1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgtttttc  1740
ggctgtagaa acagacaaat ggatttcatc tacgaagatg aactgaataa ctttgtagat  1800
caaggagtta tttcagagtt gataatggct ttttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggcaagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                         2079

SEQ ID NO: 90
MTSALYASDL FKQLKSIMGT DSLSDDVVLV IATTSLALVA GFVVLLWKKT TADRSGELKP    60
```

TABLE 11-continued

Sequences disclosed herein.

LMIPKSLMAK DEDDDLDLGS GKTRVSIFFG TQTGTAEGFA KALSEEIKAR YEKAAVKVID 120
LDDYAADDDQ YEEKLKKETL AFFCVATYGD GEPTDNAARF YKWFTEENER DIKLQQLAYG 180
VFALGNRQYE HFNKIGIVLD EELCKKGAKR LIEVGLGDDD QSIEDDFNAW KESLWSELDK 240
LLKDEDDKSV ATPYTAVIPE YRVVTHDPRF TTQKSMESNV ANGNTTIDIH HPCRVDVAVQ 300
KELHTHESDR SCIHLEFDIS RTGITYETGD HVGVYAENHV EIVEEAGKLL GHSLDLVFSI 360
HADKEDGSPL ESAVPPPFPG PCTLGTGLAR YADLLNPPRK SALVALAAYA TEPSEAEKLK 420
HLTSPDGKDE YSQWIVASQR SLLEVMAAFP SAKPPLGVFF AAIAPRLQPR YYSISSSPRL 480
APSRVHVTSA LVYGPTPTGR IHKGVCSTWM KNAVPAEKSH ECSGAPIFIR ASNFKLPSNP 540
STPIVMVGPG TGLAPFRGFL QERMALKEDG EELGSSLLFF GCRNRQMDFI YEDELNNFVD 600
QGVISELIMA FSREGAQKEY VQHKMMEKAA QVWDLIKEEG YLYVCGDAKG MARDVHRTLH 660
TIVQEQEGVS SSEAEAIVKK LQTEGRYLRD VW 692

SEQ ID NO: 91
*A. thaliana*
atgtcttcct cttcctcttc cagtacctct atgattgatt tgatggctgc tattattaaa 60
ggtgaaccag ttatcgtctc cgacccagca aatgcctctg cttatgaatc agttgctgca 120
gaattgtctt caatgttgat cgaaaacaga caattcgcca tgatcgtaac tacatcaatc 180
gctgttttga tcggttgtat tgtcatgttg gtatggagaa gatccggtag tggtaattct 240
aaaagagtcg aacctttgaa accattagta attaagccaa gagaagaaga aatagatgac 300
ggtagaaaga aagttacaat atttttcggt acccaaactg gtacagctga aggttttgca 360
aaagccttag gtgaagaagc taaggcaaga tacgaaaaga ctagattcaa gatagtcgat 420
ttggatgact atgccgctga tgacgatgaa tacgaagaaa agttgaagaa agaagatgtt 480
gcattttttct ttttggcaac ctatggtgac ggtgaaccaa ctgacaatgc agccagattc 540
tacaaatggt ttacagaggg taatgatcgt ggtgaatggt tgaaaaactt aaagtacggt 600
gttttcggtt tgggtaacag acaatacgaa catttcaaca aagttgcaaa ggttgtcgac 660
gatattttgg tcgaacaagg tgctcaaaga ttagtccaag taggtttggg tgacgatgac 720
caatgtatag aagatgactt tactgcctgg agagaagctt tgtggcctga attagacaca 780
atcttgagag aagaaggtga caccgccgtt gctacccat atactgctgc agtattagaa 840
tacagagttt ccatccatga tagtgaagac gcaaagttta atgatatcac tttggccaat 900
ggtaacggtt atacagtttt cgatgcacaa cacccttaca aagctaacgt tgcagtcaag 960
agagaattac atacaccaga atccgacaga agttgtatac acttggaatt tgatatcgct 1020
ggttccggtt taaccatgaa gttgggtgac catgtaggtg ttttatgcga caatttgtct 1080
gaaactgttg atgaagcatt gagattgttg gatatgtccc ctgacactta ttttagtttg 1140
cacgctgaaa aagaagatgg tacaccaatt tccagttctt taccacctcc attccctcca 1200
tgtaacttaa gaacagcctt gaccagatac gcttgcttgt tatcatcccc taaaaagtcc 1260
gccttggttg ctttagccgc tcatgctagt gatcctactg aagcagaaag attgaaacac 1320
ttagcatctc cagccggtaa agatgaatat tcaaagtggg tagttgaatc tcaaagatca 1380
ttgttagaag ttatggcaga atttccatct gccaagcctc cattaggtgt cttctttgct 1440
ggtgtagcac ctagattgca accaagattc tactcaatca gttcttcacc taagatcgct 1500
gaaactagaa ttcatgttac atgtgcatta gtctacgaaa agatgccaac cggtagaatt 1560
cacaagggtg tatgctctac ttggatgaaa aatgctgttc cttacgaaaa atcagaaaag 1620
ttgttcttag gtagaccaat cttcgtaaga caatcaaact tcaagttgcc ttctgattca 1680
aaggttccaa taatcatgat aggtcctggt acaggtttag ccccattcag aggtttcttg 1740
caagaaagat tggctttagt tgaatctggt gtcgaattag gtccttcagt tttgttcttt 1800
ggttgtagaa acagaagaat ggatttcatc tatgaagaag aattgcaaag attcgtcgaa 1860
tctggtgcat tggccgaatt atctgtagct tttcaagag aaggtccaac taaggaatac 1920
gttcaacata agatgatgga taaggcatcc gacatatgga acatgatcag tcaaggtgct 1980
tatttgtacg tttgcggtga cgcaaagggt atggccagag atgtccatag atctttgcac 2040
acaattgctc aagaacaagg ttccatggat agtaccaaag ctgaaggttt cgtaaagaac 2100
ttacaaactt ccggtagata cttgagagat gtctggtga 2139

SEQ ID NO: 92
*A. thaliana*
MSSSSSSSTS MIDLMAAIIK GEPVIVSDPA NASAYESVAA ELSSMLIENR QFAMIVTTSI 60
AVLIGCIVML VWRRSGSGNS KRVEPLKPLV IKPREEEIDD GRKKVTIFFG TQTGTAEGFA 120
KALGEEAKAR YEKTRFKIVD LDDYAADDDE YEEKLKKEDV AFFFLATYGD GEPTDNAARF 180
YKWFTEGNDR GEWLKNLKYG VFGLGNRQYE HFNKVAKVVD DILVEQGAQR LVQVGLGDDD 240
QCIEDDFTAW REALWPELDT ILREEGDTAV ATPYTAAVLE YRVSIHDSED AKFNDITLAN 300
GNGYTVFDAQ HPYKANVAVK RELHTPESDR SCIHLEFDIA GSGLTMKLGD HVGVLCDNLS 360
ETVDEALRLL DMSPDTYFSL HAEKEDGTPI SSSLPPPFPP CNLRTALTRY ACLLSSPKKS 420
ALVALAAHAS DPTEAERLKH LASPAGKDEY SKWVVESQRS LLEVMAEFPS AKPPLGVFFA 480
GVAPRLQPRF YSISSSPKIA ETRIHVTCAL VYEKMPTGRI HKGVCSTWMK NAVPYEKSEK 540
LFLGRPIFVR QSNFKLPSDS KVPIIMIGPG TGLAPERGEL QERLALVESG VELGPSVLFF 600
GCRNRRMDFI YEEELQRFVE SGALAELSVA FSREGPTKEY VQHKMMDKAS DIWNMISQGA 660
YLYVCGDAKG MARDVHRSLH TIAQEQGSMD STKAEGFVKN LQTSGRYLRD VW 712

SEQ ID NO: 93
*S. rebaudiana*
atggaagcct cttacctata catttctatt ttgcttttac tggcatcata cctgttcacc 60
actcaactta gaaggaagag cgctaatcta ccaccaaccg tgtttccatc aataccaatc 120
attggacact tatacttact caaaaagcct ctttatagaa ctttagcaaa aattgccgct 180
aagtacggac caatactgca attacaactc ggctacagac gtgttctggt gatttcctca 240
ccatcagcag cagaagagtg ctttaccaat aacgatgtaa tcttcgcaaa tagacctaag 300
acattgtttg gcaaaatagt gggtggaaca tcccttggca gtttatccta cggcgatcaa 360
tggcgtaatc taaggagagt agcttctatc gaaatcctat cagttcatag gttgaacgaa 420
tttcatgata tcagagtgga tgagaacaga ttgttaatta gaaaacttag aagttcatct 480
tctcctgtta ctcttataac agtcttttat gctctaacat tgaacgtcat tatgagaatg 540
atctctggca aaagatattt cgacagtggg gatagagaat tggaggagga aggtaagaga 600

TABLE 11-continued

Sequences disclosed herein.

```
tttcgagaaa tcttagacga aacgttgctt ctagccggtg cttctaatgt tggcgactac   660
ttaccaatat tgaactggtt gggagttaag tctcttgaaa agaaattgat cgctttgcag   720
aaaaagagag atgacttttt ccagggtttg attgaacagg ttagaaaatc tcgtggtgct   780
aaagtaggca aaggtagaaa aacgatgatc gaactcttat tatctttgca agagtcagaa   840
cctgagtact atacagatgc tatgataaga tcttttgtcc taggtctgct ggctgcaggt   900
agtgatactt cagcgggcac tatggaatgg gccatgagct tactggtcaa tcacccacat   960
gtattgaaga aagctcaagc tgaaatcgat agagttatcg gtaataacag attgattgac  1020
gagtcagaca ttggaaatat ccccttacatc gggtgtatta tcaatgaaac tctaagactc  1080
tatccagcag ggccattgtt gttcccacat gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                                1503
```

SEQ ID NO: 94

*S. rebaudiana*

```
MEASYLYISI LLLLASYLFT TQLRRKSANL PPTVFPSIPI IGHLYLLKKP LYRTLAKIAA    60
KYGPILQLQL GYRRVLVISS PSAAEECFTN NDVIFANRPK TLFGKIVGGT SLGSLSYGDQ   120
WRNLRRVASI EILSVHRLNE FHDIRVDENR LLIRKLRSSS SPVTLITVFY ALTLNVIMRM   180
ISGKRYFDSG DRELEEEGKR FREILDETLL LAGASNVGDY LPILNWLGVK SLEKKLIALQ   240
KKRDDFFQGL IEQVRKSRGA KVGKGRKTMI ELLLSLQESE PEYYTDAMIR SFVLGLLAAG   300
SDTSAGTMEW AMSLLVNHPH VLKKAQAEID RVIGNNRLID ESDIGNIPYI GCIINETLRL   360
YPAGPLLFPH ESSADCVISG YNIPRGTMLI VNQWAIHHDP KVWDDPETFK PERFQGLEGT   420
RDGFKLMPFG SGRRGCPGEG LAIRLLGMTL GSVIQCFDWE RVGDEMVDMT EGLGVTLPKA   480
VPLVAKCKPR SEMTNLLSEL                                              500
```

SEQ ID NO: 95

```
atggaagtaa cagtagctag tagtgtagcc ctgagcctgg tctttattag catagtagta    60
agatgggcat ggagtgtggt gaattgggtg tggtttaagc cgaagaagct ggaaagattt   120
ttgagggagc aaggccttaa aggcaattcc tacaggtttt tatatggaga catgaaggag   180
aactctatcc tgctcaaaca agcaagatcc aaacccatga acctctccac ctcccatgac   240
atagcacctc aagtcacccc ttttgtcgac caaaccgtga aagcttacgg taagaactct   300
tttaattggg ttggccccat accaagggtg aacataatga atccagaaga tttgaaggac   360
gtcttaacaa aaaatgttga ctttgttaag ccaatatcaa acccacttat caagttgcta   420
gctacaggta ttgcaatcta tgaaggtgag aaatggacta aacacagaag gattatcaac   480
ccaacattcc attcggagag gctaaagcgt atgttacctt catttcacca aagttgtaat   540
gagatggtca aggaatggga gagcttggtg tcaaaagagg gttcatcatg tgagttggat   600
gtctggcctt ttcttgaaaa tatgtcggca gatgtgatct cgagaacagc atttggaact   660
agctacaaaa aaggacagaa aatctttgaa ctcttgagag agcaagtaat atatgtaacg   720
aaaggctttc aaagttttta cattccagga tggaggtttc tcccaactaa gatgaacaag   780
aggatgaatg agattaacga agaaataaaa ggattaatca ggggtattat aattgacaga   840
gagcaaatca ttaaggcagg tgaagaaacc aacgatgact tattaggtgc acttatggag   900
tcaaacttga aggacattcg ggaacatggg aaaaacaaca aaaatgttgg gatgagtatt   960
gaagatgtaa ttcaggagtg taagctgttt tactttgctg ggcaagaaac cacttcagtg  1020
ttgctggctt ggacaatggt tttacttggt caaaatcaga actggcaaga tcgagcaaga  1080
caagaggttt tgcaagtctt tggaagcagc aagccagatt ttgatggtct agctcacctt  1140
aaagtcgtaa ccatgatttt gcttgaagtt cttcgattat acccaccagt cattgaactt  1200
attcgaacca ttcacaagaa aacacaactt gggaagctct cactaccaga aggagttgaa  1260
gtccgcttac caacactgct cattcaccat gacaaggaac tgtggggtga tgatgcaaac  1320
cagttcaatc cagagaggtt ttcggaagga gtttccaaag caacaaagaa ccgactctca  1380
ttcttcccct tcggagccgg tccacgcatt tgcattggac agaacttttc tatgatggaa  1440
gcaaagttgg ccttagcatt gatcttgcaa cacttcacct ttgagctttc tccatctcat  1500
gcacatgctc cttcccatcg tataaccctt caaccacagt atggtgttcg tatcatttta  1560
catcgacgtt ag                                                      1572
```

SEQ ID NO: 96

*R. suavissimus*

```
atggaagtca ctgtcgcctc ttctgtcgct ttatccttag tcttcatttc cattgtcgtc    60
agatgggctt ggtccgttgt caactgggtt tggttcaaac caaagaagtt ggaaagattc   120
ttgagagagc aaggtttgaa gggtaattct tatagattct tgtacggtga catgaaggaa   180
aattctattt tgttgaagca agccagatcc aaaccaatga acttgtctac ctctcatgat   240
attgctccac aagttactcc attcgtcgat caaactgtta aagcctacgg taagaactct   300
ttcaattggg ttggtccaat tcctagagtt aacatcatga acccagaaga tttgaaggat   360
gtcttgacca agaacgttga cttcgttaag ccaatttcca acccattgat taaattgttg   420
gctactggta ttgccattta cgaaggtgaa aagtggacta agcatagaag aatcatcaac   480
cctaccttcc actctgaaag attgaagaga atgttaccat ctttccatca atcctgtaat   540
gaaatggtta aggaatggga atccttggtt tctaaagaag gttcttcttg cgaattggat   600
gtttggccat tcttggaaaa tatgtctgct gatgtcattt ccagaaccgc tttcggtacc   660
tcctacaaga agggtcaaaa gattttcgaa ttgttgagag agcaagttat ttacgttacc   720
aagggtttcc aatccttcta catcccaggt tggagattct tgccaactaa aatgaacaag   780
cgtatgaacg agatcaacga agaaattaaa ggtttgatca gaggtattat tatcgacaga   840
gaacaaatta ttaaagctgg tgaagaaacc aacgatgatt tgttgggtgc tttgatggag   900
tccaacttga aggatattag agaacatggt aagaacaaca agaatgttgg tatgtctatt   960
gaagatgtta ttcaagaatg taagttattc tacttcgctg gtcaagagac cacttctgtt  1020
ttgttagcct ggactatggt cttgttaggt caaaaccaaa attggcaaga tagagctaga  1080
```

TABLE 11-continued

Sequences disclosed herein.

```
caagaagttt tgcaagtctt cggttcttcc aagccagact ttgatggttt ggcccacttg  1140
aaggttgtta ctatgatttt gttagaagtt ttgagattgt acccaccagt cattgagtta  1200
atcagaacca ttcataaaaa gactcaattg ggtaaattat ctttgccaga aggtgttgaa  1260
gtcagattac caaccttgtt gattcaccac gataaggaat tatggggtga cgacgctaat  1320
caatttaatc cagaaagatt ttccgaaggt gtttccaagg ctaccaaaaa ccgtttgtcc  1380
ttcttcccat ttggtgctgg tccacgtatt tgtatcggtc aaaacttttc catgatggaa  1440
gccaagttgg ctttggcttt aatcttgcaa cacttcactt tcgaattgtc tccatcccat  1500
gcccacgctc cttctcatag aatcacttta caaccacaat acggtgtcag aatcatctta  1560
cacagaagat aa                                                      1572
```

SEQ ID NO: 97
*R. suavissimus*

```
MEVTVASSVA LSLVFISIVV RWAWSVVNWV WFKPKKLERF LREQGLKGNS YRFLYGDMKE   60
NSILLKQARS KPMNLSTSHD IAPQVTPFVD QTVKAYGKNS FNWVGPIPRV NIMNPEDLKD  120
VLTKNVDFVK PISNPLIKLL ATGIAIYEGE KWTKHRRIIN PTFHSERLKR MLPSFHQSCN  180
EMVKEWESLV SKEGSSCELD VWPFLENMSA DVISRTAFGT SYKKGQKIFE LLREQVIYVT  240
KGFQSFYIPG WRFLPTKMNK RMNEINEEIK GLIRGIIIDR EQIIKAGEET NDDLLGALME  300
SNLKDIREHG KNNKNVGMSI EDVIQECKLF YFAGQETTSV LLAWTMVLLG QNQNWQDRAR  360
QEVLQVFGSS KPDFDGLAHL KVVTMILLEV LRLYPPVIEL IRTIHKKTQL GKLSLPEGVE  420
VRLPTLLIHH DKELWGDDAN QFNPERFSEG VSKATKNRLS FFPFGAGPRI CIGQNFSMME  480
AKLALALILQ HFTFELSPSH AHAPSHRITL QPQYGVRIIL HRR                    523
```

SEQ ID NO: 98

```
atggaagcat caagggctag ttgtgttgcg ctatgtgttg tttgggtgag catagtaatt    60
acattggcat ggagggtgct gaattgggtg tggttgaggc caaagaaact agaaagatgc   120
ttgagggagc aaggccttac aggcaattct tacaggcttt tgtttggaga caccaaggat   180
ctctcgaaga tgctggaaca aacacaatcc aaacccatca aactctccac ctcccatgat   240
atagcgccac gagtcacccc atttttccat cgaactgtga actctaatgg caagaattct   300
tttgtttgga tgggccctat accaagagtg cacatcatga atccagaaga tttgaaagat   360
gccttcaaca gacatgatga ttttcataag acagtaaaaa atcctatcat gaagtctcca   420
ccaccgggca ttgtaggcat tgaaggtgag caatgggcta aacacagaaa gattatcaac   480
ccagcattcc atttagagaa gctaaagggt atggtaccaa tattttacca aagttgtagc   540
gagatgatta acaaatggga gagcttggtg tccaaagaga gttcatgtga gttggatgtg   600
tggccttatc ttgaaaattt taccagcgat gtgatttccc gagctgcatt tggaagtagc   660
tatgaagagg gaaggaaaat atttcaacta ctaagagagg aagcaaaagt ttattcggta   720
gctctacgaa gtgtttacat tccaggatgg aggtttctac caaccaagca gaacaagaag   780
acgaaggaaa ttcacaatga aattaaaggc ttacttaagg gcattataaa taaaagggaa   840
gaggcgatga aggcagggga agccactaaa gatgacttac taggaatact tatggagtcc   900
aacttcaggg aaattcagga acatgggaac aacaaaaatg ctggaatgag tattgaagat   960
gtaattggag agtgtaagtt gttttacttt gctgggcaag agaccacttc ggtgttgctt  1020
gtttggacaa tgattttact aagccaaaat caggattggc aagctcgtgc aagagaagag  1080
gtcttgaaag tctttggaag caacatccca acctatgaag agctaagtca cctaaaagtt  1140
gtgaccatga ttttacttga agttcttcga ttataccccat cagtcgttgc gcttcctcga  1200
accactcaca agaaaacaca gcttggaaaa ttatcattac cagctggagt ggaagtctcc  1260
ttgcccatac tgcttgttca ccatgacaaa gagttgtggg gtgaggatgc aaatgagttc  1320
aagccagaga ggttttcaga gggagtttca aaggcaacaa agaacaaatt tacatactta  1380
cctttcggag ggggtccaag gatttgcatt ggacaaaact ttgccatggt ggaagctaaa  1440
ttggccttgg ccctgatttt acaacacttt gcctttgagc tttctccatc ctatgctcat  1500
gctccttctg cagttataac ccttcaacct caatttggtg ctcatatcat tttgcataaa  1560
cgttga                                                             1566
```

SEQ ID NO: 99

```
atggaagctt ctagagcatc ttgtgttgct ttgtgtgttg tttgggtttc catcgttatt    60
actttggctt ggagagtttt gaattgggtc tggttaagac caaaaaagtt ggaaagatgc   120
ttgagagaac aaggtttgac tggtaactct tacagattgt tgttcggtga taccaaggac   180
ttgtctaaga tgttggaaca aactcaatcc aagcctatca agttgtctac ctctcatgat   240
attgctccaa gagttactcc attcttccat agaactgtta actccaacgg taagaactct   300
tttgtttgga tgggtccaat tccaagagtc catattatga accctgaaga tttgaaggac   360
gctttcaaca gacatgatga tttccataag accgtcaaga acccaattat gaagtctcca   420
ccaccaggta tagttggtat tgaaggtgaa caatgggcca aacatagaaa gattattaac   480
ccagccttcc acttggaaaa gttgaaaggt atggttccaa tcttctacca atcctgctct   540
gaaatgatta acaagtggga atccttggtt tccaaagaat cttcctgtga attggatgtc   600
tggccatatt tggaaaactt cacctccgat gttatttcca gagctgcttt tggttcttct   660
tacgaagaag gtagaaagat cttccaatta ttgagagaag aagccaaggt ttactccgtt   720
gctttgagat ctgtttacat tccaggttgg agattcttgc caactaagca aaacaaaaag   780
accaaagaaa tccacaacga aatcaagggt ttgttgaagg gtatcatcaa caagagagaa   840
gaagctatga aggctggtga agctacaaaa gatgatttgt tgggtatctt gatggaatcc   900
aacttcagag aaatccaaga acacggtaac aacaagaatg ccggtatgtc tattgaagat   960
gttatcggtg aatgcaagtt gttctacttt gctggtcaag aaactacctc cgttttgttg  1020
gtttggacca tgattttgtt gtcccaaaat caagattggc aagctagagc tagagaagaa  1080
gtcttgaaag ttttcggttc taacatccca acctacgaag aattgtctca cttgaaggtt  1140
gtcactatga tcttgttgga agtattgaga ttataccat ccgttgttgc attgccaaga  1200
actactcata agaaaactca attgggtaaa ttgtccttgc cagctggtgt tgaagtttct  1260
ttgccaattt tgttagtcca ccacgacaaa gaattgtggg gtgaagatgc taatgaattc  1320
aagccagaaa gattctccga aggtgtttct aaagctacca agaacaagtt cacttacttg  1380
ccatttggtg gtggtccaag aatatgtatt ggtcaaaatt tcgctatggt cgaagctaaa  1440
ttggctttgg ctttgatctt gcaacatttc gctttcgaat tgtcaccatc ttatgctcat  1500
```

TABLE 11-continued

Sequences disclosed herein.

```
gctccatctg ctgttattac attgcaacca caatttggtg cccatatcat cttgcataag 1560
agataac                                                           1567

SEQ ID NO: 100
MEASRASCVA LCVVWVSIVI TLAWRVLNWV WLRPKKLERC LREQGLTGNS YRLLFGDTKD   60
LSKMLEQTQS KPIKLSTSHD IAPRVTPFFH RTVNSNGKNS FVWMGPIPRV HIMNPEDLKD  120
AFNRHDDFHK TVKNPIMKSP PPGIVGIEGE QWAKHRKIIN PAFHLEKLKG MVPIFYQSCS  180
EMINKWESLV SKESSCELDV WPYLENFTSD VISRAAFGSS YEEGRKIFQL LREEAKVYSV  240
ALRSVYIPGW RFLPTKQNKK TKEIHNEIKG LLKGIINKRE EAMKAGEATK DDLLGILMES  300
NFREIQEHGN NKNAGMSIED VIGECKLFYF AGQETTSVLL VWTMILLSQN QDWQARAREE  360
VLKVFGSNIP TYEELSHLKV VTMILLEVLR LYPSVVALPR TTHKKTQLGK LSLPAGVEVS  420
LPILLVHHDK ELWGEDANEF KPERFSEGVS KATKNKFTYL PFGGGPRICI GQNFAMVEAK  480
LALALILQHF AFELSPSYAH APSAVITLQP QFGAHIILHK R                      521

SEQ ID NO: 101
ASWVAVLSVV WVSMVIAWAW RVLNWVWLRP KKLEKCLREQ GLAGNSYRLL FGDTKDLSKM   60
LEQTQSKPIK LSTSHDIAPH VTPFFHQTVN SYGKNSFVWM GPIPRVHIMN PEDLKDTFNR  120
HDDFHKVVKN PIMKSLPQGI VGIEGEQWAK HRKIINPAFH LEKLKGMVPI FYRSCSEMIN  180
KWESLVSKES SCELDVWPYL ENFTSDVISR AAFGSSYEEG RKIFQLLREE AKIYTVAMRS  240
VYIPGWRFLP TKQNKKAKEI HNEIKGLLKG IINKREEAMK AGEATKDDLL GILMESNFRE  300
IQEHGNNKNA GMSIEDVIGE CKLFYFAGQE TTSVLLVWTM VLLSQNQDWQ ARAREEVLQV  360
FGSNIPTYEE LSQLKVVTMI LLEVLRLYPS VVALPRTTHK KTQLGKLSLP AGVEVSLPIL  420
LVHHDKELWG EDANEFKPER FSEGVSKATK NQFTYFPFGG GPRICIGQNF AMMEAKLALS  480
LILRHFALEL SPLYAHAPSV TITLQPQYGA HIILHKR                           517

SEQ ID NO: 102
MEASRPSCVA LSVVLVSIVI AWAWRVLNWV WLRPNKLERC LREQGLTGNS YRLLFGDTKE   60
ISMMVEQAQS KPIKLSTTHD IAPRVIPFSH QIVYTYGRNS FVWMGPTPRV TIMNPEDLKD  120
AFNKSDEFQR AISNPIVKSI SQGLSSLEGE KWAKHRKIIN PAFHLEKLKG MLPTFYQSCS  180
EMINKWESLV FKEGSREMDV WPYLENLTSD VISRAAFGSS YEEGRKIFQL LREEAKFYTI  240
AARSVYIPGW RFLPTKQNKR MKEIHKEVRG LLKGIINKRE DAIKAGEAAK GNLLGILMES  300
NFREIQEHGN NKNAGMSIED VIGECKLFYF AGQETTSVLL VWTLVLLSQN QDWQARAREE  360
VLQVFGTNIP TYDQLSHLKV VTMILLEVLR LYPAVVELPR TTYKKTQLGK FLLPAGVEVS  420
LHIMLAHHDK ELWGEDAKEF KPERFSEGVS KATKNQFTYF PFGAGPRICI GQNFAMLEAK  480
LALSLILQHF TFELSPSYAH APSVTITLHP QFGAHFILHK R                      521

SEQ ID NO: 103
CVALSVVLVS IVIAWAWRVL NWVWLRPNKL ERCLREQGLT GNSYRLLFGD TKEISMMVEQ   60
AQSKPIKLST THDIAPRVIP FSHQIVYTYG RNSFVWMGPT PRVTIMNPED LKDAFNKSDE  120
FQRAISNPIV KSISQGLSSL EGEKWAKHRK IINPAFHLEK LKGMLPTFYQ SCSEMINKWE  180
SLVFKEGSRE MDVWPYLENL TSDVISRAAF GSSYEEGRKI FQLLREEAKF YTIAARSVYI  240
PGWRFLPTKQ NKRMKEIHKE VRGLLKGIIN KREDAIKAGE AAKGNLLGIL MESNFREIQE  300
HGNNKNAGMS IEDVIGECKL FYFAGQETTS VLLVWTLVLL SQNQDWQARA REEVLQVFGT  360
NIPTYDQLSH LKVVTMILLE VLRLYPAVVE LPRTTYKKTQ LGKFLLPAGV EVSLHIMLAH  420
HDKELWGEDA KEFKPERFSE GVSKATKNQF TYFPFGAGPR ICIGQNFAML EAKLALSLIL  480
QHFTFELSPS YAHAPSVTIT LHPQFGAHFI LHKR                              514

SEQ ID NO: 104
MGPIPRVHIM NPEDLKDTFN RHDDFHKVVK NPIMKSLPQG IVGIEGDQWA KHRKIINPAF   60
HLEKLKGMVP IFYQSCSEMI NIWKSLVSKE SSCELDVWPY LENFTSDVIS RAAFGSSYEE  120
GRKIFQLLRE EAKVYTVAVR SVYIPGWRFL PTKQNKKTKE IHNEIKGLLK GIINKREEAM  180
KAGEATKDDL LGILMESNFR EIQEHGNNKN AGMSIEDVIG ECKLFYFAGQ ETTSVLLVWT  240
MVLLSQNQDW QARAREEVLQ VFGSNIPTYE ELSHLKVVTM ILLEVLRLYP SVVALPRTTH  300
KKTQLGKLSL PAGVEVSLPI LLVHHDKELW GEDANEFKPE RFSEGVSKAT KNQFTYFPFG  360
GGPRICIGQN FAMMEAKLAL SLILQHFTFE LSPQYSHAPS VTITLQPQYG AHLILHKR     418

SEQ ID NO: 105
atgggtttgt tcccattaga ggattcctac gcgctggtct ttgaaggact agcaataaca   60
ctggctttgt actatctact gtctttcatc tacaaaacat ctaaaaagac atgtacacct  120
cctaaagcat ctggtgaaat cattccaatt acaggaatca tattgaatct gctatctggc  180
tcaagtggtc tacctattat cttagcactt gcctctttag cagacagatg tggtcctatt  240
ttcaccatta ggctgggtat taggagagtg ctagtagtat caaattggga aatcgctaag  300
gagattttca ctacccacga tttgatagtt tctaatagac caaaatactt agccgctaag  360
attcttggtt tcaattatgt ttcattctct ttcgctccat acggcccata ttgggtcgga  420
atcagaaaga ttattgctac aaaactaatg tcttcttcca gacttcagaa gttgcaattt  480
gtaagagttt ttgaactaga aaactctatg aaatctatca gagaatcatg gaaggagaaa  540
aaggatgaag agggaaaggt attagttgag atgaaaaagt ggttctggga actgaatatg  600
aacatagtgt taaggacagt tgctggtaaa caatacactg gtacagttga tgatgccgat  660
gcaaagcgta tctccgagtt attcagagaa tggtttcact acactggcag atttgtcgtt  720
ggagacgctt ttcctttttct aggttggttg gacctgggcg gatacaaaaa gacaatggaa  780
ttagttgcta gtagattgga ctcaatggtc agtaaatggt tagatgagca tcgtaaaaag  840
caagctaacg atgacaaaaa ggaggatatg gatttcatgg atatcatgat ctccatgaca  900
gaagcaaatt caccacttga aggatacggc actgatacta ttatcaagac cacatgtatg  960
actttgattg tttcaggagt tgatacaacc tcaatcgtac ttacttgggc cttatcactt 1020
ttgttaaaca acagagatac tttgaaaaag gcacaagagg aattagatat gtgcgtaggt 1080
aaaggaagac aagtcaacga gtctgatctt gttaacttga tatacttgga agcagtgctt 1140
aaagaggctt taagacttta cccagcagcg ttcttaggcg gaccaagagc attcttggaa 1200
gattgtactg ttgctggtta tagaattcca aagggcacct gcttgttgat taacatgtgg 1260
```

TABLE 11-continued

Sequences disclosed herein.

```
aaactgcata gagatccaaa catttggagt gatccttgcg aattcaagcc agaaagattt 1320
ttgacaccta atcaaaagga tgttgatgtg atcggtatgg atttcgaatt gataccattt 1380
ggtgccggca gaagatattg tccaggtact agattggctt tacagatgtt gcatatcgta 1440
ttagcgacat tgctgcaaaa cttcgaaatg tcaacaccaa acgatgcgcc agtcgatatg 1500
actgcttctg ttggcatgac aaatgccaaa gcatcacctt tagaagtctt gctatcacct 1560
cgtgttaaat ggtcctaa 1578

SEQ ID NO: 106
MGLFPLEDSY ALVFEGLAIT LALYYLLSFI YKTSKKTCTP PKASGEHPIT GHLNLLSGSS 60
GLPHLALASL ADRCGPIFTI RLGIRRVLVV SNWEIAKEIF TTHDLIVSNR PKYLAAKILG 120
FNYVSFSFAP YGPYWVGIRK IIATKLMSSS RLQKLQFVRV FELENSMKSI RESWKEKKDE 180
EGKVLVEMKK WFWELNMNIV LRTVAGKQYT GTVDDADAKR ISELFREWFH YTGRFVVGDA 240
FPFLGWLDLG GYKKTMELVA SRLDSMVSKW LDEHRKKQAN DDKKEDMDFM DIMISMTEAN 300
SPLEGYGTDT IIKTTCMTLI VSGVDTTSIV LTWALSLLLN NRDTLKKAQE ELDMCVGKGR 360
QVNESDLVNL IYLEAVLKEA LRLYPAAFLG GPRAFLEDCT VAGYRIPKGT CLLINMWKLH 420
RDPNIWSDPC EFKPERFLTP NQKDVDVIGM DFELIPFGAG RRYCPGTRLA LQMLHIVLAT 480
LLQNFEMSTP NDAPVDMTAS VGMTNAKASP LEVLLSPRVK WS 522

SEQ ID NO: 107
atgatacaag ttttaactcc aattctactc ttcctcatct tcttcgtttt ctggaaagtc 60
tacaaacatc aaaagactaa aatcaatcta ccaccaggtt ccttcggctg gccatttttg 120
ggtgaaacct tagccttact tagagcaggc tgggattctg agccagaaag attcgtaaga 180
gagcgtatca aaaagcatgg atctccactt gttttcaaga catcactatt tggagacaga 240
ttcgctgttc tttgcggtcc agctggtaat aagtttttgt tctgcaacga aaacaaatta 300
gtggcatctt ggtggccagt ccctgtaagg aagttgttcg gtaaaagttt actcacaata 360
agaggagatg aagcaaaatg gatgagaaaa atgctattgt cttacttggg tccagatgca 420
tttgccacac attatgccgt tactatggat gttgtaacac gtagacatat tgatgtccat 480
tggaggggca aggaggaagt taatgtattt caaacagtta agttgtacgc attcgaatta 540
gcttgtagat tattcatgaa cctagatgac ccaaaccaca tcgcgaaact cggtagtctt 600
ttcaacattt tcctcaaagg gatcatcgag cttcctatag acgttcctgg aactagattt 660
tactccagta aaaaggccgc agctgccatt agaattgaat tgaaaaagct cattaaagct 720
agaaaactcg aattgaagga gggtaaggcg tcttcttcac aggacttgct ttctcatcta 780
ttaacatcac ctgatgagaa tgggatgttc ttgacagaag aggaaatagt cgataacatt 840
ctacttttgt tattcgctgg tcacgatacc tctgcactat caataacact tttgatgaaa 900
accttaggtg aacacagtga tgtgtacgac aaggttttga aggaacaatt agaaatttcc 960
aaaacaaagg aggcttggga atcactaaag tgggaagata tccagaagat gaagtactca 1020
tggtcagtaa tctgtgaagt catgagattg aatcctcctg tcatagggac atacagagag 1080
gcgttggttg atatcgacta tgctggttac actatcccaa aaggatggaa gttgcattgg 1140
tcagctgttt ctactcaaag agacgaagcc aatttcgaag atgtaactag attcgatcca 1200
tccagatttg aaggggcagg ccctactcca ttcacatttg tgcctttcgg tggaggtcct 1260
agaatgtgtt taggcaaaga gtttgccagg ttagaagtgt tagcatttct ccacaacatt 1320
gttaccaact ttaagtggga tcttctaatc cctgatgaga agatcgaata tgatccaatg 1380
gctactccag ctaagggctt gccaattaga cttcatccac accaagtcta a 1431

SEQ ID NO: 108
MIQVLTPILL FLIFFVFWKV YKHQKTKINL PPGSFGWPFL GETLALLRAG WDSEPERFVR 60
ERIKKHGSPL VFKTSLFGDR FAVLCGPAGN KFLFCNENKL VASWWPVPVR KLFGKSLLTI 120
RGDEAKWMRK MLLSYLGPDA FATHYAVTMD VVTRRHIDVH WRGKEEVNVF QTVKLYAFEL 180
ACRLFMNLDD PNHIAKLGSL FNIFLKGIIE LPIDVPGTRF YSSKKAAAAI RIELKKLIKA 240
RKLELKEGKA SSSQDLLSHL LTSPDENGMF LTEEEIVDNI LLLLFAGHDT SALSITLLMK 300
TLGEHSDVYD KVLKEQLEIS KTKEAWESLK WEDIQKMKYS WSVICEVMRL NPPVIGTYRE 360
ALVDIDYAGY TIPKGWKLHW SAVSTQRDEA NFEDVTRFDP SRFEGAGPTP FTFVPFGGGP 420
RMCLGKEFAR LEVLAFLHNI VTNFKWDLLI PDEKIEYDPM ATPAKGLPIR LHPHQV 476

SEQ ID NO: 109
atggagtctt tagtggttca tacagtaaat gctatctggt gtattgtaat cgtcgggatt 60
ttctcagttg gttatcacgt ttacggtaga gctgtggtcg aacaatggag aatgagaaga 120
tcactgaagc tacaaggtgt taaaggccca ccaccatcca tcttcaatgg taacgtctca 180
gaaatgcaac gtatccaatc cgaagctaaa cactgctctg gcgataacat tatctcacat 240
gattattctt cttcattatt cccacacttc gatcactgga gaaaacagta cggcagaatc 300
tacacatact ctactggatt aaagcaacac ttgtacatca atcatccaga aatggtgaag 360
gagctatctc agactaacac attgaacttg ggtagaatca cccatataac caaaagattg 420
aatcctatct taggtaacgg aatcataacc tctaatggtc ctcattgggc ccatcagcgt 480
agaattatcg cctacgagtt tactcatgat aagatcaagg gtatggttgg tttgatggtt 540
gagtctgcta tgcctatgtt gaataagtgg gaggagatgg taaagagagg cggagaaatg 600
ggatgcgaca taagagttga tgaggacttg aaagatgttt cagcagatgt gattgcaaaa 660
gcctgtttcg gatcctcatt ttctaaaggt aaggctattt tctctatgat aagagatttg 720
cttacagcta tcacaaagag aagtgttcta ttcagattca acggattcac tgatatggtc 780
tttgggagta aaaagcatgg tgacgttgat atagacgctt tagaaatgga attggaatca 840
tccatttggg aaactgtcaa ggaacgtgaa atagaatgta aagatactca caaaaaggat 900
ctgatgcaat tgattttgga aggggcaatg cgttcatgtg acggtaacct ttgggataaa 960
tcagcatata gaagatttgt tgtagataat tgtaaatcta tctacttcgc agggcatgat 1020
agtacagctg tctcagtgtc atggtgtttg atgttactgg ccctaaaccc atcatggcaa 1080
gttaagatcc gtgatgaaat tctgtcttct tgcaaaaatg gtattccaga tgccgaaagt 1140
atcccaaacc ttaaaacagt gactatggtt attcaagaga caatgagatt ataccctcca 1200
gcaccaatcg tcgggagaga agcctctaaa gatatcagat tgggcgatct agttgttcct 1260
aaaggcgtct gtatatggac actaatacca gctttacaca gagatcctga gatttgggga 1320
ccagatgcaa acgatttcaa accagaaaga ttttctgaag gaatttcaaa ggcttgtaag 1380
```

TABLE 11-continued

Sequences disclosed herein.

```
tatcctcaaa gttacattcc atttggtctg ggtcctagaa catgcgttgg taaaaacttt 1440
ggcatgatgg aagtaaaggt tcttgtttcc ctgattgtct ccaagttctc tttcactcta 1500
tctcctacct accaacatag tcctagtcac aaacttttag tagaaccaca acatggggtg 1560
gtaattagag tggtttaa 1578

SEQ ID NO: 110
MESLVVHTVN AIWCIVIVGI FSVGYHVYGR AVVEQWRMRR SLKLQGVKGP PPSIFNGNVS 60
EMQRIQSEAK HCSGDNIISH DYSSSLFPHF DHWRKQYGRI YTYSTGLKQH LYINHPEMVK 120
ELSQTNTLNL GRITHITKRL NPILGNGIIT SNGPHWAHQR RIIAYEFTHD KIKGMVGLMV 180
ESAMPMLNKW EEMVKRGGEM GCDIRVDEDL KDVSADVIAK ACFGSSFSKG KAIFSMIRDL 240
LTAITKRSVL FRFNGFTDMV FGSKKHGDVD IDALEMELES SIWETVKERE IECKDTHKKD 300
LMQLILEGAM RSCDGNLWDK SAYRRFVVDN CKSIYFAGHD STAVSVSWCL MLLALNPSWQ 360
VKIRDEILSS CKNGIPDAES IPNLKTVTMV IQETMRLYPP APIVGREASK DIRLGDLVVP 420
KGVCIWTLIP ALHRDPEIWG PDANDFKPER FSEGISKACK YPQSYIPFGL GPRTCVGKNF 480
GMMEVKVLVS LIVSKFSFTL SPTYQHSPSH KLLVEPQHGV VIRVV 525

SEQ ID NO: 111
atgtacttcc tactacaata cctcaacatc acaaccgttg gtgtctttgc cacattgttt 60
ctctcttatt gtttacttct ctggagaagt agagcgggta acaaaaagat tgccccagaa 120
gctgccgctg catggcctat tatcggccac ctccacttac ttgcaggtgg atcccatcaa 180
ctaccacata ttacattggg taacatggca gataagtacg gtcctgtatt cacaatcaga 240
ataggcttgc atagagctgt agttgtctca tcttgggaaa tggcaaagga atgttcaaca 300
gctaatgatc aagtgtcttc ttcaagacct gaactattag cttctaagtt gttgggttat 360
aactacgcca tgtttggttt ttcaccatac ggttcatact ggagagaaat gagaaagatc 420
atctctctcg aattactatc taattccaga ttggaactat tgaaagatgt tagagcctca 480
gaagttgtca catctattaa ggaactatac aaattgtggg cggaaaagaa gaatgagtca 540
ggattggttt ctgtcgagat gaaacaatgg ttcggagatt tgactttaaa cgtgatcttg 600
agaatggtgg ctggtaaaag atacttctcc gcgagtgacg cttcagaaaa caaacaggcc 660
cagcgttgta gaagagtctt cagagaattc ttccatctct ccggcttgtt tgtggttgct 720
gatgctatac cttttcttgg atggctcgat tggggaagac acgagaagac cttgaaaaag 780
accgccatag aaatggattc catcgcccag gagtggcttg aggaacatag acgtagaaaa 840
gattctggag atgataattc tacccaagat ttcatggacg ttatgcaatc tgtgctagat 900
ggcaaaaatc taggcggata cgatgctgat acgattaaca aggctacatg cttaactctt 960
atatcaggtg gcagtgatac tactgtagtt tctttgacat gggctcttag tcttgtgtta 1020
aacaatagag atactttgaa aaaggcacag gaagagttag acatccaagt cggtaaggaa 1080
agattggtta acgagcaaga catcagtaag ttagtttact tgcaagcaat agtaaaagag 1140
acactcagac tttatccacc aggtcctttg ggtggtttga gacaattcac tgaagattgt 1200
acactaggtg gctatcacgt ttcaaaagga actagattaa tcatgaactt atccaagatt 1260
caaaaagatc cacgtatttg gtctgatcct actgaattcc aaccagagag attccttacg 1320
actcataaag atgtcgatcc acgtggtaaa cactttgaat tcattccatt cggtgcagga 1380
agacgtgcat gtcctggtat cacattcgga ttacaagtac tacatctaac attggcatct 1440
ttcttgcatg cgtttgaatt ttcaacacca tcaaatgagc aggttaacat gagagaatca 1500
ttaggtctta cgaatatgaa atctacccca ttagaagttt tgatttctcc aagactatcc 1560
cttaattgct tcaaccttat gaaaatttga 1590

SEQ ID NO: 112
MYFLLQYLNI TTVGVFATLF LSYCLLLWRS RAGNKKIAPE AAAAWPIIGH LHLLAGGSHQ 60
LPHITLGNMA DKYGPVFTIR IGLHRAVVVS SWEMAKECST ANDQVSSSRP ELLASKLLGY 120
NYAMFGFSPY GSYWREMRKI ISLELLSNSR LELLKDVRAS EVVTSIKELY KLWAEKKNES 180
GLVSVEMKQW FGDLTLNVIL RMVAGKRYFS ASDASENKQA QRCRRVFREF FHLSGLFVVA 240
DAIPFLGWLD WGRHEKTLKK TAIEMDSIAQ EWLEEHRRRK DSGDDNSTQD FMDVMQSVLD 300
GKNLGGYDAD TINKATCLTL ISGGSDTTVV SLTWALSLVL NNRDTLKKAQ EELDIQVGKE 360
RLVNEQDISK LVYLQAIVKE TLRLYPPGPL GGLRQFTEDC TLGGYHVSKG TRLIMNLSKI 420
QKDPRIWSDP TEFQPERFLT THKDVDPRGK HFEFIPFGAG RRACPGITFG LQVLHLTLAS 480
FLHAFEFSTP SNEQVNMRES LGLTNMKSTP LEVLISPRLS SCSLYN 526

SEQ ID NO: 113
atggaaccta actttttactt gtcattacta ttgttgttcg tgaccttcat ttctttaagt 60
ctgtttttca tcttttacaa acaaaagtcc ccattgaatt tgccaccagg gaaaatgggt 120
taccctatca taggtgaaag tttagaattc ctatccacag gctggaaggg acatcctgaa 180
aagttcatat ttgatagaat gcgtaagtac agtagtgagt tattcaagac ttctattgta 240
ggcgaatcca cagttgtttg ctgtggggca gctagtaaca aattcctatt ctctaacgaa 300
aacaaactgg taactgcctg gtggccagat tctgttaaca aaatcttccc aacaacttca 360
ctggattcta atttgaagga ggaatctata aagatgagaa agttgctgcc acagttcttc 420
aaaccagaag cacttcaaag atacgtcggc gttatggatg taatcgcaca aagacatttt 480
gtcactcact gggacaacaa aaatgagatc acagtttatc cacttgctaa aagatacact 540
ttcttgcttg cgtgtagact gttcatgtct gttgaggatg aaaatcatgt ggcgaaattc 600
tcagacccat tccaactaat cgctgcaggc atcatttcac ttcctatcga tcttcctggt 660
actccattca acaaggccat aaaggcttca aatttcatta gaaaagagct gataaagatt 720
atcaaacaaa gacgtgttga tctggcagag ggtacagcat ctccaaccca ggatatcttg 780
tcacatatgc tattaacatc tgatgaaaac ggtaaatcta tgaacgagtt gaacattgcc 840
gacaagattc ttggactatt gataggaggc cacgatacag cttcagtagc ttgcacattt 900
ctagtgaagt acttaggaga attaccacat atctacgata aagtctacca agagcaaatg 960
gaaattgcca agtccaaacc tgctggggaa ttgttgaatt gggatgactt gaaaaagatg 1020
aagtattcat ggaatgtggc atgtgaggta atgagattgt caccaccttt acaaggtggt 1080
tttagagagg ctataactga ctttatgttt aacggtttct ctattccaaa agggtggaag 1140
ttatactggt ccgccaactc tacacacaaa aatgcagaat gtttcccaat gcctgagaaa 1200
ttcgatccta ccagatttga aggtaatggt ccagcgcctt atacatttgt accattcggt 1260
```

TABLE 11-continued

| Sequences disclosed herein. |
|---|
| ggaggcccta gaatgtgtcc tggaaaggaa tacgctagat tagaaatctt ggttttcatg 1320 |
| cataatctgg tcaaacgttt taagtgggaa aaggttattc cagacgaaaa gattattgtc 1380 |
| gatccattcc caatcccagc taaagatctt ccaatccgtt tgtatcctca caaagcttaa 1440 |
| |
| SEQ ID NO: 114 |
| MEPNFYLSLL LLFVTFISLS LFFIFYKQKS PLNLPPGKMG YPIIGESLEF LSTGWKGHPE 60 |
| KFIFDRMRKY SSELFKTSIV GESTVVCCGA ASNKFLFSNE NKLVTAWWPD SVNKIFPTTS 120 |
| LDSNLKEESI KMRKLLPQFF KPEALQRYVG VMDVIAQRHF VTHWDNKNEI TVYPLAKRYT 180 |
| FLLACRLFMS VEDENHVAKF SDPFQLIAAG IISLPIDLPG TPFNKAIKAS NFIRKELIKI 240 |
| IKQRRVDLAE GTASPTQDIL SHMLLTSDEN GKSMNELNIA DKILGLLIGG HDTASVACTF 300 |
| LVKYLGELPH IYDKVYQEQM EIAKSKPAGE LLNWDDLKKM KYSWNVACEV MRLSPPLQGG 360 |
| FREAITDFMF NGFSIPKGWK LYWSANSTHK NAECFPMPEK FDPTRFEGNG PAPYTFVPFG 420 |
| GGPRMCPGKE YARLEILVFM HNLVKRFKWE KVIPDEKIIV DPFPIPAKDL PIRLYPHKA 479 |
| |
| SEQ ID NO: 115 |
| atggcctctg ttactttggg ttcctggatc gtcgtccacc accataacca tcaccatcca 60 |
| tcatctatcc taactaaatc tcgttcaaga tcctgtccta ttacactaac caaaccaatc 120 |
| tcttttcgtt caaagagaac agtttcctct agtagttcta tcgtgtcctc tagtgtcgtc 180 |
| actaaggaag acaatctgag acagtctgaa ccttcttcct ttgatttcat gtcatatatc 240 |
| attactaagg cagaactagt gaataaggct cttgattcag cagttccatt aagagagcca 300 |
| ttgaaaatcc atgaagcaat gagatactct cttctagctg gcgggaagag agtcagacct 360 |
| gtactctgca tagcagcgtg cgaattagtt ggtggcgagg aatcaaccgc tatgcctgcc 420 |
| gcttgtgctg tagaaatgat tcatacaatg tcactgatac acgatgattt gccatgtatg 480 |
| gataacgatg atctgagaag gggtaagcca actaaccata aggttttcgg cgaagatgtt 540 |
| gccgtcttag ctggtgatgc tttgttatct ttcgcgttcg aacatttggc atccgcaaca 600 |
| tcaagtgatg ttgtgtcacc agtaagagta gttagagcag ttggagaact ggctaaagct 660 |
| attggaactg agggtttagt tgcaggtcaa gtcgtcgata tctcttccga aggtcttgat 720 |
| ttgaatgatg taggtcttga acatctcgaa ttcatccatc ttcacaagac agctgcactt 780 |
| ttagaagcca gtgcggttct cggcgcaatt gttggcggag ggagtgatga cgaaattgag 840 |
| agattgagga agtttgctag atgtatagga ttactgttcc aagtagtaga cgatatacta 900 |
| gatgtgacaa agtcttccaa agagttggga aaaacagctg gtaaagattt gattgccgac 960 |
| aaattgacct accctaagat tatggggcta gaaaaatcaa gagaatttgc cgagaaactc 1020 |
| aatagagagg cgcgtgatca actgttgggt ttcgattctg ataaagttgc accactctta 1080 |
| gccttagcca actacatcgc ttacagacaa aactaa 1116 |
| |
| SEQ ID NO: 116 |
| MASVTLGSWI VVHHHNHHHP SSILTKSRSR SCPITLTKPI SFRSKRTVSS SSSIVSSSVV 60 |
| TKEDNLRQSE PSSFDFMSYI ITKAELVNKA LDSAVPLREP LKIHEAMRYS LLAGGKRVRP 120 |
| VLCIAACELV GGEESTAMPA ACAVEMIHTM SLIHDDLPCM DNDDLRRGKP TNHKVFGEDV 180 |
| AVLAGDALLS FAFEHLASAT SSDVVSPVRV VRAVGELAKA IGTEGLVAGQ VVDISSEGLD 240 |
| LNDVGLEHLE FIHLHKTAAL LEASAVLGAI VGGGSDDEIE RLRKFARCIG LLFQVVDDIL 300 |
| DVTKSSKELG KTAGKDLIAD KLTYPKIMGL EKSREFAEKL NREARDQLLG FDSDKVAPLL 360 |
| ALANYIAYRQ N 371 |
| |
| SEQ ID NO: 117 |
| *R. suavissimus* |
| MATLLEHFQA MPFAIPIALA ALSWLFLFYI KVSFFSNKSA QAKLPPVPVV PGLPVIGNLL 60 |
| QLKEKKPYQT FTRWAEEYGP IYSIRTGAST MVVLNTTQVA KEAMVTRYLS ISTRKLSNAL 120 |
| KILTADKCMV AISDYNDFHK MIKRYILSNV LGPSAQKRHR SNRDTLRANV CSRLHSQVKN 180 |
| SPREAVNFRR VFEWELFGIA LKQAFGKDIE KPIYVEELGT TLSRDEIFKV LVLDIMEGAI 240 |
| EVDWRDFFPY LRWIPNTRME TKIQRLYFRR KAVMTALINE QKKRIASGEE INCYIDFLLK 300 |
| EGKTLTMDQI SMLLWETVIE TADTTMVTTE WAMYEVAKDS KRQDRLYQEI QKVCGSEMVT 360 |
| EEYLSQLPYL NAVFHETLRK HSPAALVPLR YAHEDTQLGG YYIPAGTEIA INIYGCNMDK 420 |
| HQWESPEEWK PERFLDPKFD PMDLYKTMAF GAGKRVCAGS LQAMLIACPT IGRLVQEFEW 480 |
| KLRDGEEENV DTVGLTTHKR YPMHAILKPR S 511 |
| |
| SEQ ID NO: 118 |
| *S. cerevisiae* |
| atgtcatttc aaattgaaac ggttcccacc aaaccatatg aagaccaaaa gcctggtacc 60 |
| tctggtttgc gtaagaagac aaaggtgttt aaagacgaac ctaactacac agaaaatttc 120 |
| attcaatcga tcatggaagc tattccagag ggttctaaag gtgccactct tgttgtcggt 180 |
| ggtgatgggc gttactacaa tgatgtcatt cttcataaga ttgccgctat cggtgctgcc 240 |
| aacggtatta aaaagttagt tattggccag catggtcttc tgtctacgcc agccgcttct 300 |
| cacatcatga gaacctacga ggaaaaatgt actggtggta ttatcttaac cgcctcacat 360 |
| aatccaggtg gtccagaaaa tgacatgggt attaagtata acttatccaa tgggggtcct 420 |
| gctcctgaat ccgtcacaaa tgctatttgg gagatttcca aaaagcttac cagctataag 480 |
| attatcaaag acttcccaga actagacttg ggtacgatag gcaagaacaa gaaatacggt 540 |
| ccattactcg ttgacattat cgatattaca aaagattatg tcaacttctt gaaggaaatc 600 |
| ttcgatttcg acttaatcaa gaaattcatc gataatcaac gttctactaa gaattggaag 660 |
| ttactgtttg acagtatgaa cggtgtaact ggaccatacg gtaaggctat tttcgttgat 720 |
| gaatttggtt taccggcgga tgaggtttta caaaactggc atccttctcc ggattttggt 780 |
| ggtatgcatc cagatccaaa cttaacttat gccagttcgt tagtgaaaag agtagatcgt 840 |
| gaaaagattg agtttggtgc tgcatccgat ggtgatggtg atagaaatat gatttacggt 900 |
| tacggcccat ctttcgtttc tccaggtgac tccgtcgcaa ttattgccga atatgcagct 960 |
| gaaatcccat atttcgccaa gcaaggtata tatggtctgg cccgttcatt ccctacctca 1020 |
| ggagccatag accgtgttgc caaggcccat ggtctaaact gttatgaggt cccaactggc 1080 |
| tggaaatttt tctgtgcttt gttcgacgct aaaaaattat ctatttgtgg tgaagaatcg 1140 |
| tttggtactg gttccaacca cgtaagggaa aaggacggtg tttgggccat tatggcgtgg 1200 |

TABLE 11-continued

Sequences disclosed herein.

```
ttgaacatct tggccattta caacaagcat catccggaga acgaagcttc tattaagacg 1260
atacagaatg aattctgggc aaagtacggc cgtactttct tcactcgtta tgattttgaa 1320
aaagttgaaa cagaaaaagc taacaagatt gtcgatcaat tgagagcata tgttaccaaa 1380
tcgggtgttg ttaattccgc cttcccagcc gatgagtctc ttaaggtcac cgattgtggt 1440
gatttttcat acacagattt ggacggttct gtttctgacc atcaaggttt atatgtcaag 1500
ctttccaatg gtgcaagatt cgttctaaga ttgtcaggta caggttcttc aggtgctacc 1560
attagattgt acattgaaaa atactgcgat gataaatcac aataccaaaa gacagctgaa 1620
gaatacttga agccaattat taactcggtc atcaagttct tgaactttaa acaagtttta 1680
ggaactgaag aaccaacggt tcgtacttaa 1710
```

SEQ ID NO: 119
*S. cerevisiae*

```
MSFQIETVPT KPYEDQKPGT SGLRKKTKVF KDEPNYTENF IQSIMEAIPE GSKGATLVVG 60
GDGRYYNDVI LHKIAAIGAA NGIKKLVIGQ HGLLSTPAAS HIMRTYEEKC TGGIILTASH 120
NPGGPENDMG IKYNLSNGGP APESVTNAIW EISKKLTSYK IIKDFPELDL GTIGKNKKYG 180
PLLVDIIDIT KDYVNFLKEI FDFDLIKKFI DNQRSTKNWK LLFDSMNGVT GPYGKAIFVD 240
EFGLPADEVL QNWHPSPDFG GMHPDPNLTY ASSLVKRVDR EKIEFGAASD GDGDRNMIYG 300
YGPSFVSPGD SVAIIAEYAA EIPYFAKQGI YGLARSFPTS GAIDRVAKAH GLNCYEVPTG 360
WKFFCALFDA KKLSICGEES FGTGSNHVRE KDGVWAIMAW LNILAIYNKH HPENEASIKT 420
IQNEFWAKYG RTFFTRYDFE KVETEKANKI VDQLRAYVTK SGVVNSAFPA DESLKVTDCG 480
DFSYTDLDGS VSDHQGLYVK LSNGARFVLR LSGTGSSGAT IRLYIEKYCD DKSQYQKTAE 540
EYLKPIINSV IKFLNFKQVL GTEEPTVRT 569
```

SEQ ID NO: 120
*S. cerevisiae*

```
atgtccacta agaagcacac caaaacacat tccacttatg cattcgagag caacacaaac 60
agcgttgctg cctcacaaat gagaaacgcc ttaaacaagt tggcggactc tagtaaactt 120
gacgatgctg ctcgcgctaa gtttgagaac gaactggatt cgtttttcac gcttttcagg 180
agatatttgg tagagaagtc ttctagaacc accttggaat gggacaagat caagtctccc 240
aacccggatg aagtggttaa gtatgaaatt atttctcagc agcccgagaa tgtctcaaac 300
ctttccaaat tggctgtttt gaagttgaac ggtgggctgg gtacctccat gggctgcgtt 360
ggccctaaat ctgttattga agtgagagag ggaaacacct ttttggattt gtctgttcgt 420
caaattgaat acttgaacag acagtacgat agcgacgtgc cattgttatt gatgaattct 480
ttcaacactg acaaggatac ggaacacttg attaagaagt attccgctaa cagaatcaga 540
atcagatctt tcaatcaatc caggttccca agagtctaca aggattcttt attgcctgtc 600
cccaccgaat acgattctcc actggatgct tggtatccac caggtcacgg tgatttgttt 660
gaatctttac acgtatctgg tgaactggat gccttaattg cccaaggaag agaaatatta 720
tttgtttcta acggtgacaa cttgggtgct accgtcgact taaaaatttt aaaccacatg 780
atcgagactg gtgccgaata tataatggaa ttgactgata agaccagagc cgatgttaaa 840
ggtggtactt tgatttctta cgatggtcaa gtccgtttat tggaagtcgc ccaagttcca 900
aaagaacaca ttgacgaatt caaaaatatc agaaagttta ccaacttcaa cacgaataac 960
ttatggatca atctgaaagc agtaaagagg ttgatcgaat cgagcaattt ggagatggaa 1020
atcattccaa accaaaaaac tataacaaga gacggtcatg aaattaatgt cttacaatta 1080
gaaaccgctt gtggtgctgc tatcaggcat tttgatggtg ctcacggtgt tgtcgttcca 1140
agatcaagat tcttgcctgt caagacctgt tccgatttgt tgctggttaa atcagatcta 1200
ttccgtctgg aacacggttc tttgaagtta gacccatccc gttttggtcc aaacccatta 1260
atcaagttgg gctcgcattt caaaaaggtt tctggtttta acgcaagaat ccctcacatc 1320
ccaaaaatcg tcgagctaga tcatttgacc atcactggta acgtcttttt aggtaaagat 1380
gtcactttga ggggtactgt catcatcgtt tgctccgacg gtcataaaat cgatattcca 1440
aacggctcca tattggaaaa tgttgtcgtt actggtaatt tgcaaatctt ggaacattga 1500
```

SEQ ID NO: 121
*S. cerevisiae*

```
MSTKKHTKTH STYAFESNTN SVAASQMRNA LNKLADSSKL DDAARAKFEN ELDSFFTLFR 60
RYLVEKSSRT TLEWDKIKSP NPDEVVKYEI ISQQPENVSN LSKLAVLKLN GGLGTSMGCV 120
GPKSVIEVRE GNTFLDLSVR QIEYLNRQYD SDVPLLLMNS FNTDKDTEHL IKKYSANRIR 180
IRSFNQSRFP RVYKDSLLPV PTEYDSPLDA WYPPGHGDLF ESLHVSGELD ALIAQGREIL 240
FVSNGDNLGA TVDLKILNHM IETGAEYIME LTDKTRADVK GGTLISYDGQ VRLLEVAQVP 300
KEHIDEFKNI RKFTNFNTNN LWINLKAVKR LIESSNLEME IIPNQKTITR DGHEINVLQL 360
ETACGAAIRH FDGAHGVVVP RSRFLPVKTC SDLLLVKSDL FRLEHGSLKL DPSRFGPNPL 420
IKLGSHFKKV SGFNARIPHI PKIVELDHLT ITGNVFLGKD VTLRGTVIIV CSDGHKIDIP 480
NGSILENVVV TGNLQILEH 499
```

SEQ ID NO: 122
*S. cerevisiae*

```
atgtctagtc aaacagaaag aacttttatt gcggtaaaac cagatggtgt ccagaggggc 60
ttagtatctc aaattctatc tcgttttgaa aaaaaaggtt acaaactagt tgctattaaa 120
ttagttaaag cggatgataa attactagag caacattacg cagagcatgt tggtaaacca 180
tttttcccaa agatggtatc ctttatgaag tctggtccca ttttggccac ggtctgggag 240
ggaaaagatg tggttagaca aggaagaact attcttggtg ctactaatcc tttgggcagt 300
gcaccaggta ccattagagg tgatttcggt attgacctag gcagaaacgt ctgtcacggc 360
agtgattctg ttgatagcgc tgaacgtgaa atcaatttgt ggtttaagaa ggaagagtta 420
gttgattggg aatctaatca agctaagtgg atttatgaat ga 462
```

SEQ ID NO: 123
*S. cerevisiae*

```
MSSQTERTFI AVKPDGVQRG LVSQILSRFE KKGYKLVAIK LVKADDKLLE QHYAEHVGKP 60
```

TABLE 11-continued

| Sequences disclosed herein. |
|---|
| FFPKMVSFMK SGPILATVWE GKDVVRQGRT ILGATNPLGS APGTIRGDFG IDLGRNVCHG 120<br>SDSVDSAERE INLWFKKEEL VDWESNQAEW IYE 153 |
| SEQ ID NO: 124<br>*S. rebaudiana*<br>atggctgctg ctgatactga aaagttgaac aatttgagat ccgccgtttc tggtttgacc 60<br>caaatttctg ataacgaaaa gtccggtttc atcaacttgg tcagtagata tttgtctggt 120<br>gaagctcaac acgttgaatg gtctaaaatt caaactccaa ccgataagat cgttgttcca 180<br>tacgatactt tgtctgctgt tccagaagat gctgctcaaa caaaatcttt gttggataag 240<br>ttggtcgtct tgaagttgaa cggtggtttg ggtactacta tgggttgtac tggtccaaag 300<br>tctgttatcg aagttagaaa cggtttgacc ttcttggatt tgatcgtcat ccaaatcgaa 360<br>tccttgaaca agaagtacgg ttgttctgtt cctttgttgt tgatgaactc tttcaacacc 420<br>catgaagata cccaaaagat cgtcgaaaag tactccggtt ctaacattga agttcacacc 480<br>ttcaatcaat cccaataccc aagattggtt gtcgatgaat tttgccatt gccatctaaa 540<br>ggtgaaactg gtaaagatgg ttggtatcca ccaggtcatg gtgatgtttt tccatccttg 600<br>atgaattccg gtaagttgga tgctttgttg tcccaaggta aagaatacgt tttcgttgcc 660<br>aactctgata acttgggtgc agttgttgat ttgaagatct tgaaccactt gatccaaaac 720<br>aagaacgaat actgcatgga agttactcca aagactttgg ctgatgttaa gggtggtact 780<br>ttgatttctt acgatggtaa ggttcaatta ttggaaatcg cccaagttcc agatgaacac 840<br>gttaatgaat tcaagtccat cgaaaagttt aagatcttta acactaacaa cttgtgggtc 900<br>aacttgaacg ccattaagag attggttcaa gctgatgctt tgaagatgga aattattcca 960<br>aatccaaaag aagtcaacgg tgtcaaggta ttgcaattgg aaactgctgc tggtgctgct 1020<br>attaagtttt tcgataatgc catcggtatc aacgtcccaa gatctagatt tttgcctgtt 1080<br>aaggcttcct ctgacttgtt gttagttcaa tcagacttgt acaccgaaaa ggatggttac 1140<br>gttattagaa acccagctag aaaggatcca gctaacccat ctattgaatt gggtccagaa 1200<br>ttcaaaaagg tcggtgattt cttgaagaga ttcaagtcta tcccatccat catcgaattg 1260<br>gactcattga aagtttctgg tgatgtctgg tttggttcca acgttgtttt gaaaggtaag 1320<br>gttgttgttg ctgccaaatc cggtgaaaaa ttggaaattc cagatggtgc cttgattgaa 1380<br>aacaaagaag ttcatggtgc ctccgacatt tga 1413 |
| SEQ ID NO: 125<br>*S. rebaudiana*<br>MAAADTEKLN NLRSAVSGLT QISDNEKSGF INLVSRYLSG EAQHVEWSKI QTPTDKIVVP 60<br>YDTLSAVPED AAQTKSLLDK LVVLKLNGGL GTTMGCTGPK SVIEVRNGLT FLDLIVIQIE 120<br>SLNKKYGCSV PLLLMNSFNT HEDTQKIVEK YSGSNIEVHT FNQSQYPRLV VDEFLPLPSK 180<br>GETGKDGWYP PGHGDVFPSL MNSGKLDALL SQGKEYVFVA NSDNLGAVVD LKILNHLIQN 240<br>KNEYCMEVTP KTLADVKGGT LISYDGKVQL LEIAQVPDEH VNEFKSIEKF KIFNTNNLWV 300<br>NLNAIKRLVQ ADALKMEIIP NPKEVNGVKV LQLETAAGAA IKFFDNAIGI NVPRSRFLPV 360<br>KASSDLLLVQ SDLYTEKDGY VIRNPARKDP ANPSIELGPE FKKVGDFLKR FKSIPSIIEL 420<br>DSLKVSGDVW FGSNVVLKGK VVVAAKSGEK LEIPDGALIE NKEVHGASDI 470 |
| SEQ ID NO: 126<br>*A. pullulans*<br>atgtcctctg aaatggctac tcatttgaaa cctaatggtg gtgccgaatt cgaaaaaaga 60<br>catcatggta agacccaatc ccatgttgct tttgaaaaca cttctacatc tgttgctgcc 120<br>tcccaaatga gaaatgcttt gaatactttg tgcgattccg ttactgatcc agctgaaaag 180<br>caaagattcg aaaccgaaat ggataacttc ttcgccttgt ttagaagata cttgaacgat 240<br>aaggctaagg gtaacgaaat cgaatggtct agaattgctc caccaaaacc agaacaagtt 300<br>gttgcttatc aagacttgcc tgaacaagaa tccgttgaat tcttgaacaa attggccgtc 360<br>ttgaagttga atggtggttt gggtacttct atgggttgtg ttggtccaaa gtctgttatc 420<br>gaagttagag atggtatgtc cttcttggat ttgtccgtta gacaaatcga atacttgaat 480<br>agaacctacg gtgttaacgt tccattcgtc ttgatgaatt ctttcaacac tgatgctgat 540<br>accgccaaca ttatcaaaaa gtacgaaggt cacaacatcg acatcatgac cttcaatcaa 600<br>tctagatacc caagaatctt gaaggattct ttgttgccag ctccaaaatc tgccaactct 660<br>caaatttctg attggtatcc accaggtcat ggtgacgttt ttgaatcctt gtacaactct 720<br>ggtatcttgg ataagttgtt ggaaagaggt gtcgaaatcg ttttcttgtc caatgctgat 780<br>aatttgggtg ccgttgttga tttgaagatc ttgcaacata tggttgatac caaggccgaa 840<br>tatatcatgg aattgactga taagactaag gccgatgtta agggtggtac tattattgac 900<br>tatgaaggtc aagccagatt attggaaatt gcccaagttc caaaagaaca cgtcaacgaa 960<br>ttcaagtcca tcaagaagtt taagtacttc aacaccaaca acatctggat gaacttgaga 1020<br>gctgttaaga gaatcgtcga aaacaacgaa ttggccatgg aaattatccc aaacggtaaa 1080<br>tctattccag ccgacaaaaa aggtgaagcc gatgtttcta tagttcaatt ggaaactgct 1140<br>gttggtgctg ccattagaca ttttaacaat gctcatggtg tcaacgtccc aagaagaaga 1200<br>tttttgccag ttaagacctg ctccgatttg atgttggtta agtctgactt gtacactttg 1260<br>aagcacggtc aattgattat ggacccaaat agatttggtc cagccccatt gattaagttg 1320<br>ggtggtgatt ttaagaaggt ttcctcattc caatccagaa tcccatccat tcctaaaatc 1380<br>ttggaattgg atcatttgac cattaccggt ccagttaact tgggtagagg tgttactttt 1440<br>aagggtactg ttattatcgt tgcctccgaa ggtcaaacca ttgatattcc acctggttcc 1500<br>attttggaaa acgttgttgt tcaaggttcc ttgagattat tagaacatta a 1551 |
| SEQ ID NO: 127<br>*A. pullulans*<br>MSSEMATHLK PNGGAEFEKR HHGKTQSHVA FENTSTSVAA SQMRNALNTL CDSVTDPAEK 60<br>QRFETEMDNF FALFRRYLND KAKGNEIEWS RIAPPKPEQV VAYQDLPEQE SVEFLNKLAV 120<br>LKLNGGLGTS MGCVGPKSVI EVRDGMSFLD LSVRQIEYLN RTYGVNVPFV LMNSFNTDAD 180<br>TANIIKKYEG HNIDIMTFNQ SRYPRILKDS LLPAPKSANS QISDWYPPGH GDVFESLYNS 240<br>GILDKLLERG VEIVFLSNAD NLGAVVDLKI LQHMVDTKAE YIMELTDKTK ADVKGGTIID 300<br>YEGQARLLEI AQVPKEHVNE FKSIKKFKYF NTNNIWMNLR AVKRIVENNE LAMEIIPNGK 360 |

TABLE 11-continued

Sequences disclosed herein.

```
SIPADKKGEA DVSIVQLETA VGAAIRHFNN AHGVNVPRRR FLPVKTCSDL MLVKSDLYTL   420
KHGQLIMDPN RFGPAPLIKL GGDFKKVSSF QSRIPSIPKI LELDHLTITG PVNLGRGVTF   480
KGTVIIVASE GQTIDIPPGS ILENVVVQGS LRLLEH                            516
```

SEQ ID NO: 128
*A. thaliana*

```
atggctgcta ctactgaaaa cttgccacaa ttgaaatctg ccgttgatgg tttgactgaa    60
atgtccgaat ctgaaaagtc cggtttcatc tctttggtca gtagatattt gtctggtgaa   120
gcccaacata tcgaatggtc taaaattcaa actccaaccg acgaaatcgt tgtcccatac   180
gaaaaaatga ctccagtttc tcaagatgtc gccgaaacta agaatttgtt ggataagttg   240
gtcgtcttga agttgaatgg tggtttgggt actactatgg gttgtactgg tccaaagtct   300
gttatcgaag ttagagatgg tttaaccttc ttggacttga tcgtcatcca aatcgaaaac   360
ttgaacaaca agtacggttg caaggttcca ttggtcttga tgaattcttt caacacccat   420
gatgataccc acaagatcgt tgaaaagtac accaactcca acgttgatat ccacaccttc   480
aatcaatcta agtacccaag agttgttgcc gatgaatttg ttccatggcc atctaaaggt   540
aagactgaca aagaaggttg gtatccacca ggtcatggtg atgtttttcc agctttaatg   600
aactccggta agttggatac tttcttgtcc caaggtaaag aatacgtttt cgttgccaac   660
tctgataact tgggtgctat agttgatttg accatcttga agcacttgat ccaaaacaag   720
aacgaatact gcatggaagt tactccaaag actttggctg atgttaaggg tggtactttg   780
atttcttacg aaggtaaggt tcaattattg gaaatcgccc aagttccaga tgaacacgtt   840
aatgaattca agtccatcga aaagttcaag atcttcaaca ccaacaactt gtgggttaac   900
ttgaaggcca tcaagaaatt ggttgaagct gatgctttga agatggaaat tatcccaaac   960
ccaaaagaag ttgacggtgt taaggtattg caattggaaa ctgctgctgg tgctgctatt  1020
agatttttcg ataatgccat cggtgttaac gtcccaagat ctagattttt gccagttaag  1080
gcttcctccg atttgttgtt ggttcaatct gacttgtaca ccttggttga cggttttgtt  1140
acaagaaaca aggctagaac taacccatcc aacccatcta ttgaattggg tccagaattc  1200
aaaaaggttg ccacattctt gtccagattc aagtctattc catccatcgt cgaattggac  1260
tcattgaaag tttctggtga tgtctggttt ggttcctcta tagttttgaa gggtaaggtt  1320
actgttgctg ctaaatctgg tgttaagttg gaaattccag atagagccgt tgtcgaaaac  1380
aaaaacatta acggtcctga agatttgtga                                   1410
```

SEQ ID NO: 129
*A. thaliana*

```
MAATTENLPQ LKSAVDGLTE MSESEKSGFI SLVSRYLSGE AQHIEWSKIQ TPTDEIVVPY    60
EKMTPVSQDV AETKNLLDKL VVLKLNGGLG TTMGCTGPKS VIEVRDGLTF LDLIVIQIEN   120
LNNKYGCKVP LVLMNSFNTH DDTHKIVEKY TNSNVDIHTF NQSKYPRVVA DEFVPWPSKG   180
KTDKEGWYPP GHGDVFPALM NSGKLDTFLS QGKEYVFVAN SDNLGAIVDL TILKHLIQNK   240
NEYCMEVTPK TLADVKGGTL ISYEGKVQLL EIAQVPDEHV NEFKSIEKFK IFNTNNLWVN   300
LKAIKKLVEA DALKMEIIPN PKEVDGVKVL QLETAAGAAI RFFDNAIGVN VPRSRFLPVK   360
ASSDLLLVQS DLYTLVDGFV TRNKARTNPS NPSIELGPEF KKVATFLSRF KSIPSIVELD   420
SLKVSGDVWF GSSIVLKGKV TVAAKSGVKL EIPDRAVVEN KNINGPEDL              469
```

SEQ ID NO: 130
*E. coli*

```
atggctgcta ttaacaccaa ggttaagaag gctgttattc cagttgctgg tttgggtact    60
agaatgttgc cagctacaaa agccattcca aaagaaatgt taccattggt cgataagcca   120
ttgatccaat acgttgtcaa cgaatgtatt gctgctggta ttaccgaaat cgttttggtt   180
actcactcct ccaagaactc cattgaaaat catttcgaca cctcattcga attggaagcc   240
atgttggaaa agagagtcaa gagacaatta ttggacgaag tccaatctat ttgcccacca   300
catgttacta tcatgcaagt tagacaaggt ttggctaaag gtttgggtca tgctgttttg   360
tgtgctcatc cagttgttgg tgatgaacca gttgcagtta ttttgccaga tgttatcttg   420
gacgaatacg aatccgattt gtctcaagat aacttggctg aaatgatcag aagattcgac   480
gaaactggtc actcccaaat tatggttgaa cctgttgctg atgttactgc ttatggtgtt   540
gttgattgca agggtgttga attggctcca ggtgaatctg ttccaatggt tggtgttgta   600
gaaaagccaa aagctgatgt tgctccatct aatttggcta tcgttggtag atatgttttg   660
tccgctgata tttggccttt gttggctaaa actccaccag gtgctggtga cgaaattcaa   720
ttgactgatg ctatcgacat gttgatcgaa aaagaaaccg ttgaagccta ccacatgaag   780
ggtaaatctc atgattgtgg taacaagttg ggttacatgc aagcttttgt tgaatacggt   840
atcagacata acaccttagg tactgaattc aaggcttggt tggaagaaga aatgggtatc   900
aagaagtaa                                                          909
```

SEQ ID NO: 131
*E. coli*

```
MAAINTKVKK AVIPVAGLGT RMLPATKAIP KEMLPLVDKP LIQYVVNECI AAGITEIVLV    60
THSSKNSIEN HFDTSFELEA MLEKRVKRQL LDEVQSICPP HVTIMQVRQG LAKGLGHAVL   120
CAHPVVGDEP VAVILPDVIL DEYESDLSQD NLAEMIRRFD ETGHSQIMVE PVADVTAYGV   180
VDCKGVELAP GESVPMVGVV EKPKADVAPS NLAIVGRYVL SADIWPLLAK TPPGAGDEIQ   240
LTDAIDMLIE KETVEAYHMK GKSHDCGNKL GYMQAFVEYG IRHNTLGTEF KAWLEEEMGI   300
KK                                                                 302
```

SEQ ID NO: 132
*R. suavissimus*

```
atggctgctg ttgctactga taagatctct aagttgaagt ctgaagttgc tgccttgtcc    60
caaatttctg aaaacgaaaa gtccggtttc atcaacttgg tcagtagata tttgtctggt   120
actgaagcta ctcacgttga atggtctaaa attcaaactc caaccgatga agttgttgtt   180
ccatatgata ctttggctcc aactccagaa gatccagctg aaactaagaa gttgttagat   240
aagttggtcg tcttgaagtt gaacggtggt ttgggtacta ctatgggttg tactggtcca   300
aagtctgtta tcgaagttag aaacggtttg accttcttgg atttgatcgt cattcaaatc   360
```

TABLE 11-continued

Sequences disclosed herein.

```
gaaaccttga acaacaagta cggttgtaac gttcctttgt tgttgatgaa ctctttcaac   420
acccatgatg acaccttcaa gatcgttgaa agatacacca agtccaacgt tcaaatccat   480
accttcaatc aatcccaata cccaagattg gttgtcgaag ataattctcc attgccatct   540
aagggtcaaa ctggtaaaga tggttggtat ccaccaggtc atggtgatgt tttccatct   600
ttgagaaact ccggtaagtt ggatttgttg ttatcccaag gtaaagaata cgttttcatc   660
tccaactctg ataacttggg tgcagttgtt gatttgaaga tcttgtccca tttggtccaa   720
aaaaagaacg aatactgcat ggaagttacc ccaaaaactt tggctgatgt taagggtggt   780
actttgattt cttacgaagg tagaacccaa ttattggaaa ttgcccaagt tccagatcaa   840
cacgttaacg aattcaagtc catcgaaaag ttcaagatct ttaacaccaa caatttgtgg   900
gtcaacttga acgccattaa gagattagtt gaagctgatg ccttgaaaat ggaaatcatc   960
ccaaatccaa aagaagtcga cggtattaag gtcttgcaat tggaaactgc tgctggtgct  1020
gctattagat tttcaatca tgccatcggt atcaacgtcc caagatctag atttttgcca  1080
gttaaggcta cctccgattt gttattggtt caatctgact tgtacaccgt cgaagatggt  1140
ttcgttatta gaaacactgc tagaaagaat ccagccaacc catctgttga attgggtcca  1200
gaattcaaaa aggttgccaa cttcttgtcc agattcaagt ctattccatc catcatcgaa  1260
ttggactcat tgaaggttgt tggtgatgta tggtttggtg ctggtgttgt tttgaaaggt  1320
aaggttacta ttactgctaa gccaggtgtt aagttggaaa ttccagataa ggctgtcttg  1380
gaaaacaagg atattaacgg tcctgaagat ttgtga                            1416
```

SEQ ID NO: 133
*R. suavissimus*

```
MAAVATDKIS KLKSEVAALS QISENEKSGF INLVSRYLSG TEATHVEWSK IQTPTDEVVV    60
PYDTLAPTPE DPAETKKLLD KLVVLKLNGG LGTTMGCTGP KSVIEVRNGL TFLDLIVIQI   120
ETLNNKYGCN VPLLLMNSFN THDDTFKIVE RYTKSNVQIH TFNQSQYPRL VVEDNSPLPS   180
KGQTGKDGWY PPGHGDVFPS LRNSGKLDLL LSQGKEYVFI SNSDNLGAVV DLKILSHLVQ   240
KKNEYCMEVT PKTLADVKGG TLISYEGRTQ LLEIAQVPDQ HVNEFKSIEK FKIFNTNNLW   300
VNLNAIKRLV EADALKMEII PNPKEVDGIK VLQLETAAGA AIRFFNHAIG INVPRSRFLP   360
VKATSDLLLV QSDLYTVEDG FVIRNTARKN PANPSVELGP EFKKVANFLS RFKSIPSIIE   420
LDSLKVVGDV WFGAGVVLKG KVTITAKPGV KLEIPDKAVL ENKDINGPED L            471
```

SEQ ID NO: 134
*H. vulgare*

```
atggctgctg ctgcagttgc tgctgattct aaaattgatg gtttgagaga tgctgttgcc    60
aagttgggtg aaatttctga aaacgaaaag gccggtttca tctccttggt ttctagatat   120
ttgtctggtg aagccgaaca aatcgaatgg tctaaaattc aaactccaac cgatgaagtt   180
gttgttccat atgatacttt ggctccacca cctgaagatt tggatgctat gaaggctttg   240
ttggataagt tggttgtctt gaagttgaat ggtggtttgg gtactactat gggttgtact   300
ggtccaaagt ctgttatcga agttagaaac ggtttcacct tcttggattt gatcgttatc   360
caaattgaat ccttgaacaa gaagtacggt tgctctgttc ctttgttgtt gatgaactct   420
ttcaacaccc atgatgacac ccaaaagatc gttgaaaagt actccaactc caacatcgaa   480
atccacacct tcaatcaatc tcaataccca agaatcgtca ccgaagattt tttgccattg   540
ccatctaaag gtcaaactgg taaagatggt tggtatccac caggtcatgg tgatgttttt   600
ccatctttga acaactccgg taagttggat accttgttgt ctcaaggtaa agaatacgtt   660
ttcgttgcca actctgataa cttgggtgct atcgttgata ttaagatctt gaaccacttg   720
atccacaatc aaaacgaata ctgcatggaa gttactccaa agactttggc tgatgttaag   780
ggtggtactt tgatttctta cgaaggtaga gttcaattat tggaaatcgc ccaagttcca   840
gatgaacacg ttgatgaatt caagtccatc gaaaagttca aaatcttcaa caccaacaac   900
ttgtgggtta acttgaaggc cattaagaga ttggttgatg ctgaagcttt gaaaatggaa   960
atcatcccaa accctaaaga agttgacggt gttaaggtat tgcaattgga aactgctgct  1020
ggtgctgcta ttagattctt tgaaaaagcc atcggtatca acgtcccaag atctagattt  1080
ttgccagtta aggctacctc tgacttgttg ttggttcaat cagacttgta caccttggtt  1140
gacggttacg ttattagaaa tccagctaga gttaagccat ccaacccatc tattgaattg  1200
ggtccagaat tcaagaaggt cgctaatttc ttggctagat tcaagtctat cccatccatc  1260
gttgaattgg actcattgaa agtttctggt gatgtctctt ttggttccgg tgttgttttg  1320
aagggtaatg ttactattgc tgctaaggct ggtgttaagt tggaaattcc agatggtgct  1380
gttttggaaa acaaggatat taacggtcca gaagatattt ga                      1422
```

SEQ ID NO: 135
*H. vulgare*

```
MAAAAVAADS KIDGLRDAVA KLGEISENEK AGFISLVSRY LSGEAEQIEW SKIQTPTDEV    60
VVPYDTLAPP PEDLDAMKAL LDKLVVLKLN GGLGTTMGCT GPKSVIEVRN GFTFLDLIVI   120
QIESLNKKYG CSVPLLLMNS FNTHDDTQKI VEKYSNSNIE IHTFNQSQYP RIVTEDFLPL   180
PSKGQTGKDG WYPPGHGDVF PSLNNSGKLD TLLSQGKEYV FVANSDNLGA IVDIKILNHL   240
IHNQNEYCME VTPKTLADVK GGTLISYEGR VQLLEIAQVP DEHVDEFKSI EKFKIFNTNN   300
LWVNLKAIKR LVDAEALKME IIPNPKEVDG VKVLQLETAA GAAIRFFEKA IGINVPRSRF   360
LPVKATSDLL LVQSDLYTLV DGYVIRNPAR VKPSNPSIEL GPEFKKVANF LARFKSIPSI   420
VELDSLKVSG DVSFGSGVVL KGNVTIAAKA GVKLEIPDGA VLENKDINGP EDI          473
```

SEQ ID NO: 136
*O. sativa*

```
atggctgacg aaaaattggc caaattgaga gaagctgttg ctggtttgtc tcaaatctct    60
gataacgaaa agtccggttt catttccttg gttgctagat atttgtccgg tgaagaagaa   120
catgttgaat gggctaaaat tcatacccca accgatgaag ttgttgttcc atatgatact   180
ttggaagctc caccagaaga tttggaagaa acaaaaaagt tgttgaacaa gttggccgtc   240
ttgaagttga atggtggttt gggtactact atgggttgta ctggtccaaa gtctgttatc   300
gaagttagaa acggtttcac cttcttggat ttgatcgtca tccaaatcga atccttgaac   360
aaaaagtacg gttccaacgt tcctttgttg ttgatgaact ctttcaacac ccatgaagat   420
accttgaaga tcgttgaaaa gtacaccaac tccaacatcg aagttcacac cttcaatcaa   480
```

TABLE 11-continued

Sequences disclosed herein.

```
tctcaatacc caagagttgt tgccgatgaa tttttgccat ggccatctaa aggtaagact   540
tgtaaagatg gttggtatcc accaggtcat ggtgatattt ttccatcctt gatgaacagt   600
ggtaagttgg acttgttgtt gtcccaaggt aaagaatacg ttttcattgc caactccgat   660
aacttgggtg ctatagttga tatgaagatt ttgaaccact tgatccacaa gcaaaacgaa   720
tactgtatgg aagttactcc aaagactttg gctgatgtta agggtggtac tttgatctct   780
tacgaagata aggttcaatt attggaaatc gcccaagttc cagatgctca tgttaatgaa   840
ttcaagtcca tcgaaaagtt caagatcttt aacaccaaca acttgtgggt taacttgaag   900
gccattaaga gattagttga agctgacgct ttgaagatgg aaattatccc aaacccaaaa   960
gaagttgacg gtgttaaggt attgcaattg gaaactgctg ctggtgctgc tattagattt  1020
ttcgatcatg ctatcggtat caacgtccca agatctagat tttaccagt taaggctacc  1080
tccgacttgc aattagttca atctgacttg tacaccttgg ttgatggttt cgttactaga  1140
aatccagcta gaactaatcc atccaaccca tctattgaat tgggtccaga attcaagaag  1200
gttggttgtt ttttgggtag attcaagtct atcccatcca tcgttgaatt ggacactttg  1260
aaagtttctg gtgatgtttg gttcggttcc tccattacat tgaaaggtaa ggttactatt  1320
accgctcaac caggtgttaa gttggaaatt ccagatggtg ctgtcatcga aaacaaggat  1380
attaacggtc ctgaagattt gtga                                          1404
```

SEQ ID NO: 137
*O. sativa*

```
MADEKLAKLR EAVAGLSQIS DNEKSGFISL VARYLSGEEE HVEWAKIHTP TDEVVVPYDT   60
LEAPPEDLEE TKKLLNKLAV LKLNGGLGTT MGCTGPKSVI EVRNGFTFLD LIVIQIESLN  120
KKYGSNVPLL LMNSFNTHED TLKIVEKYTN SNIEVHTFNQ SQYPRVVADE FLPWPSKGKT  180
CKDGWYPPGH GDIFPSLMNS GKLDLLLSQG KEYVFIANSD NLGAIVDMKI LNHLIHKQNE  240
YCMEVTPKTL ADVKGGTLIS YEDKVQLLEI AQVPDAHVNE FKSIEKFKIF NTNNLWVNLK  300
AIKRLVEADA LKMEIIPNPK EVDGVKVLQL ETAAGAAIRF FDHAIGINVP RSRFLPVKAT  360
SDLQLVQSDL YTLVDGFVTR NPARTNPSNP SIELGPEFKK VGCFLGRFKS IPSIVELDTL  420
KVSGDVWFGS SITLKGKVTI TAQPGVKLEI PDGAVIENKD INGPEDL                 467
```

SEQ ID NO: 138
*S. tuberosum*

```
atggctactg ctactacttt gtctccagct gatgctgaaa agttgaacaa tttgaaatct    60
gctgtcgccg gtttgaatca aatctctgaa aacgaaaagt ccggtttcat caacttggtt   120
ggtagatatt tgtctggtga agcccaacat attgactggt ctaaaattca aactccaacc   180
gatgaagttg ttgtcccata tgataagttg gctccattgt ctgaagatcc agctgaaaca   240
aaaaagttgt tggacaagtt ggtcgtcttg aagttgaatg gtggtttggg tactactatg   300
ggttgtactg gtccaaagtc tgttatcgaa gttagaaacg gtttgacctt cttggatttg   360
atcgtcaagc aaattgaagc tttgaacgct aagttcggtt gttctgttcc tttgttgttg   420
atgaactctt tcaacaccca tgatgacacc ttgaagatcg ttgaaaagta cgccaactcc   480
aacattgata tccacacctt caatcaatcc caatacccaa gattggttac cgaagatttt   540
gctccattgc catgtaaagg taactctggt aaagatggtt ggtatccacc aggtcatggt   600
gatgtttttc catccttgat gaattccggt aagttggatg ctttgttggc taagggtaaa   660
gaatacgttt tcgttgccaa ctctgataac ttgggtgcta tcgttgattt gaaaatcttg   720
aaccacttga tcttgaacaa gaacgaatac tgcatggaag ttactccaaa gactttggct   780
gatgttaagg gtggtacttt gatttcttac gaaggtaagg ttcaattatt ggaaatcgcc   840
caagttccag atgaacacgt taatgaattc aagtccatcg aaaagtttaa gatcttcaac   900
actaacaact tgtgggtcaa cttgtctgcc attaagagat tggttgaagc tgatgccttg   960
aaaatggaaa ttattccaaa cccaaaagaa gtcgatggtg tcaaagtatt gcaattggaa  1020
actgctgctg gtgctgctat taagtttttc gatagagcta ttggtgccaa cgttccaaga  1080
tctagatttt tgccagttaa ggctacctct gacttgttgt tggttcaatc agacttgtac  1140
actttgactg atgaaggtta cgttattaga aacccagcta gatccaatcc atccaaccca  1200
tctattgaat tgggtccaga attcaagaag gtagccaatt ttttgggtag attcaagtct  1260
atcccatcca tcatcgattt ggattctttg aaagttactg gtgatgtctg gtttggttct  1320
ggtgttactt tgaaaggtaa agttaccgtt gctgctaagt caggtgttaa gttggaaatt  1380
ccagatggtg ctgttattgc caacaaggat attaacggtc cagaagatat ctaa        1434
```

SEQ ID NO: 139
*S. tuberosum*

```
MATATTLSPA DAEKLNNLKS AVAGLNQISE NEKSGFINLV GRYLSGEAQH IDWSKIQTPT   60
DEVVVPYDKL APLSEDPAET KKLLDKLVVL KLNGGLGTTM GCTGPKSVIE VRNGLTFLDL  120
IVKQIEALNA KFGCSVPLLL MNSFNTHDDT LKIVEKYANS NIDIHTFNQS QYPRLVTEDF  180
APLPCKGNSG KDGWYPPGHG DVFPSLMNSG KLDALLAKGK EYVFVANSDN LGAIVDLKIL  240
NHLILNKNEY CMEVTPKTLA DVKGGTLISY EGKVQLLEIA QVPDEHVNEF KSIEKFKIFN  300
TNNLWVNLSA IKRLVEADAL KMEIIPNPKE VDGVKVLQLE TAAGAAIKFF DRAIGANVPR  360
SRFLPVKATS DLLLVQSDLY TLIDEGYVIR NPARSNPSNP SIELGPEFKK VANFLGRFKS  420
IPSIIDLDSL KVTGDVWFGS GVTLKGKVTV AAKSGVKLEI PDGAVIANKD INGPEDI     477
```

SEQ ID NO: 140

```
atgttcttgt tggttacctc ttgcttcttg ccagattctg gttcttctgt taaggtcagt    60
ttgttcatct tcggtgtctc attggtttct acctctccaa ttgatggtca aaaaccaggt   120
acttctggtt tgagaaagaa ggtcaaggtt ttcaagcaac ctaactactt ggaaaacttc   180
gttcaagcta ctttcaacgc tttgactacc gaaaaagtta agggtgctac tttggttgtt   240
tctggtgatg gtagatatta ctccgaacaa gccattcaaa tcatcgttaa gatggctgct   300
gctaacggtg ttagaagagt ttgggttggt caaaactctt tgttgtctac tccagctgtt   360
tccgccatta ttagagaaag agttggtgct gatggttcta aagctactgg tgctttcatt   420
ttgactgctt ctcataatcc aggtggtcca actgaagatt tcggtattaa gtacaacatg   480
gaaaatggtg gtccagcccc agaatctatt actgataaga tatacgaaaa caccaagacc   540
atcaaagaat acccaattgc agaagatttg ccaagagttg atatctctac tatcggtatc   600
acttctttcg aaggtcctga aggtaaattc gacgttgaag tttttgattc cgctgatgat   660
```

TABLE 11-continued

Sequences disclosed herein.

```
tacgtcaagt tgatgaagtc catcttcgac ttcgaatcca tcaagaagtt gttgtcttac   720
ccaaagttca ccttttgtta cgatgcattg catggtgttg ctggtgctta tgctcataga   780
attttcgttg aagaattggg tgctccagaa tcctctttat tgaactgtgt tccaaaagaa   840
gattttggtg gtggtcatcc agatccaaat ttgacttatg ccaaagaatt ggttgccaga   900
atgggtttgt ctaagactga tgatgctggt ggtgaaccac ctgaatttgg tgctgctgca   960
gatggtgatg ctgatagaaa tatgatcttg ggtaaaagat tcttcgtcac ccccatctgat  1020
tccgttgcta ttattgctgc taatgctgtt ggtgctattc catacttttc atccggtttg  1080
aaaggtgttg ctagatctat gccaacttct gctgctttgg atgttgttgc taagaatttg  1140
ggtttgaagt tcttcgaagt tccaactggt tggaaattct tcggtaattt gatggatgca  1200
ggtatgtgtt ctgtttgcgg tgaagaatca tttggtactg gttccgatca tatcagagaa  1260
aaggatggta tttgggctgt tttggcttgg ttgtctattt tggctcacaa gaacaaagaa  1320
accttggatg gtaatgccaa gttggttact gttgaagata tcgttagaca acattgggct  1380
acttacggta gacattacta cactagatac gactacgaaa acgttgatgc tacagctgct  1440
aaagaattga tgggtttatt ggtcaagttg caatcctcat tgccagaagt taacaagatc  1500
atcaagggta tccatcctga agttgctaat gttgcttctg ctgatgaatt cgaatacaag  1560
gatccagttg atggttccgt ttctaaacat caaggtatca gatacttgtt tgaagatggt  1620
tccagattgg ttttcagatt gtctggtaca ggttctgaag gtgctactat tagattgtac  1680
atcgaacaat acgaaaagga cgcctctaag attggtagag attctcaaga tgctttgggt  1740
ccattggttg atgttgcttt gaagttgtcc aagatgcaag aattcactgg tagatcttct  1800
ccaaccgtta ttacctga                                                1818
```

SEQ ID NO: 141

```
MFLLVTSCFL PDSGSSVKVS LFIFGVSLVS TSPIDGQKPG TSGLRKKVKV FKQPNYLENF    60
VQATFNALTT EKVKGATLVV SGDGRYYSEQ AIQIIVKMAA ANGVRRVWVG QNSLLSTPAV   120
SAIIRERVGA DGSKATGAFI LTASHNPGGP TEDFGIKYNM ENGGPAPESI TDKIYENTKT   180
IKEYPIAEDL PRVDISTIGI TSFEGPEGKF DVEVFDSADD YVKLMKSIFD FESIKKLLSY   240
PKFTFCYDAL HGVAGAYAHR IFVEELGAPE SSLLNCVPKE DFGGGHPDPN LTYAKELVAR   300
MGLSKTDDAG GEPPEFGAAA DGDADRNMIL GKRFFVTPSD SVAIIAANAV GAIPYFSSGL   360
KGVARSMPTS AALDVVAKNL GLKFFEVPTG WKFFGNLMDA GMCSVCGEES FGTGSDHIRE   420
KDGIWAVLAW LSILAHKNKE TLDGNAKLVT VEDIVRQHWA TYGRHYYTRY DYENVDATAA   480
KELMGLLVKL QSSLPEVNKI IKGIHPEVAN VASADEFEYK DPVDGSVSKH QGIRYLFEDG   540
SRLVFRLSGT GSEGATIRLY IEQYEKDASK IGRDSQDALG PLVDVALKLS KMQEFTGRSS   600
PTVIT                                                               605
```

SEQ ID NO: 142

```
atggccattc ataatagagc tggtcaacca gcacaacaat ccgatttgat taacgttgct    60
caattgaccg cccaatatta cgttttgaaa cctgaagctg gtaacgctga acatgctgtt   120
aagtttggta cttctggtca tagaggttct gctgctagac attcttttaa cgaaccacat   180
attttggcta tcgctcaagc tattgctgaa gaaagagcta agaacggtat tactggtcca   240
tgttacgttg gtaaagatac ccatgctttg tctgaaccag ctttcatttc tgttttggaa   300
gttttggctg ctaacggtgt tgatgttatc gttcaagaaa acaacggttt cactccaact   360
ccagctgttt ctaatgctat tttggttcac aacaaaaagg gtggtccatt ggctgatggt   420
atagttatta ctccatctca taacccacct gaagatggtg gtattaagta caatccacca   480
aatggtggtc cagctgatac aaatgttact aaggttgttg aagatagagc caacgctttg   540
ttagctgatg gtttgaaagg tgtcaagaga atctctttgg atgaagctat ggcttcaggt   600
catgtcaaag aacaagattt ggttcaacca ttcgttgaag gtttggctga tatagttgat   660
atggctgcta ttcaaaaggc tggtttgact ttgggtgttg atccattggg tggttctggt   720
attgaatact ggaaaagaat cggtgaatat tacaacttga acttgaccat cgtcaacgat   780
caagttgacc aaactttcag attcatgcac ttggataagg atggtgctat tagaatggac   840
tgttcttctg aatgtgctat ggctggttta ttggctttga gagataagtt cgatttggct   900
tttgctaacg atccagatta cgatagacat ggtatcgtta ctccagcagg tttgatgaat   960
ccaaatcatt acttggctgt tgccatcaac tacttgtttc aacatagacc acaatggggt  1020
aaggatgttg ctgttggtaa aactttggtt tcctccgcta tgatcgatag agttgttaac  1080
gatttgggta gaaagttggt tgaagttcca gttggtttca agtggtttgt tgacggtttg  1140
tttgatggtt cttttggttt tggtggtgaa gaatctgctg gtgcttcatt tttgagattt  1200
gatggtactc catggtccac tgacaaagat ggtattatca tgtgtttgtt ggctgctgaa  1260
attactgctg ttactggtaa gaatccacaa gaacactaca acgaattggc taagagattt  1320
ggtgctccat cttacaatag attgcaagct gctgctactt ctgctcaaaa agctgcttta  1380
tctaagttgt ccccagaaat ggtttctgct tctactttag ctggtgatcc aattacagct  1440
agattgactg ctgctccagg taatggtgct tctattggtg gtttaaaggt tatgactgat  1500
aacggttggt ttgctgcaag accatctggt actgaagatg cttacaaaat ctactgcgaa  1560
tccttcttgg gtgaagaaca tagaaagcaa attgaaaaag aagccgtcga aatcgtcagt  1620
gaagttttga agaatgccta a                                            1641
```

SEQ ID NO: 143

```
MAIHNRAGQP AQQSDLINVA QLTAQYYVLK PEAGNAEHAV KFGTSGHRGS AARHSFNEPH    60
ILAIAQAIAE ERAKNGITGP CYVGKDTHAL SEPAFISVLE VLAANGVDVI VQENNGFTPT   120
PAVSNAILVH NKKGGPLADG IVITPSHNPP EDGGIKYNPP NGGPADTNVT KVVEDRANAL   180
LADGLKGVKR ISLDEAMASG HVKEQDLVQP FVEGLADIVD MAAIQKAGLT LGVDPLGGSG   240
IEYWKRIGEY YNLNLTIVND QVDQTFRFMH LDKDGAIRMD CSSECAMAGL LALRDKFDLA   300
FANDPDYDRH GIVTPAGLMN PNHYLAVAIN YLFQHRPQWG KDVAVGKTLV SSAMIDRVVN   360
DLGRKLVEVP VGFKWFVDGL FDGSFGFGGE ESAGASFLRF DGTPWSTDKD GIIMCLLAAE   420
ITAVTGKNPQ EHYNELAKRF GAPSYNRLQA AATSAQKAAL SKLSPEMVSA STLAGDPITA   480
RLTAAPGNGA SIGGLKVMTD NGWFAARPSG TEDAYKIYCE SFLGEEHRKQ IEKEAVEIVS   540
EVLKNA                                                              546
```

SEQ ID NO: 144

*R. suavissimus*

TABLE 11-continued

Sequences disclosed herein.

```
atgtcctccg gtaagattaa gagagttcaa actactccat tcgacggtca aaaaccaggt    60
acttctggtt tgagaaagaa ggttaaggtt ttcacccaac ctaactactt gcaaaacttc   120
gttcaatcta ccttcaacgc tttgccatct gataaggtaa aggtgctag attggttgtt   180
tctggtgatg gtagatactt ctccaaagaa gccattcaaa tcatcattaa gatggctgct   240
ggtaacggtg ttaagtctgt ttgggttggt caaaatggtt tgttgtctac tccagctgtt   300
tctgctgttg ttagagaaag agttggtgct gatggttgta aagcttctgg tgctttcatt   360
ttgactgctt ctcataatcc aggtggtcca aatgaagatt tcggtatcaa gtacaacatg   420
gaaaatggtg gtccagctcc agaatctatt accaacaaaa tctacgaaaa caccacccaa   480
atcaaagaat acttgaccgt tgatttgcca gaagttgata ttactaagcc aggtgttact   540
accttcgaag ttgaaggtgg tactttcact gttgatgttt tcgattctgc ttccgattac   600
gtcaagttga tgaagtccat tttcgacttc gaatccatca gaaagttgtt gtcctctcca   660
aagttcacct tttgttttga tgcattgcat ggtgttggtg gtgcttacgc taaaagaatt   720
ttcgttgaag aattgggtgc caaagaatcc tctttgttga actgtgttcc taaagaagat   780
tttggtggtg gtcatccaga tccaaatttg acatatgcta aagaattggt cgccagaatg   840
ggtttgtcta agtctaatac tcaaaacgaa ccaccagaat ttggtgctgc tgcagatggt   900
gatgctgata gaaatatggt tttgggtaag agattcttcg ttaccccatc tgattccgtt   960
gctattattg ctgctaatgc tgttgaagct atcccatact ttctactgg tttgaaaggt  1020
gttgctagat ctatgccaac ttctgctgct ttggatgttg ttgctaaaca cttgaacttg  1080
aagttcttcg aagtaccaac tggttggaag tttttcggta atttgatgga tgctggtttg  1140
tgttctgttt gcggtgaaga atcttttggt actggttccg atcatatcag agaaaaggat  1200
ggtatttggg ctgttttggc ttggttgtca attattgcca tcaagaacaa ggataacatc  1260
ggtggtgata agttggttac cgttgaagat atcgttagaa aacattgggc tacttacggt  1320
agacattact acactagata cgattacgaa aacgttgatg ctggtaaggc taaagatttg  1380
atggcatcat tggtcaactt gcaatcatct ttgcctgaag ttaacaagat cgttaagggt  1440
atctgttccg atgttgcaaa tgttgttggt gccgatgaat tcgaatacaa ggattctgtt  1500
gatggttcca tctccaaaca tcaaggtatc agatacttgt tcgaagatgg ttcaagattg  1560
gttttcagat tgtctggtac aggttctgaa ggtgctacta ttagattgta catcgaacaa  1620
tacgaaaatg acccatccaa gatctccaga gaatcttctg aagctttggc tccattggtt  1680
gaagttgctt tgaaattgtc caagatgcaa gaattcactg gtagatcagc tccaactgtt  1740
attacctga                                                          1749
```

SEQ ID NO: 145

*R. suavissimus*

```
MSSGKIKRVQ TTPFDGQKPG TSGLRKKVKV FTQPNYLQNF VQSTFNALPS DKVKGARLVV    60
SGDGRYFSKE AIQIIIKMAA GNGVKSVWVG QNGLLSTPAV SAVVRERVGA DGCKASGAFI   120
LTASHNPGGP NEDFGIKYNM ENGGPAPESI TNKIYENTTQ IKEYLTVDLP EVDITKPGVT   180
TFEVEGGTFT VDVFDSASDY VKLMKSIFDF ESIRKLLSSP KFTFCFDALH GVGGAYAKRI   240
FVEELGAKES SLLNCVPKED FGGGHPDPNL TYAKELVARM GLSKSNTQNE PPEFGAAADG   300
DADRNMVLGK RFFVTPSDSV AIIAANAVEA IPYFSTGLKG VARSMPTSAA LDVVAKHLNL   360
KFFEVPTGWK FFGNLMDAGL CSVCGEESFG TGSDHIREKD GIWAVLAWLS IIAIKNKDNI   420
GGDKLVTVED IVRKHWATYG RHYYTRYDYE NVDAGKAKDL MASLVNLQSS LPEVNKIVKG   480
ICSDVANVVG ADEFEYKDSV DGSISKHQGI RYLFEDGSRL VFRLSGTGSE GATIRLYIEQ   540
YENDPSKISR ESSEALAPLV EVALKLSKMQ EFTGRSAPTV IT                      582
```

SEQ ID NO: 146

```
atggcctctt tcaaggttaa cagagttgaa tcctctccaa tcgaaggtca aaaaccaggt    60
acttctggtt tgagaaagaa ggttaaggtt ttcacccaac cacattactt gcacaacttc   120
gttcaatcta ctttcaacgc tttgtctgcc gaaaaagtta agggttctac tttggttgtt   180
tccggtgatg gtagatatta ctccaaggat gccattcaaa tcatcattaa gatggctgct   240
gctaacggtg ttagaagagt ttgggttggt caaaatggtt tgttgtctac tccagctgtt   300
tctgctgttg ttagagaaag agttggtgct gatggttcta aatctaacgg tgctttcatt   360
ttgactgcct ctcataatcc aggtggtcca aatgaagatt tcggtatcaa gtacaacatg   420
gaaaatggtg gtccagctcc agaaggtatt actgataaga tttttgaaaa caccaagacc   480
atcaaagaat acttcattgc tgaaggtttg ccagacgttg atatttccgc tattggtatc   540
tcttcattct ctggtccaga tggtcaattc gatgttgatg ttttcgattc ctcttccgac   600
tacgtcaaat tgatgaagtc catcttcgac ttccaatcca tcaagaagtt gattacctcc   660
ccacaatttt ctttctgtta cgatgcttta catggtgttg gtggtgctta tgctaagcca   720
atttttgttg atgaattggg tgccaaagaa tcctctttgt tgaactgtgt tcctaaagaa   780
gattttggtg gtggtcatcc agatccaaat ttgacttacg ctaaagaatt ggtttccaga   840
atgggtttgg gtaagaatcc agattctaat ccaccagaat ttggtgctgc tgcagatggt   900
gatgctgata gaaatatgat cttgggtaaa agattcttcg tcaccccatc tgattccgtt   960
gctattattg ctgctaatgc cgttcaatca atcccatact tttcatccgg tttgaaaggt  1020
gttgctagat ctatgccaac ttctgctgct ttggatgttg ttgctaagtc tttgaacttg  1080
aagttcttcg aagttccaac tggttggaag tttttcggta atttgatgga tgctggtttg  1140
tgttctgttt gcggtgaaga atcatttggt actggttccg atcatatcag agaaaaggat  1200
ggtatttggg ctgttttggc ttggttgtct attttggctc ataagaacaa ggacaacttg  1260
aacggtggta acttggttac tgttgaagat atcgttaagc aacattgggc tacttacggt  1320
agacattact acactagata cgactacgaa aacgttgatg ctggtgctgc aaaagaattg  1380
atggctcatt tggttaagtt gcaatcctcc atctctgatg ttaacacctt cattaagggt  1440
atcagatccg atgttgctaa tgttgcatct gctgatgaat tcgaatacaa ggatccagtt  1500
gacggttcta tttccaaaca tcaaggtatt agatacttgt ttgaagatgg ttccagattg  1560
gttttcagat tgtctggtac aggttctgaa ggtgctacta ttagattgta catcgaacaa  1620
tacgaaaagg attcctctaa gaccggtaga gattctcaag aagctttggc tccattagtt  1680
gaagttgcct tgaaattgtc caagatgcaa gaattcactg gtagatctgc tccaactgtt  1740
attacctga                                                          1749
```

SEQ ID NO: 147

```
MASFKVNRVE SSPIEGQKPG TSGLRKKVKV FTQPHYLHNF VQSTFNALSA EKVKGSTLVV    60
```

TABLE 11-continued

| Sequences disclosed herein. |
|---|
| SGDGRYYSKD AIQIIIKMAA ANGVRRVWVG QNGLLSTPAV SAVVRERVGA DGSKSNGAFI 120 |
| LTASHNPGGP NEDFGIKYNM ENGGPAPEGI TDKIFENTKT IKEYFIAEGL PDVDISAIGI 180 |
| SSFSGPDGQF DVDVFDSSSD YVKLMKSIFD FQSIKKLITS PQFSFCYDAL HGVGGAYAKP 240 |
| IFVDELGAKE SSLLNCVPKE DFGGGHPDPN LTYAKELVSR MGLGKNPDSN PPEFGAAADG 300 |
| DADRNMILGK RFFVTPSDSV AIIAANAVQS IPYFSSGLKG VARSMPTSAA LDVVAKSLNL 360 |
| KFFEVPTGWK FFGNLMDAGL CSVCGEESFG TGSDHIREKD GIWAVLAWLS ILAHKNKDNL 420 |
| NGGNLVTVED IVKQHWATYG RHYYTRYDYE NVDAGAAKEL MAHLVKLQSS ISDVNTFIKG 480 |
| IRSDVANVAS ADEFEYKDPV DGSISKHQGI RYLFEDGSRL VFRLSGTGSE GATIRLYIEQ 540 |
| YEKDSSKTGR DSQEALAPLV EVALKLSKMQ EFTGRSAPTV IT 582 |
| |
| SEQ ID NO: 148 |
| gcacacacca tagcttcaaa atgtttctac tcctttttta ctcttccaga ttttctcgga 60 |
| ctccgcgcat cgccgtacca cttcaaaaca cccaagcaca gcatactaaa tttcccctct 120 |
| ttcttcctct agggtgtcgt taattacccg tactaaaggt ttggaaaaga aaaaagagac 180 |
| cgcctcgttt ctttttcttc gtcgaaaaag gcaataaaaa tttttatcac gtttcttttt 240 |
| cttgaaaatt tttttttttg atttttttct ctttcgatga cctcccattg atatttaagt 300 |
| taataaacgg tcttcaattt ctcaagtttc agtttcattt ttcttgttct attacaactt 360 |
| tttttacttc ttgctcatta gaaagaaagc atagcaatct aatctaagtt ttaattacaa 420 |
| ggatcc 426 |
| |
| SEQ ID NO: 149 |
| ggaagtacct tcaaagaatg gggtcttatc ttgttttgca agtaccactg agcaggataa 60 |
| taatagaaat gataatatac tatagtagag ataacgtcga tgacttccca tactgtaatt 120 |
| gcttttagtt gtgtattttt agtgtgcaag tttctgtaaa tcgattaatt tttttttctt 180 |
| tcctcttttt attaacctta atttttattt tagattcctg acttcaactc aagacgcaca 240 |
| gatattataa catctgcata ataggcattt gcaagaatta ctcgtgagta aggaaagagt 300 |
| gaggaactat cgcatacctg catttaaaga tgccgatttg ggcgcgaatc ctttattttg 360 |
| gcttcaccct catactatta tcagggccag aaaaaggaag tgtttccctc cttcttgaat 420 |
| tgatgttacc ctcataaagc acgtggcctc ttatcgagaa agaaattacc gtcgctcgtg 480 |
| atttgtttgc aaaaagaaca aaactgaaaa aacccagaca cgctcgactt cctgtcttcc 540 |
| tattgattgc agcttccaat ttcgtcacac aacaaggtcc tagcgacggc tcacaggttt 600 |
| tgtaacaagc aatcgaaggt tctggaatgg cgggaaaggg tttagtacca catgctatga 660 |
| tgcccactgt gatctccaga gcaaagttcg ttcgatcgta ctgttactct ctctctttca 720 |
| aacagaattg tccgaatcgt gtgacaacaa cagcctgttc tcacacactc ttttcttcta 780 |
| accaaggggg tggtttagtt tagtagaacc tcgtgaaact tacatttaca tatatataaa 840 |
| cttgcataaa ttggtcaatg caagaaatac atatttggtc ttttctaatt cgtagttttt 900 |
| caagttctta gatgctttct ttttctcttt tttacagatc atcaaggaag taattatcta 960 |
| ctttttacaa caaatataaa acaa 984 |
| |
| SEQ ID NO: 150 |
| cattatcaat actgccattt caaagaatac gtaaataatt aatagtagtg attttcctaa 60 |
| ctttatttag tcaaaaaatt agccttttaa ttctgctgta acccgtacat gcccaaaata 120 |
| gggggcgggt tacacagaat atataacatc gtaggtgtct gggtgaacag tttattcctg 180 |
| gcatccacta aatataatgg agcccgcttt ttaagctggc atccagaaaa aaaaagaatc 240 |
| ccagcaccaa aatattgttt tcttcaccaa ccatcagttc ataggtccat tctcttagcg 300 |
| caactacaga gaacaggggc acaaacaggc aaaaaacggg cacaacctca atggagtgat 360 |
| gcaacctgcc tggagtaaat gatgacacaa ggcaattgac ccacgcatgt atctatctca 420 |
| ttttcttaca ccttctatta ccttctgctc tctctgattt ggaaaaagct gaaaaaaaag 480 |
| gttgaaacca gttccctgaa attattcccc tacttgacta ataagtatat aaagacggta 540 |
| ggtattgatt gtaattctgt aaatctattt cttaaacttc ttaaattcta cttttatagt 600 |
| tagtcttttt tttagtttta aaacaccaag aacttagttt cgaataaaca cacataaaca 660 |
| aacaaa 666 |
| |
| SEQ ID NO: 151 |
| gatctgggcc gtatacttac atatagtaga tgtcaagcgt aggcgcttcc cctgccggct 60 |
| gtgagggcgc cataaccaag gtatctatag accgccaatc agcaaactac ctccgtacat 120 |
| tcatgttgca cccacacatt tatacaccca gaccgcgaca aattacccat aaggttgttt 180 |
| gtgacggcgt cgtacaagag aacgtgggaa ctttttaggc tcaccaaaaa agaaagaaaa 240 |
| aatacgagtt gctgacagaa gcctcaagaa aaaaaaaatt cttcttcgac tatgctggag 300 |
| gcagagatga tcgagccggt agttaactat atatagctaa attggttcca tcaccttctt 360 |
| ttctggtgtc gctccttcta gtgctatttc tggcttttcc tatttttttt tttccatttt 420 |
| tctttctctc tttctaatat ataaattctc ttgcattttc tatttttctc tctatctatt 480 |
| ctacttgttt attcccttca aggttttttt ttaaggagta cttgttttta gaatatacgg 540 |
| tcaacgaact ataattaact aaaca 565 |
| |
| SEQ ID NO: 152 |
| agttataata atcctacgtt agtgtgagcg ggatttaaac tgtgaggacc ttaatacatt 60 |
| cagacacttc tgcggtatca ccctacttat tcccttcgag attatatcta ggaacccatc 120 |
| aggttggtgg aagattaccc gttctaagac ttttcagctt cctctattga tgttacacct 180 |
| ggacacccct tttctggcat ccagttttta atcttcagtg gcatgtgaga ttctccgaaa 240 |
| ttaattaaag caatcacaca attctctcgg ataccacctc ggttgaaact gacaggtggt 300 |
| ttgttacgca tgctaatgca aaggagccta tatacctttg gctcggctgc tgtaacaggg 360 |
| aatataaagg gcagcataat ttaggagttt agtgaacttg caacatttac tattttccct 420 |
| tcttacgtaa atatttttct ttttaattct aaatcaatct ttttcaattt tttgtttgta 480 |
| ttcttttctt gcttaaatct ataactacaa aaaacacata cataaactaa aa 532 |
| |
| SEQ ID NO: 153 |
| gatctatgcg actgggtgag catatgttcc gctgatgtga tgtgcaagat aaacaagcaa 60 |

TABLE 11-continued

| Sequences disclosed herein. |
|---|
| ggcagaaact aacttcttct tcatgtaata aacacacccc gcgtttattt acctatctct 120 |
| aaacttcaac accttatatc ataactaata tttcttgaga taagcacact gcacccatac 180 |
| cttccttaaa aacgtagctt ccagtttttg gtggttccgg cttccttccc gattccgccc 240 |
| gctaaacgca tatttttgtt gcctggtggc atttgcaaaa tgcataacct atgcatttaa 300 |
| aagattatgt atgctcttct gacttttcgt gtgatgaggc tcgtggaaaa aatgaataat 360 |
| ttatgaattt gagaacaatt ttgtgttgtt acggtatttt actatggaat aatcaatcaa 420 |
| ttgaggattt tatgcaaata tcgtttgaat atttttccga ccctttgagt acttttcttc 480 |
| ataattgcat aatattgtcc gctgcccctt tttctgttag acggtgtctt gatctacttg 540 |
| ctatcgttca acaccacctt attttctaac tatttttttt ttagctcatt tgaatcagct 600 |
| tatggtgatg gcacattttt gcataaacct agctgtcctc gttgaacata ggaaaaaaaa 660 |
| atatataaac aaggctcttt cactctcctt gcaatcagat ttgggtttgt tccctttatt 720 |
| ttcatatttc ttgtcatatt cctttctcaa ttattatttt ctactcataa cctcacgcaa 780 |
| aataacacag tcaaatctat caaaa 805 |
| |
| SEQ ID NO: 154 |
| atccgctcta accgaaaagg aaggagttag acaacctgaa gtctaggtcc ctatttattt 60 |
| tttttaatag ttatgttagt attaagaacg ttatttatat ttcaaatttt tcttttttttt 120 |
| ctgtacaaac gcgtgtacgc atgtaacatt atactgaaaa ccttgcttga gaaggttttg 180 |
| ggacgctcga ag 192 |
| |
| SEQ ID NO: 155 |
| gtagatacgt tgttgacact tctaaataag cgaatttctt atgatttatg atttttatta 60 |
| ttaaataagt tataaaaaaa ataagtgtat acaaatttta aagtgactct taggttttaa 120 |
| aacgaaaatt cttattcttg agtaactctt tcctgtaggt caggttgctt tctcaggtat 180 |
| agcatgaggt cgctc 195 |

The invention claimed is:

1. A recombinant host cell capable of producing one or more steviol glycosides or a steviol glycoside composition in a cell culture, comprising:

(a) a recombinant gene encoding a polypeptide capable of synthesizing uridine 5'-triphosphate (UTP) from uridine diphosphate (UDP);

wherein the polypeptide comprises a polypeptide having at least 90% sequence identity to the amino acid sequence set forth in SEQ ID NO:123;

(b) a recombinant gene encoding a polypeptide capable of converting glucose-6-phosphate to glucose-1-phosphate;

wherein the polypeptide comprises a polypeptide having at least 90% sequence identity to the amino acid sequence set forth in any one of SEQ ID NOs:2, 119, 141, 143, 145, or 147; and/or (c) a recombinant gene encoding a polypeptide capable of synthesizing uridine diphosphate glucose (UDP-glucose) from UTP and glucose-1-phosphate;

wherein the polypeptide comprises a polypeptide having at least 90% sequence identity to the amino acid sequence set forth in any one of SEQ ID NOs:121, 125, 127, 129, 131, 133, 135, 137, or 139.

2. The recombinant host cell of claim 1, further comprising:

(a) a gene encoding a polypeptide capable of glycosylating steviol or a steviol glycoside at its C-13 hydroxyl group thereof;

(b) a gene encoding a polypeptide capable of beta 1,3 glycosylation of the C3' of the 13-O-glucose, 19-O-glucose, or both 13-O-glucose and 19-O-glucose of a steviol glycoside;

(c) a gene encoding a polypeptide capable of glycosylating steviol or a steviol glycoside at its C-19 carboxyl group thereof; and/or (d) a gene encoding a polypeptide capable of beta 1,2 glycosylation of the C2' of the 13-O-glucose, 19-O-glucose, or both 13-O-glucose and 19-O-glucose of a steviol glycoside;

wherein at least one of the genes in items (a)-(d) is a recombinant gene.

3. The recombinant host cell of claim 2, wherein:

(a) the polypeptide capable of glycosylating steviol or a steviol glycoside at its C-13 hydroxyl group thereof comprises a polypeptide having at least 90% sequence identity to the amino acid sequence set forth in SEQ ID NO:7;

(b) the polypeptide capable of beta 1,3 glycosylation of the C3' of the 13-O-glucose, 19-O-glucose, or both 13-O-glucose and 19-O-glucose of a steviol glycoside comprises a polypeptide having at least 90% sequence identity to the amino acid sequence set forth in SEQ ID NO:9;

(c) the polypeptide capable of glycosylating steviol or a steviol glycoside at its C-19 carboxyl group thereof comprises a polypeptide having at least 90% sequence identity to the amino acid sequence set forth in SEQ ID NO:4; and/or (d) the polypeptide capable of beta 1,2 glycosylation of the C2' of the 13-O-glucose, 19-O-glucose, or both 13-O-glucose and 19-O-glucose of a steviol glycoside comprises a polypeptide having at least 90% sequence identity to the amino acid sequence set forth in any one of SEQ ID NO:11, 13, or 16.

4. The recombinant host cell of claim 2, further comprising:

(e) a gene encoding a polypeptide capable of synthesizing geranylgeranyl pyrophosphate (GGPP) from farnesyl diphosphate (FPP) and isopentenyl diphosphate (IPP);

(f) a gene encoding a polypeptide capable of synthesizing ent-copalyl diphosphate from GGPP;

(g) a gene encoding an a polypeptide capable of synthesizing ent-kaurene from ent-copalyl diphosphate;

(h) a gene encoding a polypeptide capable of synthesizing ent-kaurenoic acid from ent-kaurene;

(i) a gene encoding a polypeptide capable of reducing cytochrome P450 complex; and/or (j) a gene encoding a polypeptide capable of synthesizing steviol from ent-kaurenoic acid;

wherein at least one of the genes in items (e)-(j) is a recombinant gene.

5. The recombinant host cell of claim 4, wherein:

(e) the polypeptide capable of synthesizing geranylgeranyl pyrophosphate (GGPP) from farnesyl diphosphate (FPP) and isopentenyl diphosphate (IPP) comprises a polypeptide having at least 90% sequence identity to the amino acid sequence set forth in any one of SEQ ID NOs:20, 22, 24, 26, 28, 30, 32, or 116;

(f) the polypeptide capable of synthesizing ent-copalyl diphosphate from GGPP comprises a polypeptide having at least 90% sequence identity to the amino acid sequence set forth in any one of SEQ ID NOs:34, 36, 38, 40, 42, or 120;

(q) the polypeptide capable of synthesizing ent-kaurene from ent-copalyl diphosphate comprises a polypeptide having at least 90% sequence identity to the amino acid sequence set forth in any one of SEQ ID NOs:44, 46, 48, 50, or 52;

(h) the polypeptide capable of synthesizing ent-kaurenoic acid from ent-kaurene comprises a polypeptide having at least 90% sequence identity to the amino acid sequence set forth in any one of SEQ ID NOs:60, 62, 66, 68, 70, 72, 74, 76 or 117;

(i) the polypeptide capable of reducing cytochrome P450 complex comprises a polypeptide having at least 90% sequence identity to the amino acid sequence set forth in any one of SEQ ID NOs:78, 80, 82, 84, 86, 88, 90, or 92; and/or (j) the polypeptide capable of synthesizing steviol from ent-kaurenoic acid comprises a polypeptide having at least 90% sequence identity to the amino acid sequence set forth in any one of SEQ ID NOs:94, 97, 100-104, 106, 108, 110, 112, or 114.

6. The recombinant host cell of claim 1, wherein the recombinant host cell comprises:

(a) a gene encoding a polypeptide capable of synthesizing uridine 5'-triphosphate (UTP) from uridine diphosphate (UDP) having at least 90% sequence identity to the amino acid sequence set forth in SEQ ID NO:123;

(b) one or more genes encoding a polypeptide capable of converting glucose-6-phosphate to glucose-1-phosphate, each having at least 90% sequence identity to the amino acid sequence set forth in SEQ ID NO:2 and/or SEQ ID NO:119; and (c) a gene encoding a polypeptide capable of synthesizing UDP-glucose from UTP and glucose-1-phosphate having at least 90% sequence identity to the amino acid sequence set forth in SEQ ID NO:121.

7. The recombinant host cell of claim 1, wherein the recombinant host cell comprises:

(a) a gene encoding a polypeptide capable of synthesizing uridine 5'-triphosphate (UTP) from uridine diphosphate (UDP) having at least 90% sequence identity to the amino acid sequence set forth in SEQ ID NO:123;

(b) one or more genes encoding a polypeptide capable of converting glucose-6-phosphate to glucose-1-phosphate, each having at least 90% sequence identity to the amino acid sequence set forth in SEQ ID NO:2 and/or SEQ ID NO:119; and (c) a gene encoding a polypeptide capable of synthesizing UDP-glucose from UTP and glucose-1-phosphate having at least 90% sequence identity to the amino acid sequence set forth in SEQ ID NO:121;

wherein the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed relative to a corresponding host cell lacking the one or more recombinant genes.

8. The recombinant host cell of claim 7, wherein the gene encoding the polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed by at least 10% relative to a corresponding host cell lacking the one or more recombinant genes.

9. The recombinant host cell of claim 1, wherein expression of the one or more recombinant genes increase the amount of UDP-glucose accumulated by the cell relative to a corresponding host lacking the one or more recombinant genes.

10. The recombinant host cell of claim 9, wherein expression of the one or more recombinant genes increases the amount of UDP-glucose accumulated by the cell by at least about 10% relative to a corresponding host lacking the one or more recombinant genes.

11. The recombinant host cell of claim 1, wherein expression of the one or more recombinant genes increases an amount of the one or more steviol glycosides or the steviol glycoside composition produced by the cell relative to a corresponding host lacking the one or more recombinant genes.

12. The recombinant host cell of claim 11, wherein expression of the one or more recombinant genes increases the amount of the one or more steviol glycosides produced by the cell by at least about 5% relative to a corresponding host lacking the one or more recombinant genes.

13. The recombinant host cell of claim 11, wherein expression of the one or more recombinant genes increases the amount of rebaudioside A (RebA), rebaudioside B (RebB), rebaudioside D (RebD), and/or rebaudioside M (RebM) produced by the cell relative to a corresponding host lacking the one or more recombinant genes.

14. The recombinant host cell of claim 13, wherein expression of the one or more recombinant genes increases the amount of RebA, RebB, RebD, and/or RebM produced by the cell by at least about 5% relative to a corresponding host cell lacking the one or more recombinant genes.

15. The recombinant host cell of claim 1, wherein expression of the one or more recombinant genes increases the amount of total steviol glycosides produced by the cell by at least about 5% relative to a corresponding host lacking the one or more recombinant genes.

16. The recombinant host cell of claim 1, wherein expression of the one or more recombinant genes decreases the one of one or more steviol glycosides or the steviol glycoside composition accumulated by the cell relative to a corresponding host lacking the one or more recombinant genes.

17. The recombinant host cell of claim 16, wherein expression of the one or more recombinant genes decreases the amount of the one or more steviol glycosides accumulated by the cell by at least about 5% relative to a corresponding host lacking the one or more recombinant genes.

18. The recombinant host cell of claim 16, wherein expression of the one or more recombinant genes decreases the amount of RebB, RebD, and/or steviol-13-O-glucoside (13-SMG), accumulated by the cell relative to a corresponding host lacking the one or more recombinant genes.

19. The recombinant host cell of claim 1, wherein expression of the one or more recombinant genes decreases the amount of total steviol glycosides produced by the cell by less than 5% relative to a corresponding host lacking the one or more recombinant genes.

20. The recombinant host cell of claim 1, wherein the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-Stevioside, 1,3-stevioside (RebG), rubusoside, RebA, RebB, rebaudioside C (RebC), RebD, rebaudioside E (RebE), rebaudioside F (RebF), RebM, rebaudioside Q (RebQ), rebaudioside I (RebI), dulcoside A, and/or an isomer thereof.

21. The recombinant host cell of claim 1, wherein the recombinant host cell is a plant cell, a fungal cell, an algal cell, or a bacterial cell.

22. A method of producing one or more steviol glycosides or a steviol glycoside composition in a cell culture, comprising culturing the recombinant host cell of claim 1 in the cell culture, under conditions in which the genes are expressed, and wherein the one or more steviol glycosides or the steviol glycoside composition is produced by the recombinant host cell.

* * * * *

UNITED STATES PATENT AND TRADEMARK OFFICE

CERTIFICATE OF CORRECTION

PATENT NO. : 11,821,015 B2
APPLICATION NO. : 17/200673
DATED : November 21, 2023
INVENTOR(S) : Douchin et al.

It is certified that error appears in the above-identified patent and that said Letters Patent is hereby corrected as shown below:

In the Specification

At Column 2, Line 64:
"a gene encoding an a polypeptide capable ..." should be "a gene encoding a polypeptide capable ..."

At Column 3, Lines 42-43:
"... SEQ ID NO:40, SEQ ID NO:42, or SEQ ID NO:120;" should be "... SEQ ID NO:40 or SEQ ID NO:42;"

At Column 3, Line 61:
"k" should be "j"

At Column 4, Line 38:
"e" should be "a"

In the Claims

Claim 4, item (g), at Column 481, Line 15:
"a gene encoding an a polypeptide capable ..." should be "a gene encoding a polypeptide capable ..."

Claim 5, item (f), at Column 481, Line 36:
"38, 40, 42, or 120;" should be "38, 40, or 42;"

Claim 5, item (q), at Column 481, Line 37:
"q" should be "g"

Signed and Sealed this
Fifth Day of March, 2024

Katherine Kelly Vidal

Katherine Kelly Vidal
*Director of the United States Patent and Trademark Office*